United States Patent
Wu et al.

(10) Patent No.: US 11,713,317 B2
(45) Date of Patent: *Aug. 1, 2023

(54) TRICYCLIC HETEROCYCLIC COMPOUNDS AS STING ACTIVATORS

(71) Applicant: Incyte Corporation, Wilmington, DE (US)

(72) Inventors: Liangxing Wu, Wilmington, DE (US); Neil Lajkiewicz, Garnet Valley, PA (US); Yingda Ye, Wilmington, DE (US); Zhenwu Li, Wilmington, DE (US); Wenqing Yao, Chadds Ford, PA (US)

(73) Assignee: Incyte Corporation, Wilmington, DE (US)

(*) Notice: Subject to any disclaimer, the term of this patent is extended or adjusted under 35 U.S.C. 154(b) by 189 days.

This patent is subject to a terminal disclaimer.

(21) Appl. No.: 17/190,151

(22) Filed: Mar. 2, 2021

(65) Prior Publication Data

US 2022/0073509 A1  Mar. 10, 2022

Related U.S. Application Data

(63) Continuation of application No. 16/421,881, filed on May 24, 2019, now Pat. No. 10,947,227.

(60) Provisional application No. 62/841,587, filed on May 1, 2019, provisional application No. 62/730,610, filed on Sep. 13, 2018, provisional application No. 62/676,810, filed on May 25, 2018.

(51) Int. Cl.
*A61P 35/00* (2006.01)
*A61K 31/4184* (2006.01)
*C07D 471/04* (2006.01)

(52) U.S. Cl.
CPC .................. *C07D 471/04* (2013.01)

(58) Field of Classification Search
CPC .......................... A61P 35/00; A61K 31/4184
See application file for complete search history.

(56) References Cited

U.S. PATENT DOCUMENTS

| | | | |
|---|---|---|---|
| 5,521,184 A | 5/1996 | Zimmermann | |
| 10,875,872 B2 | 12/2020 | Wu et al. | |
| 10,947,227 B2 | 3/2021 | Wu et al. | |
| 11,008,344 B2 | 5/2021 | Wu et al. | |
| 11,427,597 B2 | 8/2022 | Wu et al. | |
| 2017/0146519 A1 | 5/2017 | DeFillipis et al. | |
| 2018/0105514 A1 | 4/2018 | Mehlmann et al. | |
| 2018/0177784 A1 | 6/2018 | Wu et al. | |
| 2018/0177870 A1 | 6/2018 | Liu et al. | |
| 2018/0179179 A1 | 6/2018 | Wu et al. | |
| 2018/0179197 A1 | 6/2018 | Wu et al. | |
| 2018/0179201 A1 | 6/2018 | Wu et al. | |
| 2018/0179202 A1 | 6/2018 | Wu et al. | |
| 2019/0300524 A1 | 10/2019 | Wu et al. | |
| 2019/0359608 A1 | 11/2019 | Wu et al. | |
| 2020/0039994 A1 | 2/2020 | Wu et al. | |
| 2020/0040009 A1 | 2/2020 | Wu et al. | |
| 2021/0163493 A1 | 6/2021 | Wu et al. | |
| 2021/0332067 A1 | 10/2021 | Wu et al. | |
| 2022/0056049 A1 | 2/2022 | Wu et al. | |

FOREIGN PATENT DOCUMENTS

| | | |
|---|---|---|
| CN | 105367617 | 3/2016 |
| CN | 107335049 | 11/2017 |
| WO | WO 2000/009495 | 2/2000 |
| WO | WO 2000/053595 | 9/2000 |
| WO | WO 2001/014402 | 3/2001 |
| WO | WO 2001/064655 | 9/2001 |
| WO | WO 2002/000196 | 1/2002 |
| WO | WO 2003/024967 | 3/2003 |
| WO | WO 2003/037347 | 5/2003 |
| WO | WO 2003/099771 | 12/2003 |
| WO | WO 2004/005281 | 1/2004 |
| WO | WO 2004/046120 | 6/2004 |
| WO | WO 2004/056786 | 7/2004 |
| WO | WO 2004/080980 | 9/2004 |
| WO | WO 2005/028444 | 3/2005 |
| WO | WO 2006/056399 | 6/2006 |
| WO | WO 2014/093936 | 6/2014 |
| WO | WO 2015/061294 | 4/2015 |
| WO | WO 2015/077354 | 5/2015 |
| WO | WO 2015/143161 | 9/2015 |
| WO | WO 2015/185565 | 12/2015 |
| WO | WO 2016/096577 | 6/2016 |
| WO | WO 2016/120305 | 8/2016 |
| WO | WO 2017/011444 | 1/2017 |
| WO | WO 2017/011622 | 1/2017 |
| WO | WO 2017/011920 | 1/2017 |
| WO | WO 2017/027645 | 2/2017 |
| WO | WO 2017/027646 | 2/2017 |
| WO | WO 2017/053537 | 3/2017 |
| WO | WO 2017/093933 | 6/2017 |
| WO | WO 2017/100305 | 6/2017 |

(Continued)

OTHER PUBLICATIONS

Atzrodt et al., "The Renaissance of H/D Exchange," Angew. Chem. Int. Ed., Oct. 4, 2007, 7744-7765. Azzoni et al., "Pegylated Interferon Alfa-2a Monotherapy Results in Suppression of HIV Type 1 Replication and Decreased Cell-Associated HIV DNA Integration," J. Infect. Dis., Oct. 2012, 207:213-222.

Barber et al., "STING: infection, inflammation and cancer," Nat Rev Immunol., Dec. 2015, 15(12):760-770.

Beutler, "TLRs and innate immunity," Blood, Feb. 12, 2009, 113:1399-1407.

Blom et al., "Preparative LC-MS Purification: Improved Compound Specific Method Optimization," J. Combi. Chem., Sep. 11, 2014, 6:874-883.

(Continued)

*Primary Examiner* — Bruck Kifle
(74) *Attorney, Agent, or Firm* — Fish & Richardson P.C.

(57) ABSTRACT

The present application provides tricyclic heterocyclic compounds that activate the STING pathway to produce interferons, which are useful in the treatment of various diseases including infectious diseases and cancer.

39 Claims, No Drawings

(56) References Cited

FOREIGN PATENT DOCUMENTS

| WO | WO 2017/106740 | 6/2017 |
|---|---|---|
| WO | WO 2017/123657 | 7/2017 |
| WO | WO 2017/123669 | 7/2017 |
| WO | WO 2017/151922 | 9/2017 |
| WO | WO 2017/161349 | 9/2017 |
| WO | WO 2017/175147 | 10/2017 |
| WO | WO 2017/175156 | 10/2017 |
| WO | WO 2017/186711 | 11/2017 |
| WO | WO 2018/060323 | 4/2018 |
| WO | WO 2018/067423 | 4/2018 |
| WO | WO 2018/234805 | 12/2018 |
| WO | WO 2018/234807 | 12/2018 |
| WO | WO 2018/234808 | 12/2018 |
| WO | WO 2019/027857 | 2/2019 |
| WO | WO 2019/027858 | 2/2019 |
| WO | WO 2019/069269 | 4/2019 |
| WO | WO 2019/069270 | 4/2019 |
| WO | WO 2019/069275 | 4/2019 |
| WO | WO 2019/134705 | 7/2019 |
| WO | WO 2019/137707 | 7/2019 |
| WO | WO 2019/219820 | 11/2019 |
| WO | WO 2020/006432 | 1/2020 |
| WO | WO 2020/132549 | 6/2020 |

OTHER PUBLICATIONS

Blom et al., "Optimizing Preparative LC-MS Configurations and Methods for Parallel Synthesis Purification," J, Combi. Chem., Jul. 29, 2003, 5:670-683.

Blom et al., "Two-Pump At Column Dilution Configuration for Preparative LC-MS," Journal of Combinatorial Chemistry, Apr. 12, 2002, 4:295-301.

Burdette et al., "STING and the innate immune response to nucleic acids in the cytosol," Nat. Immunol. Jan. 2013, 14:19-26.

Cai et al., "The cGAS-cGAMP-STING Pathway of Cytosolic DNA Sensing and Signaling," Mol. Cell Review, Apr. 24, 2014, 54:289-296.

Cavlar et al., "Species-specific detection of the antiviral small-molecule compound CMA by STING," EMBO J., May 15, 2013, 32:1440-1450.

Chen et al., "Regulation and function of the cGAS-STING pathway of cytosolic DNA sensing," Nature Immunol., Oct. 2016, 17(10):1142-1149.

Cheng et al., "Pharmacologic Activation of the Innate Immune System to Prevent Respiratory Viral Infections," Am. J. Respir. Cell. Mol. Biol. Sep. 2011, 45:480-488.

Conlon et al., "Mouse, but not Human STING, Binds and Signals in Response to the Vascular Disrupting Agent 5,6-Dimethylxanthenone-4-Acetic Acid," J Immunol., 2013, 190:5216-5225.

Corrales et al., "Direct Activation of STING in the Tumor Microenvironment Leads to Potent and Systemic Tumor Regression and Immunity," Cell Reports, May 19, 2015, 11:1018-1030.

Crosse et al., "Interferon-Stimulated Genes as Enhancers of Antiviral Innate Immune Signaling," J. Innate Immun., Nov. 30, 2017, 10:85-93.

Diprivan, Reference ID No. 4089428, retrieved from https://www.accessdata.fda.gov/drugsatfda_docs/label/2017/019627s066lbl.pdf, Apr. 2017, 54 pages.

Enomoto et al., "Factors associated with the response to interferon-based antiviral therapies for chronic hepatitis C," World J. Hepatol, Nov. 18, 2015, 7:2681-2687.

Gao et al., "Structure-Function Analysis of STING Activation by c[G(20,50)pA(30,50)p]and Targeting by Antiviral DMXAA," Cell, Aug. 13, 2013, 154(4):748-762.

Garbe et al., "Diagnosis and treatment of cutaneous melanoma: state of the art 2006*," Melanoma Res. Apr. 2007, 17:117-127.

Guo et al., "STING agonists induce an innate antiviral immune response against hepatitis B virus," Antimicrobial Agents and Chemotherapy, Dec. 15, 2014, 59:1273-1281.

Hervas-Stubbs et al., "Direct Effects of Type I Interferons on Cells of the Immune System," Clin. Cancer Res., May 1, 2011, 17:2619-2627.

International Search Report and Written Opinion in International Application No. PCT/US2019/033944, dated Sep. 19, 2019, 13 pages.

International Search Report and Written Opinion in International Application No. PCT/US2019/044499, dated Nov. 20, 2019, 13 pages.

International Search Report and Written Opinion in International Application No. PCT/US2019/044500, dated Nov. 20, 2019, 13 pages.

International Search Report and Written Opinion in International Application No. PCT/US2020/012324, dated Mar. 30, 2020, 13 pages.

International Preliminary Report on Patentability in International Application No. PCT/US2019/044499, dated Feb. 11, 2021, 7 pages.

International Preliminary Report on Patentability in International Application No. PCT/US2019/044500, dated Feb. 11, 2021, 7 pages.

International Preliminary Report on Patentability in International Application No. PCT/US2020/012324, dated Jun. 16, 2021, 8 pages.

Ishikawa et al., "STING is an endoplasmic reticulum adaptor that facilitates innate immune signalling," Nature, Oct. 2, 2018, 455:674-678.

Kerekes et al., "Aurora Kinase Inhibitors Based on the Imidazo[1,2-a]pyrazine Core: Fluorine and Deuterium Incorporation Improve Oral Absorption and Exposure," J. Med. Chem., Dec. 3, 2010, 54:201-210.

Khiar et al., "Identification of a small molecule that primes the type I interferon response to cytosolic DNA," Scientific Reports, May 31, 2017, 7:2561.

Kim et al., "Anticancer Flavonoids Are Mouse-Selective STING Agonists," ACS Chem. Biol., May 17, 2013, 8:1396-1401.

Kirkwood, "Cancer Immunotherapy: The Interferon-Experience," Semin. Oncol., Jun. 1, 2002, 29:18-26.

Kramer et al., "Antiviral Activity of 10-Carboxymethyl-9-Acridanone," Antimicrobial Agents and Chemotherapy, Feb. 1, 1976, 9:233-238.

Lane et al., "Interferon-α in Patients with Asymptomatic Human Immunodeficiency Virus (HIV) Infection: A Randomized, Placebo-Controlled Trial," Ann. Intern. Med., Jun. 1, 1990, 112:805-811.

Larkin et al., "Cutting Edge: Activation of STING in T Cells Induces Type I IFN Responses and Cell Death," J Immunol., 2017, 199:397-402.

Liu et al., "A cell-based high throughput screening assay for the discovery of cGASSTING pathway agonists," Antiviral Research, 2017, 147:37-46.

McNab et al., "Type I interferons in infectious disease," Nat Rev Immunol, Feb. 2015, 15:87-103.

Palm et al., "Pattern recognition receptors and control of adaptive immunity," Immunol Rev. Jan. 2009, 227:221-233.

Perera et al., "Activation of LPS-inducible genes by the antitumor agent 5,6-dimethylxanthenone-4-acetic acid in primary murine macrophages. Dissection of signaling pathways leading to gene induction and tyrosine phosphoiylation," J. Immunol., Nov. 15, 1994, 153:4684-4697.

Pizzocaro et al., "Interferon Adjuvant to Radical Nephrectomy in Robson Stages II and III Renal Cell Carcinoma: A Multicentric Randomized Study," J. Clin. Oncol., Jan. 15, 2001, 19:425-431.

Quesada et al., "Alpha Interferon for Induction of Remission in Hairy-Cell Leukemia," N. Engl. J. Med. Jan. 5, 1984, 310:15-18.

Ramanjulu et al., "Design of amidobenzimidazole STING receptor agonists with systemic activity," Nature, 2018, 564:439-443.

Ramanjulu et al., "Design of amidobenzimidazole STING receptor agonists with systemic activity," Nature, 2018, Supplementary Information, 66 pages.

Remington et al., "Remington's Pharmaceutical Sciences," 17th ed., 1985, p. 1418.

(56) References Cited

OTHER PUBLICATIONS

Sali et al., "Characterization of a Novel Human-Specific STING Agonist that Elicits Antiviral Activity Against Emerging Alphaviruses," PLoS Pathog., Dec. 8, 2015, 11(12):e1005324.

SciFinder Search Results, generated Jun. 27, 2018, 1 page.

SciFinder Search Results, generated Jun. 27, 2018, 22 pages.

Siu et al., "Discovery of a Novel cGAMP Competitive Ligand of the Inactive Form of STING," ACS Med Chem Lett., 2019, 10(1):92-97.

Sokolowska et al., "STING Signaling in Cancer Cells: Important or Not?" Arch Immunol Ther Exp., Jul. 26, 2017, 66:125-132.

Takeuchi et al., "Innate immunity to virus infection," Immunol Rev., Jan. 2009, 227:75-86.

Tang et al., "Benefits of Therapeutic Drug Monitoring of Vancomycin: A Systematic Review and Meta-Analysis," Plos One, Oct. 2013, 8:1-10.

Tarhini et al., "IFN-α in the Treatment of Melanoma," J. Immunol., Oct. 2012, 189:3789-3793.

Vannucchi et al., "Perspectives in Biomolecular Therapeutic Intervention in Cancer: From the Early to the New Strategies With Type I Interferons," Curr. Med. Chem., Mar. 1, 2007, 14:667-679.

Wallace et al., "The Vascular Disrupting Agent, DMXAA, Directly Activates Dendritic Cells through a MyD88-Independent Mechanism and Generates Antitumor Cytotoxic T Lymphocytes," Cancer Research, Jul. 2007, 67:7011-7019.

Xu et al., "Design, synthesis and biological evaluation of deuterated nintedanib for improving pharmacokinetic properties," J. Label Compd. Radiopharm. May 26, 2015, 58:308-312.

TRICYCLIC HETEROCYCLIC COMPOUNDS AS STING ACTIVATORS

CROSS-REFERENCE TO RELATED APPLICATIONS

This application is a continuation of U.S. patent application Ser. No. 16/421,881, filed May 24, 2019, which claims the benefit of U.S. Provisional Application Ser. Nos. 62/676,810, filed May 25, 2018, 62/730,610, filed Sep. 13, 2018, and 62/841,587, filed May 1, 2019, the disclosure of each of which is incorporated herein by reference in its entirety.

TECHNICAL FIELD

The present application provides tricyclic heterocyclic compounds that activate the STING pathway to produce interferons, which are useful in the treatment of various diseases including infectious diseases and cancer.

BACKGROUND

The innate immunity is the first line of defense against infection from foreign microorganisms including bacteria, viruses, parasites and other infectious threats, but it also responds to certain danger signals associated with cellular or tissue damage. This response is initiated by activation of so-called pattern recognition receptors that can detect different forms of foreign antigens, i.e. nucleic acids, peptides, carbohydrates, and more, which then lead to production of interferons, proinflammatory chemokines and cytokines, and anti-microbial peptides to fight infection (Palm and Medzhitov, *Immunol Rev* (2009) 227:221-233; Takeuchi and Akira, *Immunol Rev* (2009) 227:75-86; Beutler, *Blood* (2009) 113:1399-1407). STING (stimulator of interferon genes), also known as MITA, MPYS, ERIS, and TMEM173, is one of such pattern recognition receptors in the innate immune response that could detect cytosolic nucleic acids (Ishikawa and Barber, *Nature* (2008) 455:674-678). Direct binding of STING to its ligands induces a conformational change of the complex resulting in a downstream signaling cascade involving TBK1 activation, IRF-3 phosphorylation, and production of type I IFNs and other proinflammatory cytokines, such as TNF, IL-6 and IFNγ (Ishikawa and Barber, *Nature* (2008) 455:674-678).

Type I interferons play a central role in orchestrating host anti-viral response through inhibiting viral replication in infected cells, activating and enhancing antigen presentation and triggering the adaptive immune response through direct and indirect action on T and B cells (McNab et al, *Nat Rev Immunol* (2015) 15:87-103; Crosse et al, *J Innate Immun* (2018) 10:85-93). Therefore, this cytokine acts as a master regulator whose induction in the early stages of viral infection modulates downstream signaling cascades that promote both pro-inflammatory and anti-inflammatory responses. Thus type I IFNs have been evaluated as a therapeutic agent for chronic viral infection such as HCV and HIV (Enomoto and Nishiguchi, *World J Hepatol* (2015) 7:2681-2687; Azzoni et al, *J Infect Dis* (2013) 207:213-222; Lane et al, *Ann Intern Med* (1990) 112:805-11).

The use of type I interferons (IFNs) (the IFNα family and IFNβ) as potential antitumor agents has also been investigated (Kirkwood, *Semin Oncol* (2002) 29:18-26; Tarhini et al, *J Immunol* (2012) 189:3789-3793). IFNs have multiple anticancer mechanisms that include: direct inhibition on tumor cell proliferation and angiogenesis; induction of tumor-specific cytotoxic T-cells; plus other immunoregulatory effects on antibody production, natural killer (NK) cell activation, macrophage function, delayed-type hypersensitivity, and major histocompatibility complex antigen expression (Hervas-Stubbs et al, *Clin Cancer Res* (2011) 17:2619-2627; Vannucchi et al, *Curr Med Chem* (2007) 14:667-679). Anticancer activity of type I IFNs has been demonstrated in patients with hematological malignancies (e.g., hairy cell leukemia) and solid tumors (e.g., renal cell carcinoma and malignant melanoma) (Quesada et al, *N Engl J Med* (1984) 310:15-18; Pizzocaro et al, *J Clin Oncol* (2001) 19:425-431; Garbe and Eigentler, *Melanoma Res* (2007) 17:117-127), however, the results and overall efficacy have been modest. This may be due to intrinsic resistance to IFN-induced cell death, to the short half-life (~30 minutes) of intravenously or subcutaneously dosed IFN, to dose-limiting systemic toxicities, and/or to the development of neutralizing antibodies against recombinant IFN protein. Thus, the development of an agent like a STING agonist to induce production of type I interferons will be of interest to the field. Currently, there are two different classes of STING agonists: cyclic dinucleotide and small molecule.

Cyclic dinucleotides (CDNs) can directly bind and activate STING, and the complex of bacterial CDN and STING has been confirmed by X-ray crystallography recently (Burdette and Vance, *Nat Immunol* (2013) 14:19-26). In mammalian cells, the primary sensor of cyclic double stranded DNA (dsDNA), namely cyclic GMP-AMP synthetase (cGAS), can convert those cyclic dsDNA into a mammalian CDN cGAMP (cyclic guanosine monophosphate—adenosine monophosphate; Gao et al, *Cell* (2013) 154:748-762). The interaction of cGAMP and STING has also been confirmed by X-ray crystallography (Cai et al, *Mol Cell* (2014) 54:289-296). Synthetic derivatives of cGAMP have been synthesized and showed excellent cellular potency to activate both mouse and human STING in vitro, as well as demonstrated good anti-tumor efficacy in preclinical mouse models (Corrales et al, *Cell Rep* (2015) 11:1018-1030).

Small molecules that can activate STING have also been identified, DMXAA (5,6-dimethylxanthenone-4-acetic acid) and CMA (10-carboxymethyl-9-acridanone) (Perera et al, *J Immunol* (1994) 153:4684-4697; Kramer et al, *Antimicrob Agents Chemother* (1976) 9:233-238). These two chemically-unrelated compounds can activate the STING pathway, and block multiple viruses from replication (Guo et al, *Agents Chemother* (2015) 59:1273-1281; Cheng et al, *Am J Respir Cell Mol Biol* (2011) 45:480-488). Intriguingly, DMXAA demonstrates excellent anti-tumor activity in preclinical mouse models by priming CD8+ T cells responses to promote rejection of established tumors in a STING-dependent manner, inducing tumor necrosis through disruption of tumor vasculature, as well as augmenting cancer vaccine effect (Corrales et al, *Cell Rep* (2015) 11:1018-1030; Wallace et al, *Cancer Res* (2007) 67:7011-7019; Tang et al, *Plos One* (2013) 8:1-6). Unfortunately, both DMXAA and CMA were found to only bind and activate mouse STING, but not human STING (Caviar et al, *EMBO J* (2013) 32:1440-1450; Kim et al, *ACS Chem Biol* (2013) 8:1396-1401).

Hence, there is a need to develop small molecule entities that can activate human STING and induce upregulation of IRF3 and NFκB pathway, which can later lead to production of interferons and other proinflammatory cytokines and chemokines. This type of immunomodulating agents may be useful not only in infectious disease to activate innate immunity, but also in cancer, and as vaccine adjuvants. This application is directed to this need and others.

SUMMARY

The present invention relates to, inter alia, compounds of Formula (I):

$$\text{(I)}$$

or a pharmaceutically acceptable salt thereof, wherein constituent members are defined herein.

The present invention further provides pharmaceutical compositions comprising a compound of Formula (I), or a pharmaceutically acceptable salt thereof, and a pharmaceutically acceptable carrier.

The present invention further provides methods of activating STING, comprising contacting the receptor with a compound of Formula (I), or a pharmaceutically acceptable salt thereof.

The present invention further provides a compound of Formula (I), or a pharmaceutically acceptable salt thereof, for use in any of the methods described herein.

The present invention further provides use of a compound of Formula (I), or a pharmaceutically acceptable salt thereof, for the preparation of a medicament for use in any of the methods described herein.

DETAILED DESCRIPTION

Compounds

The present application provides, inter alia, compounds of Formula (I):

$$\text{(I)}$$

or a pharmaceutically acceptable salt thereof, wherein:

$R^1$ is H, $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, or 5-10 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl are each optionally substituted by 1, 2, 3, or 4 independently selected $R^8$ groups;

U is N or $CR^U$;
V is N or $CR^V$;
W is N or $CR^W$;
Q is N or $CR^Q$;

wherein U=V—W=Q is selected from $CR^U=CR^V-CR^W=CR^Q$, $N=CR^V-CR^W=CR^Q$, $CR^U=N-CR^W=CR^Q$, $CR^U=CR^V-N=CR^Q$, $CR^U=CR^V-CR^W=N$, $N=N-CR^W=CR^Q$, $CR^U=N-N=CR^Q$, $CR^U=CR^V-N=N$, $N=CR^V-CR^W=N$, $N=CR^V-N=CR^Q$, $CR^U=N-CR^W=N$, $N=N-CR^W=N$, and $N=CR^V-N=N$;

$R^U$, $R^V$, $R^W$, and $R^Q$ are each independently selected from H, D, halo, CN, $NO_2$, $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, 5-10 membered heteroaryl-$C_{1-4}$ alkyl, $OR^a$, $SR^a$, $C(=O)R^b$, $C(=O)NR^aR^d$, $C(=O)OR^a$, $OC(=O)R^b$, $OC(=O)NR^cR^d$, $NR^cR^d$, $NR^cC(=O)R^b$, $NR^cC(=O)OR^b$, $NR^cC(=O)NR^aR^d$, $C(=NR^e)R^b$, $C(=NR^e)NR^cR^d$, $NR^cC(=NR^e)NR^cR^d$, $NR^cS(=O)_2R^b$, $NR^cS(=O)_2NR^cR^d$, $S(=O)_2R^b$, and $S(=O)_2NR^cR^d$, wherein said $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl are each optionally substituted by 1, 2, 3, or 4 independently selected $R^8$ groups;

each $R^a$, $R^c$, and $R^d$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^8$ groups;

each $R^b$ is independently selected from $C_{1-6}$ alkyl, $C_{1-6}$ haloalkyl, $C_{2-6}$ alkenyl, $C_{2-6}$ alkynyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, or 3 independently selected $R^8$ groups;

each $R^e$ is independently selected from H, CN, OH, $C_{1-4}$ alkyl, and $C_{1-4}$ alkoxy;

each $R^8$ is independently selected from H, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a8}$, $SR^{a8}$, $C(=O)R^{b8}$, $C(=)NR^{c8}R^{d8}$, $C(=O)OR^{a8}$, $OC(=O)R^{b8}$, $OC(=O)NR^{c8}R^{d8}$, $NR^{c8}R^{d8}$, $NR^{c8}C(=O)R^{b8}$, $NR^{c8}C(=O)OR^{b8}$, $NR^{c8}C(=O)NR^{c8}R^{d8}$, $C(=NR^e)R^{b8}$, $C(=NR^e)NR^{c8}R^{d8}$, $NR^{c8}C(=NR^e)NR^{c8}R^{d8}$, $NR^{c8}S(=O)_2R^{b8}$, $NR^{c8}S(=O)_2NR^{c8}R^{d8}$, $S(=O)_2R^{b8}$, and $S(=O)_2NR^{c8}R^{d8}$, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted by 1, 2, 3, or 4 independently selected $R^{10}$ groups;

each $R^{a8}$, $R^{c8}$, and $R^{d8}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{10}$ groups;

each $R^{b8}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, or 3 independently selected $R^{10}$ groups;

each $R^{10}$ is independently selected from H, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a10}$, $SR^{a10}$, $C(=O)R^{b10}$, $C(=O)NR^{c10}R^{d10}$, $C(=O)OR^{a10}$, $OC(=O)R^{b10}$, $OC(=O)NR^{c10}R^{d10}$, $NR^{c10}R^{d10}$, $NR^{c10}OC(=O)R^{b10}$, $NR^{c10}C(=O)OR^{b10}$, $NR^{c10}C(=O)NR^{c10}R^{d10}$, $C(=NR^e)R^{b10}$, $C(=NR^e)NR^{c10}R^{d10}$, $NR^{c10}C(=NR^e)NR^{c10}R^{d10}$, $NR^{c10}S(=O)_2R^{b10}$, $NR^{c10}S(=O)_2NR^{c10}R^{d10}$, $S(=O)_2R^{b10}$, or $S(=O)_2NR^{c10}R^{d10}$, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted by 1, 2, 3, or 4 independently selected $R^G$ groups;

each $R^{a10}$, $R^{c10}$, and $R^{d10}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ groups;

each $R^{b10}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, or 3 independently selected $R^G$ groups;

X is N or $CR^X$;
Y is N or $CR^Y$;
Z is N or $CR^Z$;

wherein i) X, Y and Z are $CR^X$, $CR^Y$, and $CR^Z$ respectively, or ii) only one of X, Y and Z is N, or iii) only two of X, Y and Z are N; $R^X$, $R^Y$, and $R^Z$ are each independently selected from H, D, halo, CN, $NO_2$, $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, 5-10 membered heteroaryl-$C_{1-4}$ alkyl, $OR^{a0}$, $SR^{a0}$, $C(=O)R^{b0}$, $C(=O)NR^{c0}R^{d0}$, $C(=O)OR^{a0}$, $OC(=O)R^{b0}$, $OC(=O)NR^{c0}R^{d0}$, $NR^{c0}R^{d0}$, $NR^{c0}C(=O)R^{b0}$, $NR^{c0}C(=O)OR^{b0}$, $NR^{c0}C(=O)NR^{c0}R^{d0}$, $C(=NR^e)R^{b0}$, $C(=NR^e)NR^{c0}R^{d0}$, $NR^{c0}C(=NR^e)NR^{c0}R^{d0}$, $NR^{c0}S(=O)_2R^{b0}$, $NR^{c0}S(=O)_2NR^{c0}R^{d0}$, $S(=O)_2R^{b0}$, and $S(=O)_2NR^{c0}R^{d0}$, wherein said $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl are each optionally substituted by 1, 2, 3, or 4 independently selected $R^G$ groups;

each $R^{a0}$, $R^{c0}$, and $R^{d0}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^G$ groups;

each $R^{b0}$ is independently selected from $C_{1-6}$ alkyl, $C_{1-6}$ haloalkyl, $C_{2-6}$ alkenyl, $C_{2-6}$ alkynyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, or 3 independently selected $R^G$ groups;

Ring moiety A is selected from $C_{3-10}$ cycloalkyl, $C_{6-10}$ aryl, 4-10 membered heterocycloalkyl, and 5-10 membered heteroaryl, each of which is optionally substituted by 1, 2, 3, or 4 independently selected $R^A$ groups;

Ring moiety B is selected from $C_{3-10}$ cycloalkyl, $C_{6-10}$ aryl, 4-10 membered heterocycloalkyl, and 5-10 membered heteroaryl, each of which is optionally substituted by 1, 2, 3, or 4 independently selected $R^B$ groups;

n is 0 or 1;
m is 0 or 1;
s is 0 or 1;
wherein n+m+s=1 or 2;
when n is 1, $R^1$ and $R^2$ taken together form a linking group $L^1$;
when m is 1, one of $R^A$ and one of $R^B$ taken together form a linking group $L^2$;
when s is 1, $R^Q$ and $R^4$ taken together form a linking group $L^3$;

$L^1$, $L^2$, and $L^3$ are each independently selected from -R-R-, -R-R-R-, -Cy-, -R-Cy-, -Cy-R, -Cy-R-R-, and -Cy-R-R-Cy-;

each R is independently M, $C_{1-6}$ alkylene, $C_{2-6}$ alkenylene, $C_{2-6}$ alkynylene, $C_{1-6}$ alkylene-M, M-$C_{1-6}$ alkylene, $C_{1-6}$ alkylene-M-$C_{1-6}$ alkylene, M-$C_{1-6}$ alkenylene-M, $C_{2-6}$ alkenylene-M, M-$C_{2-6}$ alkenylene, $C_{2-6}$ alkenylene-M-$C_{2-6}$ alkenylene, M-$C_{2-6}$ alkenylene-M, $C_{2-6}$ alkynylene-M, M-$C_{2-6}$ alkynylene, $C_{2-6}$ alkynylene-M-$C_{2-6}$ alkynylene, or M-$C_{2-6}$ alkynylene-M, wherein each of said $C_{1-6}$ alkylene, $C_{2-6}$ alkenylene, and $C_{2-6}$ alkynylene is optionally substituted by 1, 2, 3, or 4 groups independently selected $R^G$ groups;

each Cy is independently selected from $C_{3-14}$ cycloalkyl, phenyl, 4-14 membered heterocycloalkyl, and 5-6 membered heteroaryl, each of which is optionally substituted by 1, 2, 3, or 4 independently selected $R^G$ groups;

each M is independently —O—, —S—, —C(O)—, —C(O)NR$^L$—, —C(O)O—, —OC(O)—, —OC(O)NR$^L$—, —NR$^L$—, —NR$^L$C(O)—, —NR$^L$C(O)O—, —NR$^L$C(O)NR$^L$—, —NR$^L$S(O)$_2$—, —S(O)$_2$—, —S(O)$_2$NR$^L$—, or —NR$^L$S(O)$_2$NR$^L$—; provided that when M is attached to a nitrogen atom, then M is selected from —C(O)—, —C(O)NR$^L$—, —C(O)O—, —S(O)$_2$—, or —S(O)$_2$NR$^L$—;

each $R^L$ is independently selected from H, $C_{1-3}$ alkyl, $C_{2-3}$ alkenyl, $C_{2-3}$ alkynyl, and $C_{1-3}$ haloalkyl;

each $R^A$ is independently selected from halo, CN, NO$_2$, $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, 5-10 membered heteroaryl-$C_{1-4}$ alkyl, OR$^{a1}$, SR$^{a1}$, C(=O)R$^{b1}$, C(=O)NR$^{c1}$R$^{d1}$, C(=O)OR$^{a1}$, OC(=O)R$^{b1}$, OC(=O)NR$^{c1}$R$^{d1}$, NR$^{c1}$R$^{d1}$, NR$^{c1}$C(=O)R$^{b1}$, NR$^{c1}$C(=O)OR$^{b1}$, NR$^{c1}$C(=O)NR$^{c1}$R$^{d1}$, C(=NR$^e$)R$^{b1}$, C(=NR$^e$)NR$^{c1}$R$^{d1}$, NR$^{c1}$C(=NR$^e$)NR$^{c1}$R$^{d1}$, NR$^{c1}$S(=O)$_2$NR$^{b2}$, NR$^{c1}$S(=O)$_2$NR$^{c1}$R$^{d1}$, S(=O)$_2$R$^{b1}$, and S(=O)$_2$NR$^{c1}$R$^{d1}$, wherein said $C_{1-6}$ alkyl, $C_{2-6}$ alkenyl, $C_{2-6}$ alkynyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl are each optionally substituted by 1, 2, 3, or 4 independently selected $R^{A1}$ groups;

each $R^B$ is independently selected from halo, CN, NO$_2$, $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, 5-10 membered heteroaryl-$C_{1-4}$ alkyl, OR$^{a2}$, SR$^{a2}$, C(=O)R$^{b2}$, C(=O)NR$^{c2}$R$^{d2}$, C(=O)OR$^{a2}$, OC(=O)R$^{b2}$, OC(=O)NR$^{c2}$R$^{d2}$, NR$^{c2}$R$^{d2}$, NR$^{c2}$C(=O)R$^{b2}$, NR$^{c2}$C(=O)OR$^{a2}$, NR$^{c2}$C(=O)NR$^{c2}$R$^{d2}$, C(=NR$^e$)R$^{b2}$, C(=NR$^e$)NR$^{c2}$R$^{d2}$, NR$^{c2}$C(=NR$^e$)NR$^{c2}$R$^{d2}$, NR$^{c2}$S(=O)$_2$R$^{b2}$, NR$^{c2}$S(=O)$_2$NR$^{c2}$R$^{d2}$, S(=O)$_2$R$^{b2}$, and S(=O)$_2$NR$^{c2}$R$^{d2}$, wherein said $C_{1-6}$ alkyl, $C_{2-6}$ alkenyl, $C_{2-6}$ alkynyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl are each optionally substituted by 1, 2, 3, or 4 independently selected $R^{B1}$ groups;

each $R^{a1}$, $R^{c1}$, and $R^{d1}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{A1}$ groups;

each $R^{b1}$ is independently selected from $C_{1-6}$ alkyl, $C_{1-6}$ haloalkyl, $C_{2-6}$ alkenyl, $C_{2-6}$ alkynyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, or 3 independently selected $R^{A1}$ groups;

each $R^{a2}$, $R^{c2}$, and $R^{d2}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, and 5-10 membered heteroaryl are each optionally substituted with 1, 2, 3, or 4 independently selected $R^{B1}$ groups;

each $R^{b2}$ is independently selected from $C_{1-6}$ alkyl, $C_{1-6}$ haloalkyl, $C_{2-6}$ alkenyl, $C_{2-6}$ alkynyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{i-4}$ alkyl are each optionally substituted with 1, 2, or 3 independently selected $R^{B1}$ groups;

each $R^{A1}$ and $R^{B1}$ is independently selected from H, halo, CN, NO$_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, OR$^{a12}$, SR$^{a12}$, C(=O)R$^{b12}$, C(=O)NR$^{c12}$R$^{d12}$, C(=O)OR$^{a12}$, OC(=O)R$^{b12}$, OC(=O)NR$^{c12}$R$^{d12}$, NR$^{c12}$R$^{d12}$, NR$^{c12}$C(=O)R$^{b12}$, $NR^{c12}C(=O)OR^{b12}$, $NR^{c12}C(=O)NR^{c12}R^{d12}$, $C(=NR^e)R^{b12}$, $C(=NR^e)NR^{c12}R^{d12}$, $NR^{c12}C(=NR^e)NR^{c12}R^{d12}$, $NR^{c12}S(=O)_2R^{b12}$, $NR^{c12}S(=O_2NR^{c12}R^{d12}$, $S(=O)_2R^{b12}$, and $S(=O)_2NR^{c12}R^{d12}$, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted by 1, 2, 3, or 4 independently selected $R^G$ groups;

each $R^{a12}$, $R^{c12}$, and $R^{d12}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ groups;

each $R^{b12}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, or 3 independently selected $R^G$ groups;

$R^2$ is H, $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, or 5-10 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl are each optionally substituted by 1, 2, 3, or 4 independently selected $R^{2a}$ groups;

$R^3$ is H, $C_{1-4}$ alkyl or $C_{1-4}$ haloalkyl;

$R^4$ is H, D, halo, CN, NO$_2$, $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, 5-10 membered heteroaryl-$C_{1-4}$ alkyl, $OR^{a4}$, $SR^{a4}$, $C(=O)R^{b4}$, $C(=O)NR^{c4}R^{d4}$, $C(=O)OR^{a4}$, $OC(=O)R^{b4}$, $OC(=O)NR^{c4}R^{d4}$, $NR^{c4}R^{d4}$, $NR^{c4}C(=O)R^{b4}$, $NR^{c4}C(=O)OR^{b4}$, $NR^{c4}C(=O)NR^{c4}R^{d4}$, $C(=NR^e)R^{b4}$, $C(=NR^e)NR^{c4}R^{d4}$, $NR^{c4}C(=NR^e)NR^{c4}R^{d4}$, $NR^{c4}S(=O)_2R^{b4}$, $NR^{c4}S(=O)_2NR^{c4}R^{d4}$, $S(=O)_2R^{b4}$, or $S(=O)_2NR^{c4}R^{d4}$, wherein said $C_{1-6}$ alkyl $C_{2-6}$ alkenyl, $C_{2-6}$ alkynyl $C_{3-10}$ cycloalkyl, aryl 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl are each optionally substituted by 1, 2, 3, or 4 independently selected $R^{4a}$ groups;

$R^5$ is H, D, halo, CN, NO$_2$, $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, 5-10 membered heteroaryl-$C_{1-4}$ alkyl, $OR^{a5}$, $SR^{a5}$, $C(=O)R^{b5}$, $C(=O)NR^{c5}R^{d5}$, $C(=O)OR^{a5}$, $OC(=O)R^{b5}$, $OC(=O)NR^{c5}R^{d5}$, $NR^{c5}R^{d5}$, $NR^{c5}C(=O)R^{b5}$, $NR^{c5}C(=O)OR^{b5}$, $NR^{c5}C(=O)NR^{c5}R^{d5}$, $C(=NR^e)R^{b5}$, $C(=NR^e)NR^{c5}R^{d5}$, $NR^{c5}C(=NR^e)NR^{c5}R^{d5}$, $NR^{c5}S(=O)_2R^{b5}$, $NR^{c5}S(=O)_2NR^{c5}R^{d5}$, $S(=O)_2R^{b5}$, or $S(=O)_2NR^{c5}R^{d5}$, wherein said $C_{1-6}$ alkyl, $C_{2-6}$ alkenyl, $C_{2-6}$ alkynyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl are each optionally substituted by 1, 2, 3, or 4 independently selected $R^{5a}$ groups;

$R^6$ is H, D, halo, CN, NO$_2$, $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, 5-10 membered heteroaryl-$C_{1-4}$ alkyl, $OR^{a6}$, $SR^{a6}$, $C(=O)R^{b6}$, $C(=O)NR^{c6}R^{d6}$, $C(=O)OR^{a6}$, $OC(=O)R^{b6}$, $OC(=O)NR^{c6}R^{d6}$, $NR^{c6}R^{d6}$, $NR^{c6}C(=O)R^{b6}$, $NR^{c6}C(=O)OR^{b6}$, $NR^{c6}C(=O)NR^{c6}R^{d6}$, $C(=NR^e)R^{b6}$, $C(=NR^e)NR^{c6}R^{d6}$, $NR^{c6}C(=NR^e)NR^{c6}R^{d6}$, $NR^{c6}S(=O)_2R^{b6}$, $NR^{c6}S(=O)_2NR^{c6}R^{d6}$, $S(=O)_2R^{b6}$, or $S(=O)_2NR^{c6}R^{d6}$, wherein said $C_{1-6}$ alkyl, $C_{2-6}$ alkenyl, $C_{2-6}$ alkynyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl are each optionally substituted by 1, 2, 3, or 4 independently selected $R^{6a}$ groups;

$R^7$ is H, D, halo, CN, NO$_2$, $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, 5-10 membered heteroaryl-$C_{1-4}$ alkyl, $OR^{a7}$, $SR^{a7}$, $C(=O)R^{b7}$, $C(=O)NR^{c7}R^{d7}$, $C(=O)OR^{a7}$, $OC(=O)R^{b7}$, $OC(=O)NR^{c7}R^{d7}$, $NR^{c7}R^{d7}$, $NR^{c7}C(=O)R^{b7}$, $NR^{c7}C(=O)OR^{b7}$, $NR^{c7}C(=O)NR^{c7}R^{d7}$, $C(=NR^e)R^{b7}$, $C(=NR^e)NR^{c7}R^{d7}$, $NR^{c7}C(=NR^e)NR^{c7}R^{d7}$, $NR^{c7}S(=O)_2R^{b7}$, $NR^{c7}S(=O)_2NR^{c7}R^{d7}$, $S(=O)_2R^{b7}$, or $S(=O)_2NR^{c7}R^{d7}$, wherein said $C_{1-6}$ alkyl, $C_{2-6}$ alkenyl, $C_{2-6}$ alkynyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl are each optionally substituted by 1, 2, 3, or 4 independently selected $R^{7a}$ groups;

each $R^{a4}$, $R^{c4}$, and $R^{d4}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{4a}$ groups;

each $R^{b4}$ is independently selected from $C_{1-6}$ alkyl, $C_{1-6}$ haloalkyl, $C_{2-6}$ alkenyl, $C_{2-6}$ alkynyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, or 3 independently selected $R^{4a}$ groups;

each $R^{a5}$, $R^{c5}$, and $R^{d5}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{5a}$ groups;

each $R^{b5}$ is independently selected from $C_{1-6}$ alkyl, $C_{1-6}$ haloalkyl, $C_{2-6}$ alkenyl, $C_{2-6}$ alkynyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, or 3 independently selected $R^{5a}$ groups;

each $R^{a6}$, $R^{c6}$, and $R^{d6}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{6a}$ groups;

each $R^{b6}$ is independently selected from $C_{1-6}$ alkyl, $C_{1-6}$ haloalkyl, $C_{2-6}$ alkenyl, $C_{2-6}$ alkynyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, or 3 independently selected $R^{6a}$ groups;

each $R^{a7}$, $R^{c7}$, and $R^{d7}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{7a}$ groups;

each $R^{b7}$ is independently selected from $C_{1-6}$ alkyl, $C_{1-6}$ haloalkyl, $C_{2-6}$ alkenyl, $C_{2-6}$ alkynyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl, wherein $C_{1-6}$ alkyl, $C_{2-6}$ alkenyl, $C_{2-6}$ alkynyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, or 3 independently selected $R^{7a}$ groups;

each $R^{2a}$, $R^{4a}$, $R^{5a}$, $R^{6a}$, and $R^{7a}$ are independently selected from H, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a9}$, $SR^{a9}$, $C(=O)R^{b9}$, $C(=O)NR^{c9}R^{d9}$, $C(=O)OR^{a9}$, $OC(=O)R^{b9}$, $OC(=O)NR^{c9}R^{d9}$, $NR^{c9}R^{d9}$, $NR^{c9}C(=O)R^{b9}$, $NR^{c9}C(=O)OR^{b9}$, $NR^{c9}C(=O)NR^{c9}R^{d9}$, $C(=NR^e)R^{b9}$, $C(=NR^e)NR^{c9}R^{d9}$, $NR^{c9}C(=NR^e)NR^{c9}R^{d9}$, $NR^{c9}S(=O)_2R^{b9}$, $NR^{c9}S(=O)_2NR^{c9}R^{d9}$, $S(=O)_2R^{b9}$, and $S(=O)_2NR^{c9}R^{d9}$, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted by 1, 2, 3, or 4 independently selected $R^{11}$ groups;

each $R^{a9}$, $R^{c9}$, and $R^{d9}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{11}$ groups;

each $R^{b9}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, or 3 independently selected $R^{11}$ groups;

each $R^{11}$ is independently selected from H, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a11}$, $SR^{a11}$, $C(=O)R^{b11}$, $C(=O)NR^{c11}R^{d11}$, $C(=O)OR^{a11}$, $OC(=O)R^{b11}$, $OC(=O)NR^{c11}R^{d11}$, $NR^{c11}R^{d11}$, $NR^{c11}C(=O)R^{b11}$, $NR^{c11}C(=O)OR^{b11}$, $NR^{c11}C(=O)NR^{c11}R^{d11}$, $C(=NR^e)R^{b11}$, $C(=NR^e)NR^{c11}R^{d11}$, $NR^{c11}C(=NR^e)NR^{c11}R^{d11}$, $NR^{c11}S(=O)_2R^{b11}$, $NR^{c11}S(=O)_2NR^{c11}R^{d11}$, $S(=O)_2R^{b11}$, and $S(=O)_2NR^{c11}R^{d11}$, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted by 1, 2, 3, or 4 independently selected $R^G$ groups;

each $R^{a11}$, $R^{c11}$, and $R^{d11}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ groups;

each $R^{b11}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, or 3 independently selected $R^G$ groups;

each $R^G$ is independently selected from OH, $NO_2$, CN, halo, $C_{1-3}$ alkyl, $C_{2-3}$ alkenyl, $C_{2-3}$ alkynyl, $C_{1-3}$ haloalkyl, cyano-$C_{1-3}$ alkyl, HO-$C_{1-3}$ alkyl, $C_{1-3}$ alkoxy-$C_{1-3}$ alkyl, $C_{3-7}$ cycloalkyl, $C_{1-3}$ alkoxy, $C_{1-3}$ haloalkoxy, amino, $C_{1-3}$ alkylamino, di($C_{1-3}$ alkyl)amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl)carbamyl, carboxy, $C_{1-3}$ alkylcarbonyl, $C_{1-4}$ alkoxycarbonyl, $C_{1-3}$ alkylcarbonylamino, $C_{1-3}$ alkylsulfonylamino, aminosulfonyl, $C_{1-3}$ alkylaminosulfonyl, di($C_{1-3}$ alkyl)aminosulfonyl, aminosulfonylamino, $C_{1-3}$ alkylaminosulfonylamino, di($C_{1-3}$ alkyl)aminosulfonylamino, aminocarbonylamino, $C_{1-3}$ alkylaminocarbonylamino, and di($C_{1-3}$ alkyl)aminocarbonylamino.

In some embodiments, the compound is a compound of Formula (X):

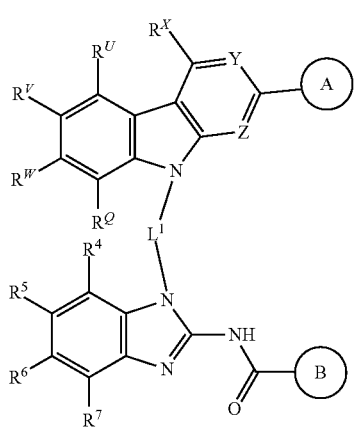

(X)

or a pharmaceutically acceptable salt thereof, wherein:

$R^U$, $R^V$, and $R^W$ are each independently selected from H, D, OH, $NO_2$, CN, halo, $C_{1-6}$ alkyl, $C_{2-6}$ alkenyl, $C_{2-6}$ alkynyl, $C_{1-6}$ haloalkyl, cyano-$C_{1-6}$ alkyl, HO-$C_{1-6}$ alkyl, $C_{1-6}$ alkoxy-$C_{1-6}$ alkyl, $C_{3-7}$ cycloalkyl, $C_{1-6}$ alkoxy, $C_{1-6}$ haloalkoxy, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-4}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

$R^Q$ is selected from H, D, halo, CN, $NO_2$, $C_{1-6}$ alkyl, -$C_{1-6}$ alkylene-$R^{80}$, -$C_{1-6}$ alkylene-$R^{90}$, -$C_{1-6}$ alkylene-$OR^{80}$, -$C_{1-6}$ alkylene-$NHR^{80}$, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, 5-10 membered heteroaryl-$C_{1-4}$ alkyl, $OR^a$, $OR^f$, $SR^a$, C(=O)$R^b$, C(=O)$NR^cR^d$, C(=O)$OR^a$, OC(=O)$R^b$, OC(=O)$NR^cR^d$, $NR^cR^d$, $NR^cC$(=O)$R^b$, $NR^cC$(=O)$OR^b$, $NR^cC$(=O)$NR^cR^d$, C(=$NR^e$)$R^b$, C(=$NR^e$)$NR^cR^d$, $NR^cC$(=$NR^e$)$NR^cR^d$, $NR^cS$(=O)$_2R^b$, $NR^cS$(=O)$_2NR^cR^d$, S(=O)$_2R^b$, and S(=O)$_2NR^cR^d$, wherein said $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl are each optionally substituted by 1, 2, 3, or 4 independently selected $R^8$ groups;

$R^a$, $R^c$, and $R^d$ are each independently selected from H, $C_{1-6}$ alkyl, $C_{1-6}$ haloalkyl, $C_{2-6}$ alkenyl, $C_{2-6}$ alkynyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^8$ groups;

$R^b$ is selected from $C_{1-6}$ alkyl, $C_{1-6}$ haloalkyl, $C_{2-6}$ alkenyl, $C_{2-6}$ alkynyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, or 3 independently selected $R^8$ groups;

each $R^c$ is independently selected from H, CN, OH, $C_{1-4}$ alkyl, and $C_{1-4}$ alkoxy;

$R^f$ is selected from $C_{1-6}$ alkyl and $C_{1-6}$ haloalkyl, which are each optionally substituted with 1 substituent selected from $R^{80}$, —$OR^{80}$, $R^{90}$, and —$NHR^{80}$;

each $R^8$ is independently selected from H, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a8}$, $SR^{a8}$, C(=O)$R^{b8}$, C(=O)$NR^{c8}R^{d8}$, C(=O)$OR^{a8}$, OC(=O)$R^{b8}$, OC(=O)$NR^{c8}R^{d8}$, $NR^{c8}R^{d8}$, $NR^{c8}C$(=O)$R^{b8}$, $NR^{c8}C$(=O)$OR^{b8}$, $NR^{c8}C$(=O)$NR^{c8}R^{d8}$, C(=$NR^e$)$R^{b8}$, C(=$NR^e$)$NR^{c8}R^{d8}$, $NR^{c8}C$(=$NR^e$)$NR^{c8}R^{d8}$, $NR^{c8}S$(=O)$_2R^{b8}$, $NR^{c8}S$ $(=O)_2NR^{c8}R^{d8}$, $S(=O)_2R^{b8}$, and $S(=O)_2NR^{c8}R^{d8}$, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted by 1, 2, 3, or 4 independently selected $R^{10}$ groups;

each $R^{a8}$, $R^{c8}$, and $R^{d8}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{10}$ groups;

each $R^{b8}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, or 3 independently selected $R^{10}$ groups;

each $R^{10}$ is independently selected from H, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a10}$, $SR^{a10}$, $C(=O)OR^{b10}$, $C(=O)NR^{c10}R^{d10}$, $C(=O)OR^{a10}$, $OC(=O)R^{b10}$, $OC(=O)NR^{c10}R^{d10}$, $NR^{c10}R^{d10}$, $NR^{c10}C(=O)R^{b10}$, $NR^{c10}C(=O)OR^{b10}$, $NR^{c10}C(=O)NR^{c10}R^{d10}$, $C(=NR^e)R^{b10}$, $C(=NR^e)NR^{c10}R^{d10}$, $NR^{c10}C(=NR^e)NR^{c10}R^{d10}$, $NR^{c10}S(=O)_2R^{b10}$, $NR^{c10}S(=O)_2NR^{c10}R^{d10}$, $S(=O)_2R^{b10}$, or $S(=O)_2NR^{c10}R^{d10}$, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted by 1, 2, 3, or 4 independently selected $R^G$ groups;

each $R^{a10}$, $R^{c10}$, and $R^{d10}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ groups;

each $R^{b10}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, or 3 independently selected $R^G$ groups;

$R^{80}$ is a linear peptide chain having 2-6 amino acids, which is optionally substituted with 1, 2, 3, or 4 independently selected $R^G$ substituents;

$R^{90}$ is a linear chain of formula $-(O-C_{2-4}$ alkylene$)_z-R^G$, wherein z is 1, 2, 3, 4, 5, or 6;

Y is N or $CR^Y$;

Z is N or $CR^Z$;

$R^X$, $R^Y$, and $R^Z$ are each independently selected from H, D, halo, CN, $NO_2$, $C_{1-6}$ alkyl, $C_{2-6}$ alkenyl, $C_{2-6}$ alkynyl, $C_{1-6}$ haloalkyl, and $C_{3-4}$ cycloalkyl;

Ring moiety A is 5-membered heteroaryl, which is optionally substituted by 1, 2, 3, or 4 independently selected $R^A$ groups;

Ring moiety B is 5-membered heteroaryl, which is optionally substituted by 1, 2, 3, or 4 independently selected $R^B$ groups;

$L^1$ is selected from -R-R- and -R-R-R-;

each R is independently M, $C_{1-6}$ alkylene, $C_{2-6}$ alkenylene, $C_{2-6}$ alkynylene, $C_{1-6}$ alkylene-M, M-$C_{1-6}$ alkylene, $C_{1-6}$ alkylene-M-$C_{1-6}$ alkylene, M-$C_{1-6}$ alkylene-M, $C_{2-6}$ alkenylene-M, M-$C_{2-6}$ alkenylene, $C_{2-6}$ alkenylene-M-$C_{2-6}$ alkenylene, M-$C_{2-6}$ alkenylene-M, $C_{2-6}$ alkynylene-M, M-$C_{2-6}$ alkynylene, $C_{2-6}$ alkynylene-M-$C_{2-6}$ alkynylene, or M-$C_{2-6}$ alkynylene-M, wherein each of said $C_{1-6}$ alkylene, $C_{2-6}$ alkenylene, and $C_{2-6}$ alkynylene is optionally substituted by 1, 2, 3, or 4 groups independently selected $R^G$ groups;

each M is independently $-O-$, $-S-$, $-C(O)-$, $-C(O)NR^L-$, $-C(O)O-$, $-OC(O)NR^L-$, $-NR^L-$, $-NR^LC(O)-$, $-NR^LC(O)O-$, $-NR^LC(O)NR^L-$, $-NR^LS(O)_2-$, $-S(O)_2-$, or $-S(O)_2NR^L-$, or $-NR^LS(O)_2NR^L-$; provided that when M is attached to a nitrogen atom, then M is selected from $-C(O)-$, $-C(O)NR^L-$, $-C(O)O-$, $-S(O)_2-$, or $-S(O)_2NR^L-$;

each $R^L$ is independently selected from H, $C_{1-3}$ alkyl, $C_{2-3}$ alkenyl, $C_{2-3}$ alkynyl, and $C_{1-3}$ haloalkyl;

each $R^A$ is independently selected from halo, CN, $NO_2$, $C_{1-6}$ alkyl, $C_{2-6}$ alkenyl, $C_{2-6}$ alkynyl, $C_{1-6}$ haloalkyl, and $C_{3-4}$ cycloalkyl, wherein said $C_{1-6}$ alkyl, $C_{2-6}$ alkenyl, $C_{2-6}$ alkynyl, $C_{1-6}$ haloalkyl, and $C_{3-4}$ cycloalkyl are each optionally substituted by 1, 2, 3, or 4 independently selected $R^G$ groups;

each $R^B$ is independently selected from halo, CN, $NO_2$, $C_{1-6}$ alkyl, $C_{2-6}$ alkenyl, $C_{2-6}$ alkynyl, $C_{1-6}$ haloalkyl, and $C_{3-4}$ cycloalkyl, wherein said $C_{1-6}$ alkyl, $C_{2-6}$ alkenyl, $C_{2-6}$ alkynyl, $C_{1-6}$ haloalkyl, and $C_{3-4}$ cycloalkyl are each optionally substituted by 1, 2, 3, or 4 independently selected $R^G$ groups;

$R^5$, $R^6$, and $R^7$ are each independently selected from H, D, OH, $NO_2$, CN, halo, $C_{1-6}$ alkyl, $C_{2-6}$ alkenyl, $C_{2-6}$ alkynyl, $C_{1-6}$ haloalkyl, cyano-$C_{1-6}$ alkyl, HO-$C_{1-6}$ alkyl, $C_{1-6}$ alkoxy-$C_{1-6}$ alkyl, $C_{3-7}$ cycloalkyl, $C_{1-6}$ alkoxy, $C_{1-6}$ haloalkoxy, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-4}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

$R^4$ is H, D, halo, CN, $NO_2$, $C_{1-6}$ alkyl, -$C_{1-6}$ alkylene-$R^{80}$, -$C_{1-6}$ alkylene-$R^{90}$, -$C_{1-6}$ alkylene-$OR^{80}$, -$C_{1-6}$ alkylene-$NHR^{80}$, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, 5-10 membered heteroaryl-$C_{1-4}$ alkyl, $OR^{a4}$, $OR^{f4}$, $SR^{a4}$, $C(=O)R^{b4}$, $C(=O)NR^{c4}R^{d4}$, $C(=O)OR^{a4}$, $OC(=O)R^{b4}$, $OC(=O)NR^{c4}R^{d4}$, $NR^{c4}R^{d4}$, $NR^{c4}C(=O)R^{b4}$, $NR^{c4}C(=O)OR^{b4}$, $NR^{c4}C(=O)NR^{c4}R^{d4}$, $C(=NR^e)R^{b4}$, $C(=NR^e)NR^{c4}R^{d4}$, $NR^{c4}C(=NR^e)NR^{c4}R^{d4}$, $NR^{c4}S(=O)_2R^{b4}$, $NR^{c4}S(=O)_2NR^{c4}R^{d4}$, $S(=O)_2R^{b4}$, or $S(=O)_2NR^{c4}R^{d4}$, wherein said $C_{1-6}$ alkyl, $C_{2-6}$ alkenyl, $C_{2-6}$ alkynyl $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl are each optionally substituted by 1, 2, 3, or 4 independently selected $R^{4a}$ groups;

each $R^{a4}$, $R^{c4}$, and $R^{d4}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{4a}$ groups;

each $R^{b4}$ is independently selected from $C_{1-6}$ alkyl, $C_{1-6}$ haloalkyl, $C_{2-6}$ alkenyl, $C_{2-6}$ alkynyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, or 3 independently selected $R^{4a}$ groups;

$R^{f4}$ is selected from $C_{1-6}$ alkyl and $C_{1-6}$ haloalkyl, which are each optionally substituted with 1 substituent selected from $R^{80}$, $R^{90}$, —$OR^{80}$, and —$NHR^{80}$;

each $R^{4a}$ is independently selected from H, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a9}$, $SR^{a9}$, $C(=O)R^{b9}$, $C(=O)NR^{c9}R^{d9}$, $C(=O)OR^{a9}$, $OC(=O)R^{b9}$, $OC(=O)NR^{c9}R^{d9}$, $NR^{c9}R^{d9}$, $NR^{c9}C(=O)R^{b9}$, $NR^{c9}C(=O)OR^{b9}$, $NR^{c9}C(=O)NR^{c9}R^{d9}$, $C(=NR^e)R^{b9}$, $C(=NR^e)NR^{c9}R^{d9}$, $NR^{c9}C(=NR^e)NR^{c9}R^{d9}$, $NR^{c9}S(=O)_2R^{b9}$, $NR^{c9}S(=O)_2NR^{c9}R^{d9}$, $S(=O)_2R^{b9}$, and $S(=O)_2NR^{c9}R^{d9}$, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted by 1, 2, 3, or 4 independently selected $R^{11}$ groups;

each $R^{a9}$, $R^{c9}$, and $R^{d9}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{-14}$ alkyl are each optionally substituted with 1, 2, 3, or 4 independently selected $R^{11}$ groups;

each $R^{b9}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, or 3 independently selected $R^{11}$ groups;

$R^{f11}$ is selected from $C_{1-6}$ alkyl and $C_{1-6}$ haloalkyl, which are each optionally substituted with 1 substituent selected from $R^{80}$, —$OR^{80}$, and —$NHR^{80}$;

each $R^{11}$ is independently selected from H, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a11}$, $SR^{a11}$, $C(=O)R^{b11}$, $C(=O)NR^{c11}R^{d11}$, $C(=O)OR^{a11}$, $OC(=O)R^{b11}$, $OC(=O)NR^{c11}R^{d11}$, $NR^{c11}R^{d11}$, $NR^{c11}C(=O)R^{b11}$, $NR^{c11}C(=O)OR^{b11}$, $NR^{c11}C(=O)NR^{c11}R^{d11}$, $C(=NR^e)R^{b11}$, $C(=NR^e)NR^{c11}R^{d11}$, $NR^{c11}C(=NR^e)NR^{c11}R^{d11}$, $NR^{c11}S(=O)_2R^{b11}$, $NR^{c11}S(=O)_2NR^{c11}R^{d11}$, $S(=O)_2R^{b11}$, and $S(=O)_2NR^{c11}R^{d11}$, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted by 1, 2, 3, or 4 independently selected $R^G$ groups;

each $R^{a11}$, $R^{c11}$, and $R^{d11}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ groups;

each $R^{b11}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl- $C_{1-4}$ alkyl, and 5-6 membered heteroaryl-$C_{1-4}$ alkyl are each optionally substituted with 1, 2, or 3 independently selected $R^G$ groups; and each $R^G$ is independently selected from H, D, OH, $NO_2$, CN, halo, $C_{1-3}$ alkyl, $C_{2-3}$ alkenyl, $C_{2-3}$ alkynyl, $C_{1-3}$ haloalkyl, cyano-$C_{1-3}$ alkyl, HO-$C_{1-3}$ alkyl, $C_{1-3}$ alkoxy-$C_{1-3}$ alkyl, $C_{3-7}$ cycloalkyl, $C_{1-3}$ alkoxy, $C_{1-3}$ haloalkoxy, amino, $C_{1-3}$ alkylamino, di($C_{1-3}$ alkyl)amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl)carbamyl, carboxy, $C_{1-3}$ alkylcarbonyl, $C_{1-4}$ alkoxycarbonyl, $C_{1-3}$ alkylcarbonylamino, $C_{1-3}$ alkylsulfonylamino, aminosulfonyl, $C_{1-3}$ alkylaminosulfonyl, di($C_{1-3}$ alkyl)aminosulfonyl, aminosulfonylamino, $C_{1-3}$ alkylaminosulfonylamino, di($C_{1-3}$ alkyl)aminosulfonylamino, aminocarbonylamino, $C_{1-3}$ alkylaminocarbonylamino, and di($C_{1-3}$ alkyl)aminocarbonylamino.

In some embodiments, $R^{80}$ is a linear peptide chain having 2-6 amino acids.

In some embodiments, $R^{80}$ is a linear peptide chain having 2-4 amino acids.

In some embodiments, $R^{80}$ is a linear peptide chain having 2-6 amino acids, wherein the amino acids are independently selected from alanine (Ala), arginine (Arg), asparagine (Asn), aspartic acid (Asp), cysteine (cys), glutamine (Gln), glutamic acid (Glu), glycine (Gly), histidine (His), isoleucine (Ile), leucine (Leu), lysine (Lys), methionine (Met), phenylalanine (Phe), proline (Pro), serine (Ser), threonine (Thr), tryptophan (Trp), tyrosine (Tyr), and valine (Val). In some embodiments, $R^{80}$ is a linear peptide chain having 2-6 amino acids independently selected from Asp, Arg, Glu, His, Lys, Ser, Thr, Asn, and Gln. In some embodiments, $R^{80}$ is a linear peptide chain having 2-6 amino acids independently selected from Asp, Arg, Glu, His, and Lys. In some embodiments, $R^{80}$ is a linear peptide chain having 2-6 amino acids independently selected from Asp and Arg. In some embodiments, $R^{80}$ is a linear peptide chain having 2-4 amino acids independently selected from Asp, Arg, Glu, His, Lys, Ser, Thr, Asn, and Gln. In some embodiments, $R^{80}$ is a linear peptide chain having 2-4 amino acids independently selected from Asp, Arg, Glu, His, and Lys. In some embodiments, $R^{80}$ is a linear peptide chain having 2-4 amino acids independently selected from Asp and Arg.

In some embodiments, U=V—W=Q is selected from $CR^U=CR^V—CR^W=CR^Q$, $N=CR^V—CR^W=CR^Q$, $CR^U=N—CR^W=CR^Q$, $CR^U=CR^V—N=CR^Q$, $CR^U=CR^V—CR^W=N$, $N=N—CR^W=CR^Q$, $CR^U=N—N=CR^Q$, $CR^U=CR^V—N=N$, $N=CR^V—CR^W=N$, $N=CR^V—N=CR^Q$, and $CR^U=N—CR^W=N$.

In some embodiments, U=V—W=Q is selected from $CR^U=CR^V—CR^W=CR^Q$, $N=CR^V—CR^W=CR^Q$, $CR^U=N—CR^W=CR^Q$, $CR^U=CR^V—N=CR^Q$, and $CR^U=CR^V—CR^W=N$.

In some embodiments, U=V—W=Q is selected from $N=N—CR^W=CR^Q$, $CR^U=N—N=CR^Q$, $CR^U=CR^V—N=N$, $N=CR^V—CR^W=N$, $N=CR^V—N=CR^Q$, and $CR^U=N—CR^W=N$.

In some embodiments, U=V-W=Q is $CR^U=CR^V—CR^W=CR^Q$.

In some embodiments, U=V—W=Q is $N=CR^V—CR^W=CR^Q$.

In some embodiments, U=V—W=Q is $CR^U=N—CR^W=CR^Q$.

In some embodiments, U=V—W=Q is $CR^U=CR^V—N=CR^Q$.

In some embodiments, U=V—W=Q is $CR^U=CR^V—CR^W=N$.

In some embodiments, U is N.

In some embodiments, U is $CR^U$.

In some embodiments, $R^U$ is H, D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^a$, $SR^a$, $C(=O)R^b$, $C(=O)NR^cR^d$, $C(=O)OR^a$, $OC(=O)R^b$, $OC(=O)NR^cR^d$, $NR^cR^d$, $NR^cC(=O)R^b$, $NR^cC(=O)OR^b$, $NR^cC(=O)NR^cR^d$, $C(=NR^e)R^b$, $C(=NR^e)NR^cR^d$, $NR^cC(=NR^e)NR^cR^d$, $NR^cS(=O)_2R^b$, $NR^cS(=O)_2NR^cR^d$, $S(=O)_2R^b$, or $S(=O)_2NR^cR^d$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted by 1, 2, 3, or 4 independently selected $R^8$ groups.

In some embodiments, $R^U$ is H, D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^a$, $SR^a$, $C(=O)R^b$, $C(=O)NR^cR^d$, $C(=O)OR^a$, $OC(=O)R^b$, $OC(=O)NR^cR^d$, $NR^cR^d$, $NR^cC(=O)R^b$, $NR^cC(=O)OR^b$, $NR^cC(=O)NR^cR^d$, $C(=NR^e)R^b$, $C(=NR^e)NR^cR^d$, $NR^cC(=NR^e)NR^cR^d$, $NR^cS(=O)_2R^b$, $NR^cS(=O)_2NR^cR^d$, $S(=O)_2R^b$, or $S(=O)_2NR^cR^d$, wherein said $C_{1-6}$ alkyl, $C_{2-6}$ alkenyl, $C_{2-6}$ alkynyl, $C_{1-6}$ haloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted by 1, 2, 3, or 4 independently selected $R^8$ groups.

In some embodiments, $R^U$ is H, D, halo, CN, $NO_2$, $C_{1-6}$ alkyl, $C_{2-6}$ alkenyl, $C_{2-6}$ alkynyl, $OR^a$, $SR^a$, $C(=O)R^b$, $C(=O)NR^cR^d$, $C(=O)OR^a$, $OC(=O)R^b$, $OC(=O)NR^cR^d$, $NR^cR^d$, $NR^cC(=O)R^b$, $NR^cC(=O)OR^b$, $NR^cC(=O)NR^cR^d$, $NR^cS(=O)_2R^b$, $NR^cS(=O)_2NR^cR^d$, $S(=O)_2R^b$, or $S(=O)_2NR^cR^d$, wherein said $C_{1-6}$ alkyl, $C_{2-6}$ alkenyl, $C_{2-6}$ alkynyl, and $C_{1-6}$ haloalkyl are each optionally substituted by 1, 2, 3, or 4 independently selected $R^8$ groups.

In some embodiments, $R^U$ is H, halo, CN, $C_{1-6}$ alkyl, $OR^a$, $C(=O)R^b$, $C(=O)NR^cR^d$, $S(=O)_2R^b$, or $S(=O)_2NR^cR^d$.

In some embodiments, $R^U$ is H, halo, CN, $C_{1-6}$ alkyl, haloalkyl, or $C(=O)NR^cR^d$, wherein $R^c$ and $R^d$ are each independently selected from H, $C_{1-6}$ alkyl, and $C_{1-6}$ haloalkyl.

In some embodiments, $R^U$ is H, halo, CN, $C_{1-6}$ alkyl, or $C_{1-6}$ haloalkyl.

In some embodiments, $R^U$ is selected from H, halo, CN, $C_{1-4}$ alkyl, or $C_{1-4}$ haloalkyl.

In some embodiments, $R^U$ is H.

In some embodiments, V is N.

In some embodiments, V is $CR^V$.

In some embodiments, $R^V$ is H, D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^a$, $SR^a$, $C(=O)R^b$, $C(=O)NR^cR^d$, $C(=O)OR^a$, $OC(=O)R^b$, $OC(=O)NR^cR^d$, $NR^cR^d$, $NR^cC(=O)R^b$, $NR^cC(=O)OR^b$, $NR^cC(=O)NR^cR^d$, $C(=NR^e)R^b$, $C(=NR^e)NR^cR^d$, $NR^cC(=NR^e)NR^cR^d$, $NR^cS(=O)_2R^b$, $NR^cS(=O)_2NR^cR^d$, $S(=O)_2R^b$, or $S(=O)_2NR^cR^d$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted by 1, 2, 3, or 4 independently selected $R^8$ groups.

In some embodiments, $R^V$ is H, D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^a$, $SR^a$, $C(=O)R^b$, $C(=O)NR^cR^d$, $C(=O)OR^a$, $OC(=O)R^b$, $OC(=O)NR^cR^d$, $NR^cR^d$, $NR^cC(=O)R^b$, $NR^cC(=O)OR^b$, $NR^cC(=O)NR^cR^d$, $C(=NR^e)R^b$, $C(=NR^e)NR^cR^d$, $NR^cC(=NR^e)NR^cR^d$, $NR^cS(=O)_2R^b$, $NR^cS(=O)_2NR^cR^d$, $S(=O)_2R^b$, or $S(=O)_2NR^cR^d$, wherein said $C_{1-6}$ alkyl, $C_{2-6}$ alkenyl, $C_{2-6}$ alkynyl, $C_{1-6}$ haloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted by 1, 2, 3, or 4 independently selected $R^8$ groups.

In some embodiments, $R^V$ is H, D, halo, CN, $NO_2$, $C_{1-6}$ alkyl, $C_{2-6}$ alkenyl, $C_{2-6}$ alkynyl, $OR^a$, $SR^a$, $C(=O)R^b$, $C(=O)NR^cR^d$, $C(=O)OR^a$, $OC(=O)R^b$, $OC(=O)NR^cR^d$, $NR^cR^d$, $NR^cC(=O)R^b$, $NR^cC(=O)OR^b$, $NR^cC(=O)NR^cR^d$, $NR^cS(=O)_2R^b$, $NR^cS(=O)_2NR^cR^d$, $S(=O)_2R^b$, or $S(=O)_2NR^cR^d$, wherein said $C_{1-6}$ alkyl, $C_{2-6}$ alkenyl, $C_{2-6}$ alkynyl, and $C_{1-6}$ haloalkyl are each optionally substituted by 1, 2, 3, or 4 independently selected $R^8$ groups.

In some embodiments, $R^V$ is H, halo, CN, $C_{1-6}$ alkyl, $OR^a$, $C(=O)R^b$, $C(=O)NR^cR^d$, $S(=O)_2R^b$, or $S(=O)_2NR^cR^d$.

In some embodiments, $R^V$ is H, halo, CN, $C_{1-6}$ alkyl, $C_{1-6}$ haloalkyl, or $C(=O)NR^cR^d$, wherein $R^c$ and $R^d$ are each independently selected from H, $C_{1-6}$ alkyl, and $C_{1-6}$ haloalkyl.

In some embodiments, $R^V$ is H, halo, CN, $C_{1-6}$ alkyl, or $C_{1-6}$ haloalkyl.

In some embodiments, $R^V$ is H, halo, CN, $C(=O)NH_2$, $C_{1-6}$ alkyl, or $C_{1-6}$ haloalkyl.

In some embodiments, $R^V$ is H, halo, CN, $C_{1-4}$ alkyl, $C_{1-4}$ haloalkyl, carbamyl, or $C_{1-4}$ alkylcarbamyl.

In some embodiments, $R^V$ is $C(=O)NR^cR^d$, wherein $R^c$ and $R^d$ are each independently selected from H, $C_{1-6}$ alkyl, and $C_{1-6}$ haloalkyl.

In some embodiments, $R^V$ is $C(=O)NH_2$.

In some embodiments, $R^V$ is H.

In some embodiments, W is N.

In some embodiments, W is $CR^W$.

In some embodiments, $R^W$ is H, D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^a$, $SR^a$, $C(=O)R^b$, $C(=O)NR^cR^d$, $C(=O)OR^a$, $OC(=O)R^b$, $OC(=O)NR^cR^d$, $NR^cR^d$, $NR^cC(=O)R^b$, $NR^cC(=O)OR^b$, $NR^cC(=O)NR^cR^d$, $C(=NR^e)R^b$, $C(=NR^e)NR^cR^d$, $NR^cC(=NR^e)NR^cR^d$, $NR^cS(=O)_2R^b$, $NR^cS(=O)_2NR^cR^d$, $S(=O)_2R^b$, or $S(=O)_2NR^cR^d$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted by 1, 2, 3, or 4 independently selected $R^8$ groups.

In some embodiments, $R^W$ is H, D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^a$, $SR^a$, $C(=O)R^b$, $C(=O)NR^cR^d$, $C(=O)OR^a$, $OC(=O)R^b$, $OC(=O)NR^cR^d$, $NR^cR^d$, $NR^cC(=O)R^b$, $NR^cC(=O)OR^b$, $NR^cC(=O)NR^cR^d$, $C(=NR^e)R^b$, $C(=NR^e)NR^cR^d$, $NR^cC(=NR^e)NR^cR^d$, $NR^cS(=O)_2R^b$, $NR^cS(=O)_2NR^cR^d$, $S(=O)_2R^b$, or $S(=O)_2NR^cR^d$, wherein said $C_{1-6}$ alkyl, $C_{2-6}$ alkenyl, $C_{2-6}$ alkynyl, $C_{1-6}$ haloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted by 1, 2, 3, or 4 independently selected $R^8$ groups.

In some embodiments, $R^W$ is H, D, halo, CN, $NO_2$, $C_{1-6}$ alkyl, $C_{2-6}$ alkenyl, $C_{2-6}$ alkynyl, $OR^a$, $SR^a$, $C(=O)R^b$, $C(=O)NR^cR^d$, $C(=O)OR^a$, $OC(=O)R^b$, $OC(=O)NR^cR^d$, $NR^cR^d$, $NR^cC(=O)R^b$, $NR^cC(=O)OR^b$, $NR^cC(=O)NR^cR^d$, $NR^cS(=O)_2R^b$, $NR^cS(=O)_2NR^cR^d$, $S(=O)_2R^b$, or $S(=O)_2NR^cR^d$, wherein said $C_{1-6}$ alkyl, $C_{2-6}$ alkenyl, $C_{2-6}$ alkynyl, and $C_{1-6}$ haloalkyl are each optionally substituted by 1, 2, 3, or 4 independently selected $R^8$ groups.

In some embodiments, $R^W$ is H, halo, CN, $C_{1-6}$ alkyl, $OR^a$, $C(=O)R^b$, $C(=O)NR^cR^d$, $S(=O)_2R^b$, or $S(=O)_2NR^cR^d$.

In some embodiments, $R^W$ is H, halo, CN, $C_{1-6}$ alkyl, $C_{1-6}$ haloalkyl, or $C(=O)NR^cR^d$, wherein $R^c$ and $R^d$ are each independently selected from H, $C_{1-6}$ alkyl, and $C_{1-6}$ haloalkyl.

In some embodiments, $R^W$ is H, halo, CN, $C_{1-6}$ alkyl, or $C_{1-6}$ haloalkyl.

In some embodiments, $R^W$ is H, halo, CN, $C_{1-4}$ alkyl, or $C_{1-4}$ haloalkyl.

In some embodiments, $R^W$ is H.

In some embodiments, Q is N.

In some embodiments, Q is $CR^Q$.

In some embodiments, $R^Q$ is H, D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^a$, $SR^a$, $C(=O)R^b$, $C(=O)NR^cR^d$, $C(=O)OR^a$, $OC(=O)R^b$, $OC(=O)NR^cR^d$, $NR^cR^d$, $NR^cC(=O)R^b$, $NR^cC(=O)OR^b$, $NR^cC(=O)NR^cR^d$, $C(=NR^e)R^b$, $C(=NR^e)NR^cR^d$, $NR^cC(=NR^e)NR^cR^d$, $NR^cS(=O)_2R^b$, $NR^cS(=O)_2NR^cR^d$, $S(=O)_2R^b$, or $S(=O)_2NR^cR^d$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted by 1, 2, 3, or 4 independently selected $R^8$ groups.

In some embodiments, $R^Q$ is H, D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^a$, $SR^a$, $C(=O)R^b$, $C(=O)NR^cR^d$, $C(=O)OR^a$, $OC(=O)R^b$, $OC(=O)NR^cR^d$, $NR^cR^d$, $NR^cC(=O)R^b$, $NR^cC(=O)OR^b$, $NR^cC(=O)NR^cR^d$, $C(=NR^e)R^b$, $C(=NR^e)NR^cR^d$, $NR^cC(=NR^e)NR^cR^d$, $NR^cS(=O)_2R^b$, $NR^cS(=O)_2NR^cR^d$, $S(=O)_2R^b$, or $S(=O)_2NR^cR^d$, wherein said $C_{1-6}$ alkyl, $C_{2-6}$ alkenyl, $C_{2-6}$ alkynyl, $C_{1-6}$ haloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted by 1, 2, 3, or 4 independently selected $R^8$ groups.

In some embodiments, $R^Q$ is H, D, halo, CN, $NO_2$, $C_{1-6}$ alkyl, $C_{2-6}$ alkenyl, $C_{2-6}$ alkynyl, $OR^a$, $SR^a$, $C(=O)R^b$, $C(=O)NR^cR^d$, $C(=O)OR^a$, $OC(=O)R^b$, $OC(=O)NR^cR^d$, $NR^cR^d$, $NR^cC(=O)R^b$, $NR^cC(=O)OR^b$, $NR^cC(=O)NR^cR^d$, $NR^cS(=O)_2R^b$, $NR^cS(=O)_2NR^cR^d$, $S(=O)_2R^b$, or $S(=O)_2NR^cR^d$, wherein said $C_{1-6}$ alkyl, $C_{2-6}$ alkenyl, $C_{2-6}$ alkynyl, and $C_{1-6}$ haloalkyl are each optionally substituted by 1, 2, 3, or 4 independently selected $R^8$ groups.

In some embodiments, $R^Q$ is H, halo, CN, $C_{1-6}$ alkyl, $OR^a$, $C(=O)R^b$, $C(=O)NR^cR^d$, $S(=O)_2R^b$, or $S(=O)_2NR^cR^d$.

In some embodiments, $R^Q$ is H, halo, CN, $C_{1-6}$ alkyl, $C_{1-6}$ haloalkyl, or $C(=O)NR^cR^d$, wherein $R^c$ and $R^d$ are each independently selected from H, $C_{1-6}$ alkyl, and $C_{1-6}$ haloalkyl.

In some embodiments, $R^Q$ is H, halo, CN, $C_{1-6}$ alkyl, or $C_{1-6}$ haloalkyl.

In some embodiments, $R^Q$ is H.

In some embodiments, $R^Q$ is H or $OR^a$.

In some embodiments, $R^Q$ is H or $OR^a$, wherein $R^a$ is selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^8$ groups; and each $R^8$ is independently selected from OH, $NO_2$, CN, halo, $C_{1-3}$ alkyl, $C_{2-3}$ alkenyl, $C_{2-3}$ alkynyl, $C_{1-3}$ haloalkyl, $C_{1-3}$ alkoxy, $C_{1-3}$ haloalkoxy, amino, $C_{1-3}$ alkylamino, and di($C_{1-3}$ alkyl)amino.

In some embodiments of Formula (X):
$R^Q$ is selected from H, $C_{1-6}$ alkyl, $OR^a$, and $OR^f$, wherein said $C_{1-6}$ alkyl is optionally substituted by 1 or 2 independently selected $R^8$ groups;
$R^a$ is selected from H, $C_{1-6}$ alkyl, $C_{1-6}$ haloalkyl, and 4-7 membered heterocycloalkyl-$C_{1-4}$ alkyl, wherein said $C_{1-6}$ alkyl and 4-7 membered heterocycloalkyl-$C_{1-4}$ alkyl are each optionally substituted with 1 or 2 independently selected $R^8$ groups;
$R^f$ is $C_{1-6}$ alkyl which is substituted with 1 substituent selected from $R^{90}$ and —$NHR^{80}$;
each $R^8$ is independently selected from H, halo, CN, $C_{1-6}$ alkyl, $C_{1-6}$ haloalkyl, $OR^{a8}$, $C(=O)OR^{a8}$, $OC(=O)R^{b8}$, $OC(=O)NR^{c8}R^{d8}$, $NR^{c8}R^{d8}$, $NR^{c8}C(=O)R^{b8}$, $NHC(=O)NHR^{d8}$, $NR^{c8}S(=O)_2R^{b8}$, and $NR^{c8}C(=O)OR^{b8}$;
each $R^{a8}$, $R^{c8}$, and $R^{d8}$ is independently selected from H, $C_{1-6}$ alkyl, $C_{1-6}$ haloalkyl, $C_{3-7}$ cycloalkyl, phenyl, 4-7 membered heterocycloalkyl, and 5-6 membered heteroaryl, wherein said $C_{1-6}$ alkyl, $C_{3-7}$ cycloalkyl, phenyl, 4-7 membered heterocycloalkyl, and 5-6 membered heteroaryl are each optionally substituted with 1 or 2 independently selected $R^{10}$ groups;
each $R^{b8}$ is independently selected from $C_{1-6}$ alkyl, $C_{1-6}$ haloalkyl, $C_{3-7}$ cycloalkyl, phenyl, 4-7 membered heterocycloalkyl, and 5-6 membered heteroaryl, wherein said $C_{1-6}$ alkyl, $C_{3-7}$ cycloalkyl, phenyl, 4-7 membered heterocycloalkyl, and 5-6 membered heteroaryl are each optionally substituted with 1 or 2 independently selected $R^{10}$ groups;
each $R^{10}$ is independently selected from H, halo, CN, $C_{1-6}$ alkyl, $C_{1-6}$ haloalkyl, $OR^{a10}$, $NR^{c10}R^{d10}$, and $C(=O)OR^{a10}$, wherein said $C_{1-6}$ alkyl is optionally substituted by 1 or 2 independently selected $R^G$ groups;
each $R^{a10}$ is independently selected from H and $C_{1-6}$ alkyl, wherein said $C_{1-6}$ alkyl is optionally substituted with 1 or 2 independently selected $R^G$ groups;
$R^{80}$ is a linear peptide chain having 2-4 amino acids; and
$R^{90}$ is a linear chain of formula —(O-$C_{2-4}$ alkylene)$_z$—$R^G$, wherein z is 1, 2, 3, or 4.

In some embodiments, $R^Q$ is H or $OR^aR^a$ is selected from H, $C_{1-6}$ alkyl, $C_{1-6}$ haloalkyl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^8$ groups; and each $R^8$ is independently selected from OH, $NO_2$, CN, halo, $C_{1-3}$ alkyl, $C_{2-3}$ alkenyl, $C_{2-3}$ alkynyl, $C_{1-3}$ haloalkyl, $C_{1-3}$ alkoxy, $C_{1-3}$ haloalkoxy, amino, $C_{1-3}$ alkylamino, and di($C_{1-3}$ alkyl)amino.

In some embodiments, $R^Q$ is H or $OR^a$, wherein $R^a$ is selected from H, $C_{1-6}$ alkyl, $C_{1-6}$ haloalkyl, and 4-7 membered heterocycloalkyl-$C_{1-4}$ alkyl, wherein said $C_{1-6}$ alkyl and 4-7 membered heterocycloalkyl-$C_{1-4}$ alkyl are each optionally substituted with 1, 2, 3, or 4 independently selected $R^8$ groups; and each $R^8$ is independently selected from OH, $NO_2$, CN, halo, $C_{1-3}$ alkyl, $C_{2-3}$ alkenyl, $C_{2-3}$ alkynyl, $C_{1-3}$ haloalkyl, $C_{1-3}$ alkoxy, $C_{1-3}$ haloalkoxy, amino, $C_{1-3}$ alkylamino, and di($C_{1-3}$ alkyl)amino.

In some embodiments, $R^Q$ is H, $OR^a$, halo, CN, $C_{1-6}$ alkyl, $C_{1-6}$ haloalkyl, or $C(=O)NR^cR^d$, wherein $R^a$ is selected from H, $C_{1-6}$ alkyl, $C_{1-6}$ haloalkyl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^8$ groups; $R^c$ and $R^d$ are each independently selected from H, $C_{1-6}$ alkyl, and $C_{1-6}$ haloalkyl; and each $R^8$ is independently selected from OH, $NO_2$, CN, halo, $C_{1-3}$ alkyl, $C_{2-3}$ alkenyl, $C_{2-3}$ alkynyl, $C_{1-3}$ haloalkyl, $C_{1-3}$ alkoxy, $C_{1-3}$ haloalkoxy, amino, $C_{1-3}$ alkylamino, and di($C_{1-3}$ alkyl)amino.

In some embodiments, $R^Q$ is H or $OR^a$, wherein $R^a$ is selected from H, $C_{1-6}$ alkyl, and 4-7 membered heterocycloalkyl-$C_{1-4}$ alkyl, wherein said $C_{1-6}$ alkyl and 4-7 membered heterocycloalkyl-$C_{1-4}$ alkyl are optionally substituted by 1 group selected from CN, OH, $C_{1-3}$ alkyl, $C_{1-3}$ alkoxy, carboxy-$C_{1-3}$ alkoxy-$C_{1-3}$-alkoxy-, carboxy-$C_{1-3}$ alkoxy-$C_{1-3}$ alkoxy-$C_{1-3}$-alkoxy-, $OC(=O)R^{a8}$, $C(=O)OR^{a8}$, $OC(=O)NHR^{d8}$, —$NHC(=O)R^{b8}$, $NHC(=O)NHR^{d8}$, $C(=O)OH$-$C_{1-6}$ alkyl-, $C(=O)OH$-$C_{1-6}$ alkoxy-$C(=O)$—and —$NHC(=O)OR^{b8}$; wherein $R^{a8}$, $R^{b8}$ and $R^{d8}$ are each independently $C_{1-3}$ alkyl, which is optionally substituted by 1 or 2 groups independently selected from carboxy and amino.

In some embodiments, $R^Q$ is H or $OR^a$, wherein $R^a$ is selected from H, $C_{1-6}$ alkyl, and 4-7 membered heterocycloalkyl-$C_{1-4}$ alkyl, wherein said $C_{1-6}$ alkyl is optionally substituted by OH or $C_{1-3}$ alkoxy.

In some embodiments, $R^Q$ is selected from H, methoxy, N-morpholinylpropoxy, methoxypropoxy, hydroxypropoxy, 3-(4-carboxybutanamido)propoxy, 3-(((2-carboxyethoxy)carbonyl)amino)propoxy, 3-(((2-carboxyethyl)carbamoyl)oxy)propoxy, 2-(2-(2-carboxyethoxy)ethoxy)ethoxy; 2-(2-(2-(2-carboxyethoxy)ethoxy)ethoxy)ethoxy; 2-(1-(3-carboxypropyl)piperidin-4-yl)ethoxy; and 2-(1-((carboxymethoxy)carbonyl)piperidin-4-yl)ethoxy.

In some embodiments, $R^Q$ is selected from H, methoxy, N-morpholinylpropoxy, methoxypropoxy, and hydroxypropoxy.

In some embodiments:

each $R^a$, $R^c$, and $R^d$ is independently selected from H, $C_{1-6}$ alkyl, $C_{1-6}$ haloalkyl, $C_{2-6}$ alkenyl, and $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^8$ groups;

each $R^b$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, or 3 independently selected $R^8$ groups; and each $R^8$ is independently selected from OH, $NO_2$, CN, halo, $C_{1-3}$ alkyl, $C_{2-3}$ alkenyl, $C_{2-3}$ alkynyl, $C_{1-3}$ haloalkyl, cyano-$C_{1-3}$ alkyl, HO-$C_{1-3}$ alkyl, $C_{1-3}$ alkoxy-$C_{1-3}$ alkyl, $C_{3-7}$ cycloalkyl, $C_{1-3}$ alkoxy, $C_{1-3}$ haloalkoxy, amino, $C_{1-3}$ alkylamino, di($C_{1-3}$ alkyl)amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl)carbamyl, carboxy, $C_{1-3}$ alkylcarbonyl, $C_{1-4}$ alkoxycarbonyl, $C_{1-3}$ alkylcarbonylamino, $C_{1-3}$ alkylsulfonylamino, aminosulfonyl, $C_{1-3}$ alkylaminosulfonyl, di($C_{1-3}$ alkyl)aminosulfonyl, aminosulfonylamino, $C_{1-3}$ alkylaminosulfonylamino, di($C_{1-3}$ alkyl)aminosulfonylamino, aminocarbonylamino, $C_{1-3}$ alkylaminocarbonylamino, and di($C_{1-3}$ alkyl)aminocarbonylamino.

In some embodiments:

each $R^a$, $R^c$, and $R^d$ is independently selected from H, $C_{1-6}$ alkyl, $C_{1-6}$ haloalkyl, $C_{2-6}$ alkenyl, and $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^8$ groups;

each $R^b$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, or 3 independently selected $R^8$ groups; and each $R^8$ is independently selected from OH, $NO_2$, CN, halo, $C_{1-3}$ alkyl, $C_{2-3}$ alkenyl, $C_{2-3}$ alkynyl, $C_{1-3}$ haloalkyl, cyano-$C_{1-3}$ alkyl, HO-$C_{1-3}$ alkyl, $C_{1-3}$ alkoxy-$C_{1-3}$ alkyl, $C_{3-7}$ cycloalkyl, $C_{1-3}$ alkoxy, $C_{1-3}$ haloalkoxy, amino, $C_{1-3}$ alkylamino, di($C_{1-3}$ alkyl)amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl)carbamyl, carboxy, $C_{1-3}$ alkylcarbonyl, $C_{1-4}$ alkoxycarbonyl, $C_{1-3}$ alkylcarbonylamino, $C_{1-3}$ alkylsulfonylamino, aminosulfonyl, $C_{1-3}$ alkylaminosulfonyl, di($C_{1-3}$ alkyl)aminosulfonyl, aminosulfonylamino, $C_{1-3}$ alkylaminosulfonylamino, di($C_{1-3}$ alkyl)aminosulfonylamino, aminocarbonylamino, $C_{1-3}$ alkylaminocarbonylamino, di($C_{1-3}$ alkyl)aminocarbonylamino, carboxy-$C_{1-3}$ alkoxy-$C_{1-3}$-alkoxy-, carboxy-$C_{1-3}$ alkoxy-$C_{1-3}$-alkoxy-$C_{1-3}$-alkoxy-, carboxy-$C_{1-3}$ alkoxy-carbonylamino-, carboxy-$C_{1-3}$ alkyl-carbonylamino-, carboxy-$C_{1-3}$ alkyl-carbamyl-, carboxy-$C_{1-3}$ alkoxycarbonyl-, and carboxy-$C_{1-3}$ alkyl-.

In some embodiments:

each $R^a$, $R^c$, and $R^d$ is independently selected from H, $C_{1-6}$ alkyl, $C_{1-6}$ haloalkyl, and 4-7 membered heterocycloalkyl-$C_{1-4}$ alkyl, wherein said $C_{1-6}$ alkyl and 4-7 membered heterocycloalkyl-$C_{1-4}$ alkyl are each optionally substituted with 1, 2, 3, or 4 independently selected $R^8$ groups;

each $R^b$ is independently selected from $C_{1-6}$ alkyl and $C_{1-6}$ haloalkyl, wherein said $C_{1-6}$ alkyl is optionally substituted with 1, 2, or 3 independently selected $R^8$ groups; and each $R^8$ is independently selected from OH, $NO_2$, CN, halo, $C_{1-3}$ alkyl, $C_{2-3}$ alkenyl, $C_{2-3}$ alkynyl, $C_{1-3}$ haloalkyl, $C_{1-3}$ alkoxy, $C_{1-3}$ haloalkoxy, amino, $C_{1-3}$ alkylamino, di($C_{1-3}$ alkyl)amino, carboxy-$C_{1-3}$ alkoxy-$C_{1-3}$-alkoxy-, carboxy-$C_{1-3}$ alkoxy-$C_{1-3}$-alkoxy-$C_{1-3}$-alkoxy-, carboxy-$C_{1-3}$ alkoxy-carbonylamino-, carboxy-$C_{1-3}$ alkyl-carbonylamino-, carboxy-$C_{1-3}$ alkyl-carbamyl-, carboxy-$C_{1-3}$ alkoxycarbonyl-, and carboxy-$C_{1-3}$ alkyl-.

In some embodiments:

each $R^a$, $R^c$, and $R^d$ is independently selected from H, $C_{1-6}$ alkyl, $C_{1-6}$ haloalkyl, and 4-7 membered heterocycloalkyl-C 1-4 alkyl, wherein said $C_{1-6}$ alkyl and 4-7 membered heterocycloalkyl-$C_{1-4}$ alkyl are each optionally substituted with 1, 2, 3, or 4 independently selected $R^8$ groups;

each $R^b$ is independently selected from $C_{1-6}$ alkyl and $C_{1-6}$ haloalkyl, wherein said $C_{1-6}$ alkyl is optionally substituted with 1, 2, or 3 independently selected $R^8$ groups; and each $R^8$ is independently selected from OH, $NO_2$, CN, halo, $C_{1-3}$ alkyl, $C_{2-3}$ alkenyl, $C_{2-3}$ alkynyl, $C_{1-3}$ haloalkyl, $C_{1-3}$ alkoxy, $C_{1-3}$ haloalkoxy, amino, $C_{1-3}$ alkylamino, and di($C_{1-3}$ alkyl)amino.

In some embodiments:

each $R^a$, $R^c$, and $R^d$ is independently selected from H, $C_{1-6}$ alkyl, and $C_{1-6}$ haloalkyl, wherein said $C_{1-6}$ alkyl is optionally substituted with 1, 2, 3, or 4 independently selected $R^8$ groups;

each $R^b$ is independently selected from $C_{1-6}$ alkyl and $C_{1-6}$ haloalkyl, wherein said $C_{1-6}$ alkyl is optionally substituted with 1, 2, or 3 independently selected $R^8$ groups; and each $R^8$ is independently selected from OH, $NO_2$, CN, halo, $C_{1-3}$ alkyl, $C_{2-3}$ alkenyl, $C_{2-3}$ alkynyl, $C_{1-3}$ haloalkyl, $C_{1-3}$ alkoxy, $C_{1-3}$ haloalkoxy, amino, $C_{1-3}$ alkylamino, and di($C_{1-3}$ alkyl)amino.

In some embodiments, $R^a$ is H, $C_{1-4}$ alkyl, $C_{1-6}$ haloalkyl, or 4-7 membered heterocycloalkyl-$C_{1-4}$ alkyl, wherein said $C_{1-4}$ alkyl and 4-7 membered heterocycloalkyl-$C_{1-4}$ alkyl, are each optionally substituted with 1, 2, or 3 groups independently selected from OH, $NO_2$, CN, halo, $C_{1-3}$ alkyl, $C_{2-3}$ alkenyl, $C_{2-3}$ alkynyl, $C_{1-3}$ haloalkyl, $C_{1-3}$ alkoxy, $C_{1-3}$ haloalkoxy, amino, $C_{1-3}$ alkylamino, di($C_{1-3}$ alkyl)amino, carboxy-$C_{1-3}$ alkoxy-$C_{1-3}$-alkoxy-, carboxy-$C_{1-3}$ alkoxy-$C_{1-3}$ -alkoxy-$C_{1-3}$-alkoxy-, carboxy-$C_{1-3}$ alkoxy-carbonylamino-, carboxy-$C_{1-3}$ alkyl-carbonylamino-, carboxy-$C_{1-3}$ alkyl-carbamyl-, carboxy-$C_{1-3}$ alkoxycarbonyl-, and carboxy-$C_{1-3}$ alkyl-.

In some embodiments, $R^a$ is H, $C_{1-4}$ alkyl, $C_{1-6}$ haloalkyl, or 4-7 membered heterocycloalkyl-$C_{1-4}$ alkyl, wherein said $C_{1-4}$ alkyl and 4-7 membered heterocycloalkyl-$C_{1-4}$ alkyl, are each optionally substituted with 1, 2, or 3 groups independently selected from OH, $NO_2$, CN, halo, $C_{1-3}$ alkyl, $C_{2-3}$ alkenyl, $C_{2-3}$ alkynyl, $C_{1-3}$ haloalkyl, $C_{1-3}$ alkoxy, $C_{1-3}$ haloalkoxy, amino, $C_{1-3}$ alkylamino, and di($C_{1-3}$ alkyl) amino.

In some embodiments, $R^a$ is H, $C_{1-4}$ alkyl, or $C_{1-6}$ haloalkyl, wherein said $C_{1-4}$ alkyl is optionally substituted with 1, 2, or 3 groups independently selected from OH, $NO_2$, CN, halo, $C_{1-3}$ alkyl, $C_{2-3}$ alkenyl, $C_{2-3}$ alkynyl, $C_{1-3}$ haloalkyl, $C_{1-3}$ alkoxy, $C_{1-3}$ haloalkoxy, amino, $C_{1-3}$ alkylamino, and di($C_{1-3}$ alkyl)amino.

In some embodiments, $R^a$ is H, $C_{1-4}$ alkyl, or 4-7 membered heterocycloalkyl-$C_{1-4}$ alkyl, wherein the $C_{1-4}$ alkyl is optionally substituted with OH, $C_{1-3}$ alkoxy, carboxy-$C_{1-3}$ alkoxy-$C_{1-3}$-alkoxy-, carboxy-$C_{1-3}$ alkoxy-$C_{1-3}$-alkoxy-$C_{1-3}$ -alkoxy-, carboxy-$C_{1-3}$ alkoxy-carbonylamino-, carboxy-$C_{1-3}$ alkyl-carbonylamino-, carboxy-$C_{1-3}$ alkyl-carbamyl-, carboxy-$C_{1-3}$ alkoxycarbonyl-, and carboxy-$C_{1-3}$ alkyl-.

In some embodiments, $R^a$ is H, $C_{1-4}$ alkyl, or 4-7 membered heterocycloalkyl-$C_{1-4}$ alkyl, wherein the $C_{1-4}$ alkyl is optionally substituted with OH or $C_{1-3}$ alkoxy.

In some embodiments, $R^a$ is H or $C_{1-4}$ alkyl.

In some embodiments, $R^c$ is H, $C_{1-4}$ alkyl, or $C_{1-6}$ haloalkyl, wherein said $C_{1-4}$ alkyl is optionally substituted with 1, 2, or 3 groups independently selected from OH, $NO_2$, CN, halo, $C_{1-3}$ alkyl, $C_{2-3}$ alkenyl, $C_{2-3}$ alkynyl, $C_{1-3}$ haloalkyl, $C_{1-3}$ alkoxy, $C_{1-3}$ haloalkoxy, amino, $C_{1-3}$ alkylamino, and di($C_{1-3}$ alkyl)amino.

In some embodiments, $R^c$ is H or $C_{1-4}$ alkyl.

In some embodiments, $R^d$ is H, $C_{1-4}$ alkyl, or $C_{1-6}$ haloalkyl, wherein said $C_{1-4}$ alkyl is optionally substituted with 1, 2, or 3 groups independently selected from OH, $NO_2$, CN, halo, $C_{1-3}$ alkyl, $C_{2-3}$ alkenyl, $C_{2-3}$ alkynyl, $C_{1-3}$ haloalkyl, $C_{1-3}$ alkoxy, $C_{1-3}$ haloalkoxy, amino, $C_{1-3}$ alkylamino, and di($C_{1-3}$ alkyl)amino.

In some embodiments, $R^d$ is H or $C_{1-4}$ alkyl.

In some embodiments, $R^b$ is $C_{1-4}$ alkyl, or $C_{1-6}$ haloalkyl, wherein said $C_{1-4}$ alkyl is optionally substituted with 1, 2, or 3 groups independently selected from OH, $NO_2$, CN, halo, $C_{1-3}$ alkyl, $C_{2-3}$ alkenyl, $C_{2-3}$ alkynyl, $C_{1-3}$ haloalkyl, $C_{1-3}$ alkoxy, $C_{1-3}$ haloalkoxy, amino, $C_{1-3}$ alkylamino, and di($C_{1-3}$ alkyl)amino.

In some embodiments, $R^b$ is $C_{1-4}$ alkyl.

In some embodiments, $R^1$ is H, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted by 1, 2, 3, or 4 independently selected $R^8$ groups.

In some embodiments, $R^1$ is H, $C_{1-6}$ alkyl, $C_{1-6}$ haloalkyl, or $C_{3-7}$ cycloalkyl, wherein said $C_{1-6}$ alkyl or $C_{3-7}$ cycloalkyl are each optionally substituted by 1, 2, 3, or 4 independently selected $R^8$ groups.

In some embodiments, $R^1$ is H, $C_{1-6}$ alkyl, or $C_{1-6}$ haloalkyl.

In some embodiments, each $R^8$ is independently selected from OH, $NO_2$, CN, halo, $C_{1-3}$ alkyl, $C_{2-3}$ alkenyl, $C_{2-3}$ alkynyl, $C_{1-3}$ haloalkyl, cyano-$C_{1-3}$ alkyl, HO-$C_{1-3}$ alkyl, $C_{1-3}$ alkoxy-$C_{1-3}$ alkyl, $C_{3-7}$ cycloalkyl, $C_{1-3}$ alkoxy, $C_{1-3}$ haloalkoxy, amino, $C_{1-3}$ alkylamino, di($C_{1-3}$ alkyl)amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl)carbamyl, carboxy, $C_{1-3}$ alkylcarbonyl, $C_{1-4}$ alkoxycarbonyl, $C_{1-3}$ alkylcarbonylamino, $C_{1-3}$ alkylsulfonylamino, aminosulfonyl, $C_{1-3}$ alkylaminosulfonyl, di($C_{1-3}$alkyl)aminosulfonyl, aminosulfonylamino, $C_{1-3}$ alkylaminosulfonylamino, di($C_{1-3}$ alkyl)aminosulfonylamino, aminocarbonylamino, $C_{1-3}$ alkylaminocarbonylamino, and di($C_{1-3}$ alkyl)aminocarbonylamino.

In some embodiments, each $R^8$ is independently selected from OH, $NO_2$, CN, halo, $C_{1-3}$ alkyl, $C_{2-3}$ alkenyl, $C_{2-3}$ alkynyl, $C_{1-3}$ haloalkyl, $C_{1-3}$ alkoxy, $C_{1-3}$ haloalkoxy, amino, $C_{1-3}$ alkylamino, and di($C_{1-3}$ alkyl)amino.

In some embodiments, $R^1$ is H, $C_{1-6}$ alkyl, $C_{1-6}$ haloalkyl, or $C_{3-7}$ cycloalkyl, wherein said $C_{1-6}$ alkyl or $C_{3-7}$ cycloalkyl are each optionally substituted by 1, 2, 3, or 4 independently selected $R^8$ groups.

In some embodiments, X is $CR^X$; Y is $CR^Y$; and Z is $CR^Z$;
In some embodiments, X is N; Y is $CR^Y$; and Z is $CR^Z$;
In some embodiments, X is $CR^X$; Y is N; and Z is $CR^Z$;
In some embodiments, X is $CR^X$; Y is $CR^Y$; and Z is N;
In some embodiments, one of X, Y and Z are N;
In some embodiments, two of X, Y and Z are N;
In some embodiments, X is N.
In some embodiments, X is $CR^X$.
In some embodiments, X is CH.
In some embodiments:

$R^X$ is selected from H, D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a0}$, $SR^{a0}$, $C(=O)R^{b0}$, $C(=O)NR^{c0}R^{d0}$, $C(=O)OR^{a0}$, $OC(=O)R^{b0}$, $OC(=O)NR^{c0}R^{d0}$, $NR^{c0}R^{d0}$, $NR^{c0}C(=O)R^{b0}$, $NR^{c0}C(=O)OR^{b0}$, $NR^{c0}C(=O)NR^{c0}R^{d0}$, $NR^{c0}S(=O)_2R^{b0}$, $NR^{c0}S(=O)_2NR^{c0}R^{d0}$, $S(=O)_2R^{b0}$, and $S(=O)_2NR^{c0}R^{d0}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted by 1, 2, 3, or 4 independently selected $R^G$ groups;

each $R^{a0}$, $R^{c0}$, and $R^{d0}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ groups; and each $R^{b0}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl are each optionally substituted with 1, 2, or 3 independently selected $R^G$ groups.

In some embodiments, $R^X$ is selected from H, D, halo, CN, $NO_2$, $C_{1-6}$ alkyl, $C_{2-6}$ alkenyl, $C_{2-6}$ alkynyl, $C_{1-6}$ haloalkyl, $OR^{a0}$, $C(=O)R^{b0}$, $C(=O)NR^{c0}R^{d0}$, $C(=O)OR^{a0}$, $OC(=O)R^{b0}$, $NR^{c0}R^{d0}$, $NR^{c0}C(=O)R^{b0}$, $NR^{c0}S(=O)_2R^{b0}$, $S(=O)_2R^{b0}$, and $S(=O)_2NR^{c0}R^{d0}$, wherein said $C_{1-6}$ alkyl, $C_{2-6}$ alkenyl, $C_{2-6}$ alkynyl, and $C_{1-6}$ haloalkyl are each optionally substituted by 1, 2, 3, or 4 independently selected $R^G$ groups;

each $R^{a0}$, $R^{c0}$, and $R^{d0}$ is independently selected from H, $C_{1-6}$ alkyl, and $C_{1-6}$ haloalkyl, wherein said $C_{1-6}$ alkyl are each optionally substituted with 1, 2, 3, or 4 independently selected $R^G$ groups; and each $R^{b0}$ is independently selected from $C_{1-6}$ alkyl and $C_{1-6}$ haloalkyl, wherein said $C_{1-6}$ alkyl is optionally substituted with 1, 2, or 3 independently selected $R^G$ groups.

In some embodiments, $R^X$ is selected from H, D, halo, CN, $C_{1-6}$ alkyl, and $C_{1-6}$ haloalkyl.

In some embodiments, $R^X$ is H or $C_{1-6}$ alkyl.

In some embodiments, Y is N.

In some embodiments, Y is $CR^Y$.

In some embodiments:

$R^Y$ is selected from H, D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a0}$, $SR^{a0}$, $C(=O)R^{b0}$, $C(=O)NR^{c0}R^{d0}$, $C(=O)OR^{a0}$, $OC(=O)R^{b0}$, $OC(=O)NR^{c0}R^{d0}$, $NR^{c0}R^{d0}$, $NR^{c0}C(=O)R^{b0}$, $NR^{c0}C(=O)OR^{b0}$, $NR^{c0}C(=O)NR^{c0}R^{d0}$, $NR^{c0}S(=O)_2R^{b0}$, $NR^{c0}S(=O)_2NR^{c0}R^{d0}$, $S(=O)_2R^{b0}$, and $S(=O)_2NR^{c0}R^{d0}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted by 1, 2, 3, or 4 independently selected $R^G$ groups;

each $R^{a0}$, $R^{c0}$, and $R^{d0}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ groups; and each $R^{b0}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl are each optionally substituted with 1, 2, or 3 independently selected $R^G$ groups.

In some embodiments, $R^X$ is selected from H, D, halo, CN, $NO_2$, $C_{1-6}$ alkyl, $C_{2-6}$ alkenyl, $C_{2-6}$ alkynyl, $C_{1-6}$ haloalkyl, $OR^{a0}$, $C(=O)R^{b0}$, $C(=O)NR^{c0}R^{d0}$, $C(=O)OR^{a0}$, $OC(=O)R^{b0}$, $NR^{c0}R^{d0}$, $NR^{c0}C(=O)R^{b0}$, $NR^{c0}S(=O)_2R^{b0}$, $S(=O)_2R^{b0}$, and $S(=O)_2NR^{c0}R^{d0}$, wherein said $C_{1-6}$ alkyl, $C_{2-6}$ alkenyl, $C_{2-6}$ alkynyl, and $C_{1-6}$ haloalkyl are each optionally substituted by 1, 2, 3, or 4 independently selected $R^G$ groups;

each $R^{a0}$, $R^{c0}$, and $R^{d0}$ is independently selected from H, $C_{1-6}$ alkyl, and $C_{1-6}$ haloalkyl, wherein said $C_{1-6}$ alkyl are each optionally substituted with 1, 2, 3, or 4 independently selected $R^G$ groups; and each $R^{b0}$ is independently selected from $C_{1-6}$ alkyl and $C_{1-6}$ haloalkyl, wherein said $C_{1-6}$ alkyl is optionally substituted with 1, 2, or 3 independently selected $R^G$ groups.

In some embodiments, $R^Y$ is selected from H, D, halo, CN, $C_{1-6}$ alkyl, and $C_{1-6}$ haloalkyl.

In some embodiments, $R^Y$ is selected from H, halo, and CN.

In some embodiments, Y is N, or $CR^Y$, wherein $R^Y$ is selected from H, halo and CN.

In some embodiments, Y is N, CH, CF or C(CN).

In some embodiments, Y is CH, CF, or C(CN).

In some embodiments, Y is CH.

In some embodiments, Z is N.

In some embodiments, Z is $CR^Z$.

In some embodiments:

$R^Z$ is selected from H, D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a0}$, $SR^{a0}$, $C(=O)R^{b0}$, $C(=O)NR^{c0}R^{d0}$, $C(=O)OR^{a0}$, $OC(=O)R^{b0}$, $OC(=O)NR^{c0}R^{d0}$, $NR^{c0}R^{d0}$, $NR^{c0}C(=O)R^{b0}$, $NR^{c0}C(=O)OR^{b0}$, $NR^{c0}C(=O)NR^{c0}R^{d0}$, $NR^{c0}S(=O)_2R^{b0}$, $NR^{c0}S(=O)_2NR^{c0}R^{d0}$, $S(=O)_2R^{b0}$, and $S(=O)_2NR^{c0}R^{d0}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted by 1, 2, 3, or 4 independently selected $R^G$ groups;

each $R^{a0}$, $R^{c0}$, and $R^{d0}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ groups; and each $R^{b0}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl are each optionally substituted with 1, 2, or 3 independently selected $R^G$ groups.

In some embodiments, $R^X$ is selected from H, D, halo, CN, $NO_2$, $C_{1-6}$ alkyl, $C_{2-6}$ alkenyl, $C_{2-6}$ alkynyl, $C_{1-6}$ haloalkyl, $OR^{a0}$, $C(=O)R^{b0}$, $C(=O)NR^{c0}R^{d0}$, $C(=O)OR^{d0}$, $OC(=O)R^{b0}$, $NR^{c0}R^{d0}$, $NR^{c0}C(=O)R^{b0}$, $NR^{c0}S(=O)_2R^{b0}$, $S(=O)_2R^{b0}$, and $S(=O)_2NR^{c0}R^{d0}$, wherein said $C_{1-6}$ alkyl, $C_{2-6}$ alkenyl, $C_{2-6}$ alkynyl, and $C_{1-6}$ haloalkyl are each optionally substituted by 1, 2, 3, or 4 independently selected $R^G$ groups;

each $R^{a0}$, $R^{c0}$, and $R^{d0}$ is independently selected from H, $C_{1-6}$ alkyl, and $C_{1-6}$ haloalkyl, wherein said $C_{1-6}$ alkyl are each optionally substituted with 1, 2, 3, or 4 independently selected $R^G$ groups; and each $R^{b0}$ is independently selected from $C_{1-6}$ alkyl and $C_{1-6}$ haloalkyl, wherein said $C_{1-6}$ alkyl is optionally substituted with 1, 2, or 3 independently selected $R^G$ groups.

In some embodiments, $R^Z$ is selected from H, D, halo, CN, $C_{1-6}$ alkyl, and $C_{1-6}$ haloalkyl.

In some embodiments, $R^Z$ is selected from H, halo, and CN.

In some embodiments, $R^Z$ is selected from H, F, and CN.

In some embodiments, Z is N, or $CR^Z$, wherein $R^Z$ is selected from H, halo and CN.

In some embodiments, Z is N, CH, CF, or C(CN).

In some embodiments, Z is CH, CF, or C(CN).

In some embodiments, Z is CH.

In some embodiments, $R^3$ is H or $C_{1-6}$ alkyl.

In some embodiments, $R^3$ is H or methyl.

In some embodiments, $R^3$ is H.

In some embodiments, $R^2$ is H, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, or 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted by 1, 2, 3, or 4 independently selected $R^{2a}$ groups.

In some embodiments, $R^2$ is H, $C_{1-6}$ alkyl, $C_{2-6}$ alkenyl, $C_{2-6}$ alkynyl, or $C_{1-6}$ haloalkyl, wherein said $C_{1-6}$ alkyl, $C_{2-6}$ alkenyl, $C_{2-6}$ alkynyl, and $C_{1-6}$ haloalkyl are each optionally substituted by 1, 2, 3, or 4 independently selected $R^{2a}$ groups.

In some embodiments, $R^2$ is H, $C_{1-6}$ alkyl, or $C_{1-6}$ haloalkyl.

In some embodiments, $R^4$ is H, D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a4}$, $SR^{a4}$, $C(=O)R^{b4}$, $C(=O)NR^{c4}R^{d4}$, $C(=O)OR^{a4}$, $OC(=O)R^{b4}$, $OC(=O)NR^{c4}R^{d4}$, $NR^{c4}R^{d4}$, $NR^{c4}C(=O)R^{b4}$, $NR^{c4}C(=O)OR^{b4}$, $NR^{c4}C(=O)NR^{c4}R^{d4}$, $NR^{c4}S(=O)_2R^{b4}$, $NR^{c4}S(=O)_2NR^{c4}R^{d4}$, $S(=O)_2R^{b4}$, or $S(=O)_2NR^{c4}R^{d4}$, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted by 1, 2, 3, or 4 independently selected $R^{4a}$ groups.

In some embodiments, $R^4$ is H, D, halo, CN, $NO_2$, $C_{1-6}$ alkyl, $C_{2-6}$ alkenyl, $C_{2-6}$ alkynyl, $C_{1-6}$ haloalkyl, $OR^{a4}$, $SR^{a4}$, $C(=O)R^{b4}$, $C(=O)NR^{c4}R^{d4}$, $C(=O)OR^{a4}$, $OC(=O)R^{b4}$, $OC(=O)NR^{c4}R^{d4}$, $NR^{c4}R^{d4}$, $NR^{c4}C(=O)R^{b4}$, $NR^{c4}C(=O)OR^{b4}$, $NR^{c4}C(=O)NR^{c4}R^{d4}$, $NR^{c4}S(=O)_2R^{b4}$, $NR^{c4}S(=O)_2NR^{c4}R^{d4}$, $S(=O)_2R^{b4}$, or $S(=O)_2NR^{c4}R^{d4}$, wherein said $C_{1-6}$ alkyl, $C_{2-6}$ alkenyl, and $C_{2-6}$ alkynyl are each optionally substituted by 1, 2, 3, or 4 independently selected $R^{4a}$ groups.

In some embodiments:

each $R^{a4}$, $R^{c4}$, and $R^{d4}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{4a}$ groups; and each $R^{b4}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{4a}$ groups.

In some embodiments:

each $R^{a4}$, $R^{c4}$, and $R^{d4}$ is independently selected from H, $C_{1-6}$ alkyl, and $C_{1-6}$ haloalkyl, wherein said $C_{1-6}$ alkyl is optionally substituted with 1, 2, 3, or 4 independently selected $R^{4a}$ groups; and each $R^{b4}$ is independently selected from $C_{1-6}$ alkyl and $C_{1-6}$ haloalkyl, wherein said $C_{1-6}$ alkyl is optionally substituted with 1, 2, 3, or 4 independently selected $R^{4a}$ groups.

In some embodiments, $R^4$ is H, $C_{1-6}$ alkyl, $C_{1-6}$ haloalkyl, or $OR^{a4}$.

In some embodiments, $R^4$ is H, $C_{1-6}$ alkyl, or $OR^{a4}$.

In some embodiments of Formula (X):

$R^4$ is selected from H, $C_{1-6}$ alkyl, $OR^{a4}$, and $OR^{f4}$, wherein said $C_{1-6}$ alkyl is optionally substituted by 1 or 2 independently selected $R^{4a}$ groups;

$R^{a4}$ is selected from H, $C_{1-6}$ alkyl, $C_{1-6}$ haloalkyl, and 4-7 membered heterocycloalkyl-$C_{1-4}$ alkyl, wherein said $C_{1-6}$ alkyl and 4-7 membered heterocycloalkyl-$C_{1-4}$ alkyl are each optionally substituted with 1 or 2 independently selected $R^{4a}$ groups;

$R^{f4}$ is $C_{1-6}$ alkyl which is substituted with 1 substituent selected from $R^{90}$ and —$NHR^{80}$;

each $R^{4a}$ is independently selected from H, halo, CN, $C_{1-6}$ alkyl, $C_{1-6}$ haloalkyl, $C(=O)OR^{a9}$, $OC(=O)R^{b9}$, $OC(=O)NR^{c9}R^{d9}$, $NR^{c9}R^{d9}$, $NR^{c9}C(=O)R^{b9}$, $NHC(=O)NHR^{d9}$, $NR^{c9}S(=O)_2R^{b9}$, and $NR^{c9}C(=O)OR^{b9}$;

each $R^{a9}$, $R^{c9}$, and $R^{d9}$ is independently selected from H, $C_{1-6}$ alkyl, $C_{1-6}$ haloalkyl, $C_{3-7}$ cycloalkyl, phenyl, 4-7 membered heterocycloalkyl, and 5-6 membered heteroaryl, wherein said $C_{1-6}$ alkyl, $C_{3-7}$ cycloalkyl, phenyl, 4-7 membered heterocycloalkyl, and 5-6 membered heteroaryl are each optionally substituted with 1 or 2 independently selected $R^{11}$ groups;

each $R^{b9}$ is independently selected from $C_{1-6}$ alkyl, $C_{1-6}$ haloalkyl, $C_{3-7}$ cycloalkyl, phenyl, 4-7 membered heterocycloalkyl, and 5-6 membered heteroaryl, wherein said $C_{1-6}$ alkyl, $C_{3-7}$ cycloalkyl, phenyl, 4-7 membered heterocycloalkyl, and 5-6 membered heteroaryl are each optionally substituted with 1 or 2 independently selected $R^{11}$ groups;

each $R^{11}$ is independently selected from H, halo, CN, $C_{1-6}$ alkyl, $C_{1-6}$ haloalkyl, $OR^{a11}$, $NR^{c11}R^{d11}$, and $C(=O)OR^{a11}$, wherein said $C_{1-6}$ alkyl is optionally substituted by 1 or 2 independently selected $R^G$ groups;

each $R^{a11}$ is independently selected from H and $C_{1-6}$ alkyl, wherein said $C_{1-6}$ alkyl is optionally substituted with 1 or 2 independently selected $R^G$ groups;

each $R^{c11}$ and $R^{d11}$ independently selected from H and $C_{1-6}$ alkyl, wherein said $C_{1-6}$ alkyl is optionally substituted with 1 or 2 independently selected $R^G$ groups;

$R^{80}$ is a linear peptide chain having 2-4 amino acids; and $R^{90}$ is a linear chain of formula $-(O-C_{2-4}\ \text{alkylene})_z-R^G$, wherein z is 1, 2, 3, or 4.

In some embodiments, $R^4$ is H, $C_{1-6}$ alkyl, or $OR^{a4}$;

wherein $R^{a4}$ is selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{4a}$ groups;

each $R^{4a}$ is independently selected from CN, halo, $C_{1-6}$ alkyl, $C_{2-6}$ alkenyl, $C_{2-6}$ alkynyl, $C_{1-6}$ haloalkyl, $OR^{a9}$, $C(=O)R^{b9}$, $C(=O)NR^{c9}R^{d9}$, $C(=O)OR^{a9}$, $OC(=O)R^{b9}$, $OC(=O)NR^{c9}R^{d9}$, $NR^{c9}R^{d9}$, $NR^{c9}C(=O)R^{b9}$, $NR^{c9}C(=O)OR^{b9}$, $NR^{c9}C(=O)NR^{c9}R^{d9}$, $NR^{c9}S(=O)_2R^{b9}$, $NR^{c9}S(=O)_2NR^{c9}R^{d9}$, and $S(=O)_2R^{b9}$;

each $R^{a9}$, $R^{c9}$, and $R^{d9}$ is independently selected from H, $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted by 1, 2, or 3 independently selected $R^{11}$ groups;

each $R^{b9}$ is independently selected from $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, each of which is optionally substituted by 1, 2, or 3 independently selected $R^{11}$ groups; and each $R^{11}$ is independently selected from OH, $NO_2$, CN, halo, $C_{1-3}$ alkyl, $C_{2-3}$ alkenyl, $C_{2-3}$ alkynyl, $C_{1-3}$ haloalkyl, $C_{1-3}$ alkoxy, $C_{1-3}$ haloalkoxy, amino, $C_{1-3}$ alkylamino, and di($C_{1-3}$ alkyl)amino.

In some embodiments, $R^4$ is H, $C_{1-6}$ alkyl, or $OR^{a4}$;

wherein $R^{a4}$ is selected from H, $C_{1-6}$ alkyl, $C_{1-6}$ haloalkyl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1 or 2 independently selected $R^{4a}$ groups;

each $R^{4a}$ is independently selected from CN, halo, $C_{1-6}$ alkyl, $C_{1-6}$ haloalkyl, $C(=O)R^{b9}$, $C(=O)NR^{c9}R^{d9}$, $C(=O)OR^{a9}$, $OC(=O)R^{b9}$, $OC(=O)NR^{c9}R^{d9}$, $NR^{c9}R^{d9}$, $NR^{c9}C(=O)R^{b9}$, $NR^{c9}S(=O)_2R^{b9}$, and $NR^{c9}S(=O)_2NR^{c9}R^{d9}$;

each $R^{a9}$, $R^{c9}$, and $R^{d9}$ independently selected from H, $C_{1-6}$ alkyl, $C_{1-6}$ haloalkyl, $C_{3-7}$ cycloalkyl, phenyl, 4-7 membered heterocycloalkyl, and 5-6 membered heteroaryl, wherein said $C_{1-6}$ alkyl, $C_{1-6}$ haloalkyl, $C_{3-7}$ cycloalkyl, phenyl, 4-7 membered heterocycloalkyl, and 5-6 membered heteroaryl are each optionally substituted by 1 or 2 independently selected $R^{11}$ groups;

each $R^{b9}$ is independently selected from $C_{1-6}$ alkyl, $C_{1-6}$ haloalkyl, $C_{3-7}$ cycloalkyl, phenyl, 4-7 membered heterocycloalkyl, and 5-6 membered heteroaryl, each of which is optionally substituted by 1, 2, or 3 independently selected $R^{11}$ groups; and each $R^{11}$ is independently selected from $C_{1-3}$ alkyl and $C_{1-3}$ haloalkyl.

In some embodiments:

$R^4$ is H, $C_{1-6}$ alkyl, $C_{1-6}$ haloalkyl, or $OR^{a4}$;

$R^{a4}$ is selected from H, $C_{1-6}$ alkyl, $C_{1-6}$ haloalkyl, and 4-7 membered heterocycloalkyl-$C_{1-4}$ alkyl, wherein said $C_{1-6}$ alkyl, and 4-7 membered heterocycloalkyl-$C_{1-4}$ alkyl are each optionally substituted with 1 or 2 independently selected $R^{4a}$ groups;

each $R^{4a}$ is selected from CN, $OR^9$, $NHR^{d9}$, $OC(=O)R^{b9}$, $OC(=O)NHR^{d9}$, $NHC(=O)R^{b9}$, $NHC(=O)OR^{b9}$, $NHC(=O)NHR^{d9}$, and $NHS(=O)_2R^{b9}$;

each $R^{a9}$ and $R^{d9}$ is independently selected from H and $C_{1-6}$ alkyl optionally substituted with 1, 2, or 3 independently selected $R^{11}$ groups;

each $R^{b9}$ is independently selected from $C_{1-6}$ alkyl and 5-6 membered heteroaryl, each of which is optionally substituted with 1, 2, or 3 independently selected $R^{11}$ groups; and each $R^{11}$ group is independently selected from $C_{1-3}$ alkyl, carboxy-$C_{1-3}$ alkoxy, carboxy, amino, and $C_{1-3}$ haloalkyl.

In some embodiments:

$R^4$ is H, $C_{1-6}$ alkyl, $C_{1-6}$ haloalkyl, or $OR^{a4}$;

$R^{a4}$ is selected from H, $C_{1-6}$ alkyl, $C_{1-6}$ haloalkyl, and 4-7 membered heterocycloalkyl-$C_{1-4}$ alkyl, wherein said $C_{1-6}$ alkyl, and 4-7 membered heterocycloalkyl-$C_{1-4}$ alkyl are each optionally substituted with 1 or 2 independently selected $R^{4a}$ groups;

each $R^{4a}$ is selected from $OR^{a9}$ and $OC(=O)R^{b9}$;

each $R^{a9}$ is independently selected from H and $C_{1-6}$ alkyl;

each $R^{b9}$ is independently selected from 5-6 membered heteroaryl, which is optionally substituted with 1, 2, or 3 independently selected $R^{11}$ groups;

and each $R^{11}$ group is independently selected from $C_{1-6}$ alkyl.

In some embodiments, $R^4$ is H, $C_{1-3}$ alkyl, or $OR^{a4}$, wherein $R^{a4}$ is selected from H, $C_{1-6}$ alkyl, and 4-7 membered heterocycloalkyl-$C_{1-4}$ alkyl, wherein said $C_{1-6}$ alkyl and 4-7 membered heterocycloalkyl-$C_{1-4}$ alkyl are optionally substituted by 1 group selected from CN, amino, OH, $C_{1-3}$ alkyl, $C_{1-3}$ alkoxy, carboxy-$C_{1-3}$ alkoxy-$C_{1-3}$-alkoxy-, carboxy-$C_{1-3}$ alkoxy- $C_{1-3}$ alkoxy-$C_{1-3}$-alkoxy-, OC(=O)$R^{a8}$, C(=O)O$R^{a8}$, OC(=O)NH$R^{d8}$, —NHC(=O)$R^{b8}$, NHC(=O)NH$R^{d8}$, C(=O)OH-$C_{1-6}$ alkyl-, C(=O)OH-$C_{1-6}$ alkoxy-C(=O)— and —NHC(=O)O$R^{b8}$; wherein $R^{a8}$, $R^{b8}$ and $R^{d8}$ are each independently $C_{1-3}$ alkyl, which is optionally substituted by 1 or 2 groups independently selected from carboxy and amino; and $R^{b8}$ is $C_{1-3}$ alkyl or 5-membered heteroaryl, which are each optionally substituted by 1 or 2 groups independently selected from $C_{1-3}$ alkyl, carboxy and amino.

In some embodiments, $R^4$ is selected from H, methyl, OH, methoxy, isopropoxy, hydroxyethoxy, hydroxypropoxy, methoxypropoxy, aminopropoxy, CN-propoxy, N-morpholinylethoxy, N-morpholinylpropoxy, (4-methylpiperazin-l-yl)propoxy, 3-(((carboxymethoxy)carbonyl)amino)propoxy, 3-(3-(carboxymethyl)ureido)propoxy, 3-(2-amino-3-carboxypropanamido)propoxy, 3-(3-carboxypropanamido)propoxy, 3-(((2-carboxyethyl)carbamoyl)oxy)propoxy, 2-(2-(2-carboxyethoxy)ethoxy)ethoxy, 3-((3-carboxypropyl)sulfonamido)propoxy, and OCH$_2$CH$_2$CH$_2$OC(O)pyrazolyl, wherein the pyrazolyl is substituted by 1 or 2 $C_{1-3}$ alkyl groups.

In some embodiments, $R^4$ is —OCH$_2$CH$_2$CH$_2$NH(Asp-Asp-Arg-Asp).

In some embodiments, $R^4$ is selected from H, methyl, OH, methoxy, hydroxypropoxy, N-morpholinylpropoxy, and OCH$_2$CH$_2$CH$_2$OC(O)pyrazolyl, wherein the pyrazolyl is substituted by 1 or 2 methyl groups.

In some embodiments, $R^5$ is H, D, halo, CN, NO$_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, O$R^{a5}$, S$R^{a5}$, C(=O)$R^{b5}$, C(=O)N$R^{c5}R^{d5}$, C(=O)O$R^{a5}$, OC(=O)$R^{b5}$, OC(=O)N$R^{c5}R^{d5}$, N$R^{c5}R^{d5}$, N$R^{c5}$C(=O)$R^{b5}$, N$R^{c5}$C(=O)O$R^{b5}$, N$R^{c5}$C(=O)N$R^{c5}R^{d5}$, N$R^{c5}$S(=O)$_2R^{b5}$, N$R^{c5}$S(=O)$_2$N$R^{c5}R^{d5}$, S(=O)$_2R^{b5}$, or S(=O)$_2$N$R^{c5}R^{d5}$, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted by 1, 2, 3, or 4 independently selected $R^{5a}$ groups.

In some embodiments, $R^5$ is H, D, halo, CN, NO$_2$, $C_{1-6}$ alkyl, $C_{2-6}$ alkenyl, $C_{2-6}$ alkynyl, $C_{1-6}$ haloalkyl, O$R^{a5}$, S$R^{a5}$, C(=O)$R^{b5}$, C(=O)N$R^{c5}R^{d5}$, C(=O)O$R^{a5}$, OC(=O)$R^{b5}$, OC(=O)N$R^{c5}R^{d5}$, N$R^{c5}R^{d5}$, N$R^{c5}$C(=O)$R^{b5}$, N$R^{c5}$C(=O)O$R^{b5}$, N$R^{c5}$C(=O)N$R^{c5}R^{d5}$, N$R^{c5}$S(=O)$_2R^{b5}$, N$R^{c5}$S(=O)$_2$N$R^{c5}R^{d5}$, S(=O)$_2R^{b5}$, or S(=O)$_2$N$R^{c5}R^{d5}$, wherein said $C_{1-6}$ alkyl, $C_{2-6}$ alkenyl, and $C_{2-6}$ alkynyl are each optionally substituted by 1, 2, 3, or 4 independently selected $R^{5a}$ groups.

In some embodiments:
each $R^{a5}$, $R^{c5}$, and $R^{d5}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{5a}$ groups; and each $R^{b5}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{5a}$ groups.

In some embodiments:
each $R^{a5}$, $R^{c5}$, and $R^{d5}$ is independently selected from H, $C_{1-6}$ alkyl, and $C_{1-6}$ haloalkyl, wherein said $C_{1-6}$ alkyl is optionally substituted with 1, 2, 3, or 4 independently selected $R^{5a}$ groups; and each $R^{b5}$ is independently selected from $C_{1-6}$ alkyl and $C_{1-6}$ haloalkyl, wherein said $C_{1-6}$ alkyl is optionally substituted with 1, 2, 3, or 4 independently selected $R^{5a}$ groups.

In some embodiments, $R^5$ is selected from H, halo, CN, $C_{1-4}$ alkyl, or $C_{1-4}$ haloalkyl.

In some embodiments, $R^5$ is H.

In some embodiments, $R^6$ is H, D, halo, CN, NO$_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, O$R^{a6}$, S$R^{a6}$, C(=O)$R^{b6}$, C(=O)N$R^{c6}R^{d6}$, C(=O)O$R^{a6}$, OC(=O)$R^{b6}$, OC(=O)N$R^{c6}R^{d6}$, N$R^{c6}R^{d6}$, N$R^{c6}$C(=O)$R^{b6}$, N$R^{c6}$C(=O)O$R^{b6}$, N$R^{c6}$C(=O)N$R^{c6}R^{d6}$, N$R^{c6}$S(=O)$_2R^{b6}$, N$R^{c6}$S(=O)$_2$N$R^{c6}R^{d6}$, S(=O)$_2R^{b6}$, or S(=O)$_2$N$R^{c6}R^{d6}$, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted by 1, 2, 3, or 4 independently selected $R^{6a}$ groups.

In some embodiments, $R^6$ is H, D, halo, CN, NO$_2$, $C_{1-6}$ alkyl, $C_{2-6}$ alkenyl, $C_{2-6}$ alkynyl, $C_{1-6}$ haloalkyl, O$R^{a6}$, S$R^{a6}$, C(=O)$R^{b6}$, C(=O)N$R^{c6}R^{d6}$, C(=O)O$R^{a6}$, OC(=O)$R^{b6}$, OC(=O)N$R^{c6}R^{d6}$, N$R^{c6}R^{d6}$, N$R^{c6}$C(=O)$R^{b6}$, N$R^{b6}$C(=O)O$R^{b6}$, N$R^{c6}$C(=O)N$R^{c6}R^{d6}$, N$R^{c6}$S(=O)$_2R^{b6}$, N$R^{c6}$S(=O)$_2$N$R^{c6}R^{d6}$, S(=O)$_2R^{b6}$, or S(=O)$_2$N$R^{c6}R^{d6}$, wherein said $C_{1-6}$ alkyl, $C_{2-6}$ alkenyl, $C_{2-6}$ alkynyl are each optionally substituted by 1, 2, 3, or 4 independently selected $R^{6a}$ groups.

In some embodiments, $R^6$ is H, halo, CN, $C_{1-4}$ alkyl, $C_{1-4}$ haloalkyl, carbamyl, and $C_{1-4}$ alkylcarbamyl.

In some embodiments, $R^6$ is H or C(=O)N$R^{c6}R^{d6}$.

In some embodiments, $R^6$ is C(=O)N$R^{c6}R^{d6}$.

In some embodiments, $R^6$ is C(=O)NH$_2$.

In some embodiments:
each $R^{a6}$, $R^{c6}$, and $R^{d6}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{6a}$ groups; and each $R^{b6}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{6a}$ groups.

In some embodiments:
each $R^{a6}$, $R^{c6}$, and $R^{d6}$ is independently selected from H, $C_{1-6}$ alkyl, and $C_{1-6}$ haloalkyl, wherein said $C_{1-6}$ alkyl is optionally substituted with 1, 2, 3, or 4 independently selected $R^{6a}$ groups; and each $R^{b6}$ is independently selected from $C_{1-6}$ alkyl and $C_{1-6}$ haloalkyl, wherein said $C_{1-6}$ alkyl is optionally substituted with 1, 2, 3, or 4 independently selected $R^{6a}$ groups.

In some embodiments, $R^7$ is H, D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a7}$, $SR^{a7}$, $C(=O)R^{b7}$, $C(=O)NR^{c7}R^{d7}$, $C(=O)OR^{a7}$, $OC(=O)R^{b7}$, $OC(=O)NR^{c7}R^{d7}$, $NR^{c7}R^{d7}$, $NR^{c7}C(=O)R^{b7}$, $NR^{c7}C(=O)OR^{b7}$, $NR^{c7}C(=O)NR^{c7}R^{d7}$, $NR^{c7}S(=O)_2R^{b7}$, $NR^{c7}S(=O)_2NR^{c7}R^{d7}$, $S(=O)_2R^{b7}$, or $S(=O)_2NR^{c7}R^{d7}$, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl are each optionally substituted by 1, 2, 3, or 4 independently selected $R^{7a}$ groups.

In some embodiments, $R^7$ is H, D, halo, CN, $NO_2$, $C_{1-6}$ alkyl, $C_{2-6}$ alkenyl, $C_{2-6}$ alkynyl, $C_{1-6}$ haloalkyl, $OR^{a7}$, $SR^{a7}$, $C(=O)R^{b7}$, $C(=O)NR^{c7}R^{d7}$, $C(=O)OR^{a7}$, $OC(=O)R^{b7}$, $OC(=O)NR^{c7}R^{d7}$, $NR^{c7}R^{d7}$, $NR^{c7}C(=O)R^{b7}$, $NR^{c7}C(=O)OR^{b7}$, $NR^{c7}C(=O)NR^{c7}R^{d7}$, $NR^{c7}S(=O)_2R^{b7}$, $NR^{c7}S(=O)_2NR^{c7}R^{d7}$, $S(=O)_2R^{b7}$, or $S(=O)_2NR^{c7}R^{d7}$, wherein said $C_{1-6}$ alkyl, $C_{2-6}$ alkenyl, and $C_{2-6}$ alkynyl are each optionally substituted by 1, 2, 3, or 4 independently selected $R^{7a}$ groups.

In some embodiments, $R^7$ is selected from H, halo, CN, $C_{1-4}$ alkyl, or $C_{1-4}$ haloalkyl.

In some embodiments, $R^7$ is H.

In some embodiments:
each $R^{a7}$, $R^{c7}$, and $R^{d7}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{7a}$ groups; and each $R^{b7}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{7a}$ groups.

In some embodiments:
each $R^{a7}$, $R^{c7}$, and $R^{d7}$ is independently selected from H, $C_{1-6}$ alkyl, and $C_{1-6}$ haloalkyl, wherein said $C_{1-6}$ alkyl is optionally substituted with 1, 2, 3, or 4 independently selected $R^{7a}$ groups; and each $R^{b7}$ is independently selected from $C_{1-6}$ alkyl and $C_{1-6}$ haloalkyl, wherein said $C_{1-6}$ alkyl is optionally substituted with 1, 2, 3, or 4 independently selected $R^{7a}$ groups.

In some embodiments, each $R^{2a}$, $R^{4a}$, $R^{5a}$, $R^{6a}$, and $R^{7a}$ are independently selected from H, halo, CN, $NO_2$, $C_{1-6}$ alkyl, $C_{2-6}$ alkenyl, $C_{3-7}$ cycloalkyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a9}$, $SR^{a9}$, $C(=O)R^{b9}$, $C(=O)NR^{c9}R^{d9}$, $C(=O)OR^{a9}$, $OC(=O)R^{b9}$, $OC(=O)NR^{c9}R^{d9}$, $NR^{c9}R^{d9}$, $NR^{c9}C(=O)R^{b9}$, $NR^{c9}C(=O)OR^{b9}$, $NR^{c9}C(=O)NR^{c9}R^{d9}$, $NR^{c9}S(=O)_2R^{b9}$, $NR^{c9}S(=O)_2NR^{c9}R^{d9}$, $S(=O)_2R^{b9}$, and $S(=O)_2NR^{c9}R^{d9}$, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted by 1, 2, 3, or 4 independently selected $R^{11}$ groups.

In some embodiments, each $R^{2a}$, $R^{4a}$, $R^{5a}$, $R^{6a}$, and $R^{7a}$ are independently selected from H, halo, CN, $NO_2$, $C_{1-6}$ alkyl, $C_{2-6}$ alkenyl, $C_{2-6}$ alkynyl, $C_{1-6}$ haloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a9}$, $SR^{a9}$, $C(=O)R^{b9}$, $C(=O)NR^{c9}R^{d9}$, $C(=O)OR^{a9}$, $OC(=O)R^{b9}$, $OC(=O)NR^{c9}R^{d9}$, $NR^{c9}R^{d9}$, $NR^{c9}C(=O)R^{b9}$, $NR^{c9}C(=O)OR^{b9}$, $NR^{c9}C(=O)NR^{c9}R^{d9}$, $NR^{c9}S(=O)_2R^{b9}$, $NR^{c9}S(=O)_2NR^{c9}R^{d9}$, $S(=O)_2R^{b9}$, and $S(=O)_2NR^{c9}R^{d9}$, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted by 1, 2, 3, or 4 independently selected $R^{11}$ groups.

In some embodiments, each $R^{2a}$, $R^{4a}$, $R^{5a}$, $R^{6a}$, and $R^{7a}$ are independently selected from H, halo, CN, $NO_2$, $C_{1-6}$ alkyl, $C_{2-6}$ alkenyl, $C_{2-6}$ alkynyl, $C_{1-6}$ haloalkyl, $OR^{a9}$, $SR^{a9}$, $C(=O)R^{b9}$, $C(=O)NR^{c9}R^{d9}$, $C(=O)OR^{a9}$, $OC(=O)R^{b9}$, $OC(=O)NR^{c9}R^{d9}$, $NR^{c9}R^{d9}$, $NR^{c9}C(=O)R^{b9}$, $NR^{c9}C(=O)OR^{b9}$, $NR^{c9}C(=O)NR^{c9}R^{d9}$, $C(=NR^e)R^{b9}$, $NR^{c9}S(=O)_2R^{b9}$, $NR^{c9}S(=O)_2NR^{c9}R^{d9}$, $S(=O)_2R^{b9}$, and $S(=O)_2NR^{c9}R^{d9}$, wherein said $C_{1-6}$ alkyl, $C_{2-6}$ alkenyl, and $C_{2-6}$ alkynyl, are each optionally substituted by 1, 2, 3, or 4 independently selected $R^{11}$ groups.

In some embodiments, each $R^{a9}$, $R^{c9}$, and $R^{d9}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl is optionally substituted with 1, 2, 3, or 4 independently selected $R^{11}$ groups; and each $R^{b9}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, or 3 independently selected $R^{11}$ groups.

In some embodiments, each $R^{a9}$, $R^{c9}$, and $R^{d9}$ is independently selected from H, $C_{1-6}$ alkyl, and $C_{1-6}$ haloalkyl, wherein said $C_{1-6}$ alkyl is optionally substituted with 1, 2, 3, or 4 independently selected $R^{11}$ groups; and each $R^{b9}$ is independently selected from $C_{1-6}$ alkyl and $C_{1-6}$ haloalkyl, wherein said $C_{1-6}$ alkyl are each optionally substituted with 1, 2, or 3 independently selected $R^{11}$ groups.

In some embodiments, each $R^{11}$ is independently selected from OH, $NO_2$, CN, halo, $C_{1-6}$ alkyl, $C_{2-6}$ alkenyl, $C_{2-6}$ alkynyl, $C_{1-6}$ haloalkyl, cyano-$C_{1-6}$ alkyl, HO-$C_{1-6}$ alkyl, $C_{1-6}$ alkoxy-$C_{1-6}$ alkyl, $C_{3-7}$ cycloalkyl, $C_{1-6}$ alkoxy, $C_{1-6}$ haloalkoxy, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-4}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

In some embodiments, each $R^{11}$ group is independently selected from $C_{1-3}$ alkyl, carboxy-$C_{1-3}$ alkoxy, carboxy, amino, and $C_{1-3}$ haloalkyl.

In some embodiments, each $R^{2a}$, $R^{4a}$, $R^{5a}$, $R^{6a}$, and $R^{7a}$ are independently selected from H, halo, CN, OH, $C_{1-6}$ alkyl, $C_{1-6}$ haloalkyl, $C_{1-6}$ alkoxy, $C_{1-6}$ haloalkoxy, amino, $C_{1-6}$ alkylamino, and di($C_{1-6}$ alkyl)amino.

In some embodiments, $R^5$, $R^6$, and $R^7$ are each independently selected from H, halo, OH, $NO_2$, CN, $C_{1-6}$ alkyl, $C_{2-6}$ alkenyl, $C_{2-6}$ alkynyl, $C_{1-6}$ haloalkyl, cyano-$C_{1-6}$ alkyl, HO-$C_{1-6}$ alkyl, $C_{1-6}$ alkoxy-$C_{1-6}$ alkyl, $C_{3-7}$ cycloalkyl, $C_{1-6}$ alkoxy, $C_{1-6}$ haloalkoxy, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-4}$ alkoxycarbonyl, $C_{1-6}$ alkylcarbonylamino, $C_{1-6}$ alkylsulfonylamino, aminosulfonyl, 1-6 alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

In some embodiments, $R^5$, $R^6$, and $R^7$ are each independently selected from H, halo, CN, OH, $C_{1-6}$ alkyl, $C_{1-6}$ haloalkyl, $C_{1-6}$ alkoxy, $C_{1-6}$ haloalkoxy, amino, $C_{1-6}$ alkylamino, di($C_{1-6}$ alkyl)amino, carbamyl, $C_{1-6}$ alkylcarbamyl, and di($C_{1-6}$ alkyl)carbamyl.

In some embodiments, $R^5$, $R^6$, and $R^7$ are each independently selected from H, $C_{1-6}$ alkyl, $C_{1-6}$ haloalkyl, $C_{1-6}$ alkoxy, carbamyl, $C_{1-6}$ alkylcarbamyl, and di($C_{1-6}$ alkyl) carbamyl.

In some embodiments, Ring moiety A is 5-10 membered heteroaryl, which is optionally substituted by 1, 2, 3, or 4 independently selected $R^A$ groups.

In some embodiments, Ring moiety A is 5-6 membered heteroaryl, which is optionally substituted by 1, 2, 3, or 4 independently selected $R^A$ groups.

In some embodiments, Ring moiety A is 5 membered heteroaryl, which is optionally substituted by 1, 2, 3, or 4 independently selected $R^A$ groups.

In some embodiments, Ring moiety A is a pyrazole ring, which is optionally substituted by 1, 2, or 3 independently selected $R^A$ groups.

In some embodiments, Ring moiety A is selected from 1-ethyl-3-methyl-1H-pyrazol-5-yl, 3-methyl-1-propyl-1H-pyrazol-5-yl, 1-ethyl-1H-pyrazol-5-yl, 1-ethyl-3-(trifluoromethyl)-1H-pyrazol-5-yl, 3-ethyl-1-methyl-1H-pyrazol-4-yl, and 1,3-dimethyl-1H-pyrazol-5-yl.

In some embodiments, each $R^A$ is independently selected from halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a1}$, $SR^{a1}$, $C(=O)R^{b1}$, $C(=O)NR^{c1}R^{d1}$, $C(=O)OR^{a1}$, $OC(=O)R^{b1}$, $OC(=O)NR^{c1}R^{d1}$, $NR^{c1}R^{d1}$, $NR^{c1}C(=O)R^{b1}$, $NR^{c1}C(=O)OR^{b1}$, $NR^{c1}C(=O)NR^{c1}R^{d1}$, $NR^{c1}S(=O)_2R^{b2}$, $NR^{c1}S(=O)_2NR^{c1}R^{d1}$, $S(=O)_2R^{b1}$, and $S(=O)_2NR^{c1}R^{d1}$, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted by 1, 2, 3, or 4 independently selected $R^{A1}$ groups.

In some embodiments, each $R^A$ is independently selected from halo, CN, $NO_2$, $C_{1-6}$ alkyl, $C_{2-6}$ alkenyl, $C_{2-6}$ alkynyl, $C_{1-6}$ haloalkyl, $C_{3-5}$ cycloalkyl, $OR^{a1}$, $SR^{a1}$, $C(=O)R^{b1}$, $C(=O)NR^{c1}R^{d1}$, $C(=O)OR^{a1}$, $OC(=O)R^{b1}$, $OC(=O)NR^{c1}R^{d1}$, $NR^{c1}R^{d1}$, $NR^{c1}C(=O)R^{b1}$, $NR^{c1}C(=O)OR^{b1}$, $NR^{c1}C(=O)NR^{c1}R^{d1}$, $C(=NR^e)R^{b1}$, $C(=NR^e)NR^{c1}R^{d1}$, $NR^{c1}C(=NR^e)NR^{c1}R^{d1}$, $NR^{c1}S(=O)_2R^{b2}$, $NR^{c1}S(=O)_2NR^{c1}R^{d1}$, $S(=O)_2R^{b1}$, and $S(=O)_2NR^{c1}R^{d1}$, wherein said $C_{1-6}$ alkyl, $C_{2-6}$ alkenyl, and $C_{2-6}$ alkynyl are each optionally substituted by 1, 2, 3, or 4 independently selected $R^{A1}$ groups.

In some embodiments, each $R^A$ is independently selected from halo, CN, $C_{1-6}$ alkyl, and $C_{1-6}$ haloalkyl.

In some embodiments, each $R^A$ is independently $C_{1-6}$ alkyl or $C_{1-6}$ haloalkyl.

In some embodiments, each $R^A$ is independently $C_{1-6}$ alkyl.

In some embodiments, Ring moiety B is selected from 1-ethyl-3-methyl-1H-pyrazol-5-yl, 3-methyl-1-propyl-1H-pyrazol-5-yl, 1-ethyl-1H-pyrazol-5-yl, 1-ethyl-3-(trifluoromethyl)-1H-pyrazol-5-yl, 3-ethyl-1-methyl-1H-pyrazol-4-yl, and 1,3-dimethyl-1H-pyrazol-5-yl.

In some embodiments, Ring moiety B is 1-ethyl-3-methyl-1H-pyrazol-5-yl.

In some embodiments:
each $R^{a1}$, $R^{c1}$, and $R^{d1}$ is independently selected from H, $C_{1-6}$ alkyl, $C_{1-6}$ haloalkyl, $C_{2-6}$ alkenyl, and $C_{2-6}$ alkynyl, wherein said $C_{1-6}$ alkyl, $C_{2-6}$ alkenyl, and $C_{2-6}$ alkynyl are each optionally substituted with 1, 2, 3, or 4 independently selected $R^{A1}$ groups; and each $R^{B1}$ is independently selected from $C_{1-6}$ alkyl, $C_{1-6}$ haloalkyl, $C_{2-6}$ alkenyl, and $C_{2-6}$ alkynyl, wherein said $C_{1-6}$ alkyl, $C_{2-6}$ alkenyl, and $C_{2-6}$ alkynyl are each optionally substituted with 1, 2, or 3 independently selected $R^{A1}$ groups.

In some embodiments, Ring moiety B is 5-10 membered heteroaryl, which is optionally substituted by 1, 2, 3, or 4 independently selected $R^B$ groups.

In some embodiments, Ring moiety B is 5-6 membered heteroaryl, which is optionally substituted by 1, 2, 3, or 4 independently selected $R^B$ groups.

In some embodiments, Ring moiety B is 5 membered heteroaryl, which is optionally substituted by 1, 2, 3, or 4 independently selected $R^B$ groups.

In some embodiments, Ring moiety B is a pyrazole ring, which is optionally substituted by 1, 2, or 3 independently selected $R^B$ groups.

In some embodiments, each $R^B$ is independently selected from halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a2}$, $SR^{a2}$, $C(=O)R^{b2}$, $C(=O)NR^{c2}R^{d2}$, $C(=O)OR^{a2}$, $OC(=O)R^{b2}$, $OC(=O)NR^{c2}R^{d2}$, $NR^{c2}R^{d2}$, $NR^{c2}C(=O)R^{b2}$, $NR^{c2}C(=O)OR^{b2}$, $NR^{c2}C(=O)NR^{c2}R^{d2}$, $NR^{c2}S(=O)_2R^{b2}$, $NR^{c2}S(=O)_2NR^{c2}R^{d2}$, $S(=O)_2R^{b2}$, and $S(=O)_2NR^{c2}R^{d2}$, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted by 1, 2, 3, or 4 independently selected $R^{B1}$ groups.

In some embodiments, each $R^B$ is independently selected from halo, CN, $NO_2$, $C_{1-6}$ alkyl, $C_{2-6}$ alkenyl, $C_{2-6}$ alkynyl, $C_{1-6}$ haloalkyl, $OR^{a2}$, $SR^{a2}$, $C(=O)R^{b2}$, $C(=O)NR^{c2}R^{d2}$, $C(=O)OR^{a2}$, $OC(=O)R^{b2}$, $OC(=O)NR^{c2}R^{d2}$, $NR^{c2}R^{d2}$, $NR^{c2}C(=O)R^{b2}$, $NR^{c2}C(=O)OR^{b2}$, $NR^{c2}C(=O)NR^{c2}R^{d2}$, $NR^{c2}S(=O)_2R^{b2}$, $NR^{c2}S(=O)_2NR^{c2}R^{d2}$, $S(=O)_2R^{b2}$, and $S(=O)_2NR^{c2}R^{d2}$, wherein said $C_{1-6}$ alkyl, $C_{2-6}$ alkenyl, and $C_{2-6}$ alkynyl are each optionally substituted by 1, 2, 3, or 4 independently selected $R^{B1}$ groups.

In some embodiments, each $R^B$ is independently selected from halo, CN, $C_{1-6}$ alkyl, and $C_{1-6}$ haloalkyl.

In some embodiments, each $R^B$ is independently $C_{1-6}$ alkyl or $C_{1-6}$ haloalkyl.

In some embodiments, each $R^B$ is independently $C_{1-6}$ alkyl.

In some embodiments:

each $R^{a2}$, $R^{c2}$, and $R^{d2}$ is independently selected from H, $C_{1-6}$ alkyl, $C_{1-6}$ haloalkyl, $C_{2-6}$ alkenyl, and $C_{2-6}$ alkynyl, wherein said $C_{1-6}$ alkyl, $C_{2-6}$ alkenyl, and $C_{2-6}$ alkynyl are each optionally substituted with 1, 2, or 3 independently selected $R^{B1}$ groups; and each $R^{b2}$ is independently selected from $C_{1-6}$ alkyl, $C_{1-6}$ haloalkyl, $C_{2-6}$ alkenyl, and $C_{2-6}$ alkynyl, wherein said $C_{1-6}$ alkyl, $C_{2-6}$ alkenyl, and $C_{2-6}$ alkynyl are each optionally substituted with 1, 2, or 3 independently selected $R^{B1}$ groups.

In some embodiments, each $R^{A1}$ and $R^{B1}$ is independently selected from H, halo, CN, $NO_2$, $C_{1-6}$ alkyl, $C_{2-6}$ alkenyl, $C_{2-6}$ alkynyl, $C_{1-6}$ haloalkyl, $OR^{a12}$, $SR^{a12}$, $C(=O)R^{b12}$, $C(=O)NR^{c12}R^{d12}$, $C(=O)OR^{a12}$, $OC(=O)R^{b12}$, $OC(=O)NR^{c12}R^{d12}$, $NR^{c12}R^{d12}$, $NR^{c12}C(=O)R^{b12}$, $NR^{c12}C(=O)OR^{b12}$, $NR^{c12}C(=O)NR^{c12}R^{d12}$, $NR^{c12}S(=O)_2R^{b12}$, $NR^{c12}S(=O)_2NR^{c12}R^{d12}$, $S(=O)_2R^{b12}$, and $S(=O)_2NR^{c12}R^{d12}$, wherein said $C_{1-6}$ alkyl, $C_{2-6}$ alkenyl, and $C_{2-6}$ alkynyl are each optionally substituted by 1, 2, 3, or 4 independently selected $R^G$ groups.

In some embodiments:

each $R^{a12}$, $R^{c12}$, and $R^{d12}$ is independently selected from H, $C_{1-6}$ alkyl, and $C_{1-6}$ haloalkyl, wherein said $C_{1-6}$ alkyl is optionally substituted with 1, 2, 3, or 4 independently selected $R^G$ groups; and each $R^{b12}$ is independently selected from $C_{1-6}$ alkyl and $C_{1-6}$ haloalkyl, wherein said $C_{1-6}$ alkyl is optionally substituted with 1, 2, or 3 independently selected $R^G$ groups.

In some embodiments, each $R^{A1}$ and $R^{B1}$ is independently selected from H, halo, CN, $C_{1-6}$ alkyl, and $C_{1-6}$ haloalkyl.

In some embodiments, $L^1$, $L^2$, and $L^3$ are each independently selected from -R-R-, -R-R-R-, -Cy-, -R-Cy-, -Cy-R-, and -R-Cy-R-.

In some embodiments, $L^1$, $L^2$, and $L^3$ are each independently selected from -R-R-, -R-R-R-, -Cy-, -R-Cy-, and -Cy-R-.

In some embodiments, $L^1$, $L^2$, and $L^3$ are each independently selected from -R-R- and -R-R-R-.

In some embodiments, $L^1$ is -R-R-R-.

In some embodiments, $L^1$ is -R-R-.

In some embodiments, $L^2$ is -R-R-R-.

In some embodiments, $L^2$ is -R-R-.

In some embodiments, $L^3$ is -R-R-R-.

In some embodiments, $L^3$ is -R-R-.

In some embodiments, R is M, $C_{1-6}$ alkylene, $C_{2-6}$ alkenylene, $C_{2-6}$ alkynylene, $C_{1-6}$ alkylene-M, or M-$C_{1-6}$ alkylene.

In some embodiments, each R is independently M, $C_{1-6}$ alkylene, $C_{2-6}$ alkenylene, or $C_{2-6}$ alkynylene.

In some embodiments, each R is independently M, $C_{1-3}$ alkylene, $C_{2-3}$ alkenylene, or $C_{2-3}$ alkynylene.

In some embodiments, each R is independently $C_{1-6}$ alkylene or $C_{2-6}$ alkenylene.

In some embodiments, each R is independently $C_{1-3}$ alkylene or $C_{2-3}$ alkenylene.

In some embodiments, each M is independently —O—, —C(O)—, —C(O)$NR^L$—, —OC(O)$NR^L$—, —$NR^L$—, —$NR^L$C(O)—, —$NR^L$C(O)O—, —$NR^L$S(O)_2—, —S(O)_2—, or —S(O)_2$NR^L$—, provided that when M is attached to a nitrogen atom, then M is selected from —C(O)—, —C(O)$NR^L$—, —C(O)O—, —S(O)_2—, or —S(O)_2$NR^L$—; and each $R^L$ is independently selected from H and $C_{1-3}$ alkyl.

In some embodiments, $L^1$ is —$CH_2$—CH=CH—$CH_2$—.

In some embodiments, $L^2$ is —$CH_2$—CH=CH—$CH_2$—.

In some embodiments, $L^3$ is —$CH_2$—CH=CH—$CH_2$—.

In some embodiments:

U is N or $CR^U$;

V is N or $CR^V$;

W is N or $CR^W$;

Q is N or $CR^Q$;

wherein U=V—W=Q is selected from $CR^U$=$CR^V$—$CR^W$=$CR^Q$, N=$CR^V$—$CR^W$=$CR^Q$, $CR^U$=N—$CR^W$=$CR^Q$, $CR^U$=$CR^V$—N=$CR^Q$, $CR^U$=$CR^V$—$CR^W$=N, N=N—$CR^W$=$CR^Q$, $CR^U$=N—N=$CR^Q$, $CR^U$=$CR^V$—N=N, N=$CR^V$—$CR^W$=N, N=$CR^V$—N=$CR^Q$, $CR^U$=N—$CR^W$=N, N=N—$CR^W$=N, and N=$CR^V$—N=N;

$R^U$, $R^V$, $R^W$, and $R^Q$ are each independently selected from H, D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl- $C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, OR$^a$, SR$^a$, C(=O)R$^b$, C(=O)NR$^c$R$^d$, C(=O)OR$^a$, OC(=O)R$^b$, OC(=O)NR$^c$R$^d$, NR$^c$R$^d$, NR$^c$C(=O)R$^b$, NR$^c$C(=O)OR$^b$, NR$^c$C(=O)NR$^c$R$^d$, C(=NR$^e$)R$^b$, C(=NR$^e$)NR$^c$R$^d$, NR$^c$C(=NR$^e$)NR$^c$R$^d$, NR$^c$S(=O)$_2$R$^b$, NR$^c$S(=O)$_2$NR$^c$R$^d$, S(=O)$_2$R$^b$, and S(=O)$_2$NR$^c$R$^d$, wherein said $C_{1-6}$ alkyl, $C_{2-6}$ alkenyl, $C_{2-6}$ alkynyl, $C_{1-6}$ haloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted by 1, 2, 3, or 4 independently selected R$^8$ groups;

each R$^8$ is independently selected from OH, NO$_2$, CN, halo, $C_{1-3}$ alkyl, $C_{2-3}$ alkenyl, $C_{2-3}$ alkynyl, $C_{1-3}$ haloalkyl, cyano-$C_{1-3}$ alkyl, HO-$C_{1-3}$ alkyl, $C_{1-3}$ alkoxy-$C_{1-3}$ alkyl, $C_{3-7}$ cycloalkyl, $C_{1-3}$ alkoxy, $C_{1-3}$ haloalkoxy, amino, $C_{1-3}$ alkylamino, di($C_{1-3}$ alkyl)amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl)carbamyl, carboxy, $C_{1-3}$ alkylcarbonyl, $C_{1-4}$ alkoxycarbonyl, $C_{1-3}$ alkylcarbonylamino, $C_{1-3}$ alkylsulfonylamino, aminosulfonyl, $C_{1-3}$ alkylaminosulfonyl, di($C_{1-3}$ alkyl)aminosulfonyl, aminosulfonylamino, $C_{1-3}$ alkylaminosulfonylamino, di($C_{1-3}$ alkyl)aminosulfonylamino, aminocarbonylamino, $C_{1-3}$ alkylaminocarbonylamino, and di($C_{1-3}$ alkyl)aminocarbonylamino;

each R$^a$, R$^c$, and R$^d$ is independently selected from H, $C_{1-6}$ alkyl, $C_{1-6}$ haloalkyl, $C_{2-6}$ alkenyl, and $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected R$^{10}$ groups;

each R$^b$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, or 3 independently selected R$^{10}$ groups;

each R$^{10}$ is independently selected from OH, NO$_2$, CN, halo, $C_{1-3}$ alkyl, $C_{2-3}$ alkenyl, $C_{2-3}$ alkynyl, $C_{1-3}$ haloalkyl, cyano-$C_{1-3}$ alkyl, HO-$C_{1-3}$ alkyl, $C_{1-3}$ alkoxy-$C_{1-3}$ alkyl, $C_{3-7}$ cycloalkyl, $C_{1-3}$ alkoxy, $C_{1-3}$ haloalkoxy, amino, $C_{1-3}$ alkylamino, di($C_{1-3}$ alkyl)amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl)carbamyl, carboxy, $C_{1-3}$ alkylcarbonyl, $C_{1-4}$ alkoxycarbonyl, $C_{1-3}$ alkylcarbonylamino, $C_{1-3}$ alkylsulfonylamino, aminosulfonyl, $C_{1-3}$ alkylaminosulfonyl, di($C_{1-3}$ alkyl)aminosulfonyl, aminosulfonylamino, $C_{1-3}$ alkylaminosulfonylamino, di($C_{1-3}$ alkyl)aminosulfonylamino, aminocarbonylamino, $C_{1-3}$ alkylaminocarbonylamino, and di($C_{1-3}$ alkyl)aminocarbonylamino;

X is N or CR$^X$;
Y is N or CR$^Y$;
Z is N or CR$^Z$;

wherein i) X, Y and Z are CR$^X$, CR$^Y$, and CR$^Z$ respectively, or ii) only one of X, Y and Z is N, or iii) only two of X, Y and Z are N;

R$^X$, R$^Y$, and R$^Z$ are each independently selected from H, D, halo, CN, NO$_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, OR$^{a0}$, SR$^{a0}$, C(=O)R$^{b0}$, C(=O)NR$^{c0}$R$^{d0}$, C(=O)OR$^{a0}$, OC(=O)R$^{b0}$, OC(=O)NR$^{c0}$R$^{d0}$, NR$^{c0}$R$^{d0}$, NR$^{c0}$C(=O)R$^{b0}$, NR$^{c0}$C(=O)OR$^{b0}$, NR$^{c0}$C(=O)NR$^{c0}$R$^{d0}$, NR$^{c0}$S(=O)$_2$R$^{b0}$, NR$^{c0}$S(=O)$_2$NR$^{c0}$R$^{d0}$, S(=O)$_2$R$^{b0}$, and S(=O)$_2$NR$^{c0}$R$^{d0}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted by 1, 2, 3, or 4 independently selected R$^G$ groups;

each R$^{a0}$, R$^{c0}$, and R$^{d0}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected R$^G$ groups;

each R$^{b0}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl are each optionally substituted with 1, 2, or 3 independently selected R$^G$ groups;

R$^1$ is H, $C_{1-6}$ alkyl, or $C_{1-6}$ haloalkyl;
R$^2$ is H, $C_{1-6}$ alkyl, or $C_{1-6}$ haloalkyl;
R$^3$ is H, $C_{1-6}$ alkyl, or $C_{1-6}$ haloalkyl;
R$^4$ is H, D, halo, CN, NO$_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, OR$^{a4}$, SR$^{a4}$, C(=O)R$^{b4}$, C(=O)NR$^{c4}$R$^{d4}$, C(=O)OR$^{a4}$, OC(=O)R$^{b4}$, OC(=O)NR$^{c4}$R$^{d4}$, NR$^{c4}$R$^{d4}$, NR$^{c4}$C(=O)R$^{b4}$, NR$^{c4}$C(=O)OR$^{b4}$, NR$^{c4}$C(=O)NR$^{c4}$R$^{d4}$, NR$^{c4}$S(=O)$_2$R$^{b4}$, NR$^{c4}$S(=O)$_2$NR$^{c4}$R$^{d4}$, S(=O)$_2$R$^{b4}$, or S(=O)$_2$NR$^{c4}$R$^{d4}$, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted by 1, 2, 3, or 4 independently selected R$^{4a}$ groups;

each R$^{a4}$, R$^{c4}$, and R$^{d4}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl- $C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{4a}$ groups;

each $R^{b4}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{4a}$ groups;

$R^5$ is H, D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a5}$, $SR^{a5}$, $C(=O)R^{b5}$, $C(=O)NR^{c5}R^{d5}$, $C(=O)OR^{a5}$, $OC(=O)R^{b5}$, $OC(=O)NR^{c5}R^{d5}$, $NR^{c5}R^{d5}$, $NR^{c5}C(=O)R^{b5}$, $NR^{c5}C(=O)OR^{b5}$, $NR^{c5}C(=O)NR^{c5}R^{d5}$, $NR^{c5}S(=O)_2R^{b5}$, $NR^{c5}S(=O)_2NR^{c5}R^{d5}$, $S(=O)_2R^{b5}$, or $S(=O)_2NR^{c5}R^{d5}$, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted by 1, 2, 3, or 4 independently selected $R^{5a}$ groups;

each $R^{a5}$, $R^{c5}$, and $R^{d5}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{5a}$ groups;

each $R^{b5}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{5a}$ groups;

$R^6$ is H, D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a6}$, $SR^{a6}$, $C(=O)R^{b6}$, $C(=O)NR^{c6}R^{d6}$, $C(=O)OR^{a6}$, $OC(=O)R^{b6}$, $OC(=O)NR^{c6}R^{d6}$, $NR^{c6}R^{d6}$, $NR^{c6}C(=O)R^{b6}$, $NR^{b6}C(=O)OR^{b6}$, $NR^{c6}C(=O)NR^{c6}R^{d6}$, $NR^{c6}S(=O)_2R^{b6}$, $NR^{c6}S(=O)_2NR^{c6}R^{d6}$, $S(=O)_2R^{b6}$, or $S(=O)_2NR^{c6}R^{d6}$, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted by 1, 2, 3, or 4 independently selected $R^{6a}$ groups;

each $R^{a6}$, $R^{c6}$, and $R^{d6}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{6a}$ groups;

each $R^{b6}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{6a}$ groups;

$R^7$ is H, D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a7}$, $SR^{a7}$, $C(=O)R^{b7}$, $C(=O)NR^{c7}R^{d7}$, $C(=O)OR^{a7}$, $OC(=O)R^{b7}$, $OC(=O)NR^{c7}R^{d7}$, $NR^{c7}R^{d7}$, $NR^{c7}C(=O)R^{b7}$, $NR^{c7}C(=O)OR^{b7}$, $NR^{c7}C(=O)NR^{c7}R^{d7}$, $NR^{c7}S(=O)_2R^{b7}$, $NR^{c7}S(=O)_2NR^{c7}R^{d7}$, $S(=O)_2R^{b7}$, or $S(=O)_2NR^{c7}R^{d7}$, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl are each optionally substituted by 1, 2, 3, or 4 independently selected $R^{7a}$ groups;

each $R^{a7}$, $R^{c7}$, and $R^{d7}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{7a}$ groups;

each $R^{b7}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{7a}$ groups;

$R^{4a}$, $R^{5a}$, $R^{6a}$, and $R^{7a}$ are independently selected from H, halo, CN, $NO_2$, $C_{1-6}$ alkyl, $C_{2-6}$ alkenyl, $C_{2-6}$ alkynyl, $C_{1-6}$ haloalkyl, $OR^{a9}$, $SR^{a9}$, $C(=O)R^{b9}$, $C(=O)NR^{c9}R^{d9}$, $C(=O)OR^{a9}$, $OC(=O)R^{b9}$, $OC(=O)NR^{c9}R^{d9}$, $NR^{c9}R^{d9}$, $NR^{c9}C(=O)R^{b9}$, $NR^{c9}C(=O)OR^{b9}$, $NR^{c9}C(=O)NR^{c9}R^{d9}$, $C(=NR^e)R^{b9}$, $NR^{c9}S(=O)_2R^{b9}$, $NR^{c9}S(=O)_2NR^{c9}R^{d9}$, $S(=O)_2R^{b9}$, and $S(=O)_2NR^{c9}R^{d9}$, wherein said $C_{1-6}$ alkyl, $C_{2-6}$ alkenyl, and $C_{2-6}$ alkynyl, are each optionally substituted by 1, 2, 3, or 4 independently selected $R^{11}$ groups;

each $R^{a9}$, $R^{c9}$, and $R^{d9}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl is optionally substituted with 1, 2, 3, or 4 independently selected $R^{11}$ groups;

each $R^{b9}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, or 3 independently selected $R^{11}$ groups;

each $R^{11}$ is independently selected from OH, $NO_2$, CN, halo, $C_{1-6}$ alkyl, $C_{2-6}$ alkenyl, $C_{2-6}$ alkynyl, $C_{1-6}$ haloalkyl, cyano-$C_{1-6}$ alkyl, HO-$C_{1-6}$ alkyl, $C_{1-6}$ alkoxy-$C_{1-6}$ alkyl, $C_{3-7}$ cycloalkyl, $C_{1-6}$ alkoxy, $C_{1-6}$ haloalkoxy, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-4}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

Ring moiety A is selected from $C_{3-10}$ cycloalkyl, $C_{6-10}$ aryl, 4-10 membered heterocycloalkyl, and 5-10 membered heteroaryl, each of which is optionally substituted by 1, 2, 3, or 4 independently selected $R^A$ groups;

Ring moiety B is selected from $C_{3-10}$ cycloalkyl, $C_{6-10}$ aryl, 4-10 membered heterocycloalkyl, and 5-10 membered heteroaryl, each of which is optionally substituted by 1, 2, 3, or 4 independently selected $R^B$ groups;

each $R^A$ is independently selected from halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a1}$, $SR^{a1}$, $C(=O)R^{b1}$, $C(=O)NR^{c1}R^{d1}$, $C(=O)OR^{a1}$, $OC(=O)R^{b1}$, $OC(=O)NR^{c1}R^{d1}$, $NR^{c1}R^{d1}$, $NR^{c1}C(=O)R^{b1}$, $NR^{c1}C(=O)OR^{b1}$, $NR^{c1}C(=O)NR^{c1}R^{d1}$, $NR^{c1}S(=O)_2R^{b2}$, $NR^{c1}S(=O)_2NR^{c1}R^{d1}$, $S(=O)_2R^{b1}$, and $S(=O)_2NR^{c1}R^{d1}$, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted by 1, 2, 3, or 4 independently selected $R^{A1}$ groups;

each $R^B$ is independently selected from halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a2}$, $SR^{a2}$, $C(=O)R^{b2}$, $C(=O)NR^{c2}R^{d2}$, $C(=O)OR^{a2}$, $OC(=O)R^{b2}$, $OC(=O)NR^{c2}R^{d2}$, $NR^{c\,2}R^{d2}$, $NR^{c2}C(=O)R^{b2}$, $NR^{c2}C(=O)OR^{b2}$, $NR^{c2}C(=O)NR^{c2}R^{d2}$, $NR^{c2}S(=O)_2R^{b2}$, $NR^{c2}S(=O)_2NR^{c2}R^{d2}$, and $S(=O)_2NR^{c2}R^{d2}$, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted by 1, 2, 3, or 4 independently selected $R^{B1}$ groups;

each $R^{A1}$ and $R^{B1}$ is independently selected from H, halo, CN, $NO_2$, $C_{1-6}$ alkyl, $C_{2-6}$ alkenyl, $C_{2-6}$ alkynyl, $C_{1-6}$ haloalkyl, $OR^{a12}$, $SR^{a12}$, $C(=O)R^{b12}$, $C(=O)NR^{c12}R^{d12}$, $C(=O)OR^{a12}$, $OC(=O)R^{b12}$, $OC(=O)NR^{c12}R^{d12}$, $NR^{c12}R^{d12}$, $NR^{c12}C(=O)R^{b12}$, $NR^{c12}C(=O)OR^{b12}$, $NR^{c12}C(=O)NR^{c12}R^{d12}$, $NR^{c12}S(=O)_2R^{b12}$, $NR^{c12}S(=O)_2NR^{c12}R^{d12}$, $S(=O)_2R^{b12}$, and $S(=O)_2NR^{c12}R^{d12}$, wherein said $C_{1-6}$ alkyl, $C_{2-6}$ alkenyl, and $C_{2-6}$ alkynyl are each optionally substituted by 1, 2, 3, or 4 independently selected $R^G$ groups;

each $R^{a12}$, $R^{c12}$, and $R^{d12}$ is independently selected from H, $C_{1-6}$ alkyl, and $C_{1-6}$ haloalkyl, wherein said $C_{1-6}$ alkyl is optionally substituted with 1, 2, 3, or 4 independently selected $R^G$ groups;

each $R^{b12}$ is independently selected from $C_{1-6}$ alkyl and $C_{1-6}$ haloalkyl, wherein said $C_{1-6}$ alkyl is optionally substituted with 1, 2, or 3 independently selected $R^G$ groups;

n is 0 or 1;

m is 0 or 1;

s is 0 or 1;

wherein n+m+s=1 or 2;

when n is 1, $R^1$ and $R^2$ taken together form a linking group $L^1$;

when m is 1, one of $R^A$ and one of $R^B$ taken together form a linking group $L^2$;

when s is 1, $R^Q$ and $R^4$ taken together form a linking group $L^3$;

$L^1$, $L^2$, and $L^3$ are each independently selected from -R-R-, -R-R-R-, -Cy-, -R-Cy-, -Cy-R-, and -R-Cy-R- ;

each R is independently M, $C_{1-6}$ alkylene, $C_{2-6}$ alkenylene, $C_{2-6}$ alkynylene, $C_{1-6}$ alkylene-M, or M-$C_{1-6}$ alkylene, wherein each of said $C_{1-6}$ alkylene, $C_{2-6}$ alkenylene, and $C_{2-6}$ alkynylene is optionally substituted by 1, 2, 3, or 4 groups independently selected $R^G$ groups;

each Cy is independently selected from $C_{3-14}$ cycloalkyl, phenyl, 4-14 membered heterocycloalkyl, and 5-6 membered heteroaryl, each of which is optionally substituted by 1, 2, 3, or 4 independently selected $R^G$ groups;

each M is independently —O—, —S—, —C(O)—, —C(O)$NR^L$—, —C(O)O—, —OC(O)$NR^L$—, —$NR^L$—, —$NR^L$C(O)—, —$NR^L$C(O)O—, —$NR^L$C(O)$NR^L$—, —$NR^L$S(O)$_2$—, —S(O)$_2$—, or —S(O)$_2$$NR^L$—, or —$NR^L$S(O)$_2NR^L$—; provided that when M is attached to a nitrogen atom, then M is selected from —C(O)—, —C(O)NR$^L$—, —C(O)O—, —S(O)$_2$—, or —S(O)$_2$NR$^L$—;

each R$^L$ is independently H or C$_{1-3}$ alkyl; and each R$^G$ is independently selected from OH, NO$_2$, CN, halo, C$_{1-3}$ alkyl, C$_{2-3}$ alkenyl, C$_{2-3}$ alkynyl, C$_{1-3}$ haloalkyl, cyano-C$_{1-3}$ alkyl, HO-C$_{1-3}$ alkyl, C$_{1-3}$ alkoxy-C$_{1-3}$ alkyl, C$_{3-7}$ cycloalkyl, C$_{1-3}$ alkoxy, C$_{1-3}$ haloalkoxy, amino, C$_{1-3}$ alkylamino, di(C$_{1-3}$ alkyl)amino, thio, C$_{1-3}$ alkylthio, C$_{1-3}$ alkylsulfinyl, C$_{1-3}$ alkylsulfonyl, carbamyl, C$_{1-3}$ alkylcarbamyl, di(C$_{1-3}$ alkyl)carbamyl, carboxy, C$_{1-3}$ alkylcarbonyl, C$_{1-4}$ alkoxycarbonyl, C$_{1-3}$ alkylcarbonylamino, C$_{1-3}$ alkylsulfonylamino, aminosulfonyl, C$_{1-3}$ alkylaminosulfonyl, di(C$_{1-3}$ alkyl)aminosulfonyl, aminosulfonylamino, C$_{1-3}$ alkylaminosulfonylamino, di(C$_{1-3}$alkyl)aminosulfonylamino, aminocarbonylamino, C$_{1-3}$ alkylaminocarbonylamino, and di(C$_{1-3}$ alkyl)aminocarbonylamino.

In some embodiments:

U is N or CR$^U$;

V is N or CR$^V$;

W is N or CR$^W$;

Q is N or CR$^Q$;

wherein U=V—W=Q is selected from CR$^U$=CR$^V$—CR$^W$=CR$^Q$, N=CR$^V$—CR$^W$=CR$^Q$, CR$^U$=N—CR$^W$=CR$^Q$, CR$^U$=CR$^V$—N=CR$^Q$, CR$^U$=CR$^V$—CR$^W$=N, N=N—CR$^W$=CR$^Q$, CR$^U$=N—N=CR$^Q$, CR$^U$=CR$^V$—N=N, N=CR$^V$—CR$^W$=N, N=CR$^V$—N=CR$^Q$, CR$^U$=N—CR$^W$=N, N=N—CR$^W$=N, and N=CR$^V$—N=N;

R$^U$, R$^V$, R$^W$, and R$^Q$ are each independently selected from H, D, halo, CN, NO$_2$, C$_{1-6}$ alkyl, C$_{2-6}$ alkenyl, C$_{2-6}$ alkynyl, C$_{1-6}$ haloalkyl, C$_{3-7}$ cycloalkyl, phenyl, 4-7 membered heterocycloalkyl, 5-6 membered heteroaryl, C$_{3-7}$ cycloalkyl-C$_{1-4}$ alkyl, phenyl-C$_{1-4}$ alkyl, 4-7 membered heterocycloalkyl-C$_{1-4}$ alkyl, 5-6 membered heteroaryl-C$_{1-4}$ alkyl, OR$^a$, SR$^a$, C(=O)R$^b$, C(=O)NR$^c$R$^d$, C(=O)OR$^a$, OC(=O)R$^b$, OC(=O)NR$^c$R$^d$, NR$^c$R$^d$, NR$^c$C(=O)R$^b$, NR$^c$C(=O)OR$^b$, NR$^c$C(=O)NR$^c$R$^d$, C(=NR$^e$)R$^b$, C(=NR$^e$)NR$^c$R$^d$, NR$^c$C(=NR$^e$)NR$^c$R$^d$, NR$^c$S(=O)$_2$R$^b$, NR$^c$S(=O)$_2$NR$^c$R$^d$, S(=O)$_2$R$^b$, and S(=O)$_2$NR$^c$R$^d$, wherein said C$_{1-6}$ alkyl, C$_{2-6}$ alkenyl, C$_{2-6}$ alkynyl, C$_{1-6}$ haloalkyl, phenyl, 4-7 membered heterocycloalkyl, 5-6 membered heteroaryl, C$_{3-7}$ cycloalkyl-C$_{1-4}$ alkyl, phenyl-C$_{1-4}$ alkyl, 4-7 membered heterocycloalkyl-C$_{1-4}$ alkyl, and 5-6 membered heteroaryl-C$_{1-4}$ alkyl are each optionally substituted by 1, 2, 3, or 4 independently selected R$^8$ groups;

each R$^8$ is independently selected from OH, NO$_2$, CN, halo, C$_{1-3}$ alkyl, C$_{2-3}$ alkenyl, C$_{2-3}$ alkynyl, C$_{1-3}$ haloalkyl, cyano-C$_{1-3}$ alkyl, HO-C$_{1-3}$ alkyl, C$_{1-3}$ alkoxy-C$_{1-3}$ alkyl, C$_{3-7}$ cycloalkyl, C$_{1-3}$ alkoxy, C$_{1-3}$ haloalkoxy, amino, C$_{1-3}$ alkylamino, di(C$_{1-3}$ alkyl)amino, thio, C$_{1-3}$ alkylthio, C$_{1-3}$ alkylsulfinyl, C$_{1-3}$ alkylsulfonyl, carbamyl, C$_{1-3}$ alkylcarbamyl, di(C$_{1-3}$ alkyl)carbamyl, carboxy, C$_{1-3}$ alkylcarbonyl, C$_{1-4}$ alkoxycarbonyl, C$_{1-3}$ alkylcarbonylamino, C$_{1-3}$ alkylsulfonylamino, aminosulfonyl, C$_{1-3}$ alkylaminosulfonyl, di(C$_{1-3}$ alkyl)aminosulfonyl, aminosulfonylamino, C$_{1-3}$ alkylaminosulfonylamino, di(C$_{1-3}$ alkyl)aminosulfonylamino, aminocarbonylamino, C$_{1-3}$ alkylaminocarbonylamino, and di(C$_{1-3}$ alkyl)aminocarbonylamino;

each R$^a$, R$^c$, and R$^d$ is independently selected from H, C$_{1-6}$ alkyl, C$_{1-6}$ haloalkyl, C$_{2-6}$ alkenyl, and C$_{2-6}$ alkynyl, C$_{3-7}$ cycloalkyl, phenyl, 4-7 membered heterocycloalkyl, 5-6 membered heteroaryl, C$_{3-7}$ cycloalkyl-C$_{1-4}$ alkyl, phenyl-C$_{1-4}$ alkyl, 4-7 membered heterocycloalkyl-C$_{1-4}$ alkyl, and 5-6 membered heteroaryl-C$_{1-4}$ alkyl, wherein said C$_{1-6}$ alkyl, C$_{2-6}$ alkenyl, C$_{2-6}$ alkynyl, C$_{3-7}$ cycloalkyl, phenyl, 4-7 membered heterocycloalkyl, 5-6 membered heteroaryl, C$_{3-7}$ cycloalkyl-C$_{1-4}$ alkyl, phenyl-C$_{1-4}$ alkyl, 4-7 membered heterocycloalkyl-C$_{1-4}$ alkyl, and 5-6 membered heteroaryl-C$_{1-4}$ alkyl are each optionally substituted with 1, 2, 3, or 4 independently selected R$^8$ groups;

each R$^b$ is independently selected from C$_{1-6}$ alkyl, C$_{1-6}$ haloalkyl, C$_{2-6}$ alkenyl, C$_{2-6}$ alkynyl, C$_{3-7}$ cycloalkyl, phenyl, 4-7 membered heterocycloalkyl, 5-6 membered heteroaryl, C$_{3-7}$ cycloalkyl-C$_{1-4}$ alkyl, phenyl-C$_{1-4}$ alkyl, 4-7 membered heterocycloalkyl-C$_{1-4}$ alkyl, and 5-6 membered heteroaryl-C$_{1-4}$ alkyl, wherein said C$_{1-6}$ alkyl, C$_{2-6}$ alkenyl, C$_{2-6}$ alkynyl, C$_{3-7}$ cycloalkyl, phenyl, 4-7 membered heterocycloalkyl, 5-6 membered heteroaryl, C$_{3-7}$ cycloalkyl-C$_{1-4}$ alkyl, phenyl-C$_{1-4}$ alkyl, 4-7 membered heterocycloalkyl-C$_{1-4}$ alkyl, and 5-6 membered heteroaryl-C$_{1-4}$ alkyl are each optionally substituted with 1, 2, or 3 independently selected R$^8$ groups;

each R$^e$ is independently selected from H, CN, OH, C$_{1-4}$ alkyl, and C$_{1-4}$ alkoxy;

X is N or CR$^X$;

Y is N or CR$^Y$;

Z is N or CR$^Z$;

wherein i) X, Y and Z are CR$^X$, CR$^Y$, and CR$^Z$ respectively, or ii) only one of X, Y and Z is N, or iii) only two of X, Y and Z are N;

R$^X$, R$^Y$, and R$^Z$ are each independently selected from H, D, halo, CN, NO$_2$, C$_{1-6}$ alkyl, C$_{2-6}$ alkenyl, C$_{2-6}$ alkynyl, C$_{1-6}$ haloalkyl, OR$^{a0}$, C(=O)R$^{b0}$, C(=O)NR$^{c0}$R$^{d0}$, C(=O)OR$^{a0}$, OC(=O)R$^{b0}$, NR$^{c0}$R$^{d0}$, NR$^{c0}$C(=O)R$^{b0}$, NR$^{c0}$S(=O)$_2$R$^{b0}$, S(=O)$_2$R$^{b0}$, and S(=O)$_2$NR$^{c0}$R$^{d0}$, wherein said C$_{1-6}$ alkyl, C$_{2-6}$ alkenyl, C$_{2-6}$ alkynyl, and C$_{1-6}$ haloalkyl are each optionally substituted by 1, 2, 3, or 4 independently selected R$^G$ groups;

each R$^{a0}$, R$^{c0}$, and R$^{d0}$ is independently selected from H, C$_{1-6}$ alkyl, and C$_{1-6}$ haloalkyl, wherein said C$_{1-6}$ alkyl are each optionally substituted with 1, 2, 3, or 4 independently selected R$^G$ groups;

each R$^{b0}$ is independently selected from C$_{1-6}$ alkyl and C$_{1-6}$ haloalkyl, wherein said C$_{1-6}$ alkyl is optionally substituted with 1, 2, or 3 independently selected R$^G$ groups.

R$^1$ is H, C$_{1-6}$ alkyl, or C$_{1-6}$ haloalkyl;

R$^2$ is H, C$_{1-6}$ alkyl, or C$_{1-6}$ haloalkyl;

R$^3$ is H, C$_{1-6}$ alkyl, or C$_{1-6}$ haloalkyl;

R$^4$ is H, D, halo, CN, NO$_2$, C$_{1-6}$ alkyl, C$_{2-6}$ alkenyl, C$_{2-6}$ alkynyl, C$_{1-6}$ haloalkyl, C$_{3-7}$ cycloalkyl, phenyl, 4-7 membered heterocycloalkyl, 5-6 membered heteroaryl, C$_{3-7}$ cycloalkyl-C$_{1-4}$ alkyl, phenyl-C$_{1-4}$ alkyl, 4-7 membered heterocycloalkyl-C$_{1-4}$ alkyl, 5-6 membered heteroaryl-C$_{1-4}$ alkyl, OR$^{a4}$, SR$^{a4}$, C(=O)R$^{b4}$, C(=O)NR$^{c4}$R$^{d4}$, C(=O)OR$^{a4}$, OC(=O)R$^{b4}$, OC(=O)NR$^{c4}$R$^{d4}$, NR$^{c4}$R$^{d4}$, NR$^{c4}$C(=O)R$^{b4}$, NR$^{c4}$C(=O)OR$^{b4}$, NR$^{c4}$C(=O)NR$^{c4}$R$^{d4}$, NR$^{c4}$S(=O)$_2$R$^{b4}$, NR$^{c4}$S(=O)$_2$NR$^{c4}$R$^{d4}$, S(=O)$_2$R$^{b4}$, or S(=O)$_2$NR$^{c4}$R$^{d4}$, wherein said C$_{1-6}$ alkyl, C$_{2-6}$ alkenyl, C$_{2-6}$ alkynyl, C$_{3-7}$ cycloalkyl, phenyl, 4-7 membered heterocycloalkyl, 5-6 membered heteroaryl, C$_{3-7}$ cycloalkyl-C$_{1-4}$ alkyl, phenyl-C$_{1-4}$ alkyl, 4-7 membered heterocycloalkyl-C$_{1-4}$ alkyl, and 5-6 membered heteroaryl-C$_{1-4}$ alkyl are each optionally substituted by 1, 2, 3, or 4 independently selected R$^{4a}$ groups;

each R$^{a4}$, R$^{c4}$, and R$^{d4}$ is independently selected from H, C$_{1-6}$ alkyl, C$_{1-6}$ haloalkyl, C$_{2-6}$ alkenyl, C$_{2-6}$ alkynyl, C$_{3-7}$ cycloalkyl, phenyl, 4-7 membered heterocycloalkyl, 5-6 membered heteroaryl, C$_{3-7}$ cycloalkyl-C$_{1-4}$ alkyl, phenyl-C$_{1-4}$ alkyl, 4-7 membered heterocycloalkyl-C$_{1-4}$ alkyl, and 5-6 membered heteroaryl-C$_{1-4}$ alkyl, wherein said C$_{1-6}$ alkyl, C$_{2-6}$ alkenyl, C$_{2-6}$ alkynyl, C$_{3-7}$ cycloalkyl, phenyl, 4-7 membered heterocycloalkyl, 5-6 membered heteroaryl, C$_{3-7}$ cycloalkyl-C$_{1-4}$ alkyl, phenyl-C$_{1-4}$ alkyl, 4-7 membered heterocycloalkyl-C$_{1-4}$ alkyl, and 5-6 membered heteroaryl-C$_{1-4}$ alkyl are each optionally substituted with 1, 2, 3, or 4 independently selected $R^{4a}$ groups;

each $R^{b4}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{4a}$ groups;

$R^5$ is H, D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a5}$, $SR^{a5}$, $C(=O)R^{b5}$, $C(=O)NR^{c5}R^{d5}$, $C(=O)OR^{a5}$, $OC(=O)R^{b5}$, $OC(=O)NR^{c5}R^{d5}$, $NR^{c5}R^{d5}$, $NR^{c5}C(=O)R^{b5}$, $NR^{c5}C(=O)OR^{b5}$, $NR^{c5}C(=O)NR^{c5}R^{d5}$, $NR^{c5}S(=O)_2R^{b5}$, $NR^{c5}S(=O)_2NR^{c5}R^{d5}$, $S(=O)_2R^{b5}$, or $S(=O)_2NR^{c5}R^{d5}$, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted by 1, 2, 3, or 4 independently selected $R^{5a}$ groups;

each $R^{a5}$, $R^{c5}$, and $R^{d5}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{5a}$ groups;

each $R^{b5}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{5a}$ groups;

$R^6$ is H, D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a6}$, $SR^{a6}$, $C(=O)R^{b6}$, $C(=O)NR^{c6}R^{d6}$, $C(=O)OR^{a6}$, $OC(=O)R^{b6}$, $OC(=O)NR^{c6}R^{d6}$, $NR^{c6}R^{d6}$, $NR^{c6}C(=O)R^{b6}$, $NR^{b6}C(=O)OR^{b6}$, $NR^{c6}C(=O)NR^{c6}R^{d6}$, $NR^{c6}S(=O)_2R^{b6}$, $NR^{c6}S(=O)_2NR^{c6}R^{d6}$, $S(=O)_2R^{b6}$, or $S(=O)_2NR^{c6}R^{d6}$, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted by 1, 2, 3, or 4 independently selected $R^{6a}$ groups;

each $R^{a6}$, $R^{c6}$, and $R^{d6}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{6a}$ groups;

each $R^{b6}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{6a}$ groups;

$R^7$ is H, D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a7}$, $SR^{a7}$, $C(=O)R^{b7}$, $C(=O)NR^{c7}R^{d7}$, $C(=O)OR^{a7}$, $OC(=O)R^{b7}$, $OC(=O)NR^{c7}R^{d7}$, $NR^{c7}R^{d7}$, $NR^{c7}C(=O)R^{b7}$, $NR^{c7}C(=O)OR^{b7}$, $NR^{c7}C(=O)NR^{c7}R^{d7}$, $NR^{c7}S(=O)_2R^{b7}$, $NR^{c7}S(=O)_2NR^{c7}R^{d7}$, $S(=O)_2R^{b7}$, or $S(=O)_2NR^{c7}R^{d7}$, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl are each optionally substituted by 1, 2, 3, or 4 independently selected $R^{7a}$ groups;

each $R^{a7}$, $R^{c7}$, and $R^{d7}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{7a}$ groups;

each $R^{b7}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{7a}$ groups;

$R^{4a}$, $R^{5a}$, $R^{6a}$, and $R^{7a}$ are independently selected from H, halo, CN, $NO_2$, $C_{1-6}$ alkyl, $C_{2-6}$ alkenyl, $C_{2-6}$ alkynyl, $C_{1-6}$ haloalkyl, $OR^{a9}$, $SR^{a9}$, $C(=O)R^{b9}$, $C(=O)NR^{c9}R^{d9}$, $C(=O)OR^{a9}$, $OC(=O)R^{b9}$, $OC(=O)NR^{c9}R^{d9}$, $NR^{c9}R^{d9}$, $NR^{c9}C(=O)R^{b9}$, $NR^{c9}C(=O)OR^{b9}$, $NR^{c9}C(=O)NR^{c9}R^{d9}$, $C(=NR^e)R^{b9}$, $NR^{c9}S(=O)_2R^{b9}$, $NR^{c9}S(=O)_2NR^{c9}R^{d9}$, $S(=O)_2R^{b9}$, and $S(=O)_2NR^{c9}R^{d9}$, wherein said $C_{1-6}$ alkyl, $C_{2-6}$ alkenyl, and $C_{2-6}$ alkynyl, are each optionally substituted by 1, 2, 3, or 4 independently selected $R^{11}$ groups;

each $R^{a9}$, $R^{c9}$, and $R^{d9}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl is optionally substituted with 1, 2, 3, or 4 independently selected $R^{11}$ groups;

each $R^{b9}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, or 3 independently selected $R^{11}$ groups;

each $R^{11}$ is independently selected from OH, $NO_2$, CN, halo, $C_{1-6}$ alkyl, $C_{2-6}$ alkenyl, $C_{2-6}$ alkynyl, $C_{1-6}$ haloalkyl, cyano-$C_{1-6}$ alkyl, HO-$C_{1-6}$ alkyl, $C_{1-6}$ alkoxy-$C_{1-6}$ alkyl, $C_{3-7}$ cycloalkyl, $C_{1-6}$ alkoxy, $C_{1-6}$ haloalkoxy, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-4}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

Ring moiety A is selected from $C_{3-7}$ cycloalkyl, phenyl, 4-7 membered heterocycloalkyl, and 5-6 membered heteroaryl, each of which is optionally substituted by 1, 2, 3, or 4 independently selected $R^A$ groups;

Ring moiety B is selected from $C_{3-7}$ cycloalkyl, phenyl, 4-7 membered heterocycloalkyl, and 5-6 membered heteroaryl, each of which is optionally substituted by 1, 2, 3, or 4 independently selected $R^B$ groups;

each $R^A$ is independently selected from halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a1}$, $SR^{a1}$, $C(=O)R^{b1}$, $C(=O)NR^{c1}R^{d1}$, $C(=O)OR^{a1}$, $OC(=)R^{b1}$, $OC(=O)NR^{c1}R^{d1}$, $NR^{c1}R^{d1}$, $NR^{c1}C(=O)R^{b1}$, $NR^{c1}C(=O)OR^{b1}$, $NR^{c1}C(=O)NR^{c1}R^{d1}$, $NR^{c1}S(=O)_2R^{b2}$, $NR^{c1}S(=O)_2NR^{c1}R^{d1}$, $S(=O)_2R^{b1}$, and $S(=O)_2NR^{c1}R^{d1}$, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted by 1, 2, 3, or 4 independently selected $R^{A1}$ groups;

each $R^B$ is independently selected from halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a2}$, $SR^{a2}$, $C(=O)R^{b2}$, $C(=O)NR^{c2}R^{d2}$, $C(=O)OR^{a2}$, $OC(=O)R^{b2}$, $OC(=O)NR^{c2}R^{d2}$, $NR^{c2}R^{d2}$, $NR^{c2}C(=O)R^{b2}$, $NR^{c2}C(=O)OR^{b2}$, $NR^{c2}C(=O)NR^{c2}R^{d2}$, $NR^{c2}S(=O)_2R^{b2}$, $NR^{c2}S(=O)_2NR^{c2}R^{d2}$, and $S(=O)_2NR^{c2}R^{d2}$, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted by 1, 2, 3, or 4 independently selected $R^{B1}$ groups;

each $R^{A1}$ and $R^{B1}$ is independently selected from H, halo, CN, $NO_2$, $C_{1-6}$ alkyl, $C_{2-6}$ alkenyl, $C_{2-6}$ alkynyl, $C_{1-6}$ haloalkyl, $OR^{a12}$, $SR^{a12}$, $C(=O)R^{b12}$, $C(=O)NR^{c12}R^{d12}$, $C(=O)OR^{a12}$, $OC(=O)R^{b12}$, $OC(=O)NR^{c12}R^{d12}$, $NR^{c12}R^{d12}$, $NR^{c12}C(=O)R^{b12}$, $NR^{c12}C(=O)OR^{b12}$, $NR^{c12}C(=O)NR^{c12}R^{d12}$, $NR^{c12}S(=O)_2R^{b12}$, $NR^{c12}S(=O)_2NR^{c12}R^{d12}$, $S(=O)_2R^{b12}$, and $S(=O)_2NR^{c12}R^{d12}$, wherein said $C_{1-6}$ alkyl, $C_{2-6}$ alkenyl, and $C_{2-6}$ alkynyl are each optionally substituted by 1, 2, 3, or 4 independently selected $R^G$ groups;

each $R^{a12}$, $R^{c12}$, and $R^{d12}$ is independently selected from H, $C_{1-6}$ alkyl, and $C_{1-6}$ haloalkyl, wherein said $C_{1-6}$ alkyl is optionally substituted with 1, 2, 3, or 4 independently selected $R^G$ groups;

each $R^{b12}$ is independently selected from $C_{1-6}$ alkyl and $C_{1-6}$ haloalkyl, wherein said $C_{1-6}$ alkyl is optionally substituted with 1, 2, or 3 independently selected $R^G$ groups;

n is 0 or 1;
m is 0 or 1;
s is 0 or 1;
wherein n+m+s=1 or 2;
when n is 1, $R^1$ and $R^2$ taken together form a linking group $L^1$;
when m is 1, one of $R^A$ and one of $R^B$ taken together form a linking group $L^2$;
when s is 1, $R^Q$ and $R^4$ taken together form a linking group $L^3$;

$L^1$, $L^2$, and $L^3$ are each independently selected from -R-R-, -R-R-R-, -Cy-, -R-Cy-, -Cy-R-, and -R-Cy-R-;

each R is independently M, $C_{1-6}$ alkylene, $C_{2-6}$ alkenylene, $C_{2-6}$ alkynylene, $C_{1-6}$ alkylene-M, or M-$C_{1-6}$ alkylene, wherein each of said $C_{1-6}$ alkylene, $C_{2-6}$ alkenylene, and $C_{2-6}$ alkynylene is optionally substituted by 1, 2, 3, or 4 groups independently selected $R^G$ groups;

each Cy is independently selected from $C_{3-14}$ cycloalkyl, phenyl, 4-14 membered heterocycloalkyl, and 5-6 membered heteroaryl, each of which is optionally substituted by 1, 2, 3, or 4 independently selected $R^G$ groups;

each M is independently —O—, —S—, —C(O)—, —C(O)NR$^L$—, —C(O)O—, —OC(O)NR$^L$—, —NR$^L$—, —NR$^L$C(O)—, —NR$^L$C(O)O—, —NR$^L$C(O)NR$^L$—, —NR$^L$S(O)$_2$—, —S(O)$_2$—, or —S(O)$_2$NR$^L$—, or —NR$^L$S(O)$_2$NR$^L$—; provided that when M is attached to a nitrogen atom, then M is selected from —C(O)—, —C(O)NR$^L$—, —C(O)O—, —S(O)$_2$—, or —S(O)$_2$NR$^L$—;

each $R^L$ is independently H or $C_{1-3}$ alkyl; and each $R^G$ is independently selected from OH, $NO_2$, CN, halo, $C_{1-3}$ alkyl, $C_{2-3}$ alkenyl, $C_{2-3}$ alkynyl, $C_{1-3}$ haloalkyl, cyano-$C_{1-3}$ alkyl, HO-$C_{1-3}$ alkyl, $C_{1-3}$ alkoxy-$C_{1-3}$ alkyl, $C_{3-7}$ cycloalkyl, $C_{1-3}$ alkoxy, $C_{1-3}$ haloalkoxy, amino, $C_{1-3}$ alkylamino, di($C_{1-3}$ alkyl)amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl)carbamyl, carboxy, $C_{1-3}$ alkylcarbonyl, $C_{1-4}$ alkoxycarbonyl, $C_{1-3}$ alkylcarbonylamino, $C_{1-3}$ alkylsulfonylamino, aminosulfonyl, $C_{1-3}$ alkylaminosulfonyl, di($C_{1-3}$ alkyl)aminosulfonyl, aminosulfonylamino, $C_{1-3}$ alkylaminosulfonylamino, di($C_{1-3}$ alkyl)aminosulfonylamino, aminocarbonylamino, $C_{1-3}$ alkylaminocarbonylamino, and di($C_{1-3}$ alkyl)aminocarbonylamino.

In some embodiments:

U is N or $CR^U$;
V is N or $CR^V$;
W is N or $CR^W$;
Q is N or $CR^Q$;

wherein U=V—W=Q is selected from $CR^U=CR^V—CR^W=CR^Q$, $N=CR^V—CR^W=CR^Q$, $CR^U=N—CR^W=CR^Q$, $CR^U=CR^V—N=CR^Q$, $CR^U=CR^V—CR^W=N$, $N=N—CR^W=CR^Q$, $CR^U=N—N=CR^Q$, $CR^U=CR^V—N=N$, $N=CR^V—CR^W=N$, $N=CR^V—N=CR^Q$, $CR^U=N—CR^W=N$, $N=N—CR^W=N$, and $N=CR^V—N=N$;

$R^U$, $R^V$, $R^W$, and $R^Q$ are each independently selected from H, D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^a$, $SR^a$, $C(=O)R^b$, $C(=O)NR^cR^d$, $C(=O)OR^a$, $OC(=O)R^b$, $OC(=O)NR^cR^d$, $NR^cR^d$, $NR^cC(=O)R^b$, $NR^cC(=O)OR^b$, $NR^cC(=O)NR^cR^d$, $C(=NR^e)R^b$, $C(=NR^e)NR^cR^d$, $NR^cC(=NR^e)NR^cR^d$, $NR^cS(=O)_2R^b$, $NR^cS(=O)_2NR^cR^d$, $S(=O)_2R^b$, and $S(=O)_2NR^cR^d$, wherein said $C_{1-6}$ alkyl, $C_{2-6}$ alkenyl, $C_{2-6}$ alkynyl, $C_{1-6}$ haloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl are each optionally substituted by 1, 2, 3, or 4 independently selected $R^8$ groups;

each $R^8$ is independently selected from OH, $NO_2$, CN, halo, $C_{1-3}$ alkyl, $C_{2-3}$ alkenyl, $C_{2-3}$ alkynyl, $C_{1-3}$ haloalkyl, cyano-$C_{1-3}$ alkyl, HO-$C_{1-3}$ alkyl, $C_{1-3}$ alkoxy-$C_{1-3}$ alkyl, $C_{3-7}$ cycloalkyl, $C_{1-3}$ alkoxy, $C_{1-3}$ haloalkoxy, amino, $C_{1-3}$ alkylamino, di($C_{1-3}$ alkyl)amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl)carbamyl, carboxy, $C_{1-3}$ alkylcarbonyl, $C_{1-4}$ alkoxycarbonyl, $C_{1-3}$ alkylcarbonylamino, $C_{1-3}$ alkylsulfonylamino, aminosulfonyl, $C_{1-3}$ alkylaminosulfonyl, di($C_{1-3}$ alkyl)aminosulfonyl, aminosulfonylamino, $C_{1-3}$ alkylaminosulfonylamino, di($C_{1-3}$ alkyl)aminosulfonylamino, aminocarbonylamino, $C_{1-3}$ alkylaminocarbonylamino, and di($C_{1-3}$ alkyl)aminocarbonylamino;

each $R^a$, $R^c$, and $R^d$ is independently selected from H, $C_{1-6}$ alkyl, $C_{1-6}$ haloalkyl, $C_{2-6}$ alkenyl, and $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{10}$ groups;

each $R^b$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, or 3 independently selected $R^{10}$ groups;

each $R^{10}$ is independently selected from OH, $NO_2$, CN, halo, $C_{1-3}$ alkyl, $C_{2-3}$ alkenyl, $C_{2-3}$ alkynyl, $C_{1-3}$ haloalkyl, cyano-$C_{1-3}$ alkyl, HO-$C_{1-3}$ alkyl, $C_{1-3}$ alkoxy-$C_{1-3}$ alkyl, $C_{3-7}$ cycloalkyl, $C_{1-3}$ alkoxy, $C_{1-3}$ haloalkoxy, amino, $C_{1-3}$ alkylamino, di($C_{1-3}$ alkyl)amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl)carbamyl, carboxy, $C_{1-3}$ alkylcarbonyl, $C_{1-4}$ alkoxycarbonyl, $C_{1-3}$ alkylcarbonylamino, $C_{1-3}$ alkylsulfonylamino, aminosulfonyl, $C_{1-3}$ alkylaminosulfonyl, di($C_{1-3}$ alkyl)aminosulfonyl, aminosulfonylamino, $C_{1-3}$ alkylaminosulfonylamino, di($C_{1-3}$ alkyl)aminosulfonylamino, aminocarbonylamino, $C_{1-3}$ alkylaminocarbonylamino, and di($C_{1-3}$ alkyl)aminocarbonylamino;

X is N or $CR^X$;
Y is N or $CR^Y$;
Z is N or $CR^Z$;

wherein i) X, Y and Z are $CR^X$, $CR^Y$, and $CR^Z$ respectively, or ii) only one of X, Y and Z is N, or iii) only two of X, Y and Z are N;

$R^X$, $R^Y$, and $R^Z$ are each independently selected from H, D, halo, CN, $C_{1-6}$ alkyl, and $C_{1-6}$ haloalkyl;

$R^1$ is H, $C_{1-6}$ alkyl, or $C_{1-6}$ haloalkyl;
$R^2$ is H, $C_{1-6}$ alkyl, or $C_{1-6}$ haloalkyl;
$R^3$ is H, $C_{1-6}$ alkyl, or $C_{1-6}$ haloalkyl;
$R^4$ is H, D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a4}$, $SR^{a4}$, $C(=O)R^{b4}$, $C(=O)NR^{c4}R^{d4}$, $C(=O)OR^{a4}$, $OC(=O)R^{b4}$, $OC(=O)NR^{c4}R^{d4}$, $NR^{c4}R^{d4}$, $NR^{c4}C(=O)R^{b4}$, $NR^{c4}C(=O)OR^{b4}$, $NR^{c4}C(=O)NR^{c4}R^{d4}$, $NR^{c4}S(=O)_2R^{b4}$, $NR^{c4}S(=O)_2NR^{c4}R^{d4}$, $S(=O)_2R^{b4}$, or $S(=O)_2NR^{c4}R^{d4}$, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted by 1, 2, 3, or 4 independently selected $R^{4a}$ groups;

each $R^{a4}$, $R^{c4}$, and $R^{d4}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{4a}$ groups;

each $R^{b4}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{4a}$ groups;

$R^5$ is H, D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a5}$, $SR^{a5}$, $C(=O)R^{b5}$, $C(=O)NR^{c5}R^{d5}$, $C(=O)OR^{a5}$, $OC(=O)R^{b5}$, $OC(=O)NR^{c5}R^{d5}$, $NR^{c5}R^{d5}$, $NR^{c5}C(=O)R^{b5}$, $NR^{c5}C(=O)OR^{b5}$, $NR^{c5}C(=O)NR^{c5}R^{d5}$, $NR^{c5}S(=O)_2R^{b5}$, $NR^{c5}S(=O)_2NR^{c5}R^{d5}$, $S(=O)_2R^{b5}$, or $S(=O)_2NR^{c5}R^{d5}$, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted by 1, 2, 3, or 4 independently selected $R^{5a}$ groups;

each $R^{a5}$, $R^{c5}$, and $R^{d5}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{5a}$ groups;

each $R^{b5}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{5a}$ groups;

$R^6$ is H, D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a6}$, $SR^{a6}$, $C(=O)R^{a6}$, $C(=O)NR^{c6}R^{d6}$, $C(=O)OR^{a6}$, $OC(=O)R^{b6}$, $OC(=O)NR^{c6}R^{d6}$, $NR^{c6}R^{d6}$, $NR^{c6}C(=O)R^{b6}$, $NR^{c6}C(=O)OR^{b6}$, $NR^{c6}C(=O)NR^{c6}R^{d6}$, $NR^{c6}S(=O)_2R^{b6}$, $NR^{c6}S(=O)_2NR^{c6}R^{d6}$, $S(=O)_2R^{b6}$, or $S(=O)_2NR^{c6}R^{d6}$, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted by 1, 2, 3, or 4 independently selected $R^{6a}$ groups;

each $R^{a6}$, $R^{c6}$, and $R^{d6}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{6a}$ groups;

each $R^{b6}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{6a}$ groups;

$R^7$ is H, D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a7}$, $SR^{a7}$, $C(=O)R^{b7}$, $C(=O)NR^{c7}R^{d7}$, $C(=O)OR^{a7}$, $OC(=O)R^{b7}$, $OC(=O)NR^{c7}R^{d7}$, $NR^{c7}R^{d7}$, $NR^{c7}C(=O)R^{b7}$, $NR^{c7}C(=O)OR^{b7}$, $NR^{c7}C(=O)NR^{c7}R^{d7}$, $NR^{c7}S(=O)_2R^{b7}$, $NR^{c7}S(=O)_2NR^{c7}R^{d7}$, $S(=O)_2R^{b7}$, or $S(=O)_2NR^{c7}R^{d7}$, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl are each optionally substituted by 1, 2, 3, or 4 independently selected $R^{7a}$ groups;

each $R^{a7}$, $R^{c7}$, and $R^{d7}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{7a}$ groups;

each $R^{b7}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{7a}$ groups;

$R^{4a}$, $R^{5a}$, $R^{6a}$, and $R^{7a}$ are independently selected from H, halo, CN, $NO_2$, $C_{1-6}$ alkyl, $C_{2-6}$ alkenyl, $C_{2-6}$ alkynyl, $C_{1-6}$ haloalkyl, $OR^{a9}$, $SR^{a9}$, $C(=O)R^{b9}$, $C(=O)NR^{c9}R^{d9}$, $C(=O)OR^{a9}$, $OC(=O)R^{b9}$, $OC(=O)NR^{c9}R^{d9}$, $NR^{c9}R^{d9}$, $NR^{c9}C(=O)R^{b9}$, $NR^{c9}C(=O)OR^{b9}$, $NR^{c9}C(=O)NR^{c9}R^{d9}$, $C(=NR^e)R^{b9}$, $NR^{c9}S(=O)R^{b9}$, $NR^{c9}S(=O)_2NR^{c9}R^{d9}$, $S(=O)_2R^{b9}$, and $S(=O)_2NR^{c9}R^{d9}$, wherein said $C_{1-6}$ alkyl, $C_{2-6}$ alkenyl, and $C_{2-6}$ alkynyl, are each optionally substituted by 1, 2, 3, or 4 independently selected $R^{11}$ groups;

each $R^{a9}$, $R^{c9}$, and $R^{d9}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl is optionally substituted with 1, 2, 3, or 4 independently selected $R^{11}$ groups;

each $R^{b9}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, or 3 independently selected $R^{11}$ groups;

each is independently selected from OH, $NO_2$, CN, halo, $C_{1-6}$ alkyl, $C_{2-6}$ alkenyl, $C_{2-6}$ alkynyl, $C_{1-6}$ haloalkyl, cyano-$C_{1-6}$ alkyl, HO-$C_{1-6}$ alkyl, $C_{1-6}$ alkoxy-$C_{1-6}$ alkyl, $C_{3-7}$ cycloalkyl, $C_{1-6}$ alkoxy, $C_{1-6}$ haloalkoxy, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-4}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

Ring moiety A is selected from $C_{3-7}$ cycloalkyl, phenyl, 4-7 membered heterocycloalkyl, and 5-6 membered heteroaryl, each of which is optionally substituted by 1, 2, 3, or 4 independently selected $R^A$ groups;

Ring moiety B is selected from $C_{3-7}$ cycloalkyl, phenyl, 4-7 membered heterocycloalkyl, and 5-6 membered heteroaryl, each of which is optionally substituted by 1, 2, 3, or 4 independently selected $R^B$ groups;

each $R^A$ is independently selected from halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a1}$, $SR^{a1}$, $C(=O)R^{b1}$, $C(=O)NR^{c1}R^{d1}$, $C(=O)OR^{a1}$, $OC(=O)R^{b1}$, $OC(=O)NR^{c1}R^{d1}$, $NR^{c1}R^{d1}$, $NR^{c1}C(=O)R^{b1}$, $NR^{c1}C(=O)OR^{b1}$, $NR^{c1}C(=O)NR^{c1}R^{d1}$, $NR^{c1}S(=O)_2R^{b2}$, $NR^{c1}S(=O)_2NR^{c1}R^{d1}$, $S(=O)_2R^{b1}$, and $S(=O)_2NR^{c1}R^{d1}$, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted by 1, 2, 3, or 4 independently selected $R^{41}$ groups;

each $R^B$ is independently selected from halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a2}$, $SR^{a2}$, $C(=O)R^{b2}$, $C(=O)NR^{c2}R^{d2}$, $C(=O)OR^{a2}$, $OC(=O)R^{b2}$, $OC(=O)NR^{c2}R^{d2}$, $NR^{c2}R^{d2}$, $NR^{c2}R^{d2}$, $NR^{c2}C(=O)R^{b2}$, $NR^{c2}C(=O)OR^{b2}$, $NR^{c2}C(=O)NR^{c2}R^{d2}$, $NR^{c2}S(=O)_2R^{b2}$, $NR^{c2}S(=O)_2NR^{c2}R^{d2}$, $S(=O)_2R^{b2}$, and $S(=O)_2NR^{c2}R^{d2}$, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-Ci-4 alkyl are each optionally substituted by 1, 2, 3, or 4 independently selected $R^{B1}$ groups;

each $R^{41}$ and $R^{B1}$ is independently selected from H, halo, CN, $NO_2$, $C_{1-6}$ alkyl, $C_{2-6}$ alkenyl, $C_{2-6}$ alkynyl, $C_{1-6}$ haloalkyl, $OR^{a12}$, $SR^{a12}$, $C(=O)R^{b12}$, $C(=O)NR^{c12}R^{d12}$, $C(=O)OR^{a12}$, $OC(=O)R^{b12}$, $OC(=O)NR^{c12}R^{d12}$, $NR^{c12}R^{d12}$, $NR^{c12}C(=O)R^{b12}$, $NR^{b12}C(=O)OR^{b12}$, $NR^{c12}C(=O)NR^{c12}R^{d12}$, $NR^{c12}S(=O)_2R^{b12}$, $NR^{c12}S(=O)_2NR^{c12}R^{d12}$, $S(=O)_2R^{b12}$, and $S(=O)_2NR^{c12}R^{d12}$, wherein said $C_{1-6}$ alkyl, $C_{2-6}$ alkenyl, and $C_{2-6}$ alkynyl are each optionally substituted by 1, 2, 3, or 4 independently selected $R^G$ groups;

each $R^{a12}$, $R^{c12}$, and $R^{d12}$ is independently selected from H, $C_{1-6}$ alkyl, and $C_{1-6}$ haloalkyl, wherein said $C_{1-6}$ alkyl is optionally substituted with 1, 2, 3, or 4 independently selected $R^G$ groups;

each $R^{b12}$ is independently selected from $C_{1-6}$ alkyl and $C_{1-6}$ haloalkyl, wherein said $C_{1-6}$ alkyl is optionally substituted with 1, 2, or 3 independently selected $R^G$ groups;

n is 0 or 1;

m is 0 or 1;

s is 0 or 1;

wherein n+m+s=1 or 2;

when n is 1, $R^1$ and $R^2$ taken together form a linking group $L^1$;

when m is 1, one of $R^A$ and one of $R^B$ taken together form a linking group $L^2$;

when s is 1, $R^Q$ and $R^4$ taken together form a linking group $L^3$;

$L^1$, $L^2$, and $L^3$ are each independently selected from -R-R-, -R-R-R-, -Cy-, -R-Cy-, -Cy-R-, and -R-Cy-R-;

each R is independently M, $C_{1-6}$ alkylene, $C_{2-6}$ alkenylene, $C_{2-6}$ alkynylene, $C_{1-6}$ alkylene-M, or M-$C_{1-6}$ alkylene, wherein each of said $C_{1-6}$ alkylene, $C_{2-6}$ alkenylene, and $C_{2-6}$ alkynylene is optionally substituted by 1, 2, 3, or 4 groups independently selected $R^G$ groups;

each Cy is independently selected from $C_{3-14}$ cycloalkyl, phenyl, 4-14 membered heterocycloalkyl, and 5-6 membered heteroaryl, each of which is optionally substituted by 1, 2, 3, or 4 independently selected $R^G$ groups;

each M is independently —O—, —S—, —C(O)—, —C(O)NR$^L$—, —C(O)O—, —OC(O)NR$^L$—, —NR$^L$—, —NR$^L$C(O)—, —NR$^L$C(O)O—, —NR$^L$C(O)NR$^L$—, —NR$^L$S(O)$_2$—, —S(O)$_2$—, or —S(O)$_2$NR$^L$—, or —NR$^L$S(O)$_2$NR$^L$—; provided that when M is attached to a nitrogen atom, then M is selected from —C(O)—, —C(O)NR$^L$—, —C(O)O—, —S(O)$_2$—, or —S(O)$_2$NR$^L$—;

each $R^L$ is independently H or $C_{1-3}$ alkyl; and each $R^G$ is independently selected from OH, $NO_2$, CN, halo, $C_{1-3}$ alkyl, $C_{2-3}$ alkenyl, $C_{2-3}$ alkynyl, $C_{1-3}$ haloalkyl, cyano-$C_{1-3}$ alkyl, HO-$C_{1-3}$ alkyl, $C_{1-3}$alkoxy-$C_{1-3}$ alkyl, $C_{3-7}$ cycloalkyl, $C_{1-3}$ alkoxy, $C_{1-3}$haloalkoxy, amino, $C_{1-3}$ alkylamino, di($C_{1-3}$alkyl)amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl)carbamyl, carboxy, $C_{1-3}$ alkylcarbonyl, $C_{1-4}$ alkoxycarbonyl, $C_{1-3}$ alkylcarbonylamino, $C_{1-3}$ alkylsulfonylamino, aminosulfonyl, $C_{1-3}$alkylaminosulfonyl, di($C_{1-3}$alkyl)aminosulfonyl, aminosulfonylamino, $C_{1-3}$ alkylaminosulfonylamino, di($C_{1-3}$ alkyl)aminosulfonylamino, aminocarbonylamino, $C_{1-3}$ alkylaminocarbonylamino, and di($C_{1-3}$ alkyl)aminocarbonylamino.

In some embodiments:

U is N or $CR^U$;
V is N or $CR^V$;
W is N or $CR^W$;
Q is N or $CR^Q$;
wherein U=V—W=Q is selected from $CR^U$=$CR^V$—$CR^W$=$CR^Q$, N=$CR^V$—$CR^W$=$CR^Q$, $CR^U$=N—$CR^W$=$CR^Q$, $CR^U$=$CR^V$—N=$CR^Q$, $CR^U$=$CR^V$—$CR^W$=N, N=N—$CR^W$=$CR^Q$, $CR^U$=N—N=$CR^Q$, $CR^U$=$CR^V$—N=N, N=$CR^V$—$CR^W$=N, N=$CR^V$—N=$CR^Q$, $CR^U$=N—$CR^W$=N, N=N—$CR^W$=N, and N=$CR^V$—N=N;

$R^U$, $R^V$, $R^W$, and $R^Q$ are each independently selected from H, D, halo, CN, $NO_2$, $C_{1-6}$ alkyl, $C_{2-6}$ alkenyl, $C_{2-6}$ alkynyl, $OR^a$, $SR^a$, $C(=O)R^b$, $C(=O)NR^cR^d$, $C(=O)OR^a$, $OC(=O)R^b$, $OC(=O)NR^cR^d$, $NR^cR^d$, $NR^cC(=O)R^b$, $NR^cC(=O)OR^b$, $NR^cC(=O)NR^cR^d$, $NR^cS(=O)_2R^b$, $NR^cS(=O)_2NR^cR^d$, $S(=O)_2R^b$, or $S(=O)_2NR^cR^d$, wherein said $C_{1-6}$ alkyl, $C_{2-6}$ alkenyl, $C_{2-6}$ alkynyl, and $C_{1-6}$ haloalkyl are each optionally substituted by 1, 2, 3, or 4 independently selected $R^8$ groups;

each $R^8$ is independently selected from OH, $NO_2$, CN, halo, $C_{1-3}$ alkyl, $C_{2-3}$ alkenyl, $C_{2-3}$ alkynyl, $C_{1-3}$ haloalkyl, cyano-$C_{1-3}$ alkyl, HO-$C_{1-3}$ alkyl, $C_{1-3}$ alkoxy-$C_{1-3}$ alkyl, $C_{3-7}$ cycloalkyl, $C_{1-3}$ alkoxy, $C_{1-3}$ haloalkoxy, amino, $C_{1-3}$ alkylamino, di($C_{1-3}$ alkyl)amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl)carbamyl, carboxy, $C_{1-3}$ alkylcarbonyl, $C_{1-4}$ alkoxycarbonyl, $C_{1-3}$ alkylcarbonylamino, $C_{1-3}$ alkylsulfonylamino, aminosulfonyl, $C_{1-3}$ alkylaminosulfonyl, di($C_{1-3}$ alkyl)aminosulfonyl, aminosulfonylamino, $C_{1-3}$ alkylaminosulfonylamino, di($C_{1-3}$ alkyl)aminosulfonylamino, aminocarbonylamino, $C_{1-3}$ alkylaminocarbonylamino, and di($C_{1-3}$ alkyl)aminocarbonylamino;

each $R^a$, $R^c$, and $R^d$ is independently selected from H, $C_{1-6}$ alkyl, and $C_{1-6}$ haloalkyl, wherein said $C_{1-6}$ alkyl is optionally substituted with 1, 2, 3, or 4 independently selected $R^{10}$ groups;

each $R^b$ is independently selected from $C_{1-6}$ alkyl and $C_{1-6}$ haloalkyl, wherein said $C_{1-6}$ alkyl is optionally substituted with 1, 2, or 3 independently selected $R^{10}$ groups; and each $R^{10}$ is independently selected from OH, $NO_2$, CN, halo, $C_{1-3}$ alkyl, $C_{2-3}$ alkenyl, $C_{2-3}$ alkynyl, $C_{1-3}$ haloalkyl, $C_{1-3}$ alkoxy, $C_{1-3}$ haloalkoxy, amino, $C_{1-3}$ alkylamino, and di($C_{1-3}$ alkyl)amino;

X is N or $CR^X$;
Y is N or $CR^Y$;
Z is N or $CR^Z$;
wherein i) X, Y and Z are $CR^X$, $CR^Y$, and $CR^Z$ respectively, or ii) only one of X, Y and Z is N, or iii) only two of X, Y and Z are N;

$R^X$, $R^Y$, and $R^Z$ are each independently selected from H, D, halo, CN, $C_{1-6}$ alkyl, and $C_{1-6}$ haloalkyl;

$R^1$ is H, $C_{1-6}$ alkyl, or $C_{1-6}$ haloalkyl;
$R^2$ is H, $C_{1-6}$ alkyl, or $C_{1-6}$ haloalkyl;
$R^3$ is H, $C_{1-6}$ alkyl, or $C_{1-6}$ haloalkyl;
$R^4$ is H, D, halo, CN, $NO_2$, $C_{1-6}$ alkyl, $C_{2-6}$ alkenyl, $C_{2-6}$ alkynyl, $C_{1-6}$ haloalkyl, $OR^{a4}$, $SR^{a4}$, $C(=O)R^{b4}$, $C(=O)NR^{c4}R^{d4}$, $C(=O)OR^{a4}$, $OC(=O)R^{b4}$, $OC(=O)NR^{c4}R^{d4}$, $NR^{c4}R^{d4}$, $NR^{c4}C(=O)R^{b4}$, $NR^{c4}C(=O)OR^{b4}$, $NR^{c4}C(=O)NR^{c4}R^{d4}$, $NR^{c4}S(=O)_2R^{b4}$, $NR^{c4}S(=O)_2NR^{c4}R^{d4}$, $S(=O)_2R^{b4}$, or $S(=O)_2NR^{c4}R^{d4}$, wherein said $C_{1-6}$ alkyl, $C_{2-6}$ alkenyl, and $C_{2-6}$ alkynyl are each optionally substituted by 1, 2, 3, or 4 independently selected $R^{4a}$ groups;

each $R^{a4}$, $R^{c4}$, and $R^{d4}$ is independently selected from H, $C_{1-6}$ alkyl, and $C_{1-6}$ haloalkyl, wherein said $C_{1-6}$ alkyl is optionally substituted with 1, 2, 3, or 4 independently selected $R^{4a}$ groups;

each $R^{b4}$ is independently selected from $C_{1-6}$ alkyl and $C_{1-6}$ haloalkyl, wherein said $C_{1-6}$ alkyl is optionally substituted with 1, 2, 3, or 4 independently selected $R^{4a}$ groups;

each $R^{a5}$, $R^{c5}$, and $R^{d5}$ is independently selected from H, $C_{1-6}$ alkyl, and $C_{1-6}$ haloalkyl, wherein said $C_{1-6}$ alkyl is optionally substituted with 1, 2, 3, or 4 independently selected $R^{5a}$ groups;

each $R^{b5}$ is independently selected from $C_{1-6}$ alkyl and $C_{1-6}$ haloalkyl, wherein said $C_{1-6}$ alkyl is optionally substituted with 1, 2, 3, or 4 independently selected $R^{5a}$ groups;

$R^6$ is H, D, halo, CN, $NO_2$, $C_{1-6}$ alkyl, $C_{2-6}$ alkenyl, $C_{2-6}$ alkynyl, $C_{1-6}$ haloalkyl, $OR^{a6}$, $SR^{a6}$, $C(=O)R^{b6}$, $C(=O)NR^{c6}R^{d6}$, $C(=O)OR^{a6}$, $OC(=O)R^{b6}$, $OC(=O)NR^{c6}R^{d6}$, $NR^{c6}R^{d6}$, $NR^{c6}C(=O)R^{b6}$, $NR^{c6}C(=O)OR^{b6}$, $NR^{c6}C(=O)NR^{c6}R^{d6}$, $NR^{c6}S(=O)_2R^{b6}$, $NR^{c6}S(=O)_2NR^{c6}R^{d6}$, $S(=O)_2R^{b6}$, or $S(=O)2NR^{c6}R^{d6}$, wherein said $C_{1-6}$ alkyl, $C_{2-6}$ alkenyl, and $C_{2-6}$ alkynyl are each optionally substituted by 1, 2, 3, or 4 independently selected $R^{6a}$ groups;

each $R^{a6}$, $R^{c6}$, and $R^{d6}$ is independently selected from H, $C_{1-6}$ alkyl, and $C_{1-6}$ haloalkyl, wherein said $C_{1-6}$ alkyl is optionally substituted with 1, 2, 3, or 4 independently selected $R^{6a}$ groups;

each $R^{b6}$ is independently selected from $C_{1-6}$ alkyl and $C_{1-6}$ haloalkyl, wherein said $C_{1-6}$ alkyl is optionally substituted with 1, 2, 3, or 4 independently selected $R^{6a}$ groups;

$R^7$ is H, D, halo, CN, $NO_2$, $C_{1-6}$ alkyl, $C_{2-6}$ alkenyl, $C_{2-6}$ alkynyl, $C_{1-6}$ haloalkyl, $OR^{a7}$, $SR^{a7}$, $C(=O)R^{b7}$, $C(=O)NR^{c7}R^{d7}$, $C(=O)OR^{a7}$, $OC(=O)R^{b7}$, $OC(=O)NR^{c7}R^{d7}$, $NR^{c7}R^{d7}$, $NR^{c7}C(=O)R^{b7}$, $NR^{c7}C(=O)OR^{b7}$, $NR^{c7}C(=O)NR^{c7}R^{d7}$, $NR^{c7}S(=O)_2R^{b7}$, $NR^{c7}S(=O)_2NR^{c7}R^{d7}$, $S(=O)_2R^{b7}$, or $S(=O)_2NR^{c7}R^{d7}$, wherein said $C_{1-6}$ alkyl, $C_{2-6}$ alkenyl, and $C_{2-6}$ alkynyl are each optionally substituted by 1, 2, 3, or 4 independently selected $R^{7a}$ groups;

each $R^{a7}$, $R^{c7}$, and $R^{d7}$ is independently selected from H, $C_{1-6}$ alkyl, and $C_{1-6}$ haloalkyl, wherein said $C_{1-6}$ alkyl is optionally substituted with 1, 2, 3, or 4 independently selected $R^{7a}$ groups;

each $R^{b7}$ is independently selected from $C_{1-6}$ alkyl and $C_{1-6}$ haloalkyl, wherein said $C_{1-6}$ alkyl is optionally substituted with 1, 2, 3, or 4 independently selected $R^{7a}$ groups;

$R^{4a}$, $R^{5a}$, $R^{6a}$, and $R^{7a}$ are independently selected from halo, CN, $NO_2$, $C_{1-6}$ alkyl, $C_{2-6}$ alkenyl, $C_{2-6}$ alkynyl, $C_{1-6}$ haloalkyl, $OR^{a9}$, $SR^{a9}$, $C(=O)R^{b9}$, $C(=O)NR^{c9}R^{d9}$, $C(=O)OR^{a9}$, $OC(=O)R^{b9}$, $OC(=O)NR^{c9}R^{d9}$, $NR^{c9}R^{d9}$, $NR^{c9}C(=O)R^{b9}$, $NR^{c9}C(=O)OR^{b9}$, $NR^{c9}C(=O)NR^{c9}R^{d9}$, $C(=NR^e)R^{b9}$, $NR^{c9}S(=O)_2R^{b9}$, $NR^{c9}S(=O)_2NR^{c9}R^{d9}$, $S(=O)_2R^{b9}$, and $S(=O)_2NR^{c9}R^{d9}$, wherein said $C_{1-6}$ alkyl, $C_{2-6}$ alkenyl, and $C_{2-6}$ alkynyl,are each optionally substituted by 1, 2, 3, or 4 independently selected $R^{11}$ groups;

each $R^{a9}$, $R^{c9}$, and $R^{d9}$ is independently selected from H, $C_{1-6}$ alkyl, and $C_{1-6}$ haloalkyl, wherein said $C_{1-6}$ alkyl is optionally substituted with 1, 2, 3, or 4 independently selected $R^{11}$ groups;

each $R^{b9}$ is independently selected from $C_{1-6}$ alkyl and $C_{1-6}$ haloalkyl, wherein said $C_{1-6}$ alkyl are each optionally substituted with 1, 2, or 3 independently selected $R^{11}$ groups;

each is independently selected from OH, $NO_2$, CN, halo, $C_{1-6}$ alkyl, $C_{2-6}$ alkenyl, $C_{2-6}$ alkynyl, $C_{1-6}$ haloalkyl, cyano-$C_{1-6}$ alkyl, HO-$C_{1-6}$ alkyl, $C_{1-6}$ alkoxy-$C_{1-6}$ alkyl, $C_{3-7}$ cycloalkyl, $C_{1-6}$ alkoxy, $C_{1-6}$ haloalkoxy, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-4}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

Ring moiety A is selected from phenyl, 4-6 membered heterocycloalkyl, and 5-6 membered heteroaryl, each of which is optionally substituted by 1, 2, 3, or 4 independently selected $R^A$ groups;

Ring moiety B is selected from phenyl, 4-6 membered heterocycloalkyl, and 5-6 membered heteroaryl, each of which is optionally substituted by 1, 2, 3, or 4 independently selected $R^B$ groups;

each $R^A$ is independently selected from halo, CN, $NO_2$, $C_{1-6}$ alkyl, $C_{2-6}$ alkenyl, $C_{2-6}$ alkynyl, $C_{1-6}$ haloalkyl, $C_{3-5}$ cycloalkyl, $OR^{a1}$, $SR^{a1}$, $C(=O)R^{b1}$, $C(=O)NR^{c1}R^{d1}$, $C(=O)OR^{a1}$, $OC(=O)R^{b1}$, $OC(=O)NR^{c1}R^{d1}$, $NR^{c1}R^{d1}$, $NR^{c1}C(=O)R^{b1}$, $NR^{c1}C(=O)OR^{b1}$, $NR^{c1}C(=O)NR^{c1}R^{d1}$, $C(=NR^e)R^{b1}$, $C(=NR^e)NR^{c1}R^{d1}$, $NR^{c1}C(=NR^e)NR^{c1}R^{d1}$, $NR^{c1}S(=O)_2R^{b2}$, $NR^{c1}S(=O)_2NR^{c1}R^{d1}$, $S(=O)_2R^{b1}$, and $S(=O)_2NR^{c1}R^{d1}$, wherein said $C_{1-6}$ alkyl, $C_{2-6}$ alkenyl, and $C_{2-6}$ alkynyl are each optionally substituted by 1, 2, 3, or 4 independently selected $R^{A1}$ groups;

each $R^B$ is independently selected from halo, CN, $NO_2$, $C_{1-6}$ alkyl, $C_{2-6}$ alkenyl, $C_{2-6}$ alkynyl, $C_{1-6}$ haloalkyl, $C_{3-5}$ cycloalkyl, $OR^{a1}$, $SR^{a1}$, $C(=O)R^{b1}$, $C(=O)NR^{c1}R^{d1}$, $C(=O)OR^{a1}$, $OC(=O)R^{b1}$, $OC(=O)NR^{c1}R^{d1}$, $NR^{c1}R^{d1}$, $NR^{c1}C(=O)R^{b1}$, $NR^{c1}C(=O)OR^{b1}$, $NR^{c1}C(=O)NR^{c1}R^{d1}$, $C(=NR^e)R^{b1}$, $C(=NR^e)NR^{c1}R^{d1}$, $NR^{c1}C(=NR^e)NR^{c1}R^{d1}$, $NR^{c1}S(=O)_2R^{b2}$, $NR^{c1}S(=O)_2NR^{c1}R^{d1}$, $S(=O)_2R^{b1}$, and $S(=O)_2NR^{c1}R^{d1}$, wherein said $C_{1-6}$ alkyl, $C_{2-6}$ alkenyl, and $C_{2-6}$ alkynyl are each optionally substituted by 1, 2, 3, or 4 independently selected $R^{B1}$ groups;

each $R^{a12}$, $R^{c12}$, and $R^{d12}$ is independently selected from H, $C_{1-6}$ alkyl, and $C_{1-6}$ haloalkyl, wherein said $C_{1-6}$ alkyl is optionally substituted with 1, 2, 3, or 4 independently selected $R^G$ groups;

each $R^{b12}$ is independently selected from $C_{1-6}$ alkyl and $C_{1-6}$ haloalkyl, wherein said $C_{1-6}$ alkyl is optionally substituted with 1, 2, or 3 independently selected $R^G$ groups;

each $R^{A1}$ and $R^{B1}$ is independently selected from H, halo, CN, $C_{1-6}$ alkyl, and $C_{1-6}$ haloalkyl;

n is 0 or 1;
m is 0 or 1;
s is 0 or 1;
wherein n+m+s=1 or 2;

when n is 1, $R^1$ and $R^2$ taken together form a linking group $L^1$;

when m is 1, one of $R^A$ and one of $R^B$ taken together form a linking group $L^2$;

when s is 1, $R^Q$ and $R^4$ taken together form a linking group $L^3$;

$L^1$, $L^2$, and $L^3$ are each independently selected from -R-R-, -R-R-R-, -Cy-, -R-Cy-, -Cy-R-, and -R-Cy-R-;

each R is independently M, $C_{1-6}$ alkylene, $C_{2-6}$ alkenylene, $C_{2-6}$ alkynylene, $C_{1-6}$ alkylene-M, or M-$C_{1-6}$ alkylene, wherein each of said $C_{1-6}$ alkylene, $C_{2-6}$ alkenylene, and $C_{2-6}$ alkynylene is optionally substituted by 1, 2, 3, or 4 groups independently selected $R^G$ groups;

each Cy is independently selected from $C_{3-14}$ cycloalkyl, phenyl, 4-14 membered heterocycloalkyl, and 5-6 membered heteroaryl, each of which is optionally substituted by 1, 2, 3, or 4 independently selected $R^G$ groups;

each M is independently —O—, —C(O)—, —C(O)$NR^L$—, —OC(O)$NR^L$—, —$NR^L$—, —$NR^L$C(O)—, —$NR^L$C(O)O—, —$NR^L$S(O)$_2$—, —S(O)$_2$—, or —S(O)$_2NR^L$—, provided that when M is attached to a nitrogen atom, then M is selected from —C(O)—, —C(O)$NR^L$—, —C(O)O—, —S(O)$_2$—, or —S(O)$_2NR^L$—;

each $R^L$ is independently selected from H and $C_{1-3}$ alkyl; and each $R^G$ is independently selected from OH, $NO_2$, CN, halo, $C_{1-3}$ alkyl, $C_{2-3}$ alkenyl, $C_{2-3}$ alkynyl, $C_{1-3}$ haloalkyl, cyano-$C_{1-3}$ alkyl, HO-$C_{1-3}$ alkyl, $C_{1-3}$ alkoxy-$C_{1-3}$ alkyl, $C_{3-7}$ cycloalkyl, $C_{1-3}$ alkoxy, $C_{1-3}$ haloalkoxy, amino, $C_{1-3}$ alkylamino, di($C_{1-3}$ alkyl)amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl)carbamyl, carboxy, $C_{1-3}$ alkylcarbonyl, $C_{1-4}$ alkoxycarbonyl, $C_{1-3}$ alkylcarbonylamino, $C_{1-3}$ alkylsulfonylamino, aminosulfonyl, $C_{1-3}$ alkylaminosulfonyl, di($C_{1-3}$ alkyl)aminosulfonyl, aminosulfonylamino, $C_{1-3}$ alkylaminosulfonylamino, di($C_{1-3}$ alkyl)aminosulfonylamino, aminocarbonylamino, $C_{1-3}$ alkylaminocarbonylamino, and di($C_{1-3}$ alkyl)aminocarbonylamino.

In some embodiments:
U is $CR^U$;
V is $CR^V$;
W is $CR^W$;
Q is $CR^Q$;
$R^U$ is H, halo, CN, $C_{1-6}$ alkyl, $C_{1-6}$ haloalkyl, or C(=O)$NR^cR^d$;
$R^V$ is H, halo, CN, $C_{1-6}$ alkyl, $C_{1-6}$ haloalkyl, or C(=O)$NR^cR^d$;
$R^W$ is H, halo, CN, $C_{1-6}$ alkyl, $C_{1-6}$ haloalkyl, or C(=O)$NR^cR^d$;
$R^Q$ is H, halo, CN, $C_{1-6}$ alkyl, $C_{1-6}$ haloalkyl, or C(=O)$NR^cR^d$;
each $R^c$ and $R^d$ is independently selected from H, $C_{1-6}$ alkyl, and $C_{1-6}$ haloalkyl;
X is $CR^X$;
$R^X$ is selected from H, D, halo, CN, $C_{1-6}$ alkyl, and $C_{1-6}$ haloalkyl;
Y is N;
Z is N;
$R^1$ is H, $C_{1-6}$ alkyl, or $C_{1-6}$ haloalkyl;
$R^2$, $R^4$, $R^5$, $R^6$, and $R^7$ are each independently selected from H, halo, CN, OH, $C_{1-6}$ alkyl, $C_{1-6}$ haloalkyl, $C_{1-6}$ alkoxy, $C_{1-6}$ haloalkoxy, amino, $C_{1-6}$ alkylamino, di($C_{1-6}$ alkyl)amino, carbamyl, $C_{1-6}$ alkylcarbamyl, and di($C_{1-6}$ alkyl)carbamyl;
$R^3$ is H;
Ring moiety A is a pyrazole ring, which is optionally substituted by 1, 2, or 3 independently selected $R^A$ groups;
Ring moiety B is a pyrazole ring, which is optionally substituted by 1, 2, or 3 independently selected $R^B$ groups;
each $R^A$ is independently selected from halo, CN, $C_{1-6}$ alkyl, and $C_{1-6}$ haloalkyl;
each $R^B$ is independently selected from halo, CN, $C_{1-6}$ alkyl, and $C_{1-6}$ haloalkyl;
n is 0 or 1;
m is 0 or 1;
s is 0 or 1;
wherein n+m+s=1 or 2;
when n is 1, $R^1$ and $R^2$ taken together form a linking group $L^1$;
when m is 1, one of $R^A$ and one of $R^B$ taken together form a linking group $L^2$;
when s is 1, $R^Q$ and $R^4$ taken together form a linking group $L^3$;
$L^1$ is —$CH_2$—CH=CH—$CH_2$—;
$L^2$ is —$CH_2$—CH=CH—$CH_2$—; and
$L^3$ is —$CH_2$—CH=CH—$CH_2$—.

In some embodiments:

U is $CR^U$;
V is $CR^V$;
W is $CR^W$;
Q is $CR^Q$;
$R^U$ is H, halo, CN, $C_{1-6}$ alkyl, $C_{1-6}$ haloalkyl, $C_{1-6}$ alkoxy, $C_{1-6}$ haloalkoxy, or $C(=O)NR^cR^d$;
$R^V$ is H, halo, CN, $C_{1-6}$ alkyl, $C_{1-6}$ haloalkyl, $C_{1-6}$ alkoxy, $C_{1-6}$ haloalkoxy, or $C(=O)NR^cR^d$;
$R^W$ is H, halo, CN, $C_{1-6}$ alkyl, $C_{1-6}$ haloalkyl, $C_{1-6}$ alkoxy, $C_{1-6}$ haloalkoxy, or $C(=O)NR^cR^d$;
$R^Q$ is H, halo, CN, $C_{1-6}$ alkyl, $C_{1-6}$ haloalkyl, $OR^a$, or $C(=O)NR^cR^d$;
$R^a$ is selected from H, $C_{1-6}$ alkyl, $C_{1-6}$ haloalkyl, $C_{2-6}$ alkenyl, and $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^8$ groups;
each $R^8$ is independently selected from OH, $NO_2$, CN, halo, $C_{1-3}$ alkyl, $C_{2-3}$ alkenyl, $C_{2-3}$ alkynyl, $C_{1-3}$ haloalkyl, $C_{1-3}$ alkoxy, $C_{1-3}$ haloalkoxy, amino, $C_{1-3}$ alkylamino, and di($C_{1-3}$ alkyl)amino;
each $R^c$ and $R^d$ is independently selected from H, $C_{1-6}$ alkyl, and $C_{1-6}$ haloalkyl;
X is $CR^X$;
Y is $CR^Y$ or N;
Z is $CR^Z$ or N;
$R^X$ is selected from H, D, halo, CN, $C_{1-6}$ alkyl, and $C_{1-6}$ haloalkyl;
$R^3$ is H;
$R^5$, $R^6$, and $R^7$ are each independently selected from H, halo, CN, OH, $C_{1-6}$ alkyl, $C_{1-6}$ haloalkyl, $C_{1-6}$ alkoxy, $C_{1-6}$ haloalkoxy, amino, $C_{1-6}$ alkylamino, di($C_{1-6}$ alkyl)amino, carbamyl, $C_{1-6}$ alkylcarbamyl, and di($C_{1-6}$ alkyl)carbamyl;
$R^4$ is H, $C_{1-6}$ alkyl, or $OR^{a4}$;
$R^{a4}$ is selected from H, $C_{1-6}$ alkyl, $C_{1-6}$ haloalkyl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1 or 2 independently selected $R^{4a}$ groups;
each $R^{4a}$ is independently selected from CN, halo, $C_{1-6}$ alkyl, $C_{2-6}$ alkenyl, $C_{2-6}$ alkynyl, $C_{1-6}$ haloalkyl, $OR^{a9}$, $C(=O)R^{b9}$, $C(=O)NR^{c9}R^{d9}$, $C(=O)OR^{a9}$, $OC(=O)R^{b9}$, $OC(=O)NR^{c9}R^{d9}$, $NR^{c9}R^{d9}$, $NR^{c9}C(=O)R^{b9}$, $NR^{c9}C(=O)OR^{b9}$, $NR^{c9}C(=O)NR^{c9}R^{d9}$, $NR^{c9}S(=O)_2R^{b9}$, $NR^{c9}S(=O)_2NR^{c9}R^{d9}$, and $S(=O)_2R^{b9}$;
each $R^{a9}$, $R^{c9}$, and $R^{d9}$ independently selected from H, $C_{1-6}$ alkyl, $C_{1-6}$ haloalkyl, $C_{3-7}$ cycloalkyl, phenyl, 4-7 membered heterocycloalkyl, and 5-6 membered heteroaryl, wherein said $C_{1-6}$ alkyl, $C_{1-6}$ haloalkyl, $C_{3-7}$ cycloalkyl, phenyl, 4-7 membered heterocycloalkyl, and 5-6 membered heteroaryl are each optionally substituted by 1 or 2 independently selected $R^{11}$ groups;
each $R^{b9}$ is independently selected from $C_{1-6}$ alkyl, $C_{1-6}$ haloalkyl, $C_{3-7}$ cycloalkyl, phenyl, 4-7 membered heterocycloalkyl, and 5-6 membered heteroaryl, each of which is optionally substituted by 1, 2, or 3 independently selected $R^{11}$ groups;
each $R^{11}$ is independently selected from $C_{1-3}$ alkyl and $C_{1-3}$ haloalkyl;
Ring moiety A is a pyrazole ring, which is optionally substituted by 1, 2, or 3 independently selected $R^A$ groups;
Ring moiety B is a pyrazole ring, which is optionally substituted by 1, 2, or 3 independently selected $R^B$ groups;
each $R^A$ is independently selected from halo, CN, $C_{1-6}$ alkyl, and $C_{1-6}$ haloalkyl;
each $R^B$ is independently selected from halo, CN, $C_{1-6}$ alkyl, and $C_{1-6}$ haloalkyl;
n is 1;
m is 0;
s is 0;
$R^1$ and $R^2$ taken together form a linking group $L^1$; and
$L^1$ is $-CH_2-CH=CH-CH_2-$.

In some embodiments:
U is $CR^U$;
V is $CR^V$;
W is $CR^W$;
Q is $CR^Q$;
$R^U$ is H, halo, CN, $C_{1-6}$ alkyl, $C_{1-6}$ haloalkyl, $C_{1-6}$ alkoxy, $C_{1-6}$ haloalkoxy, or $C(=O)NR^cR^d$;
$R^V$ is H, halo, CN, $C_{1-6}$ alkyl, $C_{1-6}$ haloalkyl, $C_{1-6}$ alkoxy, $C_{1-6}$ haloalkoxy, or $C(=O)NR^cR^d$;
$R^W$ is H, halo, CN, $C_{1-6}$ alkyl, $C_{1-6}$ haloalkyl, $C_{1-6}$ alkoxy, $C_{1-6}$ haloalkoxy, or $C(=O)NR^cR^d$;
$R^Q$ is H, halo, CN, $C_{1-6}$ alkyl, $C_{1-6}$ haloalkyl, $OR^a$, or $C(=O)NR^cR^d$;
$R^a$ is selected from H, $C_{1-6}$ alkyl, $C_{1-6}$ haloalkyl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1 or 2 independently selected $R^8$ groups;
each $R^8$ is independently selected from OH, $NO_2$, CN, halo, $C_{1-3}$ alkyl, $C_{2-3}$ alkenyl, $C_{2-3}$ alkynyl, $C_{1-3}$ haloalkyl, $C_{1-3}$ alkoxy, $C_{1-3}$ haloalkoxy, amino, $C_{1-3}$ alkylamino, and di($C_{1-3}$ alkyl)amino;
each $R^c$ and $R^d$ is independently selected from H, $C_{1-6}$ alkyl, and $C_{1-6}$ haloalkyl;
X is $CR^X$;
Y is $CR^Y$ or N;
Z is $CR^Z$ or N;
$R^X$ is selected from H, D, halo, CN, $C_{1-6}$ alkyl, and $C_{1-6}$ haloalkyl;
$R^3$ is H;
$R^5$, $R^6$, and $R^7$ are each independently selected from H, halo, CN, OH, $C_{1-6}$ alkyl, $C_{1-6}$ haloalkyl, $C_{1-6}$ alkoxy, $C_{1-6}$ haloalkoxy, amino, $C_{1-6}$ alkylamino, di($C_{1-6}$ alkyl)amino, carbamyl, $C_{1-6}$ alkylcarbamyl, and di($C_{1-6}$ alkyl)carbamyl;
$R^4$ is H, $C_{1-6}$ alkyl, or $OR^{a4}$;
$R^{a4}$ is selected from H, $C_{1-6}$ alkyl, $C_{1-6}$ haloalkyl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1 or 2 independently selected $R^{4a}$ groups;
each $R^{4a}$ is independently selected from CN, $OR^{a9}$, $C(=O)R^{b9}$, $C(=O)NR^{c9}R^{d9}$, $C(=O)OR^{a9}$, $OC(=O)R^{b9}$, OC(=O)NR$^{c9}$R$^{d9}$, NR$^{c9}$R$^{d9}$, NR$^{c9}$C(=O)R$^{b9}$, and NR$^{c9}$S(=O)$_2$R$^{b9}$, NR$^{c9}$S(=O)$_2$NR$^{c9}$R$^{d9}$;

each R$^{a9}$, R$^{c9}$, and R$^{d9}$ independently selected from H, C$_{1-6}$ alkyl, C$_{1-6}$ haloalkyl, C$_{3-7}$ cycloalkyl, phenyl, 4-7 membered heterocycloalkyl, and 5-6 membered heteroaryl, wherein said C$_{1-6}$ alkyl, C$_{1-6}$ haloalkyl, C$_{3-7}$ cycloalkyl, phenyl, 4-7 membered heterocycloalkyl, and 5-6 membered heteroaryl are each optionally substituted by 1 or 2 independently selected R$^{11}$ groups;

each R$^{b9}$ is independently selected from C$_{1-6}$ alkyl, C$_{1-6}$ haloalkyl, C$_{3-7}$ cycloalkyl, phenyl, 4-7 membered heterocycloalkyl, and 5-6 membered heteroaryl, each of which is optionally substituted by 1, 2, or 3 independently selected groups;

each R$^{11}$ is independently selected from C$_{1-3}$ alkyl and C$_{1-3}$ haloalkyl;

Ring moiety A is a pyrazole ring, which is optionally substituted by 1, 2, or 3 independently selected R$^A$ groups;

Ring moiety B is a pyrazole ring, which is optionally substituted by 1, 2, or 3 independently selected R$^B$ groups;

each R$^A$ is independently selected from halo, CN, C$_{1-6}$ alkyl, and C$_{1-6}$ haloalkyl;

each R$^B$ is independently selected from halo, CN, C$_{1-6}$ alkyl, and C$_{1-6}$ haloalkyl;

n is 1;

m is 0;

s is 0;

R$^1$ and R$^2$ taken together form a linking group L$^1$; and

L$^1$ is —CH$_2$—CH=CH—CH$_2$—.

The following formulas can be combined with any of the aforementioned embodiments.

In some embodiments, the compound is a compound of Formula (II):

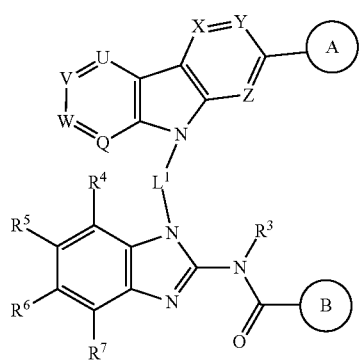

or a pharmaceutically acceptable salt thereof.

In some embodiments, the compound is a compound of Formula (III):

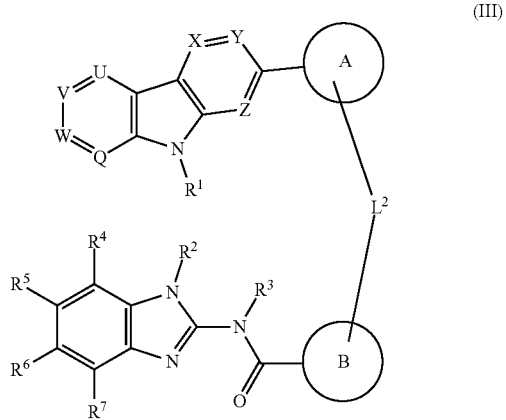

or a pharmaceutically acceptable salt thereof.

In some embodiments, the compound is a compound of Formula (IV):

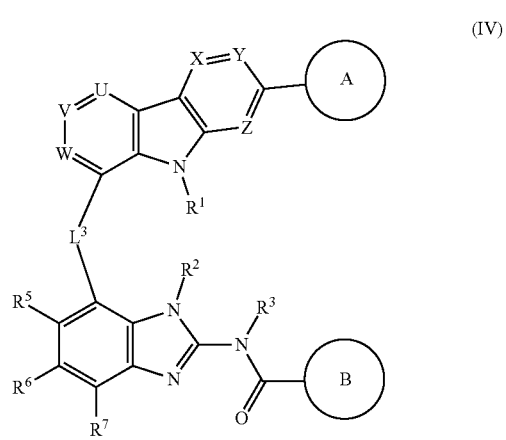

or a pharmaceutically acceptable salt thereof.

In some embodiments, the compound is a compound of Formula (V):

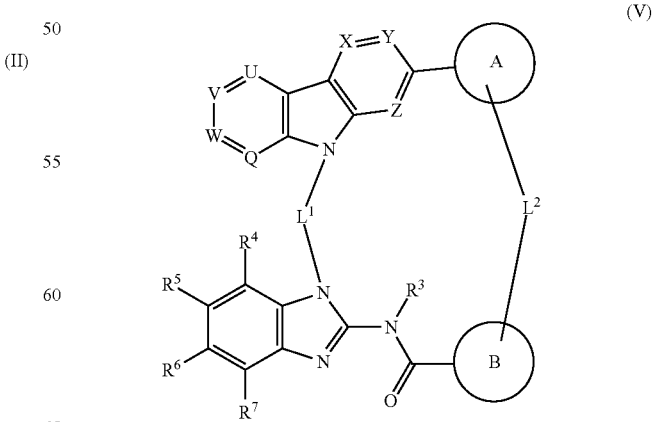

or a pharmaceutically acceptable salt thereof.

In some embodiments, the compound is a compound of Formula (VI):

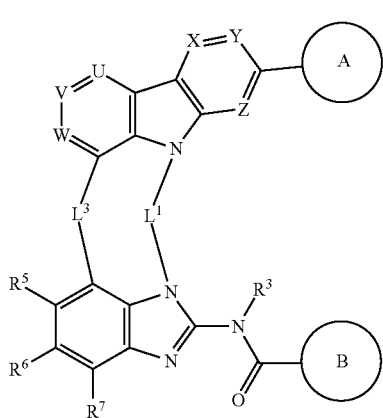

(VI)

or a pharmaceutically acceptable salt thereof.

In some embodiments, the compound is a compound of Formula (VII):

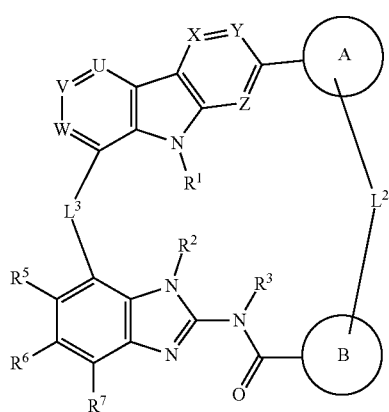

(VII)

or a pharmaceutically acceptable salt thereof.

In some embodiments, the compound is a compound of Formula (IIa):

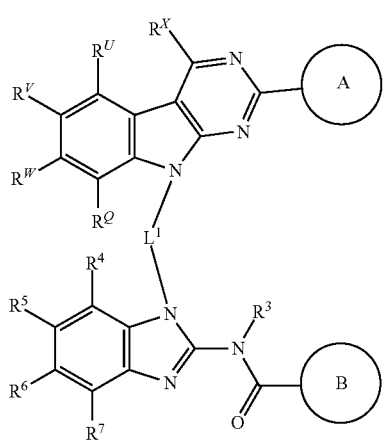

(IIa)

or a pharmaceutically acceptable salt thereof.

In some embodiments, the compound is a compound of Formula (IIIa):

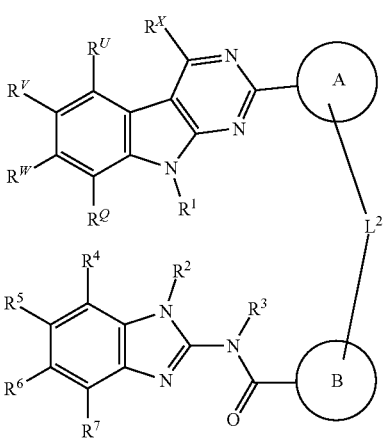

(IIIa)

or a pharmaceutically acceptable salt thereof.

In some embodiments, the compound is a compound of Formula (IVa):

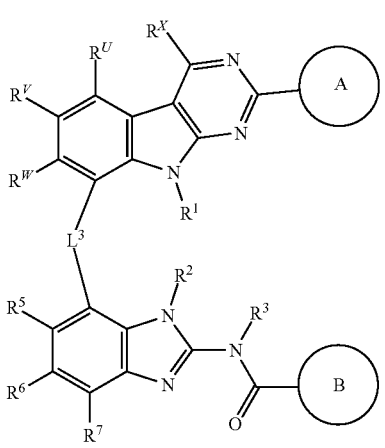

(IVa)

or a pharmaceutically acceptable salt thereof.

In some embodiments, the compound is a compound of Formula (Va):

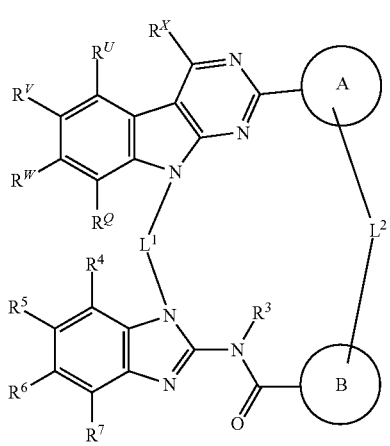

(Va)

or a pharmaceutically acceptable salt thereof.

In some embodiments, the compound is a compound of Formula (VIa):

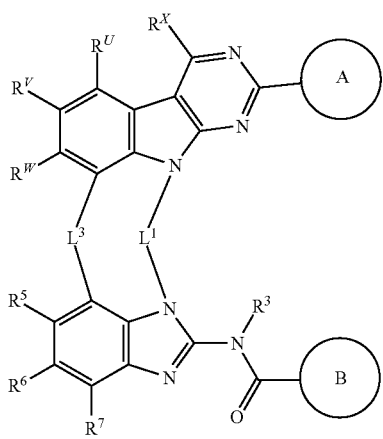

(VIa)

or a pharmaceutically acceptable salt thereof.

In some embodiments, the compound is a compound of Formula (VIIa):

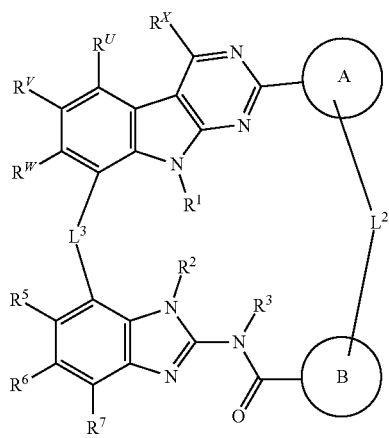

(VIIa)

or a pharmaceutically acceptable salt thereof.

In some embodiments, the compound is a compound of Formula (VIII):

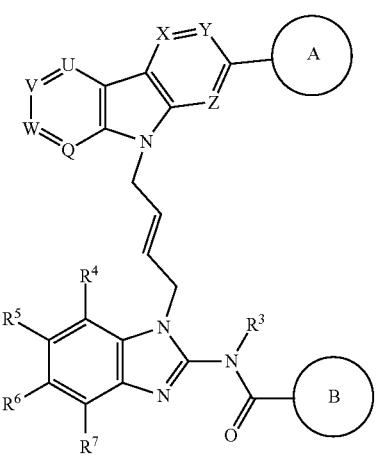

(VIII)

or a pharmaceutically acceptable salt thereof.

In some embodiments, the compound is a compound of Formula (IX):

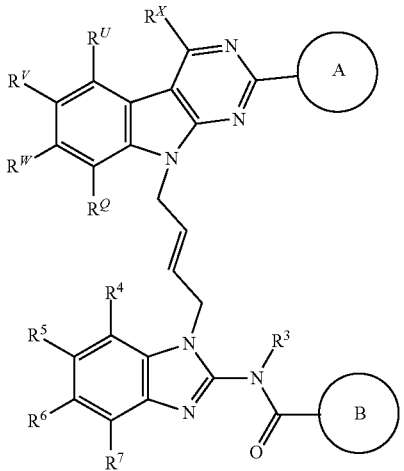

(IX)

or a pharmaceutically acceptable salt thereof.

In some embodiments of the compounds of Formula (X):

$R^V$ is H, halo, CN, $C_{1-4}$ alkyl, $C_{1-4}$ haloalkyl, carbamyl, or $C_{1-4}$ alkylcarbamyl;

$R^U$ and $R^W$ are each independently selected from H, halo, CN, $C_{1-4}$ alkyl, and $C_{1-4}$ haloalkyl;

$R^Q$ is selected from H, $C_{1-6}$ alkyl, $OR^a$, and $OR^f$, wherein said $C_{1-6}$ alkyl is optionally substituted by 1 or 2 independently selected $R^8$ groups;

$R^a$ is selected from H, $C_{1-6}$ alkyl, $C_{1-6}$ haloalkyl, and 4-7 membered heterocycloalkyl-$C_{1-4}$ alkyl, wherein said $C_{1-6}$ alkyl and 4-7 membered heterocycloalkyl-$C_{1-4}$ alkyl are each optionally substituted with 1 or 2 independently selected $R^8$ groups;

$R^f$ is $C_{1-6}$ alkyl which is substituted with 1 substituent selected from $R^{90}$ and —$NHR^{80}$;

each $R^8$ is independently selected from H, halo, CN, $C_{1-6}$ alkyl, $C_{1-6}$ haloalkyl, $OR^{a8}$, $C(=O)OR^{a8}$, $OC(=O)R^{b8}$, $OC(=O)NR^{c8}R^{d8}$, $NR^{c8}R^{d8}$, $NR^{c8}C(=O)R^{b8}$, $NHC(=O)NHR^{d8}$, $NR^{c8}S(=O)_2R^{b8}$, and $NR^{c8}C(=O)OR^{b8}$;

each $R^{a8}$, $R^{c8}$, and $R^{d8}$ is independently selected from H, $C_{1-6}$ alkyl, $C_{1-6}$ haloalkyl, $C_{3-7}$ cycloalkyl, phenyl, 4-7 membered heterocycloalkyl, and 5-6 membered heteroaryl, wherein said $C_{1-6}$ alkyl, $C_{3-7}$ cycloalkyl, phenyl, 4-7 membered heterocycloalkyl, and 5-6 membered heteroaryl are each optionally substituted with 1 or 2 independently selected $R^{10}$ groups;

each $R^{b8}$ is independently selected from $C_{1-6}$ alkyl, $C_{1-6}$ haloalkyl, $C_{3-7}$ cycloalkyl, phenyl, 4-7 membered heterocycloalkyl, and 5-6 membered heteroaryl, wherein said $C_{1-6}$ alkyl, $C_{3-7}$ cycloalkyl, phenyl, 4-7 membered heterocycloalkyl, and 5-6 membered heteroaryl are each optionally substituted with 1 or 2 independently selected $R^{10}$ groups;

each $R^{10}$ is independently selected from H, halo, CN, $C_{1-6}$ alkyl, $C_{1-6}$ haloalkyl, $OR^{a10}$, $NR^{c10}R^{d10}$, and $C(=O)OR^{a10}$, wherein said $C_{1-6}$ alkyl is optionally substituted by 1 or 2 independently selected $R^G$ groups;

each $R^{a10}$ is independently selected from H and $C_{1-6}$ alkyl, wherein said $C_{1-6}$ alkyl is optionally substituted with 1 or 2 independently selected $R^G$ groups;

$R^{80}$ is a linear peptide chain having 2-4 amino acids;

$R^{90}$ is a linear chain of formula —(O-$C_{2-4}$ alkylene)$_z$— $R^G$, wherein z is 1, 2, 3, or 4;

Y is N or $CR^Y$;

Z is N or $CR^Z$;

wherein at least one of Y or Z is N;

$R^X$, $R^Y$, and $R^Z$ are each independently selected from H, halo, CN, $C_{1-3}$ alkyl, and $C_{1-3}$ haloalkyl;

Ring moiety A is a pyrazole ring, which is optionally substituted by 1, 2, or 3 independently selected $R^A$ groups;

Ring moiety B is a pyrazole ring, which is optionally substituted by 1, 2, or 3 independently selected $R^B$ groups;

$L^1$ is selected from -R-R- and -R-R-R-;

each R is independently $C_{1-3}$ alkylene or $C_{2-3}$ alkenylene;

each $R^A$ is independently selected from $C_{1-6}$ alkyl and $C_{1-6}$ haloalkyl;

each $R^B$ is independently selected from $C_{1-6}$ alkyl and $C_{1-6}$ haloalkyl;

$R^4$ is selected from H, $C_{1-6}$ alkyl, $OR^{a4}$, and $OR^{f4}$, wherein said $C_{1-6}$ alkyl is optionally substituted by 1 or 2 independently selected $R^{4a}$ groups;

$R^6$ is H, halo, CN, $C_{1-4}$ alkyl, $C_{1-4}$ haloalkyl, carbamyl, or $C_{1-4}$ alkylcarbamyl;

$R^5$ and $R^7$ are each independently selected from H, halo, CN, $C_{1-4}$ alkyl, and $C_{1-4}$ haloalkyl;

$R^{a4}$ is selected from H, $C_{1-6}$ alkyl, $C_{1-6}$ haloalkyl, and 4-7 membered heterocycloalkyl-$C_{1-4}$ alkyl, wherein said $C_{1-6}$ alkyl and 4-7 membered heterocycloalkyl-$C_{1-4}$ alkyl are each optionally substituted with 1 or 2 independently selected $R^8$ groups;

$R^{f4}$ is $C_{1-6}$ alkyl which is substituted with 1 substituent selected from $R^{90}$ and —$NHR^{80}$;

each $R^{4a}$ is independently selected from H, halo, CN, $C_{1-6}$ alkyl, $C_{1-6}$ haloalkyl, $OR^{a9}$, $C(=O)OR^{a9}$, $OC(=O)R^{b9}$, $OC(=O)NR^{c9}R^{d9}$, $NR^{c9}R^{d9}$, $NR^{c9}C(=O)R^{b9}$, $NHC(=O)NHR^{d9}$, $NR^{c9}S(=O)_2R^{b9}$, and $NR^{c9}C(=O)OR^{b9}$;

each $R^{a9}$, $R^{c9}$, and $R^{d9}$ is independently selected from H, $C_{1-6}$ alkyl, $C_{1-6}$ haloalkyl, $C_{3-7}$ cycloalkyl, phenyl, 4-7 membered heterocycloalkyl, and 5-6 membered heteroaryl, wherein said $C_{1-6}$ alkyl, $C_{3-7}$ cycloalkyl, phenyl, 4-7 membered heterocycloalkyl, and 5-6 membered heteroaryl are each optionally substituted with 1 or 2 independently selected $R^{11}$ groups;

each $R^{b9}$ is independently selected from $C_{1-6}$ alkyl, $C_{1-6}$ haloalkyl, $C_{3-7}$ cycloalkyl, phenyl, 4-7 membered heterocycloalkyl, and 5-6 membered heteroaryl, wherein said $C_{1-6}$ alkyl, $C_{3-7}$ cycloalkyl, phenyl, 4-7 membered heterocycloalkyl, and 5-6 membered heteroaryl are each optionally substituted with 1 or 2 independently selected $R^{11}$ groups;

each $R^{11}$ is independently selected from H, halo, CN, $C_{1-6}$ alkyl, $C_{1-6}$ haloalkyl, $OR^{a11}$, $NR^{c11}R^{d11}$, and $C(=O)OR^{a11}$, wherein said $C_{1-6}$ alkyl is optionally substituted by 1 or 2 independently selected $R^G$ groups;

each $R^{a11}$ is independently selected from H and $C_{1-6}$ alkyl, wherein said $C_{1-6}$ alkyl is optionally substituted with 1 or 2 independently selected $R^G$ groups;

each $R^{c11}$ and $R^{d11}$ independently selected from H and $C_{1-6}$ alkyl, wherein said $C_{1-6}$ alkyl is optionally substituted with 1 or 2 independently selected $R^G$ groups;

each $R^G$ is independently selected from H, D, OH, $NO_2$, CN, halo, $C_{1-3}$ alkyl, $C_{2-3}$ alkenyl, $C_{2-3}$ alkynyl, $C_{1-3}$ haloalkyl, cyano-$C_{1-3}$ alkyl, HO-$C_{1-3}$ alkyl, $C_{1-3}$ alkoxy-$C_{1-3}$ alkyl, $C_{3-7}$ cycloalkyl, $C_{1-3}$ alkoxy, $C_{1-3}$ haloalkoxy, amino, $C_{1-3}$ alkylamino, di($C_{1-3}$ alkyl)amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl)carbamyl, carboxy, $C_{1-3}$ alkylcarbonyl, $C_{1-4}$ alkoxycarbonyl, $C_{1-3}$ alkylcarbonylamino, $C_{1-3}$ alkylsulfonylamino, aminosulfonyl, $C_{1-3}$ alkylaminosulfonyl, di($C_{1-3}$ alkyl)aminosulfonyl, aminosulfonylamino, $C_{1-3}$ alkylaminosulfonylamino, di($C_{1-3}$ alkyl)aminosulfonylamino, aminocarbonylamino, $C_{1-3}$ alkylaminocarbonylamino, and di($C_{1-3}$ alkyl)aminocarbonylamino.

In some embodiments of the compounds of Formula (X):

$R^V$ is H or carbamyl;

$R^U$ and $R^W$ are each independently selected from H, halo, CN, and $C_{1-3}$ alkyl;

$R^Q$ is selected from H, $C_{1-6}$ alkyl, $OR^a$, and $OR^f$;

$R^a$ is selected from H, $C_{1-6}$ alkyl, $C_{1-6}$ haloalkyl, and 4-7 membered heterocycloalkyl-$C_{1-4}$ alkyl, wherein said $C_{1-6}$ alkyl and 4-7 membered heterocycloalkyl-$C_{1-4}$ alkyl are each optionally substituted with 1 or 2 independently selected $R^8$ groups;

each $R^8$ is independently selected from H, halo, CN, $C_{1-6}$ alkyl, $C_{1-6}$ haloalkyl, $OR^{a8}$, $C(=O)OR^{a8}$, $OC(=O)R^{b8}$, $OC(=O)NR^{c8}R^{d8}$, $NR^{c8}R^{d8}$, $NR^{c8}C(=O)R^{b8}$, $NHC(=O)NHR^{d8}$, $NR^{c8}S(=O)_2R^{b8}$, and $NR^{c8}C(=O)OR^{b8}$;

each $R^{a8}$, $R^{c8}$, and $R^{d8}$ is independently selected from H, $C_{1-6}$ alkyl, and $C_{1-6}$ haloalkyl, wherein said $C_{1-6}$ alkyl is optionally substituted with 1 or 2 independently selected $R^{10}$ groups;

each $R^{b8}$ is independently selected from $C_{1-6}$ alkyl, $C_{1-6}$ haloalkyl, and 5-membered heteroaryl, wherein said $C_{1-6}$ alkyl and 5-membered heteroaryl are each optionally substituted with 1 or 2 independently selected $R^{10}$ groups;

each $R^{10}$ is independently selected from H, halo, CN, $C_{1-6}$ alkyl, $C_{1-6}$ haloalkyl, $OR^{a10}$, $NR^{c10}R^{d10}$, and $C(=O)OR^{a10}$, wherein said $C_{1-6}$ alkyl is optionally substituted by 1 or 2 independently selected $R^G$ groups;

each $R^{a10}$ is independently selected from H and $C_{1-6}$ alkyl, wherein said $C_{1-6}$ alkyl is optionally substituted with 1 or 2 independently selected $R^G$ groups;

Y is N or $CR^Y$;

Z is N or $CR^Z$;

wherein at least one of Y or Z is N;

$R^X$, $R^Y$, and $R^Z$ are each independently selected from H, halo, CN, $C_{1-3}$ alkyl, and $C_{1-3}$ haloalkyl;

Ring moiety A is a pyrazole ring, which is optionally substituted by 1 or 2 independently selected $R^A$ groups;

Ring moiety B is a pyrazole ring, which is optionally substituted by 1 or 2 independently selected $R^B$ groups;

$L^1$ is $C_{3-6}$ alkenylene;

each $R^A$ is independently selected from $C_{1-6}$ alkyl and $C_{1-6}$ haloalkyl;

each $R^B$ is independently selected from $C_{1-6}$ alkyl and $C_{1-6}$ haloalkyl;

$R^4$ is selected from H, $C_{1-6}$ alkyl, $OR^{a4}$, and $OR^{f4}$, wherein said $C_{1-6}$ alkyl is optionally substituted by 1 or 2 independently selected $R^{4a}$ groups;

$R^6$ is H or carbamyl;

$R^5$ and $R^7$ are each independently selected from H, halo, CN, and $C_{1-3}$ alkyl;

$R^{a4}$ is selected from H, $C_{1-6}$ alkyl, $C_{1-6}$ haloalkyl, and 4-7 membered heterocycloalkyl-$C_{1-4}$ alkyl, wherein said $C_{1-6}$ alkyl and 4-7 membered heterocycloalkyl-$C_{1-4}$ alkyl are each optionally substituted with 1 or 2 independently selected $R^{4a}$ groups;

$R^{f4}$ is $C_{1-6}$ alkyl which is substituted with 1 substituent selected from $R^{90}$ and $-NHR^{80}$;

each $R^{4a}$ is independently selected from H, halo, CN, $C_{1-6}$ alkyl, $C_{1-6}$ haloalkyl, $OR^{a9}$, $OC(=O)R^{b9}$, $OC(=O)NR^{c9}R^{d9}$, $NR^{c9}R^{d9}$, $NR^{c9}C(=O)R^{b9}$, $NHC(=O)NHR^{d9}$, $NR^{c9}S(=O)_2R^{b9}$, and $NR^{c9}C(=O)OR^{b9}$;

$R^{80}$ is a linear peptide chain having 2-4 amino acids;

$R^{90}$ is a linear chain of formula $-(O-C_{2-4}$ alkylene$)_z-R^G$, wherein z is 1, 2, 3, or 4;

each $R^{a9}$, $R^{c9}$, and $R^{d9}$ is independently selected from H, $C_{1-6}$ alkyl, and $C_{1-6}$ haloalkyl, wherein said $C_{1-6}$ alkyl is optionally substituted with 1 or 2 independently selected $R^{11}$ groups;

each $R^{b9}$ is independently $C_{1-6}$ alkyl, which is optionally substituted with 1 or 2 independently selected $R^{11}$ groups;

each $R^{11}$ is independently selected from H, halo, CN, $C_{1-6}$ alkyl, $C_{1-6}$ haloalkyl, $OR^{a11}$, $NR^{c11}R^{d11}$ and $C(=O)OR^{a11}$, wherein said $C_{1-6}$ alkyl is optionally substituted by 1 or 2 independently selected $R^G$ groups;

each $R^{a11}$ is independently selected from H and $C_{1-6}$ alkyl, wherein said $C_{1-6}$ alkyl is optionally substituted with 1 or 2 independently selected $R^G$ groups;

each $R^{c11}$ and $R^{d11}$ independently selected from H and $C_{1-6}$ alkyl, wherein said $C_{1-6}$ alkyl is optionally substituted with 1 or 2 independently selected $R^G$ groups; and each $R^G$ is independently selected from H, OH, CN, halo, $C_{1-3}$ alkyl, $C_{1-3}$ alkoxy, $C_{1-3}$ amino, $C_{1-3}$ alkylamino, di($C_{1-3}$ alkyl)amino, and carboxy.

In further embodiments of the compounds of Formula (X), Ring moiety A is a pyrazole ring, which is optionally substituted by 1 or 2 independently selected $R^A$ groups; Ring moiety B is a pyrazole ring, which is optionally substituted by 1 or 2 independently selected $R^B$ groups; each $R^A$ and $R^B$ is independently selected from $C_{1-4}$ alkyl; and $L^1$ is $-CH_2-CH=CH-CH_2-$.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

The term "n-membered" where n is an integer typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

As used herein, the phrase "optionally substituted" means unsubstituted or substituted. The substituents are independently selected, and substitution may be at any chemically accessible position. As used herein, the term "substituted" means that a hydrogen atom is removed and replaced by a substituent. A single divalent substituent, e.g., oxo, can replace two hydrogen atoms. It is to be understood that substitution at a given atom is limited by valency, that the designated atom's normal valency is not exceeded, and that the substitution results in a stable compound.

As used herein, the phrase "each 'variable' is independently selected from" means substantially the same as wherein "at each occurance 'variable' is selected from."

When any variable (e.g., $R^8$) occurs more than one time in any constituent or formula for a compound, its definition at each occurrence is independent of its definition at every other occurrence. Thus, for example, if a group is shown to be substituted with 1, 2, 3, or 4 $R^8$, then said group may optionally be substituted with up to four $R^8$ groups and $R^8$ at each occurrence is selected independently from the definition of $R^8$. Also, combinations of substituents and/or variables are permissible only if such combinations result in stable compounds; for example the combination of a first M group and second M group in the combination of two R groups are permissible only if such combinations of M-M result in stable compounds.

Throughout the definitions, the term "$C_{n-m}$" indicates a range which includes the endpoints, wherein n and m are integers and indicate the number of carbons. Examples include $C_{1-4}$, $C_{1-6}$, and the like.

As used herein, the term "$C_{n-m}$ alkyl", employed alone or in combination with other terms, refers to a saturated hydrocarbon group that may be straight-chain or branched, having n to m carbons. Examples of alkyl moieties include, but are not limited to, chemical groups such as methyl (Me), ethyl (Et), n-propyl (n-Pr), isopropyl (iPr), n-butyl, tert-butyl, isobutyl, sec-butyl; higher homologs such as 2-methyl-1-butyl, n-pentyl, 3-pentyl, n-hexyl, 1,2,2-trimethylpropyl, and the like. In some embodiments, the alkyl group contains from 1 to 6 carbon atoms, from 1 to 4 carbon atoms, from 1 to 3 carbon atoms, or 1 to 2 carbon atoms.

As used herein, "$C_{n-m}$ alkenyl" refers to an alkyl group having one or more double carbon-carbon bonds and having n to m carbons. Example alkenyl groups include, but are not limited to, ethenyl, n-propenyl, isopropenyl, n-butenyl, sec-butenyl, and the like. In some embodiments, the alkenyl moiety contains 2 to 6, 2 to 4, or 2 to 3 carbon atoms.

As used herein, "$C_{n-m}$ alkynyl" refers to an alkyl group having one or more triple carbon-carbon bonds and having n to m carbons. Example alkynyl groups include, but are not limited to, ethynyl, propyn-1-yl, propyn-2-yl, and the like. In some embodiments, the alkynyl moiety contains 2 to 6, 2 to 4, or 2 to 3 carbon atoms. As used herein, the term "$C_{n-m}$ alkoxy", employed alone or in combination with other terms, refers to a group of formula —O-alkyl, wherein the alkyl group has n to m carbons. Example alkoxy groups include, but are not limited to, methoxy, ethoxy, propoxy (e.g., n-propoxy and isopropoxy), butoxy (e.g., n-butoxy and tert-butoxy), and the like. In some embodiments, the alkyl group has 1 to 6, 1 to 4, or 1 to 3 carbon atoms.

As used herein, the term "amino" refers to a group of formula —$NH_2$.

As used herein, the term "aryl," employed alone or in combination with other terms, refers to an aromatic hydrocarbon group, which may be monocyclic or polycyclic (e.g., having 2, 3 or 4 fused rings). The term "$C_{n-m}$ aryl" refers to an aryl group having from n to m ring carbon atoms. Aryl groups include, e.g., phenyl, naphthyl, anthracenyl, phenanthrenyl, indanyl, indenyl, and the like. In some embodiments, the aryl group has from 5 to 10 carbon atoms. In some embodiments, the aryl group is phenyl or naphthyl. In some embodiments, the aryl is phenyl.

As used herein, "halo" refers to F, Cl, Br, or I. In some embodiments, halo is F, Cl, or Br. In some embodiments, halo is F or Cl. In some embodiments, halo is F. In some embodiments, halo is Cl.

As used herein, "$C_{n-m}$ haloalkoxy" refers to a group of formula —O-haloalkyl having n to m carbon atoms. Example haloalkoxy groups include $OCF_3$ and $OCHF_2$. In some embodiments, the haloalkoxy group is fluorinated only. In some embodiments, the alkyl group has 1 to 6, 1 to 4, or 1 to 3 carbon atoms.

As used herein, the term "$C_{n-m}$ haloalkyl", employed alone or in combination with other terms, refers to an alkyl group having from one halogen atom to 2s+1 halogen atoms which may be the same or different, where "s" is the number of carbon atoms in the alkyl group, wherein the alkyl group has n to m carbon atoms. In some embodiments, the haloalkyl group is fluorinated only. In some embodiments, the alkyl group has 1 to 6, 1 to 4, or 1 to 3 carbon atoms. Example haloalkyl groups include $CF_3$, $C_2F_5$, $CHF_2$, $CH_2F$, $CCl_3$, $CHCl_2$, $C_2Cl_5$ and the like.

As used herein, the term "thio" refers to a group of formula —SH.

As used herein, the term "carbamyl" to a group of formula —$C(O)NH_2$.

As used herein, the term "carbonyl", employed alone or in combination with other terms, refers to a —C(O)— group.

As used herein, the term "$C_{n-m}$ alkylamino" refers to a group of formula —NH(alkyl), wherein the alkyl group has n to m carbon atoms. In some embodiments, the alkyl group has 1 to 6, 1 to 4, or 1 to 3 carbon atoms.

As used herein, the term "$C_{n-m}$ alkoxycarbonyl" refers to a group of formula —C(O)O-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylcarbonyl" refers to a group of formula —C(O)-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylcarbonylamino" refers to a group of formula —NHC(O)-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfonylamino" refers to a group of formula —$NHS(O)_2$-alkyl, wherein the alkyl group has n to m carbon atoms. In some embodiments, the alkyl group has 1 to 6, 1 to 4, or 1 to 3 carbon atoms.

As used herein, the term "aminosulfonyl" refers to a group of formula —$S(O)_2NH_2$.

As used herein, the term "$C_{n-m}$ alkylaminosulfonyl" refers to a group of formula —$S(O)_2$NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminosulfonyl" refers to a group of formula —$S(O)_2N(alkyl)_2$, wherein each alkyl group independently has n to m carbon atoms. In some embodiments, each alkyl group has, independently, 1 to 6, 1 to 4, or 1 to 3 carbon atoms.

As used herein, the term "aminosulfonylamino" refers to a group of formula —$NHS(O)_2NH_2$.

As used herein, the term "$C_{n-m}$ alkylaminosulfonylamino" refers to a group of formula —$NHS(O)_2$NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminosulfonylamino" refers to a group of formula —$NHS(O)_2N(alkyl)_2$, wherein each alkyl group independently has n to m carbon atoms. In some embodiments, each alkyl group has, independently, 1 to 6, 1 to 4, or 1 to 3 carbon atoms.

As used herein, the term "aminocarbonylamino", employed alone or in combination with other terms, refers to a group of formula —$NHC(O)NH_2$.

As used herein, the term "$C_{n-m}$ alkylaminocarbonylamino" refers to a group of formula —NHC(O)NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminocarbonylamino" refers to a group of formula —$NHC(O)N(alkyl)_2$, wherein each alkyl group independently has n to m carbon atoms. In some embodiments, each alkyl group has, independently, 1 to 6, 1 to 4, or 1 to 3 carbon atoms.

As used herein, the term "$C_{n-m}$ alkylcarbamyl" refers to a group of formula —C(O)—NH(alkyl), wherein the alkyl group has n to m carbon atoms. In some embodiments, the alkyl group has 1 to 6, 1 to 4, or 1 to 3 carbon atoms.

As used herein, the term "$C_{n-m}$ alkylthio" refers to a group of formula —S-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfinyl" refers to a group of formula —S(O)-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfonyl" refers to a group of formula —S(O)$_2$-alkyl, wherein the alkyl group has n to m carbon atoms. In some embodiments, the alkyl group has 1 to 6, 1 to 4, or 1 to 3 carbon atoms.

As used herein, the term "cyano-$C_{1-6}$ alkyl" refers to a group of formula -($C_{1-6}$ alkylene)—CN.

As used herein, the term "HO-$C_{1-6}$ alkyl" refers to a group of formula -($C_{1-6}$ alkylene)—OH.

As used herein, the term "$C_{1-6}$ alkoxy-$C_{1-6}$ alkyl" refers to a group of formula -($C_{1-6}$ alkylene)—O($C_{1-6}$ alkyl).

As used herein, the term "carboxy" refers to a group of formula —C(O)OH.

As used herein, the term "di($C_{n-m}$-alkyl)amino" refers to a group of formula —N(alkyl)$_2$, wherein the two alkyl groups each has, independently, n to m carbon atoms. In some embodiments, each alkyl group independently has 1 to 6, 1 to 4, or 1 to 3 carbon atoms.

As used herein, the term "di($C_{n-m}$-alkyl)carbamyl" refers to a group of formula —C(O)N(alkyl)$_2$, wherein the two alkyl groups each has, independently, n to m carbon atoms. In some embodiments, each alkyl group independently has 1 to 6, 1 to 4, or 1 to 3 carbon atoms.

As used herein, the term "$C_{n-m}$ alkylcarbonyloxy" is a group of formula —OC(O)-alkyl, wherein the alkyl group has n to m carbon atoms.

As used herein, "aminocarbonyloxy" is a group of formula —OC(O)—NH$_2$.

As used herein, "$C_{n-m}$ alkylaminocarbonyloxy" is a group of formula —OC(O)—NH-alkyl, wherein the alkyl group has n to m carbon atoms.

As used herein, "di($C_{n-m}$ alkyl)aminocarbonyloxy" is a group of formula —OC(O)—N(alkyl)$_2$, wherein each alkyl group has, independently, n to m carbon atoms.

As used herein $C_{n-m}$ alkoxycarbonylamino refers to a group of formula —NHC(O)—O-alkyl, wherein the alkyl group has n to m carbon atoms.

As used herein, "cycloalkyl" refers to non-aromatic cyclic hydrocarbons including cyclized alkyl and alkenyl groups. Cycloalkyl groups can include mono- or polycyclic (e.g., having 2, 3 or 4 fused rings) groups, spirocycles, and bridged rings (e.g., a bridged bicycloalkyl group). Ring-forming carbon atoms of a cycloalkyl group can be optionally substituted by oxo or sulfido (e.g., C(O) or C(S)). Also included in the definition of cycloalkyl are moieties that have one or more aromatic rings fused (i.e., having a bond in common with) to the cycloalkyl ring, for example, benzo or thienyl derivatives of cyclopentane, cyclohexane, and the like. A cycloalkyl group containing a fused aromatic ring can be attached through any ring-forming atom including a ring-forming atom of the fused aromatic ring. Cycloalkyl groups can have 3, 4, 5, 6, 7, 8, 9, 10, 11, 12, 13 or 14 ring-forming carbons (i.e., $C_{3-14}$). In some embodiments, the cycloalkyl is a $C_{3-14}$ monocyclic or bicyclic cycloalkyl. In some embodiments, the cycloalkyl is a $C_{3-7}$ monocyclic cycloalkyl. In some embodiments, the cycloalkyl is a $C_{4-7}$ monocyclic cycloalkyl. In some embodiments, the cycloalkyl is a $C_{4-10}$ spirocycle or bridged cycloalkyl (e.g., a bridged bicycloalkyl group). Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, cubane, adamantane, bicyclo[1.1.1]pentyl, bicyclo[2.1.1]hexyl, bicyclo[2.2.1]heptanyl, bicyclo[3.1.1]heptanyl, bicyclo [2.2.2]octanyl, spiro[3.3]heptanyl, and the like. In some embodiments, cycloalkyl is cyclopropyl, cyclobutyl, cyclopentyl, or cyclohexyl.

As used herein, "heteroaryl" refers to a monocyclic or polycyclic (e.g., having 2, 3, or 4 fused rings) aromatic heterocycle having at least one heteroatom ring member selected from N, O, S and B. In some embodiments, the heteroaryl ring has 1, 2, 3, or 4 heteroatom ring members independently selected from N, O, S and B. In some embodiments, any ring-forming N in a heteroaryl moiety can be an N-oxide. In some embodiments, the heteroaryl is a 5-10 membered monocyclic or bicyclic heteroaryl having 1, 2, 3, or 4 heteroatom ring members independently selected from N, O, S and B. In some embodiments, the heteroaryl is a 5-10 membered monocyclic or bicyclic heteroaryl having 1, 2, 3, or 4 heteroatom ring members independently selected from N, O, S and B. In some embodiments, the heteroaryl is a 5-10 membered monocyclic or bicyclic heteroaryl having 1, 2, 3, or 4 heteroatom ring members independently selected from N, O, and S. In some embodiments, the heteroaryl is a 5-6 monocyclic heteroaryl having 1 or 2 heteroatom ring members independently selected from N, O, S and B. In some embodiments, the heteroaryl is a 5-6 monocyclic heteroaryl having 1 or 2 heteroatom ring members independently selected from N, O, and S. In some embodiments, the heteroaryl group contains 5-10 or 5-6 ring-forming atoms. In some embodiments, the heteroaryl group has 1 to 4 ring-forming heteroatoms, 1 to 3 ring-forming heteroatoms, 1 to 2 ring-forming heteroatoms or 1 ring-forming heteroatom. When the heteroaryl group contains more than one heteroatom ring member, the heteroatoms may be the same or different. Example heteroaryl groups include, but are not limited to, pyridine, pyrimidine, pyrazine, pyridazine, pyrrole, pyrazole, azolyl, oxazole, isoxazole, thiazole, isothiazole, imidazole, furan, thiophene, triazole, tetrazole, thiadiazole, quinoline, isoquinoline, indole, benzothiophene, benzofuran, benzisoxazole, imidazo[1,2-b]thiazole, purine, triazine, thieno[3,2-b]pyridine, imidazo[1,2-a]pyridine, 1,5-naphthyridine, 1H-pyrazolo[4,3-b]pyridine, and the like.

A five-membered heteroaryl is a heteroaryl group having five ring-formimg atoms wherein one or more (e.g., 1, 2, or 3) of the ring-forming atoms are independently selected from N, O, S or B. Exemplary five-membered ring heteroaryls are thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, 1,3,4-oxadiazolyl and 1,2-dihydro-1,2-azaborine.

A six-membered heteroaryl ring is a heteroaryl with a ring having six ring atoms wherein one or more (e.g., 1, 2, or 3) ring atoms are independently selected from N, O, S and B. Exemplary six-membered ring heteroaryls are pyridyl, pyrazinyl, pyrimidinyl, triazinyl and pyridazinyl.

As used herein, "heterocycloalkyl" refers to monocyclic or polycyclic heterocycles having at least one non-aromatic ring (saturated or partially unsaturated ring), wherein one or more of the ring-forming carbon atoms of the heterocycloalkyl is replaced by a heteroatom selected from N, O, S and B, wherein the ring-forming carbon atoms and heteroatoms of a heterocycloalkyl group can be optionally substituted by one or more oxo or sulfido (e.g., C(O), S(O), C(S), or S(O)$_2$, etc.). Heterocycloalkyl groups include monocyclic and polycyclic (e.g., having 2, 3 or 4 fused rings) systems. Included in heterocycloalkyl are monocyclic and polycyclic 3-14 or 4-14 membered heterocycloalkyl groups. Heterocycloalkyl groups can also include spirocycles and bridged rings (e.g., a 5-14 membered bridged biheterocycloalkyl ring having one or more of the ring-forming carbon atoms replaced by a heteroatom selected from N, O, S and B). The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds. Also included in the definition of heterocycloalkyl are moieties that have one or more aromatic rings fused (i.e., having a bond in common with) to the non-aromatic heterocyclic ring, for example, benzo or thienyl derivatives of piperidine, morpholine, azepine, etc. A heterocycloalkyl group containing a fused aromatic ring can be attached through any ring-forming atom including a ring-forming atom of the fused aromatic ring. In some embodiments, the heterocycloalkyl group contains 3 to 14 ring-forming atoms, 4 to 14 ring-forming atoms, 3 to 7 ring-forming atoms, or 5 to 6 ring-forming atoms. In some embodiments, the heterocycloalkyl group has 1 to 4 heteroatoms, 1 to 3 heteroatoms, 1 to 2 heteroatoms or 1 heteroatom. In some embodiments, the heterocycloalkyl is a monocyclic 4-6 membered heterocycloalkyl having 1 or 2 heteroatoms independently selected from N, O, S and B and having one or more oxidized ring members.

In some embodiments, the heterocycloalkyl is a monocyclic or bicyclic 5-10 membered heterocycloalkyl having 1, 2, 3, or 4 heteroatoms independently selected from N, O, S and B and having one or more oxidized ring members. In some embodiments, the heterocycloalkyl is a monocyclic or bicyclic 5-10 membered heterocycloalkyl having 1, 2, 3, or 4 heteroatoms independently selected from N, O, and S and having one or more oxidized ring members. In some embodiments, the heterocycloalkyl is a monocyclic 5-6 membered heterocycloalkyl having 1, 2, 3, or 4 heteroatoms independently selected from N, O, and S and having one or more oxidized ring members. Example heterocycloalkyl groups include pyrrolidin-2-one, 1,3-isoxazolidin-2-one, pyranyl, tetrahydropyran, oxetanyl, azetidinyl, morpholino, thiomorpholino, piperazinyl, tetrahydrofuranyl, tetrahydrothienyl, piperidinyl, pyrrolidinyl, isoxazolidinyl, isothiazolidinyl, pyrazolidinyl, oxazolidinyl, thiazolidinyl, imidazolidinyl, azepanyl, benzazapene, azabicyclo[3.1.0]hexanyl, diazabicyclo[3.1.0]hexanyl, oxabicyclo[2.1.1]hexanyl, azabicyclo[2.2.1]heptanyl, diazabicyclo[2.2.1]heptanyl, azabicyclo[3.1.1]heptanyl, diazabicyclo[3.1.1]heptanyl, azabicyclo [3.2.1]octanyl, diazabicyclo[3.2.1]octanyl, oxabicyclo[2.2.2]octanyl, azabicyclo[2.2.2]octanyl, azaadamantanyl, diazaadamantanyl, oxa-adamantanyl, azaspiro[3.3]heptanyl, diazaspiro[3.3]heptanyl, oxa-azaspiro[3.3]heptanyl, azaspiro[3.4]octanyl, diazaspiro[3.4]octanyl, oxa-azaspiro[3.4]octanyl, azaspiro[2.5]octanyl, diazaspiro[2.5]octanyl, azaspiro[4.4]nonanyl, diazaspiro[4.4]nonanyl, oxa-azaspiro[4.4]nonanyl, azaspiro[4.5]decanyl, diazaspiro[4.5]decanyl, diazaspiro[4.4]nonanyl, oxa-diazaspiro[4.4]nonanyl and the like. In some embodiments, example heterocycloalkyl group are pyrrolidonyl, pyrrolidin-2-one, 1,3-isoxazolidin-2-one, pyranyl, tetrahydropuran, oxetanyl, azetidinyl, morpholinyl, thiomorpholino, piperazinyl, tetrahydrofuranyl, tetrahydrothienyl, piperidinyl, pyrrolidinyl, isoxazolidinyl, isothiazolidinyl, pyrazolidinyl, oxazolidinyl, thiazolidinyl, imidazolidinyl, azepanyl, and 1,2,3,4-tetrahydroisoquinoline As used herein, "$C_{o-p}$ cycloalkyl-$C_{n-m}$ alkyl-" refers to a group of formula cycloalkyl-alkylene-, wherein the cycloalkyl has o to p carbon atoms and the alkylene linking group has n to m carbon atoms.

As used herein "$C_{o-p}$ aryl-$C_{n-m}$ alkyl-" refers to a group of formula aryl-alkylene-, wherein the aryl has o to p carbon atoms and the alkylene linking group has n to m carbon atoms.

As used herein, "heteroaryl-$C_{n-m}$ malkyl-" refers to a group of formula heteroaryl-alkylene-, wherein alkylene linking group has n to m carbon atoms.

As used herein "heterocycloalkyl-$C_{n-m}$ alkyl-" refers to a group of formula heterocycloalkyl-alkylene-, wherein alkylene linking group has n to m carbon atoms.

As used herein, an "alkyl linking group" is a bivalent straight chain or branched alkyl linking group ("alkylene group"). For example, "$C_{o-p}$ cycloalkyl-$C_{n-m}$ alkyl-", "$C_{o-p}$ aryl-$C_{n-m}$ alkyl-", "phenyl-$C_{n-m}$ alkyl-", "heteroaryl-$C_{n-m}$ alkyl-", and "heterocycloalkyl-$C_{n-m}$ alkyl-" contain alkyl linking groups. Examples of "alkyl linking groups" or "alkylene groups" include methylene, ethan-1,1-diyl, ethan-1,2-diyl, propan-1,3-dilyl, propan-1,2-diyl, propan-1,1-diyl and the like.

As used herein, the term "one of $R^A$ and one of $R^B$ taken together form a linking group $L^2$" means i) ring moiety A has been substituted with at least one $R^A$ group ortho to the bond connecting ring A to the tricyclic heterocycle containing X, Y, and Z, ii) ring moiety B has been substituted with at least one $R^B$ group ortho to the bond connecting ring B to the —$NR^3$—C(=O)-amide, and iii) taken together $R^A$ and $R^B$ form the linking group $L^2$ the definition of which is independent of the definitions of subsitutents $R^A$ and $R^B$ before combination.

At certain places, the definitions or embodiments refer to specific rings (e.g., an azetidine ring, a pyridine ring, etc.). Unless otherwise indicated, these rings can be attached to any ring member provided that the valency of the atom is not exceeded. For example, an azetidine ring may be attached at any position of the ring, whereas a pyridin-3-yl ring is attached at the 3-position.

As used herein, the term "oxo" refers to an oxygen atom (i.e., =O) as a divalent substituent, forming a carbonyl group when attached to a carbon (e.g., C=O or C(O)), or attached to a nitrogen or sulfur heteroatom forming a nitroso, sulfinyl or sulfonyl group.

The compounds described herein can be asymmetric (e.g., having one or more stereocenters). All stereoisomers, such as enantiomers and diastereomers, are intended unless otherwise indicated. Compounds of the present disclosure that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds of the present disclosure are described and may be isolated as a mixture of isomers or as separated isomeric forms. In some embodiments, the compound has the (R)-configuration. In some embodiments, the compound has the (S)-configuration.

Resolution of racemic mixtures of compounds can be carried out by any of numerous methods known in the art. An example method includes fractional recrystallizaion using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as (3-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Compounds provided herein also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone—enol pairs, amide-imidic acid pairs, lactam—lactim pairs, enamine—imine pairs, and annular forms where a proton can occupy two or more positions of a heterocyclic system, for example, 1H- and 3H-imidazole, 1H-, 2H- and 4H-1,2,4-triazole, 1H- and 2H-isoindole, 2-hydroxypyridine and 2-pyridone, and 1H- and 2H-pyrazole. Tautomeric forms can be in equilibrium or sterically locked into one form by appropriate substitution.

All compounds, and pharmaceutically acceptable salts thereof, can be found together with other substances such as water and solvents (e.g. hydrates and solvates) or can be isolated.

In some embodiments, preparation of compounds can involve the addition of acids or bases to affect, for example, catalysis of a desired reaction or formation of salt forms such as acid addition salts.

In some embodiments, the compounds provided herein, or salts thereof, are substantially isolated. By "substantially isolated" is meant that the compound is at least partially or substantially separated from the environment in which it was formed or detected. Partial separation can include, for example, a composition enriched in the compounds provided herein. Substantial separation can include compositions containing at least about 50%, at least about 60%, at least about 70%, at least about 80%, at least about 90%, at least about 95%, at least about 97%, or at least about 99% by weight of the compounds provided herein, or salt thereof. Methods for isolating compounds and their salts are routine in the art.

The term "compound" as used herein is meant to include all stereoisomers, geometric isomers, tautomers, and isotopes of the structures depicted. Compounds herein identified by name or structure as one particular tautomeric form are intended to include other tautomeric forms unless otherwise specified.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present application also includes pharmaceutically acceptable salts of the compounds described herein. The present disclosure also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present disclosure include the conventional non-toxic salts of the parent compound formed, for example, from non-toxic inorganic or organic acids. The pharmaceutically acceptable salts of the present disclosure can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (ACN) are preferred. Lists of suitable salts are found in *Remington's Pharmaceutical Sciences,* 17th ed., Mack Publishing Company, Easton, Pa., 1985, p. 1418 and *Journal of Pharmaceutical Science,* 66, 2 (1977), each of which is incorporated herein by reference in its entirety.

Synthesis

As will be appreciated, the compounds provided herein, including salts and stereoisomers thereof, can be prepared using known organic synthesis techniques and can be synthesized according to any of numerous possible synthetic routes.

Compounds of formula 1-10 can be synthesized using a process shown in Scheme 1. Nucleophilic aromatic substitution of an appropriately functionalized nitro-halo-phenyl compound 1-1 with an amine containing a linker group $L^1$ 1-2 can afford compound 1-3. Reduction of the aromatic nitro group followed by ring closing reaction with cyanogen bromide can provide the aminobenzimidazole 1-5. Amide coupling of compound 1-5 with carboxylic acid 1-6 can generate the aminobenzimidazole 1-7. Removal of the Boc protecting group in 1-7 can afford the amine 1-8 which can be converted to the alcohol 1-9 under Sandmeyer conditions. The compound 1-10 could be achieved by reacting the alcohol 1-9 with phosphorus (III) bromide.

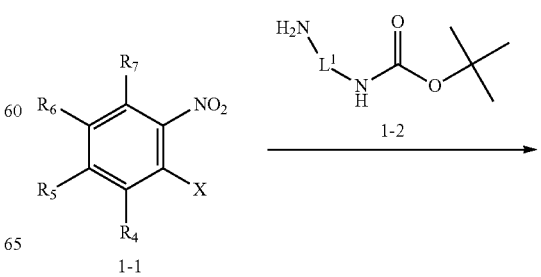

-continued

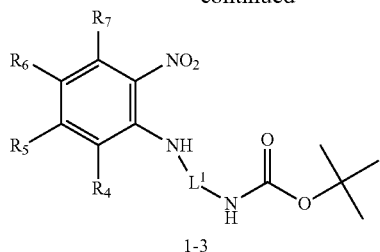
1-3

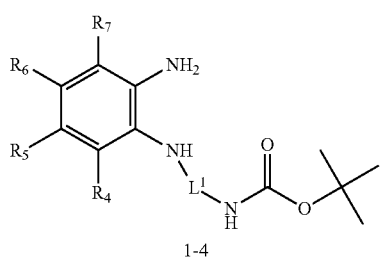
1-4

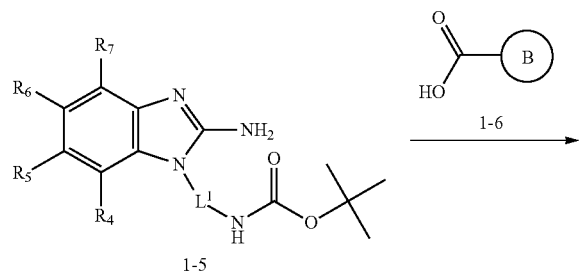
1-5

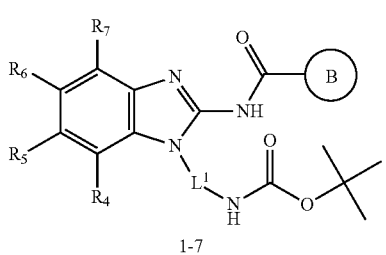
1-7

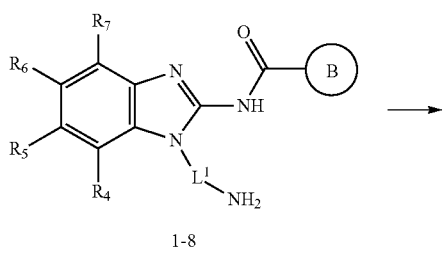
1-8

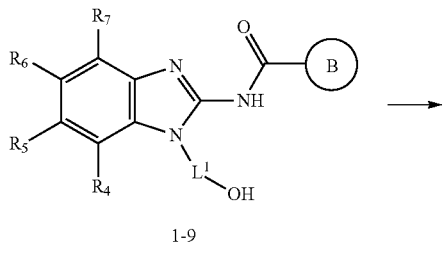
1-9

-continued

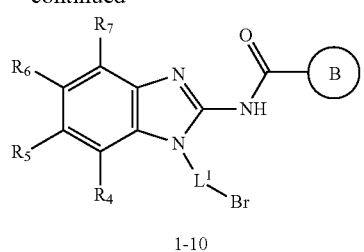
1-10

Compounds of formula 2-8 can be synthesized using a process shown in Scheme 2. Palladium-catalyzed cross-coupling reactions of the appropriate aryl halides and boronic acids/esters can produce the biaryl compounds of formula 2-5. Under deoxygenation conditions, the in-situ generated nitrene from compound 2-5 can insert into the adjacent aromatic C—H bond and afford the tricyclic compound 2-6. Suzuki coupling of the aryl-Cl 2-6 with aromatic boronic ester 2-7 can furnish the compounds of formula 2-8.

Scheme 2

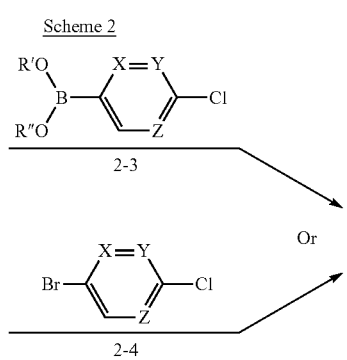

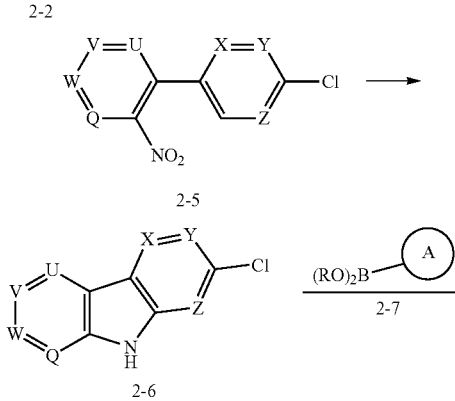

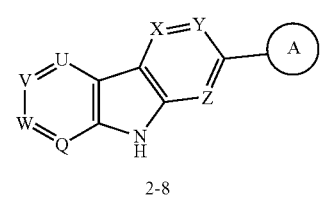
2-8

As shown in Scheme 3, reactions of compounds 3-1 and 3-2 under basic conditions can afford the compound of formula 3-3.

Scheme 3

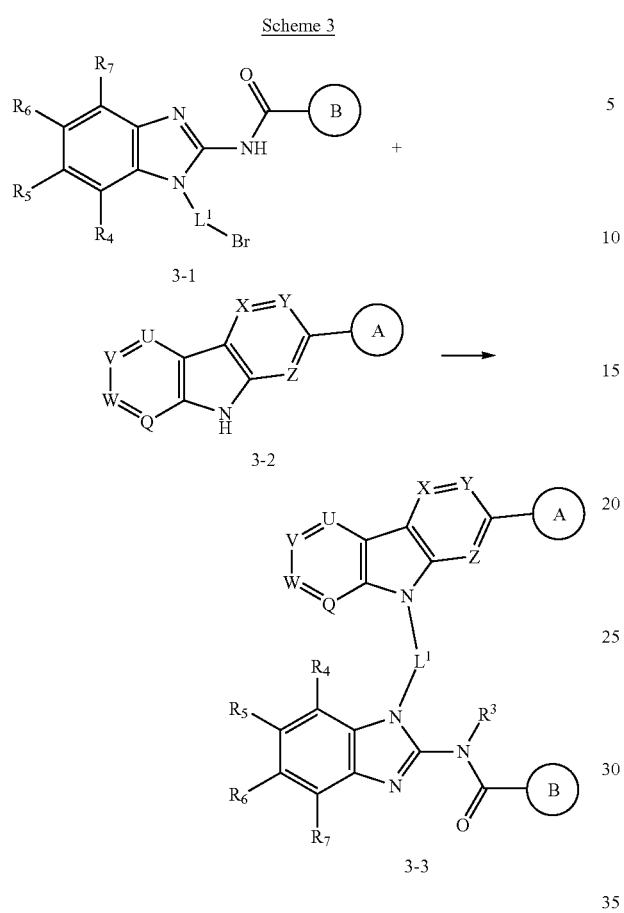

Compounds of formula 4-7 can be synthesized using a process shown in Scheme 4. Reagents 4-1 and 4-2 can be coupled with the suitable linker to form compound 4-3. Two consecutive palladium-catalyzed cross-coupling reactions of the aryl halides and boronic acids/esters can provide compounds of formula 4-5. Under deoxygenation conditions, the in-situ generated nitrene can insert into the adjacent aromatic C—H bond and afford the tricyclic compound 4-6. Finally, N-functionalization on the tricycle can generate the target molecule 4-7.

Scheme 4

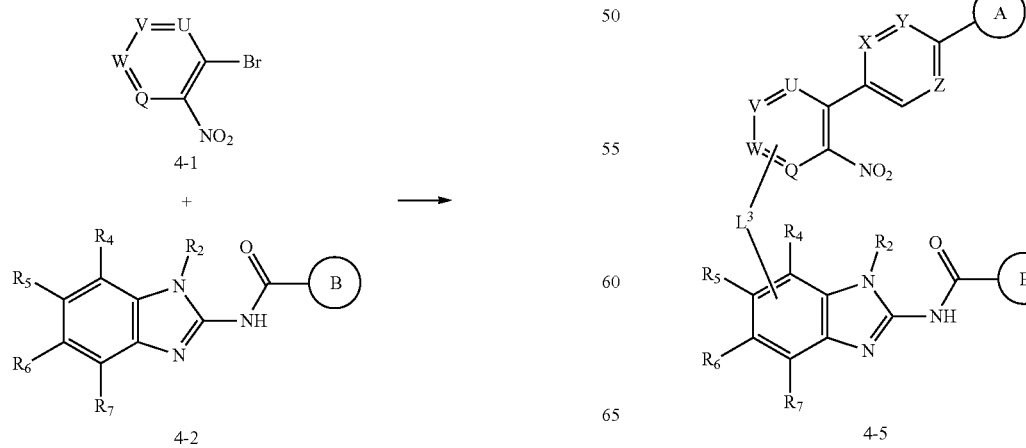

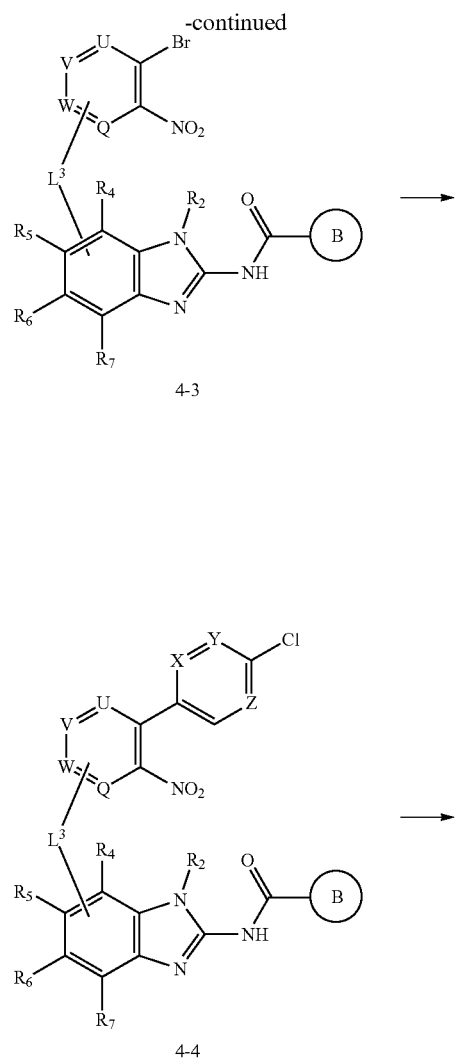

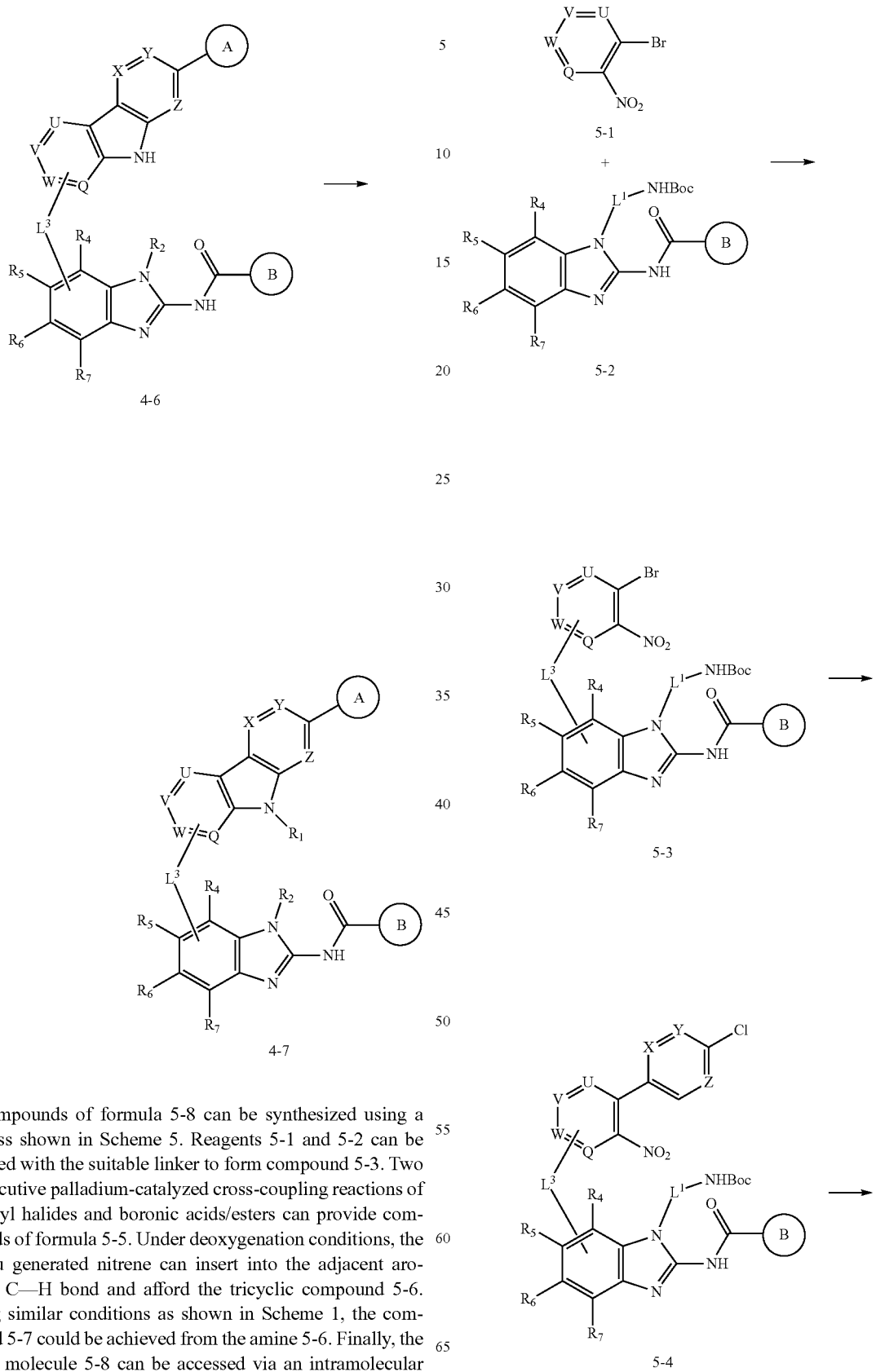

Compounds of formula 5-8 can be synthesized using a process shown in Scheme 5. Reagents 5-1 and 5-2 can be coupled with the suitable linker to form compound 5-3. Two consecutive palladium-catalyzed cross-coupling reactions of the aryl halides and boronic acids/esters can provide compounds of formula 5-5. Under deoxygenation conditions, the in-situ generated nitrene can insert into the adjacent aromatic C—H bond and afford the tricyclic compound 5-6. Using similar conditions as shown in Scheme 1, the compound 5-7 could be achieved from the amine 5-6. Finally, the target molecule 5-8 can be accessed via an intramolecular substitution reaction.

91
-continued
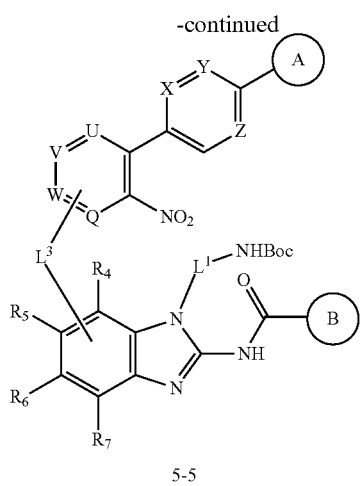
5-5
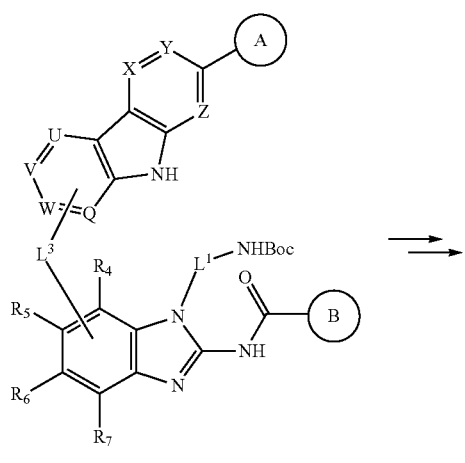
5-6
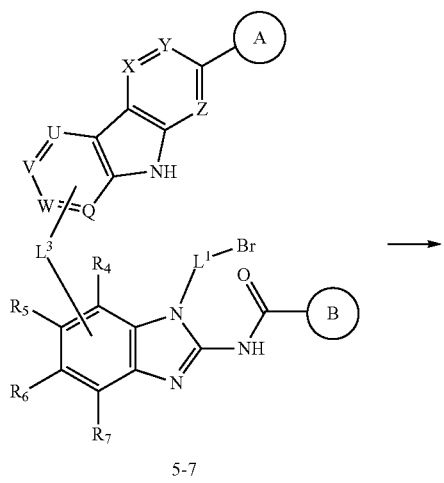
5-7
92
-continued
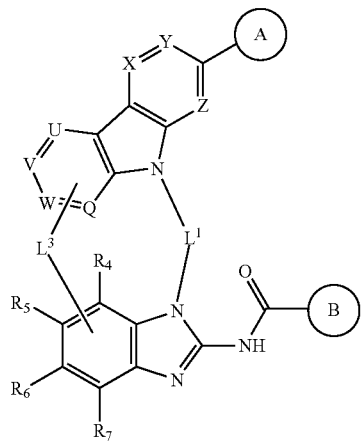
5-8
Compounds of formula 6-5 can be synthesized using a process shown in Scheme 6. Reagents 6-1 and 6-2 can be coupled with the suitable linker to form compound 6-3. Amide coupling of molecule 6-3 with 2-amino-benzimidazole 6-4 can generate the target molecule 6-5.
Scheme 6
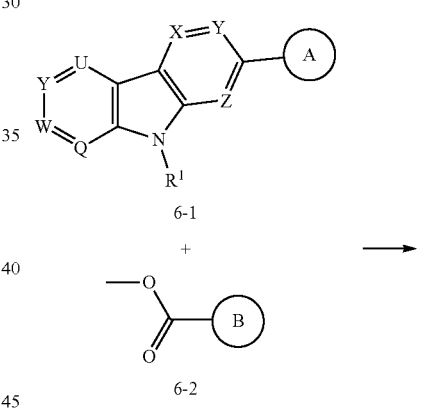
6-1
+
6-2
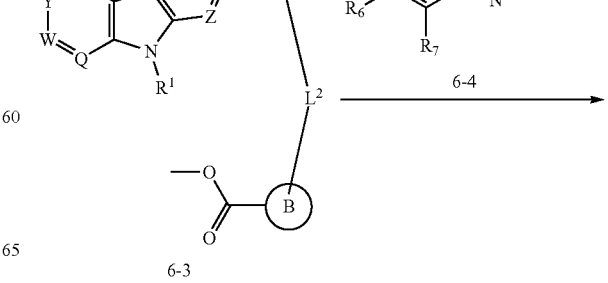
6-3

-continued

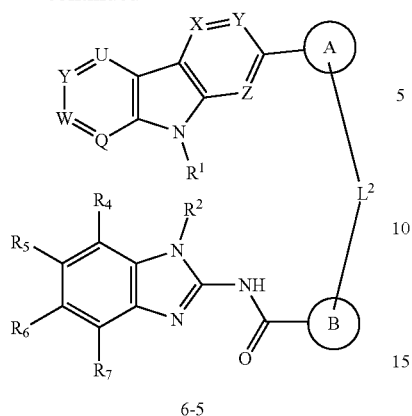

6-5

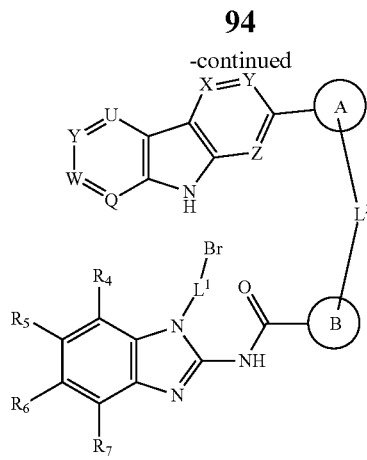

7-4

Compounds of formula 7-5 can be synthesized using a process shown in Scheme 7. Reagents 7-1 and 7-2 can be coupled with the suitable linker to form compound 7-3. Using similar conditions as shown in Scheme 1, the compound 7-4 could be achieved from the amine 7-3. Finally, target compounds 7-5 can be accessed via an intramolecular substitution step under basic conditions.

Scheme 7

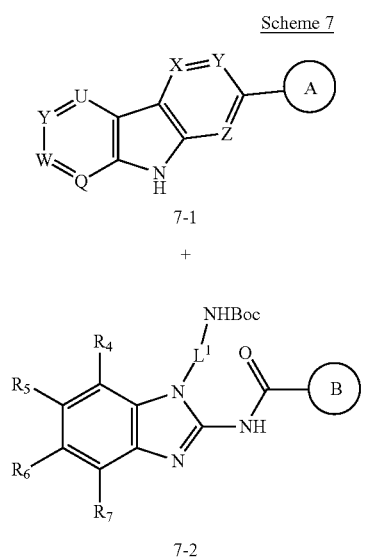

7-5

Compounds of formula 8-6 can be synthesized using a process shown in Scheme 8. Reagents 8-1 and 8-2 can be coupled with the suitable linker to form compound 8-3. Next, reagent 8-3 could be further coupled with compound 8-4 by linker $L^3$ to access intermediate 8-5. Finally, target compounds 8-6 can be accessed via an intramolecular amide coupling step.

Scheme 8

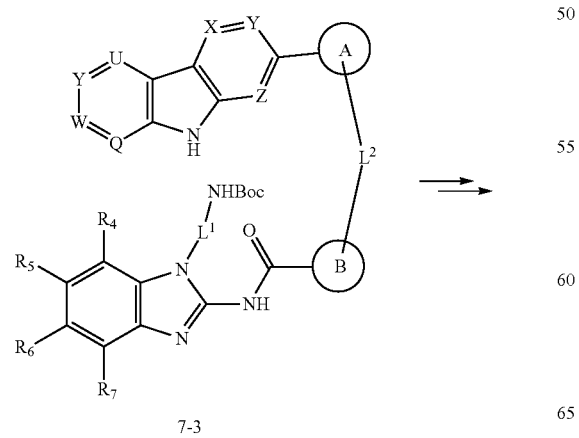

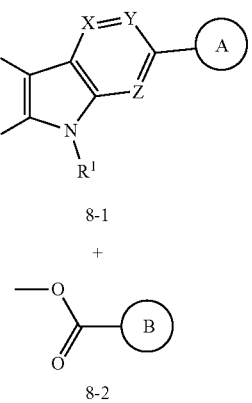

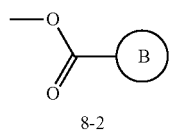

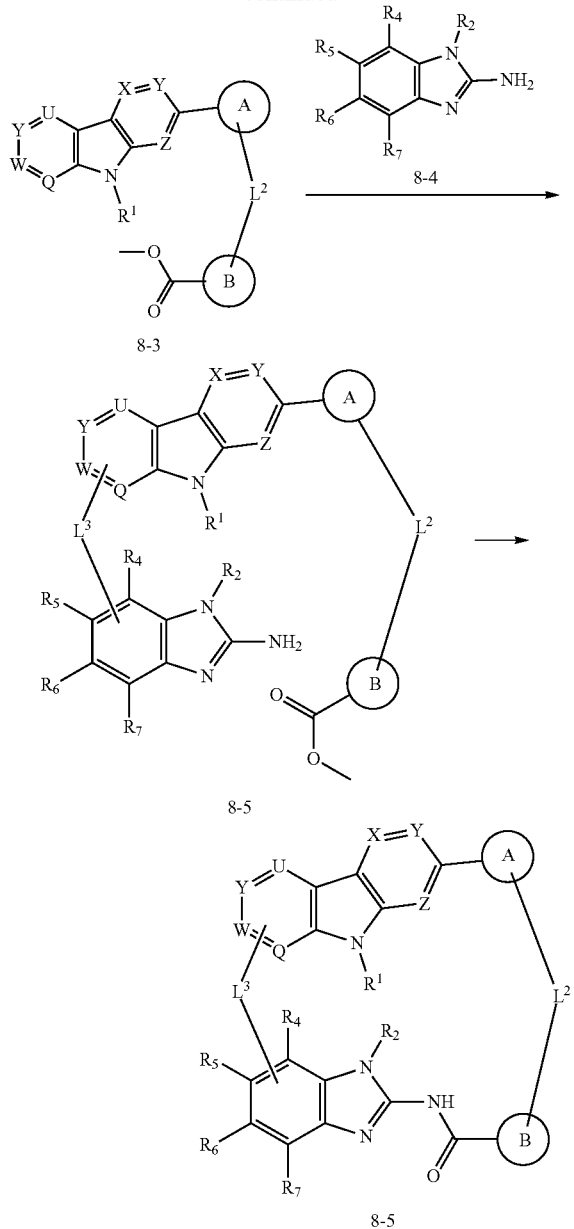

Methods of Use

Compounds of the present disclosure can activate STING-mediated IRF3 and NFκB signaling pathways to produce type I interferons and proinflammatory chemokines and cytokines and, thus, are useful in treating infectious diseases and cancer. In certain embodiments, the compounds of the present disclosure, or pharmaceutically acceptable salts or stereoisomers thereof, are useful for therapeutic administration to enhance, stimulate and/or increase immunity in cancer, chronic infection or sepsis, including enhancement of response to vaccination. In some embodiments, the present disclosure provides a method for inducing STING-mediated IRF3 and NFκB pathway activation. The method includes administering to an individual or a patient a compound of Formula (I) or of any of the formulas as described herein, or of a compound as recited in any of the claims and described herein, or a pharmaceutically acceptable salt or a stereoisomer thereof. The compounds of the present disclosure can be used alone, in combination with other agents or therapies or as an adjuvant or neoadjuvant for the treatment of diseases or disorders, including cancer or infection diseases. For the uses described herein, any of the compounds of the disclosure, including any of the embodiments thereof, may be used.

The compounds of the present disclosure activate STING, resulting in IRF3 and NFκB upregulation and production of IFNs and other cytokines. The production of those interferons and proinflammatory cytokines can enhance the immune response to cancerous cells and infectious diseases in mammals, including humans. In some embodiments, the present disclosure provides treatment of an individual or a patient in vivo using a compound of Formula (I) or a salt or stereoisomer thereof such that growth of cancerous tumors is inhibited. A compound of Formula (I) or of any of the formulas as described herein, or a compound as recited in any of the claims and described herein, or a salt or stereoisomer thereof, can be used to inhibit the growth of cancerous tumors. Alternatively, a compound of Formula (I) or of any of the formulas as described herein, or a compound as recited in any of the claims and described herein, or a salt or stereoisomer thereof, can be used in conjunction with other agents or standard cancer treatments, as described below. In one embodiment, the present disclosure provides a method for inhibiting growth of tumor cells in vitro. The method includes contacting the tumor cells in vitro with a compound of Formula (I) or of any of the formulas as described herein, or of a compound as recited in any of the claims and described herein, or of a salt or stereoisomer thereof. In another embodiment, the present disclosure provides a method for inhibiting growth of tumor cells in an individual or a patient. The method includes administering to the individual or patient in need thereof a therapeutically effective amount of a compound of Formula (I) or of any of the formulas as described herein, or of a compound as recited in any of the claims and described herein, or a salt or a stereoisomer thereof.

In some embodiments, provided herein is a method for treating cancer. The method includes administering to a patient in need thereof, a therapeutically effective amount of a compound of Formula (I) or any of the formulas as described herein, a compound as recited in any of the claims and described herein, or a salt thereof. Examples of cancers include those whose growth may be inhibited using compounds of the disclosure and cancers typically responsive to immunotherapy.

In some embodiments, the present disclosure provides a method of enhancing, stimulating and/or increasing the immune response in a patient. The method includes administering to the patient in need thereof a therapeutically effective amount of a compound of Formula (I) or any of the formulas as described herein, a compound or composition as recited in any of the claims and described herein, or a salt thereof.

Examples of cancers that are treatable using the compounds of the present disclosure include, but are not limited to, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, endometrial cancer, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or urethra, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations of said cancers. The compounds of the present disclosure are also useful for the treatment of metastatic cancers.

In some embodiments, cancers treatable with compounds of the present disclosure include melanoma (e.g., metastatic malignant melanoma), renal cancer (e.g. clear cell carcinoma), prostate cancer (e.g. hormone refractory prostate adenocarcinoma), breast cancer, colon cancer, lung cancer (e.g. non-small cell lung cancer and small cell lung cancer), squamous cell head and neck cancer, urothelial cancer (e.g. bladder) and cancers with high microsatellite instability (MSI$^{high}$). Additionally, the disclosure includes refractory or recurrent malignancies whose growth may be inhibited using the compounds of the disclosure.

In some embodiments, cancers that are treatable using the compounds of the present disclosure include, but are not limited to, solid tumors (e.g., prostate cancer, colon cancer, esophageal cancer, endometrial cancer, ovarian cancer, uterine cancer, renal cancer, hepatic cancer, pancreatic cancer, gastric cancer, breast cancer, lung cancer, cancers of the head and neck, thyroid cancer, glioblastoma, sarcoma, bladder cancer, etc.), hematological cancers (e.g., lymphoma, leukemia such as acute lymphoblastic leukemia (ALL), acute myelogenous leukemia (AML), chronic lymphocytic leukemia (CLL), chronic myelogenous leukemia (CML), DLBCL, mantle cell lymphoma, Non-Hodgkin lymphoma (including relapsed or refractory NHL and recurrent follicular), Hodgkin lymphoma or multiple myeloma) and combinations of said cancers.

In some embodiments, cancers that are treatable using the compounds of the present disclosure include, but are not limited to, cholangiocarcinoma, bile duct cancer, triple negative breast cancer, rhabdomyosarcoma, small cell lung cancer, leiomyosarcoma, hepatocellular carcinoma, Ewing's sarcoma, brain cancer, brain tumor, astrocytoma, neuroblastoma, neurofibroma, basal cell carcinoma, chondrosarcoma, epithelioid sarcoma, eye cancer, Fallopian tube cancer, gastrointestinal cancer, gastrointestinal stromal tumors, hairy cell leukemia, intestinal cancer, islet cell cancer, oral cancer, mouth cancer, throat cancer, laryngeal cancer, lip cancer, mesothelioma, neck cancer, nasal cavity cancer, ocular cancer, ocular melanoma, pelvic cancer, rectal cancer, renal cell carcinoma, salivary gland cancer, sinus cancer, spinal cancer, tongue cancer, tubular carcinoma, urethral cancer, and ureteral cancer.

In some embodiments, the compounds of the present disclosure can be used to treat sickle cell disease and sickle cell anemia.

In some embodiments, diseases and indications that are treatable using the compounds of the present disclosure include, but are not limited to hematological cancers, sarcomas, lung cancers, gastrointestinal cancers, genitourinary tract cancers, liver cancers, bone cancers, nervous system cancers, gynecological cancers, and skin cancers.

Exemplary hematological cancers include lymphomas and leukemias such as acute lymphoblastic leukemia (ALL), acute myelogenous leukemia (AML), acute promyelocytic leukemia (APL), chronic lymphocytic leukemia (CLL), chronic myelogenous leukemia (CML), diffuse large B-cell lymphoma (DLBCL), mantle cell lymphoma, Non-Hodgkin lymphoma (including relapsed or refractory NHL and recurrent follicular), Hodgkin lymphoma, myeloproliferative diseases (e.g., primary myelofibrosis (PMF), polycythemia vera (PV), and essential thrombocytosis (ET)), myelodysplasia syndrome (MDS), T-cell acute lymphoblastic lymphoma (T-ALL) and multiple myeloma (MM).

Exemplary sarcomas include chondrosarcoma, Ewing's sarcoma, osteosarcoma, rhabdomyosarcoma, angiosarcoma, fibrosarcoma, liposarcoma, myxoma, rhabdomyoma, rhabdosarcoma, fibroma, lipoma, harmatoma, and teratoma.

Exemplary lung cancers include non-small cell lung cancer (NSCLC), small cell lung cancer, bronchogenic carcinoma (squamous cell, undifferentiated small cell, undifferentiated large cell, adenocarcinoma), alveolar (bronchiolar) carcinoma, bronchial adenoma, chondromatous hamartoma, and mesothelioma.

Exemplary gastrointestinal cancers include cancers of the esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma), and colorectal cancer.

Exemplary genitourinary tract cancers include cancers of the kidney (adenocarcinoma, Wilm's tumor [nephroblastoma]), bladder and urethra (squamous cell carcinoma, transitional cell carcinoma, adenocarcinoma), prostate (adenocarcinoma, sarcoma), and testis (seminoma, teratoma, embryonal carcinoma, teratocarcinoma, choriocarcinoma, sarcoma, interstitial cell carcinoma, fibroma, fibroadenoma, adenomatoid tumors, lipoma).

Exemplary liver cancers include hepatoma (hepatocellular carcinoma), cholangiocarcinoma, hepatoblastoma, angiosarcoma, hepatocellular adenoma, and hemangioma.

Exemplary bone cancers include, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma, and giant cell tumors Exemplary nervous system cancers include cancers of the skull (osteoma, hemangioma, granuloma, xanthoma, osteitis deformans), meninges (meningioma, meningiosarcoma, gliomatosis), brain (astrocytoma, meduoblastoma, glioma, ependymoma, germinoma (pinealoma), glioblastoma, glioblastoma multiform, oligodendroglioma, schwannoma, retinoblastoma, congenital tumors), and spinal cord (neurofibroma, meningioma, glioma, sarcoma), as well as neuroblastoma and Lhermitte-Duclos disease.

Exemplary gynecological cancers include cancers of the uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), and fallopian tubes (carcinoma).

Exemplary skin cancers include melanoma, basal cell carcinoma, squamous cell carcinoma, Kaposi's sarcoma, moles dysplastic nevi, lipoma, angioma, dermatofibroma, and keloids. In some embodiments, diseases and indications that are treatable using the compounds of the present disclosure include, but are not limited to, sickle cell disease (e.g., sickle cell anemia), triple-negative breast cancer (TNBC), myelodysplastic syndromes, testicular cancer, bile duct cancer, esophageal cancer, and urothelial carcinoma.

Induction of type I interferons and other proinflammatory cytokines/chemokines with compounds of the present disclosure can also be used for treating infections such as viral, bacteria, fungus and parasite infections. The present disclosure provides a method for treating infections such as viral infections. The method includes administering to a patient in need thereof, a therapeutically effective amount of a compound of Formula (I) or any of the formulas as described herein, a compound as recited in any of the claims and described herein, a salt thereof. Examples of viruses causing infections treatable by methods of the present disclosure include, but are not limit to, human immunodeficiency virus, human papillomavirus, influenza, hepatitis A, B, C or D viruses, adenovirus, poxvirus, herpes simplex viruses, human cytomegalovirus, severe acute respiratory syndrome virus, ebola virus, and measles virus. In some embodiments, viruses causing infections treatable by methods of the present disclosure include, but are not limit to, hepatitis (A, B, or C), herpes virus (e.g., VZV, HSV-1, HAV-6, HSV-II, and CMV, Epstein Barr virus), adenovirus, influenza virus, flaviviruses, echovirus, rhinovirus, coxsackie virus, cornovirus, respiratory syncytial virus, mumpsvirus, rotavirus, measles virus, rubella virus, parvovirus, vaccinia virus, HTLV virus, dengue virus, papillomavirus, molluscum virus, poliovirus, rabies virus, JC virus, tuberculosis and arboviral encephalitis virus.

The present disclosure provides a method for treating bacterial infections. The method includes administering to a patient in need thereof, a therapeutically effective amount of a compound of Formula (I) or any of the formulas as described herein, a compound as recited in any of the claims and described herein, or a salt thereof. Non-limiting examples of pathogenic bacteria causing infections treatable by methods of the disclosure include chlamydia, rickettsial bacteria, mycobacteria, staphylococci, streptococci, pneumonococci, meningococci and conococci, klebsiella, proteus, serratia, pseudomonas, legionella, diphtheria, salmonella, bacilli, cholera, tetanus, botulism, anthrax, plague, leptospirosis, and Lyme's disease bacteria.

The present disclosure provides a method for treating fungus infections. The method includes administering to a patient in need thereof, a therapeutically effective amount of a compound of Formula (I) or any of the formulas as described herein, a compound as recited in any of the claims and described herein, or a salt thereof. Non-limiting examples of pathogenic fungi causing infections treatable by methods of the disclosure include *Candida* (*albicans, krusei, glabrata, tropicalis,* etc.), *Cryptococcus neoformans, Aspergillus* (*fumigatus, niger,* etc.), Genus *Mucorales* (*mucor, absidia, rhizophus*), *Sporothrix schenkii, Blastomyces dermatitidis, Paracoccidioides brasiliensis, Coccidioides immitis* and *Histoplasma capsulatum.*

The present disclosure provides a method for treating parasite infections. The method includes administering to a patient in need thereof, a therapeutically effective amount of a compound of Formula (I) or any of the formulas as described herein, a compound as recited in any of the claims and described herein, or a salt thereof. Non-limiting examples of pathogenic parasites causing infections treatable by methods of the disclosure include *Entamoeba histolytica, Balantidium coli, Naegleriafowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma gondi,* and *Nippostrongylus brasiliensis.*

The present disclosure provides a method for treating neurodegenerative diseases or disorders. The method includes administering to a patient in need thereof, a therapeutically effective amount of a compound of Formula (I) or any of the formulas as described herein, a compound as recited in any of the claims and described herein, or a salt thereof. Non-limiting examples of neurodegenerative diseases or disorders include Alzheimer's disease, Parkinson's disease, Huntington's disease, prion disease, Motor neurone diseases, Spinocerebellar ataxia and Spinal muscular atrophy.

It is believed that compounds of Formula (I), or any of the embodiments thereof, may possess satisfactory pharmacological profile and promising biopharmaceutical properties, such as toxicological profile, metabolism and pharmacokinetic properties, solubility, and permeability. It will be understood that determination of appropriate biopharmaceutical properties is within the knowledge of a person skilled in the art, e.g., determination of cytotoxicity in cells or inhibition of certain targets or channels to determine potential toxicity.

The terms "individual" or "patient," used interchangeably, refer to any animal, including mammals, preferably mice, rats, other rodents, rabbits, dogs, cats, swine, cattle, sheep, horses, or primates, and most preferably humans.

The phrase "therapeutically effective amount" refers to the amount of active compound or pharmaceutical agent that elicits the biological or medicinal response in a tissue, system, animal, individual or human that is being sought by a researcher, veterinarian, medical doctor or other clinician.

As used herein, the term "treating" or "treatment" refers to one or more of (1) inhibiting the disease; e.g., inhibiting a disease, condition or disorder in an individual who is experiencing or displaying the pathology or symptomatology of the disease, condition or disorder (i.e., arresting further development of the pathology and/or symptomatology); and (2) ameliorating the disease; e.g., ameliorating a disease, condition or disorder in an individual who is experiencing or displaying the pathology or symptomatology of the disease, condition or disorder (i.e., reversing the pathology and/or symptomatology) such as decreasing the severity of disease.

In some embodiments, the compounds of the invention are useful in preventing or reducing the risk of developing any of the diseases referred to herein; e.g., preventing or reducing the risk of developing a disease, condition or disorder in an individual who may be predisposed to the disease, condition or disorder but does not yet experience or display the pathology or symptomatology of the disease. Compounds of the present disclosure can activate STING-mediated IRF3 and NFκB signaling pathways to produce type I interferons and proinflammatory chemokines and cytokines and, thus, are useful in treating infectious diseases and cancer. In certain embodiments, the compounds of the present disclosure, or pharmaceutically acceptable salts or stereoisomers thereof, are useful for therapeutic administration to enhance, stimulate and/or increase immunity in cancer, chronic infection or sepsis, including enhancement of response to vaccination. In some embodiments, the present disclosure provides a method for inducing STING-mediated IRF3 and NFκB pathway activation. The method includes administering to an individual or a patient a compound of Formula (I) or of any of the formulas as described herein, or of a compound as recited in any of the claims and described herein, or a pharmaceutically acceptable salt or a stereoisomer thereof. The compounds of the present disclosure can be used alone, in combination with other agents or therapies or as an adjuvant or neoadjuvant for the treatment of diseases or disorders, including cancer or infection diseases. For the uses described herein, any of the compounds of the disclosure, including any of the embodiments thereof, may be used.

The compounds of the present disclosure activate STING, resulting in IRF3 and NFκB upregulation and production of IFNs and other cytokines. The production of those interferons and proinflammatory cytokines can enhance the immune response to cancerous cells and infectious diseases in mammals, including humans. In some embodiments, the present disclosure provides treatment of an individual or a patient in vivo using a compound of Formula (I) or a salt or stereoisomer thereof such that growth of cancerous tumors is inhibited. A compound of Formula (I) or of any of the formulas as described herein, or a compound as recited in any of the claims and described herein, or a salt or stereoisomer thereof, can be used to inhibit the growth of cancerous tumors. Alternatively, a compound of Formula (I) or of any of the formulas as described herein, or a compound as recited in any of the claims and described herein, or a salt or stereoisomer thereof, can be used in conjunction with other agents or standard cancer treatments, as described below. In one embodiment, the present disclosure provides a method for inhibiting growth of tumor cells in vitro. The method includes contacting the tumor cells in vitro with a compound of Formula (I) or of any of the formulas as described herein, or of a compound as recited in any of the claims and described herein, or of a salt or stereoisomer thereof. In another embodiment, the present disclosure provides a method for inhibiting growth of tumor cells in an individual or a patient. The method includes administering to the individual or patient in need thereof a therapeutically effective amount of a compound of Formula (I) or of any of the formulas as described herein, or of a compound as recited in any of the claims and described herein, or a salt or a stereoisomer thereof.

In some embodiments, provided herein is a method for treating cancer. The method includes administering to a patient in need thereof, a therapeutically effective amount of a compound of Formula (I) or any of the formulas as described herein, a compound as recited in any of the claims and described herein, or a salt thereof. Examples of cancers include those whose growth may be inhibited using compounds of the disclosure and cancers typically responsive to immunotherapy.

In some embodiments, the present disclosure provides a method of enhancing, stimulating and/or increasing the immune response in a patient. The method includes administering to the patient in need thereof a therapeutically effective amount of a compound of Formula (I) or any of the formulas as described herein, a compound or composition as recited in any of the claims and described herein, or a salt thereof.

Examples of cancers that are treatable using the compounds of the present disclosure include, but are not limited to, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, endometrial cancer, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or urethra, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations of said cancers. The compounds of the present disclosure are also useful for the treatment of metastatic cancers.

In some embodiments, cancers treatable with compounds of the present disclosure include melanoma (e.g., metastatic malignant melanoma), renal cancer (e.g. clear cell carcinoma), prostate cancer (e.g. hormone refractory prostate adenocarcinoma), breast cancer, colon cancer, lung cancer (e.g. non-small cell lung cancer and small cell lung cancer), squamous cell head and neck cancer, urothelial cancer (e.g. bladder) and cancers with high microsatellite instability ($MSI^{high}$). Additionally, the disclosure includes refractory or recurrent malignancies whose growth may be inhibited using the compounds of the disclosure.

In some embodiments, cancers that are treatable using the compounds of the present disclosure include, but are not limited to, solid tumors (e.g., prostate cancer, colon cancer, esophageal cancer, endometrial cancer, ovarian cancer, uterine cancer, renal cancer, hepatic cancer, pancreatic cancer, gastric cancer, breast cancer, lung cancer, cancers of the head and neck, thyroid cancer, glioblastoma, sarcoma, bladder cancer, etc.), hematological cancers (e.g., lymphoma, leukemia such as acute lymphoblastic leukemia (ALL), acute myelogenous leukemia (AML), chronic lymphocytic leukemia (CLL), chronic myelogenous leukemia (CML), DLBCL, mantle cell lymphoma, Non-Hodgkin lymphoma (including relapsed or refractory NHL and recurrent follicular), Hodgkin lymphoma or multiple myeloma) and combinations of said cancers.

In some embodiments, cancers that are treatable using the compounds of the present disclosure include, but are not limited to, cholangiocarcinoma, bile duct cancer, triple negative breast cancer, rhabdomyosarcoma, small cell lung cancer, leiomyosarcoma, hepatocellular carcinoma, Ewing's sarcoma, brain cancer, brain tumor, astrocytoma, neuroblastoma, neurofibroma, basal cell carcinoma, chondrosarcoma, epithelioid sarcoma, eye cancer, Fallopian tube cancer, gastrointestinal cancer, gastrointestinal stromal tumors, hairy cell leukemia, intestinal cancer, islet cell cancer, oral cancer, mouth cancer, throat cancer, laryngeal cancer, lip cancer, mesothelioma, neck cancer, nasal cavity cancer, ocular cancer, ocular melanoma, pelvic cancer, rectal cancer, renal cell carcinoma, salivary gland cancer, sinus cancer, spinal cancer, tongue cancer, tubular carcinoma, urethral cancer, and ureteral cancer.

In some embodiments, the compounds of the present disclosure can be used to treat sickle cell disease and sickle cell anemia.

In some embodiments, diseases and indications that are treatable using the compounds of the present disclosure include, but are not limited to hematological cancers, sarcomas, lung cancers, gastrointestinal cancers, genitourinary tract cancers, liver cancers, bone cancers, nervous system cancers, gynecological cancers, and skin cancers.

Exemplary hematological cancers include lymphomas and leukemias such as acute lymphoblastic leukemia (ALL), acute myelogenous leukemia (AML), acute promyelocytic leukemia (APL), chronic lymphocytic leukemia (CLL), chronic myelogenous leukemia (CML), diffuse large B-cell lymphoma (DLBCL), mantle cell lymphoma, Non-Hodgkin lymphoma (including relapsed or refractory NHL and recurrent follicular), Hodgkin lymphoma, myeloproliferative diseases (e.g., primary myelofibrosis (PMF), polycythemia vera (PV), and essential thrombocytosis (ET)), myelodysplasia syndrome (MDS), T-cell acute lymphoblastic lymphoma (T-ALL) and multiple myeloma (MM).

Exemplary sarcomas include chondrosarcoma, Ewing's sarcoma, osteosarcoma, rhabdomyosarcoma, angiosarcoma, fibrosarcoma, liposarcoma, myxoma, rhabdomyoma, rhabdosarcoma, fibroma, lipoma, harmatoma, and teratoma.

Exemplary lung cancers include non-small cell lung cancer (NSCLC), small cell lung cancer, bronchogenic carcinoma (squamous cell, undifferentiated small cell, undifferentiated large cell, adenocarcinoma), alveolar (bronchiolar) carcinoma, bronchial adenoma, chondromatous hamartoma, and mesothelioma.

Exemplary gastrointestinal cancers include cancers of the esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma), and colorectal cancer.

Exemplary genitourinary tract cancers include cancers of the kidney (adenocarcinoma, Wilm's tumor [nephroblastoma]), bladder and urethra (squamous cell carcinoma, transitional cell carcinoma, adenocarcinoma), prostate (adenocarcinoma, sarcoma), and testis (seminoma, teratoma, embryonal carcinoma, teratocarcinoma, choriocarcinoma, sarcoma, interstitial cell carcinoma, fibroma, fibroadenoma, adenomatoid tumors, lipoma).

Exemplary liver cancers include hepatoma (hepatocellular carcinoma), cholangiocarcinoma, hepatoblastoma, angiosarcoma, hepatocellular adenoma, and hemangioma.

Exemplary bone cancers include, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma, and giant cell tumors Exemplary nervous system cancers include cancers of the skull (osteoma, hemangioma, granuloma, xanthoma, osteitis deformans), meninges (meningioma, meningiosarcoma, gliomatosis), brain (astrocytoma, meduoblastoma, glioma, ependymoma, germinoma (pinealoma), glioblastoma, glioblastoma multiform, oligodendroglioma, schwannoma, retinoblastoma, congenital tumors), and spinal cord (neurofibroma, meningioma, glioma, sarcoma), as well as neuroblastoma and Lhermitte-Duclos disease.

Exemplary gynecological cancers include cancers of the uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), and fallopian tubes (carcinoma).

Exemplary skin cancers include melanoma, basal cell carcinoma, squamous cell carcinoma, Kaposi's sarcoma, moles dysplastic nevi, lipoma, angioma, dermatofibroma, and keloids. In some embodiments, diseases and indications that are treatable using the compounds of the present disclosure include, but are not limited to, sickle cell disease (e.g., sickle cell anemia), triple-negative breast cancer (TNBC), myelodysplastic syndromes, testicular cancer, bile duct cancer, esophageal cancer, and urothelial carcinoma.

Induction of type I interferons and other proinflammatory cytokines/chemokines with compounds of the present disclosure can also be used for treating infections such as viral, bacteria, fungus and parasite infections. The present disclosure provides a method for treating infections such as viral infections. The method includes administering to a patient in need thereof, a therapeutically effective amount of a compound of Formula (I) or any of the formulas as described herein, a compound as recited in any of the claims and described herein, a salt thereof. Examples of viruses causing infections treatable by methods of the present disclosure include, but are not limit to, human immunodeficiency virus, human papillomavirus, influenza, hepatitis A, B, C or D viruses, adenovirus, poxvirus, herpes simplex viruses, human cytomegalovirus, severe acute respiratory syndrome virus, ebola virus, and measles virus. In some embodiments, viruses causing infections treatable by methods of the present disclosure include, but are not limit to, hepatitis (A, B, or C), herpes virus (e.g., VZV, HSV-1, HAV-6, HSV-II, and CMV, Epstein Barr virus), adenovirus, influenza virus, flaviviruses, echovirus, rhinovirus, coxsackie virus, cornovirus, respiratory syncytial virus, mumpsvirus, rotavirus, measles virus, rubella virus, parvovirus, vaccinia virus, HTLV virus, dengue virus, papillomavirus, molluscum virus, poliovirus, rabies virus, JC virus, tuberculosis and arboviral encephalitis virus.

The present disclosure provides a method for treating bacterial infections. The method includes administering to a patient in need thereof, a therapeutically effective amount of a compound of Formula (I) or any of the formulas as described herein, a compound as recited in any of the claims and described herein, or a salt thereof. Non-limiting examples of pathogenic bacteria causing infections treatable by methods of the disclosure include chlamydia, rickettsial bacteria, mycobacteria, staphylococci, streptococci, pneumonococci, meningococci and conococci, klebsiella, proteus, serratia, pseudomonas, legionella, diphtheria, salmonella, bacilli, cholera, tetanus, botulism, anthrax, plague, leptospirosis, and Lyme's disease bacteria.

The present disclosure provides a method for treating fungus infections. The method includes administering to a patient in need thereof, a therapeutically effective amount of a compound of Formula (I) or any of the formulas as described herein, a compound as recited in any of the claims and described herein, or a salt thereof. Non-limiting examples of pathogenic fungi causing infections treatable by methods of the disclosure include *Candida* (*albicans, krusei, glabrata, tropicalis*, etc.), *Cryptococcus neoformans, Aspergillus* (*fumigatus, niger*, etc.), Genus *Mucorales* (*mucor, absidia, rhizophus*), *Sporothrix schenkii, Blastomyces dermatitidis, Paracoccidioides brasiliensis, Coccidioides immitis* and *Histoplasma capsulatum.*

The present disclosure provides a method for treating parasite infections. The method includes administering to a patient in need thereof, a therapeutically effective amount of a compound of Formula (I) or any of the formulas as described herein, a compound as recited in any of the claims and described herein, or a salt thereof. Non-limiting examples of pathogenic parasites causing infections treatable by methods of the disclosure include *Entamoeba histolytica, Balantidium coli, Naegleriafowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma gondi*, and *Nippostrongylus brasiliensis.*

The present disclosure provides a method for treating neurodegenerative diseases or disorders. The method includes administering to a patient in need thereof, a therapeutically effective amount of a compound of Formula (I) or any of the formulas as described herein, a compound as recited in any of the claims and described herein, or a salt thereof. Non-limiting examples of neurodegenerative diseases or disorders include Alzheimer's disease, Parkinson's disease, Huntington's disease, prion disease, Motor neurone diseases, Spinocerebellar ataxia and Spinal muscular atrophy.

It is believed that compounds of Formula (I), or any of the embodiments thereof, may possess satisfactory pharmacological profile and promising biopharmaceutical properties, such as toxicological profile, metabolism and pharmacokinetic properties, solubility, and permeability. It will be understood that determination of appropriate biopharmaceutical properties is within the knowledge of a person skilled in the art, e.g., determination of cytotoxicity in cells or inhibition of certain targets or channels to determine potential toxicity.

The terms "individual" or "patient," used interchangeably, refer to any animal, including mammals, preferably mice, rats, other rodents, rabbits, dogs, cats, swine, cattle, sheep, horses, or primates, and most preferably humans.

The phrase "therapeutically effective amount" refers to the amount of active compound or pharmaceutical agent that elicits the biological or medicinal response in a tissue, system, animal, individual or human that is being sought by a researcher, veterinarian, medical doctor or other clinician.

As used herein, the term "treating" or "treatment" refers to one or more of (1) inhibiting the disease; e.g., inhibiting a disease, condition or disorder in an individual who is experiencing or displaying the pathology or symptomatology of the disease, condition or disorder (i.e., arresting further development of the pathology and/or symptomatology); and (2) ameliorating the disease; e.g., ameliorating a disease, condition or disorder in an individual who is experiencing or displaying the pathology or symptomatology of the disease, condition or disorder (i.e., reversing the pathology and/or symptomatology) such as decreasing the severity of disease.

In some embodiments, the compounds of the invention are useful in preventing or reducing the risk of developing any of the diseases referred to herein; e.g., preventing or reducing the risk of developing a disease, condition or disorder in an individual who may be predisposed to the disease, condition or disorder but does not yet experience or display the pathology or symptomatology of the disease.

Combination Therapies

I. Immune-Checkpoint Therapies

Compounds of the present disclosure can be used in combination with one or more inhibitors or agonists of an immune checkpoint molecule for the treatment of diseases, such as cancer or infections. Exemplary immune checkpoint molecules such as CBL-B, CD20, CD27, CD28, CD40, CD122, CD96, CD73, CD47, CD160, KIR, LAIR1, 2B4, TGF beta, GITR, CSF1R, JAK, PI3K delta, PI3K gamma, TAM, arginase, HPK1, CD137 (also known as 4-1BB), ICOS, A2AR, IDO, B7-H3, B7-H4, BTLA, CTLA-4, LAG3, TIM3, TIGIT, CD112R, VISTA, PD-1, PD-L1 and PD-L2. In some embodiments, the compounds of the present disclosure can be used in combination with an inhibitor of an immune checkpoint molecule. In some embodiments, the compounds of the present disclosure can be used in combination with an agonist of an immune checkpoint molecule. In some embodiments, the inhibitor or agonist of the immune checkpoint molecule is an antibody, or antigen-binding fragment thereof. In some embodiments, the inhibitor or agonist of the immune checkpoint molecule is a small molecule, or a pharmaceutically acceptable salt thereof. In some embodiments, the immune checkpoint molecule is a stimulatory checkpoint molecule selected from CD27, CD28, CD40, ICOS, OX40, GITR and CD137. In some embodiments, the immune checkpoint molecule is an inhibitory checkpoint molecule selected from A2AR, B7-H3, B7-H4, BTLA, CTLA-4, IDO, KIR, LAG3, PD-1, TIM3, TIGIT, and VISTA. In some embodiments, the compounds provided herein can be used in combination with one or more inhibitors of an immune checkpoint molecule selected from KIR inhibitors, TIGIT inhibitors, LAIR1 inhibitors, CD160 inhibitors, 2B4 inhibitors and TGF beta inhibitors.

In some embodiments, the inhibitor of an immune checkpoint molecule is anti-PD1 antibody, anti-PD-L1 antibody, or anti-CTLA-4 antibody.

In some embodiments, the inhibitor of an immune checkpoint molecule is an inhibitor of PD-1, e.g., an anti-PD-1 monoclonal antibody. Antibodies that bind to human PD-1 include nivolumab, pembrolizumab, cemiplimab, spartalizumab, camrelizumab, cetrelimab, toripalimab, sintilimab, AB122, AMP-224, JTX-4014, BGB-108, BCD-100, BAT1306, LZM009, AK105, HLX10, and TSR-042. In some embodiments, the anti-PD-1 monoclonal antibody is nivolumab, pembrolizumab (also known as MK-3475), pidilizumab, SHR-1210, PDR001, MGA012, PDR001, AB122, or AMP-224. In some embodiments, the anti-PD-1 monoclonal antibody is nivolumab or pembrolizumab. In some embodiments, the anti-PD1 antibody is pembrolizumab.

In some embodiments, the anti-PD-1 monoclonal antibody is MGA012. In some embodiments, the anti-PD1 antibody is SHR-1210. Other anti-cancer agent(s) include antibody therapeutics such as 4-1BB (e.g. urelumab, utomilumab).

In some embodiments, the inhibitor of an immune checkpoint molecule is an inhibitor of PD-L1, e.g., an anti-PD-L1 monoclonal antibody. Antibodies that bind to human PD-L1 include atezolizumab, avelumab, durvalumab, tislelizumab, BMS-935559, MEDI4736, FAZ053, KN035, CS1001, SHR-1316, CBT-502, A167, STI-A101, CK-301, BGB-A333, MSB-2311, HLX20, and LY3300054. In some embodiments, the anti-PD-L1 monoclonal antibody is BMS-935559, MEDI4736, MPDL3280A (also known as RG7446), durvalumab (Imfinzi®), or MSB0010718C. In some embodiments, the anti-PD-L1 monoclonal antibody is MPDL3280A or MEDI4736. In some embodiments, the inhibitor of an immune checkpoint molecule is an inhibitor of PD-1 and PD-L1, e.g., an anti-PD-1/PD-L1 bispecific antibody. In some embodiments, the anti-PD-1/PD-L1 is MCLA-136.

In some embodiments, the inhibitor of an immune checkpoint molecule is an inhibitor of CTLA-4, e.g., an anti-CTLA-4 antibody. In some embodiments, the inhibitor of CTLA-4 is ipilimumab, tremelimumab, AGEN1884, or CP-675,206. In some embodiments, the inhibitor of an immune checkpoint molecule is an inhibitor of PD-L1 and CTLA-4, e.g., an anti-PD-L1/CTLA-4 bispecific antibody. Bispecific antibodies that bind to PD-L1 and CTLA-4 include AK104.

In some embodiments, the inhibitor of an immune checkpoint molecule is an inhibitor of LAG3, e.g., an anti-LAG3 antibody. In some embodiments, the inhibitor of LAG3is BMS-986016, LAG525, INCAGN2385, or eftilagimod alpha (IMP321).

In some embodiments, the agonist of CD137 is urelumab. In some embodiments, the agonist of CD137 is utomilumab.

In some embodiments, the inhibitor of an immune checkpoint molecule is an inhibitor of CD73. In some embodiments, the inhibitor of CD73 is oleclumab or MEDI9447.

In some embodiments, the inhibitor of an immune checkpoint molecule is an inhibitor of TIGIT. In some embodiments, the inhibitor of TIGIT is OMP-31M32.

In some embodiments, the inhibitor of an immune checkpoint molecule is an inhibitor of VISTA. In some embodiments, the inhibitor of VISTA is JNJ-61610588 or CA-170.

In some embodiments, the inhibitor of an immune checkpoint molecule is an inhibitor of B7-H3. In some embodiments, the inhibitor of B7-H3 is enoblituzumab, MGD009, or 8H9.

In some embodiments, the inhibitor of an immune checkpoint molecule is an inhibitor of KIR. In some embodiments, the inhibitor of KIR is lirilumab or IPH4102.

In some embodiments, the inhibitor of an immune checkpoint molecule is an inhibitor of A2aR. In some embodiments, the inhibitor of A2aR is CPI-444.

In some embodiments, the inhibitor of an immune checkpoint molecule is an inhibitor of TGF-beta. In some embodiments, the inhibitor of TGF-beta is trabedersen, galusertinib, or M7824.

In some embodiments, the inhibitor of an immune checkpoint molecule is an inhibitor of PI3K-gamma. In some embodiments, the inhibitor of PI3K-gamma is IPI-549.

In some embodiments, the inhibitor of an immune checkpoint molecule is an inhibitor of CD47. In some embodiments, the inhibitor of CD47 is Hu5F9-G4 or TTI-621.

In some embodiments, the inhibitor of an immune checkpoint molecule is an inhibitor of CD70. In some embodiments, the inhibitor of CD70 is cusatuzumab or BMS-936561.

In some embodiments, the inhibitor of an immune checkpoint molecule is an inhibitor of TIM3, e.g., an anti-TIM3 antibody. In some embodiments, the inhibitor of TIM3 antibody is INCAGN2390, MBG453, or TSR-022.

In some embodiments, the inhibitor of an immune checkpoint molecule is an inhibitor of CD20, e.g., an anti-CD20 antibody. In some embodiments, the anti-CD20 antibody is obinutuzumab or rituximab.

In some embodiments, the inhibitor of an immune checkpoint molecule is a small molecule that binds to PD-L1, or a pharmaceutically acceptable salt thereof. In some embodiments, the inhibitor of an immune checkpoint molecule is a small molecule that binds to and internalizes PD-L1, or a pharmaceutically acceptable salt thereof. In some embodiments, the inhibitor of an immune checkpoint molecule is a compound selected from those in US 2018/0179201, US 2018/0179197, US 2018/0179179, US 2018/0179202, US 2018/0177784, US 2018/0177870, U.S. Ser. No. 16/369,654 (filed Mar. 29, 2019), and U.S. Ser. No. 62/688,164 (filed May 11, 2019), or a pharmaceutically acceptable salt thereof, each of which is incorporated herein by reference in its entirety.

In some embodiments, the agonist of an immune checkpoint molecule is an agonist of OX40, CD27, CD28, GITR, ICOS, CD40, TLR7/8, and CD137 (also known as 4-1BB).

In some embodiments, the agonist of an immune checkpoint molecule is an agonist of GITR. In some embodiments, the agonist of GITR is TRX518, MK-4166, INCAGN1876, MK-1248, AMG228, BMS-986156, GWN323, MEDI1873, or MEDI6469.

In some embodiments, the agonist of an immune checkpoint molecule is an agonist of OX40, e.g., OX40 agonist antibody or OX40L fusion protein. In some embodiments, the agonist of OX40 is INCAGN01949, MEDI0562 (tavolimab), MOXR-0916, PF-04518600, GSK3174998, BMS-986178, or 9B12. In some embodiments, the OX40L fusion protein is MEDI6383.

In some embodiments, the agonist of an immune checkpoint molecule is an agonist of CD40. In some embodiments, the agonist of CD40 is CP-870893, ADC-1013, CDX-1140, SEA-CD40, RO7009789, JNJ-64457107, APX-005M, or Chi Lob 7/4.

In some embodiments, the agonist of an immune checkpoint molecule is an agonist of ICOS. In some embodiments, the agonist of ICOS is GSK-3359609, JTX-2011, or MEDI-570.

In some embodiments, the agonist of an immune checkpoint molecule is an agonist of CD28. In some embodiments, the agonist of CD28 is theralizumab.

In some embodiments, the agonist of an immune checkpoint molecule is an agonist of CD27. In some embodiments, the agonist of CD27 is varlilumab.

In some embodiments, the agonist of an immune checkpoint molecule is an agonist of TLR7/8. In some embodiments, the agonist of TLR7/8 is MEDI9197.

The compounds of the present disclosure can be used in combination with bispecific antibodies. In some embodiments, one of the domains of the bispecific antibody targets PD-1, PD-L1, CTLA-4, GITR, OX40, TIM3, LAG3, CD137, ICOS, CD3 or TGFβ receptor. In some embodiments, the bispecific antibody binds to PD-1 and PD-L1. In some embodiments, the bispecific antibody that binds to PD-1 and PD-L1 is MCLA-136. In some embodiments, the bispecific antibody binds to PD-L1 and CTLA-4. In some embodiments, the bispecific antibody that binds to PD-L1 and CTLA-4 is AK104. In some embodiments, the bispecific antibody binds to PD-L1 and CD137. In some embodiments, the bispecific antibody that binds to PD-L1 and CD137 is MCLA-145.

In some embodiments, the compounds of the disclosure can be used in combination with one or more metabolic enzyme inhibitors. In some embodiments, the metabolic enzyme inhibitor is an inhibitor of IDO1, TDO, or arginase. Examples of IDO1 inhibitors include epacadostat, NLG919, BMS-986205, PF-06840003, IOM2983, RG-70099 and LY338196.

As provided throughout, the additional compounds, inhibitors, agents, etc. can be combined with the present compound in a single or continuous dosage form, or they can be administered simultaneously or sequentially as separate dosage forms.

II. Cancer Therapies

Cancer cell growth and survival can be impacted by dysfunction in multiple biological pathways. Thus, it may be useful to combine inhibitors of different mechanisms, such as enzyme inhibitors, signal transduction inhibitors, inhibitors of chromatin dynamics or modulators of immune responses, to treat such conditions. Targeting more than one signaling pathway (or more than one biological molecule involved in a given signaling pathway) may reduce the likelihood of drug-resistance arising in a cell population, or reduce the toxicity of treatment.

The compounds of the present disclosure can be used in combination with one or more other enzyme/protein/receptor inhibitor therapies for the treatment of diseases, such as cancer, infections, and other diseases or disorder described herein. Examples of diseases and indications treatable with combination therapies include those as described herein. Examples of cancers include solid tumors and non-solid tumors, such as liquid tumors, blood cancers. Examples of infections include viral infections, bacterial infections, fungus infections or parasite infections. For example, the compounds of the present disclosure can be combined with one or more inhibitors of the following kinases for the treatment of cancer: Akt1, Akt2, Akt3, BCL2, CDK, TGF-βR,, PKA, PKG, PKC, CaM-kinase, phosphorylase kinase, MEKK, ERK, MAPK, mTOR, EGFR, HER2, HER3, HER4, INS-R, IDH2, IGF-1R, IR-R, PDGFαR, PDGFβR, PI3K (alpha, beta, gamma, delta, and multiple or selective), CSF1R, KIT, FLK-II, KDR/FLK-1, FLK-4, flt-1, FGFR1, FGFR2, FGFR3, FGFR4, c-Met, PARP, Ron, Sea, TRKA, TRKB, TRKC, TAM kinases (Axl, Mer, Tyro3), FLT3, VEGFR/Flt2, Flt4, EphA1, EphA2, EphA3, EphB2, EphB4, Tie2, Src, Fyn, Lck, Fgr, Btk, Fak, SYK, FRK, JAK, ABL, ALK and B-Raf. In some embodiments, the compounds of the present disclosure can be combined with one or more of the following inhibitors for the treatment of cancer or infections. Non-limiting examples of inhibitors that can be combined with the compounds of the present disclosure for treatment of cancer and infections include an FGFR inhibitor (FGFR1, FGFR2, FGFR3 or FGFR4, e.g., pemigatinib (INCY54828), INCB62079), an EGFR inhibitor (also known as ErB-1 or HER-1; e.g. erlotinib, gefitinib, vandetanib, orsimertinib, cetuximab, necitumumab, or panitumumab), a VEGFR inhibitor or pathway blocker (e.g. bevacizumab, pazopanib, sunitinib, sorafenib, axitinib, regorafenib, ponatinib, cabozantinib, vandetanib, ramucirumab, lenvatinib, ziv-aflibercept), a PARP inhibitor (e.g. olaparib, rucaparib, veliparib or niraparib), a JAK inhibitor (JAK1 and/or JAK2, e.g., ruxolitinib, baricitinib, itacitinib (INCB39110), an IDO inhibitor (e.g., epacadostat, NLG919, or BMS-986205, MK7162), an LSD1 inhibitor (e.g., INCB59872 and INCB60003), a TDO inhibitor, a PI3K-delta inhibitor (e.g., parsaclisib (INCB50465) and INCB50797), a PI3K-gamma inhibitor such as PI3K-gamma selective inhibitor, a Pim inhibitor (e.g., INCB53914), a CSF1R inhibitor, a TAM receptor tyrosine kinases (Tyro-3, Axl, and Mer), an adenosine receptor antagonist (e.g., A2a/A2b receptor antagonist), an HPK1 inhibitor, a chemokine receptor inhibitor (e.g. CCR2 or CCR5 inhibitor), a SHP1/2 phosphatase inhibitor, a histone deacetylase inhibitor (HDAC) such as an HDAC8 inhibitor, an angiogenesis inhibitor, an interleukin receptor inhibitor, bromo and extra terminal family members inhibitors (for example, bromodomain inhibitors or BET inhibitors such as INCB54329 and INCB57643), or combinations thereof.

In some embodiments, the compound or salt described herein is administered with a PI3Kδ inhibitor. In some embodiments, the compound or salt described herein is administered with a JAK inhibitor. In some embodiments, the compound or salt described herein is administered with a JAK1 or JAK2 inhibitor (e.g., baricitinib or ruxolitinib). In some embodiments, the compound or salt described herein is administered with a JAK1 inhibitor. In some embodiments, the compound or salt described herein is administered with a JAK1 inhibitor, which is selective over JAK2.

Example antibodies for use in combination therapy include but are not limited to Trastuzumab (e.g. anti-HER2), Ranibizumab (e.g. anti-VEGF-A), Bevacizumab (trade name Avastin, e.g. anti-VEGF, Panitumumab (e.g. anti-EGFR), Cetuximab (e.g. anti-EGFR), Rituxan (anti-CD20) and antibodies directed to c-MET.

One or more of the following agents may be used in combination with the compounds of the present disclosure and are presented as a non-limiting list: a cytostatic agent, taxotere, taxol, etoposide, irinotecan, camptostar, epothilones, 5-fluorouracil, methoxtrexate, cyclophosphamide, SCH 66336, R115777, L778,123, BMS 214662, IRESSA™ (gefitinib), TARCEVA™ (erlotinib), antibodies to EGFR, intron, ara-C, adriamycin, cytoxan, chlormethine, pipobroman, triethylenemelamine, triethylenethiophosphoramine, 6-mercaptopurine, 6-thioguanine, fludarabine phosphate, leucovirin, ELOXATIN™ (oxaliplatin), pentostatine, vindesine, mithramycin, deoxycoformycin, L-asparaginase, teniposide 17.alpha.-ethinylestradiol, diethylstilbestrol, testosterone, prednisone, fluoxymesterone, megestrolacetate, methylprednisolone, methyltestosterone, prednisolone, triamcinolone, chlorotrianisene, hydroxyprogesterone, aminoglutethimide, medroxyprogesteroneacetate, leuprolide, flutamide, goserelin, hydroxyurea, amsacrine, navelbene, anastrazole, tetrazole, reloxafine, droloxafine, hexamethylmelamine, avastin, HERCEPTIN™ (trastuzumab), BEXXAR™ (tositumomab), VELCADE™ (bortezomib), ZEVALIN™ (ibritumomab tiuxetan), TRISENOX™ (arsenic trioxide), XELODA™ (capecitabine), porfimer, ERBITUX™ (cetuximab), lerozole, ifosfomide, C225 (cetuximab), Campath (alemtuzumab), aphidicolon, rituxan, tezacitabine, Sml1, pentostatin, triapine, didox, trimidox, amidox, 3-AP, and MDL-101,731.

The compounds of the present disclosure can further be used in combination with other methods of treating cancers, for example by chemotherapy, irradiation therapy, tumor-targeted therapy, adjuvant therapy, immunotherapy or surgery. Examples of immunotherapy include cytokine treatment (e.g., interferons, GM-CSF, G-CSF, IL-2), CRS-207 immunotherapy, cancer vaccine, monoclonal antibody, bispecific or multi-specific antibody, antibody drug conjugate, adoptive T cell transfer, Toll receptor agonists, RIG-I agonists, oncolytic virotherapy and immunomodulating small molecules, including thalidomide or JAK1/2 inhibitor, PI3Kδ inhibitor and the like.

The compounds can be administered in combination with one or more anti-cancer drugs, such as a chemotherapeutic agent. Examples of chemotherapeutics include any of: abarelix, aldesleukin, alemtuzumab, alitretinoin, allopurinol, altretamine, anastrozole, arsenic trioxide, asparaginase, azacitidine, bevacizumab, bexarotene, baricitinib, bleomycin, bortezomib, busulfan intravenous, busulfan oral, calusterone, capecitabine, carboplatin, carmustine, cetuximab, chlorambucil, cisplatin, cladribine, clofarabine, cyclophosphamide, cytarabine, dacarbazine, dactinomycin, dalteparin sodium, dasatinib, daunorubicin, decitabine, denileukin, denileukin diftitox, dexrazoxane, docetaxel, doxorubicin, dromostanolone propionate, eculizumab, epirubicin, erlotinib, estramustine, etoposide phosphate, etoposide, exemestane, fentanyl citrate, filgrastim, floxuridine, fludarabine, fluorouracil, fulvestrant, gefitinib, gemcitabine, gemtuzumab ozogamicin, goserelin acetate, histrelin acetate, ibritumomab tiuxetan, idarubicin, ifosfamide, imatinib mesylate, interferon alfa 2a, irinotecan, lapatinib ditosylate, lenalidomide, letrozole, leucovorin, leuprolide acetate, levamisole, lomustine, meclorethamine, megestrol acetate, melphalan, mercaptopurine, methotrexate, methoxsalen, mitomycin C, mitotane, mitoxantrone, nandrolone phenpropionate, nelarabine, nofetumomab, oxaliplatin, paclitaxel, pamidronate, panitumumab, pegaspargase, pegfilgrastim, pemetrexed disodium, pentostatin, pipobroman, plicamycin, procarbazine, quinacrine, rasburicase, rituximab, ruxolitinib, sorafenib, streptozocin, sunitinib, sunitinib maleate, tamoxifen, temozolomide, teniposide, testolactone, thalidomide, thioguanine, thiotepa, topotecan, toremifene, tositumomab, trastuzumab, tretinoin, uracil mustard, valrubicin, vinblastine, vincristine, vinorelbine, vorinostat and zoledronate.

Additional examples of chemotherapeutics include proteosome inhibitors (e.g., bortezomib), thalidomide, revlimid, and DNA-damaging agents such as melphalan, doxorubicin, cyclophosphamide, vincristine, etoposide, carmustine, and the like.

Example steroids include corticosteroids such as dexamethasone or prednisone.

Example Bcr-Abl inhibitors include imatinib mesylate (GLEEVAC™), nilotinib, dasatinib, bosutinib, and ponatinib, and pharmaceutically acceptable salts. Other example suitable Bcr-Abl inhibitors include the compounds, and pharmaceutically acceptable salts thereof, of the genera and species disclosed in U.S. Pat. No. 5,521,184, WO 04/005281, and U.S. Ser. No. 60/578,491.

Example suitable Flt-3 inhibitors include midostaurin, lestaurtinib, linifanib, sunitinib, sunitinib, maleate, sorafenib, quizartinib, crenolanib, pacritinib, tandutinib, PLX3397 and ASP2215, and their pharmaceutically acceptable salts. Other example suitable Flt-3 inhibitors include compounds, and their pharmaceutically acceptable salts, as disclosed in WO 03/037347, WO 03/099771, and WO 04/046120.

Example suitable RAF inhibitors include dabrafenib, sorafenib, and vemurafenib, and their pharmaceutically acceptable salts. Other example suitable RAF inhibitors include compounds, and their pharmaceutically acceptable salts, as disclosed in WO 00/09495 and WO 05/028444.

Example suitable FAK inhibitors include VS-4718, VS-5095, VS-6062, VS-6063, BI853520, and GSK2256098, and their pharmaceutically acceptable salts. Other example suitable FAK inhibitors include compounds, and their pharmaceutically acceptable salts, as disclosed in WO 04/080980, WO 04/056786, WO 03/024967, WO 01/064655, WO 00/053595, and WO 01/014402.

In some embodiments, the compounds of the disclosure can be used in combination with one or more other kinase inhibitors including imatinib, particularly for treating patients resistant to imatinib or other kinase inhibitors.

In some embodiments, the compounds of the disclosure can be used in combination with a chemotherapeutic in the treatment of cancer, and may improve the treatment response as compared to the response to the chemotherapeutic agent alone, without exacerbation of its toxic effects. In some embodiments, the compounds of the disclosure can be used in combination with a chemotherapeutic provided herein. For example, additional pharmaceutical agents used in the treatment of multiple myeloma, can include, without limitation, melphalan, melphalan plus prednisone [MP], doxorubicin, dexamethasone, and Velcade (bortezomib). Further additional agents used in the treatment of multiple myeloma include Bcr-Abl, Flt-3, RAF and FAK kinase inhibitors. In some embodiments, the agent is an alkylating agent, a proteasome inhibitor, a corticosteroid, or an immunomodulatory agent. Examples of an alkylating agent include cyclophosphamide (CY), melphalan (MEL), and bendamustine. In some embodiments, the proteasome inhibitor is carfilzomib. In some embodiments, the corticosteroid is dexamethasone (DEX). In some embodiments, the immunomodulatory agent is lenalidomide (LEN) or pomalidomide (POM). In some embodiments, a corticosteroid such as dexamethasone is administered to a patient in combination with the compounds of the disclosure where the dexamethasone is administered intermittently as opposed to continuously.

In some embodiments, the compounds of the disclosure can be used in combination with an inhibitor of JAK or PI3Kδ. The agents can be combined with the present compound in a single or continuous dosage form, or the agents can be administered simultaneously or sequentially as separate dosage forms.

Other anti-cancer agent(s) include antibody therapeutics such as trastuzumab (Herceptin), antibodies to costimulatory molecules such as CTLA-4 (e.g., ipilimumab), 4-1BB (e.g. urelumab, utomilumab), antibodies to PD-1 and PD-L1, or antibodies to cytokines (IL-10, TGF-β, etc.). Examples of antibodies to PD-1 and/or PD-L1 that can be combined with compounds of the present disclosure for the treatment of cancer or infections such as viral, bacteria, fungus and parasite infections include, but are not limited to nivolumab, pembrolizumab, atezolizumab, durvalumab, avelumab, cemiplimab, spartalizumab, camrelizumab, cetrelimab, toripalimab, sintilimab, AB122, AMP-224, JTX-4014, BGB-108, BCD-100, BAT1306, LZM009, AK105, HLX10, TSR-042, tislelizumab, BMS-935559, MEDI4736, FAZ053, KN035, CS1001, SHR-1316, CBT-502, A167, STI-A101, CK-301, BGB-A333, MSB-2311, HLX20, LY3300054, MCLA-136, and SHR-1210.

The compounds of the present disclosure can further be used in combination with one or more anti-inflammatory agents, steroids, immunosuppressants or therapeutic antibodies.

The compounds of Formula (I) or any of the formulas as described herein, a compound as recited in any of the claims and described herein, or salts thereof can be combined with another immunogenic agent, such as cancerous cells, purified tumor antigens (including recombinant proteins, peptides, and carbohydrate molecules), cells, and cells transfected with genes encoding immune stimulating cytokines. Non-limiting examples of tumor vaccines that can be used include peptides of melanoma antigens, such as peptides of gp100, MAGE antigens, Trp-2, MARTI and/or tyrosinase, or tumor cells transfected to express the cytokine GM-CSF.

The compounds of Formula (I) or any of the formulas as described herein, a compound as recited in any of the claims and described herein, or salts thereof can be used in combination with a vaccination protocol for the treatment of cancer. In some embodiments, the tumor cells are transduced to express GM-CSF. In some embodiments, tumor vaccines include the proteins from viruses implicated in human cancers such as Human Papilloma Viruses (HPV), Hepatitis Viruses (HBV and HCV) and Kaposi's Herpes Sarcoma Virus (KHSV). In some embodiments, the compounds of the present disclosure can be used in combination with tumor specific antigen such as heat shock proteins isolated from tumor tissue itself. In some embodiments, the compounds of Formula (I) or any of the formulas as described herein, a compound as recited in any of the claims and described herein, or salts thereof can be combined with dendritic cells immunization to activate potent anti-tumor responses.

The compounds of the present disclosure can be used in combination with bispecific macrocyclic peptides that target Fc alpha or Fc gamma receptor-expressing effectors cells to tumor cells. The compounds of the present disclosure can also be combined with macrocyclic peptides that activate host immune responsiveness.

In some further embodiments, combinations of the compounds of the disclosure with other therapeutic agents can be administered to a patient prior to, during, and/or after a bone marrow transplant or stem cell transplant. The compounds of the present disclosure can be used in combination with bone marrow transplant for the treatment of a variety of tumors of hematopoietic origin.

The compounds of Formula (I) or any of the formulas as described herein, a compound as recited in any of the claims and described herein, or salts thereof can be used in combination with vaccines, to stimulate the immune response to pathogens, toxins, and self antigens. Examples of pathogens for which this therapeutic approach may be particularly useful, include pathogens for which there is currently no effective vaccine, or pathogens for which conventional vaccines are less than completely effective. These include, but are not limited to, HIV, Hepatitis (A, B, & C), Influenza, Herpes, Giardia, Malaria, Leishmania, *Staphylococcus aureus, Pseudomonas Aeruginosa*.

Viruses causing infections treatable by methods of the present disclosure include, but are not limit to human papillomavirus, influenza, hepatitis A, B, C or D viruses, adenovirus, poxvirus, herpes simplex viruses, human cytomegalovirus, severe acute respiratory syndrome virus, ebola virus, measles virus, herpes virus (e.g., VZV, HSV-1, HAV-6, HSV-II, and CMV, Epstein Barr virus), flaviviruses, echovirus, rhinovirus, coxsackie virus, cornovirus, respiratory syncytial virus, mumpsvirus, rotavirus, measles virus, rubella virus, parvovirus, vaccinia virus, HTLV virus, dengue virus, papillomavirus, molluscum virus, poliovirus, rabies virus, JC virus and arboviral encephalitis virus.

Pathogenic bacteria causing infections treatable by methods of the disclosure include, but are not limited to, chlamydia, rickettsial bacteria, mycobacteria, staphylococci, streptococci, pneumonococci, meningococci and conococci, klebsiella, proteus, serratia, pseudomonas, legionella, diphtheria, salmonella, bacilli, cholera, tetanus, botulism, anthrax, plague, leptospirosis, and Lyme's disease bacteria.

Pathogenic fungi causing infections treatable by methods of the disclosure include, but are not limited to, *Candida* (*albicans, krusei, glabrata, tropicalis*, etc.), *Cryptococcus neoformans, Aspergillus* (*fumigatus, niger*, etc.), Genus *Mucorales* (*mucor, absidia, rhizophus*), *Sporothrix schenkii, Blastomyces dermatitidis, Paracoccidioides brasiliensis, Coccidioides immitis* and *Histoplasma capsulatum*.

Pathogenic parasites causing infections treatable by methods of the disclosure include, but are not limited to, *Entamoeba histolytica, Balantidium coli, Naegleriafowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma gondi*, and *Nippostrongylus brasiliensis*.

When more than one pharmaceutical agent is administered to a patient, they can be administered simultaneously, separately, sequentially, or in combination (e.g., for more than two agents).

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR, e.g., 1996 edition, Medical Economics Company, Montvale, N.J.), the disclosure of which is incorporated herein by reference as if set forth in its entirety.

Pharmaceutical Formulations and Dosage Forms

When employed as pharmaceuticals, the compounds of the disclosure can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral, or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This disclosure also includes pharmaceutical compositions which contain, as the active ingredient, the compound of the disclosure or a pharmaceutically acceptable salt thereof, in combination with one or more pharmaceutically acceptable carriers (excipients). In some embodiments, the composition is suitable for topical administration. In making the compositions of the disclosure, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

The compounds of the disclosure may be milled using known milling procedures such as wet milling to obtain a particle size appropriate for tablet formation and for other formulation types. Finely divided (nanoparticulate) preparations of the compounds of the disclosure can be prepared by processes known in the art, e.g., see International App. No. WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the disclosure can be formulated so as to provide quick, sustained or delayed release of the active ingredient after administration to the patient by employing procedures known in the art.

The compositions can be formulated in a unit dosage form, each dosage containing from about 5 to about 1000 mg (1 g), more usually about 100 to about 500 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

In some embodiments, the compositions of the disclosure contain from about 5 to about 50 mg of the active ingredient. One having ordinary skill in the art will appreciate that this embodies compositions containing about 5 to about 10, about 10 to about 15, about 15 to about 20, about 20 to about 25, about 25 to about 30, about 30 to about 35, about 35 to about 40, about 40 to about 45, or about 45 to about 50 mg of the active ingredient.

In some embodiments, the compositions of the disclosure contain from about 50 to about 500 mg of the active ingredient. One having ordinary skill in the art will appreciate that this embodies compositions containing about 50 to about 100, about 100 to about 150, about 150 to about 200, about 200 to about 250, about 250 to about 300, about 350 to about 400, or about 450 to about 500 mg of the active ingredient.

In some embodiments, the compositions of the disclosure contain from about 500 to about 1000 mg of the active ingredient. One having ordinary skill in the art will appreciate that this embodies compositions containing about 500 to about 550, about 550 to about 600, about 600 to about 650, about 650 to about 700, about 700 to about 750, about 750 to about 800, about 800 to about 850, about 850 to about 900, about 900 to about 950, or about 950 to about 1000 mg of the active ingredient.

Similar dosages may be used of the compounds described herein in the methods and uses of the disclosure.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present disclosure. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, about 0.1 to about 1000 mg of the active ingredient of the present disclosure.

The tablets or pills of the present disclosure can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present disclosure can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face mask, tert, or intermittent positive pressure breathing machine. Solution, suspension, or powder compositions can be administered orally or nasally from devices which deliver the formulation in an appropriate manner.

Topical formulations can contain one or more conventional carriers. In some embodiments, ointments can contain water and one or more hydrophobic carriers selected from, for example, liquid paraffin, polyoxyethylene alkyl ether, propylene glycol, white Vaseline, and the like. Carrier compositions of creams can be based on water in combination with glycerol and one or more other components, e.g. glycerinemonostearate, PEG-glycerinemonostearate and cetylstearyl alcohol. Gels can be formulated using isopropyl alcohol and water, suitably in combination with other components such as, for example, glycerol, hydroxyethyl cellulose, and the like. In some embodiments, topical formulations contain at least about 0.1, at least about 0.25, at least about 0.5, at least about 1, at least about 2, or at least about 5 wt % of the compound of the disclosure. The topical formulations can be suitably packaged in tubes of, for example, 100 g which are optionally associated with instructions for the treatment of the select indication, e.g., psoriasis or other skin condition.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of a compound of the present disclosure can vary according to, for example, the particular use for which the treatment is made, the manner of administration of the compound, the health and condition of the patient, and the judgment of the prescribing physician. The proportion or concentration of a compound of the disclosure in a pharmaceutical composition can vary depending upon a number of factors including dosage, chemical characteristics (e.g., hydrophobicity), and the route of administration. For example, the compounds of the disclosure can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compositions of the disclosure can further include one or more additional pharmaceutical agents such as a chemotherapeutic, steroid, anti-inflammatory compound, or immunosuppressant, examples of which are listed herein.

Labeled Compounds and Assay Methods

Another aspect of the present disclosure relates to labeled compounds of the disclosure (radio-labeled, fluorescent-labeled, etc.) that would be useful not only in imaging techniques but also in assays, both in vitro and in vivo, for localizing and quantitating STING in tissue samples, including human, and for identifying STING activators by inhibition binding of a labeled compound. Substitution of one or more of the atoms of the compounds of the present disclosure can also be useful in generating differentiated ADME (Adsorption, Distribution, Metabolism and Excretion.) Accordingly, the present disclosure includes STING assays that contain such labeled or substituted compounds.

The present disclosure further includes isotopically-labeled compounds of the disclosure. An "isotopically" or "radio-labeled" compound is a compound of the disclosure where one or more atoms are replaced or substituted by an atom having an atomic mass or mass number different from the atomic mass or mass number typically found in nature (i.e., naturally occurring). Suitable radionuclides that may be incorporated in compounds of the present disclosure include but are not limited to $^2$H (also written as D for deuterium), $^3$H (also written as T for tritium), $^{11}$C, $^{13}$, $^{14}$, $^{13}$N, $^{15}$N, $^{15}$O, $^{17}$O, $^{18}$O, $^{18}$F, $^{35}$S, $^{36}$Cl, $^{82}$Br, $^{75}$Br, $^{76}$Br, $^{123}$I, $^{124}$I, $^{125}$I and $^{131}$I. For example, one or more hydrogen atoms in a compound of the present disclosure can be replaced by deuterium atoms (e.g., one or more hydrogen atoms of a $C_{1-6}$ alkyl group of Formula (I) can be optionally substituted with deuterium atoms, such as —$CD_3$ being substituted for —$CH_3$). In some embodiments, alkyl groups in Formula (I) can be perdeuterated.

One or more constituent atoms of the compounds presented herein can be replaced or substituted with isotopes of the atoms in natural or non-natural abundance. In some embodiments, the compound includes at least one deuterium atom. In some embodiments, the compound includes two or more deuterium atoms. In some embodiments, the compound includes 1-2, 1-3, 1-4, 1-5, or 1-6 deuterium atoms. In some embodiments, all of the hydrogen atoms in a compound can be replaced or substituted by deuterium atoms.

In some embodiments, 1, 2, 3, 4, 5, 6, 7, or 8 hydrogen atoms, attached to carbon atoms of "alkyl", "alkenyl", "alkynyl", "aryl", "phenyl", "cycloalkyl", "heterocycloalkyl", or "heteroaryl" substituents or "-$C_{1}$-alkyl-", "alkylene", "alkenylene" and "alkynylene" linking groups, as described herein, are optionally replaced by deuterium atoms.

Synthetic methods for including isotopes into organic compounds are known in the art (Deuterium Labeling in Organic Chemistry by Alan F. Thomas (New York, N.Y., Appleton-Century-Crofts, 1971; The Renaissance of H/D Exchange by Jens Atzrodt, Volker Derdau, Thorsten Fey and Jochen Zimmermann, Angew. Chem. Int. Ed. 2007, 7744-7765; The Organic Chemistry of Isotopic Labelling by James R. Hanson, Royal Society of Chemistry, 2011). Isotopically labeled compounds can be used in various studies such as NMR spectroscopy, metabolism experiments, and/or assays.

Substitution with heavier isotopes, such as deuterium, may afford certain therapeutic advantages resulting from greater metabolic stability, for example, increased in vivo half-life or reduced dosage requirements, and hence may be preferred in some circumstances. (see e.g., A. Kerekes et. al. *J. Med. Chem.* 2011, 54, 201-210; R. Xu et. al. *J. Label Compd. Radiopharm.* 2015, 58, 308-312). In particular, substitution at one or more metabolism sites may afford one or more of the therapeutic advantages.

The radionuclide that is incorporated in the instant radio-labeled compounds will depend on the specific application of that radio-labeled compound. For example, for in vitro STING labeling and competition assays, compounds that incorporate $^3$H, $^{14}$C, $^{82}$Br, $^{125}$I, $^{131}$I or $^{35}$S can be useful. For radio-imaging applications $^{11}$C, $^{18}$F, $^{125}$I, $^{123}$I, $^{124}$I, $^{131}$I, $^{75}$Br, $^{76}$Br or $^{77}$Br can be useful.

It is understood that a "radio-labeled" or "labeled compound" is a compound that has incorporated at least one radionuclide. In some embodiments, the radionuclide is selected from the group consisting of $^3$H, $^{14}$C, $^{125}$I, $^{35}$S and $^{83}$Br.

The present disclosure can further include synthetic methods for incorporating radio-isotopes into compounds of the disclosure. Synthetic methods for incorporating radio-isotopes into organic compounds are well known in the art, and an ordinary skill in the art will readily recognize the methods applicable for the compounds of disclosure.

A labeled compound of the disclosure can be used in a screening assay to identify/evaluate compounds. For example, a newly synthesized or identified compound (i.e., test compound) which is labeled can be evaluated for its ability to bind activate STING by monitoring its concentration variation when contacting with STING, through tracking of the labeling. For example, a test compound (labeled) can be evaluated for its ability to reduce binding of another compound which is known to bind to STING (i.e., standard compound). Accordingly, the ability of a test compound to compete with the standard compound for binding to STING directly correlates to its binding affinity. Conversely, in some other screening assays, the standard compound is labeled and test compounds are unlabeled. Accordingly, the concentration of the labeled standard compound is monitored in order to evaluate the competition between the standard compound and the test compound, and the relative binding affinity of the test compound is thus ascertained.

Kits

The present disclosure also includes pharmaceutical kits useful, for example, in the treatment or prevention of STING-associated diseases or disorders (such as, e.g., cancer, an inflammatory disease, a cardiovascular disease, or a neurodegenerative disease) which include one or more containers containing a pharmaceutical composition comprising a therapeutically effective amount of a compound of the disclosure. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results.

EXAMPLES

Preparatory LC-MS purifications of some of the compounds prepared were performed on Waters mass directed fractionation systems. The basic equipment setup, protocols, and control software for the operation of these systems have been described in detail in the literature (see e.g. "Two-Pump At Column Dilution Configuration for Preparative LC-MS", K. Blom, *J. Combi. Chem.*, 4, 295 (2002); "Optimizing Preparative LC-MS Configurations and Methods for Parallel Synthesis Purification", K. Blom, R. Sparks, J. Doughty, G. Everlof, T. Hague, A. Combs, *J. Combi. Chem.*, 5, 670 (2003); and "Preparative LC-MS Purification: Improved Compound Specific Method Optimization", K. Blom, B. Glass, R. Sparks, A. Combs, *J. Combi. Chem.*, 6, 874-883 (2004)). The compounds separated were typically subjected to analytical liquid chromatography mass spectrometry (LCMS) for purity analysis under the following conditions: Instrument; Agilent 1100 series, LC/MSD, Column: Waters Sunfire™ $C_{18}$ 5 µm, 2.1×50 mm, Buffers: mobile phase A: 0.025% TFA in water and mobile phase B: acetonitrile; gradient 2% to 80% of B in 3 minutes with flow rate 2.0 mL/minute.

Some of the compounds prepared were also separated on a preparative scale by reverse-phase high performance liquid chromatography (RP-HPLC) with MS detector or flash chromatography (silica gel) as indicated in the Examples. Typical preparative reverse-phase high performance liquid chromatography (RP-HPLC) column conditions are as follows:

pH=2 purifications: Waters Sunfire™ $C_{18}$ 5 µm, 30×100 mm or Waters XBridge™ $C_{18}$ 5 µm, 30×100 mm column, eluting with mobile phase A: 0.1% TFA (trifluoroacetic acid) in water and mobile phase B: acetonitrile; the flow rate was 60 mL/minute, the separating gradient was optimized for each compound using the Compound Specific Method Optimization protocol as described in the literature (see e.g. "Preparative LCMS Purification: Improved Compound Specific Method Optimization", K. Blom, B. Glass, R. Sparks, A. Combs, *J. Comb. Chem.*, 6, 874-883 (2004)).

pH=10 purifications: Waters XBridge™ $C_{18}$ 5 µm, 30×100 mm column, eluting with mobile phase A: 0.1% $NH_4OH$ in water and mobile phase B: acetonitrile; the flow rate was 60 mL/minute, the separating gradient was optimized for each compound using the Compound Specific Method Optimization protocol as described in the literature (see e.g. "Preparative LCMS Purification: Improved Compound Specific Method Optimization", K. Blom, B. Glass, R. Sparks, A. Combs, *J. Comb. Chem.*, 6, 874-883 (2004)).

Example 1. (E)-9-(4-(5-carbamoyl-2-(1-ethyl-3-methyl-1H-pyrazole-5-carboxamido)-7-methyl-1H-benzo[d]imidazol-1-yl)but-2-enyl)-2-(1-ethyl-3-methyl-1H-pyrazol-5-yl)-9H-pyrimido[4,5-b]indole-6-carboxamide

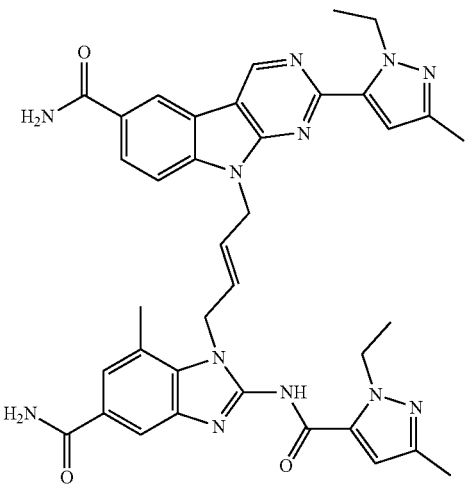 [SMILES: CCn1nc(C)cc1C(=O)Nc1nc2cc(C(N)=O)cc(C)c2n1C/C=C/Cn1c2ccc(C(N)=O)cc2c2cnc(-c3cc(C)nn3CC)nc21]

Step 1: 4-fluoro-3-methyl-5-nitrobenzamide

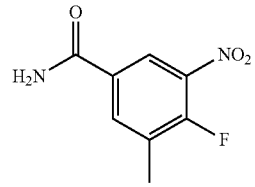

At 0° C., a mixture of nitric acid (2.51 ml, 39.2 mmol) and sulfuric acid (2.173 ml, 40.8 mmol) was added dropwise over 10 min into a solution of 4-fluoro-3-methylbenzamide (4.46 g, 29.1 mmol) in sulfuric acid (13.97 ml, 262 mmol). The mixture was stirred for 1.5 h while slowly warming up to room temperature. The mixture was slowly poured into ice water (50 mL), and the precipitated solid was filtered and then washed with water (50 mL). The resulting solid residue was dried to provide the desired product as a white solid. LC-MS calculated for $C_8H_8FN_2O_3$ (M+H)$^+$: m/z=199.04; found 199.2

Step 2: (E)-tert-butyl 4-(4-carbamoyl-2-methyl-6-nitrophenylamino)but-2-enylcarbamate

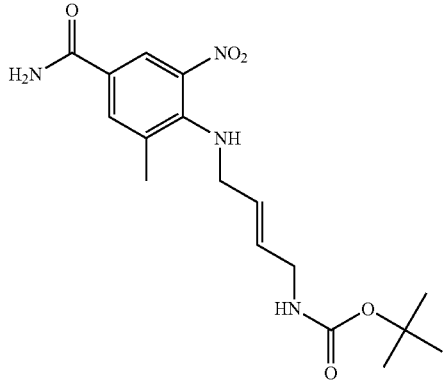

To a solution of 4-fluoro-3-methyl-5-nitrobenzamide (0.400 g, 2.019 mmol) and tert-butyl (E)-(4-aminobut-2-en-1-yl)carbamate (0.376 g, 2.019 mmol) (Ark Pharm, cat #AK308564) in dry DMSO (2.019 ml) was added $K_2CO_3$ (0.614 g, 4.44 mmol). The resulting yellow solution was stirred at room temperature for 1 h. The reaction mixture was diluted with water (15 mL) dropwise. The precipitated solid was filtered and then washed with water (10 mL). The resulting solid residue was dried to provide the desired product as a yellow solid. LC-MS calculated for $C_{17}H_{24}N_4NaO_5$ (M+Na)$^+$: m/z=387.2; found 387.2.

Step 3: (E)-tert-butyl 4-(2-amino-4-carbamoyl-6-methylphenylamino)but-2-enylcarbamate

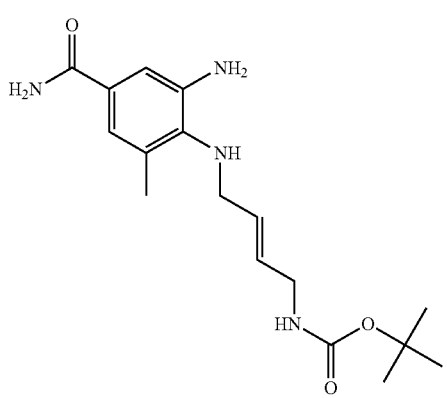 [SMILES: Cc1cc(C(N)=O)cc([N+](=O)[O-])c1NC/C=C/CNC(=O)OC(C)(C)C]

To a solution of tert-butyl (E)-(4-((4-carbamoyl-2-methyl-6-nitrophenyl)amino)but-2-en-1-yl)carbamate (220 mg, 0.604 mmol) in dioxane (1509 μl) and water (503 μl) was added ammonium chloride (226 mg, 4.23 mmol) and zinc (276 mg, 4.23 mmol) at 0° C. The reaction mixture was stirred at room temperature for 1 h, after which time it was filtered through a Celite® bed. The filtrate was partitioned between DCM and water. The organic layer was separated, dried over MgSO$_4$, filtered, and concentrated to provide the product. LC-MS calculated for $C_{17}H_{26}N_4NaO_3$ (M+Na)$^+$: m/z=357.2 ; found 357.3.

Step 4: (E)-tert-butyl 4-(2-amino-5-carbamoyl-7-methyl-1H-benzo[d]imidazol-1-yl)but-2-enylcarbamate

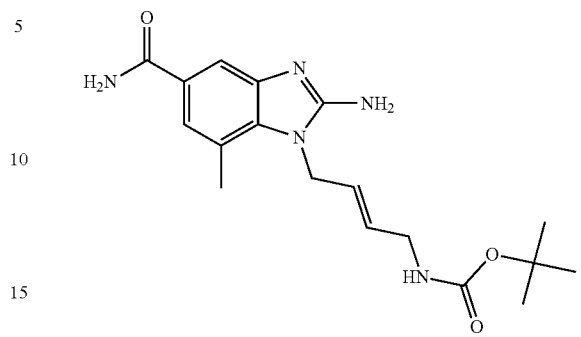

To a solution of tert-butyl (E)-(4-((2-amino-4-carbamoyl-6-methylphenyl)amino)but-2-en-1-yl)carbamate (0.201 g, 0.60 mmol) in MeOH (2.000 ml) was added cyanogen bromide (0.047 ml, 0.900 mmol). The reaction mixture was stirred at room temperature for 1 h. The mixture was diluted with DCM, and washed with water and brine. The organic phase was dried over MgSO$_4$ before filtering. The filtrate was concentrated and purified by flash chromatography on a silica gel column eluting with 0 to 8% MeOH in DCM to afford the desired product. LC-MS calculated for $C_{18}H_{26}N_5O_3$ (M+H)$^+$: m/z=360.2; found 360.3.

Step 5: (E)-tert-butyl 4-(5-carbamoyl-2-(1-ethyl-3-methyl-1H-pyrazole-5-carboxamido)-7-methyl-1H-benzo[d]imidazol-1-yl)but-2-enylcarbamate

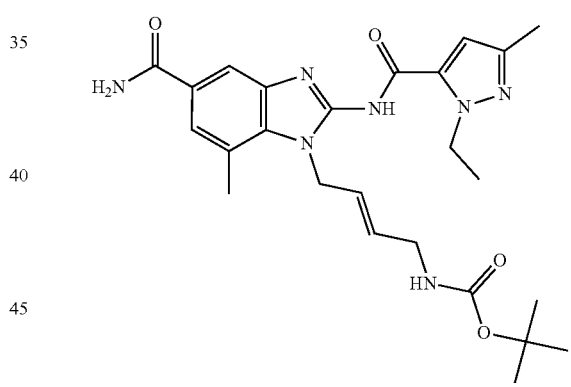

A mixture of 1-ethyl-3-methyl-1H-pyrazole-5-carboxylic acid (Combi-Blocks, cat #QB-0979: 93 mg, 0.60 mmol), tert-butyl (E)-(4-(2-amino-5-carbamoyl-7-methyl-1H-benzo[d]imidazol-1-yl)but-2-en-1-yl)carbamate (216 mg, 0.600 mmol), 2-(3H-[1,2,3]triazolo[4,5-b]pyridin-3-yl)-1,1,3,3-tetramethylisouronium hexafluorophosphate(V) (274 mg, 0.720 mmol), and N,N-Diisopropylethylamine (209 μ, 1.200 mmol) in DMF (2000 μl) was stirred at room temperature for 2 h. The mixture was concentrated under reduced pressure. The mixture was then diluted with DCM and water, and the layers were separated. The aqeous layer was further extracted with DCM and the combined organic layers were washed with brine, dried over Na$_2$SO$_4$, filtered, and concentrated in vacuo. The crude residue was purified by flash chromatography on a silica gel column eluting with 0 to 8% MeOH in DCM to afford the desired product. LC-MS calculated for $C_{25}H_{34}N_7O_4$ (M+H)$^+$: m/z=496.3 ; found 496.3.

Step 6: (E)-1-(4-aminobut-2-enyl)-2-(1-ethyl-3-methyl-1H-pyrazole-5-carboxamido)-7-methyl-1H-benzo[d]imidazole-5-carboxamide

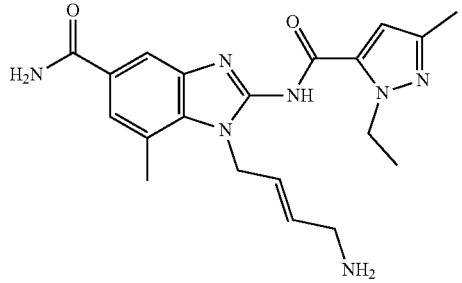 [SMILES: CCn1nc(C)cc1C(=O)Nc1nc2cc(C(N)=O)cc(C)c2n1C/C=C/CN]

To a solution of tert-butyl (E)-(4-(5-carbamoyl-2-(1-ethyl-3-methyl-1H-pyrazole-5-carboxamido)-7-methyl-1H-benzo[d]imidazol-1-yl)but-2-en-1-yl)carbamate (180.0 mg, 0.363 mmol) in DCM (2.0 mL) was added TFA (0.2 mL). The resulting solution was stirred at room temperature for 0.5 h. The reaction mixture was quenched by NaHCO$_3$ aqueous solution then extracted with DCM. The organic phases were combined and dried over MgSO$_4$, then filtered. The filtrate was concentrated and used directly in the next step without further purification. For characterization purposes, the crude material was purified by prep HPLC (pH=2, water+TFA) to provide the desired compound as its TFA salt. LC-MS calculated for $C_{20}H_{26}N_7O_2$ (M+H)$^+$: m/z=396.2; found 396.3. $^1$H NMR (400 MHz, DMSO) δ 12.91 (s, 1H), 7.87 (m, 2H), 7.69 (br s, 2H), 7.57 (s, 1H), 7.30 (s, 1H), 6.64 (s, 1H), 6.10 (dt, J=16.0, 4.8 Hz, 1H), 5.33 (dt, J=16.0, 6.4 Hz, 1H), 5.06 (brs, 2H), 4.59 (q, J=6.8 Hz, 2H), 3.42 (dt, J=6.4 Hz, 4.8 Hz, 2H), 2.63 (s, 3H), 2.16 (s, 3H), 1.34 (t, J=6.8 Hz, 3H).

Step 7: (E)-2-(1-ethyl-3-methyl-1H-pyrazole-5-carboxamido)-1-(4-hydroxybut-2-enyl)-7-methyl-1H-benzo[d]imidazole-5-carboxamide

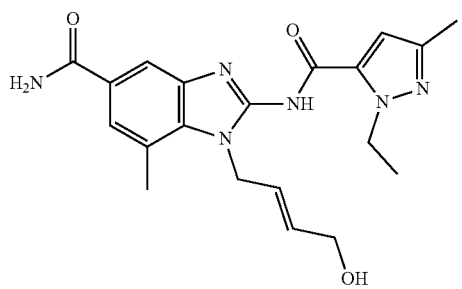 [SMILES: CCn1nc(C)cc1C(=O)Nc1nc2cc(C(N)=O)cc(C)c2n1C/C=C/CO]

To a mixture of (E)-1-(4-aminobut-2-en-1-yl)-2-(1-ethyl-3-methyl-1H-pyrazole-5-carboxamido)-7-methyl-1H-benzo[d]imidazole-5-carboxamide (180.0 mg, 0.455 mmol) and KBr (108 mg, 0.910 mmol) in water (228 µl) was added sodium nitrite (62.8 mg, 0.910 mmol). The mixture was stirred at 70° C. for 2 h. After cooling to rt, the mixture was diluted with DCM, and washed with water and brine. The organic phase was dried over MgSO$_4$ before filtering. The filtrate was concentrated to afford the desired product. LC-MS calculated for $C_{20}H_{25}N_6O_3$ (M+H)$^+$: m/z=397.2; found 397.2.

Step 8: (E)-1-(4-bromobut-2-enyl)-2-(1-ethyl-3-methyl-1H-pyrazole-5-carboxamido)-7-methyl-1H-benzo[d]imidazole-5-carboxamide

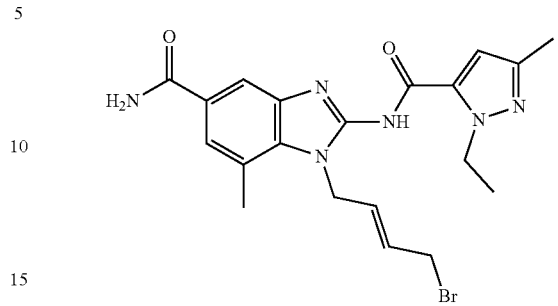

To a solution of (E)-2-(1-ethyl-3-methyl-1H-pyrazole-5-carboxamido)-1-(4-hydroxybut-2-enyl)-7-methyl-1H-benzo[d]imidazole-5-carboxamide (180.0 mg, 0.455 mmol) in THF (2.0 mL) was added PBr$_3$ (86 µl, 0.910 mmol) dropwise. The resulting solution was stirred at room temperature for 10 h. The reaction mixture was quenched by NaHCO$_3$ aqueous solution then extracted with DCM. The organic phases were combined and dried over MgSO$_4$, then filtered. The crude residue was purified by flash chromatography on a silica gel column eluting with 0 to 10% MeOH in DCM to afford the desired product. LC-MS calculated for $C_{20}H_{24}BrN_6O_2$ (M+H)$^+$: m/z=459.1, 461.1; found 459.1, 461.1.

Step 9: 3-(2-chloropyrimidin-5-yl)-4-nitrobenzamide

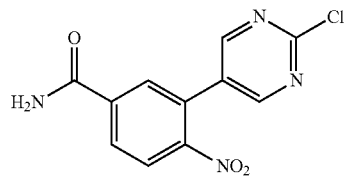 [SMILES: NC(=O)c1ccc([N+](=O)[O-])c(-c2cnc(Cl)nc2)c1]

To a solution of 3-bromo-4-nitrobenzamide (Matrix Scientific, cat #184225: 600.0 mg, 2.449 mmol), (2-chloropyrimidin-5-yl)boronic acid (Combi-Blocks, cat #BB-5457: 388 mg, 2.449 mmol), and sodium carbonate (519 mg, 4.90 mmol) in dioxane (2 mL) and water (0.4 mL) was added dichloro[1,1'-bis(diphenylphosphino)ferrocene]palladium (II) dichloromethane adduct (120 mg, 0.147 mmol). The vial was flushed with nitrogen, and the reaction was stirred at 100° C. for 1 h. The reaction mixture was quenched by NH$_4$OH aqueous solution then extracted with DCM. The organic phases were combined and dried over MgSO$_4$, then filtered. The crude residue was purified by flash chromatography on a silica gel column eluting with 0 to 8% MeOH in DCM to afford the desired product. LC-MS calculated for $C_{11}H_8ClN_4O_3$ (M+H)$^+$: m/z=279.0; found 279.0.

Step 10: 2-chloro-9H-pyrimido[4,5-b]indole-6-carboxamide

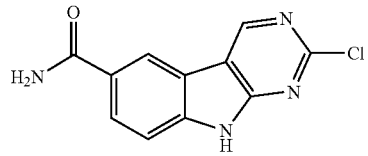 [SMILES: NC(=O)c1ccc2[nH]c3nc(Cl)ncc3c2c1]

A mixture of 3-(2-chloropyrimidin-5-yl)-4-nitrobenzamide (320.0 mg, 1.148 mmol) and 1,2-bis(diphenylphosphino)ethane (572 mg, 1.435 mmol) was dissolved in 1,2-dichlorobenzene (3828 µl). The vial was flushed with nitrogen before heating at 160° C. for 1 h. After removal of the solvent under vacuum, the reaction mixture was extracted with DCM and water. The organic phases were combined and dried over MgSO$_4$, filtered, then concentrated under reduced pressure. The crude residue was purified by flash chromatography on a silica gel column eluting with 0 to 8% MeOH in DCM to afford the desired product. LC-MS calculated for $C_{11}H_8ClN_4O$ (M+H)$^+$: m/z=247.0; found 247.0.

Step 11: 2-(1-ethyl-3-methyl-1H-pyrazol-5-yl)-9H-pyrimido[4,5-b]indole-6-carboxamide

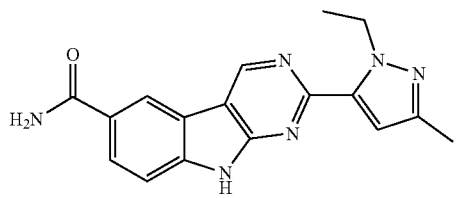 [SMILES: CCn1nc(C)cc1-c1ncc2c(n1)[nH]c1ccc(C(N)=O)cc12]

To a solution of 2-chloro-9H-pyrimido[4,5-b]indole-6-carboxamide (60.0 mg, 0.243 mmol), 1-ethyl-3-methyl-5-(4,4,5,5-tetramethyl-1,3,2-dioxaborolan-2-yl)-1H-pyrazole (Enamine, cat #EN300-207291: 57.4 mg, 0.243 mmol), and sodium carbonate (51.6 mg, 0.487 mmol) in dioxane (676 µl) and water (135 µl) was added dichloro[1,1'-bis(diphenylphosphino)ferrocene]palladium (II) dichloromethane adduct (11.92 mg, 0.015 mmol). The vial was flushed with nitrogen, and the reaction was stirred at 100° C. for 1 h. The reaction mixture was quenched by NH$_4$OH aqueous solution then extracted with DCM. The organic phases were combined and dried over MgSO$_4$, then filtered. The crude residue was purified by flash chromatography on a silica gel column eluting with 0 to 8% MeOH in DCM to afford the desired product. LC-MS calculated for $C_{17}H_{17}N_6O$ (M+H)$^+$: m/z=321.1; found 321.1.

Step 12: (E)-9-(4-(5-carbamoyl-2-(1-ethyl-3-methyl-1H-pyrazole-5-carboxamido)-7-methyl-1H-benzo[d]imidazol-1-yl)but-2-enyl)-2-(1-ethyl-3-methyl-1H-pyrazol-5-yl)-9H-pyrimido[4,5-b]indole-6-carboxamide A mixture of 2-(1-ethyl-3-methyl-1H-pyrazol-5-yl)-9H-pyrimido[4,5-b]indole-6-carboxamide (5.0 mg, 0.016 mmol), (E)-1-(4-bromobut-2-en-1-yl)-2-(1-ethyl-3-methyl-1H-pyrazole-5-carboxamido)-7-methyl-1H-benzo[d]imidazole-5-carboxamide (7.17 mg, 0.016 mmol), and cesium carbonate (11.19 mg, 0.034 mmol) was stirred in DMF (156 µ) at 50° C. for 1 h. The reaction mixture was diluted with MeOH and purified by prep-HPLC (pH=2, acetonitrile/water+TFA) to give the desired product as its TFA salt. LC-MS calculated for $C_{37}H_{39}H_{12}O_3$ (M+H)$^+$: m/z=699.3; found 699.3.

Example 2. (E)-1-(4-(2-(1-ethyl-3-methyl-1H-pyrazol-5-yl)-9H-pyrimido[4,5-b]indol-9-yl)but-2-enyl)-2-(1-ethyl-3-methyl-1H-pyrazole-5-carboxamido)-7-methyl-1H-benzo[d]imidazole-5-carboxamide

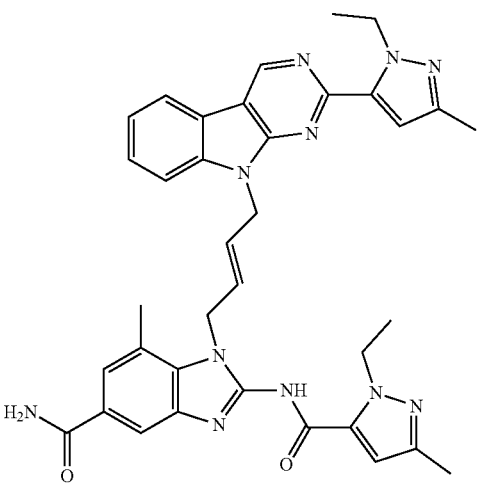 [SMILES: CCn1nc(C)cc1C(=O)Nc1nc2cc(C(N)=O)cc(C)c2n1C/C=C/Cn1c2ccccc2c2cnc(-c3cc(C)nn3CC)nc21]

Step 1: 2-(1-ethyl-3-methyl-1H-pyrazol-5-yl)-9H-pyrimido[4,5-b]indole

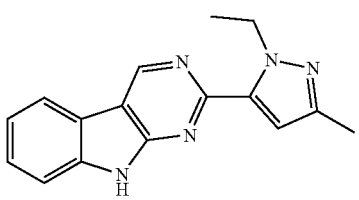 [SMILES: CCn1nc(C)cc1-c1ncc2c(n1)[nH]c1ccccc12]

This compound was prepared using similar procedures as described for Example 1, Step 9 to Step 11 with 1-bromo-2-nitrobenzene (Aldrich, cat #365424) replacing 3-bromo-4-nitrobenzamide. LC-MS calculated for $C_{16}H_{16}N_5$ (M+H)$^+$: m/z=278.2; found 278.2.

Step 2: (E)-1-(4-(2-(1-ethyl-3-methyl-1H-pyrazol-5-yl)-9H-pyrimido[4,5-b]indol-9-yl)but-2-enyl)-2-(1-ethyl-3-methyl-1H-pyrazole-5-carboxamido)-7-methyl-1H-benzo[d]imidazole-5-carboxamide A mixture of 2-(1-ethyl-3-methyl-1H-pyrazol-5-yl)-9H-pyrimido[4,5-b]indole (5.0 mg, 0.018 mmol), (E)-1-(4-bromobut-2-en-1-yl)-2-(1-ethyl-3-methyl-1H-pyrazole-5-carboxamido)-7-methyl-1H-benzo[d]imidazole-5-carboxamide (8.28 mg, 0.018 mmol), and cesium carbonate (12.92 mg, 0.040 mmol) was stirred in DMF (60.1 µl) at 50° C. for 1 h. The reaction mixture was diluted with MeOH and purified by prep-HPLC (pH=2, acetonitrile/water+TFA) to give the desired product as its TFA salt. LC-MS calculated for $C_{36}H_{38}N_{11}O_2$ (M+H)$^+$: m/z=656.3; found 656.3.

Example 3. (E)-9-(4-(5-carbamoyl-2-(1-ethyl-3-methyl-1H-pyrazole-5-carboxamido)-7-methyl-1H-benzo[d]imidazol-1-yl)but-2-enyl)-2-(1,3-dimethyl-1H-pyrazol-5-yl)-9H-pyrimido[4,5-b]indole-6-carboxamide

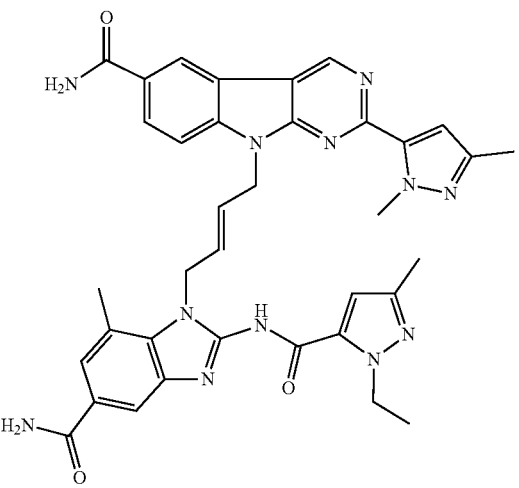 [SMILES: CCn1nc(C)cc1C(=O)Nc1nc2cc(C(N)=O)cc(C)c2n1C/C=C/Cn1c2ccc(C(N)=O)cc2c2cnc(-c3cc(C)nn3C)nc21]

Step 1: 2-(1,3-dimethyl-1H-pyrazol-5-yl)-9H-pyrimido[4,5-b]indole-6-carboxamide

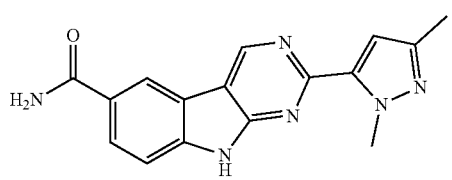 [SMILES: Cc1cc(-c2ncc3c(n2)[nH]c2ccc(C(N)=O)cc23)n(C)n1]

This compound was prepared using similar procedures as described for Example 1, Step 11 with 1,3-dimethyl-5-(4,4,5,5-tetramethyl-1,3,2-dioxaborolan-2-yl)-1H-pyrazole (Combi-Blocks, cat #PN-6021) replacing 1-ethyl-3-methyl-5-(4,4,5,5-tetramethyl-1,3,2-dioxaborolan-2-yl)-1H-pyrazole. LC-MS calculated for $C_{16}H_{15}N_6O$ (M+H)⁺: m/z=307.2; found 307.2.

Step 2: (E)-9-(4-(5-carbamoyl-2-(1-ethyl-3-methyl-1H-pyrazole-5-carboxamido)-7-methyl-1H-benzo[d]imidazol-1-yl)but-2-enyl)-2-(1,3-dimethyl-1H-pyrazol-5-yl)-9H-pyrimido[4,5-b]indole-6-carboxamide A mixture of 2-(1,3-dimethyl-1H-pyrazol-5-yl)-9H-pyrimido[4,5-b]indole-6-carboxamide (5.0 mg, 0.016 mmol), (E)-1-(4-bromobut-2-en-1-yl)-2-(1-ethyl-3-methyl-1H-pyrazole-5-carboxamido)-7-methyl-1H-benzo[d]imidazole-5-carboxamide (7.50 mg, 0.016 mmol), and cesium carbonate (11.70 mg, 0.036 mmol) was stirred in DMF (54.4 μl) at 50° C. for 1 h. The reaction mixture was diluted with MeOH and purified by prep-HPLC (pH=2, acetonitrile/water+TFA) to give the desired product as its TFA salt. LC-MS calculated for $C_{36}H_{37}N_{12}O_3$ (M+H)⁺: m/z=685.3; found 685.3. ¹H NMR (600 MHz, DMSO) δ 9.50 (s, 1H), 8.81 (s, 1H), 8.05 (d, J=8.6 Hz, 1H), 7.83 (s, 1H), 7.71 (d, J=8.6 Hz, 1H), 7.46 (s, 1H), 6.79 (s, 1H), 6.45 (s, 1H), 5.91 (dt, J=15.6, 4.8 Hz, 1H), 5.66 (dt, J=15.6, 4.8 Hz, 1H), 5.13 (d, J=4.8 Hz, 2H), 4.95 (d, J=4.8 Hz, 2H), 4.49 (q, J=7.0 Hz, 3H), 4.17 (s, 3H), 2.46 (s, 3H), 2.20 (s, 3H), 2.10 (s, 3H), 1.24 (t, J=7.0 Hz, 2H).

Example 4. (E)-9-(4-(5-carbamoyl-2-(1-ethyl-3-methyl-1H-pyrazole-5-carboxamido)-7-methoxy-1H-benzo[d]imidazol-1-yl)but-2-enyl)-2-(1-ethyl-3-methyl-1H-pyrazol-5-yl)-9H-pyrimido[4,5-b]indole-6-carboxamide

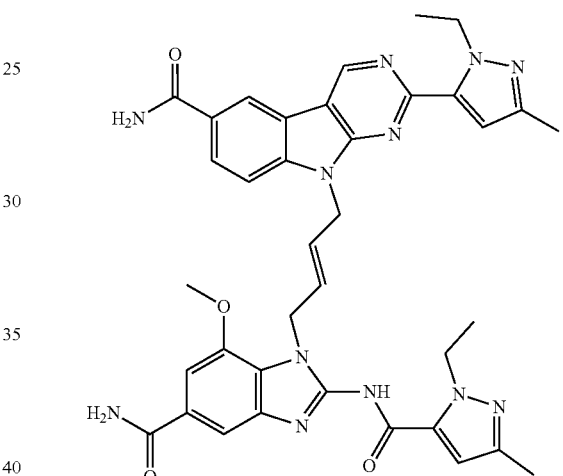

Step 1: 4-fluoro-3-methoxy-5-nitrobenzamide

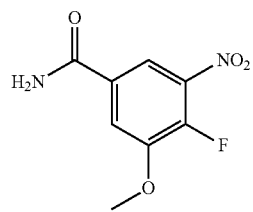

Methyl 4-fluoro-3-methoxy-5-nitrobenzoate (4.0 g, 17.45 mmol) was stirred in ammonium hydroxide (42.8 ml, 1100 mmol) at room temperature for 10 h. The solid was filtered and rinsed with cold water. The resulting solid residue was dried to provide the desired product as a light yellow solid. LC-MS calculated for $C_8H_8FN_2O_4$ (M+H)⁺: m/z=215.04; found 215.2

Step 2: (E)-tert-butyl 4-(4-carbamoyl-2-methoxy-6-nitrophenylamino)but-2-enylcarbamate

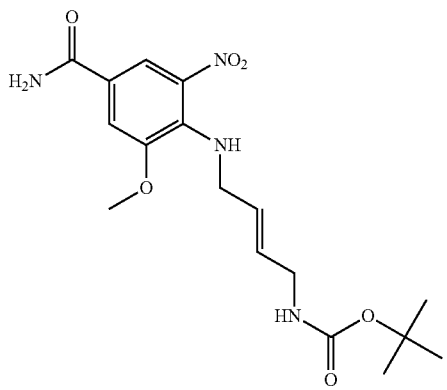 [SMILES: COc1cc(C(N)=O)cc([N+](=O)[O-])c1NC/C=C/CNC(=O)OC(C)(C)C]

To a solution of 4-fluoro-3-methoxy-5-nitrobenzamide (300.0 mg, 1.401 mmol), tert-butyl (E)-(4-aminobut-2-en-1-yl)carbamate (391 mg, 2.101 mmol) in dry DMSO (2335 µl) was added $K_2CO_3$ (387 mg, 2.80 mmol). The resulting solution was heated at 70° C. for 12 h. The mixture was concentrated under reduced pressure, and then extracted with DCM and water. The combined organic layers were dried, filtered, and concentrated in vacuo. The crude residue was purified by flash chromatography on a silica gel column to afford the desired product. LC-MS calculated for $C_{17}H_{24}N_4NaO_6$ (M+Na)$^+$: m/z=403.2; found 403.2.

Step 3: (E)-1-(4-bromobut-2-en-1-yl)-2-(1-ethyl-3-methyl-1H-pyrazole-5-carboxamido)-7-methoxy-1H-benzo[d]imidazole-5-carboxamide

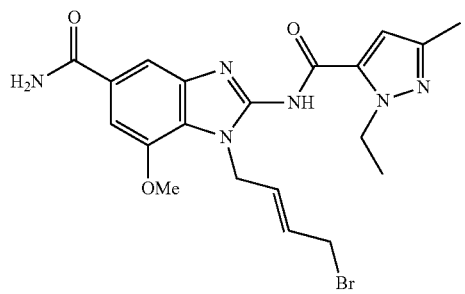 [SMILES: CCn1nc(C)cc1C(=O)Nc1nc2cc(C(N)=O)cc(OC)c2n1C/C=C/CBr]

This compound was prepared using similar procedures as described for Example 1, Step 3-8 with (E)-tert-butyl 4-(4-carbamoyl-2-methoxy-6-nitrophenylamino)but-2-enylcarbamate replacing (E)-(4-((4-carbamoyl-2-methyl-6-nitrophenyl)amino)but-2-en-1-yl)carbamate. LC-MS calculated for $C_{20}H_{24}BrN_6O_3$ (M+H)$^+$: m/z=475.1, 477.1; found 475.1, 477.1.

Step 4: (E)-9-(4-(5-carbamoyl-2-(1-ethyl-3-methyl-1H-pyrazole-5-carboxamido)-7-methoxy-1H-benzo[d]imidazol-1-yl)but-2-enyl)-2-(1-ethyl-3-methyl-1H-pyrazol-5-yl)-9H-pyrimido[4,5-b]indole-6-carboxamide A mixture of 2-(1-ethyl-3-methyl-1H-pyrazol-5-yl)-9H-pyrimido[4,5-b]indole carboxamide (5.0 mg, 0.016 mmol), (E)-1-(4-bromobut-2-en-1-yl)-2-(1-ethyl-3-methyl-1H-pyrazole-5-carboxamido)-7-methoxy-1H-benzo[d]imidazole-5-carboxamide (7.42 mg, 0.016 mmol), and cesium carbonate (11.19 mg, 0.034 mmol) was stirred in DMF (52.0 µl) at 50° C. for 1 h. The reaction mixture was diluted with MeOH and purified by prep-HPLC (pH=2, acetonitrile/water+TFA) to give the desired product as its TFA salt. LC-MS calculated for $C_{37}H_{39}N_{12}O_4$ (M+H)$^+$: m/z=715.3; found 715.3.

Example 5. (E)-9-(4-(5-carbamoyl-2-(1-ethyl-3-methyl-1H-pyrazole-5-carboxamido)-7-methyl-1H-benzo[d]imidazol-1-yl)but-2-en-1-yl)-2-(1-ethyl-3-methyl-1H-pyrazol-5-yl)-9H-pyrido[2,3-b]indole-6-carboxamide

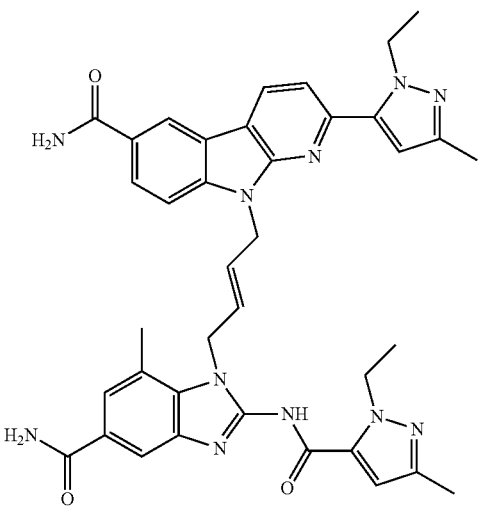 [SMILES: CCn1nc(C)cc1C(=O)Nc1nc2cc(C(N)=O)cc(C)c2n1C/C=C/Cn1c2ccc(C(N)=O)cc2c2ccc(-c3cc(C)nn3CC)nc21]

Step 1: 3-(6-(1-ethyl-3-methyl-1H-pyrazol-5-yl)pyridin-3-yl)-4-nitrobenzonitrile

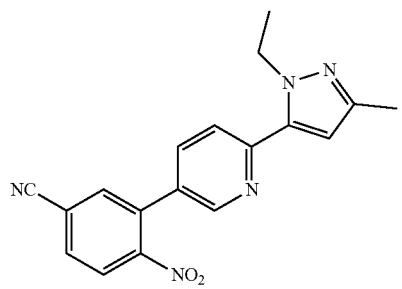 [SMILES: CCn1nc(C)cc1-c1ccc(-c2cc(C#N)ccc2[N+](=O)[O-])cn1]

To a degasseed solution of 3-bromo-4-nitrobenzonitrile (J&W PharmLab, cat #05R0293: 50 mg, 0.220 mmol) and 2-chloro-5-(4,4,5,5-tetramethyl-1,3,2-dioxaborolan-2-yl)pyridine (Aldrich, cat #659843: 52.8 mg, 0.220 mmol) in dioxane (587 µl)and water (147 µl) was added dichloro[1,1'-bis(diphenylphosphino)ferrocene]palladium (II) dichloromethane adduct (8.99 mg, 0.011 mmol) and sodium carbonate (46.7 mg, 0.440 mmol). The reaction was stirred at 100° C. for 2 h. 1-Ethyl-3-methyl-5-(4,4,5,5-tetramethyl-1,3,2-dioxaborolan-2-yl)-1H-pyrazole (Enamine Ltd, cat #EN300-207291: 52.0 mg, 0.220 mmol) was added. The reaction mixture was heated to 100° C. for another 1 h. $H_2O$ (2 mL) was added to the reaction mixture, followed by extraction with ethyl acetate (2 mL×5). The combined organic layers were dried with $Na_2SO_4$, filtered and concentrated. The crude product was used directly without further purification. LC-MS calculated for $C_{18}H_{16}N_5O_2$ (M+H)$^+$: m/z=334.1; found 334.2.

Step 2: 2-(1-ethyl-3-methyl-1H-pyrazol-5-yl)-9H-pyrido[2,3-b]indole-6-carbonitrile

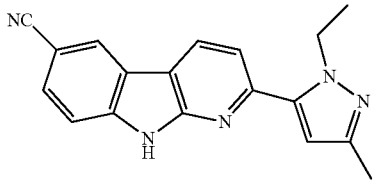 [SMILES: CCn1nc(C)cc1-c1ccc2c(n1)[nH]c1ccc(C#N)cc12]

To a solution of above crude 3-(6-(1-ethyl-3-methyl-1H-pyrazol-5-yl)pyridin-3-yl)-4-nitrobenzonitrile in 1,2-dichlorobenzene (1 mL) was added dppe (132 mg, 0.330 mmol). The reaction mixture was heated to 160° C. for 3 h, then the solvent was removed under vacuum. The crude product was used directly without further purification. LC-MS calculated for $C_{18}H_{16}N_5$ (M+H)$^+$: m/z=302.1; found 302.2.

Step 3: 2-(1-ethyl-3-methyl-1H-pyrazol-5-yl)-9H-pyrido[2,3-b]indole-6-carboxamide

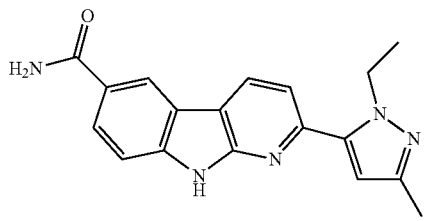 [SMILES: CCn1nc(C)cc1-c1ccc2c(n1)[nH]c1ccc(C(N)=O)cc12]

The above crude 2-(1-ethyl-3-methyl-1H-pyrazol-5-yl)-9H-pyrido[2,3-b]indole-6-carbonitrile was dissolved in EtOH (0.8 mL) and water (0.2 mL). Ghaffar-Parkins cat. (5 mg) was added and the resulting mixture was heated at 95° C. for 4 h to afford 2-(1-ethyl-3-methyl-1H-pyrazol-5-yl)-9H-pyrido[2,3-b]indole-6-carboxamide as the major regioselective isomer. The reaction mixture was diluted with MeOH then purified by prep-HPLC (pH=2, acetonitrile/water+TFA) to give the desired product as the TFA salt. LC-MS calculated for $C_{18}H18N_5O$ (M+H)$^+$: m/z=320.1; found 320.2. $^1$H NMR (500 MHz, DMSO-d6) δ 12.13 (s, 1H), 8.75 (s, 1H), 8.57 (d, J=8.0 Hz, 1H), 8.01 (dd, J=8.5, 1.6 Hz, 2H), 7.97-7.93 (m, 1H), 7.60 (d, J=8.0 Hz, 1H), 7.52 (d, J=8.5 Hz, 1H), 7.37-7.15 (m, 1H), 6.58 (s, 1H), 4.64 (q, J=7.1 Hz, 2H), 2.21 (s, 3H), 1.37 (t, J=7.1 Hz, 3H).

Step 4: (E)-9-(4-(5-carbamoyl-2-(1-ethyl-3-methyl-1H-pyrazole-5-carboxamido)-7-methyl-1H-benzo[d]imidazol-1-yl)but-2-en-1-yl)-2-(1-ethyl-3-methyl-1H-pyrazol-5-yl)-9H-pyrido[2,3-b]indole-6-carboxamide A mixture of 2-(1-ethyl-3-methyl-1H-pyrazol-5-yl)-9H-pyrido[2,3-b]indole-6-carboxamide (3.5 mg, 0.011 mmol), (E)-1-(4-bromobut-2-en-1-yl)-2-(1-ethyl-3-methyl-1H-pyrazole-5-carboxamido)-7-methyl-1H-benzo[d]imidazole-5-carboxamide (5.0 mg, 0.011 mmol), and cesium carbonate (12.92 mg, 0.040 mmol) was stirred in DMF (60.1 µl) at r.t. for 1 h. The reaction mixture was diluted with MeOH and purified by prep-HPLC (pH=2, acetonitrile/water+TFA) to give the desired product as its TFA salt. LC-MS calculated for $C_{38}H_{40}N_{11}O_3$ (M+H)$^+$: m/z=698.3; found 698.3.

Example 6. (E)-9-(4-(5-carbamoyl-2-(1-ethyl-3-methyl-1H-pyrazole-5-carboxamido)-7-methyl-1H-benzo[d]imidazol-1-yl)but-2-enyl)-2-(3-methyl-1-propyl-1H-pyrazol-5-yl)-9H-pyrimido[4,5-b]indole-6-carboxamide

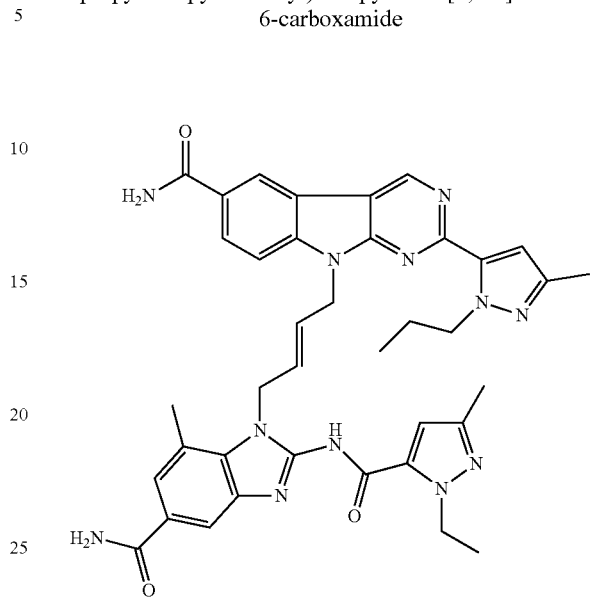

Step 1: 2-(3-methyl-1-propyl-1H-pyrazol-5-yl)-9H-pyrimido[4,5-b]indole-6-carboxamide

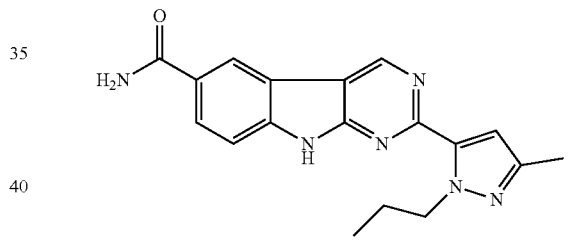

This compound was prepared using similar procedures as described for Example 1, Step 11 with 3-methyl-1-propyl-5-(4,4,5,5-tetramethyl-1,3,2-dioxaborolan-2-yl)-1H-pyrazole (Combi-Blocks, cat #FM-3989) replacing 1-ethyl-3-methyl-5-(4,4,5,5-tetramethyl-1,3,2-dioxaborolan-2-yl)-1H-pyrazole. LC-MS calculated for $C_{18}H_{19}N_6O$ (M+H)$^+$: m/z=335.2; found 335.2.

Step 2: (E)-9-(4-(5-carbamoyl-2-(1-ethyl-3-methyl-1H-pyrazole-5-carboxamido)-7-methyl-1H-benzo[d]imidazol-1-yl)but-2-enyl)-2-(3-methyl-1-propyl-1H-pyrazol-5-yl)-9H-pyrimido[4,5-b]indole-6-carboxamide A mixture of 2-(3-methyl-1-propyl-1H-pyrazol-5-yl)-9H-pyrimido[4,5-b]indole-6-carboxamide (6.68 mg, 0.02 mmol), (E)-1-(4-bromobut-2-en-1-yl)-2-(1-ethyl-3-methyl-1H-pyrazole-5-carboxamido)-7-methyl-1H-benzo[d]imidazole-5-carboxamide (Example 1, Step 8; 9.18 mg, 0.02 mmol), and cesium carbonate (14.32 mg, 0.044 mmol) was stirred in DMF (0.2 mL) at 50° C. for 1 h. The reaction mixture was diluted with MeOH and purified by prep-HPLC (pH=2, acetonitrile/water+TFA) to give the desired product as its TFA salt. LC-MS calculated for $C_{38}H_{41}N_{12}O_3$ (M+H)$^+$: m/z=713.3; found 713.4.

Example 7. (E)-9-(4-(5-carbamoyl-2-(1-ethyl-3-methyl-1H-pyrazole-5-carboxamido)-7-methyl-1H-benzo[d]imidazol-1-yl)but-2-enyl)-2-(1-ethyl-1H-pyrazol-5-yl)-9H-pyrimido [4,5-b]indole-6-carboxamide

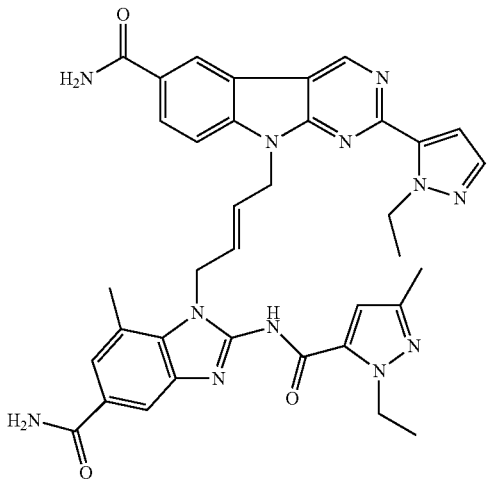 [SMILES: CCn1nc(C)cc1C(=O)Nc1nc2cc(C(N)=O)cc(C)c2n1C/C=C/Cn1c2ccc(C(N)=O)cc2c2cnc(-c3ccnn3CC)nc21]

Step 1: 2-(1-ethyl-1H-pyrazol-5-yl)-9H-pyrimido[4,5-b]indole-6-carboxamide

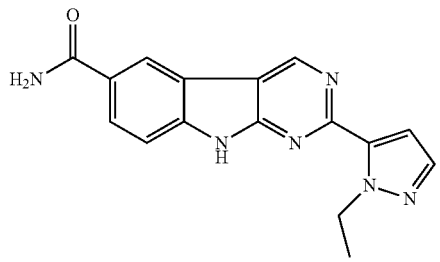 [SMILES: CCn1nccc1-c1ncc2c(n1)[nH]c1ccc(C(N)=O)cc12]

This compound was prepared using similar procedures as described for Example 1, Step 11 with 1-ethyl-5-(4,4,5,5-tetramethyl-1,3,2-dioxaborolan-2-yl)-1H-pyrazole (Combi-Blocks, cat #PN-6476) replacing 1-ethyl-3-methyl-5-(4,4,5,5-tetramethyl-1,3,2-dioxaborolan-2-yl)-1H-pyrazole. LC-MS calculated for $C_{16}H_{15}N_6O$ (M+H)$^+$: m/z=307.1; found 307.1.

Step 2: (E)-9-(4-(5-carbamoyl-2-(1-ethyl-3-methyl-1H-pyrazole-5-carboxamido)-7-methyl-1H-benzo[d]imidazol-1-yl)but-2-enyl)-2-(1-ethyl-1H-pyrazol-5-yl)-9H-pyrimido[4,5-b]indole-6-carboxamide A mixture of 2-(1-ethyl-1H-pyrazol-5-yl)-9H-pyrimido[4,5-b]indole-6-carboxamide (6.12 mg, 0.02 mmol), (E)-1-(4-bromobut-2-en-1-yl)-2-(1-ethyl-3-methyl-1H-pyrazole-5-carboxamido)-7-methyl-1H-benzo[d]imidazole-5-carboxamide (Example 1, Step 8: 9.18 mg, 0.02 mmol), and cesium carbonate (14.32 mg, 0.044 mmol) was stirred in DMF (0.2 mL) at 50° C. for 1 h. The reaction mixture was diluted with MeOH and purified by prep-HPLC (pH=2, acetonitrile/water+TFA) to give the desired product as its TFA salt. LC-MS calculated for $C_{36}H_{37}N_{12}O_3$ (M+H)$^+$: m/z=685.3; found 685.4.

Example 8. (E)-9-(4-(5-carbamoyl-2-(1-ethyl-3-methyl-1H-pyrazole-5-carboxamido)-7-methyl-1H-benzo[d]imidazol-1-yl)but-2-enyl)-2-(3-ethyl-1-methyl-1H-pyrazol-4-yl)-9H-pyrimido[4,5-b]indole-6-carboxamide

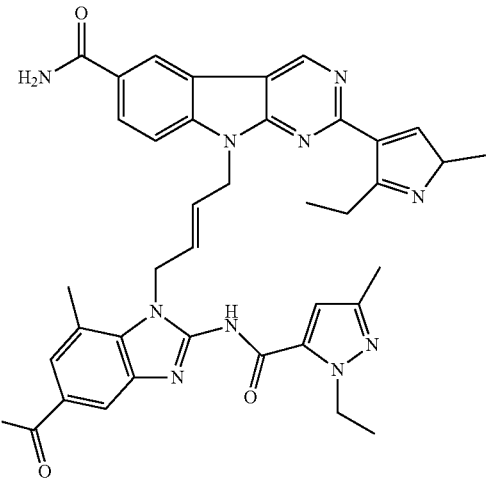

Step 1: 2-(3-ethyl-1-methyl-1H-pyrazol-4-yl)-9H-pyrimido[4,5-b]indole-6-carboxamide

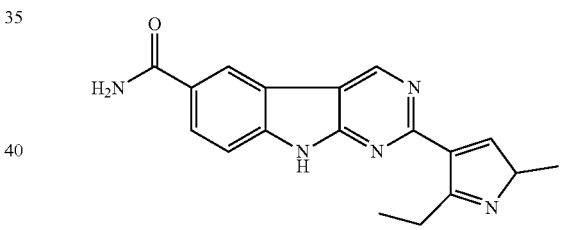

This compound was prepared using similar procedures as described for Example 1, Step 11 with 3-ethyl-1-methyl-4-(4,4,5,5-tetramethyl-1,3,2-dioxaborolan-2-yl)-1H-pyrazole (AstaTech, cat #P17340) replacing 1-ethyl-3-methyl-5-(4,4,5,5-tetramethyl-1,3,2-dioxaborolan-2-yl)-1H-pyrazole. LC-MS calculated for $C_{17}H_{17}N_6O$ (M+H)$^+$: m/z=321.1; found 321.1.

Step 2: (E)-9-(4-(5-carbamoyl-2-(1-ethyl-3-methyl-1H-pyrazole-5-carboxamido)-7-methyl-1H-benzo[d]imidazol-1-yl)but-2-enyl)-2-(3-ethyl-1-methyl-1H-pyrazol-4-yl)-9H-pyrimido[4,5-b]indole-6-carboxamide A mixture of 2-(3-ethyl-1-methyl-1H-pyrazol-4-yl)-9H-pyrimido[4,5-b]indole-6-carboxamide (6.4 mg, 0.02 mmol), (E)-1-(4-bromobut-2-en-1-yl)-2-(1-ethyl-3-methyl-1H-pyrazole-5-carboxamido)-7-methyl-1H-benzo[d]imidazole-5-carboxamide (Example 1, Step 8: 9.18 mg, 0.02 mmol), and cesium carbonate (14.32 mg, 0.044 mmol) was stirred in DMF (0.2 mL) at 50° C. for 1 h. The reaction mixture was diluted with MeOH and purified by prep-HPLC (pH=2, acetonitrile/water+TFA) to give the desired product as its TFA salt. LC-MS calculated for $C_{37}H_{39}N_{12}O_3$ (M+H)$^+$: m/z=699.3; found 699.4.

135

Example 9. (E)-9-(4-(5-carbamoyl-2-(1-ethyl-3-methyl-1H-pyrazole-5-carboxamido)-7-methyl-1H-benzo[d]imidazol-1-yl)but-2-enyl)-2-(1-ethyl-3-(trifluoromethyl)-1H-pyrazol-5-yl)-9H-pyrimido[4,5-b]indole-6-carboxamide

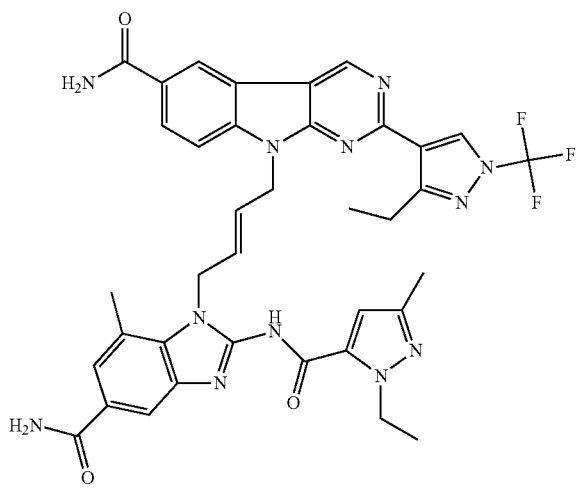 [SMILES: CCc1nn(C(F)(F)F)cc1-c1ncc2c3cc(C(N)=O)ccc3n(C/C=C/Cn3c(NC(=O)c4cc(C)nn4CC)nc4cc(C(N)=O)cc(C)c43)c2n1]

Step 1: 2-(1-ethyl-3-(trifluoromethyl)-1H-pyrazol-5-yl)-9H-pyrimido[4,5-b]indole-6-carboxamide

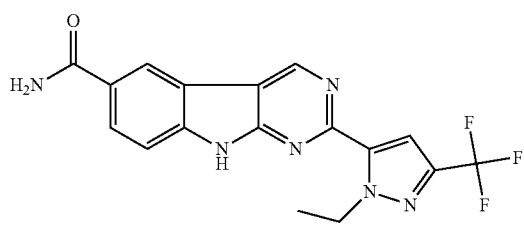 [SMILES: CCn1nc(C(F)(F)F)cc1-c1ncc2c(n1)[nH]c1ccc(C(N)=O)cc12]

This compound was prepared using similar procedures as described for Example 1, Step 11 with 1-ethyl-5-(4,4,5,5-tetramethyl-1,3,2-dioxaborolan-2-yl)-3-(trifluoromethyl)-1H-pyrazole replacing 1-ethyl-3-methyl-5-(4,4,5,5-tetramethyl-1,3,2-dioxaborolan-2-yl)-1H-pyrazole. LC-MS calculated for $C_{17}H_{14}F_3N_6O$ $(M+H)^+$: m/z=375.1; found 375.1.

Step 2: (E)-9-(4-(5-carbamoyl-2-(1-ethyl-3-methyl-1H-pyrazole-5-carboxamido)-7-methyl-1H-benzo[d]imidazol-1-yl)but-2-enyl)-2-(1-ethyl-3-(trifluoromethyl)-1H-pyrazol-5-yl)-9H-pyrimido[4,5-b]indole-6-carboxamide A mixture of 2-(1-ethyl-3-(trifluoromethyl)-1H-pyrazol-5-yl)-9H-pyrimido[4,5-b]indole-6-carboxamide (8.96 mg, 0.024 mmol), (E)-1-(4-bromobut-2-en-1-yl)-2-(1-ethyl-3-methyl-1H-pyrazole-5-carboxamido)-7-methyl-1H-benzo[d]imidazole-5-carboxamide (Example 1, Step 8: 11 mg, 0.024 mmol), and cesium carbonate (17.2 mg, 0.053 mmol) was stirred in DMF (0.2 mL) at 50° C. for 1 h. The reaction mixture was diluted with MeOH and purified by prep-HPLC (pH=2, acetonitrile/water+TFA) to give the desired product as its TFA salt. LC-MS calculated for $C_{37}H_{36}F_3N_{12}O_3$ $(M+H)^+$: m/z=753.3; found 753.4.

136

Example 10. (E)-9-(4-(5-carbamoyl-2-(1-ethyl-3-methyl-1H-pyrazole-5-carboxamido)-7-methyl-1H-benzo[d]imidazol-1-yl)but-2-enyl)-2-(1-ethyl-3-methyl-1H-pyrazol-5-yl)-8-methoxy-9H-pyrimido[4,5-b]indole-6-carboxamide

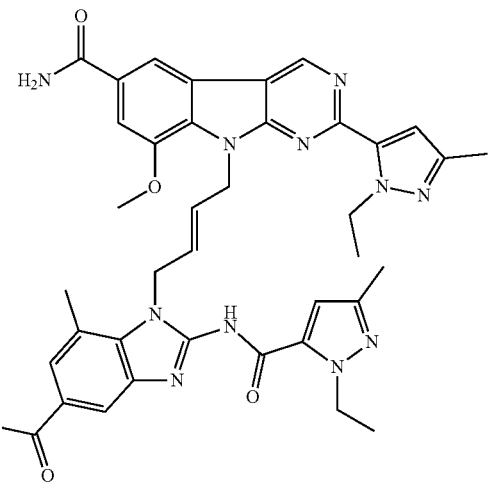

Step 1: 3-bromo-5-fluoro-4-nitrobenzamide

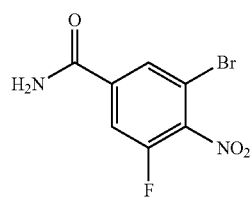 [SMILES: NC(=O)c1cc(F)c([N+](=O)[O-])c(Br)c1]

Methyl 3-bromo-5-fluoro-4-nitrobenzoate (AstaTech, cat #AB9640: 5.0 g, 17.98 mmol) was stirred in ammonium hydroxide (44.1 ml, 1133 mmol) at room temperature for 10 h. The solid was filtered and rinsed with cold water. The resulting solid residue was dried to provide the desired product as a light yellow solid.

Step 2: 3-bromo-5-methoxy-4-nitrobenzamide

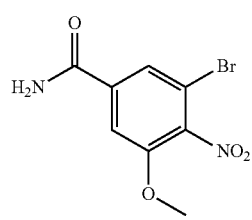

To a stirred solution of 3-bromo-5-fluoro-4-nitrobenzamide (1.0 g, 3.80 mmol) in MeOH (19.01 ml) was added sodium methoxide (1.232 g, 5.70 mmol). The reaction mixture was stirred at 60° C. for 0.5 h. The reaction mixture was concentrated under reduced pressure. The residue was dissolved in water, and then extracted with DCM. The combined organic layers were dried, filtered, and concentrated in vacuo. The crude product was used directly without further purification. LC-MS calculated for $C_8H_8BrN_2O_4$ $(M+H)^+$: m/z=275.0, 277.0; found 275.0, 277.0.

Step 3: 3-(2-(1-ethyl-3-methyl-1H-pyrazol-5-yl)pyrimidin-5-yl)-5-methoxy-4-nitrobenzamide

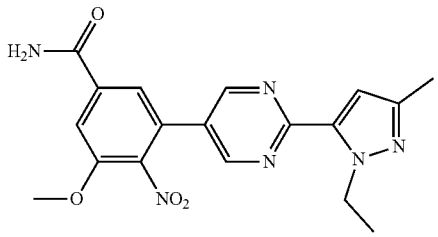 [SMILES: CCn1nc(C)cc1-c1ncc(-c2cc(C(N)=O)cc(OC)c2[N+](=O)[O-])cn1]

To a degassed solution of (2-chloropyrimidin-5-yl)boronic acid (Combi-Blocks, cat #BB-5457: 82 mg, 0.52 mmol) and 3-bromo-5-methoxy-4-nitrobenzamide (143 mg, 0.520 mmol) in dioxane (1733 µl) and water (347 µl) was added dichloro[1,1'-bis(diphenylphosphino)ferrocene]palladium (II) dichloromethane adduct (25.5 mg, 0.031 mmol) and sodium carbonate (110 mg, 1.040 mmol). The reaction was stirred at 100° C. for 2 h. Then, 1-ethyl-3-methyl-5-(4,4,5,5-tetramethyl-1,3,2-dioxaborolan-2-yl)-1H-pyrazole (Enamine Ltd, cat #EN300-207291; 123.0 mg, 0.520 mmol) was added. The reaction mixture was heated to 100° C. for another 1 h. H$_2$O was added to the reaction mixture, and the reaction was extracted with DCM. The combined organic layers were dried with Na$_2$SO$_4$, filtered and concentrated. The crude residue was purified by flash chromatography on a silica gel column eluting with 0 to 8% MeOH in DCM to afford the desired product. LC-MS calculated for C$_{18}$H$_{19}$N$_6$O$_4$ (M+H)$^+$: m/z=383.1; found 383.2.

Step 4: 2-(1-ethyl-3-methyl-1H-pyrazol-5-yl)-8-methoxy-9H-pyrimido[4,5-b]indole-6-carboxamide

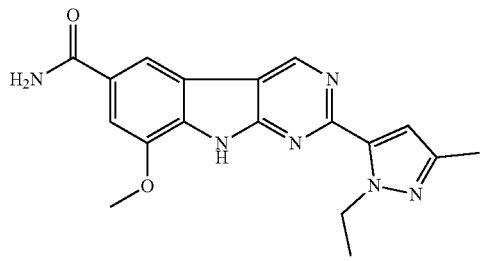 [SMILES: CCn1nc(C)cc1-c1ncc2c(n1)[nH]c1c(OC)cc(C(N)=O)cc12]

A mixture of 3-(2-(1-ethyl-3-methyl-1H-pyrazol-5-yl)pyrimidin-5-yl)-5-methoxy-4-nitrobenzamide (280.0 mg, 0.732 mmol) and 1,2-bis(diphenylphosphino)ethane (365 mg, 0.915 mmol) was dissolved in 1,2-dichlorobenzene (2.4 mL). The vial was flushed with nitrogen before heating at 160° C. for 1 h. After removal of the solvent under vacuum, the reaction mixture was extracted with DCM and water. The organic phases were combined and dried over MgSO$_4$, filtered, then concentrated under reduced pressure. The crude residue was purified by flash chromatography on a silica gel column eluting with 0 to 8% MeOH in DCM to afford the desired product. LC-MS calculated for C$_{18}$H$_{19}$N$_6$O$_2$ (M+H)$^+$: m/z=351.1; found 351.1.

Step 5: (E)-9-(4-(5-carbamoyl-2-(1-ethyl-3-methyl-1H-pyrazole-5-carboxamido)-7-methyl-1H-benzo[d]imidazol-1-yl)but-2-enyl)-2-(1-ethyl-3-methyl-1H-pyrazol-5-yl)-8-methoxy-9H-pyrimido[4,5-b]indole-6-carboxamide A mixture of 2-(1-ethyl-3-methyl-1H-pyrazol-5-yl)-8-methoxy-9H-pyrimido[4,5-b]indole-6-carboxamide (7.0 mg, 0.02 mmol), (E)-1-(4-bromobut-2-en-1-yl)-2-(1-ethyl-3-methyl-1H-pyrazole-5-carboxamido)-7-methyl-1H-benzo[d]imidazole-5-carboxamide (Example 1, Step 8; 9.18 mg, 0.02 mmol), and cesium carbonate (14.32 mg, 0.044 mmol) was stirred in DMF (0.2 mL) at 50° C. for 1 h. The reaction mixture was diluted with MeOH and purified by prep-HPLC (pH=2, acetonitrile/water+TFA) to give the desired product as its TFA salt. LC-MS calculated for C$_{38}$H$_{41}$N$_{12}$O$_4$ (M+H)$^+$: m/z=729.3; found 729.4.

Example 11. (E)-9-(4-(5-carbamoyl-2-(1-ethyl-3-methyl-1H-pyrazole-5-carboxamido)-7-methyl-1H-benzo[d]imidazol-1-yl)but-2-enyl)-2-(1-ethyl-3-methyl-1H-pyrazol-5-yl)-8-(3-morpholinopropoxy)-9H-pyrimido[4,5-b]indole-6-carboxamide

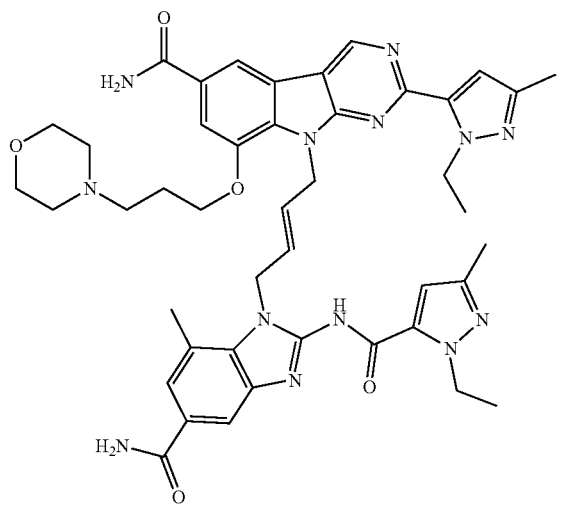 [SMILES: CCn1nc(C)cc1C(=O)Nc1nc2cc(C(N)=O)cc(C)c2n1C/C=C/Cn1c2nc(-c3cc(C)nn3CC)ncc2c2cc(C(N)=O)cc(OCCCN3CCOCC3)c21]

Step 1: 3-bromo-5-(3-morpholinopropoxy)-4-nitrobenzamide

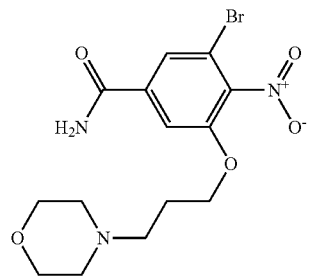 [SMILES: NC(=O)c1cc(Br)c([N+](=O)[O-])c(OCCCN2CCOCC2)c1]

To a stirred solution of 3-morpholinopropan-1-ol (Combi-Blocks, cat #OR-5079: 0.121 g, 0.836 mmol) in THF (2.79 ml) was added sodium hydride (0.067 g, 1.673 mmol). The reaction mixture was stirred at room temperature for 10 min. To the solution of sodium alkoxide was then added 3-bromo-5-fluoro-4-nitrobenzamide (0.220 g, 0.836 mmol). The mixture was heated at 60° C. for 0.5 h. The reaction mixture was concentrated under reduced pressure, and then extracted with DCM and water. The combined organic layers were dried, filtered, and concentrated in vacuo. The crude product was used directly without further purification. LC-MS calculated for C$_{14}$H$_{19}$BrN$_3$O$_5$ (M+H)$^+$: m/z=388.0, 390.0; found 388.1, 390.1.

Step 2: 3-(2-(1-ethyl-3-methyl-1H-pyrazol-5-yl)pyrimidin-5-yl)-5-(3-morpholinopropoxy)-4-nitrobenzamide

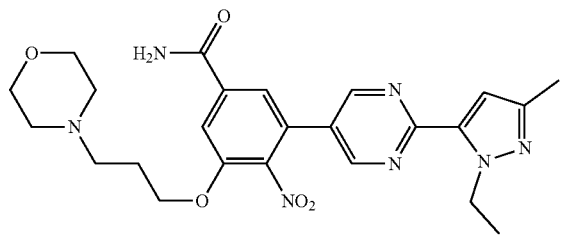 [SMILES: CCn1nc(C)cc1-c1ncc(-c2cc(C(N)=O)cc(OCCCN3CCOCC3)c2[N+](=O)[O-])cn1]

This compound was prepared using similar procedures as described for Example 10, Step 3 with 3-bromo-5-(3-morpholinopropoxy)-4-nitrobenzamide replacing 3-bromo-5-methoxy-4-nitrobenzamide. LC-MS calculated for $C_{24}H_{30}N_7O_5$ (M+H)$^+$: m/z=496.2; found 496.3.

Step 3: 2-(1-ethyl-3-methyl-1H-pyrazol-5-yl)-8-(3-morpholinopropoxy)-9H-pyrimido[4,5-b]indole-6-carboxamide

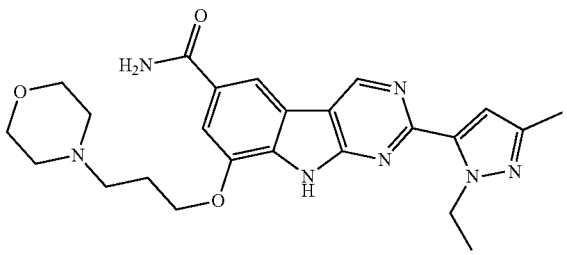 [SMILES: CCn1nc(C)cc1-c1ncc2c(n1)[nH]c1c(OCCCN3CCOCC3)cc(C(N)=O)cc12]

This compound was prepared using similar procedures as described for Example 10, Step 4 with 3-(2-(1-ethyl-3-methyl-1H-pyrazol-5-yl)pyrimidin-5-yl)-5-(3-morpholinopropoxy)-4-nitrobenzamide replacing 3-(2-(1-ethyl-3-methyl-1H-pyrazol-5-yl)pyrimidin-5-yl)-5-methoxy-4-nitrobenzamide. LC-MS calculated for $C_{24}H_{30}N_7O_3$ (M+H)$^+$: m/z=464.2; found 464.3.

Step 4: (E)-9-(4-(5-carbamoyl-2-(1-ethyl-3-methyl-1H-pyrazole-5-carboxamido)-7-methyl-1H-benzo[d]imidazol-1-yl)but-2-enyl)-2-(1-ethyl-3-methyl-1H-pyrazol-5-yl)-8-(3-morpholinopropoxy)-9H-pyrimido[4,5-b]indole-6-carboxamide A mixture of 2-(1-ethyl-3-methyl-1H-pyrazol-5-yl)-8-(3-morpholinopropoxy)-9H-pyrimido[4,5-b]indole-6-carboxamide (7.0 mg, 0.015 mmol), (E)-1-(4-bromobut-2-en-1-yl)-2-(1-ethyl-3-methyl-1H-pyrazole-5-carboxamido)-7-methyl-1H-benzo[d]imidazole-5-carboxamide (Example 1, Step 8; 6.94 mg, 0.015 mmol), and cesium carbonate (10.82 mg, 0.033 mmol) was stirred in DMF (0.2 mL) at 50° C. for 1 h. The reaction mixture was diluted with MeOH and purified by prep-HPLC (pH=2, acetonitrile/water+TFA) to give the desired product as its TFA salt. LC-MS calculated for $C_{44}H_{52}N_{13}O_5$ (M+H)$^+$: m/z=842.4; found 842.4.

Example 12. (E)-9-(4-(5-carbamoyl-2-(1-ethyl-3-methyl-1H-pyrazole-5-carboxamido)-7-methyl-1H-benzo[d]imidazol-1-yl)but-2-enyl)-2-(1-ethyl-3-methyl-1H-pyrazol-5-yl)-8-(3-methoxypropoxy)-9H-pyrimido[4,5-b]indole-6-carboxamide

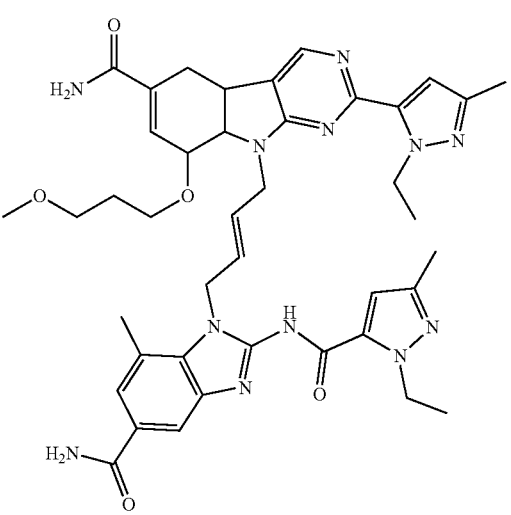

Step 1: 3-bromo-5-(3-methoxypropoxy)-4-nitrobenzamide

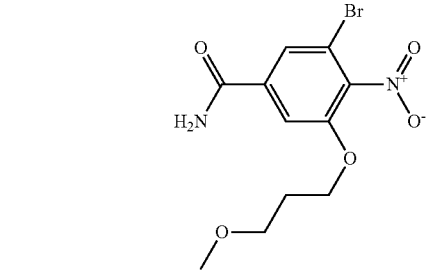 [SMILES: COCCCOc1cc(C(N)=O)cc(Br)c1[N+](=O)[O-]]

This compound was prepared using similar procedures as described for Example 11, Step 1 with 3-methoxypropan-1-ol (Aldrich, cat #38457) replacing 3-morpholinopropan-1-ol. LC-MS calculated for $C_{11}H_{14}BrN_2O_5$ (M+H)$^+$: m/z=333.0, 335.0; found 333.0, 335.0.

Step 2: 3-(2-(1-ethyl-3-methyl-1H-pyrazol-5-yl)pyrimidin-5-yl)-5-(3-methoxypropoxy)-4-nitrobenzamide

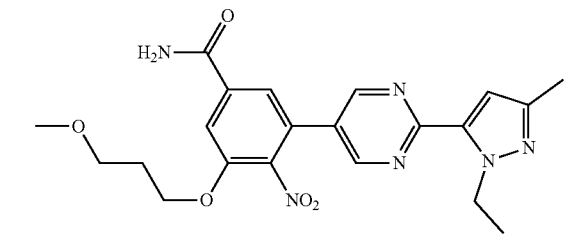

This compound was prepared using similar procedures as described for Example 10, Step 3 with 3-bromo-5-(3-methoxypropoxy)-4-nitrobenzamide replacing 3-bromo-5-methoxy-4-nitrobenzamide. LC-MS calculated for $C_{21}H_{25}N_6O_5$ (M+H)$^+$: m/z=441.2; found 441.3.

Step 3: 2-(1-ethyl-3-methyl-1H-pyrazol-5-yl)-8-(3-methoxypropoxy)-9H-pyrimido[4,5-b]indole-6-carboxamide

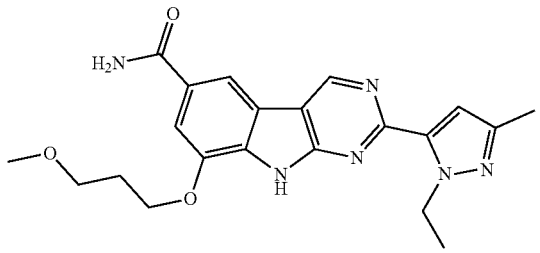

This compound was prepared using similar procedures as described for Example 10, Step 4 with 3-(2-(1-ethyl-3-methyl-1H-pyrazol-5-yl)pyrimidin-5-yl)-5-(3-methoxypropoxy)-4-nitrobenzamide replacing 3-(2-(1-ethyl-3-methyl-1H-pyrazol-5-yl)pyrimidin-5-yl)-5-methoxy-4-nitrobenzamide. LC-MS calculated for $C_{21}H_{25}N_6O_3$ (M+H)$^+$: m/z=409.2; found 409.2.

Step 4: (E)-9-(4-(5-carbamoyl-2-(1-ethyl-3-methyl-1H-pyrazole-5-carboxamido)-7-methyl-1H-benzo[d]imidazol-1-yl)but-2-enyl)-2-(1-ethyl-3-methyl-1H-pyrazol-5-yl)-8-(3-methoxypropoxy)-9H-pyrimido[4,5-b]indole-6-carboxamide A mixture of 2-(1-ethyl-3-methyl-1H-pyrazol-5-yl)-8-(3-methoxypropoxy)-9H-pyrimido[4,5-b]indole-6-carboxamide (7.0 mg, 0.015 mmol), (E)-1-(4-bromobut-2-en-1-yl)-2-(1-ethyl-3-methyl-1H-pyrazole-5-carboxamido)-7-methyl-1H-benzo[d]imidazole-5-carboxamide (Example 1, Step 8: 6.94 mg, 0.015 mmol), and cesium carbonate (10.82 mg, 0.033 mmol) was stirred in DMF (0.2 mL) at 50° C. for 1 h. The reaction mixture was diluted with MeOH and purified by prep-HPLC (pH=2, acetonitrile/water+TFA) to give the desired product as its TFA salt. LC-MS calculated for $C_{41}H_{47}N_{12}O_5$ (M+H)$^+$: m/z=787.4; found 787.4.

Example 13. (E)-9-(4-(5-carbamoyl-2-(1-ethyl-3-methyl-1H-pyrazole-5-carboxamido)-7-methyl-1H-benzo[d]imidazol-1-yl)but-2-enyl)-2-(1-ethyl-3-methyl-1H-pyrazol-5-yl)-8-(3-hydroxypropoxy)-9H-pyrimido[4,5-b]indole-6-carboxamide

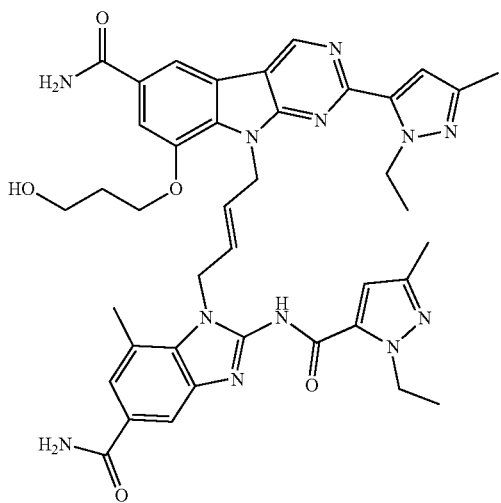 [SMILES: CCn1nc(C)cc1C(=O)Nc1nc2cc(C(N)=O)cc(C)c2n1C/C=C/Cn1c2nc(-c3cc(C)nn3CC)ncc2c2cc(C(N)=O)cc(OCCCO)c21]

Step 1: 3-bromo-5-(3-(tert-butyldimethylsilyloxy)propoxy)-4-nitrobenzamide

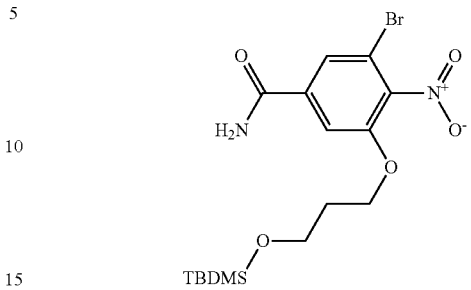

This compound was prepared using similar procedures as described for Example 11, Step 1 with 3-((tert-butyldimethylsilyl)oxy)propan-1-ol (Combi-Blocks, cat #QH-3826) replacing 3-morpholinopropan-1-ol. LC-MS calculated for $C_{16}H_{26}BrN_2O_5Si$ (M+H)$^+$: m/z=433.1, 435.1; found 433.2, 435.2.

Step 2: 3-(3-(tert-butyldimethylsilyloxy)propoxy)-5-(2-(1-ethyl-3-methyl-1H-pyrazol-5-yl)pyrimidin-5-yl)-4-nitrobenzamide

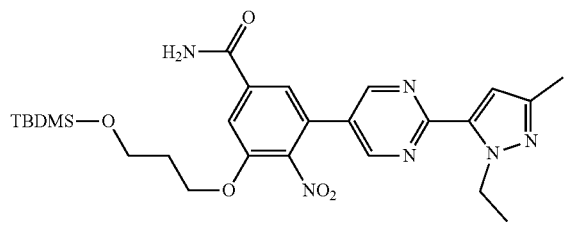

This compound was prepared using similar procedures as described for Example 10, Step 3 with 3-bromo-5-(3-(tert-butyldimethylsilyloxy)propoxy)-4-nitrobenzamide replacing 3-bromo-5-methoxy-4-nitrobenzamide. LC-MS calculated for $C_{26}H_{37}N_6O_5Si$ (M+H)$^+$: m/z=541.3; found 541.3.

Step 3: 8-(3-(tert-butyldimethylsilyloxy)propoxy)-2-(1-ethyl-3-methyl-1H-pyrazol-5-yl)-9H-pyrimido[4,5-b]indole-6-carboxamide

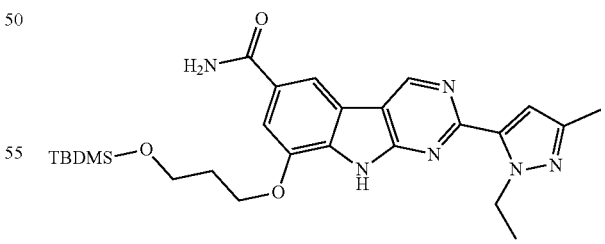

This compound was prepared using similar procedures as described for Example 10, Step 4 with 3-(3-(tert-butyldimethylsilyloxy)propoxy)-5-(2-(1-ethyl-3-methyl-1H-pyrazol-5-yl)pyrimidin-5-yl)-4-nitrobenzamide replacing 3-(2-(1-ethyl-3-methyl-1H-pyrazol-5-yl)pyrimidin-5-yl)-5-methoxy-4-nitrobenzamide. LC-MS calculated for $C_{26}H_{37}N_6O_3Si$ (M+H)$^+$: m/z=509.3; found 509.3.

Step 4: (E)-9-(4-(5-carbamoyl-2-(1-ethyl-3-methyl-1H-pyrazole-5-carboxamido)-7-methyl-1H-benzo[d]imidazol-1-yl)but-2-enyl)-2-(1-ethyl-3-methyl-1H-pyrazol-5-yl)-8-(3-hydroxypropoxy)-9H-pyrimido[4,5-b]indole-6-carboxamide A mixture of 28-(3-(tert-butyldimethylsilyloxy)propoxy)-2-(1-ethyl-3-methyl-1H-pyrazol-5-yl)-9H-pyrimido[4,5-b]indole-6-carboxamide (7.63 mg, 0.015 mmol), (E)-1-(4-bromobut-2-en-1-yl)-2-(1-ethyl-3-methyl-1H-pyrazole-5-carboxamido)-7-methyl-1H-benzo[d]imidazole-5-carboxamide (6.89 mg, 0.015 mmol), and cesium carbonate (10.75 mg, 0.033 mmol) was stirred in DMF (0.2 mL) at 50° C. for 1 h. The primary alcohol was deprotected during the process. Otherwise, the TBS group could be removed with the addition of 4 equivalents of HCl (0.015 mL of 4 M HCl in dioxane), followed by stirring at room temperature for 1 h. The reaction mixture was diluted with MeOH and purified by prep-HPLC (pH=2, acetonitrile/water+TFA) to give the desired product as its TFA salt. LC-MS calculated for $C_{40}H_{45}N_{12}O_5$ (M+H)$^+$: m/z=773.4; found 773.4.

Example 14. (E)-9-(4-(5-carbamoyl-2-(1-ethyl-3-methyl-1H-pyrazole-5-carboxamido)-7-methyl-1H-benzo[d]imidazol-1-yl)but-2-enyl)-2-(1-ethyl-3-methyl-1H-pyrazol-5-yl)-8-methoxy-9H-pyrido[2,3-b]indole-6-carboxamide

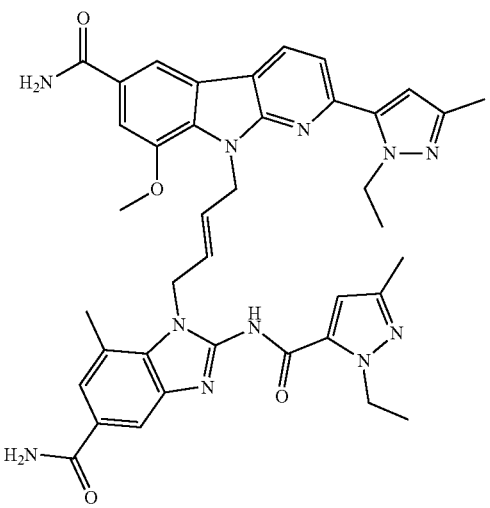 [SMILES: CCn1nc(C)cc1C(=O)Nc1nc2cc(C(N)=O)cc(C)c2n1C/C=C/Cn1c2nc(-c3cc(C)nn3CC)ccc2c2cc(C(N)=O)cc(OC)c21]

Step 1: 3-(6-(1-ethyl-3-methyl-1H-pyrazol-5-yl)pyridin-3-yl)-5-methoxy-4-nitrobenzamide

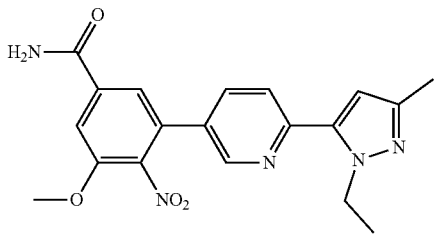

This compound was prepared using similar procedures as described for Example 10, Step 3 with 2-chloro-5-(4,4,5,5-tetramethyl-1,3,2-dioxaborolan-2-yl)pyridine replacing (2-chloropyrimidin-5-yl)boronic acid. LC-MS calculated for $C_{19}H_{20}N_5O_4$ (M+H)$^+$: m/z=382.1; found 382.3.

Step 2: 2-(1-ethyl-3-methyl-1H-pyrazol-5-yl)-8-methoxy-9H-pyrido[2,3-b]indole-6-carboxamide

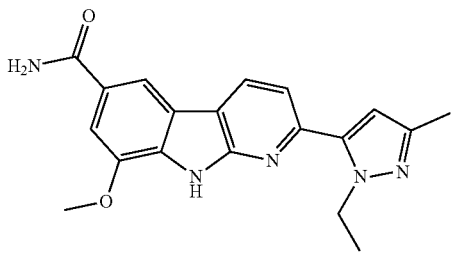 [SMILES: CCn1nc(C)cc1-c1ccc2c(n1)[nH]c1c(OC)cc(C(N)=O)cc12]

This compound was prepared using similar procedures as described for Example 10, Step 4 with 3-(6-(1-ethyl-3-methyl-1H-pyrazol-5-yl)pyridin-3-yl)-5-methoxy-4-nitrobenzamide replacing 3-(2-(1-ethyl-3-methyl-1H-pyrazol-5-yl)pyrimidin-5-yl)-5-methoxy-4-nitrobenzamide. Two isomers were formed. The reaction mixture was diluted with MeOH and purified by prep-HPLC (pH=2, acetonitrile/water+TFA) to give the desired product as its TFA salt. LC-MS calculated for $C_{19}H_{20}N_5O_2$ (M+H)$^+$: m/z=350.2; found 350.2. $^1$H NMR (500 MHz, DMSO) δ 12.26 (s, 1H), 8.53 (d, J=8.1 Hz, 1H), 8.39 (s, 1H), 7.59 (s, 1H), 7.57 (d, J=8.1 Hz, 1H), 6.58 (s, 1H), 4.65 (q, J=7.1 Hz, 2H), 4.04 (s, 3H), 2.21 (s, 3H), 1.36 (t, J=7.1 Hz, 3H).

Step 3: (E)-9-(4-(5-carbamoyl-2-(1-ethyl-3-methyl-1H-pyrazole-5-carboxamido)-7-methyl-1H-benzo[d]imidazol-1-yl)but-2-enyl)-2-(1-ethyl-3-methyl-1H-pyrazol-5-yl)-8-methoxy-9H-pyrido[2,3-b]indole-6-carboxamide A mixture of 2-(1-ethyl-3-methyl-1H-pyrazol-5-yl)-8-methoxy-9H-pyrido[2,3-b]indole-6-carboxamide (7.0 mg, 0.02 mmol), (E)-1-(4-bromobut-2-en-1-yl)-2-(1-ethyl-3-methyl-1H-pyrazole-5-carboxamido)-7-methyl-1H-benzo[d]imidazole-5-carboxamide (9.18 mg, 0.02 mmol), and cesium carbonate (14.32 mg, 0.044 mmol) was stirred in DMF (0.2 mL) at 50° C. for 1 h. The reaction mixture was diluted with MeOH and purified by prep-HPLC (pH=2, acetonitrile/water+TFA) to give the desired product as its TFA salt. LC-MS calculated for $C_{39}H_{42}N_{11}O_4$ (M+H)$^+$: m/z=728.3; found 728.4.

Example 15. (E)-3-((5-carbamoyl-1-(4-(6-carbamoyl-2-(1-ethyl-3-methyl-1H-pyrazol-5-yl)-8-methoxy-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propyl 1-ethyl-3-methyl-1H-pyrazole-5-carboxylate

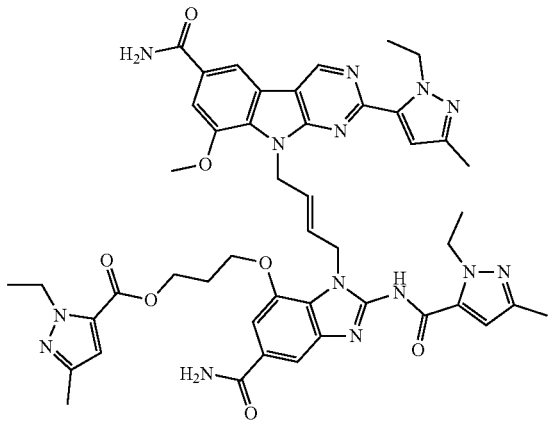 [SMILES: CCn1nc(C)cc1C(=O)Nc1nc2cc(C(N)=O)cc(OCCCOC(=O)c3cc(C)nn3CC)c2n1C/C=C/Cn1c2nc(-c3cc(C)nn3CC)ncc2c2cc(C(N)=O)cc(OC)c21]

Step 1: 4-chloro-3-hydroxy-5-nitrobenzamide

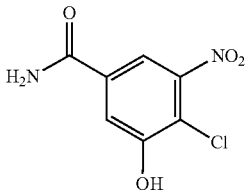 [SMILES: NC(=O)c1cc(O)c(Cl)c([N+](=O)[O-])c1]

In a round-bottomed flask, 4-chloro-3-methoxy-5-nitrobenzamide (Astatech, cat #97780: 1.0 g, 4.34 mmol) was dissolved in DCM. 1M BBr$_3$ in DCM (13.01 ml, 13.01 mmol) was added to the reaction mixture dropwise, then was refluxed for 12 h. The reaction mixture was cooled and then was poured into ice water. After stirring for 30 min, the reaction mixture was filtered and the filter cake was rinsed with water and dried to provide the desired compound as a white solid. LC-MS calculated for $C_7H_6ClN_2O_4$ (M+H)$^+$: m/z=217.0; found 216.9.

Step 2: 3-(3-((tert-butyldimethylsilyl)oxy)propoxy)-4-chloro-5-nitrobenzamide

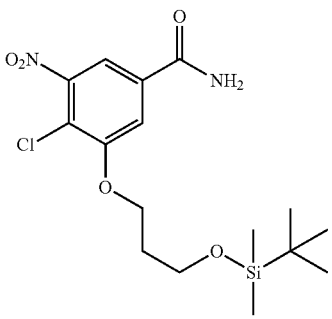 [SMILES: CC(C)(C)[Si](C)(C)OCCCOc1cc(C(N)=O)cc([N+](=O)[O-])c1Cl]

To a suspension of 4-chloro-3-hydroxy-5-nitrobenzamide (211.0 mg, 0.974 mmol), and cesium carbonate (476 mg, 1.461 mmol) in DMF (3247 µl) was added (3-bromopropoxy)(tert-butyl)dimethylsilane (Aldrich, cat #429066: 271 µl, 1.169 mmol). The reaction was then sealed and heated to 50° C. with stirring for 12 h. After cooling with an ice bath, the product was triturated with cold water, filtered, and dried to provide the desired product as a yellow solid. LC-MS calculated for $C_{16}H_{26}ClN_2O_5Si$ (M+H)+: m/z=389.1; found 389.1.

Step 3: tert-butyl (E)-(4-((2-(3-((tert-butyldimethylsilyl)oxy)propoxy)-4-carbamoyl-6-nitrophenyl)amino)but-2-en-1-yl)carbamate

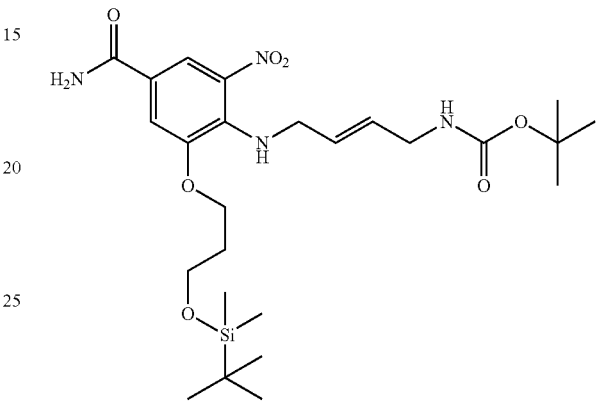

To a vial was added 3-(3-((tert-butyldimethylsilyl)oxy)propoxy)-4-chloro-5-nitrobenzamide (1.004 g, 2.58 mmol), tert-butyl (E)-(4-aminobut-2-en-1-yl)carbamate (Ark Pharm, cat #AK308564: 0.481 g, 2.58 mmol), DMSO (12.91 ml), and DIPEA (2.254 ml, 12.91 mmol). The mixture was sealed, then heated at 100° C. overnight with stirring. After cooling to rt, the mixture was diluted with water and extracted with CHCl$_3$/IPA (3:1). The combined organic extracts were dried over MgSO$_4$, filtered, and concentrated in vacuo to provide the desired product as a brown oil. LC-MS calculated for $C_{25}H_{43}N_4O_7Si$ (M+Na)$^+$: m/z=561.3; found 561.3.

Step 4: tert-butyl (E)-(4-((2-amino-6-(3-((tert-butyldimethylsilyl)oxy)propoxy)-4-carbamoylphenyl)amino)but-2-en-1-yl)carbamate

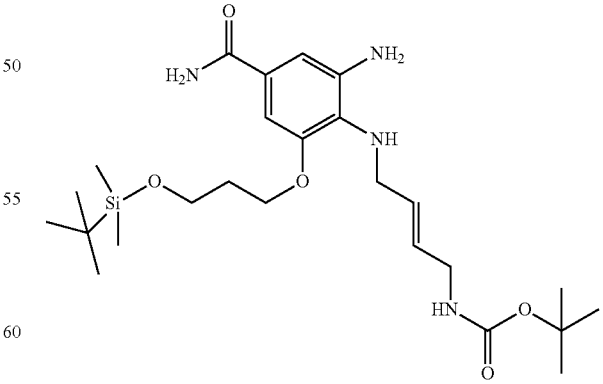

This compound was prepared using similar procedures as described for Example 1, Step 3 with tert-butyl (E)-(4-((2-(3-((tert-butyldimethylsilyl)oxy)propoxy)-4-carbamoyl-6-nitrophenyl)amino)but-2-en-1-yl)carbamate replacing tert-butyl (E)-(4-((4-carbamoyl-2-methyl-6-nitrophenyl)amino)but-2-en-1-yl)carbamate. LC-MS calculated for $C_{25}H_{45}N_4O_5Si$ (M+H)$^+$: m/z=509.3; found 509.3.

Step 5: tert-butyl (E)-(4-(2-amino-5-carbamoyl-7-(3-hydroxypropoxy)-1H-benzo[d]imidazol-1-yl)but-2-en-1-yl)carbamate

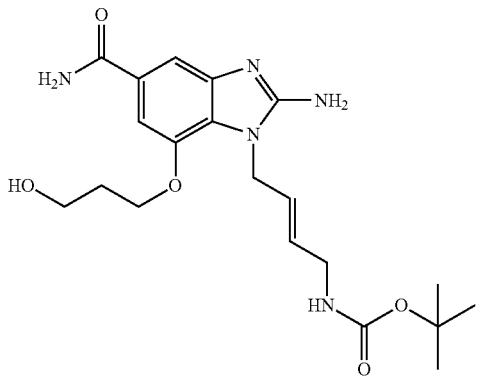 [SMILES: CC(C)(C)OC(=O)NC/C=C/Cn1c(N)nc2cc(C(N)=O)cc(OCCCO)c21]

This compound was prepared using similar procedures as described for Example 1, Step 4 with tert-butyl (E)-(4-((2-amino-6-(3-((tert-butyldimethylsilyl)oxy)propoxy)-4-carbamoylphenyl)amino)but-2-en-1-yl)carbamate replacing tert-butyl (E)-(4-((2-amino-4-carbamoyl-6-methylphenyl)amino)but-2-en-1-yl)carbamate. LC-MS calculated for $C_{20}H_{30}N_5O_5$ (M+H)$^+$: m/z=420.2; found 420.3.

Step 6: (E)-3-((1-(4-((tert-butoxycarbonyl)amino)but-2-en-1-yl)-5-carbamoyl-2-(1-ethyl-3-methyl-1H-pyrazole-5-carboxamido)-1H-benzo[d]imidazol-7-yl)oxy)propyl 1-ethyl-3-methyl-1H-pyrazole-5-carboxylate

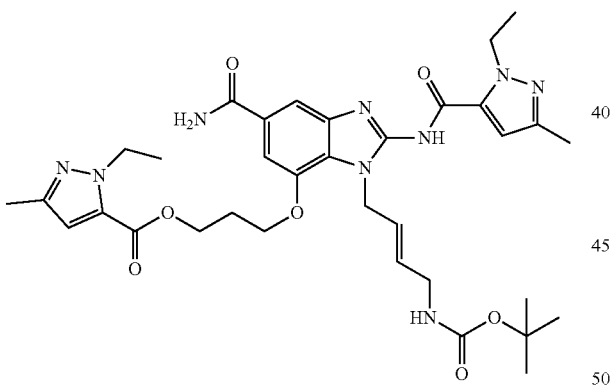

To a solution of 1-ethyl-3-methyl-1H-pyrazole-5-carboxylic acid (Combi-Blocks, cat #QB-0979: 0.336 g, 2.179 mmol) in DMF (4.95 ml) at rt was added HATU (0.911 g, 2.397 mmol) and DIPEA (0.951 ml, 5.45 mmol). The mixture was stirred for 15 min, then a solution of tert-butyl (E)-(4-(2-amino-5-carbamoyl-7-(3-hydroxypropoxy)-1H-benzo[d]imidazol-1-yl)but-2-en-1-yl)carbamate (0.457 g, 1.089 mmol) in DMF (0.495 ml) was added and stirred overnight. The reaction was concentrated, and was diluted with water. The aqueous mixture was extracted with DCM (3×20 mL). The combined organic layers were washed with brine, dried over MgSO$_4$, filtered, and concentrated. The product was purified by column chromatography (15% MeOH/DCM) to provide the desired product as a white solid. LC-MS calculated for $C_{34}H_{46}N_9O_7$ (M+H)$^+$: m/z=692.3; found 692.4.

Step 7: (E)-3-((1-(4-aminobut-2-en-1-yl)-5-carbamoyl-2-(1-ethyl-3-methyl-1H-pyrazole-5-carboxamido)-1H-benzo[d]imidazol-7-yl)oxy)propyl 1-ethyl-3-methyl-1H-pyrazole-5-carboxylate

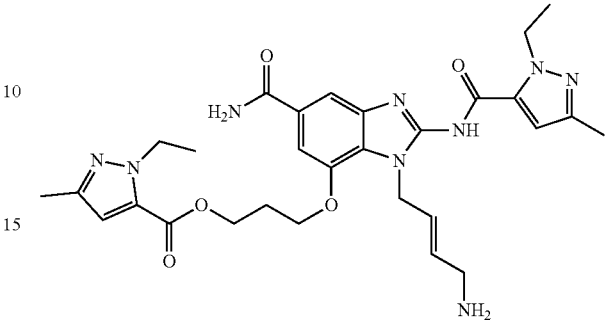

This compound was prepared using similar procedures as described for Example 1, Step 6 with (E)-3-((1-(4-((tert-butoxycarbonyl)amino)but-2-en-1-yl)-5-carbamoyl-2-(1-ethyl-3-methyl-1H-pyrazole-5-carboxamido)-1H-benzo[d]imidazol-7-yl)oxy)propyl 1-ethyl-3-methyl-1H-pyrazole-5-carboxylate replacing tert-butyl (E)-(4-(5-carbamoyl-2-(1-ethyl-3-methyl-1H-pyrazole-5-carboxamido)-7-methyl-1H-benzo[d]imidazol-1-yl)but-2-en-1-yl)carbamate. LC-MS calculated for $C_{29}H_{38}N_9O_5$ (M+H)$^+$: m/z=592.3; found 592.4.

Step 8: (E)-3-((5-carbamoyl-2-(1-ethyl-3-methyl-1H-pyrazole-5-carboxamido)-1-(4-hydroxybut-2-en-1-yl)-1H-benzo[d]imidazol-7-yl)oxy)propyl 1-ethyl-3-methyl-1H-pyrazole-5-carboxylate

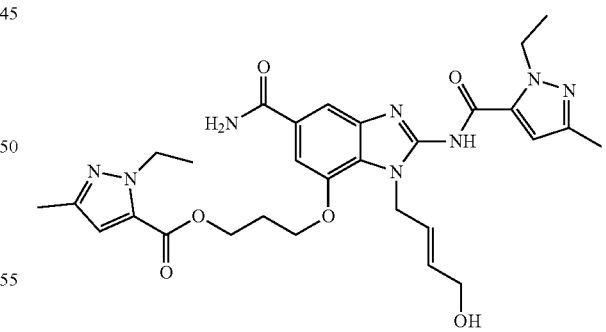

This compound was prepared using similar procedures as described for Example 1, Step 7 with (E)-3-((1-(4-aminobut-2-en-1-yl)-5-carbamoyl-2-(1-ethyl-3-methyl-1H-pyrazole-5-carboxamido)-1H-benzo[d]imidazol-7-yl)oxy)propyl 1-ethyl-3-methyl-1H-pyrazole-5-carboxylate replacing (E)-1-(4-aminobut-2-en-1-yl)-2-(1-ethyl-3-methyl-1H-pyrazole-5-carboxamido)-7-methyl-1H-benzo[d]imidazole-5-carboxamide. LC-MS calculated for $C_{29}H_{37}N_8O_6$ (M+H)$^+$: m/z=593.3; found 593.4.

Step 9: (E)-3-((1-(4-bromobut-2-en-1-yl)-5-carbamoyl-2-(1-ethyl-3-methyl-1H-pyrazole-5-carboxamido)-1H-benzo[d]imidazol-7-yl)oxy)propyl 1-ethyl-3-methyl-1H-pyrazole-5-carboxylate This compound was prepared using similar procedures as described for Example 1, Step 8 with (E)-3-carbamoyl-2-(1-ethyl-3-methyl-1H-pyrazole-5-carboxamido)-1-(4-hydroxybut-2-en-1-yl)-1H-benzo[d]imidazol-7-yl)oxy)propyl 1-ethyl-3-methyl-1H-pyrazole-5-carboxylate replacing (E)-2-(1-ethyl-3-methyl-1H-pyrazole-5-carboxamido)-1-(4-hydroxybut-2-enyl)-7-methyl-1H-benzo[d]imidazole-5-carboxamide. LC-MS calculated for $C_{29}H_{36}BrN_8O_5$ (M+H)$^+$: m/z=655.2/657.2; found 655.3/657.3.

Step 10: (E)-3-((5-carbamoyl-1-(4-(6-carbamoyl-2-(1-ethyl-3-methyl-1H-pyrazol-5-yl)-8-methoxy-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propyl 1-ethyl-3-methyl-1H-pyrazole-5-carboxylate To a mixture of (E)-3-((1-(4-bromobut-2-en-1-yl)-5-carbamoyl-2-(1-ethyl-3-methyl-1H-pyrazole-5-carboxamido)-1H-benzo[d]imidazol-7-yl)oxy)propyl 1-ethyl-3-methyl-1H-pyrazole-5-carboxylate (24 mg, 0.037 mmol) and 2-(1-ethyl-3-methyl-1H-pyrazol-5-yl)-8-methoxy-9H-pyrimido[4,5-b]indole-6-carboxamide (Example 10, Step 4: 12.83 mg, 0.037 mmol) in DMF (366 µl) was added DIPEA (19.18 µl, 0.110 mmol). After stirring for 20 min, $Cs_2CO_3$ (35.8 mg, 0.110 mmol) was added. The mixture was stirred at rt overnight. 180 uL of the reaction mixture was removed and diluted with TFA/water, then purified by prep-HPLC (pH=2, acetonitrile/water+TFA) to give the desired product as the TFA salt. LC-MS calculated for $C_{47}H_{54}N_{14}O_7$ (M+2H)$^{2+}$: m/z=463.2; found 463.3.

Example 16. (E)-9-(4-(5-carbamoyl-2-(1-ethyl-3-methyl-1H-pyrazole-5-carboxamido)-7-(3-hydroxypropoxy)-1H-benzo[d]imidazol-1-yl)but-2-en-1-yl)-2-(1-ethyl-3-methyl-1H-pyrazol-5-yl)-8-methoxy-9H-pyrimido[4,5-b]indole-6-carboxamide

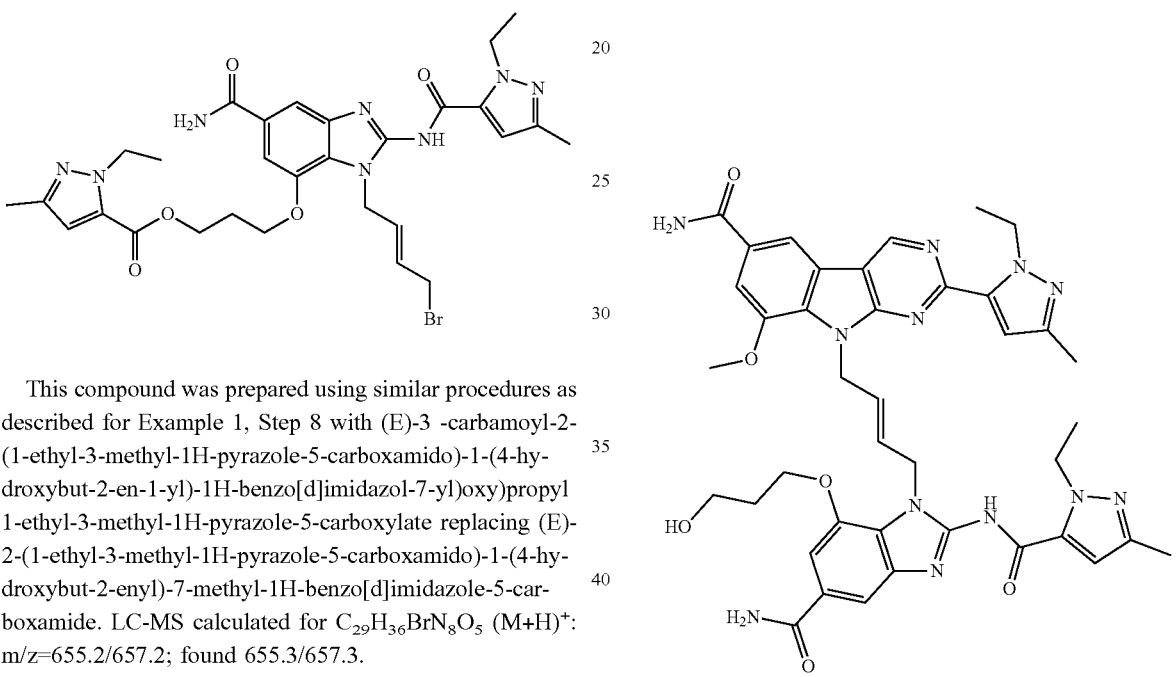

To a mixture of (E)-3-((1-(4-bromobut-2-en-1-yl)-5-carbamoyl-2-(1-ethyl-3-methyl-1H-pyrazole-5-carboxamido)-1H-benzo[d]imidazol-7-yl)oxy)propyl 1-ethyl-3-methyl-1H-pyrazole-5-carboxylate (Example 15, Step 9: 24 mg, 0.037 mmol) and 2-(1-ethyl-3-methyl-1H-pyrazol-5-yl)-8-methoxy-9H-pyrimido[4,5-b]indole-6-carboxamide (Example 10, Step 4: 12.83 mg, 0.037 mmol) in DMF (366 ul) was added DIPEA (19.18 µl, 0.110 mmol). After 20 min, $Cs_2CO_3$ (35.8 mg, 0.110 mmol) was added. The mixture was stirred at rt overnight. 180 uL of the reaction mixture was removed and purified to provide Example 15. To the remaining reaction mixture was added aqueous 1 N sodium hydroxide (36.6 µl, 0.037 mmol). The mixture was stirred for 15 min, then was diluted with MeCN, TFA, then water. The resulting solution was purified by prep-HPLC (pH=2, acetonitrile/water+TFA) to give the desired product as the TFA salt. LC-MS calculated for $C_{40}H_{45}N_{12}O_6$ (M+H)$^+$: m/z=789.4; found 789.3.

Example 17. (E)-3-((5-carbamoyl-1-(4-(6-carbam-oyl-2-(1-ethyl-3-methyl-1H-pyrazol-5-yl)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propyl 1-ethyl-3-methyl-1H-pyrazole-5-carboxylate

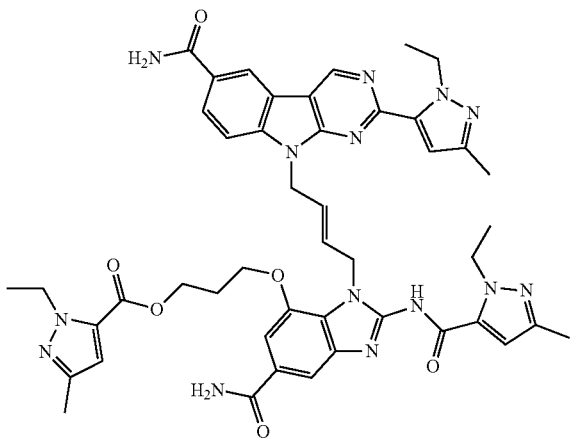 [SMILES: CCn1nc(C)cc1C(=O)Nc1nc2cc(C(N)=O)cc(OCCCOC(=O)c3cc(C)nn3CC)c2n1C/C=C/Cn1c2ccc(C(N)=O)cc2c2cnc(-c3cc(C)nn3CC)nc21]

This compound was prepared using similar procedures as described for Example 15, Step 10 with 2-(1-ethyl-3-methyl-1H-pyrazol-5-yl)-9H-pyrimido[4,5-b]indole-6-carboxamide (Example 1, Step 11) replacing 2-(1-ethyl-3-methyl-1H-pyrazol-5-yl)-8-methoxy-9H-pyrimido[4,5-b]indole-6-carboxamide. An aliquot of the reaction mixture was diluted with TFA/water, then purified by prep-HPLC (pH=2, acetonitrile/water+TFA) to give the desired product as the TFA salt. LC-MS calculated for $C_{46}H_{51}N_{14}O_6$ $(M+H)^+$: m/z=895.4; found 895.4.

Example 18. (E)-9-(4-(5-carbamoyl-2-(1-ethyl-3-methyl-1H-pyrazole-5-carboxamido)-7-(3-hydroxypropoxy)-1H-benzo[d]imidazol-1-yl)but-2-en-1-yl)-2-(1-ethyl-3-methyl-1H-pyrazol-5-yl)-9H-pyrimido[4,5-b]indole-6-carboxamide

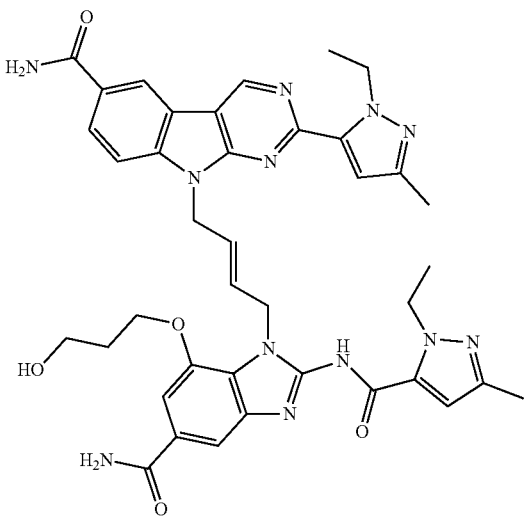 [SMILES: CCn1nc(C)cc1C(=O)Nc1nc2cc(C(N)=O)cc(OCCCO)c2n1C/C=C/Cn1c2ccc(C(N)=O)cc2c2cnc(-c3cc(C)nn3CC)nc21]

This compound was prepared using similar procedures as described for Example 16 with 2-(1-ethyl-3-methyl-1H-pyrazol-5-yl)-9H-pyrimido[4,5-b]indole-6-carboxamide (Example 1, Step 11) replacing 2-(1-ethyl-3-methyl-1H-pyrazol-5-yl)-8-methoxy-9H-pyrimido[4,5-b]indole-6-carboxamide. The reaction mixture was diluted with TFA/water, then purified by prep-HPLC (pH=2, acetonitrile/water+TFA) to give the desired product as the TFA salt. LC-MS calculated for $C_{39}H_{43}N_{12}O_5$ $(M+H)^+$: m/z=759.3; found 759.3.

Example 19. (E)-3-((5-carbamoyl-1-(4-(6-carbamoyl-2-(1-ethyl-3-methyl-1H-pyrazol-5-yl)-8-(3-morpholinopropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propyl 1-ethyl-3-methyl-1H-pyrazole-5-carboxylate

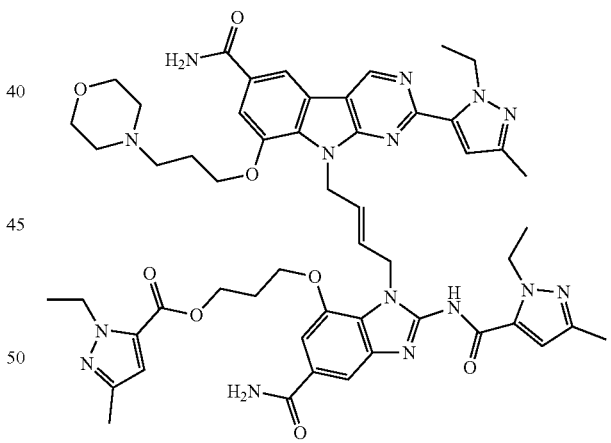

This compound was prepared using similar procedures as described for Example 15, Step 10 with 2-(1-ethyl-3-methyl-1H-pyrazol-5-yl)-8-(3-morpholinopropoxy)-9H-pyrimido[4,5-b]indole-6-carboxamide (Example 11, Step 3) replacing 2-(1-ethyl-3-methyl-1H-pyrazol-5-yl)-8-methoxy-9H-pyrimido[4,5-b]indole-6-carboxamide. An aliquot of the reaction mixture was diluted with TFA/water, then purified by prep-HPLC (pH=2, acetonitrile/water+TFA) to give the desired product as the TFA salt. LC-MS calculated for $C_{53}H_{65}N_{15}O_8$ $(M+2H)^{2+}$: m/z=519.8; found 519.9.

Example 20. (E)-9-(4-(5-carbamoyl-2-(1-ethyl-3-methyl-1H-pyrazole-5-carboxamido)-7-(3-hydroxypropoxy)-1H-benzo[d]imidazol-1-yl)but-2-en-1-yl)-2-(1-ethyl-3-methyl-1H-pyrazol-5-yl)-8-(3-morpholinopropoxy)-9H-pyrimido[4,5-b]indole-6-carboxamide

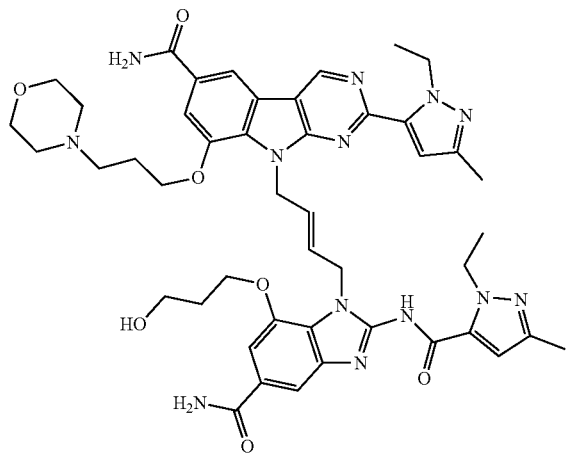 [SMILES: CCn1nc(C)cc1C(=O)Nc1nc2cc(C(N)=O)cc(OCCCO)c2n1C/C=C/Cn1c2nc(-c3cc(C)nn3CC)ncc2c2cc(C(N)=O)cc(OCCCN3CCOCC3)c21]

This compound was prepared using similar procedures as described for Example 16 with 2-(1-ethyl-3-methyl-1H-pyrazol-5-yl)-8-(3-morpholinopropoxy)-9H-pyrimido[4,5-b]indole-6-carboxamide (Example 11, Step 3) replacing 2-(1-ethyl-3-methyl-1H-pyrazol-5-yl)-8-methoxy-9H-pyrimido[4,5-b]indole-6-carboxamide. The reaction mixture was diluted with TFA/water, then purified by prep-HPLC (pH=2, acetonitrile/water+TFA) to give the desired product as the TFA salt. LC-MS calculated for $C_{46}H_{57}N_{13}O_7$ $(M+H)^{2+}$: m/z=451.7; found 451.8.

Example 21. (E)-3-((5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propyl 1-ethyl-3-methyl-1H-pyrazole-5-carboxylate

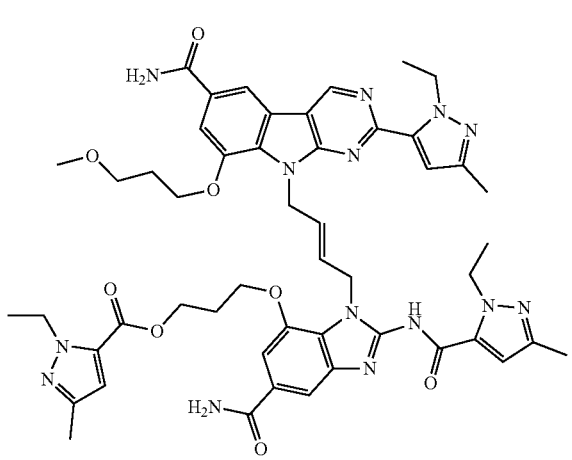 [SMILES: CCn1nc(C)cc1C(=O)Nc1nc2cc(C(N)=O)cc(OCCCOC(=O)c3cc(C)nn3CC)c2n1C/C=C/Cn1c2nc(-c3cc(C)nn3CC)ncc2c2cc(C(N)=O)cc(OCCCOC)c21]

This compound was prepared using similar procedures as described for Example 15, Step 10 with 2-(1-ethyl-3-methyl-1H-pyrazol-5-yl)-8-(3-methoxypropoxy)-9H-pyrimido[4,5-b]indole-6-carboxamide (Example 12, Step 3) replacing 2-(1-ethyl-3-methyl-1H-pyrazol-5-yl)-8-methoxy-9H-pyrimido[4,5-b]indole-6-carboxamide. An aliquot of the reaction mixture was diluted with TFA/water, then purified by prep-HPLC (pH=2, acetonitrile/water+TFA) to give the desired product as the TFA salt. LC-MS calculated for $C_{50}H_{60}N_{14}O_8$ $(M+2H)^{2+}$: m/z=492.2; found 492.3.

Example 22. (E)-9-(4-(5-carbamoyl-2-(1-ethyl-3-methyl-1H-pyrazole-5-carboxamido)-7-(3-hydroxypropoxy)-1H-benzo[d]imidazol-1-yl)but-2-en-1-yl)-2-(1-ethyl-3-methyl-1H-pyrazol-5-yl)-8-(3-methoxypropoxy)-9H-pyrimido[4,5-b]indole-6-carboxamide

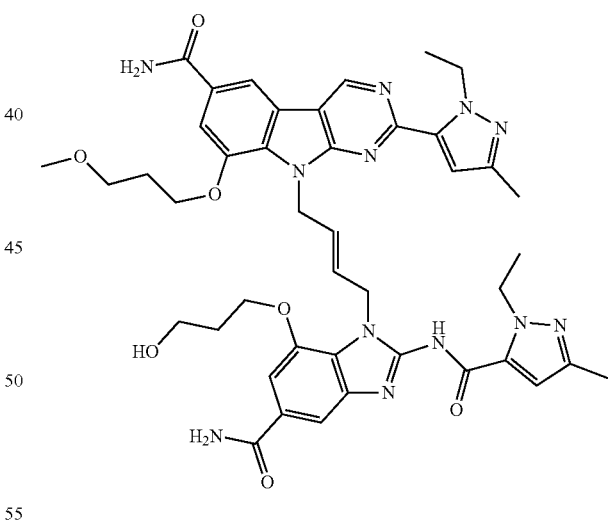

This compound was prepared using similar procedures as described for Example 16 with 2-(1-ethyl-3-methyl-1H-pyrazol-5-yl)-8-(3-methoxypropoxy)-9H-pyrimido[4,5-b]indole-6-carboxamide (Example 12, Step 3) replacing 2-(1-ethyl-3-methyl-1H-pyrazol-5-yl)-8-methoxy-9H-pyrimido[4,5-b]indole-6-carboxamide. The remaining reaction mixture was diluted with TFA/water, then purified by prep-HPLC (pH=2, acetonitrile/water+TFA) to give the desired product as the TFA salt. LC-MS calculated for $C_{43}H_{51}N_{12}O_7$ $(M+H)^+$: m/z=847.4; found 847.4.

Example 23. (E)-5-(4-(5-carbamoyl-2-(1-ethyl-3-methyl-1H-pyrazole-5-carboxamido)-7-methyl-1H-benzo[d]imidazol-1-yl)but-2-en-1-yl)-3-(1-ethyl-3-methyl-1H-pyrazol-5-yl)-4-fluoro-5H-pyrido[4,3-b]indole-8-carboxamide

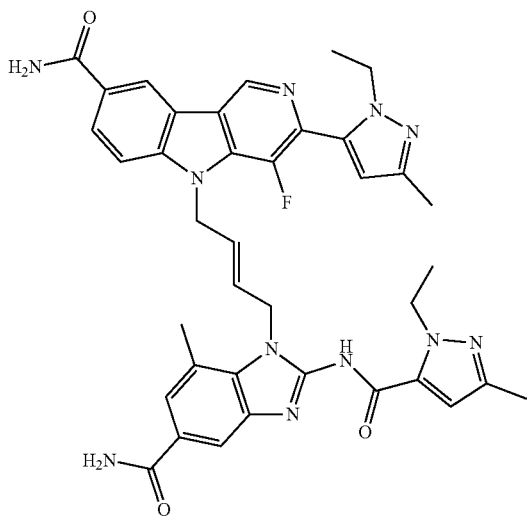 [SMILES: CCn1nc(C)cc1C(=O)Nc1nc2cc(C(N)=O)cc(C)c2n1C/C=C/Cn1c2ccc(C(N)=O)cc2c2cnc(-c3cc(C)nn3CC)c(F)c21]

Step 1: 3-(6-chloro-5-fluoropyridin-3-yl)-4-nitrobenzamide

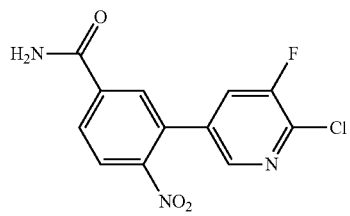 [SMILES: NC(=O)c1ccc([N+](=O)[O-])c(-c2cnc(Cl)c(F)c2)c1]

This compound was prepared using similar procedures as described for Example 1, Step 9 with 2-chloro-3-fluoro-5-(4,4,5,5-tetramethyl-1,3,2-dioxaborolan-2-yl)pyridine (Astatech, cat #33955) replacing (2-chloropyrimidin-5-yl)boronic acid. LC-MS calculated for $C_{12}H_8ClFN_3O_3$ (M+H)$^+$: m/z=296.0; found 296.1.

Step 2: 3-(6-(1-ethyl-3-methyl-1H-pyrazol-5-yl)-5-fluoropyridin-3-yl)-4-nitrobenzamide

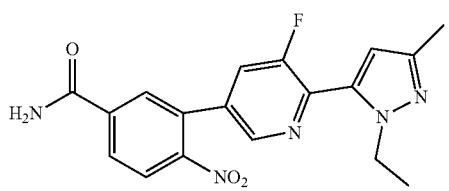 [SMILES: CCn1nc(C)cc1-c1ncc(-c2cc(C(N)=O)ccc2[N+](=O)[O-])cc1F]

This compound was prepared using similar procedures as described for Example 1, Step 11 with 3-(6-chloro-5-fluoropyridin-3-yl)-4-nitrobenzamide replacing 2-chloro-9H-pyrimido[4,5-b]indole-6-carboxamide. LC-MS calculated for $C_{18}H_{17}FN_5O_3$ (M+H)$^+$: m/z=370.1; found 370.1.

Step 3: 3-(1-ethyl-3-methyl-1H-pyrazol-5-yl)-4-fluoro-5H-pyrido[4,3-b]indole-8-carboxamide and 2-(1-ethyl-3-methyl-1H-pyrazol-5-yl)-3-fluoro-9H-pyrido[2,3-b]indole-6-carboxamide

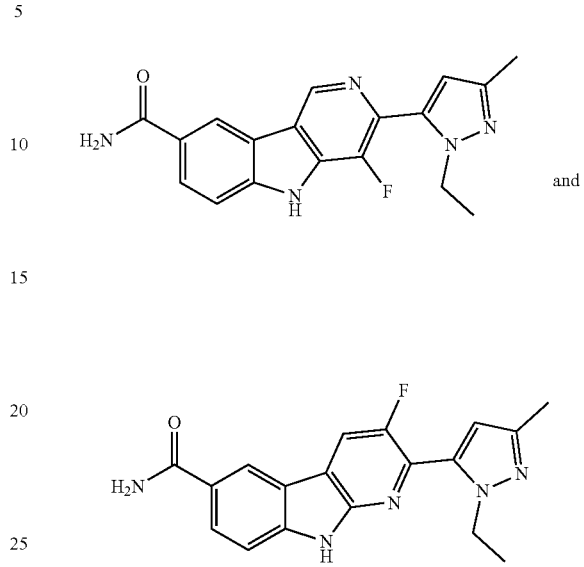

This compound was prepared using similar procedures as described for Example 1, Step 10 with 3-(6-(1-ethyl-3-methyl-1H-pyrazol-5-yl)-5-fluoropyridin-3-yl)-4-nitrobenzamide replacing 3-(2-chloropyrimidin-5-yl)-4-nitrobenzamide. After cooling to rt, the reaction was concentrated under reduced pressure and purified by flash chromatography (15% MeOH/DCM) with 2-(1-ethyl-3-methyl-1H-pyrazol-5-yl)-3-fluoro-9H-pyrido[2,3-b]indole-6-carboxamide eluting first (major product) and 3-(1-ethyl-3-methyl-1H-pyrazol-5-yl)-4-fluoro-5H-pyrido[4,3-b]indole-8-carboxamide eluting second (minor product). LC-MS calculated for $C_{18}H_{17}FN_5O$ (M+H)$^+$: m/z=338.1; found 338.2. Major product: $^1$H NMR (400 MHz, MeOD) δ 8.69 (s, 1H), 8.37 (d, J=10.5 Hz, 1H), 8.05 (dd, J=8.6, 1.6 Hz, 1H), 7.56 (d, J=8.6 Hz, 1H), 6.56 (d, J=4.0 Hz, 1H), 4.56 (q, J=7.1 Hz, 2H), 3.35 (s, 2H), 2.32 (s, 3H), 1.44 (t, J=7.1 Hz, 3H). Minor product: $^1$H NMR (400 MHz, MeOD) δ 9.22 (s, 1H), 8.81 (s, 1H), 8.11 (dd, J=8.6, 1.4 Hz, 1H), 7.65 (d, J=8.6 Hz, 1H), 6.48 (d, J=2.3 Hz, 1H), 4.40 (q, J=7.1 Hz, 2H), 2.33 (s, 3H), 1.36 (t, J=7.1 Hz, 3H).

Step 4: (E)-5-(4-(5-carbamoyl-2-(1-ethyl-3-methyl-1H-pyrazole-5-carboxamido)-7-methyl-1H-benzo[d]imidazol-1-yl)but-2-en-1-yl)-3-(1-ethyl-3-methyl-1H-pyrazol-5-yl)-4-fluoro-5H-pyrido[4,3-b]indole-8-carboxamide To a mixture of (E)-1-(4-bromobut-2-en-1-yl)-2-(1-ethyl-3-methyl-1H-pyrazole-5-carboxamido)-7-methyl-1H-benzo[d]imidazole-5-carboxamide (Example 1, Step 8:10 mg, 0.022 mmol) and 3-(1-ethyl-3-methyl-1H-pyrazol-5-yl)-4-fluoro-5H-pyrido[4,3-b]indole-8-carboxamide (7.34 mg, 0.022 mmol) in DMF (218 μl) was added DIPEA (11.41 μl, 0.065 mmol). After 20 min, Cs$_2$CO$_3$ (21.28 mg, 0.065 mmol) was added. The mixture was stirred at rt overnight. The reaction was diluted with TFA/water, then purified by prep-HPLC (pH=2, acetonitrile/water+TFA) to give the desired product as the TFA salt. LC-MS calculated for $C_{38}H_{39}FN_{11}O_3$ (M+H)$^+$: m/z=716.3; found 716.3.

Example 24. (E)-9-(4-(5-carbamoyl-2-(1-ethyl-3-methyl-1H-pyrazole-5-carboxamido)-7-methyl-1H-benzo[d]imidazol-1-yl)but-2-en-1-yl)-2-(1-ethyl-3-methyl-1H-pyrazol-5-yl)-3-fluoro-9H-pyrido[2,3-b]indole-6-carboxamide

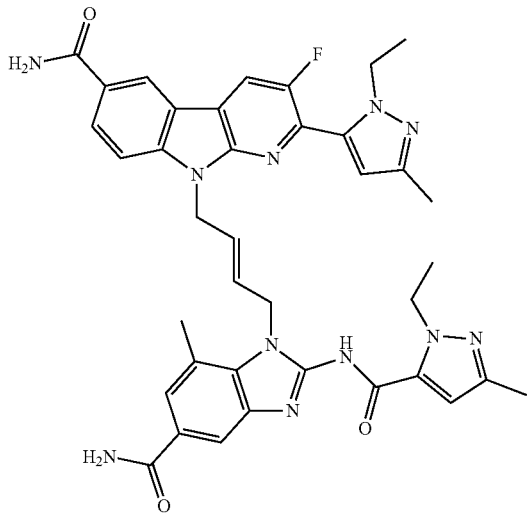 [SMILES: CCn1nc(C)cc1C(=O)Nc1nc2cc(C(N)=O)cc(C)c2n1C/C=C/Cn1c2ccc(C(N)=O)cc2c2cc(F)c(-c3cc(C)nn3CC)nc21]

This compound was prepared using similar procedures as described for Example 23, Step 4 with 2-(1-ethyl-3-methyl-1H-pyrazol-5-yl)-3-fluoro-9H-pyrido[2,3-b]indole-6-carboxamide (Example 23, Step 3) replacing 3-(1-ethyl-3-methyl-1H-pyrazol-5-yl)-4-fluoro-5H-pyrido[4,3-b]indole-8-carboxamide. LC-MS calculated for $C_{38}H_{39}FN_{11}O_3$ (M+H)$^+$: m/z=716.3; found 716.3.

Example 25. (E)-9-(4-(5-carbamoyl-2-(1-ethyl-3-methyl-1H-pyrazole-5-carboxamido)-7-methyl-1H-benzo[d]imidazol-1-yl)but-2-en-1-yl)-3-cyano-2-(1-ethyl-3-methyl-1H-pyrazol-5-yl)-9H-pyrido[2,3-b]indole-6-carboxamide

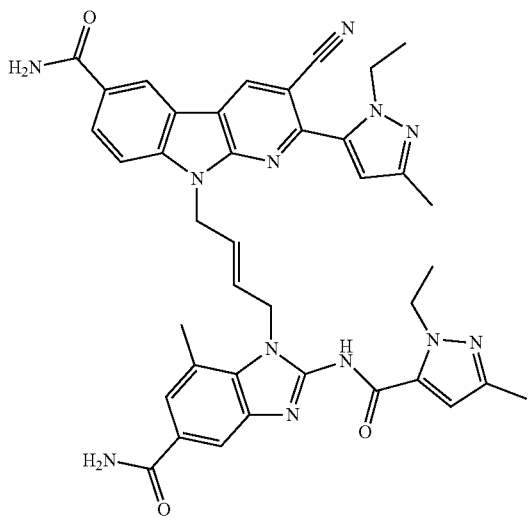 [SMILES: CCn1nc(C)cc1C(=O)Nc1nc2cc(C(N)=O)cc(C)c2n1C/C=C/Cn1c2ccc(C(N)=O)cc2c2cc(C#N)c(-c3cc(C)nn3CC)nc21]

Step 1: (6-chloro-5-cyanopyridin-3-yl)boronic acid

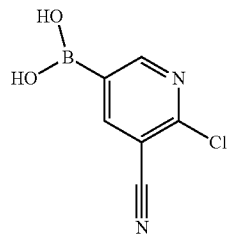 [SMILES: N#Cc1cc(B(O)O)cnc1Cl]

To a vial was added 5-bromo-2-chloronicotinonitrile (Aldrich, cat #759716: 0.500 g, 2.299 mmol), bis(pinacolato)diboron (0.701 g, 2.76 mmol), potassium acetate (0.564 g, 5.75 mmol), dichloro[1,1'-bis(diphenylphosphino)ferrocene]palladium (II) dichloromethane adduct (0.188 g, 0.230 mmol), 1,4-dioxane (5.75 ml), and a stir bar. The mixture was sparged with nitrogen for 2 min, then was sealed and heated at 110° C. for 1 h with stirring. After cooling, the mixture was filtered through Celite® and purified using flash chromatography (5% MeOH/DCM). LC-MS calculated for $C_6H_5BClN_2O_2$ (M+H)$^+$: m/z=183.0; found 183.0.

Step 2: 3-(6-chloro-5-cyanopyridin-3-yl)-4-nitrobenzamide

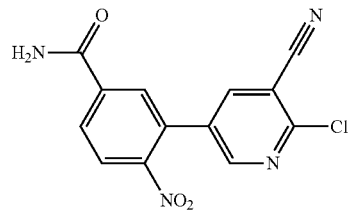 [SMILES: N#Cc1cc(-c2cc(C(N)=O)ccc2[N+](=O)[O-])cnc1Cl]

This compound was prepared using similar procedures as described for Example 1, Step 9 with (6-chloro-5-cyanopyridin-3-yl)boronic acid replacing (2-chloropyrimidin-5-yl)boronic acid. LC-MS calculated for $C_{13}H_8ClN_4O_3$ (M+H)$^+$: m/z=303.0; found 302.8.

Step 3: 3-(5-cyano-6-(1-ethyl-3-methyl-1H-pyrazol-5-yl)pyridin-3-yl)-4-nitrobenzamide

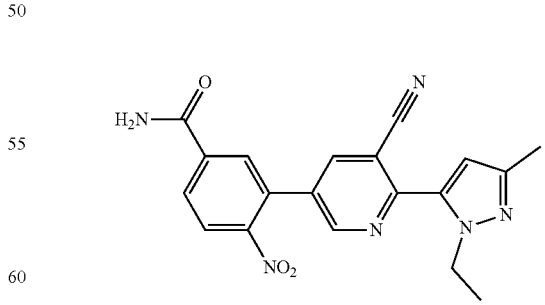

This compound was prepared using similar procedures as described for Example 1, Step 11 with 3-(6-chloro-5-cyanopyridin-3-yl)-4-nitrobenzamide replacing 2-chloro-9H-pyrimido[4,5-b]indole-6-carboxamide. LC-MS calculated for $C_{19}H_{17}N_6O_3$ (M+H)$^+$: m/z=377.1; found 377.1.

Step 4: 3-cyano-2-(1-ethyl-3-methyl-1H-pyrazol-5-yl)-9H-pyrido[2,3-b]indole-6-carboxamide and 4-cyano-3-(1-ethyl-3-methyl-1H-pyrazol-5-yl)-5H-pyrido[4,3-b]indole-8-carboxamide

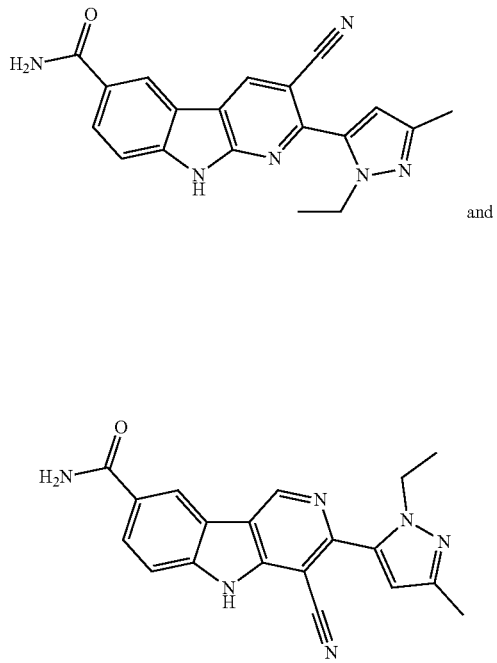

and

This compound was prepared using similar procedures as described for Example 1, Step 10 with 3-(5-cyano-6-(1-ethyl-3-methyl-1H-pyrazol-5-yl)pyridin-3-yl)-4-nitrobenzamide replacing 3-(2-chloropyrimidin-5-yl)-4-nitrobenzamide. After cooling to rt, the reaction was concentrated under reduced pressure and purified by flash chromatography (15% MeOH/DCM) with 3-cyano-2-(1-ethyl-3-methyl-1H-pyrazol-5-yl)-9H-pyrido[2,3-b]indole-6-carboxamide eluting first (major product) and 4-cyano-3-(1-ethyl-3-methyl-1H-pyrazol-5-yl)-5H-pyrido[4,3-b]indole-8-carboxamide eluting second (minor product). LC-MS calculated for $C_{19}H_{17}N_6O$ (M+H)$^+$: m/z=345.1; found 345.2.

Step 5: (E)-9-(4-(5-carbamoyl-2-(1-ethyl-3-methyl-1H-pyrazole-5-carboxamido)-7-methyl-1H-benzo[d]imidazol-1-yl)but-2-en-1-yl)-3-cyano-2-(1-ethyl-3-methyl-1H-pyrazol-5-yl)-9H-pyrido[2,3-b]indole-6-carboxamide This compound was prepared using similar procedures as described for Example 23, Step 4 with 3-cyano-2-(1-ethyl-3-methyl-1H-pyrazol-5-yl)-9H-pyrido[2,3-b]indole-6-carboxamide replacing 3-(1-ethyl-3-methyl-1H-pyrazol-5-yl)-4-fluoro-5H-pyrido[4,3-b]indole-8-carboxamide. $^1$H NMR (600 MHz, DMSO) δ 12.82 (s, 1H), 9.18 (s, 1H), 8.87 (s, 1H), 8.15-8.07 (m, 1H), 8.02 (s, 1H), 7.86 (s, 1H), 7.82 (s, 1H), 7.77 (d, J=8.6 Hz, 1H), 7.46 (s, 1H), 7.39 (s, 1H), 7.27 (s, 1H), 6.65 (s, 1H), 6.41 (s, 1H), 5.84 (dt, J=15.6, 4.8 Hz, 1H), 5.55 (dt, J=15.6, 5.4 Hz, 1H), 5.14 (d, J=4.8 Hz, 2H), 4.91 (brs, 2H), 4.46 (q, J=6.6 Hz, 2H), 4.11 (q, J=7.2 Hz, 2H), 2.42 (s, 3H), 2.24 (s, 3H), 2.10 (s, 3H), 1.21 (t, J=7.2 Hz, 3H), 1.17 (t, J=6.6 Hz, 3H). LC-MS calculated for $C_{39}H_{39}N_{12}O_3$ (M+H)$^+$: m/z=723.3; found 723.3.

Example 26. (E)-5-(4-(5-carbamoyl-2-(1-ethyl-3-methyl-1H-pyrazole-5-carboxamido)-7-methyl-1H-benzo[d]imidazol-1-yl)but-2-en-1-yl)-4-cyano-3-(1-ethyl-3-methyl-1H-pyrazol-5-yl)-5H-pyrido[4,3-b]indole-8-carboxamide

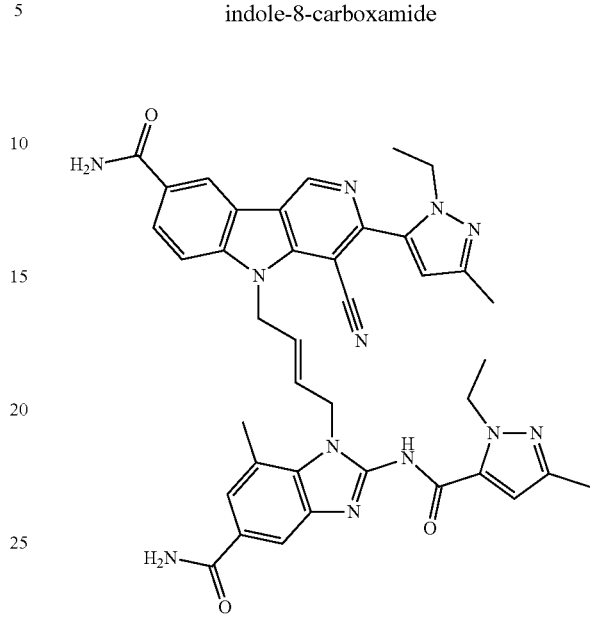

This compound was prepared using similar procedures as described for Example 23, Step 4 with 4-cyano-3-(1-ethyl-3-methyl-1H-pyrazol-5-yl)-5H-pyrido[4,3-b]indole-8-carboxamide (Example 25, Step 4) replacing 3-(1-ethyl-3-methyl-1H-pyrazol-5-yl)-4-fluoro-5H-pyrido[4,3-b]indole-8-carboxamide. LC-MS calculated for $C_{39}H_{39}N_{12}O_3$ (M+H)$^+$: m/z=723.3; found 723.3.

Example 27. (E)-9-(4-(5-carbamoyl-2-(1-ethyl-3-methyl-1H-pyrazole-5-carboxamido)-7-(3-morpholinopropoxy)-1H-benzo[d]imidazol-1-yl)but-2-en-1-yl)-2-(1-ethyl-3-methyl-1H-pyrazol-5-yl)-8-(3-methoxypropoxy)-9H-pyrimido[4,5-b]indole-6-carboxamide

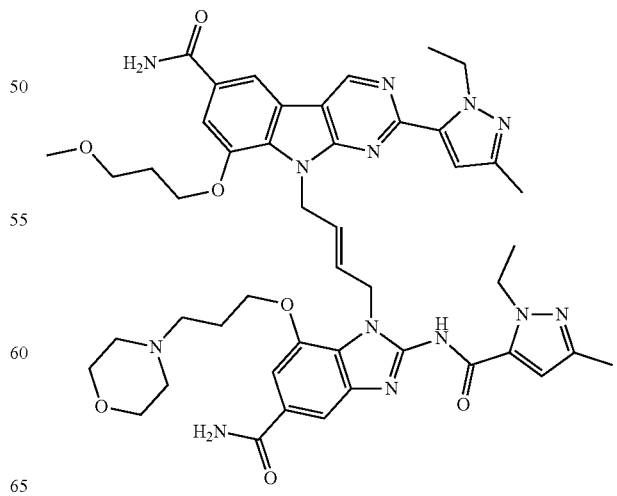

Step 1: (E)-9-(4-(5-carbamoyl-2-(1-ethyl-3-methyl-1H-pyrazole-5-carboxamido)-7-(3-oxopropoxy)-1H-benzo[d]imidazol-1-yl)but-2-en-1-yl)-2-(1-ethyl-3-methyl-1H-pyrazol-5-yl)-8-(3-methoxypropoxy)-9H-pyrimido[4,5-b]indole-6-carboxamide

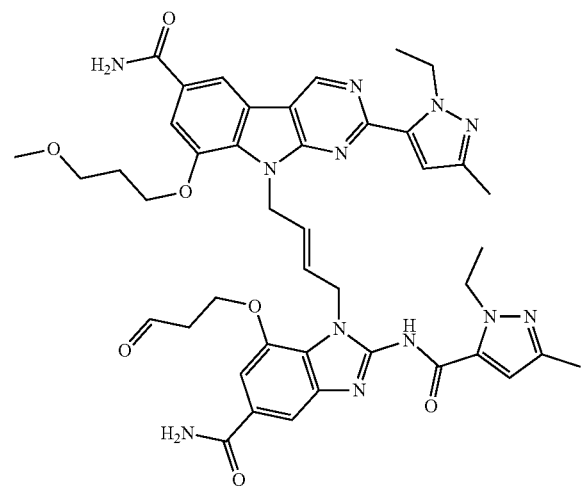

To a vial was added (E)-9-(4-(5-carbamoyl-2-(1-ethyl-3-methyl-1H-pyrazole-5-carboxamido)-7-(3-hydroxy-propoxy)-1H-benzo[d]imidazol-1-yl)but-2-en-1-yl)-2-(1-ethyl-3-methyl-1H-pyrazol-5-yl)-8-(3-methoxypropoxy)-9H-pyrimido[4,5-b]indole-6-carboxamide (Example 22: 0.025 g, 0.030 mmol), DMF (0.295 ml), and a stir bar. The mixture was cooled to 0° C., and DMP (0.025 g, 0.059 mmol) and water (4.25 µl, 0.236 mmol) were added. The reaction was gradually warmed up to rt, stirring overnight. After cooling to 0° C., ice and sodium bicarbonate were added, followed by saturated aqueous sodium thiosulfate. The reaction was extracted with chloroform/ipa (3:1), dried over MgSO$_4$, filtered, and concentrated under reduced pressure. The crude product was used directly in the next step without further purification. LC-MS calculated for $C_{43}H_{49}N_{12}O_7(M+H)^+$: m/z=845.4; found 845.3.

Step 2: (E)-9-(4-(5-carbamoyl-2-(1-ethyl-3-methyl-1H-pyrazole-5-carboxamido)-7-(3-morpholinopropoxy)-1H-benzo[d]imidazol-1-yl)but-2-en-1-yl)-2-(1-ethyl-3-methyl-1H-pyrazol-5-yl)-8-(3-methoxypropoxy)-9H-pyrimido[4,5-b]indole-6-carboxamide To a vial was added (E)-9-(4-(5-carbamoyl-2-(1-ethyl-3-methyl-1H-pyrazole-5-carboxamido)-7-(3-oxopropoxy)-1H-benzo[d]imidazol-1-yl)but-2-en-1-yl)-2-(1-ethyl-3-methyl-1H-pyrazol-5-yl)-8-(3-methoxypropoxy)-9H-pyrimido[4,5-b]indole-6-carboxamide (0.025 g, 0.030 mmol), DMF (0.592 ml), DIPEA (0.016 ml, 0.089 mmol), and morpholine (7.73 µl, 0.089 mmol). Sodium cyanoborohydride (5.58 mg, 0.089 mmol) was then added and the reaction was stirred for 1 h. The reaction was diluted with TFA/water, then purified by prep-HPLC (pH=2, acetonitrile/water+TFA) to give the desired product as the TFA salt. LC-MS calculated for $C_{47}H_{59}N_{13}O_7$ $(M+2H)^{2+}$: m/z=458.7; found 458.7.

Example 28. (E)-9-(4-(5-carbamoyl-2-(1-ethyl-3-methyl-1H-pyrazole-5-carboxamido)-7-hydroxy-1H-benzo[d]imidazol-1-yl)but-2-en-1-yl)-2-(1-ethyl-3-methyl-1H-pyrazol-5-yl)-8-(3-methoxypropoxy)-9H-pyrimido[4,5-b]indole-6-carboxamide

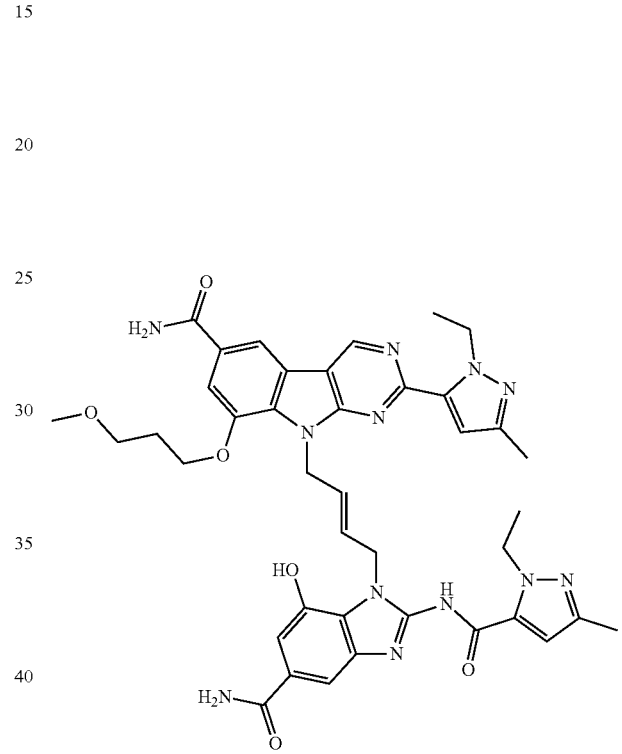

This compound was prepared as a by-product from Example 27, Step 2, wherein (E)-9-(4-(5-carbamoyl-2-(1-ethyl-3-methyl-1H-pyrazole-5-carboxamido)-7-(3-oxopropoxy)-1H-benzo[d]imidazol-1-yl)but-2-en-1-yl)-2-(1-ethyl-3-methyl-1H-pyrazol-5-yl)-8-(3-methoxypropoxy)-9H-pyrimido[4,5-b]indole-6-carboxamide undergoes a retro-Michael reaction. The reaction was diluted with TFA/water, then purified by prep-HPLC (pH=2, acetonitrile/water+TFA) to give the desired product as the TFA salt. $^1$H NMR (600 MHz, DMSO) δ 12.67 (s, 1H), 10.34 (s, 1H), 9.48 (s, 1H), 8.42 (d, J=1.2 Hz, 1H), 8.04 (s, 1H), 7.78 (s, 1H), 7.60 (d, J=1.2 Hz, 1H), 7.41 (s, 1H), 7.36 (s, 1H), 7.19 (s, 1H), 7.10 (s, 1H), 6.79 (s, 1H), 6.37 (s, 1H), 5.94 (m, 1H), 5.85-5.68 (m, 1H), 5.27 (d, J=4.8 Hz, 2H), 4.89 (d, J=6.0 Hz, 2H), 4.60 (q, J=7.2 Hz, 2H), 4.44 (q, J=6.9 Hz, 2H), 4.12 (t, J=6.3 Hz, 2H), 3.35 (t, J=6.3 Hz, 2H), 3.16 (s, 3H), 2.19 (s, 3H), 2.05 (s, 3H), 1.86 (tt, J=6.3, 6.3 Hz, 2H), 1.26 (t, J=6.9 Hz, 3H), 1.18 (t, J=7.2 Hz, 3H). LC-MS calculated for $C_{40}H_{45}N_{12}O_6$ $(M+H)^+$: m/z=789.4; found 789.3.

Example 29. (E)-9-(4-(5-carbamoyl-7-(3-cyanopropoxy)-2-(1-ethyl-3-methyl-1H-pyrazole-5-carboxamido)-1H-benzo[d]imidazol-1-yl)but-2-en-1-yl)-2-(1-ethyl-3-methyl-1H-pyrazol-5-yl)-8-(3-methoxypropoxy)-9H-pyrimido[4,5-b]indole-6-carboxamide

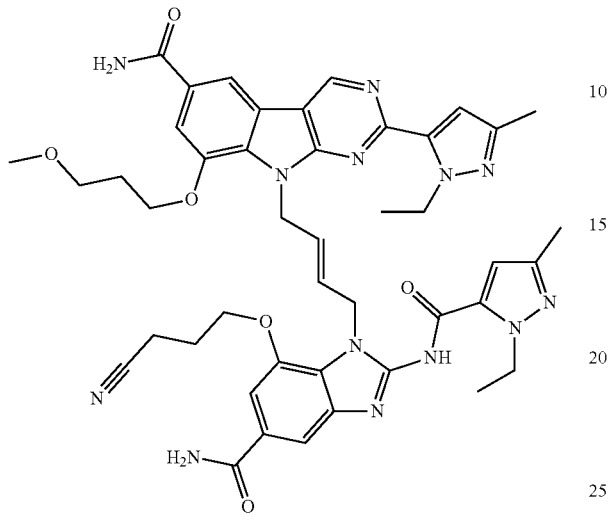

To a vial was added (E)-9-(4-(5-carbamoyl-2-(1-ethyl-3-methyl-1H-pyrazole-5-carboxamido)-7-hydroxy-1H-benzo[d]imidazol-1-yl)but-2-en-1-yl)-2-(1-ethyl-3-methyl-1H-pyrazol-5-yl)-8-(3-methoxypropoxy)-9H-pyrimido[4,5-b]indole-6-carboxamide (Example 28: 1.9 mg, 2.409 μmol), DMF (0.241 ml), cesium carbonate (1.726 mg, 5.30 μmol), 4-bromobutanenitrile (Combi-Blocks, cat #QE-2324: 0.239 μl, 2.409 μmol) and a stir bar. The mixture was stirred at rt for 15 min, then heated at 50° C. for 10 min. After cooling to rt, the mixture was diluted with MeCN, and purified by prep HPLC (pH=2, MeCN/water+TFA) to provide the desired compound as the TFA salt. LC-MS calculated for $C_{44}H_{50}N_{13}O_6$ $(M+H)^+$: m/z=856.4; found 856.4.

Example 30. (E)-9-(4-(5-carbamoyl-2-(1-ethyl-3-methyl-1H-pyrazole-5-carboxamido)-7-isopropoxy-1H-benzo[d]imidazol-1-yl)but-2-en-1-yl)-2-(1-ethyl-3-methyl-1H-pyrazol-5-yl)-8-(3-methoxypropoxy)-9H-pyrimido[4,5-b]indole-6-carboxamide

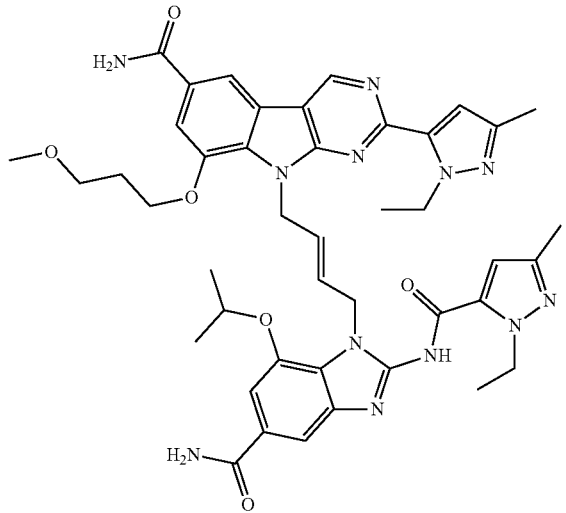

This compound was prepared using similar procedures as described for Example 29 with 2-bromopropane (Aldrich, cat #B78114) replacing 4-bromobutanenitrile. After cooling to rt, the mixture was diluted with MeCN, and purified by prep HPLC (pH=2, MeCN/water+TFA) to provide the desired compound as the TFA salt. LC-MS calculated for $C_{43}H_{51}N_{12}O_6$ $(M+H)^+$: m/z=831.4; found 831.3.

Example 31. (E)-9-(4-(5-carbamoyl-2-(1-ethyl-3-methyl-1H-pyrazole-5-carboxamido)-7-(3-(4-methylpiperazin-1-yl)propoxy)-1H-benzo[d]imidazol-1-yl)but-2-en-1-yl)-2-(1-ethyl-3-methyl-1H-pyrazol-5-yl)-8-(3-methoxypropoxy)-9H-pyrimido[4,5-b]indole-6-carboxamide

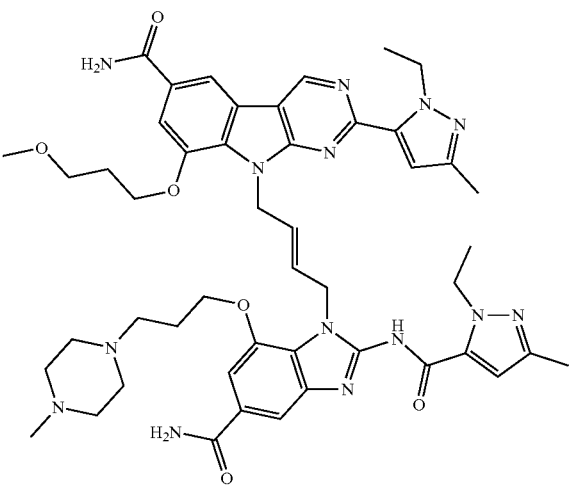

This compound was prepared using similar procedures as described for Example 27, Step 2 with 1-methylpiperazine (Aldrich, cat #130001) replacing morpholine. The reaction was diluted with MeCN, and purified by prep HPLC (pH=2, MeCN/water+TFA) to provide the desired compound as the TFA salt. LC-MS calculated for $C_{48}H_{62}N_{14}O_6$ $(M+2H)^{2+}$: m/z=465.2; found 465.5.

Example 32. (E)-9-(4-(5-carbamoyl-2-(1-ethyl-3-methyl-1H-pyrazole-5-carboxamido)-7-(3-hydroxypropoxy)-1H-benzo[d]imidazol-1-yl)but-2-en-1-yl)-2-(1-ethyl-3-methyl-1H-pyrazol-5-yl)-3-fluoro-9H-pyrido[2,3-b]indole-6-carboxamide

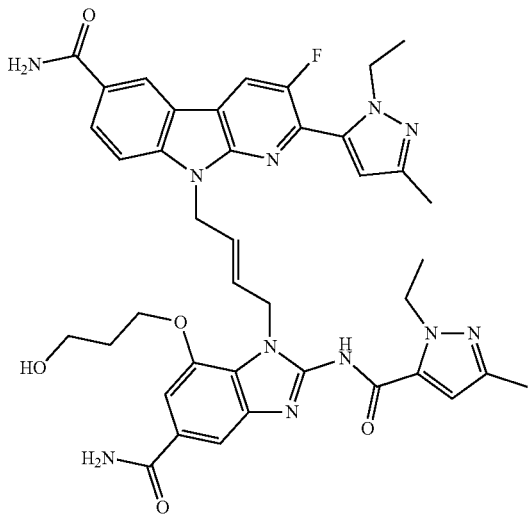 [SMILES: CCn1nc(C)cc1C(=O)Nc1nc2cc(C(N)=O)cc(OCCCO)c2n1C/C=C/Cn1c2ccc(C(N)=O)cc2c2cc(F)c(-c3cc(C)nn3CC)nc21]

Step 1: (E)-3-((5-carbamoyl-1-(4-(6-carbamoyl-2-(1-ethyl-3-methyl-1H-pyrazol-5-yl)-3-fluoro-9H-pyrido[2,3-b]indol-9-yl)but-2-en-1-yl)-2-(1-ethyl-3-methyl-1H-pyrazole-5-carboxamido)-1H-benzo[d]imidazol-7-yl)oxy)propyl 1-ethyl-3-methyl-1H-pyrazole-5-carboxylate

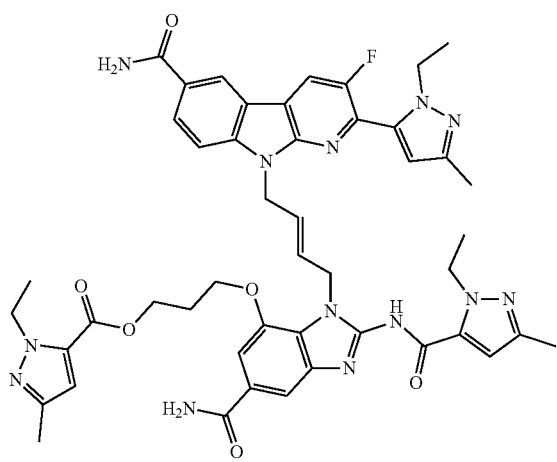 [SMILES: CCn1nc(C)cc1C(=O)Nc1nc2cc(C(N)=O)cc(OCCCOC(=O)c3cc(C)nn3CC)c2n1C/C=C/Cn1c2ccc(C(N)=O)cc2c2cc(F)c(-c3cc(C)nn3CC)nc21]

This compound was prepared using similar procedures as described for Example 15, Step 10 with 2-(1-ethyl-3-methyl-1H-pyrazol-5-yl)-3-fluoro-9H-pyrido[2,3-b]indole-6-carboxamide (Example 23, Step 3) replacing 2-(1-ethyl-3-methyl-1H-pyrazol-5-yl)-8-methoxy-9H-pyrimido[4,5-b]indole-6-carboxamide. LC-MS calculated for $C_{47}H_{52}FN_{13}O_6$ $(M+2H)^{2+}$: m/z=456.7; found 457.0.

Step 2: (E)-9-(4-(5-carbamoyl-2-(1-ethyl-3-methyl-1H-pyrazole-5-carboxamido)-7-(3-hydroxypropoxy)-1H-benzo[d]imidazol-1-yl)but-2-en-1-yl)-2-(1-ethyl-3-methyl-1H-pyrazol-5-yl)-3-fluoro-9H-pyrido[2,3-b]indole-6-carboxamide To a solution of (E)-3-((5-carbamoyl-1-(4-(6-carbamoyl-2-(1-ethyl-3-methyl-1H-pyrazol-5-yl)-3-fluoro-9H-pyrido[2,3-b]indol-9-yl)but-2-en-1-yl)-2-(1-ethyl-3-methyl-1H-pyrazole-5-carboxamido)-1H-benzo[d]imidazol-7-yl)oxy)propyl 1-ethyl-3-methyl-1H-pyrazole-5-carboxylate (15.3 mg, 0.017 mmol) in DMF (0.168 ml) was added 1 N aqueous sodium hydroxide (0.0336 ml, 0.034 mmol). The mixture was stirred for 15 min at rt and was diluted with MeCN and water, and purified by prep HPLC (pH=2, MeCN/water+TFA) to provide the desired product as the TFA salt. LC-MS calculated for $C_{40}H_{43}FN_{11}O_5$ $(M+H)^+$: m/z=776.3; found 776.3.

Example 33. (E)-9-(4-(7-(3-aminopropoxy)-5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazol-5-yl)-8-(3-methoxypropoxy)-9H-pyrimido[4,5-b]indole-6-carboxamide

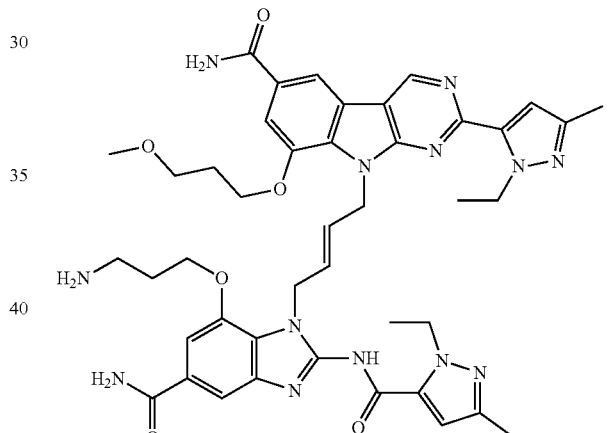

Step 1: tert-butyl (3-(5-carbamoyl-2-chloro-3-nitrophenoxy)propyl)carbamate

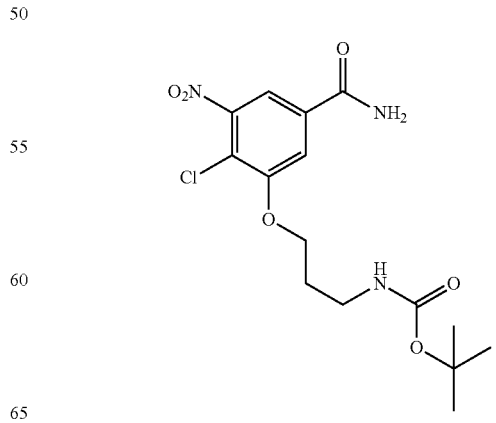

This compound was prepared using similar procedures as described for Example 15, Step 2 with tert-butyl (3-bromopropyl)carbamate (Aldrich, cat #17356) replacing (3-bromopropoxy)(tert-butyl)dimethylsilane. LC-MS calculated for $C_{11}H_{13}ClN_3O_6$ (M–$C_4H_7$)$^+$: m/z=318.0; found 318.0.

Step 2: (E)-2-(4-bromobut-2-en-1-yl)isoindoline-1,3-dione

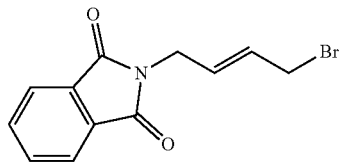 [SMILES: O=C1c2ccccc2C(=O)N1C/C=C/CBr]

A solution of (E)-1,4-dibromobut-2-ene (Aldrich, cat #D39207: 23.10 g, 108 mmol) and potassium carbonate (16.42 g, 119 mmol) in DMF (50.0 ml) at room temperature was treated with phthalimide, potassium salt (Aldrich, cat #160385: 10 g, 54.0 mmol). The reaction mixture was stirred at rt for 24 h, filtered, and concentrated in vacuo. The resulting oil was diluted with ethyl acetate (200 mL), washed with PBS buffer (2×100 mL), dried over MgSO$_4$, filtered and concentrated in vacuo. The crude oil was purified by column chromatography (0-20% ethyl acetate/hexanes). LC-MS calculated for $C_{12}H_{11}BrNO_2$ (M+H)$^+$: m/z=280.0/282.0; found 280.1/282.1.

Step 3: (E)-9-(4-(1,3-dioxoisoindolin-2-yl)but-2-en-1-yl)-2-(1-ethyl-3-methyl-1H-pyrazol-5-yl)-8-(3-methoxypropoxy)-9H-pyrimido[4,5-b]indole-6-carboxamide

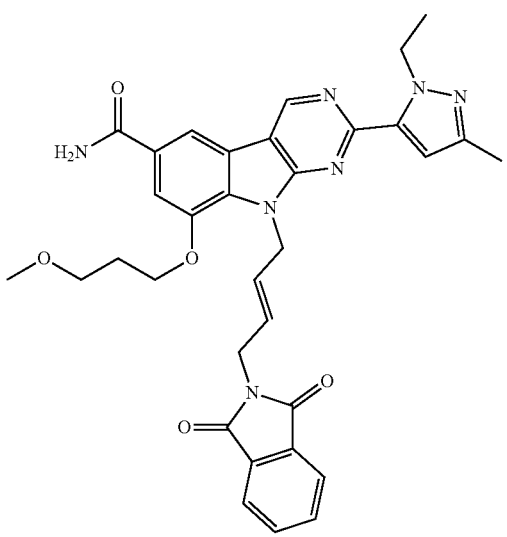

To a solution of (E)-2-(4-bromobut-2-en-1-yl)isoindoline-1,3-dione (0.034 g, 0.122 mmol) and 2-(1-ethyl-3-methyl-1H-pyrazol-5-yl)-8-(3-methoxypropoxy)-9H-pyrimido[4,5-b]indole-6-carboxamide (Example 12, Step 3: 0.05 g, 0.122 mmol) in DMF (0.769 ml) was added DIPEA (0.064 ml, 0.367 mmol) and cesium carbonate (0.120 g, 0.367 mmol). The mixture was stirred at rt overnight. After cooling with an ice bath, water was added, and the reaction was extracted with 3:1 CHCl$_3$/IPA. The combined organic extracts were dried over MgSO$_4$, filtered, and purified by silica gel chromatography (0-10% MeOH/DCM) to provide the desired product as a white solid. LC-MS calculated for $C_{33}H_{34}N_7O_5$ (M+H)$^+$: m/z=608.3; found 608.3.

Step 4: (E)-9-(4-aminobut-2-en-1-yl)-2-(1-ethyl-3-methyl-1H-pyrazol-5-yl)-8-(3-methoxypropoxy)-9H-pyrimido[4,5-b]indole-6-carboxamide

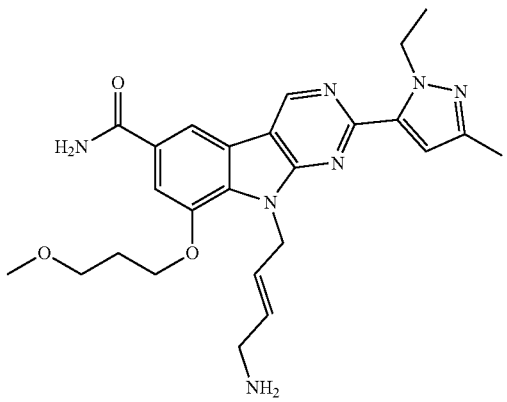

To a solution of (E)-9-(4-(1,3-dioxoisoindolin-2-yl)but-2-en-1-yl)-2-(1-ethyl-3-methyl-1H-pyrazol-5-yl)-8-(3-methoxypropoxy)-9H-pyrimido[4,5-b]indole-6-carboxamide (0.036 g, 0.059 mmol) in ethanol (0.846 ml) at room temperature was added hydrazine monohydrate (0.029 ml, 0.592 mmol). After 10 min of stirring at rt, the reaction mixture was warmed to 60° C. for 2 h, then cooled to 0° C. in an ice bath. The resulting slurry was filtered, and the filtrate was concentrated in vacuo. The resulting solid was purified by flash chromatography (6% NH$_4$OH in methanol). LC-MS calculated for $C_{25}H_{32}N_7O_3$ (M+H)$^+$: m/z=478.2; found 478.3.

Step 5: tert-butyl (E)-(3-(5-carbamoyl-2-((4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)amino)-3-nitrophenoxy)propyl)carbamate

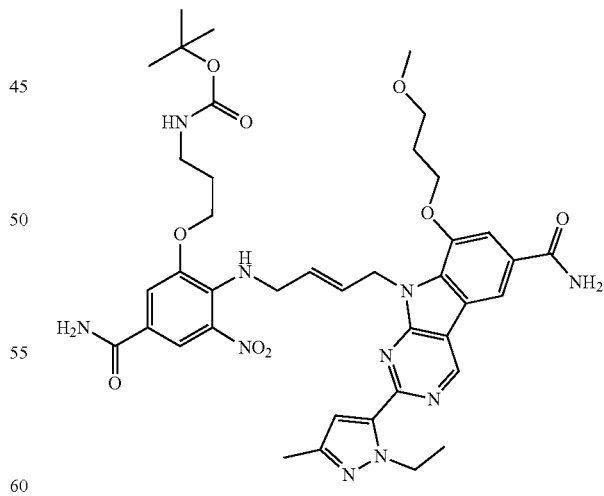

To a vial was added tert-butyl (3-(5-carbamoyl-2-chloro-3-nitrophenoxy)propyl)carbamate (0.121 g, 0.324 mmol), (E)-9-(4-aminobut-2-en-1-yl)-2-(1-ethyl-3-methyl-1H-pyrazol-5-yl)-8-(3-methoxypropoxy)-9H-pyrimido[4,5-b]indole-6-carboxamide (0.155 g, 0.324 mmol), EtOH (1.619 ml), and DIPEA (0.283 ml, 1.619 mmol). The mixture was sealed, then heated at 120° C. overnight with stirring. After cooling to rt, the mixture was concentrated under reduced pressure and purified by silica gel chromatography (15% MeOH/DCM). LC-MS calculated for $C_{40}H_{51}N_{10}O_9$ $(M+H)^+$: m/z=815.4; found 815.5.

Step 6: tert-butyl (E)-(3-(3-amino-5-carbamoyl-2-((4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)amino)phenoxy)propyl)carbamate

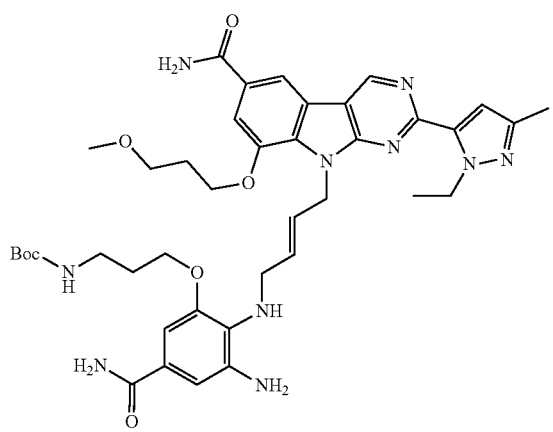 [SMILES: CCn1nc(C)cc1-c1ncc2c3cc(C(N)=O)cc(OCCCOC)c3n(C/C=C/CNc3c(N)cc(C(N)=O)cc3OCCCNC(=O)OC(C)(C)C)c2n1]

To a vial was added a stir bar, tert-butyl (E)-(3-(5-carbamoyl-2-((4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)amino)-3-nitrophenoxy)propyl)carbamate (0.040 g, 0.049 mmol), ammonium chloride (0.018 g, 0.344 mmol), and zinc (0.022 g, 0.344 mmol). 1,4-Dioxane (0.736 ml) and water (0.245 ml) were added and the mixture was stirred at rt for 10 min. The resulting mixture was filtered and extracted with $CHCl_3/IPA$ (3:1). The combined organic extracts were dried over $MgSO_4$, filtered, and concentrated in vacuo. The crude product was used directly in the next step without further purification. LC-MS calculated for $C_{40}H_{53}N_{10}O_7$ $(M+H)^+$: m/z=785.4; found 785.5.

Step 7: tert-butyl (E)-(3-((2-amino-5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-1H-benzo[d]imidazol-7-yl)oxy)propyl)carbamate

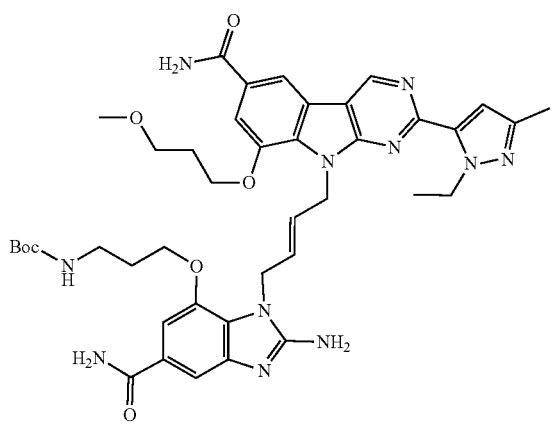 [SMILES: CCn1nc(C)cc1-c1ncc2c3cc(C(N)=O)cc(OCCCOC)c3n(C/C=C/Cn3c(N)nc4cc(C(N)=O)cc(OCCCNC(=O)OC(C)(C)C)c43)c2n1]

This compound was prepared using similar procedures as described for Example 1, Step 4 with tert-butyl (E)-(3-(3-amino-5-carbamoyl-2-((4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)amino)phenoxy)propyl)carbamate replacing tert-butyl (E)-(4-((2-amino-4-carbamoyl-6-methylphenyl)amino)but-2-en-1-yl)carbamate. LC-MS calculated for $C_{41}H_{52}N_{11}O_7$ $(M+H)^+$: m/z=810.4; found 810.4.

Step 8: tert-butyl (E)-(3-((5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propyl)carbamate

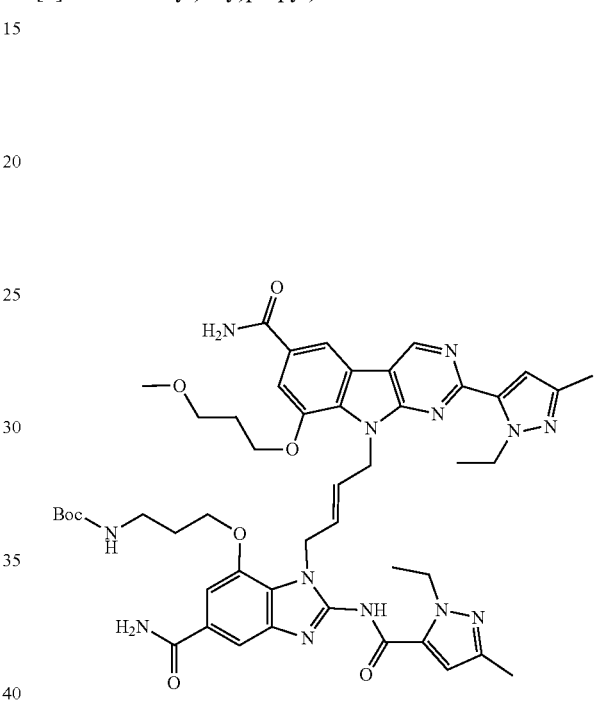

This compound was prepared using similar procedures as described for Example 15, Step 6 with tert-butyl (E)-(3-((2-amino-5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-1H-benzo[d]imidazol-7-yl)oxy)propyl)carbamate replacing tert-butyl (E)-(4-(2-amino-5-carbamoyl-7-(3-hydroxypropoxy)-1H-benzo[d]imidazol-1-yl)but-2-en-1-yl)carbamate. LC-MS calculated for $C_{48}H_{60}N_{13}O_8$ $(M+H)^+$: m/z=946.5; found 946.6.

Step 9: (E)-9-(4-(7-(3-aminopropoxy)-5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazol-5-yl)-8-(3-methoxypropoxy)-9H-pyrimido[4,5-b]indole-6-carboxamide To a solution of tert-butyl (E)-(3-((5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propyl)carbamate (0.050 g, 0.053 mmol) in 1,4-dioxane (0.528 ml) was added 4.0 M HCl in dioxane (0.132 ml, 0.528 mmol). The mixture was stirred for 15 min, then was diluted with MeCN/water and purified by prep HPLC (pH=2, MeCN/water+TFA) to provide the desired compound as the TFA salt. LC-MS calculated for $C_{43}H_{52}N_{13}O_6$ $(M+H)^+$: m/z=846.4; found 846.4.

Example 34. (E)-5-((3-((5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propyl)amino)-5-oxopentanoic acid

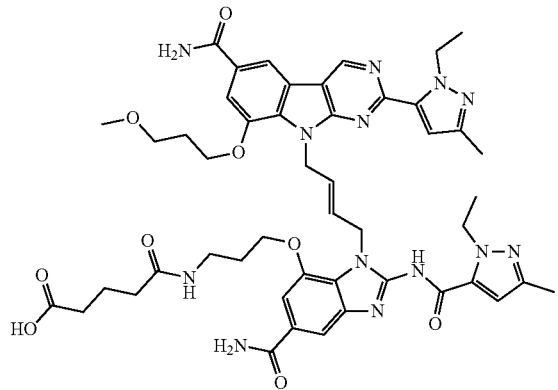 [SMILES: CCn1nc(C)cc1C(=O)Nc1nc2cc(C(N)=O)cc(OCCCNC(=O)CCCC(=O)O)c2n1C/C=C/Cn1c2nc(-c3cc(C)nn3CC)ncc2c2cc(C(N)=O)cc(OCCCOC)c21]

Step 1: methyl (E)-5-((3-((5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propyl)amino)-5-oxopentanoate

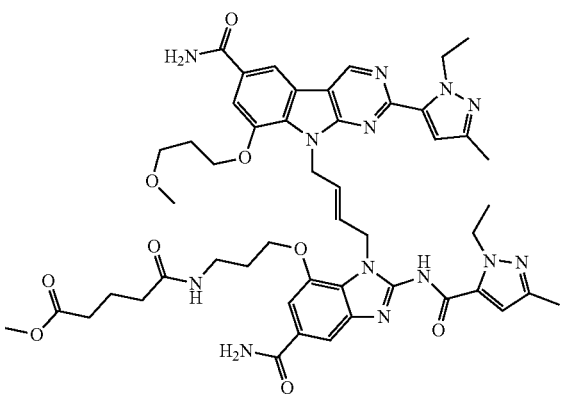

In a 1 dram vial, (E)-9-(4-(7-(3-aminopropoxy)-5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazol-5-yl)-8-(3-methoxypropoxy)-9H-pyrimido[4,5-b]indole-6-carboxamide (6 mg, 7.09 μmol) was dissolved in DMF (709 μl). Mono-methyl glutarate (Aldrich, cat #M47353: 2.67 μl, 0.021 mmol), DIPEA (3.72 μl, 0.021 mmol) and BOP (9.41 mg, 0.021 mmol) were added to the reaction mixture sequentially. After 15 min, the reaction mixture was concentrated to dryness and used directly in the next step without further purification. LC-MS calculated for $C_{49}H_{60}N_{13}O_9$ (M+H)$^+$: m/z=974.5; found 974.6.

Step 2: (E)-5-((3-((5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propyl)amino)-5-oxopentanoic acid In a 1 dram vial, methyl (E)-5-((3-((5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propyl)amino)-5-oxopentanoate (6.91 mg, 7.09 μmol) was dissolved in THF (0.140 ml), MeOH (0.071 ml), and 2.0 N LiOH (70.9 μl, 0.142 mmol). The mixture was stirred at rt for 15 min, then the reaction was diluted in MeCN/water and purified by prep HPLC (pH=2, MeCN/water+TFA) to provide the desired compound as the TFA salt. $^1$H NMR (600 MHz, DMSO) δ 12.78 (s, 1H), 9.48 (s, 1H), 8.41 (d, J=1.2 Hz, 1H), 8.04 (s, 1H), 7.92 (s, 1H), 7.79-7.64 (m, 1H), 7.61 (s, 1H), 7.56 (s, 1H), 7.35 (s, 1H), 7.31 (s, 1H), 7.23 (s, 1H), 6.79 (s, 1H), 6.41 (s, 1H), 5.86 (m, 1H), 5.74-5.68 (m, 1H), 5.27-5.24 (m, 2H), 4.89-4.87 (m, 2H), 4.63-4.58 (m, 2H), 4.46 (m, 2H), 4.04 (t, J=6.4 Hz, 2H), 3.89-3.84 (m, 2H), 3.31 (t, J=6.3 Hz, 2H), 3.15 (s, 3H), 2.97-2.93 (m, 2H), 2.19 (s, 3H), 2.15 (t, J=7.4 Hz, 2H), 2.07 (s, 3H), 2.02-1.97 (m, 2H), 1.78 (dt, J=12.3, 6.4 Hz, 2H), 1.63 (dt, J=14.8, 7.5 Hz, 2H), 1.53-1.45 (m, 2H), 1.27 (t, J=7.1 Hz, 3H), 1.20 (t, J=7.1 Hz, 3H). LC-MS calculated for $C_{48}H_{59}N_{13}O_9$ (M+2H)$^{2+}$: m/z=480.7; found 480.9.

Example 35. (E)-2-((5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)ethyl 1-ethyl-3-methyl-1H-pyrazole-5-carboxylate

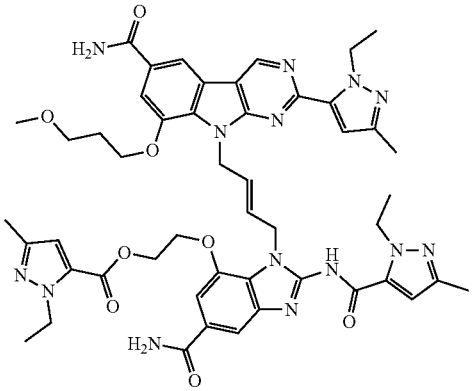

Step 1: 3-(2-((tert-butyldimethylsilyl)oxy)ethoxy)-4-chloro-5-nitrobenzamide

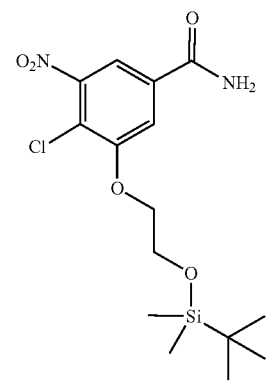 [SMILES: CC(C)(C)[Si](C)(C)OCCOc1cc(C(N)=O)cc([N+](=O)[O-])c1Cl]

This compound was prepared using similar procedures as described for Example 15, Step 2 with (2-bromoethoxy)(tert-butyl)dimethylsilane (Aldrich, cat #428426) replacing (3-bromopropoxy)(tert-butyl)dimethylsilane. LC-MS calculated for $C_{15}H_{24}ClN_2O_5Si$ (M+H)$^+$: m/z=375.1; found 375.3.

Step 2: tert-butyl (E)-(4-((2-(2-((tert-butyldimethylsilyl)oxy)ethoxy)-4-carbamoyl-6-nitrophenyl)amino)but-2-en-1-yl)carbamate

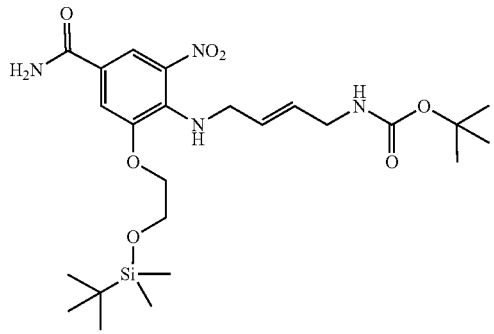 [SMILES: CC(C)(C)OC(=O)NC/C=C/CNc1c(OCCO[Si](C)(C)C(C)(C)C)cc(C(N)=O)cc1[N+](=O)[O-]]

This compound was prepared using similar procedures as described for Example 15, Step 3 with 3-(2-(((tert-butyldimethylsilyl)oxy)ethoxy)-4-chloro-5-nitrobenzamide replacing 3-(3-(((tert-butyldimethylsilyl)oxy)propoxy)-4-chloro-5-nitrobenzamide. LC-MS calculated for $C_{24}H_{40}N_4NaO_7Si$ (M+Na)$^+$: m/z=547.3; found 547.3.

Step 3: tert-butyl (E)-(4-((2-amino-6-(2-((tert-butyldimethylsilyoxy)ethoxy)-4-carbamoylphenyl)amino)but-2-en-1-yl)carbamate

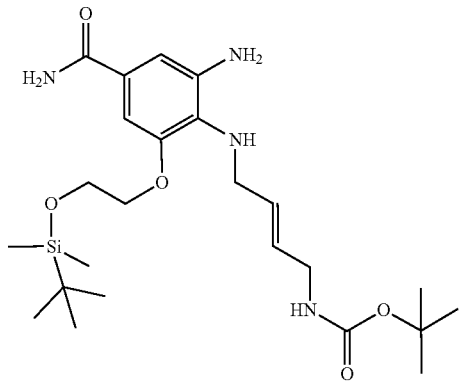 [SMILES: CC(C)(C)OC(=O)NC/C=C/CNc1c(N)cc(C(N)=O)cc1OCCO[Si](C)(C)C(C)(C)C]

This compound was prepared using similar procedures as described for Example 1, Step 3 with tert-butyl (E)-(4-((2-(2-((tert-butyldimethylsilyl)oxy)ethoxy)-4-carbamoyl-6-nitrophenyl)amino)but-2-en-1-yl)carbamate replacing tert-butyl (E)-(4-((4-carbamoyl-2-methyl-6-nitrophenyl)amino)but-2-en-1-yl)carbamate. LC-MS calculated for $C_{24}H_{43}N_4O_5Si$ (M+H)$^+$: m/z=495.3; found 495.4.

Step 4: tert-butyl (E)-(4-(2-amino-5-carbamoyl-7-(2-hydroxyethoxy)-1H-benzo[d]imidazol-1-yl)but-2-en-1-yl)carbamate

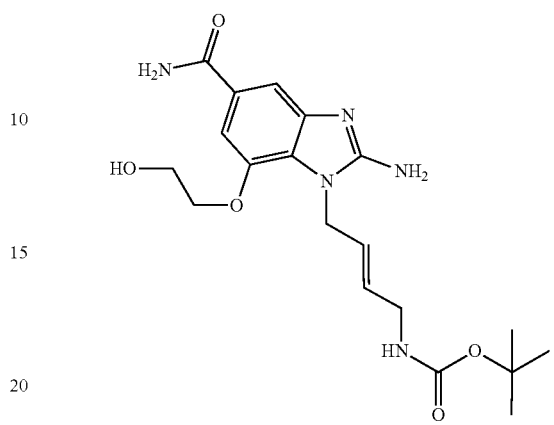

This compound was prepared using similar procedures as described for Example 1, Step 4 with tert-butyl (E)-(4-((2-amino-6-(2-((tert-butyldimethylsilyl)oxy)ethoxy)-4-carbamoylphenyl)amino)but-2-en-1-yl)carbamate replacing tert-butyl (E)-(4-((2-amino-4-carbamoyl-6-methylphenyl)amino)but-2-en-1-yl)carbamate. LC-MS calculated for $C_{19}H_{28}N_5O_5$ (M+H)$^+$: m/z=406.2; found 406.2.

Step 5: (E)-2-((1-(4-(((tert-butoxycarbonyl)amino)but-2-en-1-yl)-5-carbamoyl-2-(1-ethyl-3-methyl-1H-pyrazole-5-carboxamido)-1H-benzo[d]imidazol-7-yl)oxy)ethyl 1-ethyl-3-methyl-1H-pyrazole-5-carboxylate

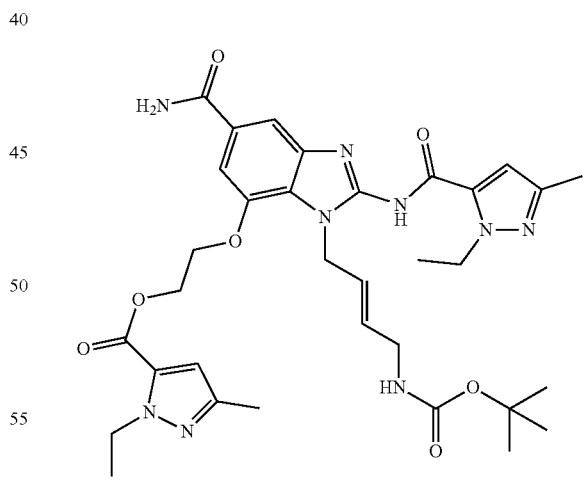

This compound was prepared using similar procedures as described for Example 15, Step 6 with tert-butyl (E)-(4-(2-amino-5-carbamoyl-7-(2-hydroxyethoxy)-1H-benzo[d]imidazol-1-yl)but-2-en-1-yl)carbamate replacing tert-butyl (E)-(4-(2-amino-5-carbamoyl-7-(3-hydroxypropoxy)-1H-benzo[d]imidazol-1-yl)but-2-en-1-yl)carbamate. LC-MS calculated for $C_{33}H_{44}N_9O_7$ (M+H)$^+$: m/z=678.3; found 678.4.

Step 6: (E)-2-((1-(4-aminobut-2-en-1-yl)-5-carbamoyl-2-(1-ethyl-3-methyl-1H-pyrazole-5-carboxamido)-1H-benzo[d]imidazol-7-yl)oxy)ethyl 1-ethyl-3-methyl-1H-pyrazole-5-carboxylate

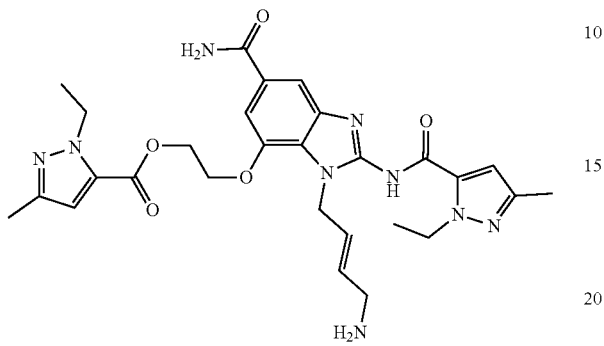

This compound was prepared using similar procedures as described for Example 1, Step 6 with (E)-2-((1-(4-((tert-butoxycarbonyl)amino)but-2-en-1-yl)-5-carbamoyl-2-(1-ethyl-3-methyl-1H-pyrazole-5-carboxamido)-1H-benzo[d]imidazol-7-yl)oxy)ethyl 1-ethyl-3-methyl-1H-pyrazole-5-carboxylate replacing tert-butyl (E)-(4-(5-carbamoyl-2-(1-ethyl-3 -methyl-1H-pyrazole-5-carboxamido)-7-methyl-1H-benzo[d]imidazol-1-yl)but-2-en-1-yl)carbamate.
LC-MS calculated for $C_{28}H_{36}N_9O_5$ $(M+H)^+$: m/z=578.3; found 578.2.

Step 7: (E)-2-((5-carbamoyl-2-(1-ethyl-3-methyl-1H-pyrazole-5-carboxamido)-1-(4-hydroxybut-2-en-1-yl)-1H-benzo[d]imidazol-7-yl)oxy)ethyl 1-ethyl-3-methyl-1H-pyrazole-5-carboxylate

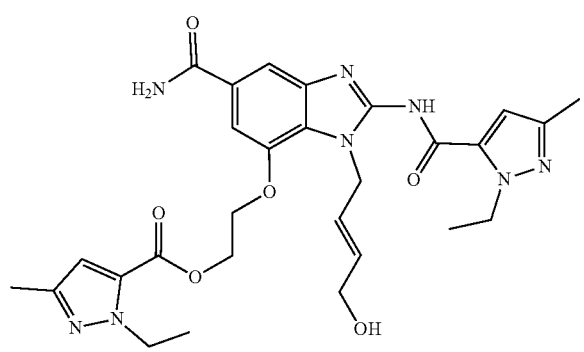

This compound was prepared using similar procedures as described for Example 1, Step 7 with (E)-2-((1-(4-aminobut-2-en-1-yl)-5-carbamoyl-2-(1-ethyl-3-methyl-1H-pyrazole-5-carboxamido)-1H-benzo[d]imidazol-7-yl)oxy)ethyl 1-ethyl-3-methyl-1H-pyrazole-5-carboxylate replacing (E)-1-(4-aminobut-2-en-1-yl)-2-(1-ethyl-3-methyl-1H-pyrazole-5-carboxamido)-7-methyl-1H-benzo[d]imidazole-5-carboxamide. LC-MS calculated for $C_{28}H_{35}N_8O_6$ $(M+H)^+$: m/z=579.3; found 579.3.

Step 8: (E)-2-((1-(4-bromobut-2-en-1-yl)-5-carbamoyl-2-(1-ethyl-3-methyl-1H-pyrazole-5-carboxamido)-1H-benzo[d]imidazol-7-yl)oxy)ethyl 1-ethyl-3-methyl-1H-pyrazole-5-carboxylate

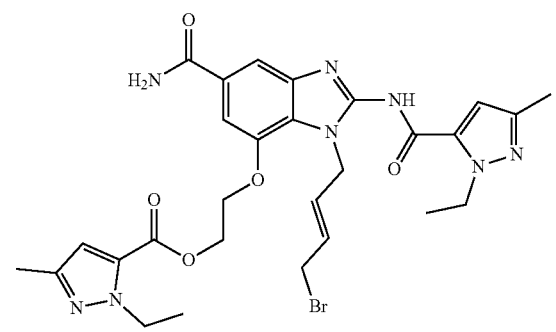

This compound was prepared using similar procedures as described for Example 1, Step 8 with (E)-2-(1-carbamoyl-2-(1-ethyl-3-methyl-1H-pyrazole-5-carboxamido)-1-(4-hydroxybut-2-en-1-yl)-1H-benzo[d]imidazol-7-yl)oxy)ethyl 1-ethyl-3-methyl-1H-pyrazole-5-carboxylate replacing (E)-2-(1-ethyl-3-methyl-1H-pyrazole-5-carboxamido)-1-(4-hydroxybut-2-enyl)-7-methyl-1H-benzo[d]imidazole-5-carboxamide. LC-MS calculated for $C_{28}H_{34}BrN_8O_5$ $(M+H)^+$: m/z=641.2/643.2; found 641.3/643.3.

Step 9: (E)-2-((5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)ethyl 1-ethyl-3-methyl-1H-pyrazole-5-carboxylate To a mixture of (E)-2-((1-(4-bromobut-2-en-1-yl)-5-carbamoyl-2-(1-ethyl-3-methyl-1H-pyrazole-5-carboxamido)-1H-benzo[d]imidazol-7-yl)oxy)ethyl 1-ethyl-3-methyl-1H-pyrazole-5-carboxylate (120 mg, 0.187 mmol) and 2-(1-ethyl-3-methyl-1H-pyrazol-5-yl)-8-(3-methoxypropoxy)-9H-pyrimido[4,5-b]indole-6-carboxamide (76 mg, 0.187 mmol) in DMF (1871 μl) was added DIPEA (98 μl, 0.561 mmol). After 5 min, Cs$_2$CO$_3$ (183 mg, 0.561 mmol) was added. The mixture was stirred at rt overnight. The reaction mixture was diluted with TFA/water, then purified by prep-HPLC (pH=2, acetonitrile/water+TFA) to give the desired product as the TFA salt. LC-MS calculated for $C_{49}H_{57}N_{14}O_8$ $(M+H)^+$: m/z=969.4; found 969.4.

Example 36. (E)-9-(4-(5-carbamoyl-2-(1-ethyl-3-methyl-1H-pyrazole-5-carboxamido)-7-(2-hydroxyethoxy)-1H-benzo[d]imidazol-1-yl)but-2-en-1-yl)-2-(1-ethyl-3-methyl-1H-pyrazol-5-yl)-8-(3-methoxypropoxy)-9H-pyrimido[4,5-b]indole-6-carboxamide

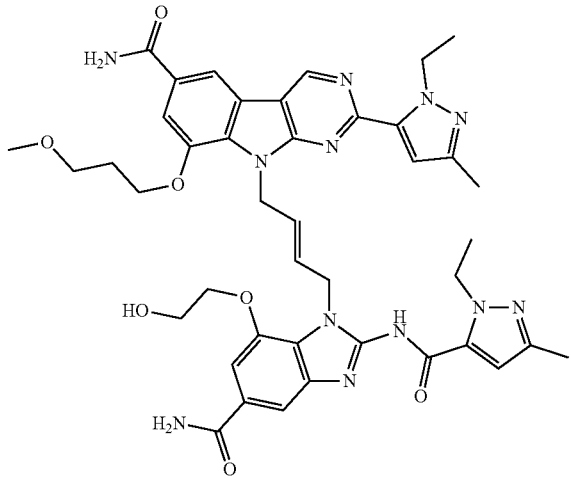

This compound was prepared using similar procedures as described for Example 32, Step 2 with (E)-2-((5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)ethyl 1-ethyl-3-methyl-1H-pyrazole-5-carboxylate (Example 35, Step 9) replacing (E)-3-((5-carbamoyl-1-(4-(6-carbamoyl-2-(1-ethyl-3-methyl-1H-pyrazol-5-yl)-3-fluoro-9H-pyrido[2,3-b]indol-9-yl)but-2-en-1-yl)-2-(1-ethyl-3-methyl-1H-pyrazole-5-carboxamido)-1H-benzo[d]imidazol-7-yl)oxy)propyl 1-ethyl-3-methyl-1H-pyrazole-5-carboxylate. $^1$H NMR (600 MHz, DMSO) δ 12.77 (s, 1H), 9.49 (s, 1H), 8.42 (m, 1H), 8.04 (s, 1H), 7.93 (s, 1H), 7.62 (s, 1H), 7.57 (s, 1H), 7.35 (s, 1H), 7.31 (s, 1H), 7.26 (s, 1H), 6.79 (s, 1H), 6.40 (s, 1H), 5.94 (m, 1H), 5.75-5.67 (m, 1H), 5.26 (d, J=4.8 Hz, 2H), 4.90 (d, J=5.6 Hz, 2H), 4.61 (dd, J=14.1, 7.0 Hz, 2H), 4.46 (d, J=6.5 Hz, 2H), 4.10-4.01 (m, 2H), 3.95-3.86 (m, 2H), 3.35 (m, 2H), 3.30 (m, 2H), 3.15 (d, J=4.9 Hz, 3H), 2.19 (s, 3H), 2.07 (s, 3H), 1.85-1.77 (m, 2H), 1.32-1.24 (m, 3H), 1.20 (t, J=7.1 Hz, 3H). LC-MS calculated for $C_{42}H_{49}N_{12}O_7$ (M+H)$^+$: m/z=833.4; found 833.4.

Example 37. (6S,9S,12S,15S)-15-amino-1-((5-carbamoyl-1-((E)-4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)-6,9-bis(carboxymethyl)-12-(3-guanidinopropyl)-5,8,11,14-tetraoxo-4,7,10,13-tetraazaheptadecan-17-oic acid

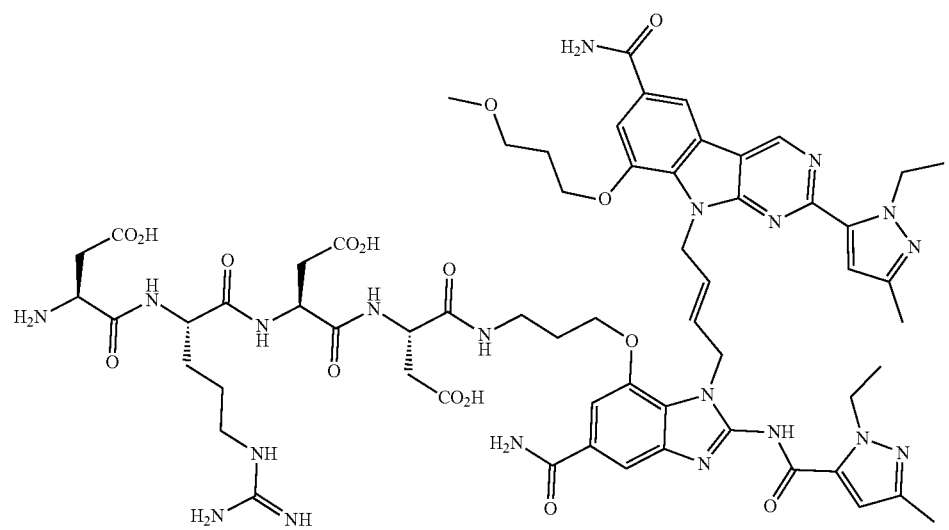 [SMILES: CCn1nc(C)cc1C(=O)Nc1nc2cc(C(N)=O)cc(OCCCNC(=O)[C@H](CC(=O)O)NC(=O)[C@H](CC(=O)O)NC(=O)[C@H](CCCNC(=N)N)NC(=O)[C@@H](N)CC(=O)O)c2n1C/C=C/Cn1c2nc(-c3cc(C)nn3CC)ncc2c2cc(C(N)=O)cc(OCCCOC)c21]

Step 1: tert-butyl (6S,9S,12S,15S)-15-amino-6,9-bis(2-(tert-butoxy)-2-oxoethyl)-1-((5-carbamoyl-1-((E)-4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)-5,8,11,14-tetraoxo-12-(3-(3-((2,2,4,6,7-pentamethyl-2,3-dihydrobenzofuran-5-yl)sulfonyl)guanidino)propyl)-4,7,10,13-tetraazaheptadecan-17-oate

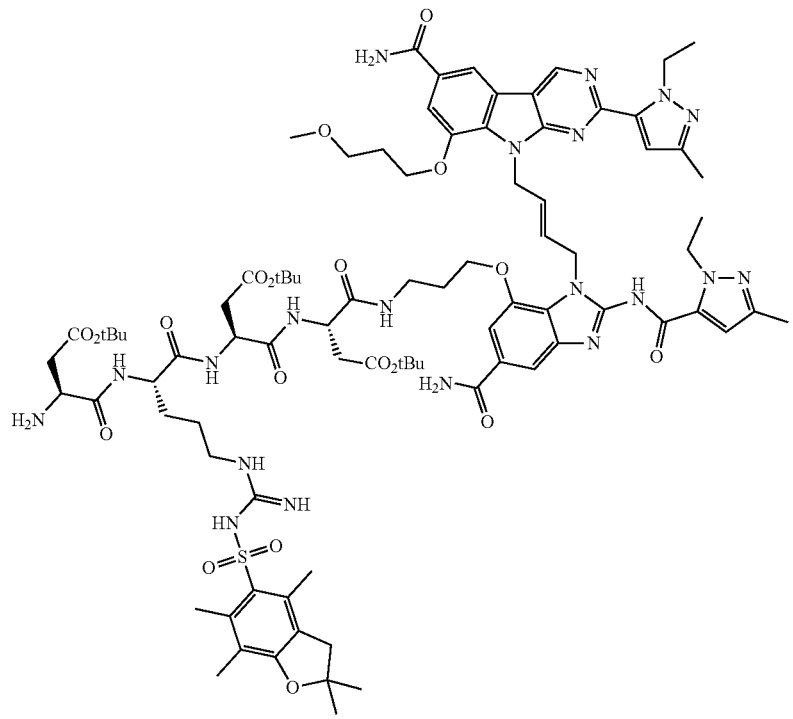 [SMILES: CCn1nc(C)cc1C(=O)Nc1nc2cc(C(N)=O)cc(OCCCNC(=O)[C@H](CC(=O)OC(C)(C)C)NC(=O)[C@H](CC(=O)OC(C)(C)C)NC(=O)[C@H](CCCNC(=N)NS(=O)(=O)c3c(C)c(C)c4c(c3C)CC(C)(C)O4)NC(=O)[C@@H](N)CC(=O)OC(C)(C)C)c2n1C/C=C/Cn1c2nc(-c3cc(C)nn3CC)ncc2c2cc(C(N)=O)cc(OCCCOC)c21]

In a 1 dram vial, (E)-9-(4-(7-(3-aminopropoxy)-5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazol-5-yl)-8-(3-methoxypropoxy)-9H-pyrimido[4,5-b]indole-6-carboxamide (Example 33, Step 9: 37 mg, 0.044 mmol) was dissolved in DMF (875 µl). Fmoc-Asp(OtBu)-Arg(Pbf)-Asp(OtBu)-Asp(OtBu)-OH (Peptides International, cat #PCS-33379-PI: 73.5 mg, 0.066 mmol), DIPEA (38.2 µl, 0.219 mmol) and BOP (38.7 mg, 0.087 mmol) were added to the reaction mixture sequentially. After stirring for 15 min, piperidine (0.1 mL) was added. After 30 min, the reaction mixture was diluted with MeOH then purified by prep-HPLC (pH=2, acetonitrile/water+TFA) to give the desired product as the TFA salt. LC-MS calculated for $C_{86}H_{120}O_{19}S$ (M+2H)$^{2+}$: m/z=884.4; found 884.5.

Step 2: (6S,9S,12S,15S)-15-amino-1-((5-carbamoyl-1-((E)-4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)-6,9-bis(carboxymethyl)-12-(3-guanidinopropyl)-5,8,11,14-tetraoxo-4,7,10,13-tetraazaheptadecan-17-oic acid Tert-butyl (6S,9S,12S,15S)-15-amino-6,9-bis(2-(tert-butoxy)-2-oxoethyl)-1-((5-carbamoyl-1-((E)-4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)-5,8,11,14-tetraoxo-12-(3-(3-((2,2,4,6,7-pentamethyl-2,3-dihydrobenzofuran-5-yl)sulfonyl)guanidino)propyl)-4,7,10,13-tetraazaheptadecan-17-oate (5 mg, 2.83 mop was stirred in TFA (0.5 mL) for 5 min. The reaction was diluted with MeCN then purified by prep HPLC (pH=2, MeCN/water+TFA) to provide the desired compound as the TFA salt. $^1$H NMR (600 MHz, DMSO) δ 12.78 (s, 1H), 9.48 (s, 1H), 8.59 (d, J=7.2 Hz, 1H), 8.41 (s, 1H), 8.26 (d, J=7.2 Hz, 1H), 8.18-8.06 (ovrlp m, 3H), 8.05 (s, 1H), 7.93 (s, 1H), 7.72 (m, 1H), 7.60 (s, 1H), 7.57 (s, 1H), 7.45 (s, 1H), 7.36 (s, 1H), 7.34 (s, 1H), 7.23 (s, 1H), 6.79 (s, 1H), 6.37 (s, 1H), 5.85 (m, 1H), 5.69 (m, 1H), 5.26 (s, 2H), 4.87 (s, 2H), 4.61 (m, 2H), 4.52 (dd, J=13.6, 7.4 Hz, 1H), 4.43 (ovrlp m, 4H), 4.27 (dd, J=13.6, 7.4 Hz, 1H), 4.12 (s, 1H), 4.09-4.00 (m, 2H), 3.89 (m, 2H), 3.31 (dd, J=6.3, 6.3 Hz, 2H), 3.15 (s, 3H), 3.10-3.00 (ovrlp m, 3H), 2.96 (m, 1H), 2.83 (dd, J=17.8, 3.3 Hz, 1H), 2.76-2.62 (ovrlp m, 2H), 2.567-2.50 (m, 3H), 2.20 (s, 3H), 2.06 (s, 3H), 1.83-1.73 (m, 2H), 1.65 (m, 1H), 1.55-1.42 (m, 4H), 1.33-1.24 (m, 3H), 1.21-1.16 (m, 3H). LC-MS calculated for $C_{61}H_{80}N_{20}O_{16}$ (M+2H)$^{2+}$: m/z=674.3; found 674.5.

181

Example 38. (E)-9-(4-(5-carbamoyl-2-(1-ethyl-3-methyl-1H-pyrazole-5-carboxamido)-7-(2-morpholinoethoxy)-1H-benzo[d]imidazol-1-yl)but-2-en-1-yl)-2-(1-ethyl-3-methyl-1H-pyrazol-5-yl)-8-(3-methoxypropoxy)-9H-pyrimido[4,5-b]indole-6-carboxamide

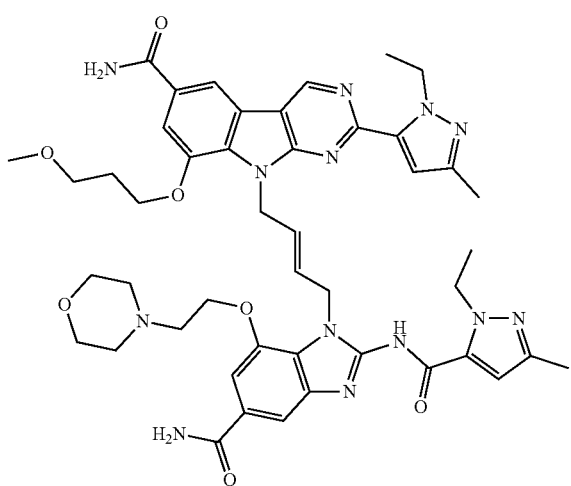

To a vial was added (E)-9-(4-(5-carbamoyl-2-(1-ethyl-3-methyl-1H-pyrazole-5-carboxamido)-7-(2-hydroxyethoxy)-1H-benzo[d]imidazol-1-yl)but-2-en-1-yl)-2-(1-ethyl-3-methyl-1H-pyrazol-5-yl)-8-(3-methoxypropoxy)-9H-pyrimido[4,5-b]indole-6-carboxamide (Example 36: 0.003 g, 3.60 µmol), DMF (0.360 ml), and a stir bar. The mixture was cooled to 0° C., and DMP (3.06 mg, 7.20 µmol) and water (0.519 µl, 0.029 mmol) were added. The mixture was warmed to rt and stirred overnight. To this mixture was then added morpholine (0.941 µl, 10.81 µmol), acetic acid (3.09 µl, 0.054 mmol), then sodium cyanoborohydride (0.453 mg, 7.20 µmol). After stirring for 15 min, the reaction was diluted with water/MeCN and purified by prep HPLC (pH=2, MeCN/water+TFA) to provide the desired compound as the TFA salt. LC-MS calculated for $C_{46}H_{57}N_{13}O_7$ $(M+2H)^{2+}$: m/z=451.7; found 451.7.

182

Example 39. (E)-3-(((3-((5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propyl)carbamoyl)oxy)propanoic acid

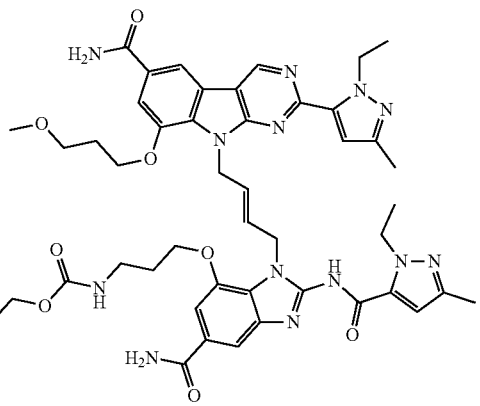

Step 1: tert-butyl 3-(((4-nitrophenoxy)carbonyl)oxy)propanoate

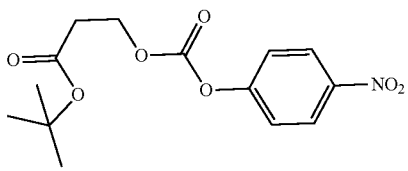 [SMILES: CC(C)(C)OC(=O)CCOC(=O)Oc1ccc([N+](=O)[O-])cc1]

To a solution of tert-butyl 3-hydroxypropanoate (Aldrich, cat #90218: 0.247 g, 1.69 mmol) and N-methylmorpholine (0.539 ml, 4.90 mmol) in dry THF (8.5 ml) was added 4-nitrophenyl carbonochloridate (Aldrich, cat #160210: 0.681 g, 3.38 mmol) at 0° C. and the resulting mixture was stirred at rt for 1 h. After completion of the reaction, the reaction was cooled to 0° C. and water was added. The aqueous phase was extracted with $CH_2Cl_2$. The organic extracts were dried over $MgSO_4$, filtered, and the solvent was removed. The crude mixture was purified by flash-chromatography (1:8 EtOAc/hexanes) to afford the desired product as an oil. LC-MS calculated for $C_{14}H_{17}NNaO_7$ $(M+Na)^+$: m/z=334.1; found 334.0.

Step 2: tert-butyl (E)-3-(((3-((5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propyl)carbamoyl)oxy)propanoate

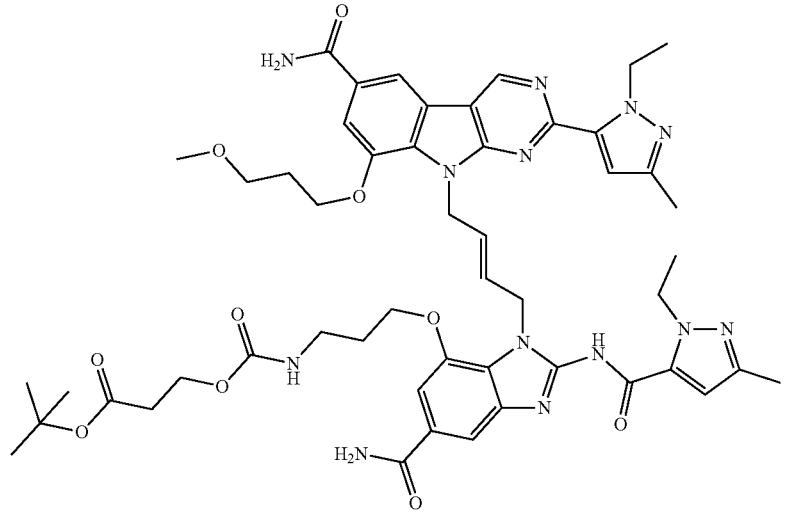 [SMILES: CCn1nc(C)cc1C(=O)Nc1nc2cc(C(N)=O)cc(OCCCNC(=O)OCCC(=O)OC(C)(C)C)c2n1C/C=C/Cn1c2nc(-c3cc(C)nn3CC)ncc2c2cc(C(N)=O)cc(OCCCOC)c21]

To a solution of (E)-9-(4-(7-(3-aminopropoxy)-5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazol-5-yl)-8-(3-methoxypropoxy)-9H-pyrimido[4,5-b]indole-6-carboxamide (Example 33, Step 9: 0.015 g, 0.018 mmol) in DMF (0.177 ml) was added DIPEA (9.29 0.053 mmol). After cooling to 0° C., tert-butyl 3-(((4-nitrophenoxy)carbonyl)oxy)propanoate (5.52 mg, 0.018 mmol) was added and the mixture was warmed to rt and stirred for 1 h. The mixture was cooled to 0° C. and quenched with water. The reaction was extracted with CHCl$_3$/IPA (3:1) and the combined organic layers were dried over MgSO$_4$, filtered, and concentrated under reduced pressure. The crude product was used directly in the next step without further purification. LC-MS calculated for C$_{51}$H$_{64}$N$_{13}$O$_{10}$ (M+H)$^+$: m/z=1018.5; found 1018.6.

Step 3: (E)-3-(((3-((5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propyl)carbamoyl)oxy)propanoic acid This compound was prepared using similar procedures as described for Example 37, Step 2 with tert-butyl (E)-3-(((3-((5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propyl)carbamoyl)oxy)propanoate replacing tert-butyl (6S,9S,12S,15S)-15-amino-6,9-bis(2-(tert-butoxy)-2-oxoethyl)-1-((5-carbamoyl-14(E)-4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)-5,8,11,14-tetraoxo-12-(3-(3-((2,2,4,6,7-pentamethyl-2,3-dihydrobenzofuran-5-yl)sulfonyl)guanidino)propyl)-4,7,10,13-tetraazaheptadecan-17-oate. $^1$H NMR (600 MHz, DMSO) δ 12.78 (s, 1H), 9.47 (s, 1H), 8.41 (d, J=1.2 Hz, 1H), 8.03 (s, 1H), 7.93 (s, 1H), 7.62 (s, 1H), 7.56 (d, J=1.2 Hz, 1H), 7.35 (s, 1H), 7.31 (s, 1H), 7.24 (d, J=0.6 Hz, 1H), 7.10 (t, J=5.7 Hz, 1H), 6.79 (s, 1H), 6.40 (s, 1H), 5.85 (m, 1H), 5.72 (dt, J=15.6, 5.4 Hz, 1H), 5.25 (d, J=4.8 Hz, 2H), 4.87 (d, J=5.4 Hz, 2H), 4.61 (q, J=6.9 Hz, 2H), 4.45 (1, J=6.9 Hz, 2H), 4.03 (ovrlp dt, J=11.4, 6.6 Hz, 4H), 3.88 (t, J=6.3 Hz, 2H), 3.31 (t, J=6.0 Hz, 2H), 3.15 (s, 3H), 2.89 (m, 2H), 2.46 (t, J=6.0 Hz, 2H), 2.19 (s, 3H), 2.07 (s, 3H), 1.78 (dt, J=12.6, 6.3 Hz, 2H), 1.52 (dt, J=12.6, 6.3 Hz, 2H), 1.27 (t, J=6.9 Hz, 3H), 1.20 (t, J=6.9 Hz, 3H). LC-MS calculated for C$_{47}$H$_{57}$N$_{13}$O$_{10}$ (M+2H)$^{2+}$: m/z=481.7; found 481.5.

Example 40. (E)-2-(((3-((5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propyl)carbamoyl)oxy)acetic acid

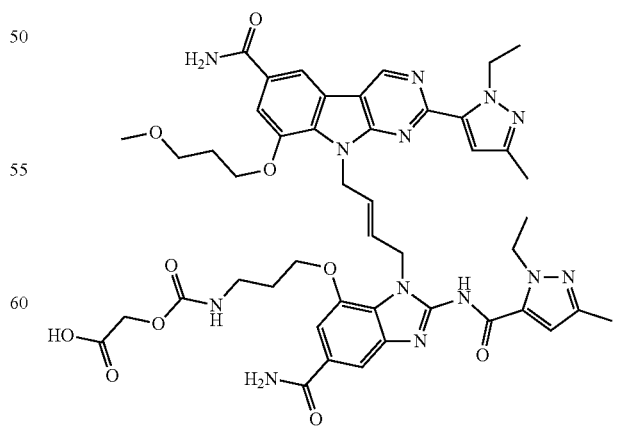

Step 1: methyl 2-(((4-nitrophenoxy)carbonyl)oxy)acetate

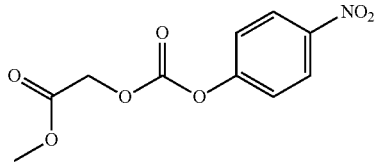 [SMILES: COC(=O)COC(=O)Oc1ccc([N+](=O)[O-])cc1]

This compound was prepared using similar procedures as described for Example 39, Step 1 with methyl 2-hydroxyacetate (Aldrich, cat #325260) replacing 3-hydroxypropanoate. The crude product was purified using silica gel chromatography (0-24% EtOAc/hexanes) to provide the desired compound as an oil. LC-MS calculated for $C_{10}H_{10}NO_7$ (M+H)$^+$: m/z=256.0; found 256.1.

Step 2: methyl (E)-2-(((3-((5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propyl)carbamoyl)oxy)acetate

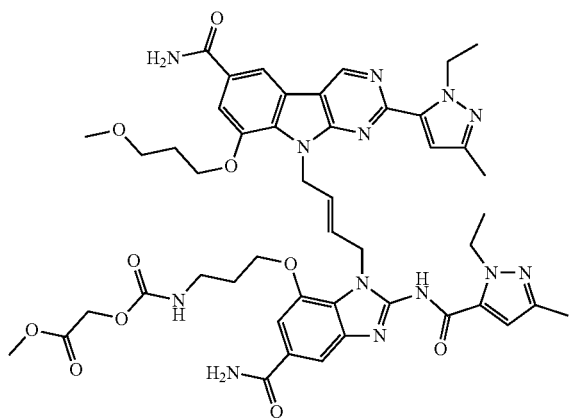

This compound was prepared using similar procedures as described for Example 39, Step 2 with methyl 2-(((4-nitrophenoxy)carbonyl)oxy)acetate replacing tert-butyl 3-(((4-nitrophenoxy)carbonyl)oxy)propanoate. LC-MS calculated for $C_{47}H_{56}N_{13}O_{10}$ (M+H)$^+$: m/z=962.4; found 962.5.

Step 3: (E)-2-(((3-((5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propyl)carbamoyl)oxy)acetic acid This compound was prepared using similar procedures as described for Example 34, Step 2 with methyl (E)-2-(((3-((5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propyl)carbamoyl)oxy)acetate replacing methyl (E)-5-((3-((5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propyl)amino)-5-oxopentanoate. $^1$H NMR (600 MHz, DMSO) δ 12.77 (s, 1H), 9.47 (s, 1H), 8.41 (d, J=1.2 Hz, 1H), 8.02 (s, 1H), 7.93 (s, 1H), 7.61 (s, 1H), 7.57 (s, 1H), 7.37-7.29 (ovrlp m, 2H), 7.24 (s, 1H), 6.79 (s, 1H), 6.39 (s, 1H), 5.85 (m, 1H), 5.74-5.67 (m, 1H), 5.25 (d, J=4.2 Hz, 2H), 4.87 (d, J=4.2 Hz, 2H), 4.61 (q, J=7.2 Hz, 2H), 4.48-4.41 (m, 2H), 4.36 (s, 2H), 4.05 (t, J=5.7 Hz, 2H), 3.90 (t, J=5.7 Hz, 2H), 3.31 (t, J=5.7 Hz, 2H), 3.15 (s, 3H), 2.92 (m, 3H), 2.19 (s, 3H), 2.07 (s, 2H), 1.78 (tt, J=5.7, 5.7 Hz, 2H), 1.56-1.50 (m, 2H), 1.26 (t, J=7.2 Hz, 3H), 1.19 (t, J=7.2 Hz, 3H). LC-MS calculated for $C_{46}H_{55}N_{13}O_{10}$ (M+2H)$^{2+}$: m/z=474.7; found 474.8.

Example 41. (E)-((3-((5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propyl)carbamoyl)glycine

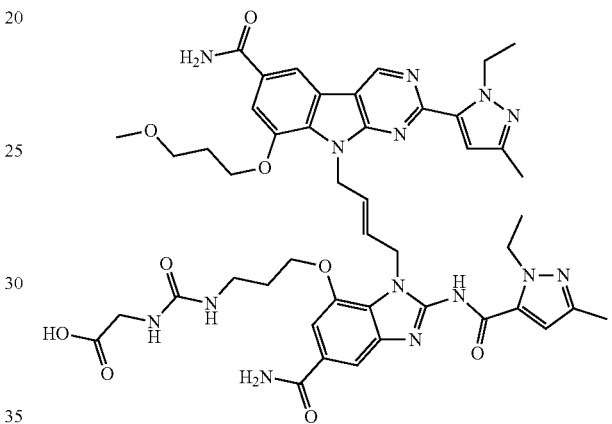

To a vial was added (E)-9-(4-(7-(3-aminopropoxy)-5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazol-5-yl)-8-(3-methoxypropoxy)-9H-pyrimido[4,5-b]indole-6-carboxamide (Example 33, Step 9: 0.015 g, 0.018 mmol), DIPEA (9.29 μl, 0.053 mmol), then ethyl 2-isocyanatoacetate (Aldrich, cat #238627: 2.98 μl, 0.027 mmol). The mixture was stirred at rt overnight, and then was concentrated under reduced pressure. To the resulting crude mixture was added THF (0.180 ml, 2.199 mmol), MeOH (0.089 ml, 2.199 mmol), and aqueous 2 M LiOH (0.089 ml, 0.177 mmol). The mixture was stirred for 15 min at rt and was then diluted with water and purified by prep HPLC (pH=2, MeCN/water+TFA) to provide the desired product as the TFA salt. $^1$H NMR (600 MHz, DMSO) δ 12.77 (s, 1H), 9.48 (s, 1H), 8.41 (d, J=1.5Hz, 1H), 8.04 (s, 1H), 7.93 (s, 1H), 7.61 (s, 1H), 7.57 (d, J=1.5 Hz, 1H), 7.35 (s, 1H), 7.31 (s, 1H), 7.25 (s, 1H), 6.79 (s, 1H), 6.39 (s, 1H), 6.13 (t, J=6.0 Hz, 1H), 5.99 (t, J=5.4 Hz, 1H), 5.86 (m, 1H), 5.73-5.67 (m, 1H), 5.26 (d, J=4.8 Hz, 2H), 4.87 (d, J=4.8 Hz, 2H), 4.60 (q, J=7.2 Hz, 2H), 4.45 (br q, J=6.9 Hz, 2H), 4.05 (t, J=6.6 Hz, 2H), 3.88 (t, J=6.0 Hz, 2H), 3.64 (d, J=5.4 Hz, 11H), 3.27 (t, J=6.0 Hz, 2H), 3.15 (s, 3H), 2.94 (m, 2H), 2.19 (s, 3H), 2.07 (s, 3H), 1.78 (tt, J=6.6, 6.0 Hz, 2H), 1.49 (tt, J=6.0, 6.0 Hz, 2H), 1.26 (t, J=7.2 Hz, 3H), 1.19 (t, J=6.9 Hz, 3H). LC-MS calculated for $C_{46}H_{55}N_{14}O_9$ (M+H)$^+$: m/z=947.4; found 947.4.

Example 42

(S,E)-3-amino-4-((3-((5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propyl)amino)-4-oxobutanoic acid

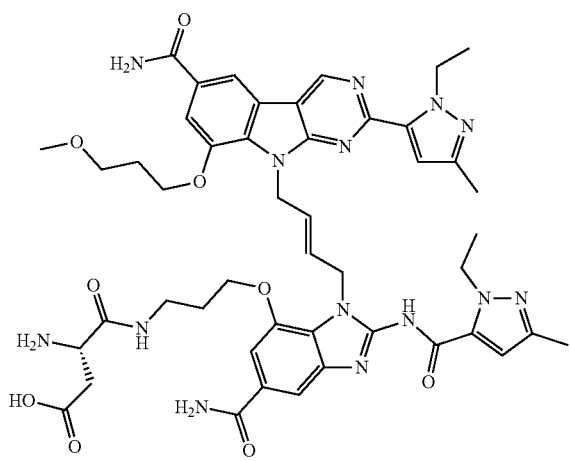 [SMILES: CCn1nc(C)cc1C(=O)Nc1nc2cc(C(N)=O)cc(OCCCNC(=O)[C@@H](N)CC(=O)O)c2n1C/C=C/Cn1c2nc(-c3cc(C)nn3CC)ncc2c2cc(C(N)=O)cc(OCCCOC)c21]

Step 1: methyl (S,E)-3-amino-4-((3-((5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propyl)amino)-4-oxobutanoate

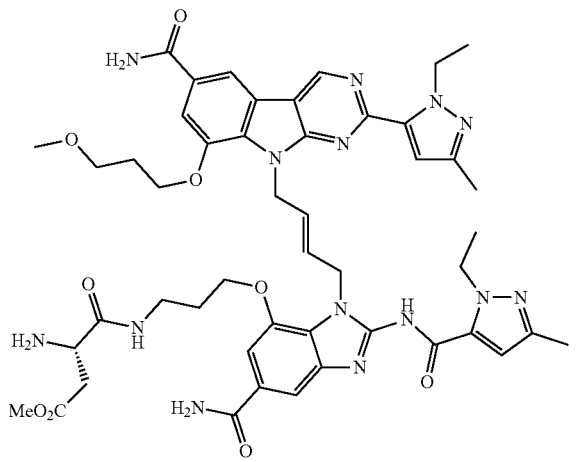

In a 1 dram vial, (E)-9-(4-(7-(3-aminopropoxy)-5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazol-5-yl)-8-(3-methoxypropoxy)-9H-pyrimido[4,5-b]indole-6-carboxamide (Example 33, Step 9: 10 mg, 0.012 mmol) was dissolved in DMF (236 µl). (S)-2-((((9H-fluoren-9-yl)methoxy)carbonyl)amino)-4-methoxy-4-oxobutanoic acid (Aurum Pharmatech, cat #B-7268: 8.73 mg, 0.024 mmol), DIPEA (10.32 µl, 0.059 mmol) and BOP (10.46 mg, 0.024 mmol) were added to the reaction mixture sequentially. After 15 min, piperidine (0.1 mL) was added. After 1 h, the reaction mixture was diluted with MeOH then purified by prep-HPLC (pH=2, acetonitrile/water+TFA) to give the desired product as the TFA salt. LC-MS calculated for $C_{48}H_{60}N_{14}O_9$ $(M+2H)^{2+}$: m/z=488.2; found 488.5.

Step 2: (S,E)-3-amino-4-((3-((5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propyl)amino)-4-oxobutanoic acid This compound was prepared using similar procedures as described for Example 34, Step 2 with methyl (S,E)-3-amino-4-((3-((5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propyl)amino)-4-oxobutanoate replacing methyl (E)-5-((3-((5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propyl)amino)-5-oxopentanoate. LC-MS calculated for $C_{47}H_{58}N_{14}O_9$ $(M+2H)^{2+}$: m/z=481.2; found 481.3.

Example 43. (E)-3-(((3-((5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propoxy)carbonyl)amino)propanoic acid

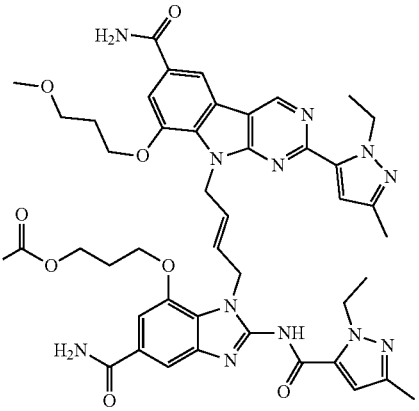

Step 1: tert-butyl (E)-(4-(5-carbamoyl-2-(1-ethyl-3-methyl-1H-pyrazole-5-carboxamido)-7-(3-hydroxypropoxy)-1H-benzo[d]imidazol-1-yl)but-2-en-1-yl)carbamate

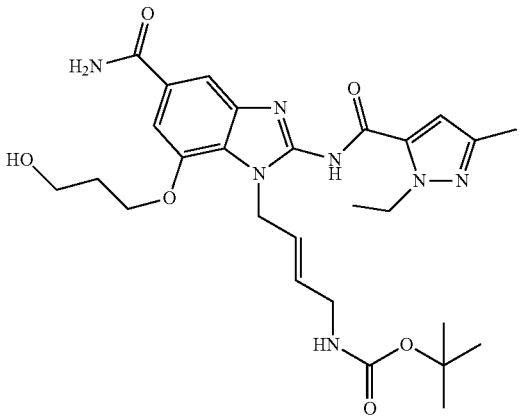 [SMILES: CCn1nc(C)cc1C(=O)Nc1nc2cc(C(N)=O)cc(OCCCO)c2n1C/C=C/CNC(=O)OC(C)(C)C]

To a solution of (E)-3-((1-(4-((tert-butoxycarbonyl)amino)but-2-en-1-yl)-5-carbamoyl-2-(1-ethyl-3-methyl-1H-pyrazole-5-carboxamido)-1H-benzo[d]imidazol-7-yl)oxy)propyl 1-ethyl-3-methyl-1H-pyrazole-5-carboxylate (Example 15, Step 6: 0.406 g, 0.587 mmol) in THF (1.956 ml) and MeOH (0.978 ml) was added 2 M LiOH (0.880 ml, 1.761 mmol). The reaction was stirred at rt for 15 min, then water and DCM were added and the layers were separated. The aqueous layer was further extracted with DCM, and the combined organic layers were dried over MgSO$_4$, filtered, and concentrated under reduced pressure. The crude product was used directly in the next step without further purification. LC-MS calculated for $C_{27}H_{38}N_7O_6$ (M+H)$^+$: m/z=556.3; found 556.5.

Step 2: ethyl (E)-3-(((3-((1-(4-((tert-butoxycarbonyl)amino)but-2-en-1-yl)-5-carbamoyl-2-(1-ethyl-3-methyl-1H-pyrazole-5-carboxamido)-1H-benzo[d]imidazol-7-yl)oxy)propoxy)carbonyl)amino)propanoate

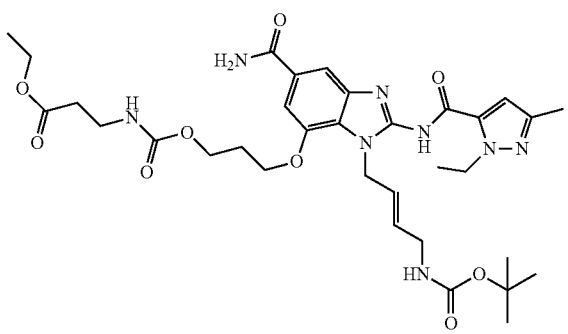 [SMILES: CCOC(=O)CCNC(=O)OCCCOc1cc(C(N)=O)cc2nc(NC(=O)c3cc(C)nn3CC)n(C/C=C/CNC(=O)OC(C)(C)C)c12]

To a solution of tert-butyl (E)-(4-(5-carbamoyl-2-(1-ethyl-3-methyl-1H-pyrazole-5-carboxamido)-7-(3-hydroxypropoxy)-1H-benzo[d]imidazol-1-yl)but-2-en-1-yl)carbamate (0.050 g, 0.090 mmol) and DIPEA (0.024 ml, 0.135 mmol) in THF (0.900 ml) was added ethyl 3-isocyanatopropionate (Aldrich, cat #479012: 0.012 ml, 0.090 mmol). The reaction was stirred at 70° C. overnight. After cooling to rt, the reaction was diulted with water and CHCl$_3$/IPA (3:1), and the layers were separated. The aqueous layer was further extracted and the combined organic extracts were dried over MgSO$_4$, filtered, and concentrated under reduced pressure. The crude product was purified by silica gel chromatography (30% MeOH/DCM). LC-MS calculated for $C_{33}H_{47}N_8O_9$ (M+H)$^+$: m/z=699.3; found 699.7.

Step 3: ethyl (E)-3-(((3-((1-(4-aminobut-2-en-1-yl)-5-carbamoyl-2-(1-ethyl-3-methyl-1H-pyrazole-5-carboxamido)-1H-benzo[d]imidazol-7-yl)oxy)propoxy)carbonyl)amino)propanoate

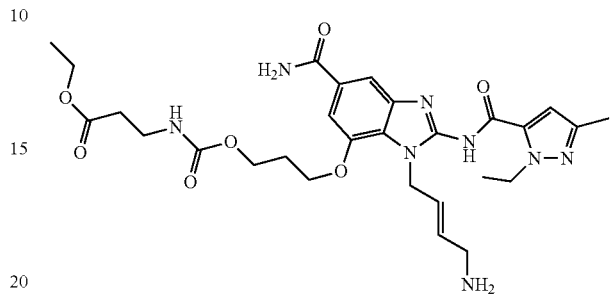

To a solution of ethyl (E)-3-(((3-((1-(4-((tert-butoxycarbonyl)amino)but-2-en-1-yl)-5-carbamoyl-2-(1-ethyl-3-methyl-1H-pyrazole-5-carboxamido)-1H-benzo[d]imidazol-7-yl)oxy)propoxy)carbonyl)amino)propanoate (0.066 g, 0.094 mmol) in dioxane (0.945 ml) was added 4 M HCl in dioxane (0.236 ml, 0.945 mmol). The reaction was stirred for 1 h, then was concentrated under reduced pressure and used directly in the next step without further purification. LC-MS calculated for $C_{28}H_{39}N_8O_7$ (M+H)$^+$: m/z=599.3; found 599.3.

Step 4: ethyl (E)-3-(((3-((5-carbamoyl-2-(1-ethyl-3-methyl-1H-pyrazole-5-carboxamido)-1-(4-hydroxybut-2-en-1-yl)-1H-benzo[d]imidazol-7-yl)oxy)propoxy)carbonyl)amino)propanoate

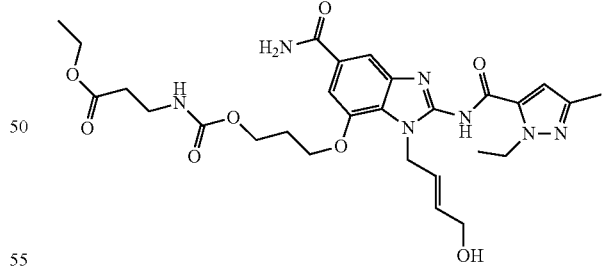

This compound was prepared using similar procedures as described for Example 1, Step 7 with ethyl (E)-3-(((3-((1-(4-aminobut-2-en-1-yl)-5-carbamoyl-2-(1-ethyl-3-methyl-1H-pyrazole-5 -carboxamido)-1H-benzo[d]imidazol-7-yl)oxy)propoxy)carbonyl)amino)propanoate replacing (E)-1-(4-aminobut-2-en-1-yl)-2-(1-ethyl-3-methyl-1H-pyrazole-5-carboxamido)-7-methyl-1H-benzo[d]imidazole-5-carboxamide. The crude product was purified using silica gel chromatography (20% MeOH/DCM). LC-MS calculated for $C_{28}H_{38}N_7O_8$ (M+H)$^+$: m/z=600.3; found 600.3.

Step 5: ethyl (E)-3-(((3-((5-carbamoyl-2-(1-ethyl-3-methyl-1H-pyrazole-5-carboxamido)-1-(4-((methylsulfonyl)oxy)but-2-en-1-yl)-1H-benzo[d]imidazol-7-yl)oxy)propoxy)carbonyl)amino)propanoate

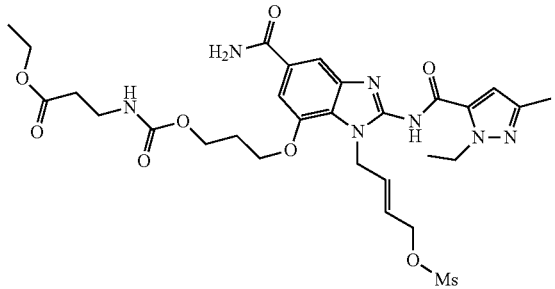 [SMILES: CCOC(=O)CCNC(=O)OCCCOc1cc(C(N)=O)cc2nc(NC(=O)c3cc(C)nn3CC)n(C/C=C/COS(C)(=O)=O)c12]

To a vial was added ethyl (E)-3-(((3-((5-carbamoyl-2-(1-ethyl-3-methyl-1H-pyrazole-5-carboxamido)-1-(4-hydroxybut-2-en-1-yl)-1H-benzo[d]imidazol-7-yl)oxy)propoxy)carbonyl)amino)propanoate (0.028 g, 0.047 mmol), THF (0.467 ml), Et$_3$N (9.76 0.070 mmol), then Ms-Cl (4.37 μl, 0.056 mmol). After stirring at rt for 1 h, the reaction was quenched with aqueous saturated sodium bicarbonate, and extracted with CHCl$_3$/IPA (3:1). The combined organic layers were dried over MgSO$_4$, filtered, and concentrated under reduced pressure. The crude product was used directly in the next step without further purification. LC-MS calculated for $C_{29}H_{40}N_7O_{10}S$ (M+H)$^+$: m/z=678.3; found 678.3.

Step 6: ethyl (E)-3-(((3-((5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propoxy)carbonyl)amino)propanoate

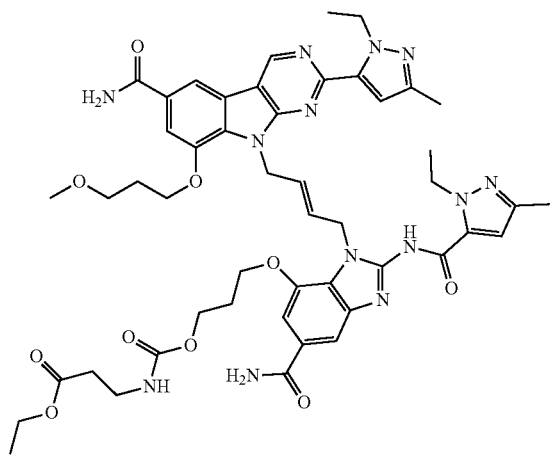 [SMILES: CCOC(=O)CCNC(=O)OCCCOc1cc(C(N)=O)cc2nc(NC(=O)c3cc(C)nn3CC)n(C/C=C/Cn3c4nc(-c5cc(C)nn5CC)ncc4c4cc(C(N)=O)cc(OCCCOC)c43)c12]

To a solution of ethyl (E)-3-(((3-((5-carbamoyl-2-(1-ethyl-3-methyl-1H-pyrazole-5-carboxamido)-1-(4-((methylsulfonyl)oxy)but-2-en-1-yl)-1H-benzo[d]imidazol-7-yl)oxy)propoxy)carbonyl)amino)propanoate (0.030 g, 0.044 mmol) in DMF (0.443 ml) was added 2-(1-ethyl-3-methyl-1H-pyrazol-5-yl)-8-(3-methoxypropoxy)-9H-pyrimido[4,5-b]indole-6-carboxamide (Example 12, Step 3: 0.018 g, 0.044 mmol) and cesium carbonate (0.043 g, 0.133 mmol). The mixture was stirred for 3 h at rt, and was then diluted with water. The mixture was extracted with CHCl$_3$/IPA (3:1) and the combined organic extracts were dried over MgSO$_4$, filtered, and concentrated under reduced pressure. The crude product was used directly in the next step without further purification. LC-MS calculated for $C_{49}H_{60}N_{13}O_{10}$ (M+H)$^+$: m/z=990.4; found 990.0.

Step 7: (E)-3-(((3-((5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propoxy)carbonyl)amino)propanoic acid To a solution of ethyl (E)-3-(((3-((5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propoxy)carbonyl)amino)propanoate was added THF (0.440 mL), MeOH (0.221 mL) and aqueous 2 M LiOH (0.221 ml, 0.443 mmol). After stirring 15 min at rt, the mixture was diluted with water, and purified by prep HPLC (pH=2, MeCN/water+TFA) to provide the desired compound as the TFA salt. LC-MS calculated for $C_{47}H_{56}N_{13}O_{10}$ (M+H)$^+$: m/z=962.4; found 962.4.

Example 44. (E)-3-(2-(2-((5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)ethoxy)ethoxy)propanoic acid

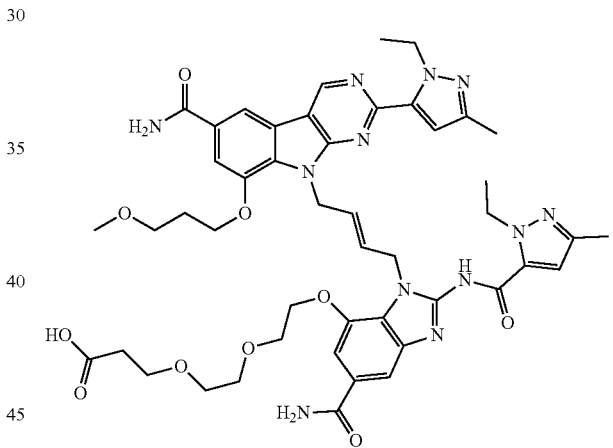

Step 1: tert-butyl 3-(2-(2-(5-carbamoyl-2-chloro-3-nitrophenoxy)ethoxy)ethoxy)propanoate

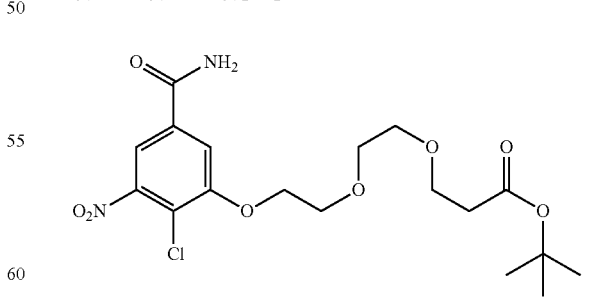

To a suspension of 4-chloro-3-hydroxy-5-nitrobenzamide (0.200 g, 0.923 mmol), and cesium carbonate (0.451 g, 1.385 mmol) in DMF (2.309 ml) was added tert-butyl 3-(2-(2-bromoethoxy)ethoxy)propanoate (Combi-Blocks, cat #QD-1308: 0.329 g, 1.108 mmol). After stirring at 50° C.

for 4 h, the reaction was diluted with water and DCM, and the layers were separated. The aqueous layer was further extracted with DCM, and the combined organic layers were dried over MgSO$_4$, filtered, and concentrated under reduced pressure. The resulting crude oil was purified by silica gel chromatography (5% MeOH/DCM). LC-MS calculated for C$_{18}$H$_{25}$ClN$_2$NaO$_8$ (M+Na)$^+$: m/z=455.1; found 455.1.

Step 2: (E)-2-(4-hydroxybut-2-en-1-yl)isoindoline-1,3-dione

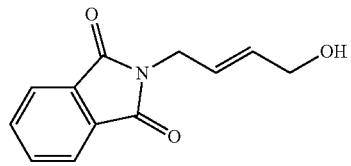 [SMILES: O=C1c2ccccc2C(=O)N1C/C=C/CO]

To a solution of (E)-but-2-ene-1,4-diol (Astatech, cat #70835: 1.198 g, 13.59 mmol) in tetrahydrofuran (34.0 ml) was added triphenylphosphine (3.57 g, 13.59 mmol). After cooling to 0° C., isoindoline-1,3-dione (1.0 g, 6.80 mmol) was added. A 40% wt/v solution of DEAD (5.92 ml, 13.59 mmol) in toluene was added dropwise and the reaction was warmed up to rt with stirring for 1 h. The reaction was concentrated and purified by silica gel column to provide the desired product (0->5% MeOH/DCM). LC-MS calculated for C$_{12}$H$_{12}$NO$_3$ (M+H)$^+$: m/z=218.1; found 218.1.

Step 3: (E)-2-(4-((tert-butyldimethylsilyl)oxy)but-2-en-1-yl)isoindoline-1,3-dione

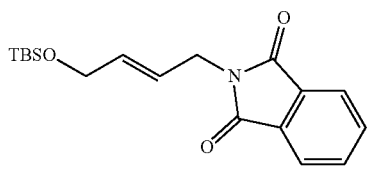 [SMILES: CC(C)(C)[Si](C)(C)OC/C=C/CN1C(=O)c2ccccc2C1=O]

To a mixture of (E)-2-(4-hydroxybut-2-en-1-yl)isoindoline-1,3-dione (1.5 g, 6.91 mmol) and Et$_3$N (1.444 ml, 10.36 mmol) in DCM (69.1 ml) was added TBS-Cl (1.249 g, 8.29 mmol). The mixture was stirred at rt for 16 h and was then concentrated under reduced pressure. Saturated aqueous NaHCO$_3$ was added to the reaction mixture followed by extraction with dichloromethane (3 times). The combined organic layers were dried over Na$_2$SO$_4$, filtered and concentrated. The crude product was added to a silica gel column and was eluted with ethyl acetate/hexane from 0% to 40% to give (E)-2-(4-((tert-butyldimethylsilyl)oxy)but-2-en-1-yl)isoindoline-1,3-dione (2.03 g, 6.12 mmol, 89% yield) as a colorless oil. LC-MS calculated for C$_{18}$H$_{27}$NO$_4$Si (M+NH$_4$)$^+$: m/z=349.2; found 349.3.

Step 4: (E)-4-((tert-butyldimethylsilyl)oxy)but-2-en-1-amine

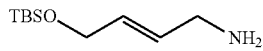

To a solution of (E)-2-(4-((tert-butyldimethylsilyl)oxy)but-2-en-1-yl)isoindoline-1,3-dione (2.02 g, 6.09 mmol) in DCM (30.5 ml) and MeOH (30.5 ml) was added hydrazine monohydrate (4.43 ml, 91 mmol). After heating for 2 h at 40° C., the mixture was filtered to remove the precipitated phthalhydrazide. The filtrate was washed with aqueous saturated NaHCO$_3$ and dried over MgSO$_4$, filtered and concentrated under reduced pressure. The crude product was used without further purification. LC-MS calculated for C$_{10}$H$_{24}$NOSi (M+H)$^+$: m/z=202.2; found 202.2.

Step 5: tert-butyl (E)-3-(2-(2-(2-((4-((tert-butyldimethylsilyl)oxy)but-2-en-1-yl)amino)-5-carbamoyl-3-narophenoxy)ethoxy)ethoxy)propanoate

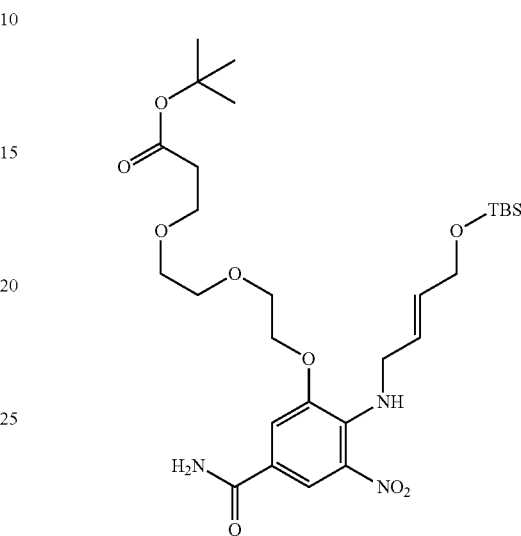

To a solution of tert-butyl 3-(2-(2-(5-carbamoyl-2-chloro-3-nitrophenoxy)ethoxy)ethoxy)propanoate (0.400 g, 0.924 mmol) in ethanol (4.62 ml) was added DIPEA (0.807 ml, 4.62 mmol) and (E)-4-((tert-butyldimethylsilyl)oxy)but-2-en-1-amine (0.186 g, 0.924 mmol). The resulting mixture was heated at 120° C. overnight. After cooling, the reaction was concentrated, and purified by silica gel column (10% MeOH/DCM). LC-MS calculated for C$_{28}$H$_{48}$N$_3$O$_9$Si (M+H)$^+$: m/z=598.3; found 598.3.

Step 6: tert-butyl (E)-3-(2-(2-(3-amino-2-((4-((tert-butyldimethylsilyl)oxy)but-2-en-1-yl)amino)-5-carbamoylphenoxy)ethoxy)ethoxy)propanoate

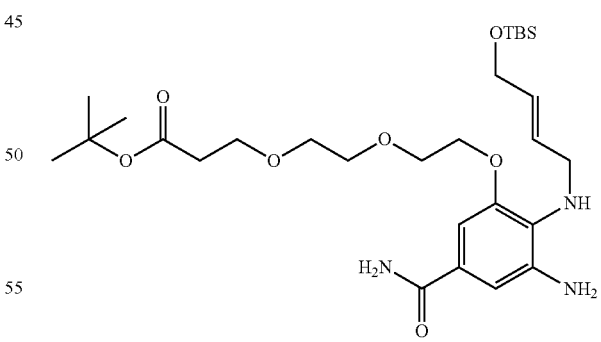

To a solution of tert-butyl (E)-3-(2-(2-(2-((4-((tert-butyldimethylsilyl)oxy)but-2-en-1-yl)amino)-5-carbamoyl-3-nitrophenoxy)ethoxy)ethoxy)propanoate (0.480 g, 0.803 mmol) in MeOH (12.04 ml) was added sodium hydrosulfite (0.699 g, 4.01 mmol) in water (2.53 ml, 141 mmol) and 30% aq. ammonium hydroxide (1.303 ml, 10.04 mmol) at 0° C. The reaction mixture was warmed to room temperature. After 10 min, H$_2$O was added to the reaction mixture followed by extraction with DCM. The combined organic layers were dried over MgSO₄, filtered and concentrated under reduced pressure. The crude product was used directly in the next step without further purification. LC-MS calculated for $C_{28}H_{50}N_3O_7Si$ (M+H)⁺: m/z=568.3; found 568.4.

Step 7: tert-butyl (E)-3-(2-(2-((2-amino-5-carbamoyl-1-(4-hydroxybut-2-en-1-yl)-1H-benzo[d]imidazol-7-yl)oxy)ethoxy)ethoxy)propanoate

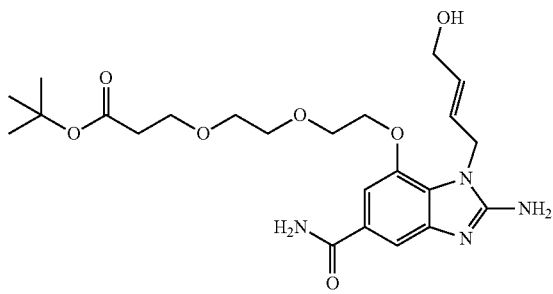 [SMILES: CC(C)(C)OC(=O)CCOCCOCCOc1cc(C(N)=O)cc2nc(N)n(C/C=C/CO)c12]

To a solution of tert-butyl (E)-3-(2-(2-(3-amino-2-((4-((tert-butyldimethylsilyl)oxy)but-2-en-1-yl)amino)-5-carbamoylphenoxy)ethoxy)ethoxy)propanoate (0.312 g, 0.549 mmol) in MeOH (2.75 ml) was added cyanogen bromide (0.144 ml, 2.75 mmol). The mixture was stirred for 2 d, and was then concentrated under reduced pressure. The resulting oil was used directly in the next step without further purification. LC-MS calculated for $C_{23}H_{35}N_4O_7$ (M+H)⁺: m/z=479.2; found 479.4.

Step 8: (E)-4-(7-(2-(2-(3-(tert-butoxy)-3-oxopropoxy)ethoxy)ethoxy)-5-carbamoyl-2-(1-ethyl-3-methyl-1H-pyrazole-5-carboxamido)-1H-benzo[d]imidazol-1-yl)but-2-en-1-yl 1-ethyl-3-methyl-1H-pyrazole-5-carboxylate

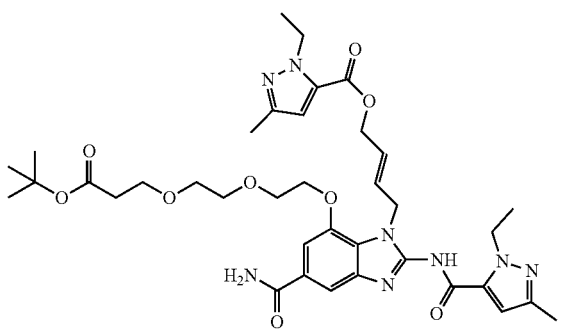 [SMILES: CCn1nc(C)cc1C(=O)Nc1nc2cc(C(N)=O)cc(OCCOCCOCCC(=O)OC(C)(C)C)c2n1C/C=C/COC(=O)c1cc(C)nn1CC]

To a solution of tert-butyl (E)-3-(2-(2-((2-amino-5-carbamoyl-1-(4-hydroxybut-2-en-1-yl)-1H-benzo[d]imidazol-7-yl)oxy)ethoxy)ethoxy)propanoate (0.263 g, 0.549) in DMF (5 mL) was added DIPEA (0.768 ml, 4.40 mmol), 1-ethyl-3-methyl-1H-pyrazole-5-carboxylic acid (Combi-Blocks, cat #QB-0979: 0.254 g, 1.648 mmol) and benzotriazol-1-yloxytris(dimethylamino)-phosphonium hexafluorophosphate (0.729 g, 1.648 mmol). After 1 h, H₂O was added to the reaction mixture followed by extraction with ethyl acetate (5 mL×3). The combined organic layers were dried over MgSO₄, filtered and concentrated under reduced pressure. The crude product was added to a silica gel column and was eluted with methanol/dichloromethane from 0% to 10% to give (E)-4-(7-(2-(2-(3-(tert-butoxy)-3-oxopropoxy)ethoxy)ethoxy)-5-carbamoyl-2-(1-ethyl-3-methyl-1H-pyrazole-5-carboxamido)-1H-benzo [d]imidazol-1-yl)but-2-en-1-yl 1-ethyl-3-methyl-1H-pyrazole-5-carboxylate as a brown foam. LC-MS calculated for $C_{37}H_{51}N_8O_9$ (M+H)⁺: m/z=751.4; found 751.3.

Step 9: tert-butyl (E)-3-(2-(2-((5-carbamoyl-2-(1-ethyl-3-methyl-1H-pyrazole-5-carboxamido)-1-(4-hydroxybut-2-en-1-yl)-1H-benzo[d]imidazol-7-yl)oxy)ethoxy)ethoxy)propanoate

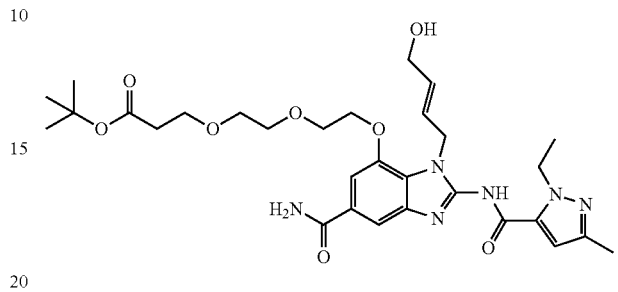

To a solution of (E)-4-(7-(2-(2-(3-(tert-butoxy)-3-oxopropoxy)ethoxy)ethoxy)-5-carbamoyl-2-(1-ethyl-3-methyl-1H-pyrazole-5-carboxamido)-1H-benzo[d]imidazol-1-yl)but-2-en-1-yl 1-ethyl-3-methyl-1H-pyrazole-5-carboxylate (0.413 g, 0.550 mmol) in THF (1.833 ml) and MeOH (0.917 ml) was added 2 N LiOH (1.375 ml, 2.75 mmol). After stirring for 2 h at rt, the reaction was extracted with CHCl₃/IPA (3:1). The combined organic extracts were dried over MgSO₄, filtered, and concentrated under reduced pressure. The resulting oil was purified by silica gel chromatography (15% MeOH/DCM) to provide the desired product as a beige foam. LC-MS calculated for $C_{30}H_{43}N_6O_8$ (M+H)⁺: m/z=615.3; found 615.3.

Step 10: tert-butyl (E)-3-(2-(2-((1-(4-bromobut-2-en-1-yl)-5-carbamoyl-2-(1-ethyl-3-methyl-1H-pyrazole-5-carboxamido)-1H-benzo[d]imidazol-7-yl)oxy)ethoxy)ethoxy)propanoate

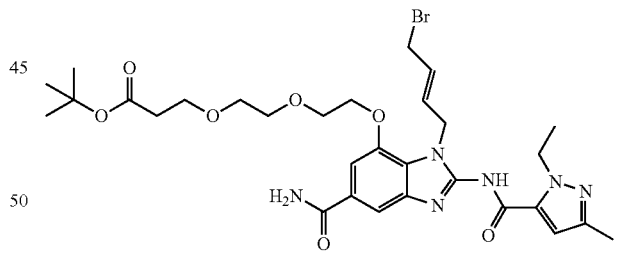

To a solution of tert-butyl (E)-3-(2-(2-((5-carbamoyl-2-(1-ethyl-3-methyl-1H-pyrazole-5-carboxamido)-1-(4-hydroxybut-2-en-1-yl)-1H-benzo[d]imidazol-7-yl)oxy)ethoxy)ethoxy)propanoate (0.153 g, 0.249 mmol) in THF (1.833 ml) was added PBr₃ (0.052 ml, 0.550 mmol) at 0° C. The reaction was warmed to rt and stirred for 15 min. After cooling to 0° C. the reaction was quenched with aqueous saturated sodium bicarbonate. The reaction was extracted with DCM, and the combined organic extracts were dried over MgSO₄, filtered, and concentrated. The resulting brown oil was then used directly in the next step. LC-MS calculated for $C_{30}H42BrN_6O_7$ (M+H)⁺: m/z=677.2/679.2; found 677.2/679.2.

Step 11: tert-butyl (E)-3-(2-(2-((5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)ethoxy)ethoxy)propanoate

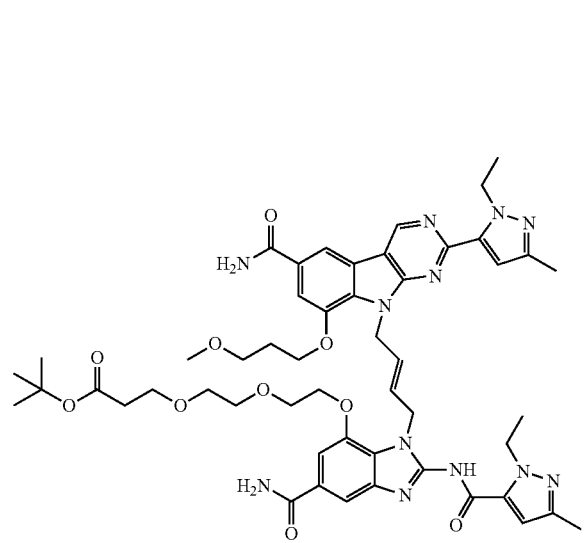 [SMILES: CCn1nc(C)cc1C(=O)Nc1nc2cc(C(N)=O)cc(OCCOCCOCCC(=O)OC(C)(C)C)c2n1C/C=C/Cn1c2nc(-c3cc(C)nn3CC)ncc2c2cc(C(N)=O)cc(OCCCOC)c21]

To a solution of tert-butyl (E)-3-(2-(2-((1-(4-bromobut-2-en-1-yl)-5-carbamoyl-2-(1-ethyl-3-methyl-1H-pyrazole-5-carboxamido)-1H-benzo[d]imidazol-7-yl)oxy)ethoxy)ethoxy)propanoate (0.020 g, 0.030 mmol) and 2-(1-ethyl-3-methyl-1H-pyrazol-5-yl)-8-(3-methoxypropoxy)-9H-pyrimido[4,5-b]indole-6-carboxamide (Example 12, Step 3: 0.012 g, 0.030 mmol) in DMF (0.295 mL) was added $Cs_2CO_3$ (0.029 g, 0.089 mmol). The mixture was stirred at rt for 30 min. The mixture was diluted with water and EtOAc. The layers were separated, and the organic layer was washed with 10% brine (2×), brine, then dried over $MgSO_4$. The combined organic layers were filtered and concentrated under reduced pressure. The resulting crude oil was used directly in the next step without further purification. LC-MS calculated for $C_{51}H_{66}N_{12}O_{10}$ $(M+2H)^{2+}$: m/z=503.2; found 503.5.

Step 12: (E)-3-(2-(2-((5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)ethoxy)ethoxy)propanoic acid To a vial was added tert-butyl (E)-3-(2-(2-((5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)ethoxy)ethoxy)propanoate (0.030 mg, 0.030 mmol) and TFA (0.2 mL, 2.60 mmol). The mixture was stirred for 15 min, and was then diluted with MeCN and water and purified by prep HPLC (pH=2, MeCN/water+TFA) to provide the desired product as the TFA salt. LC-MS calculated for $C_{47}H_{57}N_{12}O_{10}$ $(M+H)^+$: m/z=949.4; found 949.4.

Example 45. (E)-4-(N-(3-((5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propyl)sulfamoyl)butanoic acid

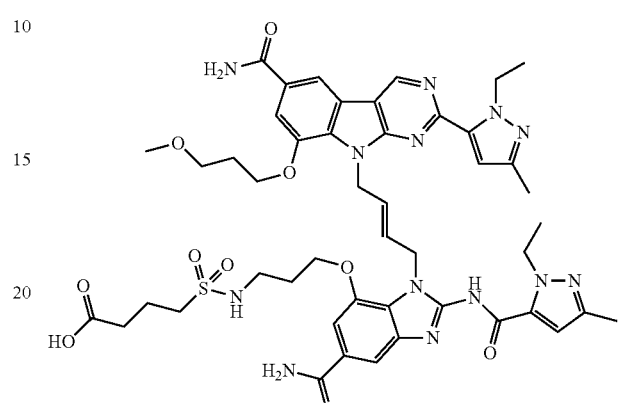

Step 1: methyl (E)-4-(N-(3-((5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propyl)sulfamoyl)butanoate

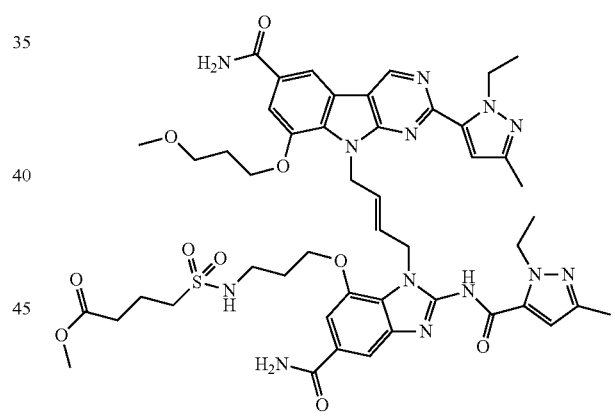

To a solution of (E)-9-(4-(7-(3-aminopropoxy)-5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazol-5-yl)-8-(3-methoxypropoxy)-9H-pyrimido[4,5-b]indole-6-carboxamide (Example 33, Step 9: 0.020 g, 0.024 mmol) in THF (0.236 ml)/DMF (0.236 ml) was added $Et_3N$ (9.89 μl, 0.071 mmol) then methyl 4-(chlorosulfonyl)butanoate (Enamine, cat #EN300-31554: 4.74 mg, 0.024 mmol) dropwise. After stirring for 1 h at rt, the reaction was quenched with aqueous saturated sodium bicarbonate, and was extracted with 3:1 $CHCl_3$/IPA. The combined organic layers were dried over $MgSO_4$, filtered, and concentrated under reduced pressure, and the crude product was used directly in the next step without further purification. LC-MS calculated for $C_{48}H_{60}N_{13}O_{10}S$ $(M+H)^+$: m/z=1010.4; found 1010.2.

Step 2: (E)-4-(N-(3-((5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propyl)sulfamoyl)butanoic acid To a solution of methyl (E)-4-(N-(3-((5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propyl)sulfamoyl)butanoate (0.024 g, 0.024 mmol) in THF (0.572 mL) and MeOH (0.236) was added aqueous 2 N LiOH (0.236 ml, 0.473 mmol). After stirring for 15 min, the mixture was diulted with water and MeCN and was purified by prep HPLC (pH 32 2, MeCN/water+TFA) to provide the desired compound as the TFA salt. LC-MS calculated for $C_{47}H_{58}N_{13}O_{10}S$ (M+H)$^+$: m/z=996.4; found 996.2.

Example 46. (E)-5-(3-(6-carbamoyl-9-(4-(5-carbamoyl-2-(1-ethyl-3-methyl-1H-pyrazole-5-carboxamido)-7-methoxy-1H-benzo[d]imidazol-1-yl)but-2-enyl)-2-(1-ethyl-3-methyl-1H-pyrazol-5-yl)-9H-pyrimido[4,5-b]indol-8-yloxy)propylamino)-5-oxopentanoic acid

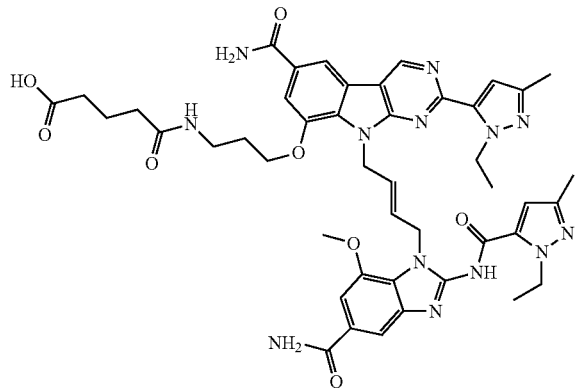 [SMILES: CCn1nc(C)cc1C(=O)Nc1nc2cc(C(N)=O)cc(OC)c2n1C/C=C/Cn1c2nc(-c3cc(C)nn3CC)ncc2c2cc(C(N)=O)cc(OCCCNC(=O)CCCC(=O)O)c21]

Step 1: tert-butyl 3-(3-bromo-5-carbamoyl-2-nitrophenoxy)propylcarbamate

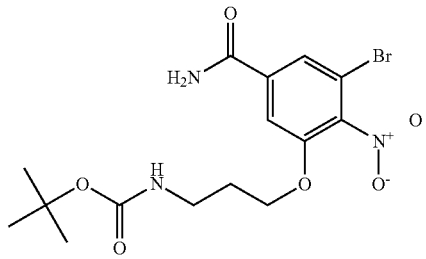

This compound was prepared using similar procedures as described for Example 11, Step 1 with tert-butyl 3-hydroxypropylcarbamate (Aldrich, cat #416444) replacing 3-morpholinopropan-1-ol. LC-MS calculated for $C_{15}H_{21}BrN_3O_6$ (M+H)$^+$: m/z=418.1, 420.1; found 318.1, 320.1.

Step 2: tert-butyl (3-(5-carbamoyl-3-(2-(1-ethyl-3-methyl-1H-pyrazol-5-yl)pyrimidin-5-yl)-2-nitrophenoxy)propyl)carbamate

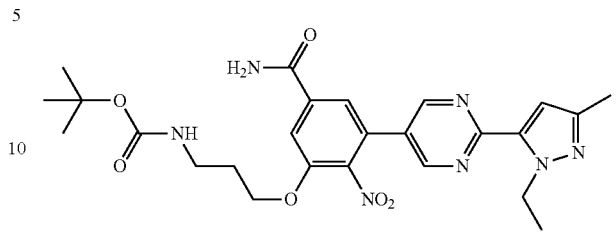

This compound was prepared using similar procedures as described for Example 10, Step 3 with tert-butyl 3-(3-bromo-5-carbamoyl-2-nitrophenoxy)propylcarbamate replacing 3-bromo-5-methoxy-4-nitrobenzamide. LC-MS calculated for $C_{25}H_{32}N_7O_6$ (M+H)$^+$: m/z=526.2; found 526.2.

Step 3: tert-butyl 3-(6-carbamoyl-2-(1-ethyl-3-methyl-1H-pyrazol-5-yl)-9H-pyrimido[4,5-b]indol-8-yloxy)propylcarbamate

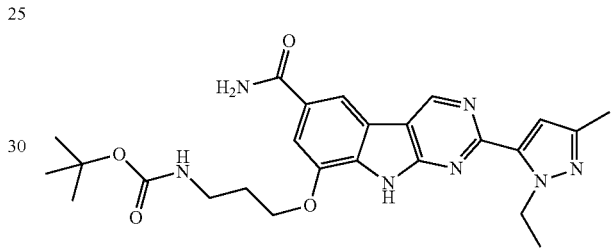

This compound was prepared using similar procedures as described for Example 10, Step 4 with tert-butyl (3-(5-carbamoyl-3-(2-(1-ethyl-3-methyl-1H-pyrazol-5-yl)pyrimidin-5-yl)-2-nitrophenoxy)propyl)carbamate replacing 3-(2-(1-ethyl-3-methyl-1H-pyrazol-5-yl)pyrimidin-5-yl)-5-methoxy-4-nitrobenzamide. LC-MS calculated for $C_{25}H_{32}N_7O_4$ (M+H)$^+$: m/z=494.2; found 494.3.

Step 4: (E)-tert-butyl 3-(6-carbamoyl-9-(4-(5-carbamoyl-2-(1-ethyl-3-methyl-1H-pyrazole-5-carboxamido)-7-methoxy-1H-benzo[d]imidazol-1-yl)but-2-enyl)-2-(1-ethyl-3-methyl-1H-pyrazol-5-yl)-9H-pyrimido[4,5-b]indol-8-yloxy)propylcarbamate

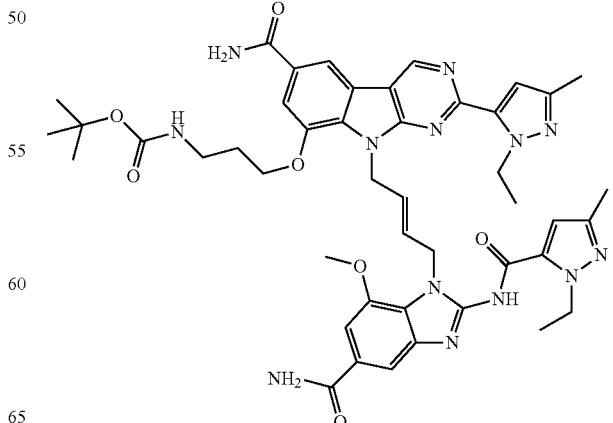

This compound was prepared using similar procedures as described for Example 4, Step 4 with tert-butyl 3-(6-carbamoyl-2-(1-ethyl-3-methyl-1H-pyrazol-5-yl)-9H-pyrimido[4,5-b]indol-8-yloxy)propylcarbamate replacing 2-(1-ethyl-3-methyl-1H-pyrazol-5-yl)-9H-pyrimido[4,5-b]indole-6-carboxamide. The mixture was diluted with DCM, and was washed with water and brine. The organic phase was dried over MgSO$_4$ before filtering. The filtrate was concentrated and purified by flash chromatography on a silica gel column eluting with 0 to 20% MeOH in DCM to afford the desired product. LC-MS calculated for $C_{45}H_{54}N_{13}O_7$ (M+H)$^+$: m/z=888.4; found 888.4.

Step 5: (E)-8-(3-aminopropoxy)-9-(4-(5-carbamoyl-2-(1-ethyl-3-methyl-1H-pyrazole-5-carboxamido)-7-methoxy-1H-benzo[d]imidazol-1-yl)but-2-enyl)-2-(1-ethyl-3-methyl-1H-pyrazol-5-yl)-9H-pyrimido[4,5-b]indole-6-carboxamide

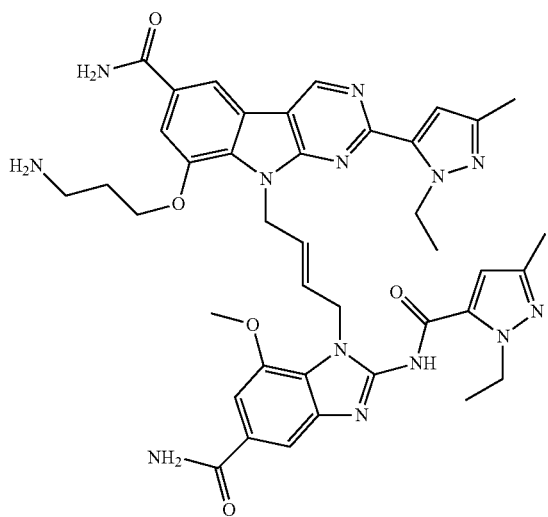 [SMILES: CCn1nc(C)cc1C(=O)Nc1nc2cc(C(N)=O)cc(OC)c2n1C/C=C/Cn1c2nc(-c3cc(C)nn3CC)ncc2c2cc(C(N)=O)cc(OCCCN)c21]

This compound was prepared using similar procedures as described for Example 33, Step 9 with (E)-tert-butyl 3-(6-carbamoyl-9-(4-(5-carbamoyl-2-(1-ethyl-3-methyl-1H-pyrazole-5-carboxamido)-7-methoxy-1H-benzo[d]imidazol-1-yl)but-2-enyl)-2-(1-ethyl-3-methyl-1H-pyrazol-5-yl)-9H-pyrimido[4,5-b]indol-8-yloxy)propylcarbamate replacing tert-butyl (E)-(3-((5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propyl)carbamate. The reaction mixture was concentrated and used in the next step without further purification. LC-MS calculated for $C_{40}H_{46}N_{13}O_5$ (M+H)$^+$: m/z=788.4; found 788.4.

Step 6: (E)-methyl 5-(3-(6-carbamoyl-9-(4-(5-carbamoyl-2-(1-ethyl-3-methyl-1H-pyrazole-5-carboxamido)-7-methoxy-1H-benzo[d]imidazol-1-yl)but-2-enyl)-2-(1-ethyl-3-methyl-1H-pyrazol-5-yl)-9H-pyrimido[4,5-b]indol-8-yloxy)propylamino)-5-oxopentanoate This compound was prepared using similar procedures as described for Example 34, Step 1 with (E)-8-(3-aminopropoxy)-9-(4-(5-carbamoyl-2-(1-ethyl-3-methyl-1H-pyrazole-5-carboxamido)-7-methoxy-1H-benzo[d]imidazol-1-yl)but-2-enyl)-2-(1-ethyl-3-methyl-1H-pyrazol-5-yl)-9H-pyrimido[4,5-b]indole-6-carboxamide replacing (E)-9-(4-(7-(3-aminopropoxy)-5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazol-5-yl)-8-(3-methoxypropoxy)-9H-pyrimido[4,5-b]indole-6-carboxamide. LC-MS calculated for $C_{46}H_{54}N_{13}O_8$ (M+H)$^+$: m/z=916.4; found 916.4.

Step 7: (E)-5-(3-(6-carbamoyl-9-(4-(5-carbamoyl-2-(1-ethyl-3-methyl-1H-pyrazole-5-carboxamido)-7-methoxy-1H-benzo[d]imidazol-1-yl)but-2-enyl)-2-(1-ethyl-3-methyl-1H-pyrazol-5-yl)-9H-pyrimido[4,5-b]indol-8-yloxy)propylamino)-5-oxopentanoic acid This compound was prepared using similar procedures as described for Example 34, Step 2 with (E)-methyl 5-(3-(6-carbamoyl-9-(4-(5-carbamoyl-2-(1-ethyl-3-methyl-1H-pyrazole-5-carboxamido)-7-methoxy-1H-benzo[d]imidazol-1-yl)but-2-enyl)-2-(1-ethyl-3-methyl-1H-pyrazol-5-yl)-9H-pyrimido[4,5-b]indol-8-yloxy)propylamino)-5-oxopentanoate replacing methyl (E)-5-((3-((5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propyl)amino)-5-oxopentanoate. The reaction mixture was diluted with MeOH and purified by prep-HPLC (pH=2, acetonitrile/water+TFA) to give the desired product as its TFA salt. LC-MS calculated for $C_{45}H_{52}N_{13}O_8$ (M+H)$^+$: m/z=902.4; found 902.4.

Example 47. (E)-3-(3-(6-carbamoyl-9-(4-(5-carbamoyl-2-(1-ethyl-3-methyl-1H-pyrazole-5-carboxamido)-7-methoxy-1H-benzo[d]imidazol-1-yl)but-2-enyl)-2-(1-ethyl-3-methyl-1H-pyrazol-5-yl)-9H-pyrimido[4,5-b]indol-8-yloxy)propylcarbamoyloxy) propanoic acid

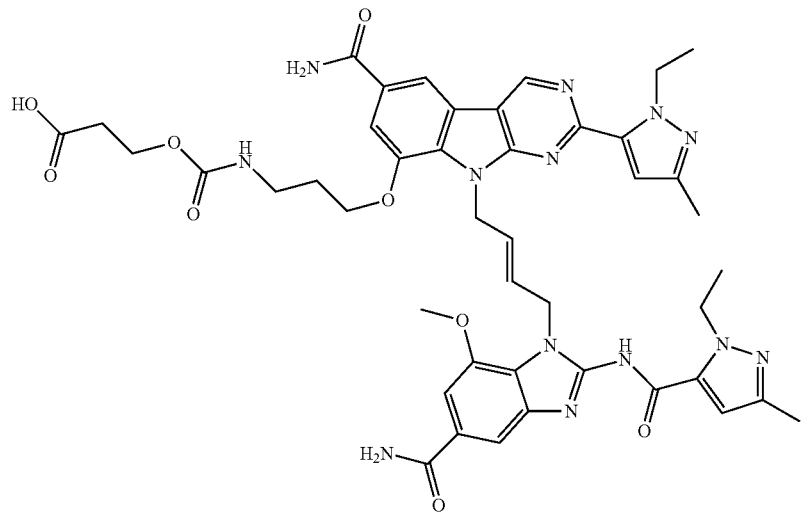 [SMILES: CCn1nc(C)cc1C(=O)Nc1nc2cc(C(N)=O)cc(OC)c2n1C/C=C/Cn1c2nc(-c3cc(C)nn3CC)ncc2c2cc(C(N)=O)cc(OCCCNC(=O)OCCC(=O)O)c21]

Step 1: (E)-tert-butyl 3-(3-(6-carbamoyl-9-(4-(5-carbamoyl-2-(1-ethyl-3-methyl-1H-pyrazole-5-carboxamido)-7-methoxy-1H-benzo[d]imidazol-1-yl)but-2-enyl)-2-(1-ethyl-3-methyl-1H-pyrazol-5-yl)-9H-pyrimido[4,5-b]indol-8-yloxy)propylcarbamoyloxy)propanoate

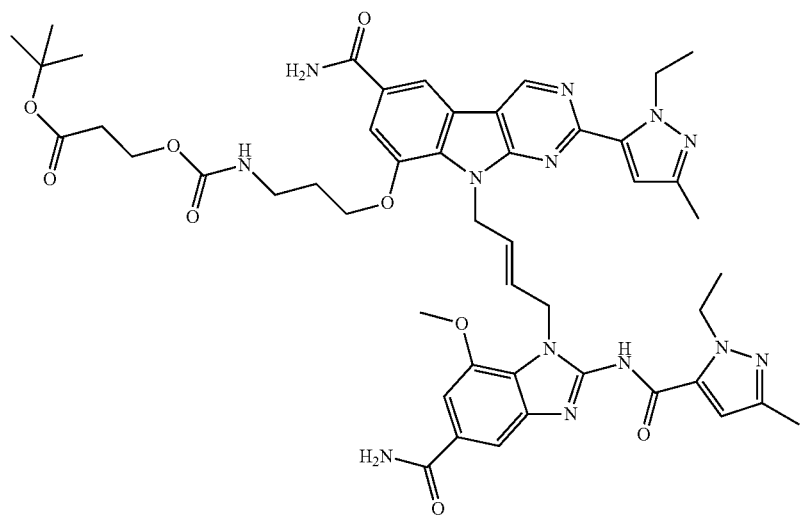 [SMILES: CCn1nc(C)cc1C(=O)Nc1nc2cc(C(N)=O)cc(OC)c2n1C/C=C/Cn1c2nc(-c3cc(C)nn3CC)ncc2c2cc(C(N)=O)cc(OCCCNC(=O)OCCC(=O)OC(C)(C)C)c21]

This compound was prepared using similar procedures as described for Example 39, Step 2 with (E)-8-(3-aminopropoxy)-9-(4-(5-carbamoyl-2-(1-ethyl-3-methyl-1H-pyrazole-5-carboxamido)-7-methoxy-1H-benzo[d]imidazol-1-yl)but-2-enyl)-2-(1-ethyl-3-methyl-1H-pyrazol-5-yl)-9H-pyrimido[4,5-b]indole-6-carboxamide (Example 46, Step 5) replacing (E)-9-(4-(7-(3-aminopropoxy)-5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazol-5-yl)-8-(3-methoxypropoxy)-9H-pyrimido[4,5-b]indole-6-carboxamide. LC-MS calculated for $C_{48}H_{58}N_{13}O_9$ $(M+H)^+$: m/z=960.4; found 960.5.

Step 2: (E)-3-(3-(6-carbamoyl-9-(4-(5-carbamoyl-2-(1-ethyl-3-methyl-1H-pyrazole-5-carboxamido)-7-methoxy-1H-benzo[d]imidazol-1-yl)but-2-enyl)-2-(1-ethyl-3-methyl-1H-pyrazol-5-yl)-9H-pyrimido[4,5-b]indol-8-yloxy)propylcarbamoyloxy)propanoic acid This compound was prepared using similar procedures as described for Example 37, Step 2 with (E)-tert-butyl 3-(3-(6-carbamoyl-9-(4-(5-carbamoyl-2-(1-ethyl-3-methyl-1H-pyrazole-5-carboxamido)-7-methoxy-1H-benzo[d]imidazol-1-yl)but-2-enyl)-2-(1-ethyl-3-methyl-1H-pyrazol-5-yl)-9H-pyrimido[4,5-b]indol-8-yloxy)propylcarbamoyloxy)propanoate replacing tert-butyl (6S,9S,12S,15S)-15-amino-6,9-bis(2-(tert-butoxy)-2-oxoethyl)-1-((5-carbamoyl-1-((E)-4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)-5,8,11,14-tetraoxo-12-(3-(3-((2,2,4,6,7-pentamethyl-2,3-dihydrobenzofuran-5-yl)sulfonyl)guanidino)propyl)-4,7,10,13-tetraazaheptadecan-17-oate. The reaction mixture was diluted with MeOH and purified by prep-HPLC (pH=2, acetonitrile/water+TFA) to give the desired product as its TFA salt. LC-MS calculated for $C_{44}H_{50}N_{13}O_9$ $(M+H)^+$: m/z=904.4; found 904.5.

Example 48. (E)-5-(3-(6-carbamoyl-9-(4-(5-carbamoyl-2-(1-ethyl-3-methyl-1H-pyrazole-5-carboxamido)-7-(3-hydroxypropoxy)-1H-benzo[d]imidazol-1-yl)but-2-enyl)-2-(1-ethyl-3-methyl-1H-pyrazol-5-yl)-9H-pyrimido[4,5-b]indol-8-yloxy)propylamino)-5-oxopentanoic acid

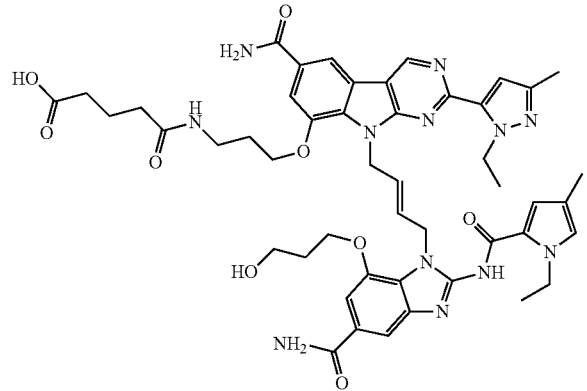

Step 1: (E)-3-(1-(4-(8-(3-(tert-butoxycarbonylamino)propoxy)-6-carbamoyl-2-(1-ethyl-3-methyl-1H-pyrazol-5-yl)-9H-pyrimido[4,5-b]indol-9-yl)but-2-enyl)-5-carbamoyl-2-(1-ethyl-3-methyl-1H-pyrazole-5-carboxamido)-1H-benzo[d]imidazol-7-yloxy)propyl 1-ethyl-3-methyl-1H-pyrazole-5-carboxylate

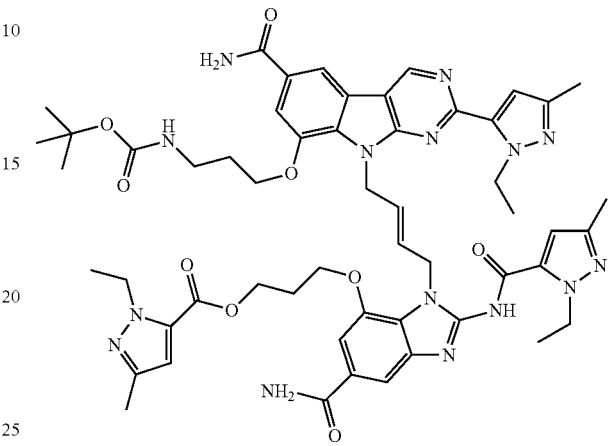

This compound was prepared using similar procedures as described for Example 15, Step 10 with tert-butyl 3-(6-carbamoyl-2-(1-ethyl-3-methyl-1H-pyrazol-5-yl)-9H-pyrimido[4,5-b]indol-8-yloxy)propylcarbamate (Example 46, Step 3) replacing 2-(1-ethyl-3-methyl-1H-pyrazol-5-yl)-8-methoxy-9H-pyrimido[4,5-b]indole-6-carboxamide.
LC-MS calculated for $C_{54}H_{66}N_{15}O_9$ $(M+H)^+$: m/z=1068.5; found 1068.8.

Step 2: (E)-3-(1-(4-(8-(3-aminopropoxy)-6-carbamoyl-2-(1-ethyl-3-methyl-1H-pyrazol-5-yl)-9H-pyrimido[4,5-b]indol-9-yl)but-2-enyl)-5-carbamoyl-2-(1-ethyl-3-methyl-1H-pyrazole-5-carboxamido)-1H-benzo[d]imidazol-7-yloxy)propyl 1-ethyl-3-methyl-1H-pyrazole-5-carboxylate

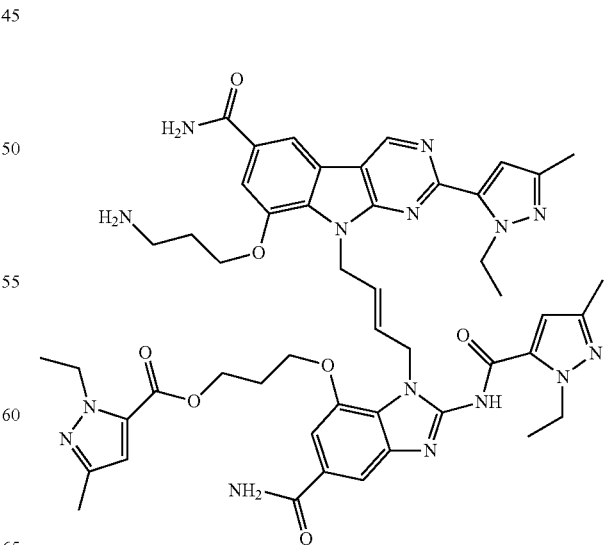

This compound was prepared using similar procedures as described for Example 33, Step 9 with (E)-3-(1-(4-(8-(3-(tert-butoxycarbonylamino)propoxy)-6-carbamoyl-2-(1-ethyl-3-methyl-1H-pyrazol-5-yl)-9H-pyrimido[4,5-b]indol-9-yl)but-2-enyl)-5-carbamoyl-2-(1-ethyl-3-methyl-1H-pyrazole-5-carboxamido)-1H-benzo[d]imidazol-7-yloxy) propyl 1-ethyl-3-methyl-1H-pyrazole-5-carboxylate replacing tert-butyl (E)-(3-((5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propyl)carbamate. The reaction mixture was concentrated and used in the next step without further purification. LC-MS calculated for $C_{49}H_{58}N_{15}O_7$ $(M+H)^+$: m/z=968.5; found 968.6.

Step 3: (E)-3-(5-carbamoyl-1-(4-(6-carbamoyl-2-(1-ethyl-3-methyl-1H-pyrazol-5-yl)-8-(3-(5-methoxy-5-oxopentanamido)propoxy)-9H-pyrimido[4,5-b]indol-9-yl)but-2-enyl)-2-(1-ethyl-3-methyl-1H-pyrazole-5-carboxamido)-1H-benzo[d]imidazol-7-yloxy)propyl 1-ethyl-3-methyl-1H-pyrazole-5-carboxylate

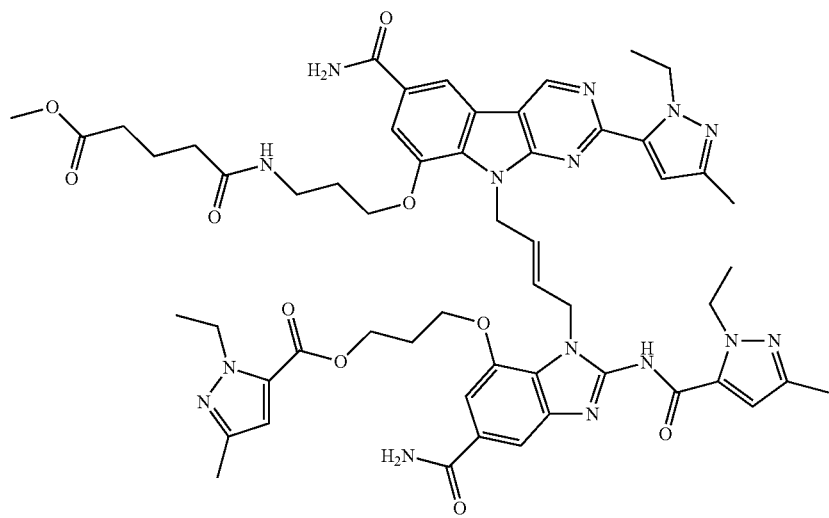

This compound was prepared using similar procedures as described for Example 34, Step 1 with (E)-3-(1-(4-(8-(3-aminopropoxy)-6-carbamoyl-2-(1-ethyl-3-methyl-1H-pyrazol-5-yl)-9H-pyrimido[4,5-b]indol-9-yl)but-2-enyl)-5-carbamoyl-2-(1-ethyl-3-methyl-1H-pyrazole-5-carboxamido)-1H-benzo[d]imidazol-7-yloxy)propyl 1-ethyl-3-methyl-1H-pyrazole-5-carboxylate replacing (E)-9-(4-(7-(3-aminopropoxy)-5-carbamoyl-2-(1-ethyl-3-methyl-1H-pyrazole-5-carboxamido)-1H-benzo [d]imidazol-1-yl)but-2-en-1-yl)-2-(1-ethyl-3-methyl-1H-pyrazol-5-yl)-8-(3-methoxypropoxy)-9H-pyrimido[4,5-b]indole-6-carboxamide. LC-MS calculated for $C_{55}H_{66}N_{15}O_{10}$ (M+H)$^+$: m/z=1096.5; found 1096.8.

Step 4: (E)-5-(3-(6-carbamoyl-9-(4-(5-carbamoyl-2-(1-ethyl-3-methyl-1H-pyrazole-5-carboxamido)-7-(3-hydroxypropoxy)-1H-benzo[d]imidazol-1-yl)but-2-enyl)-2-(1-ethyl-3-methyl-1H-pyrazol-5-yl)-9H-pyrimido[4,5-b]indol-8-yloxy)propylamino)-5-oxopentanoic acid This compound was prepared using similar procedures as described for Example 34, Step 2 with (E)-3-(5-carbamoyl-1-(4-(6-carbamoyl-2-(1-ethyl-3-methyl-1H-pyrazol-5-yl)-8-(3-(5-methoxy-5-oxopentanamido)propoxy)-9H-pyrimido[4,5-b]indol-9-yl)but-2-enyl)-2-(1-ethyl-3-methyl-1H-pyrazole-5-carboxamido)-1H-benzo[d]imidazol-7-yloxy)propyl 1-ethyl-3-methyl-1H-pyrazole-5-carboxylate replacing methyl (E)-5-((3-((5-carbamoyl-1-(4-(6-carbamoyl-2-(1-ethyl-3-methyl-1H-pyrazol-5-yl)-8-(3-methoxypropoxy)-9H-pyrimido[4,5 -b]indol-9-yl)but-2-en-1-yl)-2-(1-ethyl-3-methyl-1H-pyrazole-5-carboxamido)-1H-benzo[d]imidazol-7-yl)oxy)propyl)amino)-5-oxopentanoate. The reaction mixture was diluted with MeOH and purified by prep-HPLC (pH=2, acetonitrile/water+TFA) to give the desired product as its TFA salt. LC-MS calculated for $C_{47}H_{56}N_{13}O_9$ (M+H)$^+$: m/z=946.4; found 946.6.

Example 49. (E)-3-(3-(6-carbamoyl-9-(4-(5-carbamoyl-2-(1-ethyl-3-methyl-1H-pyrazole-5-carboxamido)-7-(3-hydroxypropoxy)-1H-benzo[d]imidazol-1-yl)but-2-enyl)-2-(1-ethyl-3-methyl-1H-pyrazol-5-yl)-9H-pyrimido[4,5-b]indol-8-yloxy) propylcarbamoyloxy)propanoic acid

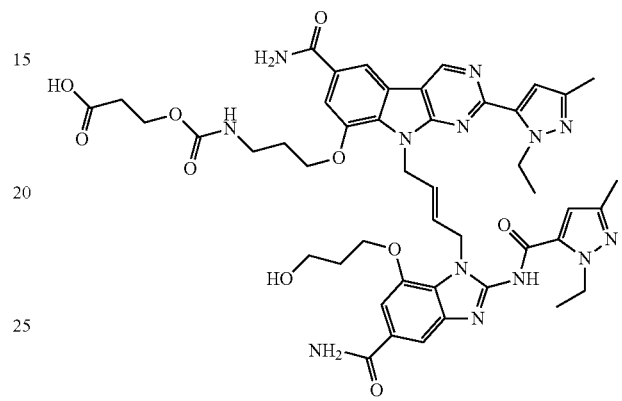

Step 1: (E)-3-(1-(4-(8-(3-(((3-tert-butoxy-3-oxopropoxy)carbonylamino)propoxy)-6-carbamoyl-2-(1-ethyl-3-methyl-1H-pyrazol-5-yl)-9H-pyrimido[4,5-b]indol-9-yl)but-2-enyl)-5-carbamoyl-2-(1-ethyl-3-methyl-1H-pyrazole-5-carboxamido)-1H-benzo[d]imidazol-7-yloxy)propyl 1-ethyl-3-methyl-1H-pyrazole-5-carboxylate

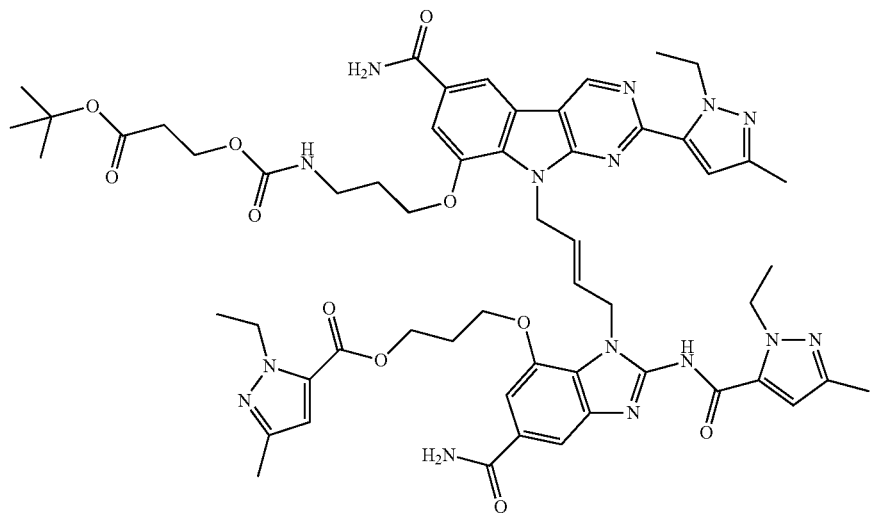 [SMILES: CCn1nc(C)cc1C(=O)Nc1nc2cc(C(N)=O)cc(OCCCOC(=O)c3cc(C)nn3CC)c2n1C/C=C/Cn1c2nc(-c3cc(C)nn3CC)ncc2c2cc(C(N)=O)cc(OCCCNC(=O)OCCC(=O)OC(C)(C)C)c21]

This compound was prepared using similar procedures as described for Example 39, Step 2 with (E)-3-(1-(4-(8-(3-aminopropoxy)-6-carbamoyl-2-(1-ethyl-3-methyl-1H-pyrazol-5-yl)-9H-pyrimido[4,5-b]indol-9-yl)but-2-enyl)-5-carbamoyl-2-(1-ethyl-3-methyl-1H-pyrazole-5-carboxamido)-1H-benzo[d]imidazol-7-yloxy)propyl 1-ethyl-3-methyl-1H-pyrazole-5-carboxylate (Example 48, Step 2) replacing (E)-9-(4-(7-(3-aminopropoxy)-5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazol-5-yl)-8-(3-methoxypropoxy)-9H-pyrimido[4,5-b]indole-6-carboxamide. LC-MS calculated for $C_{57}H_{70}N_{15}O_{11}$ (M+H)$^+$: m/z=1140.5; found 1140.6.

Step 2: (E)-3-(3-(6-carbamoyl-9-(4-(5-carbamoyl-7-(3-(1-ethyl-3-methyl-1H-pyrazole-5-carbonyloxy)propoxy)-2-(1-ethyl-3-methyl-1H-pyrazole-5-carboxamido)-1H-benzo[d]imidazol-1-yl)but-2-enyl)-2-(1-ethyl-3-methyl-1H-pyrazol-5-yl)-9H-pyrimido[4,5-b]indol-8-yloxy)propylcarbamoyloxy)propanoic acid This compound was prepared using similar procedures as described for Example 34, Step 2 with (E)-3-(3-(6-carbamoyl-9-(4-(5-carbamoyl-7-(3-(1-ethyl-3-methyl-1H-pyrazole-5-carbonyloxy)propoxy)-2-(1-ethyl-3-methyl-1H-pyrazole-5-carboxamido)-1H-benzo[d]imidazol-1-yl)but-2-enyl)-2-(1-ethyl-3-methyl-1H-pyrazol-5-yl)-9H-pyrimido[4,5-b]indol-8-yloxy)propylcarbamoyloxy)propanoic acid replacing methyl (E)-5-((3-((5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propyl)amino)-5-oxopentanoate. The reaction mixture was diluted with MeOH and purified by prep-HPLC (pH=2, acetonitrile/water+TFA) to give the desired product as its TFA salt. LC-MS calculated for $C_{46}H_{54}N_{13}O_{10}$ (M+H)$^+$: m/z=948.4; found 948.5.

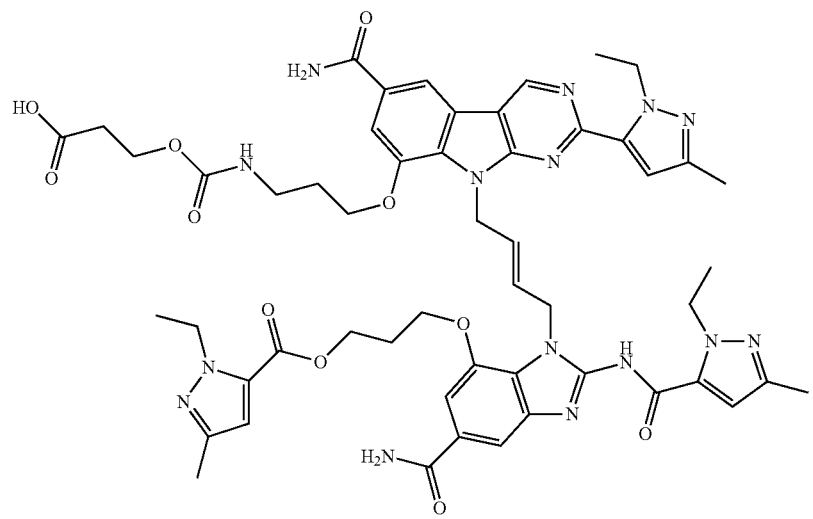 [SMILES: CCn1nc(C)cc1C(=O)Nc1nc2cc(C(N)=O)cc(OCCCOC(=O)c3cc(C)nn3CC)c2n1C/C=C/Cn1c2nc(-c3cc(C)nn3CC)ncc2c2cc(C(N)=O)cc(OCCCNC(=O)OCCC(=O)O)c21]

This compound was prepared using similar procedures as described for Example 37, Step 2 with (E)-3-(1-(4-(8-(3-((3-tert-butoxy-3-oxopropoxy)carbonylamino)propoxy)-6-carbamoyl-2-(1-ethyl-3-methyl-1H-pyrazol-5-yl)-9H-pyrimido[4,5-b]indol-9-yl)but-2-enyl)-5-carbamoyl-2-(1-ethyl-3-methyl-1H-pyrazole-5-carboxamido)-1H-benzo[d]imidazol-7-yloxy)propyl 1-ethyl-3-methyl-1H-pyrazole-5-carboxylate replacing tert-butyl (6S,9S,12S,15S)-15-amino-6,9-bis(2-(tert-butoxy)-2-oxoethyl)-1-((5-carbamoyl-1-((E)-4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo [d]imidazol-7-yl)oxy)-5,8,11,14-tetraoxo-12-(3-(3-((2,2,4,6,7-pentamethyl-2,3-dihydrobenzofuran-5-yl)sulfonyl)guanidino)propyl)-4,7,10,13-tetraazaheptadecan-17-oate. The reaction mixture was concentrated and used in the next step without further purification. LC-MS calculated for $C_{53}H_{62}N_{15}O_{11}$ (M+H)$^+$: m/z=1084.5; found 1084.7.

Step 3: (E)-3-(3-(6-carbamoyl-9-(4-(5-carbamoyl-2-(1-ethyl-3-methyl-1H-pyrazole-5-carboxamido)-7-(3-hydroxypropoxy)-1H-benzo[d]imidazol-1-yl)but-2-enyl)-2-(1-ethyl-3-methyl-1H-pyrazol-5-yl)-9H-pyrimido[4,5-b]indol-8-yloxy)propylcarbamoyloxy)propanoic acid Example 50. (E)-5-(3-(6-carbamoyl-9-(4-(5-carbamoyl-2-(1-ethyl-3-methyl-1H-pyrazole-5-carboxamido)-7-(3-methoxypropoxy)-1H-benzo[d]imidazol-1-yl)but-2-enyl)-2-(1-ethyl-3-methyl-1H-pyrazol-5-yl)-9H-pyrimido[4,5-b]indol-8-yloxy)propylamino)-5-oxopentanoic acid

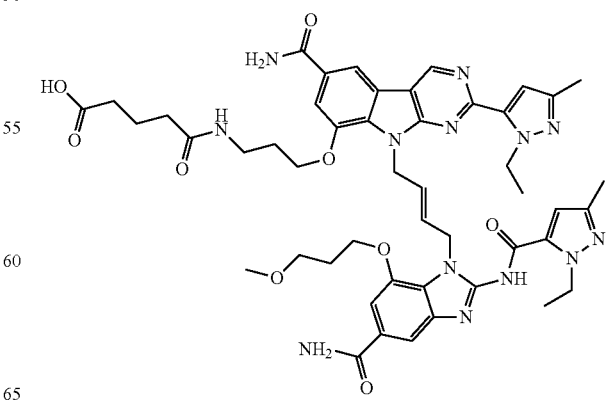

Step 1: 4-chloro-3-(3-methoxypropoxy)-5-nitrobenzamide

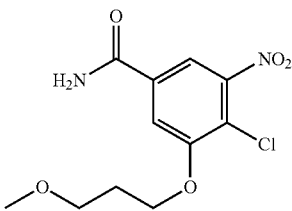 [SMILES: COCCCOc1cc(C(N)=O)cc([N+](=O)[O-])c1Cl]

This compound was prepared using similar procedures as described for Example 15, Step 2 with 3-methoxypropan-1-ol (Aldrich, cat #38457) replacing (3-bromopropoxy)(tert-butyl)dimethylsilane. LC-MS calculated for $C_{11}H_{14}ClN_2O_5$ (M+H)$^+$: m/z=289.1; found 289.0.

Step 2: (E)-tert-butyl 4-(4-carbamoyl-2-(3-methoxy-propoxy)-6-nitrophenylamino)but-2-enylcarbamate

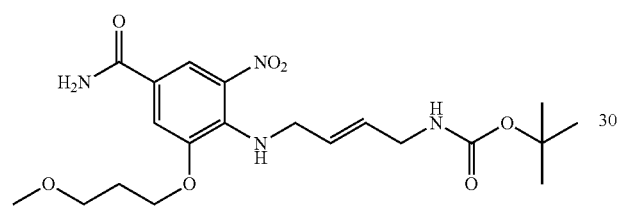

This compound was prepared using similar procedures as described for Example 15, Step 3 with 4-chloro-3-(3-methoxypropoxy)-5-nitrobenzamide replacing 3-(3-((tert-butyldimethylsilyl)oxy)propoxy)-4-chloro-5-nitrobenz-amide. LC-MS calculated for $C_{20}H_{30}N_4NaO_7$ (M+Na)$^+$: m/z=461.2; found 461.2.

Step 3: (E)-tert-butyl 4-(2-amino-4-carbamoyl-6-(3-methoxypropoxy)phenylamino)but-2-enylcarbamate

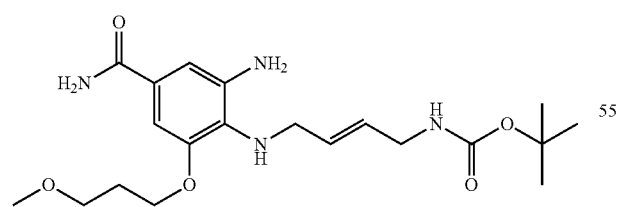

This compound was prepared using similar procedures as described for Example 1, Step 3 with tert-butyl (E)-tert-butyl 4-(4-carbamoyl-2-(3-methoxypropoxy)-6-nitrophe-nylamino)but-2-enylcarbamate replacing tert-butyl (E)-(4-(4(4-carbamoyl-2-methyl-6-nitrophenyl)amino)but-2-en-1-yl)carbamate. LC-MS calculated for $C_{20}H_{33}N_4O_5$ (M+H)$^+$: m/z=409.2; found 409.2.

Step 4: (E)-tert-butyl 4-(2-amino-5-carbamoyl-7-(3-methoxypropoxy)-1H-benzo[d]imidazol-1-yl)but-2-enyl-carbamate

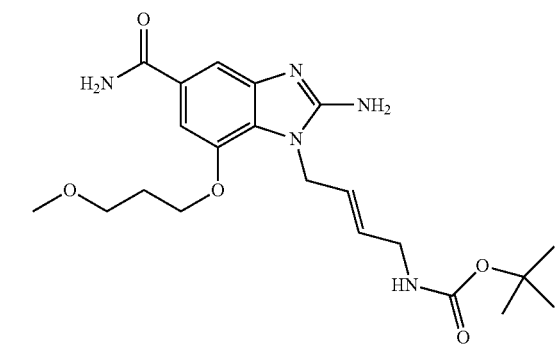 [SMILES: COCCCOc1cc(C(N)=O)cc2nc(N)n(C/C=C/CNC(=O)OC(C)(C)C)c12]

This compound was prepared using similar procedures as described for Example 1, Step 4 with (E)-tert-butyl 4-(2-amino-4-carbamoyl-6-(3-methoxypropoxy)phenylamino)but-2-enylcarbamate replacing tert-butyl (E)-(4-((2-amino-4-carbamoyl-6-methylphenyl)amino)but-2-en-1-yl)carbamate. LC-MS calculated for $C_{21}H_{32}N_5O_5$ (M+H)$^+$: m/z=434.2; found 434.5.

Step 5: (E)-tert-butyl 4-(5-carbamoyl-2-(1-ethyl-3-methyl-1H-pyrazole-5-carboxamido)-7-(3-methoxypropoxy)-1H-benzo[d]imidazol-1-yl)but-2-enylcarbamate

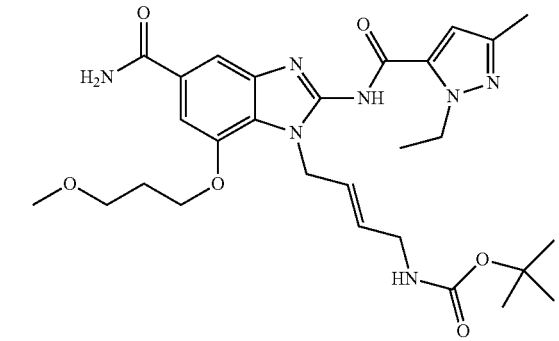 [SMILES: CCn1nc(C)cc1C(=O)Nc1nc2cc(C(N)=O)cc(OCCCOC)c2n1C/C=C/CNC(=O)OC(C)(C)C]

This compound was prepared using similar procedures as described for Example 1, Step 5 with (E)-tert-butyl 4-(2-amino-5-carbamoyl-7-(3-methoxypropoxy)-1H-benzo[d]imidazol-1-yl)but-2-enylcarbamate replacing (E)-tert-butyl 4-(2-amino-5-carbamoyl-7-methyl-1H-benzo[d]imidazol-1-yl)but-2-enylcarbamate. LC-MS calculated for $C_{28}H_{40}N_7O_6$ (M+H)$^+$: m/z=570.3; found 570.4.

Step 6: (E)-1-(4-aminobut-2-enyl)-2-(1-ethyl-3-methyl-1H-pyrazole-5-carboxamido)-7-(3-methoxypropoxy)-1H-benzo[d]imidazole-5-carboxamide

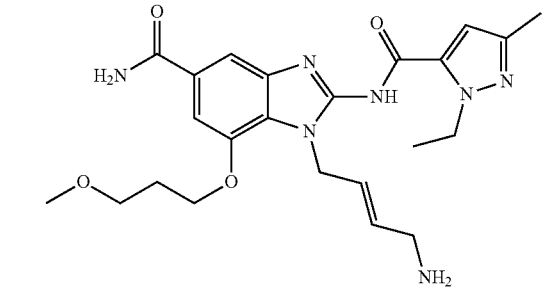

This compound was prepared using similar procedures as described for Example 1, Step 6 with (E)-tert-butyl 4-(5-carbamoyl-2-(1-ethyl-3-methyl-1H-pyrazole-5-carboxamido)-7-(3-methoxypropoxy)-1H-benzo[d]imidazol-1-yl)but-2-enylcarbamate replacing tert-butyl (E)-(4-(5-carbamoyl-2-(1-ethyl-3-methyl-1H-pyrazole-5-carboxamido)-7-methyl-1H-benzo[d]imidazol-1-yl)but-2-en-1-yl)carbamate. LC-MS calculated for $C_{23}H_{32}N_7O_4$ (M+H)$^+$: m/z=470.2; found 470.3.

Step 7: (E)-2-(1-ethyl-3-methyl-1H-pyrazole-5-carboxamido)-1-(4-hydroxybut-2-enyl)-7-(3-methoxypropoxy)-1H-benzo[d]imidazole-5-carboxamide This compound was prepared using similar procedures as described for Example 1, Step 8 with (E)-2-(1-ethyl-3-methyl-1H-pyrazole-5-carboxamido)-1-(4-hydroxybut-2-enyl)-7-(3-methoxypropoxy)-1H-benzo[d]imidazole-5-carboxamide replacing (E)-2-(1-ethyl-3-methyl-1H-pyrazole-5-carboxamido)-1-(4-hydroxybut-2-enyl)-7-methyl-1H-benzo[d]imidazole-5-carboxamide. LC-MS calculated for $C_{23}H_{30}BrN_6O_4$ (M+H)$^+$: m/z=533.1/535.1; found 533.1/535.1.

Step 9: (E)-tert-butyl 3-(6-carbamoyl-9-(4-(5-carbamoyl-2-(1-ethyl-3-methyl-1H-pyrazole-5-carboxamido)-7-(3-methoxypropoxy)-1H-benzo[d]imidazol-1-yl)but-2-enyl)-2-(1-ethyl-3-methyl-1H-pyrazol-5-yl)-9H-pyrimido[4,5-b]indol-8-yloxy)propylcarbamate

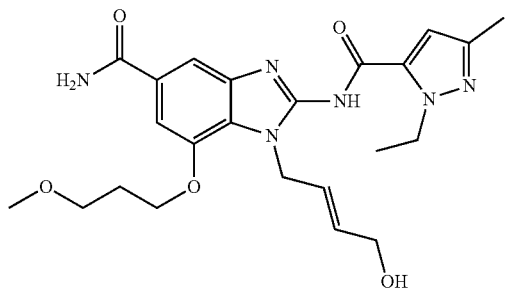

This compound was prepared using similar procedures as described for Example 1, Step 7 with (E)-1-(4-aminobut-2-enyl)-2-(1-ethyl-3-methyl-1H-pyrazole-5-carboxamido)-7-(3-methoxypropoxy)-1H-benzo[d]imidazole-5-carboxamide replacing (E)-1-(4-aminobut-2-en-1-yl)-2-(1-ethyl-3-methyl-1H-pyrazole-5-carboxamido)-7-methyl-1H-benzo[d]imidazole-5-carboxamide. LC-MS calculated for $C_{23}H_{31}N_6O_5$ (M+H)$^+$: m/z=471.2; found 471.3.

Step 8: (E)-1-(4-bromobut-2-enyl)-2-(1-ethyl-3-methyl-1H-pyrazole-5-carboxamido)-7-(3-methoxypropoxy)-1H-benzo[d]imidazole-5-carboxamide

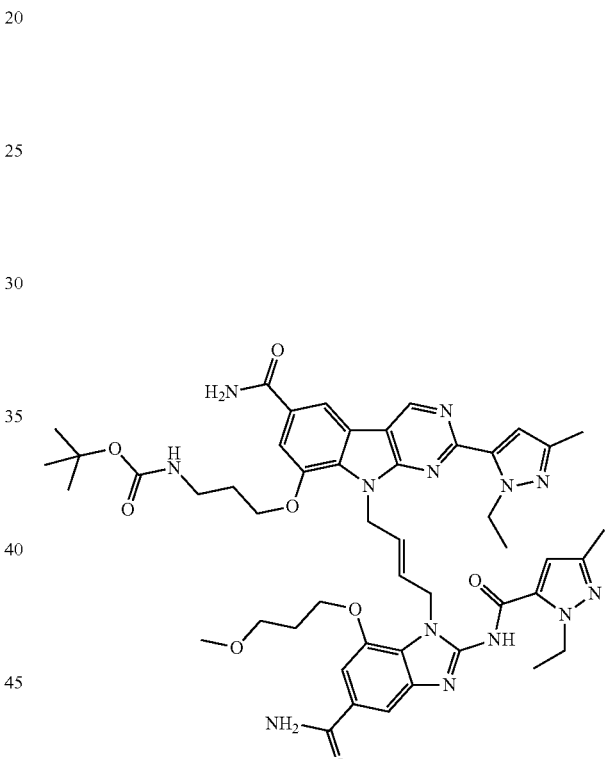

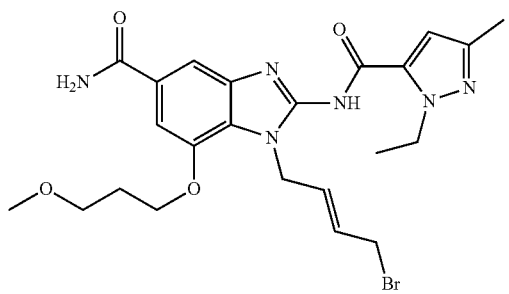

To a mixture of tert-butyl (3-((6-carbamoyl-2-(1-ethyl-3-methyl-1H-pyrazol-5-yl)-9H-pyrimido[4,5-b]indol-8-yl)oxy)propyl)carbamate (Example 46, Step 3, 35.0 mg, 0.071 mmol), and (E)-1-(4-bromobut-2-en-1-yl)-2-(1-ethyl-3-methyl-1H-pyrazole-5-carboxamido)-7-(3-methoxypropoxy)-1H-benzo[d]imidazole-5-carboxamide (37.8 mg, 0.071 mmol) in DMF (0.4 mL) was added Cs$_2$CO$_3$ (50.8 mg, 0.156 mmol). The mixture was stirred at 50° C. for 1 hour. The reaction mixture was concentrated and purified by flash chromatography on a silica gel column eluting with 0 to 20% MeOH in DCM to afford the desired product. LC-MS calculated for $C_{48}H_{60}N_{13}O_8$ (M+H)$^+$: m/z=946.5; found 946.5.

Step 10: (E)-8-(3-aminopropoxy)-9-(4-(5-carbamoyl-2-(1-ethyl-3-methyl-1H-pyrazole-5-carboxamido)-7-(3-methoxypropoxy)-1H-benzo[d]imidazol-1-yl)but-2-enyl)-2-(1-ethyl-3-methyl-1H-pyrazol-5-yl)-9H-pyrimido[4,5-b]indole-6-carboxamide

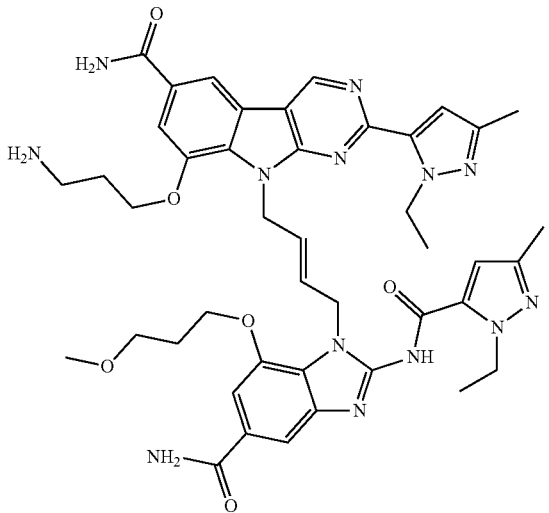 [SMILES: CCn1nc(C)cc1C(=O)Nc1nc2cc(C(N)=O)cc(OCCCOC)c2n1C/C=C/Cn1c2nc(-c3cc(C)nn3CC)ncc2c2cc(C(N)=O)cc(OCCCN)c21]

This compound was prepared using similar procedures as described for Example 33, Step 9 with (E)-tert-butyl 3-(6-carbamoyl-9-(4-(5-carbamoyl-2-(1-ethyl-3-methyl-1H-pyrazole-5-carboxamido)-7-(3-methoxypropoxy)-1H-benzo[d]imidazol-1-yl)but-2-enyl)-2-(1-ethyl-3-methyl-1H-pyrazol-5-yl)-9H-pyrimido[4,5-b]indol-8-yloxy)propylcarbamate replacing tert-butyl (E)-(3-((5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propyl)carbamate. The reaction mixture was concentrated and used in the next step without further purification. LC-MS calculated for $C_{43}H_{52}N_{13}O_6$ $(M+H)^+$: m/z=846.4; found 846.5.

Step 11: (E)-methyl 5-(3-(6-carbamoyl-9-(4-(5-carbamoyl-2-(1-ethyl-3-methyl-1H-pyrazole-5-carboxamido)-7-(3-methoxypropoxy)-1H-benzo[d]imidazol-1-yl)but-2-enyl)-2-(1-ethyl-3-methyl-1H-pyrazol-5-yl)-9H-pyrimido[4,5-b]indol-8-yloxy)propylamino)oxopentanoate This compound was prepared using similar procedures as described for Example 34, Step 1 with (E)-8-(3-aminopropoxy)-9-(4-(5-carbamoyl-2-(1-ethyl-3-methyl-1H-pyrazole-5-carboxamido)-7-(3-methoxypropoxy)-1H-benzo[d]imidazol-1-yl)but-2-enyl)-2-(1-ethyl-3-methyl-1H-pyrazol-5-yl)-9H-pyrimido[4,5-b]indole-6-carboxamide replacing (E)-9-(4-(7-(3-aminopropoxy)-5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazol-5-yl)-8-(3-methoxypropoxy)-9H-pyrimido[4,5-b]indole-6-carboxamide. LC-MS calculated for $C_{49}H_{60}N_{13}O_9$ $(M+H)^+$: m/z=974.5; found 974.8.

Step 12: (E)-5-(3-(6-carbamoyl-9-(4-(5-carbamoyl-2-(1-ethyl-3-methyl-1H-pyrazole-5-carboxamido)-7-(3-methoxypropoxy)-1H-benzo[d]imidazol-1-yl)but-2-enyl)-2-(1-ethyl-3-methyl-1H-pyrazol-5-yl)-9H-pyrimido[4,5-b]indol-8-yloxy)propylamino)-5-oxopentanoic acid This compound was prepared using similar procedures as described for Example 34, Step 2 with (E)-methyl 5-(3-(6-carbamoyl-9-(4-(5-carbamoyl-2-(1-ethyl-3-methyl-1H-pyrazole-5-carboxamido)-7-(3-methoxypropoxy)-1H-benzo[d]imidazol-1-yl)but-2-enyl)-2-(1-ethyl-3-methyl-1H-pyrazol-5-yl)-9H-pyrimido[4,5-b]indol-8-yloxy)propylamino)-5-oxopentanoate replacing methyl (E)-5-((3-((5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propyl)amino)-5-oxopentanoate. The reaction mixture was diluted with MeOH and purified by prep-HPLC (pH=2, acetonitrile/water+TFA) to give the desired product as its TFA salt. LC-MS calculated for $C_{48}H_{58}N_{13}O_9$ $(M+H)^+$: m/z=960.4; found 960.5.

Example 51. (E)-3-(3-(6-carbamoyl-9-(4-(5-carbamoyl-2-(1-ethyl-3-methyl-1H-pyrazole-5-carboxamido)-7-(3-methoxypropoxy)-1H-benzo[d]imidazol-1-yl)but-2-enyl)-2-(1-ethyl-3-methyl-1H-pyrazol-5-yl)-9H-pyrimido[4,5-b]indol-8-yloxy) propylcarbamoyloxy)propanoic acid

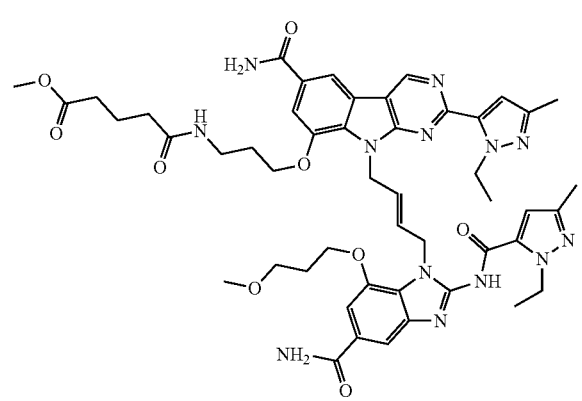

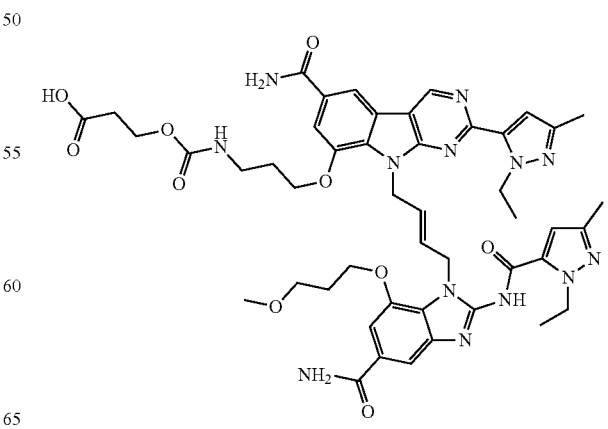

Step 1: (E)-tert-butyl 3-(3-(6-carbamoyl-9-(4-(5-carbamoyl-2-(1-ethyl-3-methyl-1H-pyrazole-5-carboxamido)-7-(3-methoxypropoxy)-1H-benzo[d]imidazol-1-yl)but-2-enyl)-2-(1-ethyl-3-methyl-1H-pyrazol-5-yl)-9H-pyrimido[4,5-b]indol-8-yloxy)propylcarbamoyloxy)propanoate

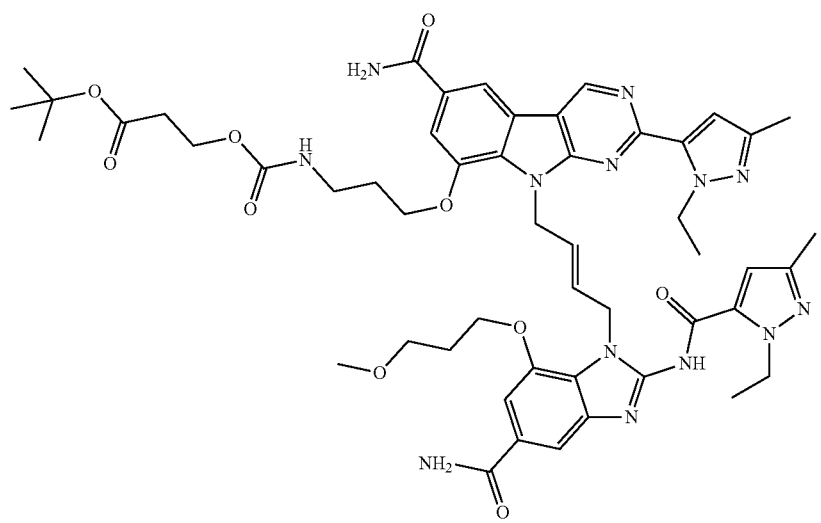 [SMILES: CCn1nc(C)cc1C(=O)Nc1nc2cc(C(N)=O)cc(OCCCOC)c2n1C/C=C/Cn1c2nc(-c3cc(C)nn3CC)ncc2c2cc(C(N)=O)cc(OCCCNC(=O)OCCC(=O)OC(C)(C)C)c21]

This compound was prepared using similar procedures as described for Example 39, Step 2 with (E)-8-(3-aminopropoxy)-9-(4-(5-carbamoyl-2-(1-ethyl-3-methyl-1H-pyrazole-5-carboxamido)-7-(3-methoxypropoxy)-1H-benzo[d]imidazol-1-yl)but-2-enyl)-2-(1-ethyl-3-methyl-1H-pyrazol-5-yl)-9H-pyrimido [4,5-b]indole-6-carboxamide (Example 50, Step 10) replacing (E)-9-(4-(7-(3-aminopropoxy)-5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazol-5-yl)-8-(3-methoxypropoxy)-9H-pyrimido[4,5-b]indole-6-carboxamide. LC-MS calculated for $C_{51}H_{64}N_{13}O_{10}$ (M+H)$^+$: m/z=1018.5; found 1018.4.

Step 2: (E)-3-(3-(6-carbamoyl-9-(4-(5-carbamoyl-2-(1-ethyl-3-methyl-1H-pyrazole-5-carboxamido)-7-(3-methoxypropoxy)-1H-benzo[d]imidazol-1-yl)but-2-enyl)-2-(1-ethyl-3-methyl-1H-pyrazol-5-yl)-9H-pyrimido[4,5-b]indol-8-yloxy)propylcarbamoyloxy)propanoic acid This compound was prepared using similar procedures as described for Example 37, Step 2 with (E)-tert-butyl 3-(3-(6-carbamoyl-9-(4-(5-carbamoyl-2-(1-ethyl-3-methyl-1H-pyrazole-5-carboxamido)-7-(3-methoxypropoxy)-1H-benzo[d]imidazol-1-yl)but-2-enyl)-2-(1-ethyl-3-methyl-1H-pyrazol-5-yl)-9H-pyrimido[4,5-b]indol-8-yloxy)propylcarbamoyloxy)propanoate replacing tert-butyl (6S,9S,12S,15S)-15-amino-6,9-bis(2-(tert-butoxy)-2-oxoethyl)-1-((5-carbamoyl-1-((E)-4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)-5,8,11,14-tetraoxo-12-(3-(3-((2,2,4,6,7-pentamethyl-2,3-dihydrobenzofuran-5-yl)sulfonyl) guanidino)propyl)-4,7,10,13-tetraazaheptadecan-17-oate. The reaction mixture was diluted with MeOH and purified by prep-HPLC (pH=2, acetonitrile/water+TFA) to give the desired product as its TFA salt. LC-MS calculated for $C_{47}H_{56}N_{13}O_{10}$ (M+H)$^+$: m/z=962.4; found 962.4.

Example 52. (E)-3-((3-(6-carbamoyl-9-(4-(5-carbamoyl-2-(1-ethyl-3-methyl-1H-pyrazole-5-carboxamido)-7-(3-methoxypropoxy)-1H-benzo[d]imidazol-1-yl)but-2-enyl)-2-(1-ethyl-3-methyl-1H-pyrazol-5-yl)-9H-pyrimido[4,5-b]indol-8-yloxy)propoxy)carbonylamino)propanoic acid

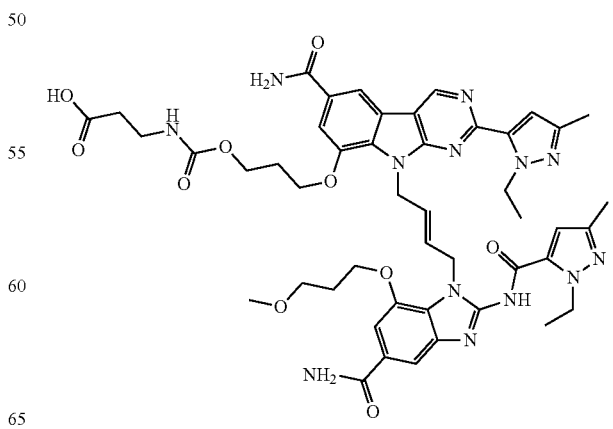

221

Step 1: (E)-8-(3-(tert-butyldimethylsilyloxy)propoxy)-9-(4-(5-carbamoyl-2-(1-ethyl-3-methyl-1H-pyrazole-5-carboxamido)-7-(3-methoxypropoxy)-1H-benzo[d]imidazol-1-yl)but-2-enyl)-2-(1-ethyl-3-methyl-1H-pyrazol-5-yl)-9H-pyrimido[4,5-b]indole-6-carboxamide

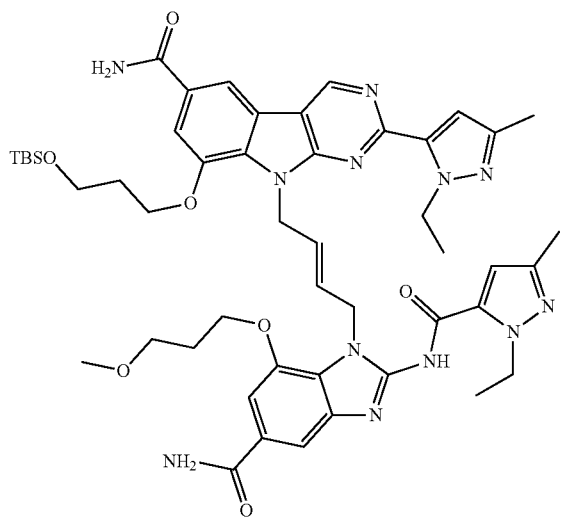 [SMILES: CCn1nc(C)cc1C(=O)Nc1nc2cc(C(N)=O)cc(OCCCOC)c2n1C/C=C/Cn1c2nc(-c3cc(C)nn3CC)ncc2c2cc(C(N)=O)cc(OCCCO[Si](C)(C)C(C)(C)C)c21]

This compound was prepared using similar procedures as described for Example 50, Step 9 with 8-(3-(tert-butyldimethylsilyloxy)propoxy)-2-(1-ethyl-3-methyl-1H-pyrazol-5-yl)-9H-pyrimido[4,5-b]indole-6-carboxamide (Example 13, Step 3) replacing tert-butyl (3-((6-carbamoyl-2-(1-ethyl-3-methyl-1H-pyrazol-5-yl)-9H-pyrimido[4,5-b]indol-8-yl)oxy)propyl)carbamate. LC-MS calculated for $C_{49}H_{65}N_{12}O_7Si$ (M+H)$^+$: m/z=961.5; found 961.6.

222

Step 2: (E)-9-(4-(5-carbamoyl-2-(1-ethyl-3-methyl-1H-pyrazole-5-carboxamido)-7-(3-methoxypropoxy)-1H-benzo[d]imidazol-1-yl)but-2-enyl)-2-(1-ethyl-3-methyl-1H-pyrazol-5-yl)-8-(3-hydroxypropoxy)-9H-pyrimido[4,5-b]indole-6-carboxamide

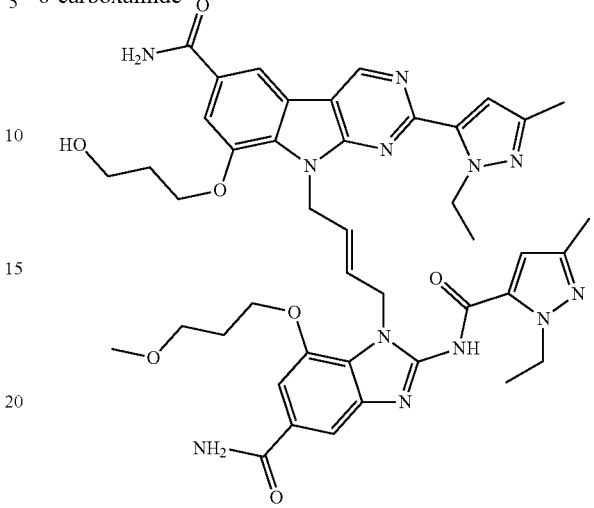

This compound was prepared using similar procedures as described in Example 33, Step 9 with (E)-8-(3-tert-butyldimethylsilyloxy)propoxy)-9-(4-(5-carbamoyl-2-(1-ethyl-3-methyl-1H-pyrazole-5-carboxamido)-7-(3-methoxypropoxy)-1H-benzo[d]imidazol-1-yl)but-2-enyl)-2-(1-ethyl-3-methyl-1H-pyrazol-5-yl)-9H-pyrimido[4,5-b]indole-6-carboxamide replacing tert-butyl (E)-(3-((5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propyl)carbamate. The reaction mixture was concentrated and used in the next step without further purification. LC-MS calculated for $C_{43}H_{51}N_{12}O_7$ (M+H)$^+$: m/z=847.4; found 847.4.

Step 3: (E)-ethyl 3-((3-(6-carbamoyl-9-(4-(5-carbamoyl-2-(1-ethyl-3-methyl-1H-pyrazole-5-carboxamido)-7-(3-methoxypropoxy)-1H-benzo[d]imidazol-1-yl)but-2-enyl)-2-(1-ethyl-3-methyl-1H-pyrazol-5-yl)-9H-pyrimido[4,5-b]indol-8-yloxy)propoxy)carbonylamino)propanoate

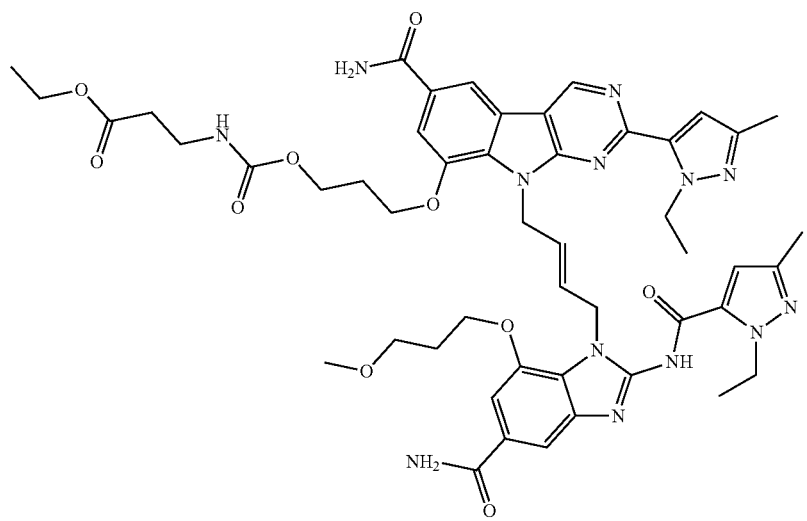 [SMILES: CCOC(=O)CCNC(=O)OCCCOc1cc(C(N)=O)cc2c3cnc(-c4cc(C)nn4CC)nc3n(C/C=C/Cn3c(NC(=O)c4cc(C)nn4CC)nc4cc(C(N)=O)cc(OCCCOC)c43)c12]

223

This compound was prepared using similar procedures as described for Example 43, Step 2 with (E)-9-(4-(5-carbamoyl-2-(1-ethyl-3-methyl-1H-pyrazole-5-carboxamido)-7-(3-methoxypropoxy)-1H-benzo[d]imidazol-1-yl)but-2-enyl)-2-(1-ethyl-3-methyl-1H-pyrazol-5-yl)-8-(3-hydroxypropoxy)-9H-pyrimido[4,5-b]indole-6-carboxamide replacing tert-butyl (E)-(4-(5-carbamoyl-2-(1-ethyl-3-methyl-1H-pyrazole-5-carboxamido)-7-(3-hydroxypropoxy)-1H-benzo[d]imidazol-1-yl)but-2-en-1-yl)carbamate. The reaction mixture was concentrated and used in the next step without further purification. LC-MS calculated for $C_{49}H_{60}N_{13}O_{10}$ (M+H)$^+$: m/z=990.5; found 990.7.

Step 4: (E)-3-((3-(6-carbamoyl-9-(4-(5-carbamoyl-2-(1-ethyl-3-methyl-1H-pyrazole-5-carboxamido)-7-(3-methoxypropoxy)-1H-benzo[d]imidazol-1-yl)but-2-enyl)-2-(1-ethyl-3-methyl-1H-pyrazol-5-yl)-9H-pyrimido[4,5-b]indol-8-yloxy)propoxy)carbonylamino)propanoic acid This compound was prepared using similar procedures as described for Example 34, Step 2 with (E)-ethyl 3-((3-(6-carbamoyl-9-(4-(5-carbamoyl-2-(1-ethyl-3-methyl-1H-pyrazole-5-carboxamido)-7-(3-methoxypropoxy)-1H-benzo[d]imidazol-1-yl)but-2-enyl)-2-(1-ethyl-3-methyl-1H-pyrazol-5-yl)-9H-pyrimido[4,5-b]indol-8-yloxy)propoxy)carbonylamino)propanoate replacing methyl (E)-5-((3-((5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propyl)amino)-5-oxopentanoate. The reaction mixture was diluted with MeOH and purified by prep-HPLC (pH=2, acetonitrile/water+TFA) to give the desired product as its TFA salt. LC-MS calculated for $C_{47}H_{56}N_{13}O_{10}$ (M+H)$^+$: m/z=962.4; found 962.6.

Example 53. (E)-3-(2-(2-(6-carbamoyl-9-(4-(5-carbamoyl-2-(1-ethyl-3-methyl-1H-pyrazole-5-carboxamido)-7-(3-methoxypropoxy)-1H-benzo[d]imidazol-1-yl)but-2-enyl)-2-(1-ethyl-3-methyl-1H-pyrazol-5-yl)-9H-pyrimido[4,5-b]indol-8-yloxy)ethoxy)ethoxy)propanoic acid

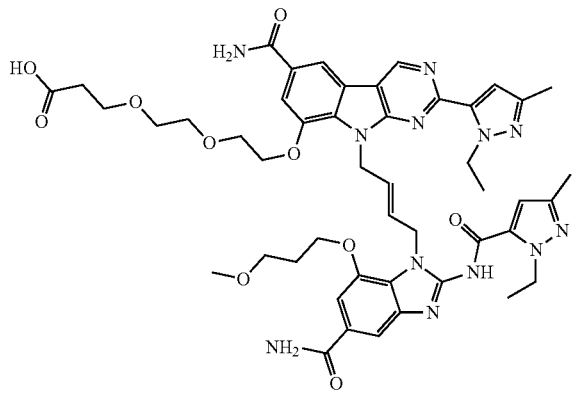 [SMILES: CCn1nc(C)cc1C(=O)Nc1nc2cc(C(N)=O)cc(OCCCOC)c2n1C/C=C/Cn1c2nc(-c3cc(C)nn3CC)ncc2c2cc(C(N)=O)cc(OCCOCCOCCC(=O)O)c21]

224

Step 1: tert-butyl 3-(2-(2-(3-bromo-5-carbamoyl-2-nitrophenoxy)ethoxy)ethoxy)propanoate

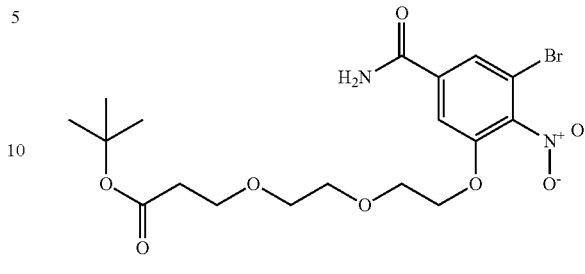

This compound was prepared using similar procedures as described for Example 11, Step 1 with tert-butyl 3-(2-(2-hydroxyethoxy)ethoxy)propanoate (Aldrich, cat #ANV00316) replacing 3-morpholinopropan-1-ol. LC-MS calculated for $C_{18}H_{25}BrN_2NaO_8$ (M+H)$^+$: m/z=499.1, 501.1; found 499.2, 501.2.

Step 2: tert-butyl 3-(2-(2-(5-carbamoyl-3-(2-(1-ethyl-3-methyl-1H-pyrazol-5-yl)pyrimidin-5-yl)-2-nitrophenoxy)ethoxy)ethoxy)propanoate

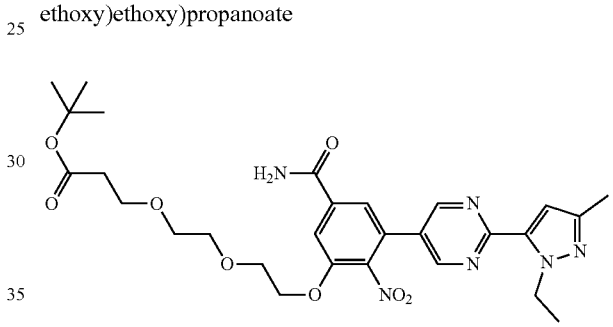

This compound was prepared using similar procedures as described for Example 10, Step 3 with tert-butyl 3-(2-(2-(3-bromo-5-carbamoyl-2-nitrophenoxy)ethoxy)ethoxy)propanoate replacing 3-bromo-5-methoxy-4-nitrobenzamide. LC-MS calculated for $C_{28}H_{37}N_6O_8$ (M+H)$^+$: m/z=585.3; found 585.2.

Step 3: tert-butyl 3-(2-(2-((6-carbamoyl-2-(1-ethyl-3-methyl-1H-pyrazol-5-yl)-9H-pyrimido[4,5-b]indol-8-yl)oxy)ethoxy)ethoxy)propanoate

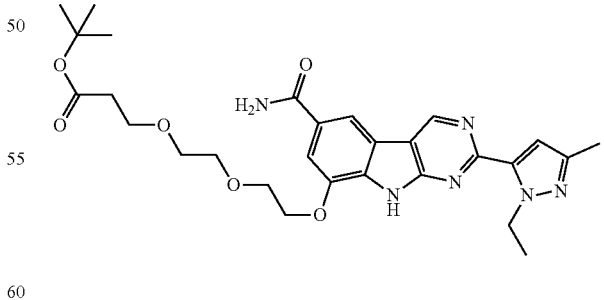

This compound was prepared using similar procedures as described for Example 10, Step 4 with tert-butyl 3-(2-(2-(5-carbamoyl-3-(2-(1-ethyl-3-methyl-1H-pyrazol-5-yl)pyrimidin-5-yl)-2-nitrophenoxy)ethoxy)ethoxy)propanoate replacing 3-(2-(1-ethyl-3-methyl-1H-pyrazol-5-yl)pyrimidin-5-yl)-5-methoxy-4-nitrobenzamide. LC-MS calculated for $C_{20}H_{37}N_6O_6$ (M+H)$^+$: m/z=553.3; found 553.3.

Step 4: (E)-tert-butyl 3-(2-(2-(6-carbamoyl-9-(4-(5-carbamoyl-2-(1-ethyl-3-methyl-1H-pyrazole-5-carboxamido)-7-(3-methoxypropoxy)-1H-benzo[d]imidazol-1-yl)but-2-enyl)-2-(1-ethyl-3-methyl-1H-pyrazol-5-yl)-9H-pyrimido[4,5-b]indol-8-yloxy)ethoxy)ethoxy)propanoate

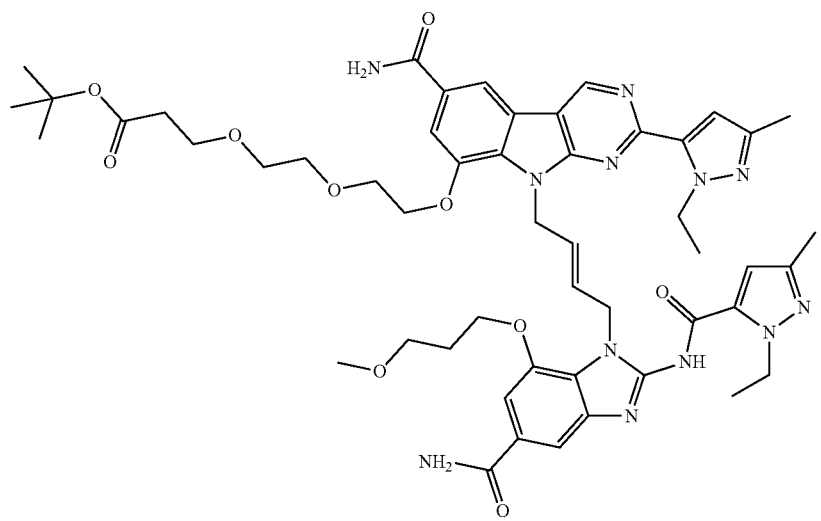 [SMILES: CCn1nc(C)cc1C(=O)Nc1nc2cc(C(N)=O)cc(OCCCOC)c2n1C/C=C/Cn1c2nc(-c3cc(C)nn3CC)ncc2c2cc(C(N)=O)cc(OCCOCCOCCC(=O)OC(C)(C)C)c21]

This compound was prepared using similar procedures as described for Example 50, Step 9 with tert-butyl 3-(2-(2-((6-carbamoyl-2-(1-ethyl-3-methyl-1H-pyrazol-5-yl)-9H-pyrimido[4,5-b]indol-8-yl)oxy)ethoxy)ethoxy)propanoate replacing tert-butyl (3-((6-carbamoyl-2-(1-ethyl-3-methyl-1H-pyrazol-5-yl)-9H-pyrimido[4,5-b]indol-8-yl)oxy)propyl)carbamate. LC-MS calculated for $C_{51}H_{65}N_{12}O_{10}$ (M+H)$^+$: m/z=1005.5; found 1005.7.

Step 5: (E)-3-(2-(2-(6-carbamoyl-9-(4-(5-carbamoyl-2-(1-ethyl-3-methyl-1H-pyrazole-5-carboxamido)-7-(3-methoxypropoxy)-1H-benzo[d]imidazol-1-yl)but-2-enyl)-2-(1-ethyl-3-methyl-1H-pyrazol-5-yl)-9H-pyrimido[4,5-b]indol-8-yloxy)ethoxy)ethoxy)propanoic acid This compound was prepared using similar procedures as described for Example 37, Step 2 with (E)-tert-butyl 3-(2-(2-(6-carbamoyl-9-(4-(5-carbamoyl-2-(1-ethyl-3-methyl-1H-pyrazole-5-carboxamido)-7-(3-methoxypropoxy)-1H-benzo[d]imidazol-1-yl)but-2-enyl)-2-(1-ethyl-3-methyl-1H-pyrazol-5-yl)-9H-pyrimido[4,5-b]indol-8-yloxy)ethoxy)ethoxy)propanoate replacing tert-butyl (6S,9S,12S,15S)-15-amino-6,9-bis(2-(tert-butoxy)-2-oxoethyl)-1-((5-carbamoyl-1-((E)-4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)-5,8,11,14-tetraoxo-12-(3-(3-((2,2,4,6,7-pentamethyl-2,3-dihydrobenzofuran-5-yl))sulfonyl)guanidino)propyl)-4,7,10,13-tetraazaheptadecan-17-oate. The reaction mixture was diluted with MeOH and purified by prep-HPLC (pH=2, acetonitrile/water+TFA) to give the desired product as its TFA salt. LC-MS calculated for $C_{47}H_{57}N_{12}O_{10}$ (M+H)$^+$: m/z=949.4; found 949.6.

Example 54. (E)-3-(2-(2-(2-(6-carbamoyl-9-(4-(5-carbamoyl-2-(1-ethyl-3-methyl-1H-pyrazole-5-carboxamido)-7-(3-methoxypropoxy)-1H-benzo[d]imidazol-1-yl)but-2-enyl)-2-(1-ethyl-3-methyl-1H-pyrazol-5-yl)-9H-pyrimido[4,5-b]indol-8-yloxy)ethoxy)ethoxy)ethoxy)propanoic acid

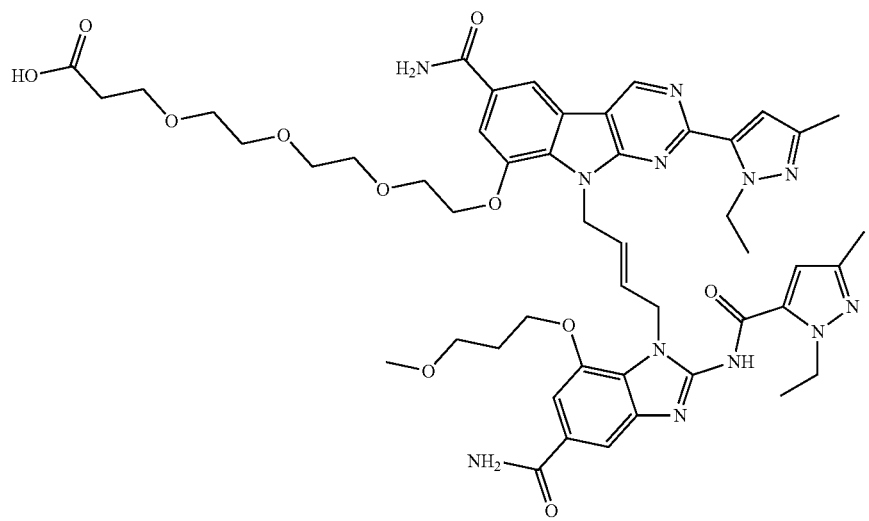 [SMILES: CCn1nc(C)cc1C(=O)Nc1nc2cc(C(N)=O)cc(OCCCOC)c2n1C/C=C/Cn1c2nc(-c3cc(C)nn3CC)ncc2c2cc(C(N)=O)cc(OCCOCCOCCOCCC(=O)O)c21]

This compound was prepared using similar procedures as described for Example 53, with tert-butyl 3-(2-(2-(2-hydroxyethoxy)ethoxy)ethoxy)propanoate (AURUM pharmatech, cat #U37808) replacing tert-butyl 3-(2-(2-hydroxyethoxy)ethoxy)propanoate in Step 1. After finishing the final step, the reaction mixture was diluted with MeOH and purified by prep-HPLC (pH=2, acetonitrile/water+TFA) to give the desired product as its TFA salt. LC-MS calculated for $C_{49}H_{61}N_{12}O_{11}$ (M+H)$^+$: m/z=993.5; found 993.6.

Example 55. (E)-4-(4-(2-(6-carbamoyl-9-(4-(5-carbamoyl-2-(1-ethyl-3-methyl-1H-pyrazole-5-carboxamido)-7-methoxy-1H-benzo[d]imidazol-1-yl)but-2-enyl)-2-(1-ethyl-3-methyl-1H-pyrazol-5-yl)-9H-pyrimido[4,5-b]indol-8-yloxy)ethyl)piperidin-1-yl)butanoic acid

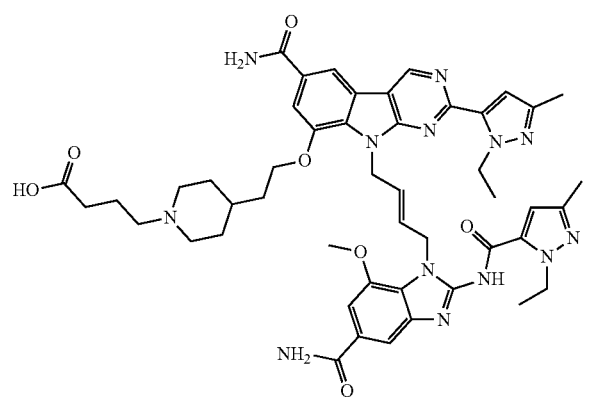 [SMILES: CCn1nc(C)cc1C(=O)Nc1nc2cc(C(N)=O)cc(OC)c2n1C/C=C/Cn1c2nc(-c3cc(C)nn3CC)ncc2c2cc(C(N)=O)cc(OCCC3CCN(CCCC(=O)O)CC3)c21]

Step 1: (E)-9-(4-(5-carbamoyl-2-(1-ethyl-3-methyl-1H-pyrazole-5-carboxamido)-7-methoxy-1H-benzo[d]imidazol-1-yl)but-2-enyl)-2-(1-ethyl-3-methyl-1H-pyrazol-5-yl)-8-(2-(piperidin-4-yl)ethoxy)-9H-pyrimido[4,5-b]indole-6-carboxamide

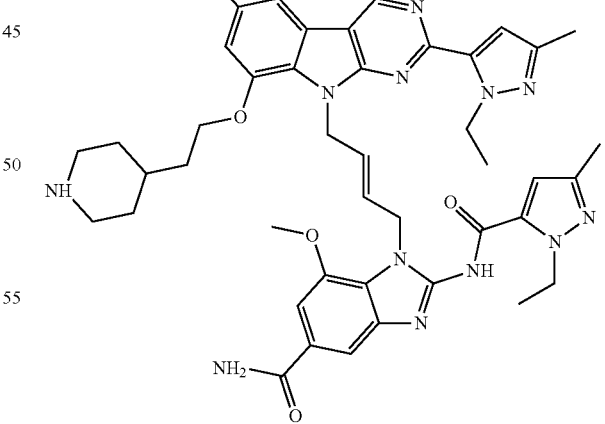

This compound was prepared using similar procedures as described for Example 46, Steps 1 to 5 with tert-butyl 4-(2-hydroxyethyl)piperidine-1-carboxylate (Matrix Scientific, cat #069039) replacing tert-butyl 3-hydroxypropylcarbamate in Step 1. LC-MS calculated for $C_{44}H_{52}N_{13}O_5$ (M+H)$^+$: m/z=842.4; found 842.6.

Step 2: (E)-4-(4-(2-(6-carbamoyl-9-(4-(5-carbamoyl-2-(1-ethyl-3-methyl-1H-pyrazole-5-carboxamido)-7-methoxy-1H-benzo[d]imidazol-1-yl)but-2-enyl)-2-(1-ethyl-3-methyl-1H-pyrazol-5-yl)-9H-pyrimido[4,5-b]indol-8-yloxy)ethyl)piperidin-1-yl)butanoic acid This compound was prepared using similar procedures as described for Example 46, Steps 6 and 7 with (E)-9-(4-(5-carbamoyl-2-(1-ethyl-3-methyl-1H-pyrazole-5-carboxamido)-7-methoxy-1H-benzo[d]imidazol-1-yl)but-2-enyl)-2-(1-ethyl-3-methyl-1H-pyrazol-5-yl)-8-(2-(piperidin-4-yl)ethoxy)-9H-pyrimido[4,5-b]indole-6-carboxamide replacing (E)-8-(3-aminopropoxy)-9-(4-(5-carbamoyl-2-(1-ethyl-3-methyl-1H-pyrazole-5-carboxamido)-7-methoxy-1H-benzo[d]imidazol-1-yl)but-2-enyl)-2-(1-ethyl-3-methyl-1H-pyrazol-5-yl)-9H-pyrimido[4,5-b]indole-6-carboxamide in Step 6. After finishing the final step, the reaction mixture was diluted with MeOH and purified by prep-HPLC (pH=2, acetonitrile/water+TFA) to give the desired product as its TFA salt. LC-MS calculated for $C_{48}H_{58}N_{13}O_7$ $(M+H)^+$: m/z=928.5; found 928.5.

Example 56. (E)-2-(4-(2-(6-carbamoyl-9-(4-(5-carbamoyl-2-(1-ethyl-3-methyl-1H-pyrazole-5-carboxamido)-7-methoxy-1H-benzo[d]imidazol-1-yl)but-2-enyl)-2-(1-ethyl-3-methyl-1H-pyrazol-5-yl)-9H-pyrimido[4,5-b]indol-8-yloxy)ethyl)piperidine-1-carbonyloxy)acetic acid

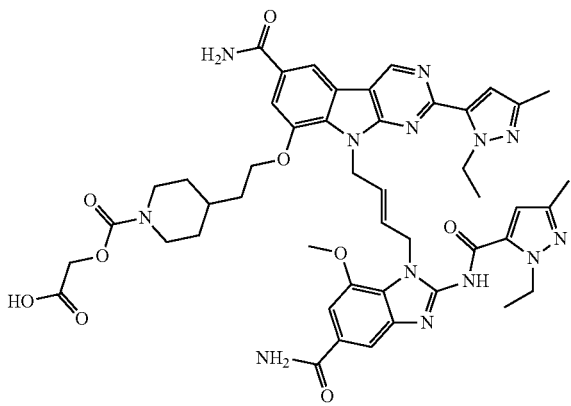 [SMILES: CCn1nc(C)cc1C(=O)Nc1nc2cc(C(N)=O)cc(OC)c2n1C/C=C/Cn1c2nc(-c3cc(C)nn3CC)ncc2c2cc(C(N)=O)cc(OCCC3CCN(C(=O)OCC(=O)O)CC3)c21]

This compound was prepared using similar procedures as described for Example 40, Steps 2 and 3, with (E)-9-(4-(5-carbamoyl-2-(1-ethyl-3-methyl-1H-pyrazole-5-carboxamido)-7-methoxy-1H-benzo[d]imidazol-1-yl)but-2-enyl)-2-(1-ethyl-3-methyl-1H-pyrazol-5-yl)-8-(2-(piperidin-4-yl)ethoxy)-9H-pyrimido[4,5-b]indole-6-carboxamide (Example 55, Step 1) replacing (E)-9-(4-(7-(3-aminopropoxy)-5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazol-5-yl)-8-(3-methoxypropoxy)-9H-pyrimido[4,5-b]indole-6-carboxamide in Step 2. After finishing the final step, the reaction mixture was diluted with MeOH and purified by prep-HPLC (pH=2, acetonitrile/water+TFA) to give the desired product as its TFA salt. LC-MS calculated for $C_{47}H_{54}N_{13}O_9$ $(M+H)^+$: m/z=944.4; found 944.5.

Example 57. (E)-3-((3-(6-carbamoyl-9-(4-(5-carbamoyl-2-(1-ethyl-3-methyl-1H-pyrazole-5-carboxamido)-7-(3-hydroxypropoxy)-1H-benzo[d]imidazol-1-yl)but-2-enyl)-2-(1-ethyl-3-methyl-1H-pyrazol-5-yl)-9H-pyrimido[4,5-b]indol-8-yloxy)propoxy)carbonylamino)propanoic acid

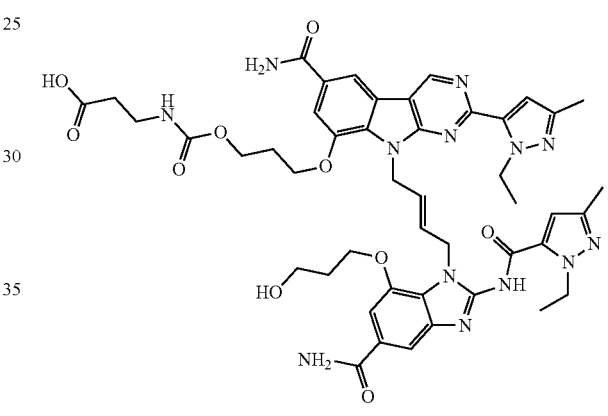

Step 1: (E)-3-(5-carbamoyl-1-(4-(6-carbamoyl-8-(3-(3-ethoxy-3-oxopropylcarbamoyloxy)propoxy)-2-(1-ethyl-3-methyl-1H-pyrazol-5-yl)-9H-pyrimido[4,5-b]indol-9-yl)but-2-enyl)-2-(1-ethyl-3-methyl-1H-pyrazole-5-carboxamido)-1H-benzo[d]imidazol-7-yloxy)propyl 1-ethyl-3-methyl-1H-pyrazole-5-carboxylate

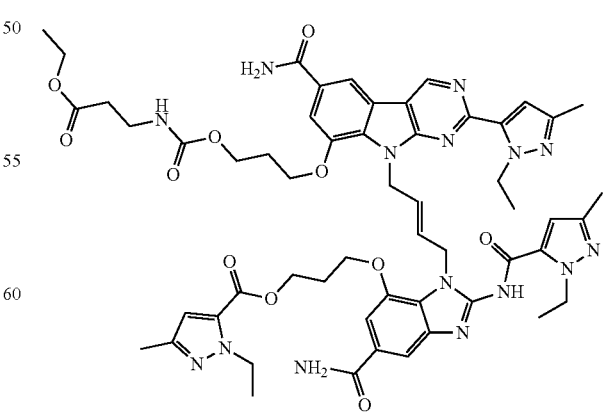

This compound was prepared using similar procedures as described for Example 52, Steps 1 to 3 with (E)-3-(1-(4-bromobut-2-enyl)-5-carbamoyl-2-(1-ethyl-3-methyl-1H-pyrazole-5-carboxamido)-1H-benzo[d]imidazol-7-yloxy)propyl 1-ethyl-3-methyl-1H-pyrazole-5-carboxylate (Example 15, Step 9) replacing (E)-1-(4-bromobut-2-enyl)-2-(1-ethyl-3-methyl-1H-pyrazole-5-carboxamido)-7-(3-methoxypropoxy)-1H-benzo[d]imidazole-5-carboxamide in Step 1.

Step 2: (E)-3-((3-(6-carbamoyl-9-(4-(5-carbamoyl-2-(1-ethyl-3-methyl-1H-pyrazole-5-carboxamido)-7-(3-hydroxypropoxy)-1H-benzo[d]imidazol-1-yl)but-2-enyl)-2-(1-ethyl-3-methyl-1H-pyrazol-5-yl)-9H-pyrimido[4,5-b]indol-8-yloxy)propoxy)carbonylamino)propanoic acid This compound was prepared using similar procedures as described for Example 34, Step 2 with (E)-3-(5-carbamoyl-1-(4-(6-carbamoyl-8-(3-(3-ethoxy-3-oxopropylcarbamoyloxy)propoxy)-2-(1-ethyl-3-methyl-1H-pyrazol-5-yl)-9H-pyrimido[4,5-b]indol-9-yl)but-2-enyl)-2-(1-ethyl-3-methyl-1H-pyrazole-5-carboxamido)-1H-benzo[d]imidazol-7-yloxy)propyl 1-ethyl-3-methyl-1H-pyrazole-5-carboxylate replacing methyl (E)-5-((3-((5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propyl)amino)-5-oxopentanoate. The reaction mixture was diluted with MeOH and purified by prep-HPLC (pH=2, acetonitrile/water+TFA) to give the desired product as its TFA salt. LC-MS calculated for $C_{46}H_{54}N_{13}O_{10}$ (M+H)$^+$: m/z=948.4; found 948.5.

Example 58. (E)-3-(((3-((5-carbamoyl-1-(4-(6-carbamoyl-8-(2-(2-(2-carboxyethoxy)ethoxy)ethoxy)-2-(1-ethyl-3-methyl-1H-pyrazol-5-yl)-9H-pyrimido[4,5-b]indol-9-yl)but-2-en-1-yl)-2-(1-ethyl-3-methyl-1H-pyrazole-5-carboxamido)-1H-benzo[d]imidazol-7y-l)oxy)propoxy)carbonyl)amino)propanoic acid

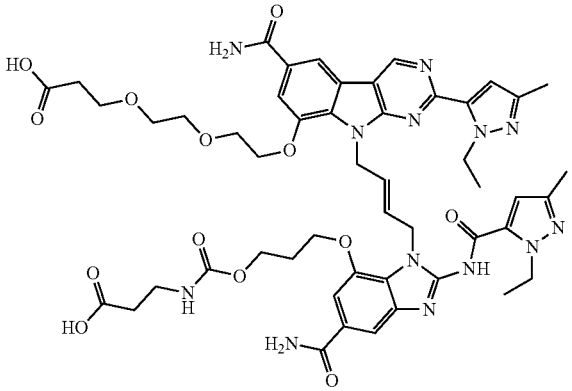 [SMILES: CCn1nc(C)cc1C(=O)Nc1nc2cc(C(N)=O)cc(OCCCOC(=O)NCCC(=O)O)c2n1C/C=C/Cn1c2nc(-c3cc(C)nn3CC)ncc2c2cc(C(N)=O)cc(OCCOCCOCCC(=O)O)c21]

Step 1: (E)-3-((1-(4-(8-(2-(2-(3-(tert-butoxy)-3-oxopropoxy)ethoxy)ethoxy)-6-carbamoyl-2-(1-ethyl-3-methyl-1H-pyrazol-5-yl)-9H-pyrimodo[4,5-b]indol-9-yl)but-2-en-1-yl)-5-carbamoyl-2-(1-ethyl-3-methyl-1H-pyrazole-5-carboxamido)-1H-benzo[d]imidazol-7-yl)oxy)propyl 1-ethyl-3-methyl-1H-pyrazole-5-carboxylate

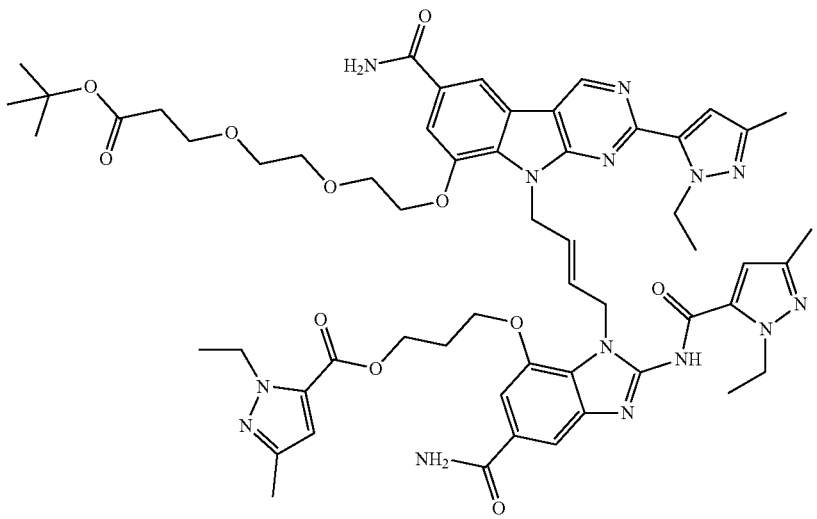 [SMILES: CCn1nc(C)cc1C(=O)Nc1nc2cc(C(N)=O)cc(OCCCOC(=O)c3cc(C)nn3CC)c2n1C/C=C/Cn1c2nc(-c3cc(C)nn3CC)ncc2c2cc(C(N)=O)cc(OCCOCCOCCC(=O)OC(C)(C)C)c21]

This compound was prepared using similar procedures as described for Example 53, Steps 1 to 3 with (E)-3-(1-(4-bromobut-2-enyl)-5-carbamoyl-2-(1-ethyl-3-methyl-1H-pyrazole-5-carboxamido)-1H-benzo[d]imidazol-7-yloxy)propyl 1-ethyl-3 -methyl-1H-pyrazole-5-carboxylate (Example 15, Step 9) replacing (E)-1-(4-bromobut-2-enyl)-2-(1-ethyl-3-methyl-1H-pyrazole-5-carboxamido)-7-(3-methoxypropoxy)-1H-benzo[d]imidazole-5-carboxamide in Step 1. LC-MS calculated for $C_{57}H_{71}N_{14}O_{11}$ $(M+H)^+$: m/z=1127.5; found 1127.2.

Step 2: tert-butyl (E)-3-(2-(2-((6-carbamoyl-9-(4-(5-carbamoyl-2-(1-ethyl-3-methyl-1H-pyrazole-5-carboxamido)-7-(3-hydroxypropoxy)-1H-benzo[d]imidazol-1-yl)but-2-en-1-yl)-2-(1-ethyl-3-methyl-1H-pyrazol-5-yl)-9H-pyrimido[4,5-b]indol-8-yl)oxy)ethoxy)ethoxy)propanoate

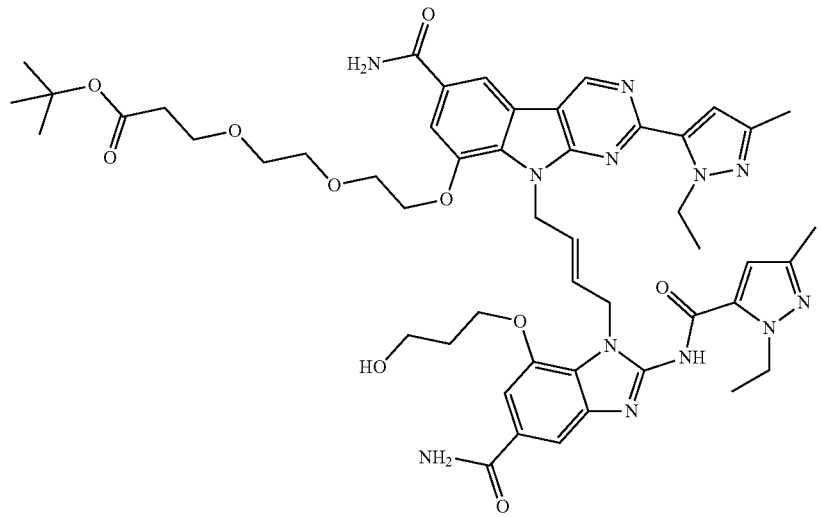 [SMILES: CCn1nc(C)cc1C(=O)Nc1nc2cc(C(N)=O)cc(OCCCO)c2n1C/C=C/Cn1c2nc(-c3cc(C)nn3CC)ncc2c2cc(C(N)=O)cc(OCCOCCOCCC(=O)OC(C)(C)C)c21]

This compound was prepared using similar procedures as described for Example 34, Step 2 with (E)-3-((1-(4-(8-(2-(2-(3-(tert-butoxy)-3-oxopropoxy)ethoxy)ethoxy)-6-carbamoyl-2-(1-ethyl-3-methyl-1H-pyrazol-5-yl)-9H-pyrimido[4,5-b]indol-9-yl)but-2-en-1-yl)-5-carbamoyl-2-(1-ethyl-3-methyl-1H-pyrazole-5-carboxamido)-1H-benzo[d]imidazol-7-yl)oxy)propyl 1-ethyl-3-methyl-1H-pyrazole-5-carboxylate replacing methyl (E)-5-((3-((5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propyl)amino)-5-oxopentanoate. LC-MS calculated for $C_{50}H_{63}N_{12}O_{10}$ $(M+H)^+$: m/z=991.5; found 991.4.

Step 3: tert-butyl (E)-3-(2-(2-((6-carbamoyl-9-(4-(5-carbamoyl-7-(3-(((3-ethoxy-3-oxopropyl)carbamoyl)oxy)propoxy)-2-(1-ethyl-3-methyl-1H-pyrazole-5-carboxamido)-1H-benzo[d]imidazol-1-yl)but-2-en-1-yl)-2-(1-ethyl-3-methyl-1H-pyrazol-5-yl)-9H-pyrimido[4,5-b]indol-8-yl)oxy)ethoxy)ethoxy)propanoate

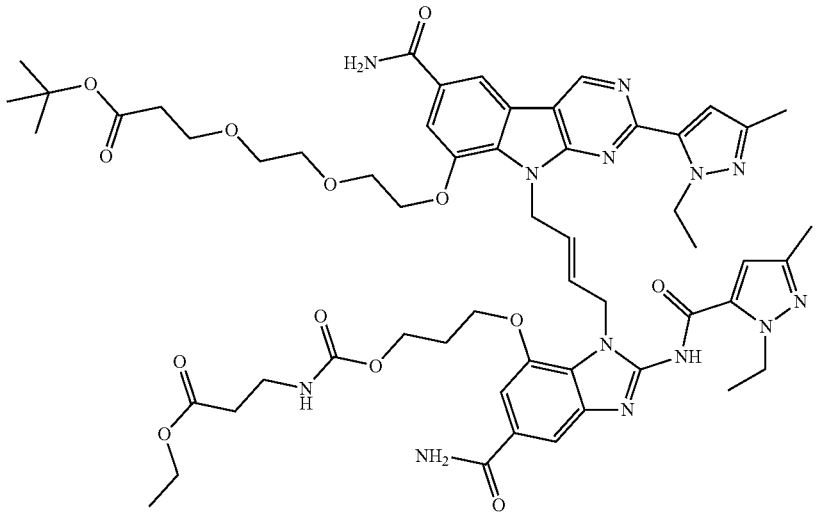 [SMILES: CCOC(=O)CCNC(=O)OCCCOc1cc(C(N)=O)cc2nc(NC(=O)c3cc(C)nn3CC)n(C/C=C/Cn3c4nc(-c5cc(C)nn5CC)ncc4c4cc(C(N)=O)cc(OCCOCCOCCC(=O)OC(C)(C)C)c43)c12]

This compound was prepared using similar procedures as described for Example 43, Step 2 with tert-butyl (E)-3-(2-(2-(((6-carbamoyl-9-(4-(5-carbamoyl-2-(1-ethyl-3-methyl-1H-pyrazole-5-carboxamido)-7-(3-hydroxypropoxy)-1H-benzo[d]imidazol-1-yl)but-2-en-1-yl)-2-(1-ethyl-3-methyl-1H-pyrazol-5-yl)-9H-pyrimido[4,5-b]indol-8-yl)oxy)ethoxy)ethoxy)propanoate replacing tert-butyl (E)-(4-(5-carbamoyl-2-(1-ethyl-3-methyl-1H-pyrazole-5-carboxamido)-7-(3-hydroxypropoxy)-1H-benzo[d]imidazol-1-yl)but-2-en-1-yl)carbamate. The reaction mixture was concentrated and used in the next step without further purification. LC-MS calculated for $C_{56}H_{72}N_{13}O_{13}$ $(M+H)^+$: m/z=1134.5; found 1134.6.

Step 4: (E)-3-(((3-((1-(4-(8-(2-(2-(3-(tert-butoxy)-3-oxopropoxy)ethoxy)ethoxy)-6-carbamoyl-2-(1-ethyl-3-methyl-1H-pyrazol-5-yl)-9H-pyrimido[4,5-b]indol-9-yl)but-2-en-1-yl)-5-carbamoyl-2-(1-ethyl-3-methyl-1H-pyrazole-5-carboxamido)-1H-benzo[d]imidazol-7-yl)oxy)propoxy)carbonyl)amino)propanoic acid

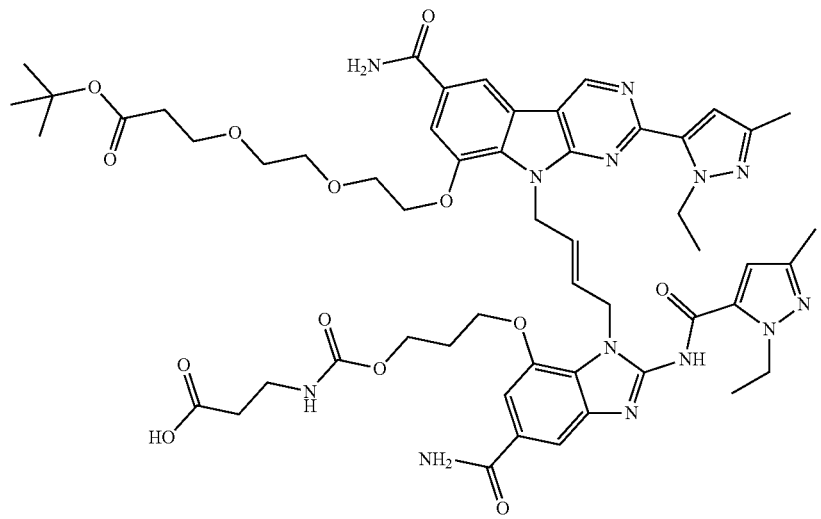 [SMILES: CCn1nc(C)cc1C(=O)Nc1nc2cc(C(N)=O)cc(OCCCOC(=O)NCCC(=O)O)c2n1C/C=C/Cn1c2nc(-c3cc(C)nn3CC)ncc2c2cc(C(N)=O)cc(OCCOCCOCCC(=O)OC(C)(C)C)c21]

This compound was prepared using similar procedures as described for Example 34, Step 2 with tert-butyl (E)-3-(2-(2-(((6-carbamoyl-9-(4-(5-carbamoyl-7-(3-(((3-ethoxy-3-oxopropyl)carbamoyl)oxy)propoxy)-2-(1-ethyl-3-methyl-1H-pyrazole-5-carboxamido)-1H-benzo[d]imidazol-1-yl)but-2-en-1-yl)-2-(1-ethyl-3-methyl-1H-pyrazol-5-yl)-9H-pyrimido[4,5-b]indol-8-yl)oxy)ethoxy)ethoxy)propanoate replacing methyl (E)-5-((3-((5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propyl)amino)-5-oxopentanoate. LC-MS calculated for $C_{54}H_{68}N_{13}O_{13}$ $(M+H)^+$: m/z=1106.5; found 1106.7.

Step 5: (E)-3-(((3-((5-carbamoyl-1-(4-(6-carbamoyl-8-(2-(2-(2-carboxyethoxy)ethoxy)ethoxy)-2-(1-ethyl-3-methyl-1H-pyrazol-5-yl)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propoxy)carbonyl)amino)propanoic acid This compound was prepared using similar procedures as described for Example 37, Step 2 with (E)-3-(((3-((1-(4-(8-(2-(2-(3-(tert-butoxy)-3-oxopropoxy)ethoxy)ethoxy)-6-carbamoyl-2-(1-ethyl-3-methyl-1H-pyrazol-5-yl)-9H-pyrimido[4,5-b]indol-9-yl)but-2-en-1-yl)-5-carbamoyl-2-(1-ethyl-3-methyl-1H-pyrazole-5-carboxamido)-1H-benzo[d]imidazol-7-yl)oxy)propoxy)carbonyl)amino)propanoic acid replacing tert-butyl (6S,9S,12S,15S)-15-amino-6,9-bis(2-(tert-butoxy)-2-oxoethyl)-1-((5-carbamoyl-1-((E)-4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)-5,8,11,14-tetraoxo-12-(3-(3-(2,2,4,6,7-pentamethyl-2,3-dihydrobenzofuran-5-yl)sulfonyl)guanidino)propyl)-4,7,10,13-tetraazaheptadecan-17-oate. The reaction mixture was diluted with MeOH and purified by prep-HPLC (pH=2, acetonitrile/water+TFA) to give the desired product as its TFA salt. LC-MS calculated for $C_{50}H_{60}N_{13}O_{13}$ (M+H)$^+$: m/z=1050.4; found 1050.5.

Example 59. (E)-4-((3-((5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propyl)amino)-4-oxobutanoic acid

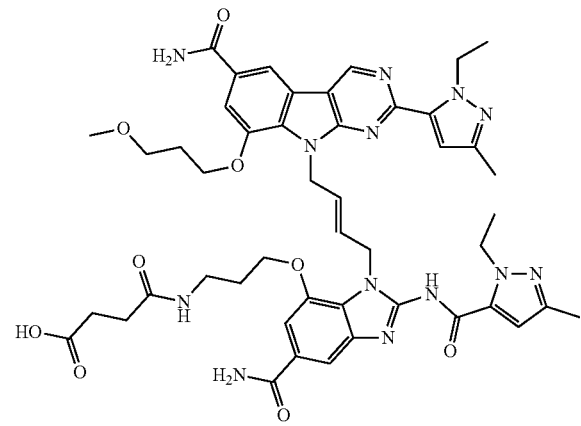 [SMILES: CCn1nc(C)cc1C(=O)Nc1nc2cc(C(N)=O)cc(OCCCNC(=O)CCC(=O)O)c2n1C/C=C/Cn1c2nc(-c3cc(C)nn3CC)ncc2c2cc(C(N)=O)cc(OCCCOC)c21]

Step 1: methyl (E)-4-((3-((5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propyl)amino)-4-oxobutanoate

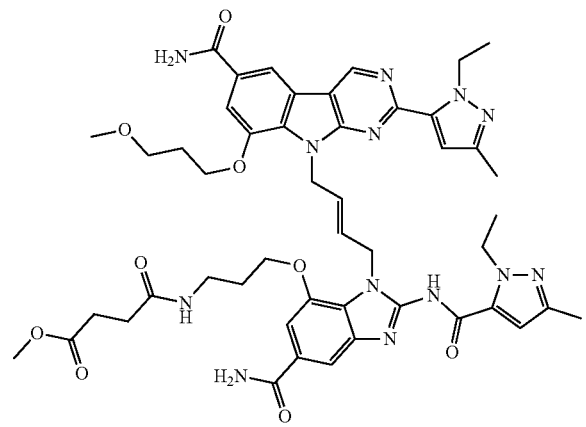

This compound was prepared using similar procedures as described for Example 34, Step 1 with mono-methyl hydrogen succinate replacing mono-methyl glutarate. LC-MS calculated for $C_{48}H_{58}N_{13}O_9$ (M+H)$^+$: m/z=960.4; found 960.5.

Step 2: (E)-4-((3-((5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propyl)amino)-4-oxobutanoic acid This compound was prepared using similar procedures as described for Example 34, Step 2 with methyl (E)-4-((3-((5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propyl)amino)-4-oxobutanoate replacing methyl (E)-5-((3-((5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propyl)amino)-5-oxopentanoate. LC-MS calculated for $C_{47}H_{56}N_{13}O_9$ (M+H)$^+$: m/z=946.4; found 946.5.

Example A. IRF3 and NF-κB Activation Assays

THP-1 Dual Cells (Invivogen) were maintained in RPMI1640 medium with addition of 10% FBS, 100 μg/ml zeocin, 10 μg/ml blasticidin. Cells were added in a 96-well flat bottom assay plate at 100,000 per well in 100 μL complete RPMI medium. Test compounds were prepared by serial dilution in complete RPMI medium and 100 μL test compounds were transferred to each corresponding well. The assay plate was incubated at 37° C., 5% $CO_2$ for 24 hours. After the overnight incubation, 20 μL of the culture supernatants were collected, followed by addition of 180 μL of QUANTI-Blue (Invivogen) to assess IRF3 activity. The amount of IRF3 activation was assessed by reading the absorbance at 620-655 nm with a microplate reader 2 hours later. The culture supernatant from the untreated THP-1 cells was used as the negative control. To determine the NF-κB activation, another 20 μL of culture supernatant were transferred to a 96-well white plate, followed by addition of 50 μL of Quanti-Luc™ assay solution (Invivogen). The amount of NF-κB activation induced by the test compounds were determined by the luminescence above the untreated control. $EC_{50}$ determination was performed by fitting the curve of percent control activity versus the log of the compound concentration using the GraphPad Prism 6.0 software.

$EC_{50}$ in activating IRF3 for the compounds of the Examples are presented in Table 1 (+ refers to an $EC_{50}$ of <1000 nM; ++ refers to an $EC_{50}$ of <200 nM) and Table 2 (A refers to an $EC_{50}$ of <50 nM; B refers to an $EC_{50}$ of >50 to 200 nM; c refers to an $EC_{50}$ of >200 to 500 nM; B refers to an $EC_{50}$ of >500 to 1000 nM).

TABLE 1

| Example No. | THP1 IRF3 $EC_{50}$ (nM) |
| --- | --- |
| 1 | + |
| 2 | + |
| 3 | + |
| 4 | + |
| 5 | + |
| 6 | ++ |
| 7 | + |
| 8 | + |
| 9 | + |
| 10 | ++ |
| 11 | ++ |
| 12 | ++ |
| 13 | ++ |
| 14 | ++ |

TABLE 1-continued

| Example No. | THP1 IRF3 EC$_{50}$ (nM) |
|---|---|
| 15 | ++ |
| 16 | ++ |
| 17 | ++ |
| 18 | ++ |
| 19 | ++ |
| 20 | ++ |
| 21 | ++ |
| 22 | ++ |
| 23 | ++ |
| 24 | ++ |
| 25 | + |
| 26 | + |
| 27 | ++ |
| 28 | ++ |

TABLE 2

| Example No. | THP1 IRF3 EC$_{50}$ (nM) |
|---|---|
| 1 | B |
| 2 | C |
| 4 | D |
| 5 | B |
| 6 | A |
| 7 | C |
| 8 | D |
| 9 | C |
| 10 | A |
| 11 | A |
| 12 | A |
| 13 | A |
| 14 | A |
| 15 | A |
| 16 | A |
| 17 | A |
| 18 | A |
| 19 | A |
| 20 | A |
| 21 | A |
| 22 | A |
| 23 | B |
| 24 | A |
| 25 | C |
| 26 | D |
| 27 | A |
| 28 | A |
| 29 | A |
| 30 | B |
| 31 | B |
| 32 | A |
| 33 | D |
| 34 | A |
| 35 | A |
| 36 | A |
| 37 | C |
| 38 | B |
| 39 | A |
| 40 | A |
| 41 | A |
| 42 | B |
| 43 | A |
| 44 | A |
| 45 | A |
| 46 | A |
| 47 | A |
| 48 | A |
| 49 | A |
| 50 | A |
| 51 | A |
| 52 | B |
| 53 | B |
| 54 | B |
| 55 | B |
| 56 | B |
| 57 | B |
| 58 | C |
| 59 | B |

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:

1. A method of treating a cancer in a subject in need thereof, wherein the cancer is selected from bladder cancer, head and neck cancer, uterine cancer (UC), prostate cancer, lung cancer, colorectal cancer, salivary gland cancer, skin cancer, breast cancer, ovarian cancer, lymphoma, pancreatic cancer, and oral cancer, comprising administering a therapeutically effective amount of a compound of Formula (IIa):

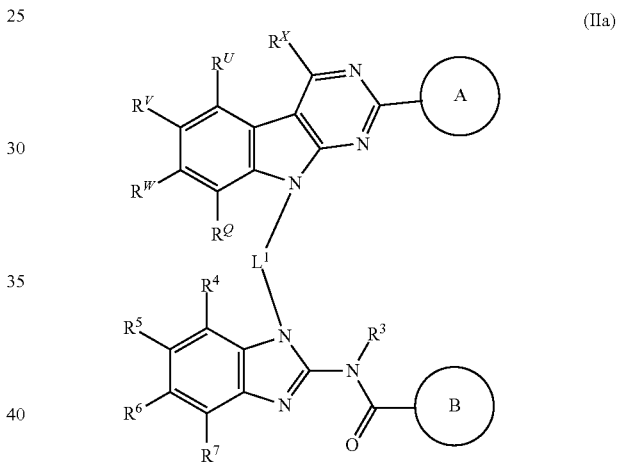

or a pharmaceutically acceptable salt thereof, wherein:

$R^U$, $R^V$, $R^W$, and $R^Q$ are each independently selected from H, D, halo, CN, NO$_2$, C$_{1-6}$ alkyl, C$_{2-6}$ alkenyl, C$_{2-6}$ alkynyl, C$_{1-6}$ haloalkyl, C$_{3-10}$ cycloalkyl, C$_{6-10}$ aryl, 4-10 membered heterocycloalkyl, 5-10 membered heteroaryl, C$_{3-10}$ cycloalkyl-C$_{1-4}$ alkyl, C$_{6-10}$ aryl-C$_{1-4}$ alkyl, 4-10 membered heterocycloalkyl-C$_{1-4}$ alkyl, 5-10 membered heteroaryl-C$_{1-4}$ alkyl, OR$^a$, SR$^a$, C(=O)R$^b$, C(=O)NR$^c$R$^d$, C(=O)OR$^a$, OC(=O)R$^b$, OC(=O)NR$^c$R$^d$, NR$^c$R$^d$, NR$^c$C(=O)R$^b$, NR$^c$C(=O)OR$^b$, NR$^c$C(=O)NR$^c$R$^d$, C(=NR$^e$)R$^b$, C(=NR$^e$)NR$^c$R$^d$, NR$^c$C(=NR$^e$)NR$^c$R$^d$, NR$^c$S(=O)$_2$R$^b$, NR$^c$S(=O)$_2$NR$^c$R$^d$, S(=O)$_2$R$^b$, and S(=O)$_2$NR$^c$R$^d$, wherein said C$_{1-6}$ alkyl, C$_{2-6}$ alkenyl, C$_{2-6}$ alkynyl, C$_{1-6}$ haloalkyl, C$_{3-10}$ cycloalkyl, C$_{6-10}$ aryl, 4-10 membered heterocycloalkyl, 5-10 membered heteroaryl, C$_{3-10}$ cycloalkyl-C$_{1-4}$ alkyl, C$_{6-10}$ aryl-C$_{1-4}$ alkyl, 4-10 membered heterocycloalkyl-C$_{1-4}$ alkyl, and 5-10 membered heteroaryl-C$_{1-4}$ alkyl are each optionally substituted by 1, 2, 3, or 4 independently selected R$^8$ groups;

each R$^a$, R$^c$, and R$^d$ is independently selected from H, C$_{1-6}$ alkyl, C$_{1-6}$ haloalkyl, C$_{2-6}$ alkenyl, C$_{2-6}$ alkynyl, C$_{3-10}$ cycloalkyl, C$_{6-10}$ aryl, 4-10 membered heterocycloalkyl, 5-10 membered heteroaryl, C$_{3-10}$ cycloalkyl- $C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^8$ groups;

each $R^b$ is independently selected from $C_{1-6}$ alkyl, $C_{1-6}$ haloalkyl, $C_{2-6}$ alkenyl, $C_{2-6}$ alkynyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, or 3 independently selected $R^8$ groups;

each $R^e$ is independently selected from H, CN, OH, $C_{1-4}$ alkyl, and $C_{1-4}$ alkoxy;

each $R^8$ is independently selected from H, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a8}$, $SR^{a8}$, $C(=O)R^{b8}$, $C(=O)NR^{c8}R^{d8}$, $C(=O)OR^{a8}$, $OC(=O)R^{b8}$, $OC(=O)NR^{c8}R^{d8}$, $NR^{c8}R^{d8}$, $NR^{c8}C(=O)R^{b8}$, $NR^{c8}C(=O)OR^{b8}$, $NR^{c8}C(=O)NR^{c8}R^{d8}$, $C(=NR^e)R^{b8}$, $C(=NR^e)NR^{c8}R^{d8}$, $NR^{c8}C(=NR^e)NR^{c8}R^{d8}$, $NR^{c8}S(=O)_2R^{b8}$, $NR^{c8}S(=O)_2NR^{c8}R^{d8}$, $S(=O)_2R^{b8}$, and $S(=O)_2NR^{c8}R^{d8}$, wherein said $C_{1-6}$ alkyl, $C_{2-6}$ alkenyl, $C_{2-6}$ alkynyl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted by 1, 2, 3, or 4 independently selected $R^{10}$ groups;

each $R^{a8}$, $R^{c8}$, and $R^{d8}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{10}$ groups;

each $R^{b8}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, or 3 independently selected $R^{10}$ groups;

each $R^{10}$ is independently selected from H, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a10}$, $SR^{a10}$, $C(=O)R^{b10}$, $C(=O)NR^{c10}R^{d10}$, $C(=O)OR^{a10}$, $OC(=O)R^{b10}$, $OC(=O)NR^{c10}R^{d10}$, $NR^{c10}R^{d10}$, $NR^{c10}C(=O)R^{b10}$, $NR^{c10}C(=O)OR^{b10}$, $NR^{c10}C(=O)NR^{c10}R^{d10}$, $C(=NR^e)R^{b10}$, $C(=NR^e)NR^{c10}R^{d10}$, $NR^{c10}C(=NR^e)NR^{c10}R^{d10}$, $NR^{c10}S(=O)_2R^{b10}$, $NR^{c10}S(=O)_2NR^{c10}R^{d10}$, $S(=O)_2R^{b10}$, or $S(=O)_2NR^{c10}R^{d10}$, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted by 1, 2, 3, or 4 independently selected $R^G$ groups;

each $R^{a10}$, $R^{c10}$, and $R^{d10}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ groups;

each $R^{b10}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, or 3 independently selected $R^G$ groups;

$R^X$ is selected from H, D, halo, CN, $NO_2$, $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_4$ alkyl, $C_{6-10}$ aryl-$C_{1-4}$ alkyl, 4-10 membered heterocycloalkyl-$C_{1-4}$ alkyl, 5-10 membered heteroaryl-$C_{14}$ alkyl, $OR^{a0}$, $SR^{a0}$, $C(=O)R^{b0}$, $C(=O)NR^{c0}R^{d0}$, $C(=O)OR^{a0}$, $OC(=O)R^{b0}$, $OC(=O)NR^{c0}R^{d0}$, $NR^{c0}R^{d0}$, $NR^{c0}C(=O)R^{b0}$, $NR^{c0}C(=O)OR^{b0}$, $NR^{c0}C(=O)NR^{c0}R^{d0}$, $C(=NR^e)R^{b0}$, $C(=NR^e)NR^{c0}R^{d0}$, $NR^{c0}C(=NR^e)NR^{c0}R^{d0}$, $NR^{c0}S(=O)_2R^{b0}$, $NR^{c0}S(=O)_2NR^{c0}R^{d0}$, $S(=O)_2R^{b0}$, and $S(=O)_2NR^{c0}R^{d0}$, wherein said $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl are each optionally substituted by 1, 2, 3, or 4 independently selected $R^G$ groups;

each $R^{a0}$, $R^{c0}$, and $R^{d0}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^G$ groups;

each $R^{b0}$ is independently selected from $C_{1-6}$ alkyl, $C_{1-6}$ haloalkyl, $C_{2-6}$ alkenyl, $C_{2-6}$ alkynyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, or 3 independently selected $R^G$ groups;

Ring moiety A is selected from $C_{3-10}$ cycloalkyl, $C_{6-10}$ aryl, 4-10 membered heterocycloalkyl, and 5-10 membered heteroaryl, each of which is optionally substituted by 1, 2, 3, or 4 independently selected $R^A$ groups;

Ring moiety B is selected from $C_{3-10}$ cycloalkyl, $C_{6-10}$ aryl, 4-10 membered heterocycloalkyl, and 5-10 membered heteroaryl, each of which is optionally substituted by 1, 2, 3, or 4 independently selected $R^B$ groups;

$L^1$ is selected from -R-R-, -R-R-R-, -Cy-, -R-Cy-, -Cy-R-, -R-Cy-R-, -R-R-Cy-, -Cy-R-R-, and -Cy-R-Cy-;

each R is independently M, $C_{1-6}$ alkylene, $C_{2-6}$ alkenylene, $C_{2-6}$ alkynylene, $C_{1-6}$ alkylene-M, M-$C_{1-6}$ alkylene, $C_{1-6}$ alkylene-M-$C_{1-6}$ alkylene, M-$C_{1-6}$ alkylene-M, $C_{2-6}$ alkenylene-M, M-$C_{2-6}$ alkenylene, $C_{2-6}$ alkenylene-M-$C_{2-6}$ alkenylene, M-$C_{2-6}$ alkenylene-M, $C_{2-6}$ alkynylene-M, M-$C_{2-6}$ alkynylene, $C_{2-6}$ alkynylene-M-$C_{2-6}$ alkynylene, or M-$C_{2-6}$ alkynylene-M, wherein each of said $C_{1-6}$ alkylene, $C_{2-6}$ alkenylene, and $C_{2-6}$ alkynylene is optionally substituted by 1, 2, 3, or 4 groups independently selected $R^G$ groups;

each Cy is independently selected from $C_{3-14}$ cycloalkyl, phenyl, 4-14 membered heterocycloalkyl, and 5-6 membered heteroaryl, each of which is optionally substituted by 1, 2, 3, or 4 independently selected $R^G$ groups;

each M is independently —O—, —S—, —C(O)—, —C(O)NR$^L$—, —C(O)O—, —OC(O)—, —C(O)NR$^L$—, —NR$^L$—, —NR$^L$C(O)—, —NR$^L$C(O)O—, —NR$^L$C(O)NR$^L$—, —NR$^L$S(O)$_2$—, —S(O)$_2$—, —S(O)$_2$NR$^L$—, or —NR$^L$S(O)$_2$NR$^L$—; provided that when M is attached to a nitrogen atom, then M is selected from —C(O)—, —C(O)NR$^L$—, —C(O)O—, —S(O)$_2$—, or —S(O)$_2$NR$^L$—;

each $R^L$ is independently selected from H, $C_{1-3}$ alkyl, $C_{2-3}$ alkenyl, $C_{2-3}$ alkynyl, and $C_{1-3}$ haloalkyl;

each $R^A$ is independently selected from halo, CN, NO$_2$, $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, 5-10 membered heteroaryl-$C_{1-4}$ alkyl, OR$^{a1}$, SR$^{a1}$, C(=O)R$^{b1}$, C(=O)NR$^{c1}$R$^{d1}$, C(=O)OR$^{a1}$, OC(=O)R$^{b1}$, OC(=O)NR$^{c1}$R$^{d1}$, NR$^{c1}$R$^{d1}$, NR$^{c1}$C(=O)R$^{b1}$, NR$^{c1}$C(=O)OR$^{b1}$, NR$^{c1}$C(=O)NR$^{c1}$R$^{d1}$, C(=NR$^e$)R$^{b1}$, C(=NR$^e$)NR$^{c1}$R$^{d1}$, NR$^{c1}$C(=NR$^e$)NR$^{c1}$R$^{d1}$, NR$^{c1}$S(=O)$_2$R$^{b2}$, NR$^{c1}$S(=O)$_2$NR$^{c1}$R$^{d1}$, (=O)$_2$R$^{b1}$, and S(=O)$_2$NR$^{c1}$R$^{d1}$, wherein said $C_{1-6}$ alkyl, $C_{2-6}$ alkenyl, $C_{2-6}$ alkynyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl are each optionally substituted by 1, 2, 3, or 4 independently selected $R^{A1}$ groups;

each $R^B$ is independently selected from halo, CN, NO$_2$, $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, 5-10 membered heteroaryl-$C_{1-4}$ alkyl, OR$^{a2}$, SR$^{a2}$, C(=O)R$^{b2}$, C(=O)NR$^{c2}$R$^{d2}$, C(=O)OR$^{a2}$, OC(=O)R$^{b2}$, OC(=O)NR$^{c2}$R$^{d2}$, NR$^{c2}$R$^{d2}$, NR$^{c2}$C(=O)R$^{b2}$, NR$^{c2}$C(=O)OR$^{b2}$, NR$^{c2}$C(=O)NR$^{c2}$R$^{d2}$, C(=NR$^e$)R$^{b2}$, C(=NR$^e$)NR$^{c2}$R$^{d2}$, NR$^{c2}$C(=NR$^e$)NR$^{c2}$R$^{d2}$, NR$^{c2}$S(=O)$_2$R$^{b2}$, NR$^{c2}$S(=O)$_2$NR$^{c2}$R$^{d2}$, S(=O)$_2$R$^{b2}$, and S(=O)$_2$NR$^{c2}$R$^{d2}$, wherein said $C_{1-6}$ alkyl, $C_{2-6}$ alkenyl, $C_{2-6}$ alkynyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl are each optionally substituted by 1, 2, 3, or 4 independently selected $R^{B1}$ groups;

each $R^{a1}$, $R^{c1}$, and $R^{d1}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{A1}$ groups;

each $R^{b1}$ is independently selected from $C_{1-6}$ alkyl, $C_{1-6}$ haloalkyl, $C_{2-6}$ alkenyl, $C_{2-6}$ alkynyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, or 3 independently selected $R^{A1}$ groups;

each $R^{a2}$, $R^{c2}$, and $R^{d2}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 independently selected $R^{B1}$ groups;

each $R^{b2}$ is independently selected from $C_{1-6}$ alkyl, $C_{1-6}$ haloalkyl, $C_{2-6}$ alkenyl, $C_{2-6}$ alkynyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, or 3 independently selected $R^{B1}$ groups;

each $R^{A1}$ and $R^{B1}$ is independently selected from H, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a12}$, $SR^{a12}$, $C(=O)R^{b12}$, $C(=O)NR^{c12}R^{d12}$, $C(=O)OR^{a12}$, $OC(=O)R^{b12}$, $OC(=O)NR^{c12}R^{d12}$, $NR^{c12}R^{d12}$, $NR^{c12}C(=O)R^{b12}$, $NR^{c12}C(=O)OR^{b12}$, $NR^{c12}C(=O)NR^{c12}R^{d12}$, $C(=NR^e)R^{b12}$, $C(=NR^e)NR^{c12}R^{d12}$, $NR^{c12}C(=NR^e)NR^{c12}R^{d12}$, $NR^{c12}S(=O)_2R^{b12}$, $NR^{c12}S(=O)_2NR^{c12}R^{d12}$, $S(=O)_2 R^{b12}$, and $S(=O)_2NR^{c12}R^{d12}$, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted by 1, 2, 3, or 4 independently selected $R^G$ groups;

each $R^{a12}$, $R^{c12}$, and $R^{d12}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ groups;

each $R^{b12}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, or 3 independently selected $R^G$ groups;

$R^3$ is H, $C_{1-4}$ alkyl or $C_{1-4}$ haloalkyl;

$R^4$ is H, D, halo, CN, $NO_2$, $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, 5-10 membered heteroaryl-$C_{1-4}$ alkyl, $OR^{a4}$, $SR^{a4}$, $C(=O)R^{b4}$, $C(=O)NR^{c4}R^{d4}$, $C(=O)OR^{a4}$, $OC(=O)R^{b4}$, $OC(=O)NR^{c4}R^{d4}$, $NR^{c4}R^{d4}$, $NR^{c4}C(=O)R^{b4}$, $NR^{c4}C(=O)OR^{b4}$, $NR^{c4}C(=O)NR^{c4}R^{d4}$, $C(=NR^e)R^{b4}$, $C(=NR^e)NR^{c4}R^{d4}$, $NR^{c4}C(=NR^e)NR^{c4}R^{d4}$, $NR^{c4}S(=O)_2R^{b4}$, $NR^{c4}S(=O)_2NR^{c4}R^{d4}$, $S(=O)_2R^{b4}$, or $S(=O)_2NR^{c4}R^{d4}$, wherein said $C_{1-6}$ alkyl, $C_{2-6}$ alkenyl, $C_{2-6}$ alkynyl $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl are each optionally substituted by 1, 2, 3, or 4 independently selected $R^{4a}$ groups;

$R^5$ is H, D, halo, CN, $NO_2$, $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, 5-10 membered heteroaryl-$C_{1-4}$ alkyl, $OR^{a5}$, $SR^{a5}$, $C(=O)R^{b5}$, $C(=O)NR^{c5}R^{d5}$, $C(=O)OR^{a5}$, $OC(=O)R^{b5}$, $OC(=O)NR^{c5}R^{d5}$, $NR^{c5}R^{d5}$, $NR^{c5}C(=O)R^{b5}$, $NR^{c5}C(=O)OR^{b5}$, $NR^{c5}C(=O)NR^{c5}R^{d5}$, $C(=NR^e)R^{b5}$, $C(=NR^e)NR^{c5}R^{d5}$, $NR^{c5}C(=NR^e)NR^{c5}R^{d5}$, $NR^{c5}S(=O)_2R^{b5}$, $NR^{c5}S(=O)_2NR^{c5}R^{d5}$, $S(=O)_2R^{b5}$, or $S(=O)_2NR^{c5}R^{d5}$, wherein said $C_{1-6}$ alkyl, $C_{2-6}$ alkenyl, $C_{2-6}$ alkynyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl are each optionally substituted by 1, 2, 3, or 4 independently selected $R^{5a}$ groups;

$R^6$ is H, D, halo, CN, $NO_2$, $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, 5-10 membered heteroaryl-$C_{1-4}$ alkyl, $OR^{a6}$, $SR^{a6}$, $C(=O)R^{b6}$, $C(=O)NR^{c6}R^{d6}$, $C(=O)OR^{a6}$, $OC(=O)R^{b6}$, $OC(=O)NR^{c6}R^{d6}$, $NR^{c6}R^{d6}$, $NR^{c6}C(=O)R^{b6}$, $NR^{c6}C(=O)OR^{b6}$, $NR^{c6}C(=O)NR^{c6}R^{d6}$, $C(=NR^e)R^{b6}$, $C(=NR^e)NR^{c6}R^{d6}$, $NR^{c6}C(=NR^e)NR^{c6}R^{d6}$, $NR^{c6}S(=O)_2R^{b6}$, $NR^{c6}S(=O)_2NR^{c6}R^{d6}$, $S(=O)_2R^{b6}$, or $S(=O)_2NR^{c6}R^{d6}$, wherein said $C_{1-6}$ alkyl, $C_{2-6}$ alkenyl, $C_{2-6}$ alkynyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl are each optionally substituted by 1, 2, 3, or 4 independently selected $R^{6a}$ groups;

$R^7$ is H, D, halo, CN, $NO_2$, $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, 5-10 membered heteroaryl-$C_{1-4}$ alkyl, $OR^{a7}$, $SR^7$, $C(=O)R^{b7}$, $C(=O)NR^{c7}R^{d7}$, $C(=O)OR^{a7}$, $OC(=O)R^{b7}$, $OC(=O)NR^{c7}R^{d7}$, $NR^{c7}R^{d7}$, $NR^{c7}C(=O)R^{b7}$, $NR^{c7}C(=O)OR^{b7}$, $NR^{c7}C(=O)NR^{c7}R^{d7}$, $C(=NR^e)R^{b7}$, $C(=NR^e)NR^{c7}R^{d7}$, $NR^{c7}C(=NR^e)NR^{c7}R^{d7}$, $NR^{c7}S(=O)_2R^{b7}$, $NR^{c7}S(=O)_2NR^{c7}R^{d7}$, $S(=O)_2R^{b7}$, or $S(=O)_2NR^{c7}R^{d7}$, wherein said $C_{1-6}$ alkyl, $C_{2-6}$ alkenyl, $C_{2-6}$ alkynyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl are each optionally substituted by 1, 2, 3, or 4 independently selected $R^{7a}$ groups;

each $R^{a4}$, $R^{c4}$, and $R^{d4}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{4a}$ groups;

each $R^{b4}$ is independently selected from $C_{1-6}$ alkyl, $C_{1-6}$ haloalkyl, $C_{2-6}$ alkenyl, $C_{2-6}$ alkynyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, or 3 independently selected $R^{4a}$ groups;

each $R^{a5}$, $R^{c5}$, and $R^{d5}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{5a}$ groups;

each $R^{b5}$ is independently selected from $C_{1-6}$ alkyl, $C_{1-6}$ haloalkyl, $C_{2-6}$ alkenyl, $C_{2-6}$ alkynyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, or 3 independently selected $R^{5a}$ groups;

each $R^{a6}$, $R^{c6}$, and $R^{d6}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{6a}$ groups;

each $R^{b6}$ is independently selected from $C_{1-6}$ alkyl, $C_{1-6}$ haloalkyl, $C_{2-6}$ alkenyl, $C_{2-6}$ alkynyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, or 3 independently selected $R^{6a}$ groups;

each $R^{a7}$, $R^{c7}$, and $R^{d7}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{7a}$ groups;

each $R^{b7}$ is independently selected from $C_{1-6}$ alkyl, $C_{1-6}$ haloalkyl, $C_{2-6}$ alkenyl, $C_{2-6}$ alkynyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, or 3 independently selected $R^{7a}$ groups;

each $R^{4a}$, $R^{5a}$, $R^{6a}$, and $R^{7a}$ are independently selected from H, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a9}$, $SR^{a9}$, $C(=O)R^{b9}$, $C(=O)NR^{c9}R^{d9}$, $C(=O)OR^{a9}$, $OC(=O)R^{b9}$, $OC(=O)NR^{c9}R^{d9}$, $NR^{c9}R^{d9}$, $NR^{c9}C(=O)R^{b9}$, $NR^{c9}C(=O)OR^{b9}$, $NR^{c9}C(=O)NR^{c9}R^{d9}$, $C(=NR^e)R^{b9}$, $C(=NR^e)NR^{c9}R^{d9}$, $NR^{c9}C(=NR^e)NR^{c9}R^{d9}$, $NR^{c9}S(=O)_2R^{b9}$, $NR^{c9}S(=O)_2NR^{c9}R^{d9}$, $S(=O)_2R^{b9}$, and $S(=O)_2NR^{c9}R^{d9}$, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted by 1, 2, 3, or 4 independently selected $R^{11}$ groups;

each $R^{a9}$, $R^{c9}$, and $R^{d9}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{11}$ groups;

each $R^{b9}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, or 3 independently selected $R^{11}$ groups;

each $R^{11}$ is independently selected from H, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a11}$, $SR^{a11}$, $C(=O)R^{b11}$, $C(=O)NR^{c11}R^{d11}$, $C(=O)OR^{a11}$, $OC(=O)R^{b11}$, $OC(=O)NR^{c11}R^{d11}$, $NR^{c11}R^{d11}$, $NR^{c11}C(=O)R^{b11}$, $NR^{c11}C(=O)OR^{b11}$, $NR^{c11}C(=O)NR^{c11}R^{d11}$, $C(=NR^e)R^{b11}$, $C(=NR^e)NR^{c11}R^{d11}$, $NR^{c11}C(=NR^e)NR^{c11}R^{d11}$, $NR^{c11}S(=O)_2R^{b11}$, $NR^{c11}S(=O)_2NR^{c11}R^{d11}$, $S(=O)_2R^{b11}$, and $S(=O)_2NR^{c11}R^{d11}$, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted by 1, 2, 3, or 4 independently selected $R^G$ groups;

each $R^{a11}$, $R^{c11}$, and $R^{d11}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ groups;

each $R^{b11}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, or 3 independently selected $R^G$ groups; and each $R^G$ is independently selected from OH, $NO_2$, CN, halo, $C_{1-3}$ alkyl, $C_{2-3}$ alkenyl, $C_{2-3}$ alkynyl, $C_{1-3}$ haloalkyl, cyano-$C_{1-3}$ alkyl, HO-$C_{1-3}$ alkyl, $C_{1-3}$ alkoxy-$C_{1-3}$ alkyl, $C_{3-7}$ cycloalkyl, $C_{1-3}$ alkoxy, $C_{1-3}$ haloalkoxy, amino, $C_{1-3}$ alkylamino, alkyl)amino, thio, $C_{1-3}$ alkylthio, $C_{1-3}$ alkylsulfinyl, $C_{1-3}$ alkyl sulfonyl, carbamyl, $C_{1-3}$ alkylcarbamyl, di($C_{1-3}$ alkyl)carbamyl, carboxy, $C_{1-3}$ alkylcarbonyl, $C_{1-4}$ alkoxycarbonyl, $C_{1-3}$ alkylcarbonylamino, $C_{1-3}$ alkylsulfonylamino, aminosulfonyl, $C_{1-3}$ alkylaminosulfonyl, di($C_{1-3}$ alkyl)aminosulfonyl, aminosulfonylamino, $C_{1-3}$ alkylaminosulfonylamino, di($C_{1-3}$ alkyl)aminosulfonylamino, aminocarbonylamino, $C_{1-3}$ alkylaminocarbonylamino, and di($C_{1-3}$ alkyl)aminocarbonylamino, wherein each heteroaryl has 1-4 heteroatom ring members each independently selected from N, O, S and B; and wherein each heterocycloalkyl has 1-4 heteroatom ring members each independently selected from N, O, S and B.

2. The method of claim 1, wherein $R^U$ is H, halo, CN, $C_{1-6}$ alkyl, $OR^a$, $C(=O)R^b$, $C(=O)NR^cR^d$, $S(=O)_2R^b$, or $S(=O)_2NR^cR^d$; and $R^w$ is H, halo, CN, $C_{1-6}$ alkyl, $OR^a$, $C(=O)R^b$, $C(=O)NR^cR^d$, $S(=O)_2R^b$, or $S(=O)_2NR^cR^d$.

3. The method of claim 1, wherein each $R^a$, $R^c$, and $R^d$ is independently selected from H, $C_{1-6}$ alkyl, and $C_{1-6}$ haloalkyl, wherein said $C_{1-6}$ alkyl is optionally substituted with 1, 2, 3, or 4 independently selected $R^8$ groups;

each $R^b$ is independently selected from $C_{1-6}$ alkyl and $C_{1-6}$ haloalkyl, wherein said $C_{1-6}$ alkyl is optionally substituted with 1, 2, or 3 independently selected $R^8$ groups; and each $R^8$ is independently selected from OH, $NO_2$, CN, halo, $C_{1-3}$ alkyl, $C_{2-3}$ alkenyl, $C_{2-3}$ alkynyl, $C_{1-3}$ haloalkyl, $C_{1-3}$ alkoxy, $C_{1-3}$ haloalkoxy, amino, $C_{1-3}$ alkylamino, and di($C_{1-3}$ alkyl)amino.

4. The method of claim 1, wherein $R^V$ is H, halo, CN, $C_{1-6}$ alkyl, $C_{1-6}$ alkoxy, $C_{1-6}$ haloalkyl, or $C(=O)NR^cR^d$, wherein $R^c$ and $R^d$ are each independently selected from H, $C_{1-6}$ alkyl, and $C_{1-6}$ haloalkyl; $R^Q$ is H or $OR^a$, wherein $R^a$ is selected from H, $C_{1-6}$ alkyl, and 4-7 membered heterocycloalkyl-$C_{1-4}$ alkyl, wherein said $C_{1-6}$ alkyl is optionally OH or $C_{1-3}$ alkoxy; and $R^X$ is selected from H, D, halo, CN, $C_{1-6}$ alkyl, and $C_{1-6}$ haloalkyl.

5. The method of claim 1, wherein $R^X$ is H or $C_{1-6}$ alkyl.

6. The method of claim 1, wherein $R^4$ is H, D, halo, CN, $NO_2$, $C_{1-6}$ alkyl, $C_{2-6}$ alkenyl, $C_{2-6}$ alkynyl, $C_{1-6}$ haloalkyl, $OR^{a4}$, $SR^{a4}$, $C(=O)R^{b4}$, $C(=O)NR^{c4}R^{d4}$, $C(=O)OR^{a4}$, $OC(=O)R^{b4}$, $OC(=O)NR^{c4}R^{d4}$, $NR^{c4}R^{d4}$, $NR^{c4}C(=O)R^{b4}$, $NR^{c4}C(=O)OR^{b4}$, $NR^{c4}C(=O)NR^{c4}R^{d4}$, $NR^{c4}S(=O)_2R^{b4}$, $NR^{c4}S(=O)_2NR^{c4}R^{d4}$, $S(=O)_2R^{b4}$, or $S(=O)_2NR^{c4}R^{d4}$, wherein said $C_{1-6}$ alkyl, $C_{2-6}$ alkenyl, and $C_{2-6}$ alkynyl are each optionally substituted by 1, 2, 3, or 4 independently selected $R^{4a}$ groups; and each $R^{a4}$, $R^{c4}$, and $R^{d4}$ is independently selected from H, $C_{1-6}$ alkyl, and $C_{1-6}$ haloalkyl, wherein said $C_{1-6}$ alkyl is optionally substituted with 1, 2, 3, or 4 independently selected $R^{4a}$ groups; and each $R^{b4}$ is independently selected from $C_{1-6}$ alkyl and $C_{1-6}$ haloalkyl, wherein said $C_{1-6}$ alkyl is optionally substituted with 1, 2, 3, or 4 independently selected $R^{4a}$ groups.

7. The method of claim 1, wherein $R^5$, $R^6$, and $R^7$ are each independently selected from H, halo, CN, OH, $C_{1-6}$ alkyl, $C_{1-6}$ haloalkyl, $C_{1-6}$ alkoxy, $C_{1-6}$ haloalkoxy, amino, $C_{1-}$ alkylamino, di($C_{1-6}$ alkyl)amino, carbamyl, $C_{1-6}$ alkylcarbamyl, and di($C_{1-6}$ alkyl)carbamyl.

8. The method of claim 1, wherein Ring moiety A and Ring B are each independently 5 membered heteroaryl, which is optionally substituted by 1, 2, 3, or 4 independently selected $R^A$ groups.

9. The method of claim 1, wherein Ring moiety A and Ring B are each independently a pyrazole ring, which is optionally substituted by 1, 2, or 3 independently selected $R^A$ groups.

10. The method of claim 1, wherein each $R^A$ is independently selected from halo, CN, $C_{1-6}$ alkyl, and $C_{1-6}$ haloalkyl; and each $R^B$ is independently selected from halo, CN, $C_{1-6}$ alkyl, and $C_{1-6}$ haloalkyl.

11. The method of claim 1, wherein $L^1$ is selected from -R-R- and -R-R-R-, wherein each R is independently $C_{1-6}$ alkylene or $C_{2-6}$ alkenylene.

12. The method of claim 1, wherein $L^1$ is —$CH_2$—CH=CH—$CH_2$—.

13. The method of claim 1, wherein:
$R^U$ is H, halo, CN, $C_{1-6}$ alkyl, $C_{1-6}$ alkoxy, $C_{1-6}$ haloalkyl, or C(=O)$NR^cR^d$;
$R^V$ is H, halo, CN, $C_{1-6}$ alkyl, $C_{1-6}$ alkoxy, $C_{1-6}$ haloalkyl, or C(=O)$NR^cR^d$;
$R^W$ is H, halo, CN, $C_{1-6}$ alkyl, $C_{1-6}$ alkoxy, $C_{1-6}$ haloalkyl, or C(=O)$NR^cR^d$;
$R^Q$ is H, halo, CN, $C_{1-6}$ alkyl, $C_{1-6}$ alkoxy, $C_{1-6}$ haloalkyl, or C(=O)$NR^cR^d$;
each $R^c$ and $R^d$ is independently selected from H, $C_{1-6}$ alkyl, and $C_{1-6}$ haloalkyl;
$R^X$ is selected from H, D, halo, CN, $C_{1-6}$ alkyl, $C_{1-6}$ alkoxy, and $C_{1-6}$ haloalkyl;
$R^4$, $R^5$, $R^6$, and $R^7$ are each independently selected from H, halo, CN, OH, $C_{1-6}$ alkyl, $C_{1-6}$ haloalkyl, $C_{1-6}$ alkoxy, $C_{1-6}$ haloalkoxy, amino, $C_{1-6}$ alkylamino, di($C_{1-6}$ alkyl)amino, carbamyl, $C_{1-6}$ alkylcarbamyl, and di($C_{1-6}$ alkyl)carbamyl;
$R^3$ is H;
Ring moiety A is a pyrazole ring, which is optionally substituted by 1, 2, or 3 independently selected $R^A$ groups;
Ring moiety B is a pyrazole ring, which is optionally substituted by 1, 2, or 3 independently selected $R^B$ groups;
each $R^A$ is independently selected from halo, CN, $C_{1-6}$ alkyl, and $C_{1-6}$ haloalkyl;
each $R^B$ is independently selected from halo, CN, $C_{1-6}$ alkyl, and $C_{1-6}$ haloalkyl; and
$L^1$ is —$CH_2$—CH=CH—$CH_2$—.

14. The method of claim 1, wherein the compound of Formula (IIa) is selected from:
(E)-9-(4-(5-carbamoyl-2-(1-ethyl-3-methyl-1H-pyrazole-5-carboxamido)-7-methyl-1H-benzo[d]imidazol-1-yl)but-2-enyl)-2-(1-ethyl-3-methyl-1H-pyrazol-5-yl)-9H-pyrimido[4,5-b]indole-6-carboxamide;
(E)-1-(4-(2-(1-ethyl-3-methyl-1H-pyrazol-5-yl)-9H-pyrimido[4,5-b]indol-9-yl)but-2-enyl)-2-(1-ethyl-3-methyl-1H-pyrazole-5-carboxamido)-7-methyl-1H-benzo[d]imidazole-5-carboxamide;
(E)-9-(4-(5-carbamoyl-2-(1-ethyl-3-methyl-1H-pyrazole-5-carboxamido)-7-methyl-1H-benzo[d]imidazol-1-yl)but-2-enyl)-2-(1,3-dimethyl-1H-pyrazol-5-yl)-9H-pyrimido[4,5-b]indole-6-carboxamide; and
(E)-9-(4-(5-carbamoyl-2-(1-ethyl-3-methyl-1H-pyrazole-5-carboxamido)-7-methoxy-1H-benzo[d]imidazol-1-yl)but-2-enyl)-2-(1-ethyl-3-methyl-1H-pyrazol-5-yl)-9H-pyrimido[4,5-b]indole-6-carboxamide;
or a pharmaceutically acceptable salt thereof.

15. The method of claim 1, wherein the compound of Formula (IIa) is selected from:
(E)-9-(4-(5-carbamoyl-2-(1-ethyl-3-methyl-1H-pyrazole-5-carboxamido)-7-methyl-1H-benzo[d]imidazol-1-yl)but-2-enyl)-2-(3-methyl-1-propyl-1H-pyrazol-5-yl)-9H-pyrimido[4,5-b]indole-6-carboxamide;
(E)-9-(4-(5-carbamoyl-2-(1-ethyl-3-methyl-1H-pyrazole-5-carboxamido)-7-methyl-1H-benzo[d]imidazol-1-yl)but-2-enyl)-2-(1-ethyl-1H-pyrazol-5-yl)-9H-pyrimido[4,5-b]indole-6-carboxamide;
(E)-9-(4-(5-carbamoyl-2-(1-ethyl-3-methyl-1H-pyrazole-5-carboxamido)-7-methyl-1H-benzo[d]imidazol-1-yl)but-2-enyl)-2-(3-ethyl-1-methyl-1H-pyrazol-4-yl)-9H-pyrimido[4,5-b]indole-6-carboxamide;
(E)-9-(4-(5-carbamoyl-2-(1-ethyl-3-methyl-1H-pyrazole-5-carboxamido)-7-methyl-1H-benzo[d]imidazol-1-yl)but-2-enyl)-2-(1-ethyl-3-(trifluoromethyl)-1H-pyrazol-5-yl)-9H-pyrimido[4,5-b]indole-6-carboxamide;
(E)-9-(4-(5-carbamoyl-2-(1-ethyl-3-methyl-1H-pyrazole-5-carboxamido)-7-methyl-1H-benzo[d]imidazol-1-yl)but-2-enyl)-2-(1-ethyl-3-methyl-1H-pyrazol-5-yl)-8-methoxy-9H-pyrimido[4,5-b]indole-6-carboxamide;
(E)-9-(4-(5-carbamoyl-2-(1-ethyl-3-methyl-1H-pyrazole-5-carboxamido)-7-methyl-1H-benzo[d]imidazol-1-yl)but-2-enyl)-2-(1-ethyl-3-methyl-1H-pyrazol-5-yl)-8-(3-morpholinopropoxy)-9H-pyrimido[4,5-b]indole-6-carboxamide;
(E)-9-(4-(5-carbamoyl-2-(1-ethyl-3-methyl-1H-pyrazole-5-carboxamido)-7-methyl-1H-benzo[d]imidazol-1-yl)but-2-enyl)-2-(1-ethyl-3-methyl-1H-pyrazol-5-yl)-8-(3-methoxypropoxy)-9H-pyrimido[4,5-b]indole-6-carboxamide;
(E)-9-(4-(5-carbamoyl-2-(1-ethyl-3-methyl-1H-pyrazole-5-carboxamido)-7-methyl-1H-benzo[d]imidazol-1-yl)but-2-enyl)-2-(1-ethyl-3-methyl-1H-pyrazol-5-yl)-8-(3-hydroxypropoxy)-9H-pyrimido[4,5-b]indole-6-carboxamide;
(E)-3-((5-carbamoyl-1-(4-(6-carbamoyl-2-(1-ethyl-3-methyl-1H-pyrazol-5-yl)-8-methoxy-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propyl 1-ethyl-3-methyl-1H-pyrazole-5-carboxylate;
(E)-9-(4-(5-carbamoyl-2-(1-ethyl-3-methyl-1H-pyrazole-5-carboxamido)-7-(3-hydroxypropoxy)-1H-benzo[d]imidazol-1-yl)but-2-en-1-yl)-2-(1-ethyl-3-methyl-1H-pyrazol-5-yl)-8-methoxy-9H-pyrimido[4,5-b]indole-6-carboxamide;
(E)-3-((5-carbamoyl-1-(4-(6-carbamoyl-2-(1-ethyl-3-methyl-1H-pyrazol-5-yl)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propyl 1-ethyl-3-methyl-1H-pyrazole-5-carboxylate;
(E)-9-(4-(5-carbamoyl-2-(1-ethyl-3-methyl-1H-pyrazole-5-carboxamido)-7-(3-hydroxypropoxy)-1H-benzo[d]imidazol-1-yl)but-2-en-1-yl)-2-(1-ethyl-3-methyl-1H-pyrazol-5-yl)-9H-pyrimido[4,5-b]indole-6-carboxamide;
(E)-3-((5-carbamoyl-1-(4-(6-carbamoyl-2-(1-ethyl-3-methyl-1H-pyrazol-5-yl)-8-(3-morpholinopropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propyl 1-ethyl-3-methyl-1H-pyrazole-5-carboxylate;
(E)-9-(4-(5-carbamoyl-2-(1-ethyl-3-methyl-1H-pyrazole-5-carboxamido)-7-(3-hydroxypropoxy)-1H-benzo[d]

imidazol-1-yl)but-2-en-1-yl)-2-(1-ethyl-3-methyl-1H-pyrazol-5-yl)-8-(3-morpholinopropoxy)-9H-pyrimido[4,5-b]indole-6-carboxamide;

(E)-3-((5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propyl 1-ethyl-3-methyl-1H-pyrazole-5-carboxylate;

(E)-9-(4-(5-carbamoyl-2-(1-ethyl-3-methyl-1H-pyrazole-5-carboxamido)-7-(3-hydroxypropoxy)-1H-benzo[d]imidazol-1-yl)but-2-en-1-yl)-2-(1-ethyl-3-methyl-1H-pyrazol-5-yl)-8-(3-methoxypropoxy)-9H-pyrimido[4,5-b]indole-6-carboxamide;

(E)-9-(4-(5-carbamoyl-2-(1-ethyl-3-methyl-1H-pyrazole-5-carboxamido)-7-(3-morpholinopropoxy)-1H-benzo[d]imidazol-1-yl)but-2-en-1-yl)-2-(1-ethyl-3-methyl-1H-pyrazol-5-yl)-8-(3-methoxypropoxy)-9H-pyrimido[4,5-b]indole-6-carboxamide; and (E)-9-(4-(5-carbamoyl-2-(1-ethyl-3-methyl-1H-pyrazole-5-carboxamido)-7-hydroxy-1H-benzo[d]imidazol-1-yl)but-2-en-1-yl)-2-(1-ethyl-3-methyl-1H-pyrazol-5-yl)-8-(3-methoxypropoxy)-9H-pyrimido[4,5-b]indole-6-carboxamide;

or a pharmaceutically acceptable salt thereof.

16. The method of claim 1, wherein the cancer is bladder cancer.

17. The method of claim 1, wherein the cancer is head and neck cancer.

18. The method of claim 17, wherein the head and neck cancer is head and neck squamous cell carcinoma (HNSCC).

19. The method of claim 1, wherein the cancer is uterine cancer (UC).

20. The method of claim 1, wherein the cancer is prostate cancer.

21. The method of claim 1, wherein the cancer is lung cancer.

22. The method of claim 21, wherein the lung cancer is small cell lung carcinoma (SCLC).

23. The method of claim 1, wherein the cancer is melanoma.

24. The method of claim 1, wherein the cancer is colorectal cancer.

25. The method of claim 1, wherein the cancer is salivary gland cancer.

26. The method of claim 1, wherein the cancer is skin cancer.

27. The method of claim 1, wherein the cancer is breast cancer.

28. The method of claim 27, wherein the breast cancer is triple-negative breast cancer.

29. The method of claim 1, wherein the cancer is ovarian cancer.

30. The method of claim 1, wherein the cancer is lymphoma.

31. The method of claim 30, wherein the lymphoma is T-cell lymphoma.

32. The method of claim 1, wherein the cancer is pancreatic cancer.

33. The method of claim 1, wherein the cancer is oral cancer.

34. A method of treating a cancer selected from the group consisting of bladder cancer, head and neck cancer, uterine cancer (UC), prostate cancer, lung cancer, melanoma, colorectal cancer, salivary gland cancer, skin cancer, breast cancer, ovarian cancer, lymphoma, pancreatic cancer, and oral cancer, in a subject in need thereof, comprising administering a therapeutically effective amount of a compound of Formula (X):

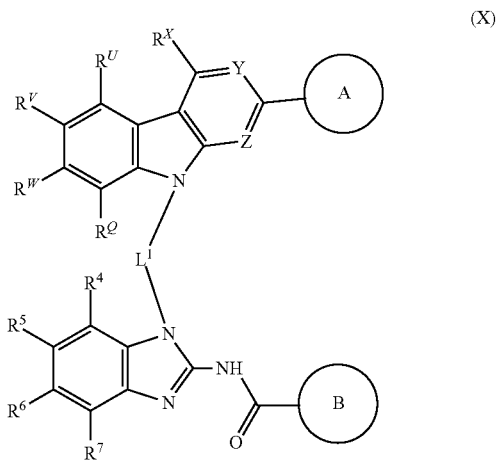

or a pharmaceutically acceptable salt thereof, wherein:

$R^U$, $R^V$, and $R^W$ are each independently selected from H, D, OH, NO$_2$, CN, halo, C$_{1-6}$ alkyl, C$_{2-6}$ alkenyl, C$_{2-6}$ alkynyl, C$_{1-6}$ haloalkyl, cyano-C$_{1-6}$ alkyl, HO-C$_{1-6}$ alkyl, C$_{1-6}$ alkoxy-C$_{1-6}$ alkyl, C$_{3-7}$ cycloalkyl, C$_{1-6}$ alkoxy, C$_{1-6}$ haloalkoxy, amino, C$_{1-6}$ alkylamino, di(C$_{1-6}$ alkyl)amino, thio, C$_{1-6}$ alkylthio, C$_{1-6}$ alkylsulfinyl, C$_{1-6}$ alkylsulfonyl, carbamyl, C$_{1-6}$ alkylcarbamyl, di(C$_{1-6}$ alkyl)carbamyl, carboxy, C$_{1-6}$ alkylcarbonyl, C$_{1-4}$ alkoxycarbonyl, C$_{1-6}$ alkylcarbonylamino, C$_{1-6}$ alkylsulfonylamino, aminosulfonyl, C$_{1-6}$ alkylaminosulfonyl, di(C$_{1-6}$ alkyl)aminosulfonyl, aminosulfonylamino, C$_{1-6}$ alkylaminosulfonylamino, di(C$_{1-6}$ alkyl)aminosulfonylamino, aminocarbonylamino, C$_{1-6}$ alkylaminocarbonylamino, and di(C$_{1-6}$ alkyl)aminocarbonylamino;

$R^Q$ is selected from H, D, halo, CN, NO$_2$, C$_{1-6}$ alkyl, -C$_{1-6}$ alkylene-R$^{80}$, -C$_{1-6}$ alkylene-R$^{90}$, -C$_{1-6}$ alkylene-OR$^{80}$, -C$_{1-6}$ alkylene-NHR$^{80}$, C$_{2-6}$ alkenyl, C$_{2-6}$ alkynyl, C$_{1-6}$ haloalkyl, C$_{3-10}$ cycloalkyl, C$_{6-10}$ aryl, 4-10 membered heterocycloalkyl, 5-10 membered heteroaryl, C$_{3-10}$ cycloalkyl-C$_{1-4}$ alkyl, C$_{6-10}$ aryl-C$_{1-4}$ alkyl, 4-10 membered heterocycloalkyl-C$_{1-4}$ alkyl, 5-10 membered heteroaryl-C$_{1-4}$ alkyl, OR$^a$, OR$^f$, SR$^a$, C(=O)R$^b$, C(=O)NR$^c$R$^d$, C(=O)OR$^a$, OC(=O)R$^b$, OC(=O)NR$^c$R$^d$, NR$^c$R$^d$, NR$^c$C(=O)R$^b$, NR$^c$C(=O)OR$^b$, NR$^c$C(=O)NR$^c$R$^d$, C(=NR$^e$)R$^b$, C(=NR$^e$)NR$^c$R$^d$, NR$^c$C(=NR$^e$)NR$^c$R$^d$, NR$^c$S(=O)$_2$R$^b$, NR$^c$S(=O)$_2$NR$^c$R$^d$, S(=O)$_2$R$^b$, and S(=O)$_2$NR$^c$R$^d$, wherein said C$_{1-6}$ alkyl, C$_{2-6}$ alkenyl, C$_{2-6}$ alkynyl, C$_{1-6}$ haloalkyl, C$_{3-10}$ cycloalkyl, C$_{6-10}$ aryl, 4-10 membered heterocycloalkyl, 5-10 membered heteroaryl, C$_{3-10}$ cycloalkyl-C$_{1-4}$ alkyl, C$_{6-10}$ aryl-C$_{1-4}$ alkyl, 4-10 membered heterocycloalkyl-C$_{1-4}$ alkyl, and 5-10 membered heteroaryl-C$_{1-4}$ alkyl are each optionally substituted by 1, 2, 3, or 4 independently selected R$^8$ groups;

$R^a$, $R^c$, and $R^d$ are each independently selected from H, C$_{1-6}$ alkyl, C$_{1-6}$ haloalkyl, C$_{2-6}$ alkenyl, C$_{2-6}$ alkynyl, C$_{3-10}$ cycloalkyl, C$_{6-10}$ aryl, 4-10 membered heterocycloalkyl, 5-10 membered heteroaryl, C$_{3-10}$ cycloalkyl-C$_{1-4}$ alkyl, C$_{6-10}$ aryl-C$_{1-4}$ alkyl, 4-10 membered heterocycloalkyl-C$_{1-4}$ alkyl, and 5-10 membered heteroaryl-C$_{1-4}$ alkyl, wherein said C$_{1-6}$ alkyl, C$_{2-6}$ alkenyl, $C_{2-6}$ alkynyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^8$ groups;

$R^b$ is selected from $C_{1-6}$ alkyl, $C_{1-6}$ haloalkyl, $C_{2-6}$ alkenyl, $C_{2-6}$ alkynyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, or 3 independently selected $R^8$ groups;

each $R^8$ is independently selected from H, CN, OH, $C_{1-4}$ alkyl, and $C_{1-4}$ alkoxy;

$R^f$ is selected from $C_{1-6}$ alkyl and $C_{1-6}$ haloalkyl, which are each optionally substituted with 1 substituent selected from $R^{80}$, —$OR^{80}$, $R^{90}$, and —$NHR^{80}$;

each $R^8$ is independently selected from H, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a8}$, $SR^{a8}$, $C(=O)R^{b8}$, $C(=O)NR^{c8}R^{d8}$, $C(=O)OR^{a8}$, $OC(=O)R^{b8}$, $OC(=O)NR^{c8}R^{d8}$, $NR^{c8}R^{d8}$, , $NR^{c8}C(=O)R^{b8}$, $NR^{c8}C(=O)OR^{b8}$, $NR^{c8}C(=O)NR^{c8}R^{d8}$, $C(=NR^e)R^{b8}$, $C(=NR^e)NR^{c8}R^{d8}$, $NR^{c8}C(=NR^e)NR^{c8}R^{d8}$, $NR^{c8}S(=O)_2R^{b8}$, $NR^{c8}S(=O)_2NR^{c8}R^{d8}$, $S(=O)_2R^{b8}$, and $S(=O)_2NR^{c8}R^{d8}$, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted by 1, 2, 3, or 4 independently selected $R^{10}$ groups;

each $R^{a8}$, $R^{c8}$, and $R^{d8}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{10}$ groups;

each $R^{b8}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, or 3 independently selected $R^{10}$ groups;

each $R^{10}$ is independently selected from H, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a10}$, $SR^{a10}$, $C(=O)R^{b10}$, $C(=O)NR^{c10}R^{d10}$, $C(=O)OR^{a10}$, $OC(=O)R^{b10}$, $OC(=O)NR^{c10}R^{d10}$, $NR^{c10}R^{d10}$, $NR^{c10}C(=O)R^{b10}$, $NR^{c10}C(=O)OR^{b10}$, $NR^{c10}C(=O)NR^{c10}R^{d10}$, $C(=NR^e)R^{b10}$, $C(=NR^e)NR^{c10}R^{d10}$, $NR^{c10}C(=NR^e)NR^{c10}R^{d10}$, $NR^{c10}S(=O)_2R^{b10}$, $NR^{c10}S(=O)_2NR^{c10}R^{d10}$, $S(=O)_2R^{b10}$, or $S(=O)_2NR^{c10}R^{d10}$, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted by 1, 2, 3, or 4 independently selected $R^G$ groups;

each $R^{a10}$, $R^{c10}$, and $R^{d10}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ groups;

each $R^{b10}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, or 3 independently selected $R^G$ groups;

$R^{80}$ is a linear peptide chain having 2-6 amino acids;

$R^{90}$ is a linear chain of formula —$(O-C_{2-4}$ alkylene)$_z$—$R^G$, wherein z is 1, 2, 3, 4, 5, or 6;

Y is N or $CR^Y$;

Z is N or $CR^Z$;

$R^X$ $R^Y$, and $R^Z$ are each independently selected from H, D, halo, CN, $NO_2$, $C_{1-6}$ alkyl, $C_{2-6}$ alkenyl, $C_{2-6}$ alkynyl, $C_{1-6}$ haloalkyl, and $C_{3-4}$ cycloalkyl;

Ring moiety A is 5-membered heteroaryl, which is optionally substituted by 1, 2, 3, or 4 independently selected $R^A$ groups;

Ring moiety B is 5-membered heteroaryl, which is optionally substituted by 1, 2, 3, or 4 independently selected $R^B$ groups;

$L^1$ is selected from -R-R- and -R-R-R-;

each R is independently M, $C_{1-6}$ alkylene, $C_{2-6}$ alkenylene, $C_{2-6}$ alkynylene, $C_{1-6}$ alkylene-M, M-$C_{1-6}$ alkylene, $C_{1-6}$ alkylene-M-$C_{1-6}$ alkylene, M-$C_{1-6}$ alkylene-M, $C_{2-6}$ alkenylene-M, M-$C_{2-6}$ alkenylene, $C_{2-6}$ alkenylene-M-$C_{2-6}$ alkenylene, M-$C_{2-6}$ alkenylene-M, $C_{2-6}$ alkynylene-M, M-$C_{2-6}$ alkynylene, $C_{2-6}$ alkynylene-M-$C_{2-6}$ alkynylene, or M-$C_{2-6}$ alkynylene-M, wherein each of said $C_{1-6}$ alkylene, $C_{2-6}$ alkenylene, and $C_{2-6}$ alkynylene is optionally substituted by 1, 2, 3, or 4 groups independently selected $R^G$ groups;

each M is independently —O—, —S—, —C(O)—, —C(O)NR$^L$—, —C(O)O—, —OC(O)—, —OC(O)NR$^L$—, —NR$^L$—, —NR$^L$C(O)—, —NR$^L$C(O)O—, —NR$^L$C(O)NR$^L$—, —NR$^L$S(O)$_2$—, —S(O)$_2$—, —S(O)$_2$NR$^L$—, or —NR$^L$S(O)$_2$NR$^L$—; provided that when M is attached to a nitrogen atom, then M is selected from —C(O)—, —C(O)NR$^L$—, —C(O)O—, —S(O)$_2$—, or —S(O)$_2$NR$^L$—;

each R$^L$ is independently selected from H, $C_{1-3}$ alkyl, $C_{2-3}$ alkenyl, $C_{2-3}$ alkynyl, and $C_{1-3}$ haloalkyl;

each R$^A$ is independently selected from halo, CN, NO$_2$, $C_{1-6}$ alkyl, $C_{2-6}$ alkenyl, $C_{2-6}$ alkynyl, $C_{1-6}$ haloalkyl, and $C_{3-4}$ cycloalkyl, wherein said $C_{1-6}$ alkyl, $C_{2-6}$ alkenyl, $C_{2-6}$ alkynyl, $C_{1-6}$ haloalkyl, and $C_{3-4}$ cycloalkyl are each optionally substituted by 1, 2, 3, or 4 independently selected R$^G$ groups;

each R$^B$ is independently selected from halo, CN, NO$_2$, $C_{1-6}$ alkyl, $C_{2-6}$ alkenyl, $C_{2-6}$ alkynyl, $C_{1-6}$ haloalkyl, and $C_{3-4}$ cycloalkyl, wherein said $C_{1-6}$ alkyl, $C_{2-6}$ alkenyl, $C_{2-6}$ alkynyl, $C_{1-6}$ haloalkyl, and $C_{3-4}$ cycloalkyl are each optionally substituted by 1, 2, 3, or 4 independently selected R$^G$ groups;

R$^5$, R$^6$, and R$^7$ are each independently selected from H, D, OH, NO$_2$, CN, halo, $C_{1-6}$ alkyl, $C_{2-6}$ alkenyl, $C_{2-6}$ alkynyl, $C_{1-6}$ haloalkyl, cyano-$C_{1-6}$ alkyl, HO-$C_{1-6}$ alkyl, $C_{1-6}$ alkoxy-$C_{1-6}$ alkyl, $C_{3-7}$ cycloalkyl, $C_{1-6}$ alkoxy, $C_{1-6}$ haloalkoxy, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-4}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

R$^4$ is H, D, halo, CN, NO$_2$, $C_{1-6}$ alkyl, -$C_{1-6}$ alkylene-R$^{80}$, -$C_{1-6}$ alkylene-R$^{90}$, -$C_{1-6}$ alkylene-OR$^{80}$, -$C_{1-6}$ alkylene-NHR$^{80}$, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, 5-10 membered heteroaryl-$C_{1-4}$ alkyl, OR$^{a4}$, OR$^{f4}$, SR$^{a4}$, C(=O)R$^{b4}$, C(=O)NR$^{c4}$R$^{d4}$, C(=O)OR$^{a4}$, OC(=O)R$^{b4}$, OC(=O)NR$^{c4}$R$^{d4}$, NR$^{c4}$R$^{d4}$, NR$^{c4}$C(=O)R$^{b4}$, NR$^{c4}$C(=O)OR$^{b4}$, NR$^{c4}$C(=O)NR$^{c4}$R$^{d4}$, C(=NR$^e$)R$^{b4}$, C(=NR$^e$)NR$^{c4}$R$^{d4}$, NR$^{c4}$C(=NR$^e$)NR$^{c4}$R$^{d4}$, NR$^{c4}$S(=O)$_2$R$^{b4}$, NR$^{c4}$S(=O)$_2$NR$^{c4}$R$^{d4}$, S(=O)$_2$R$^{b4}$, or S(=O)$_2$NR$^{c4}$R$^{d4}$, wherein said $C_{1-6}$ alkyl, $C_{2-6}$ alkenyl, $C_{2-6}$ alkynyl $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl are each optionally substituted by 1, 2, 3, or 4 independently selected R$^{4a}$ groups;

each R$^{a4}$, R$^{c4}$, and R$^{d4}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected R$^{4a}$ groups;

each R$^{b4}$ is independently selected from $C_{1-6}$ alkyl, $C_{1-6}$ haloalkyl, $C_{2-6}$ alkenyl, $C_{2-6}$ alkynyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, or 3 independently selected R$^{4a}$ groups;

R$^{f4}$ is selected from $C_{1-6}$ alkyl and $C_{1-6}$ haloalkyl, which are each optionally substituted with 1 substituent selected from R$^{80}$, R$^{90}$, —OR$^{80}$, and —NHR$^{80}$;

each R$^{4a}$ is independently selected from H, halo, CN, NO$_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, OR$^{a9}$, SR$^{a9}$, C(=O)R$^{b9}$, C(=O)NR$^{c9}$R$^{d9}$, C(=O)OR$^{a9}$, OC(=O)R$^{b9}$, OC(=O)NR$^{c9}$R$^{d9}$, NR$^{c9}$R$^{d9}$, NR$^{c9}$C(=O)R$^{b9}$, NR$^{c9}$C(=O)OR$^{b9}$, NR$^{c9}$C(=O)NR$^{c9}$R$^{d9}$, C(=NR$^e$)R$^{b9}$, C(=NR$^e$)NR$^{c9}$R$^{d9}$, NR$^{c9}$C(=NR$^e$)NR$^{c9}$R$^{d9}$, NR$^{c9}$S(=O)$_2$R$^{b9}$, NR$^{c9}$S(=O)$_2$NR$^{c9}$R$^{d9}$, S(=O)$_2$R$^{b9}$, and S(=O)$_2$NR$^{c9}$R$^{d9}$, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted by 1, 2, 3, or 4 independently selected R$^{11}$ groups;

each R$^{a9}$, R$^{c9}$, and R$^{d9}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected R$^{11}$ groups;

each R$^{b9}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, or 3 independently selected $R^{11}$ groups;

$R^{f4}$ is selected from $C_{1-6}$ alkyl and $C_{1-6}$ haloalkyl, which are each optionally substituted with 1 substituent selected from $R^{80}$, —$OR^{80}$, and —$NHR^{80}$;

each $R^{11}$ is independently selected from H, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a11}$, $SR^{a11}$, $C(=O)R^{b11}$, $C(=O)NR^{c11}R^{d11}$, $C(=O)OR^{a11}$, $OC(=O)R^{b11}$, $OC(=O)NR^{c11}R^{d11}$, $NR^{c11}R^{d11}$, $NR^{c11}C(=O)R^{b11}$, $NR^{c11}C(=O)OR^{b11}$, $NR^{c11}C(=O)NR^{c11}R^{d11}$, $C(=NR^e)R^{b11}$, $C(=NR^e)NR^{c11}R^{d11}$, $NR^{c11}C(=NR^e)NR^{c11}R^{d11}$, $NR^{c11}S(=O)_2R^{b11}$, $NR^{c11}S(=O)_2NR^{c11}R^{d11}$, $S(=O)_2R^{b11}$, and $S(=O)_2NR^{c11}R^{d11}$, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted by 1, 2, 3, or 4 independently selected $R^G$ groups;

each $R^{a11}$, $R^{c11}$, and $R^{d11}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ groups;

each $R^{b11}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, or 3 independently selected $R^G$ groups; and each $R^G$ is independently selected from H, D, OH, $NO_2$, CN, halo, $C_{1-3}$ alkyl, $C_{2-3}$ alkenyl, $C_{2-3}$ alkynyl, $C_{1-3}$ haloalkyl, cyano-$C_{1-3}$ alkyl, HO-$C_{1-3}$ alkyl, $C_{1-3}$ alkoxy-$C_{1-3}$ alkyl, $C_{3-7}$ cycloalkyl, $C_{1-3}$ alkoxy, $C_{1-3}$ haloalkoxy, amino, $C_{1-3}$ alkylamino, di($C_{1-3}$ alkyl) amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl)carbamyl, carboxy, $C_{1-3}$ alkylcarbonyl, $C_{1-4}$ alkoxycarbonyl, $C_{1-3}$ alkylcarbonylamino, $C_{1-3}$ alkylsulfonylamino, aminosulfonyl, $C_{1-3}$ alkylaminosulfonyl, di($C_{1-3}$ alkyl)aminosulfonyl, aminosulfonylamino, $C_{1-3}$ alkylaminosulfonylamino, di($C_{1-3}$ alkyl)aminosulfonylamino, aminocarbonylamino, $C_{1-3}$ alkylaminocarbonylamino, and di($C_{1-3}$ alkyl)aminocarbonylamino, wherein each heteroaryl has 1-4 heteroatom ring members each independently selected from N, O, S and B; and wherein each heterocycloalkyl has 1-4 heteroatom ring members each independently selected from N, O, S and B.

35. The method of claim 34, wherein:

$R^V$ is H or carbamyl;

$R^U$ and $R^W$ are each independently selected from H, halo, CN, and $C_{1-3}$ alkyl;

$R^Q$ is selected from H, $C_{1-6}$ alkyl, $OR^a$, and $OR^f$;

$R^a$ is selected from H, $C_{1-6}$ alkyl, $C_{1-6}$ haloalkyl, and 4-7 membered heterocycloalkyl-$C_{1-4}$ alkyl, wherein said $C_{1-6}$ alkyl and 4-7 membered heterocycloalkyl-$C_{1-4}$ alkyl are each optionally substituted with 1 or 2 independently selected $R^8$ groups;

each $R^8$ is independently selected from H, halo, CN, $C_{1-6}$ alkyl, $C_{1-6}$ haloalkyl, $OR^{a8}$, $C(=O)OR^{a8}$, $OC(=O)R^{b8}$, $OC(=O)NR^{c8}R^{d8}$, $NR^{c8}R^{d8}$, $NR^{c8}C(=O)R^{b8}$, $NHC(=O)NHR^{d8}$, $NR^{c8}S(=O)_2R^{b8}$, and $NR^{c8}C(=O)OR^{b8}$;

each $R^{a8}$, $R^{c8}$, and $R^{d8}$ is independently selected from H, $C_{1-6}$ alkyl, and $C_{1-6}$ haloalkyl, wherein said $C_{1-6}$ alkyl is optionally substituted with 1 or 2 independently selected $R^{10}$ groups;

each $R^{b8}$ is independently selected from $C_{1-6}$ alkyl, $C_{1-6}$ haloalkyl, and 5-membered heteroaryl, wherein said $C_{1-6}$ alkyl and 5-membered heteroaryl are each optionally substituted with 1 or 2 independently selected $R^{10}$ groups;

each $R^{10}$ is independently selected from H, halo, CN, $C_{1-6}$ alkyl, $C_{1-6}$ haloalkyl, $OR^{a10}$, $NR^{c10}R^{d10}$, and $C(=O)OR^{a10}$, wherein said $C_{1-6}$ alkyl is optionally substituted by 1 or 2 independently selected $R^G$ groups;

each $R^{a10}$ is independently selected from H and $C_{1-6}$ alkyl, wherein said $C_{1-6}$ alkyl is optionally substituted with 1 or 2 independently selected $R^G$ groups;

Y is N or $CR^Y$;

Z is N or $CR^Z$;

wherein at least one of Y or Z is N;

$R^X$, $R^Y$, and $R^Z$ are each independently selected from H, halo, CN, $C_{1-3}$ alkyl, and $C_{1-3}$ haloalkyl;

Ring moiety A is a pyrazole ring, which is optionally substituted by 1 or 2 independently selected $R^A$ groups;

Ring moiety B is a pyrazole ring, which is optionally substituted by 1 or 2 independently selected $R^B$ groups;

$L^1$ is $C_{3-6}$ alkenylene;

each $R^A$ is independently selected from $C_{1-6}$ alkyl and $C_{1-6}$ haloalkyl;

each $R^B$ is independently selected from $C_{1-6}$ alkyl and $C_{1-6}$ haloalkyl;

$R^4$ is selected from H, $C_{1-6}$ alkyl, $OR^{a4}$, and $OR^{f4}$, wherein said $C_{1-6}$ alkyl is optionally substituted by 1 or 2 independently selected $R^{4a}$ groups;

$R^6$ is H or carbamyl;

$R^5$ and $R^7$ are each independently selected from H, halo, CN, and $C_{1-3}$ alkyl;

$R^{a4}$ is selected from H, $C_{1-6}$ alkyl, $C_{1-6}$ haloalkyl, and 4-7 membered heterocycloalkyl-$C_{1-4}$ alkyl, wherein said $C_{1-6}$ alkyl and 4-7 membered heterocycloalkyl-$C_{1-4}$ alkyl are each optionally substituted with 1 or 2 independently selected $R^8$ groups;

$R^{f4}$ is $C_{1-6}$ alkyl which is substituted with 1 substituent selected from $R^{90}$ and —$NHR^{80}$;

each $R^{4a}$ is independently selected from H, halo, CN, $C_{1-6}$ alkyl, $C_{1-6}$ haloalkyl, $OR^{a9}$, $OC(=O)R^{b9}$, $OC(=O)$ NR$^{c9}$R$^{d9}$, NR$^{c9}$R$^{d9}$, NR$^{c9}$C(=O)R$^{b9}$, NHC(=O)NHR$^{d9}$, NR$^{c9}$S(=O)$_2$R$^{b9}$, and NR$^{c9}$C(=O)OR$^{b9}$;

R$^{80}$ is a linear peptide chain having 2-4 amino acids;

R$^{90}$ is a linear chain of formula —(O-C$_{2-4}$ alkylene)$_z$—R$^G$, wherein z is 1, 2, 3, or 4;

each R$^{a9}$, R$^{c9}$, and R$^{d9}$ is independently selected from H, C$_{1-6}$ alkyl, and C$_{1-6}$ haloalkyl, wherein said C$_{1-6}$ alkyl is optionally substituted with 1 or 2 independently selected R$^{11}$ groups;

each R$^{b9}$ is independently C$_{1-6}$ alkyl, which is optionally substituted with 1 or 2 independently selected R$^{11}$ groups;

each R$^{11}$ is independently selected from H, halo, CN, C$_{1-6}$ alkyl, C$_{1-6}$ haloalkyl, OR$^{a11}$, NR$^{c11}$R$^{d11}$ and C(=O)OR$^{a11}$, wherein said C$_{1-6}$ alkyl is optionally substituted by 1 or 2 independently selected R$^G$ groups;

each R$^{a11}$ is independently selected from H and C$_{1-6}$ alkyl, wherein said C$_{1-6}$ alkyl is optionally substituted with 1 or 2 independently selected R$^G$ groups;

each R$^{c11}$ and R$^{d11}$ independently selected from H and C$_{1-6}$ alkyl, wherein said C$_{1-6}$ alkyl is optionally substituted with 1 or 2 independently selected R$^G$ groups; and each R$^G$ is independently selected from H, OH, CN, halo, C$_{1-3}$ alkyl, C$_{1-3}$ alkoxy, C$_{1-3}$ amino, C$_{1-3}$ alkylamino, di(C$_{1-3}$ alkyl)amino, and carboxy.

36. The method of claim 35, wherein Ring moiety A is a pyrazole ring, which is optionally substituted by 1 or 2 independently selected R$^A$ groups; Ring moiety B is a pyrazole ring, which is optionally substituted by 1 or 2 independently selected R$^B$ groups;

each R$^A$ and R$^B$ is independently selected from C$_{1-4}$ alkyl; and L$^1$ is —CH$_2$—CH=CH—CH$_2$—.

37. The method of claim 34, wherein the compound of Formula (X) is selected from:

(E)-9-(4-(5-carbamoyl-7-(3-cyanopropoxy)-2-(1-ethyl-3-methyl-1H-pyrazole-5-carboxamido)-1H-benzo[d]imidazol-1-yl)but-2-en-1-yl)-2-(1-ethyl-3-methyl-1H-pyrazol-5-yl)-8-(3-methoxypropoxy)-9H-pyrimido[4,5-b]indole-6-carboxamide;

(E)-9-(4-(5-carbamoyl-2-(1-ethyl-3-methyl-1H-pyrazole-5-carboxamido)-7-isopropoxy-1H-benzo[d]imidazol-1-yl)but-2-en-1-yl)-2-(1-ethyl-3-methyl-1H-pyrazol-5-yl)-8-(3-methoxypropoxy)-9H-pyrimido[4,5-b]indole-6-carboxamide;

(E)-9-(4-(5-carbamoyl-2-(1-ethyl-3-methyl-1H-pyrazole-5-carboxamido)-7-(3-(4-methylpiperazin-1-yl)propoxy)-1H-benzo[d]imidazol-1-yl)but-2-en-1-yl)-2-(1-ethyl-3-methyl-1H-pyrazol-5-yl)-8-(3-methoxypropoxy)-9H-pyrimido[4,5-b]indole-6-carboxamide;

(E)-9-(4-(5-carbamoyl-2-(1-ethyl-3-methyl-1H-pyrazole-5-carboxamido)-7-(3-hydroxypropoxy)-1H-benzo[d]imidazol-1-yl)but-2-en-1-yl)-2-(1-ethyl-3-methyl-1H-pyrazol-5-yl)-3-fluoro-9H-pyrido[2,3-b]indole-6-carboxamide;

(E)-9-(4-(7-(3-aminopropoxy)-5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazol-5-yl)-8-(3-methoxypropoxy)-9H-pyrimido[4,5-b]indole-6-carboxamide;

(E)-5-((3-((5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propyl)amino)-5-oxopentanoic acid;

(E)-2-((5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)ethyl 1-ethyl-3-methyl-1H-pyrazole-5-carboxylate;

(E)-9-(4-(5-carbamoyl-2-(1-ethyl-3-methyl-1H-pyrazole-5-carboxamido)-7-(2-hydroxyethoxy)-1H-benzo[d]imidazol-1-yl)but-2-en-1-yl)-2-(1-ethyl-3-methyl-1H-pyrazol-5-yl)-8-(3-methoxypropoxy)-9H-pyrimido[4,5-b]indole-6-carboxamide;

(6S,9S,12S,15S)-15-amino-1-((5-carbamoyl-1-((E)-4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)-6,9-bis(carboxymethyl)-12-(3-guanidinopropyl)-5,8,11,14-tetraoxo-4,7,10,13-tetraazaheptadecan-17-oic acid;

(E)-9-(4-(5-carbamoyl-2-(1-ethyl-3-methyl-1H-pyrazole-5-carboxamido)-7-(2-morpholinoethoxy)-1H-benzo[d]imidazol-1-yl)but-2-en-1-yl)-2-(1-ethyl-3-methyl-1H-pyrazol-5-yl)-8-(3-methoxypropoxy)-9H-pyrimido[4,5-b]indole-6-carboxamide;

(E)-3-(((3-((5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propyl)carbamoyl)oxy)propanoic acid;

(E)-2-(((3-((5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propyl)carbamoyl)oxy)acetic acid;

(E)-((3-((5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propyl)carbamoyl)glycine;

(S,E)-3-amino-4-((3-((5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propyl)amino)-4-oxobutanoic acid;

(E)-3-(((3-((5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propoxy)carbonyl)amino)propanoic acid;

(E)-3-(2-(2-((5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)ethoxy)ethoxy)propanoic acid;

(E)-4-(N-(3-((5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propyl)sulfamoyl)butanoic acid;

(E)-5-(3-(6-carbamoyl-9-(4-(5-carbamoyl-2-(1-ethyl-3-methyl 1H-pyrazole-5-carboxamido)-7-methoxy-1H-benzo[d]imidazol-1-yl)but-2-enyl)-2-(1-ethyl-3- methyl-1H-pyrazol-5-yl)-9H-pyrimido[4,5-b]indol-8-yloxy)propylamino)-5-oxopentanoic acid;

(E)-3-(3-(6-carbamoyl-9-(4-(5-carbamoyl-2-(1-ethyl-3-methyl -1H-pyrazole-5-carboxamido)-7-methoxy-1H-benzo[d]imidazol-1-yl)but-2-enyl)-2-(1-ethyl-3-methyl-1H-pyrazol-5-yl)-9H-pyrimido[4,5-b]indol-8-yloxy)propylcarbamoyloxy)propanoic acid;

(E)-5-(3-(6-carbamoyl-9-(4-(5-carbamoyl-2-(1-ethyl-3-methyl-1H-pyrazole-5-carboxamido)-7-(3-hydroxy-propoxy)-1H-benzo[d]imidazol-1-yl)but-2-enyl)-2-(1-ethyl-3-methyl-1H-pyrazol-5-yl)-9H-pyrimido[4,5-b]indol-8-yloxy)propylamino)-5-oxopentanoic acid;

(E)-3-(3-(6-carbamoyl-9-(4-(5-carbamoyl-2-(1-ethyl-3-methyl-1H-pyrazole-5-carboxamido)-7-(3-hydroxy-propoxy)-1H-benzo[d]imidazol-1-yl)but-2-enyl)-2-(1-ethyl-3-methyl-1H-pyrazol-5-yl)-9H-pyrimido[4,5-b]indol-8-yloxy)propylcarbamoyloxy)propanoic acid;

(E)-5-(3-(6-carbamoyl-9-(4-(5-carbamoyl-2-(1-ethyl-3-methyl-1H-pyrazole-5-carboxamido)-7-(3-methoxy-propoxy)-1H-benzo[d]imidazol-1-yl)but-2-enyl)-2-(1-ethyl-3-methyl-1H-pyrazol-5-yl)-9H-pyrimido[4,5-b]indol-8-yloxy)propylamino)-5-oxopentanoic acid;

(E)-3-(3-(6-carbamoyl-9-(4-(5-carbamoyl-2-(1-ethyl-3-methyl-1H-pyrazole-5-carboxamido)-7-(3-methoxy-propoxy)-1H-benzo[d]imidazol-1-yl)but-2-enyl)-2-(1-ethyl-3-methyl-1H-pyrazol-5-yl)-9H-pyrimido[4,5-b]indol-8-yloxy)propylcarbamoyloxy)propanoic acid;

(E)-3-((3-(6-carbamoyl-9-(4-(5-carbamoyl-2-(1-ethyl-3-methyl-1H-pyrazole-5-carboxamido)-7-(3-methoxy-propoxy)-1H-benzo[d]imidazol-1-yl)but-2-enyl)-2-(1-ethyl-3-methyl-1H-pyrazol-5-yl)-9H-pyrimido[4,5-b]indol-8-yloxy)propoxy)carbonylamino)propanoic acid;

(E)-3-(2-(2-(6-carbamoyl-9-(4-(5-carbamoyl-2-(1-ethyl-3-methyl-1H-pyrazole-5-carboxamido)-7-(3-methoxy-propoxy)-1H-benzo[d]imidazol-1-yl)but-2-enyl)-2-(1-ethyl-3-methyl-1H-pyrazol-5-yl)-9H-pyrimido[4,5-b]indol-8-yloxy)ethoxy)ethoxy)propanoic acid;

(E)-3-(2-(2-(2-(6-carbamoyl-9-(4-(5-carbamoyl-2-(1-ethyl-3-methyl-1H-pyrazole-5-carboxamido)-7-(3-methoxypropoxy)-1H-benzo[d]imidazol-1-yl)but-2-enyl)-2-(1-ethyl-3-methyl-1H-pyrazol-5-yl)-9H-pyrimido[4,5-b]indol-8-yloxy)ethoxy)ethoxy)ethoxy)propanoic acid;

(E)-4-(4-(2-(6-carbamoyl-9-(4-(5-carbamoyl-2-(1-ethyl-3-methyl-1H-pyrazole-5-carboxamido)-7-methoxy-1H-benzo[d]imidazol-1-yl)but-2-enyl)-2-(1-ethyl-3-methyl -1H-pyrazol-5-yl)-9H-pyrimido[4,5-b]indol-8-yloxy)ethyl)piperidin-1-yl)butanoic acid;

(E)-2-(4-(2-(6-carbamoyl-9-(4-(5-carbamoyl-2-(1-ethyl-3-methyl-1H-pyrazole-5-carboxamido)-7-methoxy-1H-benzo[d]imidazol-1-yl)but-2-enyl)-2-(1-ethyl-3-methyl-1H-pyrazol-5-yl)-9H-pyrimido[4,5-b]indol-8-yloxy)ethyl)piperidine-1-carbonyloxy)acetic acid;

(E)-3-((3-(6-carbamoyl-9-(4-(5-carbamoyl-2-(1-ethyl-3-methyl-1H-pyrazole-5-carboxamido)-7-(3-hydroxy-propoxy)-1H-benzo[d]imidazol-1-yl)but-2-enyl)-2-(1-ethyl-3-methyl-1H-pyrazol-5-yl)-9H-pyrimido[4,5-b]indol-8-yloxy)propoxy)carbonylamino)propanoic acid;

(E)-3-(((3-((5-carbamoyl-1-(4-(6-carbamoyl-8-(2-(2-(2-carboxyethoxy)ethoxy)ethoxy)-2-(1-ethyl-3-methyl-1H-pyrazol-5-yl)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propoxy)carbonyl)amino)propanoic acid; and (E)-4-((3-((5-carbamoyl-1-(4-(6-carbamoyl-2-(1-ethyl-3-methyl-1H-pyrazol-5-yl)-8-(3-methoxypropoxy)-9H-pyrimido[4,5-b]indol-9-yl)but-2-en-1-yl)-2-(1-ethyl-3-methyl-1H-pyrazole-5-carboxamido)-1H-benzo[d]imidazol-7-yl)oxy)propyl)amino)-4-oxobutanoic acid;

or a pharmaceutically acceptable salt thereof.

38. The method of claim 34, wherein the compound of Formula (X) is selected from:

(E)-5-(4-(5-carbamoyl-2-(1-ethyl-3-methyl-1H-pyrazole-5-carboxamido)-7-methyl-1H-benzo[d]imidazol-1-yl)but-2-en-1-yl)-3-(1-ethyl-3-methyl-1H-pyrazol-5-yl)-4-fluoro-5H-pyrido[4,3-b]indole-8-carboxamide;

(E)-9-(4-(5-carbamoyl-2-(1-ethyl-3-methyl-1H-pyrazole-5-carboxamido)-7-methyl-1H-benzo[d]imidazol-1-yl)but-2-en-1-yl)-2-(1-ethyl-3-methyl-1H-pyrazol-5 -yl)-3-fluoro-9H-pyrido[2,3-b]indole-6-carboxamide;

(E)-9-(4-(5-carbamoyl-2-(1-ethyl-3-methyl-1H-pyrazole-5-carboxamido)-7-methyl-1H-benzo[d]imidazol-1-yl)but-2-en-1-yl)-3-cyano-2-(1-ethyl-3-methyl-1H-pyrazol-5-yl)-9H-pyrido[2,3-b]indole-6-carboxamide;

(E)-5-(4-(5-carbamoyl-2-(1-ethyl-3-methyl-1H-pyrazole-5-carboxamido)-7-methyl-1H-benzo[d]imidazol-1-yl)but-2-en-1-yl)-4-cyano-3-(1-ethyl-3-methyl-1H-pyrazol-5-yl)-5H-pyrido[4,3-b]indole-8-carboxamide;

(E)-9-(4-(5-carbamoyl-2-(1-ethyl-3-methyl-1H-pyrazole-5-carboxamido)-7-methyl-1H-benzo[d]imidazol-1-yl)but-2-en-1-yl)-2-(1-ethyl-3-methyl-1H-pyrazol-5-yl)-9H-pyrido[2,3-b]indole-6-carboxamide; and (E)-9-(4-(5-carbamoyl-2-(1-ethyl-3-methyl-1H-pyrazole-5-carboxamido)-7-methyl-1H-benzo[d]imidazol-1-yl)but-2-enyl)-2-(1-ethyl-3-methyl-1H-pyrazol-5-yl)-8-methoxy-9H-pyrido[2,3-b]indole-6-carboxamide;

or a pharmaceutically acceptable salt thereof.

39. The method of claim 34, wherein the compound of Formula (X) has the following formula:

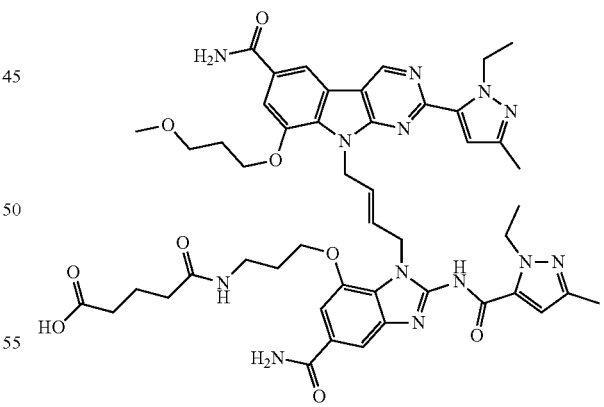

or a pharmaceutically acceptable salt thereof.

* * * * *

UNITED STATES PATENT AND TRADEMARK OFFICE
CERTIFICATE OF CORRECTION

PATENT NO. : 11,713,317 B2
APPLICATION NO. : 17/190151
DATED : August 1, 2023
INVENTOR(S) : Liangxing Wu et al.

It is certified that error appears in the above-identified patent and that said Letters Patent is hereby corrected as shown below:

In the Claims

Column 240, Line 52, Claim 1, delete "C(=O)NR$^a$R$^d$," and insert -- C(=O)NR$^c$R$^d$, --;

Column 240, Line 54, Claim 1, delete "NR$^c$C(=O)NR$^a$R$^d$," and insert -- NR$^c$C(=O)NR$^c$R$^d$, --;

Column 241, Line 33, Claim 1, delete "C(=)NR$^{c8}$R$^{d8}$," and insert -- C(=O)NR$^{c8}$R$^{d8}$, --;

Column 241, Lines 40-41, Claim 1, delete "C$_{3-7}$ cycloalkyl-C$_{1-4}$ alkyl," and insert -- C$_{3-7}$ cycloalkyl, phenyl, 4-7 membered heterocycloalkyl, 5-6 membered heteroaryl, C$_{3-7}$ cycloalkyl-C$_{1-4}$ alkyl, --;

Column 242, Line 12, Claim 1, delete "NR$^{c10}$OC(=O)R$^{b10}$," and insert -- NR$^{c10}$C(=O)R$^{b10}$, --;

Column 242, Line 24, Claim 1, delete "C$_2^-{_6}$ alkenyl," and insert -- C$_{2-6}$ alkenyl, --;

Column 242, Line 52, Claim 1, delete "cycloalkyl-C$_4$" and insert -- cycloalkyl-C$_{1-4}$ --;

Column 242, Line 54, Claim 1, delete "heteroaryl-C$_{14}$" and insert -- heteroaryl-C$_{1-4}$ --;

Column 243, Lines 55-56, Claim 1, delete "—C(O)NR$^L$—," and insert -- —OC(O)NR$^L$—, --;

Column 244, Line 8, Claim 1, delete "(=O)$_2$R$^{b1}$," and insert -- S(=O)$_2$R$^{b1}$, --;

Column 246, Line 10, Claim 1, delete "alkynyl C$_{3-10}$ cycloalkyl" and insert -- alkynyl, C$_{3-10}$ cycloalkyl --;

Column 246, Line 60, Claim 1, delete "SR$^7$," and insert -- SR$^{a7}$, --;

Column 248, Line 14, Claim 1, delete "alkynyl C$_{3-10}$" and insert -- alkynyl, C$_{3-10}$ --;

Signed and Sealed this
Nineteenth Day of September, 2023

*Katherine Kelly Vidal*
Katherine Kelly Vidal
*Director of the United States Patent and Trademark Office*

CERTIFICATE OF CORRECTION (continued)
U.S. Pat. No. 11,713,317 B2

Column 248, Lines 55-56, Claim 1, delete "C(50 O)NR$^{c9}$R$^{d9}$," and insert -- C(=O)NR$^{c9}$R$^{d9}$, --;

Column 250, Line 9, Claim 1, delete "alkyl)amino," and insert -- di(C$_{1-3}$ alkyl)amino, --;

Column 250, Line 10, Claim 1, delete "alkyl sulfonyl," and insert -- alkylsulfonyl, --;

Column 250, Line 26, Claim 2, delete "R$^w$" and insert -- R$^W$ --;

Column 255, Line 21, Claim 34, delete "R$^8$" and insert -- R$^e$ --;

Column 255, Line 33, Claim 34, delete "NR$^{c8}$R$^{d8}$, ," and insert -- NR$^{c8}$R$^{d8}$, --;

Column 256, Line 54, Claim 34, delete "R$^X$ R$^Y$" and insert -- R$^X$, R$^Y$ --;

Column 257, Lines 52-53, Claim 34, delete "C(50 O)NR$^{c4}$R$^{d4}$," and insert -- C(=O)NR$^{c4}$R$^{d4}$, --;

Column 257, Line 59, Claim 34, delete "alkynyl C$_{3-10}$" and insert -- alkynyl, C$_{3-10}$ --;

Column 260, Line 42, Claim 35, delete "R$^X$ R$^Y$" and insert -- R$^X$, R$^Y$ --;

Column 261, Line 15, Claim 35, delete "NR$^{c11}$R$^{d11}$ and" and insert -- NR$^{c11}$R$^{d11}$, and --;

Column 261, Line 36, Claim 37, delete "(3 -cyanopropoxy)" and insert -- (3-cyanopropoxy) --;

Column 262, Line 31, Claim 37, delete "-8 -(3" and insert -- -8-(3 --;

Column 262, Line 66, Claim 37, delete "methyl 1H" and insert -- methyl-1H --;

Column 263, Line 4, Claim 37, delete "methyl -1H" and insert -- methyl-1H --; and Column 264, Line 19, Claim 38, delete "5 -yl)-" and insert -- 5-yl)- --.